US010039795B2

(12) United States Patent
Koeris et al.

(10) Patent No.: US 10,039,795 B2
(45) Date of Patent: Aug. 7, 2018

(54) CODON OPTIMIZED RECOMBINANT PHAGE AND METHODS OF USING SAME

(71) Applicant: Institute for Environmental Health, Inc., Lake Forest Park, WA (US)

(72) Inventors: Michael Sandor Koeris, Natick, MA (US); Jayson L. Bowers, Cambridge, MA (US); Daniel Robert Brownell, Arlington, MA (US); Edyta Krzymanska-Olejnik, Brookline, MA (US); Robert Patrick Shivers, Watertown, MA (US); Michael Cappillino, Reading, MA (US)

(73) Assignee: Institute for Environmental Health, Inc., Lake Forest Park, WA (US)

( * ) Notice: Subject to any disclaimer, the term of this patent is extended or adjusted under 35 U.S.C. 154(b) by 71 days.

(21) Appl. No.: 14/707,847

(22) Filed: May 8, 2015

(65) Prior Publication Data

US 2015/0344930 A1 Dec. 3, 2015

Related U.S. Application Data

(60) Provisional application No. 61/991,132, filed on May 9, 2014, provisional application No. 62/044,082, filed on Aug. 29, 2014, provisional application No. 62/053,481, filed on Sep. 22, 2014, provisional application No. 62/086,445, filed on Dec. 2, 2014.

(51) Int. Cl.

| | |
|---|---|
| ***C12Q 1/70*** | (2006.01) |
| ***A61K 35/76*** | (2015.01) |
| ***C12Q 1/66*** | (2006.01) |
| ***C12Q 1/04*** | (2006.01) |
| ***C12N 7/00*** | (2006.01) |

(52) U.S. Cl.

CPC ................ *A61K 35/76* (2013.01); *C12N 7/00* (2013.01); *C12Q 1/04* (2013.01); *C12Q 1/66* (2013.01); *C12N 2795/10121* (2013.01); *C12N 2795/10132* (2013.01); *C12N 2795/10143* (2013.01); *C12N 2800/22* (2013.01); *G01N 2333/90241* (2013.01); *G01N 2458/30* (2013.01)

(58) Field of Classification Search

None

See application file for complete search history.

(56) References Cited

U.S. PATENT DOCUMENTS

| | | | | |
|---|---|---|---|---|
| 4,861,709 A | 8/1989 | Ulitzur et al. | | |
| 6,395,504 B1 * | 5/2002 | Trudil | C12Q 1/04 | 422/504 |
| 2008/0131310 A1 * | 6/2008 | Crawford | C07K 2/00 | 422/3 |
| 2009/0105195 A1 * | 4/2009 | O'Brien | A01N 25/04 | 514/56 |
| 2012/0052492 A1 * | 3/2012 | Li | C12Q 1/689 | 435/6.11 |

FOREIGN PATENT DOCUMENTS

| | | |
|---|---|---|
| WO | WO 95/32304 A1 | 11/1995 |
| WO | WO 2009/140375 A2 | 11/2009 |
| WO | WO 2014/160818 A2 | 10/2014 |

OTHER PUBLICATIONS

Patterson et al. Codon optimization of bacterial luciferase (lux ) for expression in mammalian cells. J Ind Microbiol Biotechnol (2005) 32: 115-123.*

Busch and Donnelly. Development of a Repair-Enrichment Broth for Resuscitation of Heat-Injured Listeria monocytogenes and Listeria innocua. Applied and Environmental Microbiology, Jan. 1992, p. 14-20.*

Loessner M. et al.: "Construction of luciferase reporter bacteriophage A511:: luxAB for rapid and sensitive detection of viable Listeria cells", *Applied and Environmental Microbiology, American Society for Microbiology*, vol. 62, No. 4, Apr. 1, 1996, pp. 1133-1140.

Hagens S. et al.: "Reporter bacteriophage A511:: celB transduces a hyperthermostable glycosidase from Pyrococcus furiosus for rapid and simple detection of viable Listeria cells", *Bacteriophage*, vol. 1, No. 3, May 1, 2011, pp. 143-151.

Loh J. et al.: "Comparison of firefly luciferase and NanoLuc luciferase for biophotonic labeling of group A *Streptococcus*", *Biotechnology Letters*, vol. 36, No. 4, (2013), pp. 829-834.

* cited by examiner

*Primary Examiner* — Michelle S Horning

(74) *Attorney, Agent, or Firm* — Barry L. Davison; Davis Wright Tremaine LLP

(57) ABSTRACT

Composition and methods for the detection of one or more target microbe(s) are provided. Compositions of the disclosure include at least one recombinant phage capable of infecting a target microbe, said phage comprising at least a capsid protein sequence, a ribosome binding site, and a codon-optimized marker. Compositions of the disclosure may further include an aqueous solution that enhances the ability to detect marker expression upon phage infection of the target microbe. In some embodiments the target microbe include is *Listeria*.

59 Claims, 128 Drawing Sheets
(71 of 128 Drawing Sheet(s) Filed in Color)

FIGURE 1

A511::COP2
ATGCCAAAAAATAACAAAGAAGAAGTTAAAGAAGTAAACCTTAATTCAGTACAAGAGGAT
GCGTTAAAGTCCTTTACGACTGGTTATGGTATCACACCTGATACACAAACAGATGCAGGAGC
ATTAAGACGTGAGTTCCTAGACGACCAAATCTCAATGCTTACTTGGACAGAGAATGATTTAA
CATTCTATAAAGACATCGCTAAAAAACCAGCTACATCTACAGTAGCAAAATACGATGTATA
CATGCAACATGGTAAGGTAGGTCATACTAGATTTACTCGTGAGATTGGGGTAGCACCAGTA
AGTGACCCTAACATCCGTCAAAAAACAGTAAATATGAAATTTGCTTCCGATACTAAAAACAT
CAGTATCGCAGCAGGTCTAGTAAACAACATTCAAGACCCAATGCAAATTTTGACTGACGAT
GCTATCGTAAATATTGCTAAAACAATTGAGTGGGCTTCATTCTTTGGAGATTCTGACTTATCA
GATAGCCCAGAACCACAAGCAGGACTAGAATTTGACGGCTTGGCTAAACTTATTAACCAAG
ATAACGTTCATGATGCTCGTGGAGCTAGCTTGACTGAAAGCTTGTTAAACCAAGCAGCAGTA
ATGATTAGTAAAGGTTATGGTACACCTACAGATGCTTACATGCCAGTAGGGGTTCAAGCAG
ACTTTGTTAACCAACAACTTTCTAAACAAACACAACTTGTTCGCGATAACGGAAACAACGTA
AGCGTTGGTTTCAACATCCAAGGTTTCCATTCAGCTCGTGGATTTATCAAACTTCACGGTTCT
ACAGTAATGGAAAACGAACAAATCTTAGATGAACGTATTCTTGCTTTACCAACAGCTCCACA
ACCAGCTAAGGTAACTGCAACACAAGAAGCAGGTAAAAAAGGACAATTTAGAGCAGAAGA
TTTAGCAGCACATGAATATAAAGTTGTTGTAAGTTCTGACGATGCAGAGTCTATTGCAAGTG
AAGTGGCTACAGCTACAGTTACTGCAAAAGATGACGGCGTTAAACTAGAAATCGAATTAGC
TCCAATGTATAGCTCTCGTCCACAATTCGTTTCAATCTATAGAAAAGGTGCAGAAACAGGTT
TATTCTACCTAATCGCTCGTGTACCTGCTAGCAAAGCAGAGAACAACGTAATCACTTTCTAC
GACTTAAACGACTCTATTCCTGAAACAGTAGACGTATTCGTTGGTGAAATGTCGGCTAACGT
AGTACACTTGTTTGAATTACTACCAATGATGAGATTACCTCTAGCTCAAATTAACGCATCTG
TTACATTTGCAGTTTTATGGTATGGCGCATTAGCTCTAAGAGCACCTAAGAAATGGGTACGT
ATTAGAAACGTTAAATATATTCCTGTAAAAAACGTTCATAGCAACTAATAATAAGAGGAGG
TAAATATATATGGTATTCACATTAGAAGATTTTGTAGGGGATTGGCGACAAACAGCGGGAT
ATAACTTAGATCAAGTTTTGGAACAGGGTGGAGTCTCAAGCCTCTTTCAAAATCTTGGAGTG
AGTGTTACTCCTATTCAAAGAATTGTACTATCTGGTGAAAATGGCTTAAAGATTGATATACA
TGTTATCATTCCATACGAAGGCTTATCGGGTGATCAAATGGGTCAAATTGAGAAAATCTTTA
AAGTAGTGTATCCTGTAGACGATCATCATTTCAAAGTTATTCTTCACTATGGTACGCTTGTGA
TAGACGGGGTTACACCAAATATGATTGATTACTTTGGTCGGCCGTATGAAGGCATTGCTGTT
TTTGACGGGAAAAAAATCACCGTCACTGGAACTTTATGGAATGGTAACAAAATCATTGATG
AACGTTTGATAAATCCAGATGGATCCTTACTTTTCCGCGTGACAATCAACGGAGTAACGGGC
TGGAGATTATGTGAACGTATTCTAGCATAATAATTATAGGATAATTGAATAAAAACAGTATAGAG
*AGCAGATAAATACTGCTCTCTATTTTACTAATAAGGAGGATTTAAATTGCTAAAAAATACAAACTTAG*
*CTAATTATAAAAAAGTGAATACACGGTTTGGAAATCTTAGTTTTGACGACAAAGGTATTTCTAATGAC*
*TTAACGGAAGAACAGCAAAAAGAATTAGGTAAGCTTCGAGGATTCGAATATATTAAGACAGAACAGA*
*AAACAAAAGAAGAACCTAAGAAAGAAGAACCTAAGAAAGAAGAACCTAAGAAAGAAGAACCTAAGA*
*AAGAAGAACCTAAGAAAGAAGAACCTAAGAAAGAAAGTACAGAAAATGAATTAGACAGCTTCTTAGC*
*TAAAGAGCCTTCAATCAAAGAATTAAAAGAATTTGCGAGTAAAAAAGGCATTAAAATTGAAAAAACTA*
*AGAAAAATGATATAATTGAAGAACTAAAGAGAGGGTAATGTATAATGTATGGAGGTTATGA*

Legend:
A511 cps sequence (SEQ ID NO: 19)
*Additional Stop Codons (Added by Sample6)*
Ribosome Binding Site (Added by Sample6) (SEQ ID NO: 54)
COP2 NanoLuc Sequence (Added by Sample6) (SEQ ID NO: 36)
*A511 downstream sequence (500bp)* (SEQ ID NO: 61)

FIGURE 2

LP124::COP2
ATGCCAAAAAATAACAAAGAAGAAGAAGTTAAAGAAGTAAACCTTAATTCAGTACAAGAG
GACGCGTTAAAGTCCTTTACAACTGGTTATGGTATCACACCTGATACACAAACAGATGCAGG
AGCATTAAGACGTGAGTTCCTAGACGACCAAATCTCAATGCTTACTTGGACAGAGAATGATT
TAACATTCTATAAAGACATCGCTAAAAAACCAGCTACATCTACAGTAGCAAAATACGATGT
ATACATGCAACATGGTAAGGTAGGTCATACTAGATTTACTCGTGAGATTGGGGTAGCACCA
GTAAGTGACCCTAACATCCGTCAAAAAACAGTAAACATGAAATTTGCTTCCGATACTAAAA
ACATCAGTATCGCAGCAGGTCTAGTAAACAACATTCAAGACCCAATGCAAATTTTGACTGAC
GATGCTATCGTAAATATTGCTAAAACAATTGAGTGGGCTTCATTCTTTGGAGATTCTGACTT
ATCAGATAGCCCAGAACCACAAGCAGGACTAGAATTTGACGGCTTGGCTAAACTTATTAAC
CAAGATAACGTTCATGATGCTCGTGGAGCTAGCTTGACTGAAAGCTTGTTAAACCAAGCAGC
AGTAATGATTAGTAAAGGTTATGGTACACCTACAGATGCTTACATGCCAGTAGGGGTTCAAG
CAGACTTTGTTAACCAACAACTTTCTAAACAAACACAACTTGTTCGCGATAACGGAAACAAC
GTAAGCGTTGGTTTCAACATCCAAGGTTTCCATTCAGCTCGTGGATTTATCAAACTTCACGGT
TCTACAGTAATGGAAAACGAACAAATCTTAGATGAACGTATTCTTGCTTTACCAACAGCTCC
ACAACCAGCTAAGGTAACTGCAACACAAGAAGCAGGTAAAAAAGGACAATTTAGAGCAGA
AGATTTAGCAGCACATGAATATAAAGTTGTTGTAAGTTCTGACGATGCAGAGTCTATTGCAA
GTGAAGTGGCTACAGCTACAGTTACTGCAAAAGATGACGGCGTTAAACTAGAAATCGAATT
AGCTCCAATGTATAGCTCTCGTCCACAATTCGTTTCAATCTATAGAAAAGGTGCAGAAACAG
GTTTATTCTACCTAATCGCTCGTGTACCTGCTAGCAAAGCAGAGAACAACGTAATCACTTTC
TACGACTTAAACGACTCTATTCCTGAAACAGTAGACGTATTCGTTGGTGAAATGTCGGCTAA
CGTAGTACACTTGTTTGAATTACTACCAATGATGAGATTACCTCTAGCTCAAATTAACGCAT
CTGTTACATTTGCAGTTTTATGGTATGGCGCATTAGCTCTAAGAGCACCTAAGAAATGGGTA
CGTATTAGAAACGTTAAATATATTCCTGTAAAAAACGTTCATAGCAACTAA*TAATAA*__GAGGA__
__GGTAAATATAT__ATGGTATTCACATTAGAAGATTTTGTAGGGGATTGGCGACAAACAGCGGG
ATATAACTTAGATCAAGTTTTGGAACAGGGTGGAGTCTCAAGCCTCTTTCAAAATCTTGGAG
TGAGTGTTACTCCTATTCAAAGAATTGTACTATCTGGTGAAAATGGCTTAAAGATTGATATA
CATGTTATCATTCCATACGAAGGCTTATCGGGTGATCAAATGGGTCAAATTGAGAAAATCTT
TAAAGTAGTGTATCCTGTAGACGATCATCATTTCAAAGTTATTCTTCACTATGGTACGCTTGT
GATAGACGGGGTTACACCAAATATGATTGATTACTTTGGTCGGCCGTATGAAGGCATTGCTG
TTTTTGACGGGAAAAAAATCACCGTCACTGGAACTTTATGGAATGGTAACAAAATCATTGAT
GAACGTTTGATAAATCCAGATGGATCCTTACTTTTCCGCGTGACAATCAACGGAGTAACGGG
CTGGAGATTATGTGAACGTATTCTAGCATAA*TAATTATAGGATAATTGAATAAAAACAGTATAGA*
*GAGCAGATAAATACTGCTCTCTATTTTACTAATAAGGAGGATTTAAATTGCTAAAAAATACAAACTTA*
*GCTAATTATAAAAAAGTGAATACACGGTTTGGAAATCTTAGTTTTGACGACAAAGGTATTTCTAATGA*
*CTTAACGGAAGAACAGCAAAAAGAATTAGGTAAGCTTCGAGGATTCGAATATATTAAGACAGAACAG*
*AAAACAAAAGAAGAACCTAAGAAAGAAGAACCTAAGAAAGAAGAACCTAAGAAAGAAGAACCTAAG*
*AAAGAAGAACCTAAGAAAGAAGAACCTAAGAAAGAAAGTACAGAAAATGAATTAGACAGCTTCTTAG*
*CTAAAGAGCCTTCAATCAAAGAATTAAAAGAATTTGCGAGTAAAAAAGGCATTAAAATTGAAAAAACT*
*AAGAAAAATGATATAATTGAAGAACTAAAGAGAGGGTAATGTATAATGTATGGAGGTTATGA*

Legend:
LP124 cps sequence (SEQ ID NO: 13)
*Additional Stop Codons (Added by Sample6)*
Ribosome Binding Site (Added by Sample6) (SEQ ID NO: 54)
COP2 NanoLuc Sequence (Added by Sample6) (SEQ ID NO: 36)
*LP124 downstream sequence (500bp)* (SEQ ID NO: 62)

FIGURE 3

LP40::COP2
ATGCCAAAAAATAACAAAGAAGAAGAAGTTAAAGAAGTAAACCTTAATTCAGTACAAGAG
GATGCGTTAAAGTCCTTTACAACTGGTTATGGTATCACACCTGATACACAAACAGATGCAGG
GGCACTAAGACGTGAGTTCCTAGACGACCAAATCTCAATGCTTACTTGGACAGAAAATGATT
TAACATTCTACAAAGACATCGCTAAAAAACCAGCTACATCTACAGTAGCAAAATACGATGT
GTACATGCAACACGGTAAAGTAGGTCATACTAGATTTACTCGTGAGATTGGGGTAGCACCA
GTAAGTGACCCTAACATCCGTCAAAAAACAGTAAACATGAAATTTGCTTCTGATACTAAAA
ATATTAGTATCGCAGCAGGTCTAGTAAACAACATTCAAGACCCTATGCAAATTTTGACTGAT
GATGCTATCGTAAATATCGCTAAAACAATTGAGTGGGCTTCATTCTTTGGAGATTCTGACTT
ATCAGATAGCCCAGAACCACAAGCAGGATTAGAATTTGATGGCTTGGCTAAACTTATTAACC
AAGATAACGTTCATGATGCTCGTGGAGCTAGCTTGACTGAAAGCTTGTTAAACCAAGCAGC
AGTAATGATTAGTAAAGGTTATGGTACACCTACAGATGCTTACATGCCAGTAGGGGTTCAAG
CAGACTTTGTTAACCAACAACTTTCTAAACAAACACAACTTGTTCGCGATAACGGAAACAAC
GTAAGCGTTGGTTTCAACATCCAAGGTTTCCATTCAGCTCGTGGATTTATCAAACTTCACGGT
TCTACAGTAATGGAAAACGAACAAATCTTAGATGAACGTATTCTTGCTTTACCAACAGCTCC
ACAACCAGCTAAGGTAACTGCAACACAAGAAGCAGGTAAAAAAGGACAATTTAGAGCAGA
AGATTTAGCAGCACATGAATATAAAGTTGTTGTAAGTTCTGACGATGCAGAGTCTATTGCAA
GTGAAGTGGCTACAGCTACAGTTACTGCAAAAGATGACGGCGTTAAACTAGAAATCGAATT
AGCTCCAATGTATAGCTCTCGTCCACAATTCGTTTCAATCTATAGAAAAGGTGCAGAAACAG
GTTTATTCTACCTAATCGCTCGTGTACCTGCTAGCAAAGCAGAGAACAACGTAATCACTTTC
TACGACTTAAACGACTCTATTCCTGAAACAGTAGACGTATTCGTTGGTGAAATGTCGGCTAA
CGTAGTACACTTGTTTGAATTACTACCAATGATGAGATTACCTCTAGCTCAAATTAACGCAT
CTGTTACATTTGCAGTTTTATGGTATGGCGCATTAGCTCTAAGAGCACCTAAGAAATGGGTA
CGTATTAGAAACGTTAAATATATTCCTGTAAAAAACGTTCATAGCAACTAA_TAATAA_GAGGA
GGTAAATATATATGGTATTCACATTAGAAGATTTTGTAGGGGATTGGCGACAAACAGCGGG
ATATAACTTAGATCAAGTTTTGGAACAGGGTGGAGTCTCAAGCCTCTTTCAAAATCTTGGAG
TGAGTGTTACTCCTATTCAAAGAATTGTACTATCTGGTGAAAATGGCTTAAAGATTGATATA
CATGTTATCATTCCATACGAAGGCTTATCGGGTGATCAAATGGGTCAAATTGAGAAAATCTT
TAAAGTAGTGTATCCTGTAGACGATCATCATTTCAAAGTTATTCTTCACTATGGTACGCTTGT
GATAGACGGGGTTACACCAAATATGATTGATTACTTTGGTCGGCCGTATGAAGGCATTGCTG
TTTTTGACGGGAAAAAAATCACCGTCACTGGAACTTTATGGAATGGTAACAAAATCATTGAT
GAACGTTTGATAAATCCAGATGGATCCTTACTTTTCCGCGTGACAATCAACGGAGTAACGGG
CTGGAGATTATGTGAACGTATTCTAGCATAA*TAATTATAGGATAATTGAATAAAAACAGTATAGA*
*GAGCAGATAAATACTGCTCTCTATTTTACTAATAAGGAGGATTTAAATTGCTAAAAAATACAAACTTA*
*GCTAATTATAAAAAAGTGAATACACGGTTTGGAAATCTTAGTTTTGACGACAAAGGTATTTCTAATGA*
*CTTAACGGAAGAACAGCAAAAAGAATTAGGTAAGCTTCGAGGATTCGAATATATTAAGACAGAACAG*
*AAAACAAAAGAAGAACCTAAGAAAGAAGAACCTAAGAAAGAAGAACCTAAGAAAGAAAGTACAGAA*
*AATGAATTAGACAGCTTCTTAGCTAAAGAGCCTTCAATCAAAGAATTAAAAGAATTTGCGAGTAAAAA*
*AGGCATTAAAATTGAAAAAACTAAGAAAAACGATATAATTGAAGAACTAAAGAGAGGGTAATGTATA*
*ATGTATGGAGGTTATGAAGGACAAGATTCTTACGAATACCCTTACTCACATGGGAACCCTAA*

Legend:
LP40 cps sequence (SEQ ID NO: 5)
*Additional Stop Codons (Added by Sample6)*
Ribosome Binding Site (Added by Sample6) (SEQ ID NO: 54)
COP2 NanoLuc Sequence (Added by Sample6) (SEQ ID NO: 36)
*LP40 downstream sequence (500bp)* (SEQ ID NO: 63)

| Sanitizer | Recommended use | % of recommended amount to give 50% Infection acitivity | % of recommended amount to give 50% Enzyme acitivity |
|---|---|---|---|
| F29 | 0.26% | 54% | 385% |

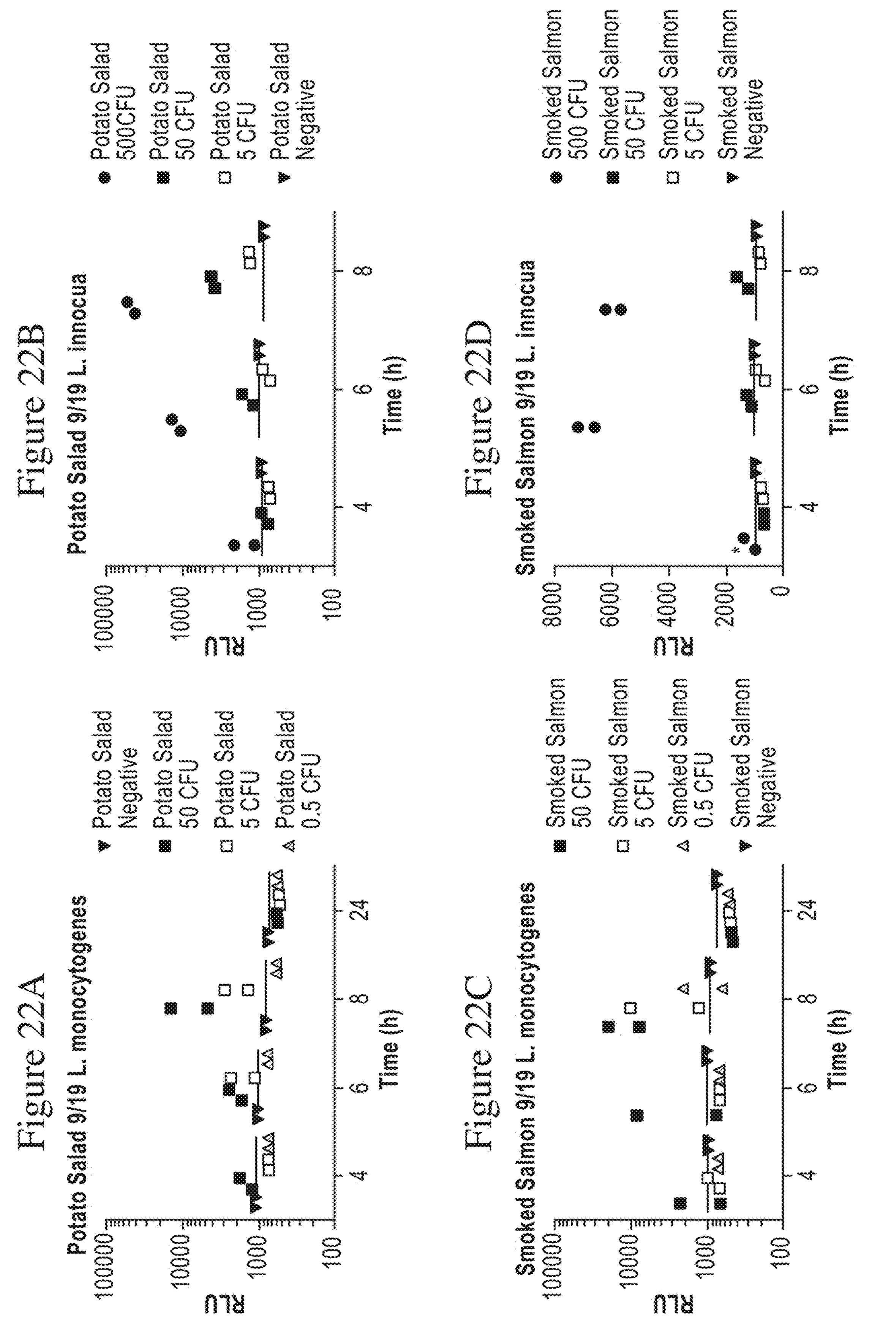
Figure 22A
Potato Salad 9/19 L. monocytogenes
RLU
100000
10000
1000
100
4
6
8
24
Time (h)
Potato Salad Negative
Potato Salad 50 CFU
Potato Salad 5 CFU
Potato Salad 0.5 CFU
Figure 22B
Potato Salad 9/19 L. innocua
RLU
100000
10000
1000
100
4
6
8
Time (h)
Potato Salad 500CFU
Potato Salad 50 CFU
Potato Salad 5 CFU
Potato Salad Negative
Figure 22C
Smoked Salmon 9/19 L. monocytogenes
RLU
100000
10000
1000
100
4
6
8
24
Time (h)
Smoked Salmon 50 CFU
Smoked Salmon 5 CFU
Smoked Salmon 0.5 CFU
Smoked Salmon Negative
Figure 22D
Smoked Salmon 9/19 L. innocua
RLU
8000
6000
4000
2000
0
4
6
8
Time (h)
Smoked Salmon 500 CFU
Smoked Salmon 50 CFU
Smoked Salmon 5 CFU
Smoked Salmon Negative

```
LP143_cps    ATGCCAAAAAATAACAAA---GAAGAAGTTAAAGAAGTAAACCTTAATTCAGTACAAGAG 57
A511_cps     ATGCCAAAAAATAACAAA---GAAGAAGTTAAAGAAGTAAACCTTAATTCAGTACAAGAG 57
LP101_cps    ATGCCAAAAAATAACAAAGAAGAAGAAGTTAAAGAAGTAAACCTTAATTCAGTACAAGAG 60
LP124_cps    ATGCCAAAAAATAACAAAGAAGAAGAAGTTAAAGAAGTAAACCTTAATTCAGTACAAGAG 60
LP99_cps     ATGCCAAAAAATAACAAAGAAGAAGAAGTTAAAGAAGTAAACCTTAATTCAGTACAAGAG 60
LP48_cps     ATGCCAAAAAATAACAAAGAAGAAGAAGTTAAAGAAGTAAACCTTAATTCAGTACAAGAG 60
LP125_cps    ATGCCAAAAAATAACAAAGAAGAAGAAGTTAAAGAAGTAAACCTTAATTCAGTACAAGAG 60
P100_cps     ATGCCAAAAAATAACAAAGAAGAAGAAGTTAAAGAAGTAAACCTTAATTCAGTACAAGAG 60
LP40_cps     ATGCCAAAAAATAACAAAGAAGAAGAAGTTAAAGAAGTAAACCTTAATTCAGTACAAGAG 60
             ******************   ***************************************

LP143_cps    GATGCGTTAAAGTCCTTTACGACTGGTTATGGTATCACACCTGATACACAAACAGATGCA 117
A511_cps     GATGCGTTAAAGTCCTTTACGACTGGTTATGGTATCACACCTGATACACAAACAGATGCA 117
LP101_cps    GACGCGTTAAAGTCCTTTACAACTGGTTATGGTATCACACCTGATACACAAACAGATGCA 120
LP124_cps    GACGCGTTAAAGTCCTTTACAACTGGTTATGGTATCACACCTGATACACAAACAGATGCA 120
LP99_cps     GACGCGTTAAAGTCCTTTACAACTGGTTATGGTATCACACCTGATACACAAACAGATGCA 120
LP48_cps     GACGCGTTAAAGTCCTTTACAACTGGTTATGGTATCACACCTGATACACAAACAGATGCA 120
LP125_cps    GACGCGTTAAAGTCCTTTACAACTGGTTATGGTATCACACCTGATACACAAACAGATGCA 120
P100_cps     GACGCGTTAAAGTCCTTTACAACTGGTTATGGTATCACACCTGATACACAAACAGATGCA 120
LP40_cps     GATGCGTTAAAGTCCTTTACAACTGGTTATGGTATCACACCTGATACACAAACAGATGCA 120
             ** ***************** ***************************************

LP143_cps    GGAGCATTAAGACGTGAGTTCCTAGACGACCAAATCTCAATGCTTACTTGGACAGAGAAT 177
A511_cps     GGAGCATTAAGACGTGAGTTCCTAGACGACCAAATCTCAATGCTTACTTGGACAGAGAAT 177
LP101_cps    GGAGCATTAAGACGTGAGTTCCTAGACGACCAAATCTCAATGCTTACTTGGACAGAGAAT 180
LP124_cps    GGAGCATTAAGACGTGAGTTCCTAGACGACCAAATCTCAATGCTTACTTGGACAGAGAAT 180
LP99_cps     GGAGCATTAAGACGTGAGTTCCTAGACGACCAAATCTCAATGCTTACTTGGACAGAGAAT 180
LP48_cps     GGAGCATTAAGACGTGAGTTCCTAGACGACCAAATCTCAATGCTTACTTGGACAGAGAAT 180
LP125_cps    GGAGCATTAAGACGTGAGTTCCTAGACGACCAAATCTCAATGCTTACTTGGACAGAGAAT 180
P100_cps     GGAGCATTAAGACGTGAGTTCCTAGACGACCAAATCTCAATGCTTACTTGGACAGAGAAT 180
LP40_cps     GGGGCACTAAGACGTGAGTTCCTAGACGACCAAATCTCAATGCTTACTTGGACAGAAAAT 180
             ** *** ************************************************* ***

LP143_cps    GATTTAACATTCTATAAAGACATCGCTAAAAAACCAGCTACATCTACAGTAGCAAAATAC 237
A511_cps     GATTTAACATTCTATAAAGACATCGCTAAAAAACCAGCTACATCTACAGTAGCAAAATAC 237
LP101_cps    GATTTAACATTCTATAAAGACATCGCTAAAAAACCAGCTACATCTACAGTAGCAAAATAC 240
LP124_cps    GATTTAACATTCTATAAAGACATCGCTAAAAAACCAGCTACATCTACAGTAGCAAAATAC 240
LP99_cps     GATTTAACATTCTATAAAGACATCGCTAAAAAACCAGCTACATCTACAGTAGCAAAATAC 240
LP48_cps     GATTTAACATTCTATAAAGACATCGCTAAAAAACCAGCTACATCTACAGTAGCAAAATAC 240
LP125_cps    GATTTAACATTCTATAAAGACATCGCTAAAAAACCAGCTACATCTACAGTAGCAAAATAC 240
P100_cps     GATTTAACATTCTATAAAGACATCGCTAAAAAACCAGCTACATCTACAGTAGCAAAATAC 240
LP40_cps     GATTTAACATTCTACAAAGACATCGCTAAAAAACCAGCTACATCTACAGTAGCAAAATAC 240
             ************** *********************************************

LP143_cps    GATGTATACATGCAACATGGTAAGGTAGGTCATACTAGATTTACTCGTGAGATTGGGGTA 297
A511_cps     GATGTATACATGCAACATGGTAAGGTAGGTCATACTAGATTTACTCGTGAGATTGGGGTA 297
LP101_cps    GATGTATACATGCAACATGGTAAGGTAGGTCATACTAGATTTACTCGTGAGATTGGGGTA 300
LP124_cps    GATGTATACATGCAACATGGTAAGGTAGGTCATACTAGATTTACTCGTGAGATTGGGGTA 300
LP99_cps     GATGTATACATGCAACATGGTAAGGTAGGTCATACTAGATTTACTCGTGAGATTGGGGTA 300
LP48_cps     GATGTATACATGCAACATGGTAAGGTAGGTCATACTAGATTTACTCGTGAGATTGGGGTA 300
LP125_cps    GATGTATACATGCAACATGGTAAGGTAGGTCATACTAGATTTACTCGTGAGATTGGGGTA 300
P100_cps     GATGTATACATGCAACATGGTAAGGTAGGTCATACTAGATTTACTCGTGAGATTGGGGTA 300
LP40_cps     GATGTGTACATGCAACACGGTAAAGTAGGTCATACTAGATTTACTCGTGAGATTGGGGTA 300
             ***** *********** ***** ************************************

LP143_cps    GCACCAGTAAGTGACCCTAACATCCGTCAAAAAACAGTAAATATGAAATTTGCTTCCGAT 357
A511_cps     GCACCAGTAAGTGACCCTAACATCCGTCAAAAAACAGTAAATATGAAATTTGCTTCCGAT 357
LP101_cps    GCACCAGTAAGTGACCCTAACATCCGTCAAAAAACAGTAAACATGAAATTTGCTTCCGAT 360
LP124_cps    GCACCAGTAAGTGACCCTAACATCCGTCAAAAAACAGTAAACATGAAATTTGCTTCCGAT 360
LP99_cps     GCACCAGTAAGTGACCCTAACATCCGTCAAAAAACAGTAAACATGAAATTTGCTTCCGAT 360
LP48_cps     GCACCAGTAAGTGACCCTAACATCCGTCAAAAAACAGTAAACATGAAATTTGCTTCCGAT 360
LP125_cps    GCACCAGTAAGTGACCCTAACATCCGTCAAAAAACAGTAAACATGAAATTTGCTTCCGAT 360
P100_cps     GCACCAGTAAGTGACCCTAACATCCGTCAAAAAACAGTAAATATGAAATTTGCTTCCGAT 360
LP40_cps     GCACCAGTAAGTGACCCTAACATCCGTCAAAAAACAGTAAACATGAAATTTGCTTCTGAT 360
             ***************************************** ************** ***
```

FIGURE 26

```
LP143_cps     ACTAAAAACATCAGTATCGCAGCAGGTCTAGTAAACAACATTCAAGACCCAATGCAAATT  417
A511_cps      ACTAAAAACATCAGTATCGCAGCAGGTCTAGTAAACAACATTCAAGACCCAATGCAAATT  417
LP101_cps     ACTAAAAACATCAGTATCGCAGCAGGTCTAGTAAACAACATTCAAGACCCAATGCAAATT  420
LP124_cps     ACTAAAAACATCAGTATCGCAGCAGGTCTAGTAAACAACATTCAAGACCCAATGCAAATT  420
LP99_cps      ACTAAAAACATCAGTATCGCAGCAGGTCTAGTAAACAACATTCAAGACCCAATGCAAATT  420
LP48_cps      ACTAAAAACATCAGTATCGCAGCAGGTCTAGTAAACAACATTCAAGACCCAATGCAAATT  420
LP125_cps     ACTAAAAACATCAGTATCGCAGCAGGTCTAGTAAACAACATTCAAGACCCAATGCAAATT  420
P100_cps      ACTAAAAACATCAGTATCGCAGCAGGTCTAGTAAACAACATTCAAGACCCAATGCAAATT  420
LP40_cps      ACTAAAAATATTAGTATCGCAGCAGGTCTAGTAAACAACATTCAAGACCCTATGCAAATT  420
              ******** ** ************************************** *********

LP143_cps     TTGACTGACGATGCTATCGTAAATATTGCTAAAACAATTGAGTGGGCTTCATTCTTTGGA  477
A511_cps      TTGACTGACGATGCTATCGTAAATATTGCTAAAACAATTGAGTGGGCTTCATTCTTTGGA  477
LP101_cps     TTGACTGACGATGCTATCGTAAATATTGCTAAAACAATTGAGTGGGCTTCATTCTTTGGA  480
LP124_cps     TTGACTGACGATGCTATCGTAAATATTGCTAAAACAATTGAGTGGGCTTCATTCTTTGGA  480
LP99_cps      TTGACTGACGATGCTATCGTAAATATTGCTAAAACAATTGAGTGGGCTTCATTCTTTGGA  480
LP48_cps      TTGACTGACGATGCTATCGTAAATATTGCTAAAACAATTGAGTGGGCTTCATTCTTTGGA  480
LP125_cps     TTGACTGACGATGCTATCGTAAATATTGCTAAAACAATTGAGTGGGCTTCATTCTTTGGA  480
P100_cps      TTGACTGACGATGCTATCGTAAATATTGCTAAAACAATTGAGTGGGCTTCATTCTTTGGA  480
LP40_cps      TTGACTGATGATGCTATCGTAAATATCGCTAAAACAATTGAGTGGGCTTCATTCTTTGGA  480
              ******** ***************** *********************************

LP143_cps     GATTCTGACTTATCAGATAGCCCAGAACCACAAGCAGGACTAGAATTTGACGGCTTGGCT  537
A511_cps      GATTCTGACTTATCAGATAGCCCAGAACCACAAGCAGGACTAGAATTTGACGGCTTGGCT  537
LP101_cps     GATTCTGACTTATCAGATAGCCCAGAACCACAAGCAGGACTAGAATTTGACGGCTTGGCT  540
LP124_cps     GATTCTGACTTATCAGATAGCCCAGAACCACAAGCAGGACTAGAATTTGACGGCTTGGCT  540
LP99_cps      GATTCTGACTTATCAGATAGCCCAGAACCACAAGCAGGACTAGAATTTGACGGCTTGGCT  540
LP48_cps      GATTCTGACTTATCAGATAGCCCAGAACCACAAGCAGGACTAGAATTTGACGGCTTGGCT  540
LP125_cps     GATTCTGACTTATCAGATAGCCCAGAACCACAAGCAGGACTAGAATTTGACGGCTTGGCT  540
P100_cps      GATTCTGACTTATCAGATAGCCCAGAACCACAAGCAGGACTAGAATTTGACGGCTTGGCT  540
LP40_cps      GATTCTGACTTATCAGATAGCCCAGAACCACAAGCAGGATTAGAATTTGATGGCTTGGCT  540
              *************************************** ********** *********

LP143_cps     AAACTTATTAACCAAGATAACGTTCATGATGCTCGTGGAGCTAGCTTGACTGAAAGCTTG  597
A511_cps      AAACTTATTAACCAAGATAACGTTCATGATGCTCGTGGAGCTAGCTTGACTGAAAGCTTG  597
LP101_cps     AAACTTATTAACCAAGATAACGTTCATGATGCTCGTGGAGCTAGCTTGACTGAAAGCTTG  600
LP124_cps     AAACTTATTAACCAAGATAACGTTCATGATGCTCGTGGAGCTAGCTTGACTGAAAGCTTG  600
LP99_cps      AAACTTATTAACCAAGATAACGTTCATGATGCTCGTGGAGCTAGCTTGACTGAAAGCTTG  600
LP48_cps      AAACTTATTAACCAAGATAACGTTCATGATGCTCGTGGAGCTAGCTTGACTGAAAGCTTG  600
LP125_cps     AAACTTATTAACCAAGATAACGTTCATGATGCTCGTGGAGCTAGCTTGACTGAAAGCTTG  600
P100_cps      AAACTTATTAACCAAGATAACGTTCATGATGCTCGTGGAGCTAGCTTGACTGAAAGCTTG  600
LP40_cps      AAACTTATTAACCAAGATAACGTTCATGATGCTCGTGGAGCTAGCTTGACTGAAAGCTTG  600
              ************************************************************

LP143_cps     TTAAACCAAGCAGCAGTAATGATTAGTAAAGGTTATGGTACACCTACAGATGCTTACATG  657
A511_cps      TTAAACCAAGCAGCAGTAATGATTAGTAAAGGTTATGGTACACCTACAGATGCTTACATG  657
LP101_cps     TTAAACCAAGCAGCAGTAATGATTAGTAAAGGTTATGGTACACCTACAGATGCTTACATG  660
LP124_cps     TTAAACCAAGCAGCAGTAATGATTAGTAAAGGTTATGGTACACCTACAGATGCTTACATG  660
LP99_cps      TTAAACCAAGCAGCAGTAATGATTAGTAAAGGTTATGGTACACCTACAGATGCTTACATG  660
LP48_cps      TTAAACCAAGCAGCAGTAATGATTAGTAAAGGTTATGGTACACCTACAGATGCTTACATG  660
LP125_cps     TTAAACCAAGCAGCAGTAATGATTAGTAAAGGTTATGGTACACCTACAGATGCTTACATG  660
P100_cps      TTAAACCAAGCAGCAGTAATGATTAGTAAAGGTTATGGTACACCTACAGATGCTTACATG  660
LP40_cps      TTAAACCAAGCAGCAGTAATGATTAGTAAAGGTTATGGTACACCTACAGATGCTTACATG  660
              ************************************************************

LP143_cps     CCAGTAGGGGTTCAAGCAGACTTTGTTAACCAACAACTTTCTAAACAAACACAACTTGTT  717
A511_cps      CCAGTAGGGGTTCAAGCAGACTTTGTTAACCAACAACTTTCTAAACAAACACAACTTGTT  717
LP101_cps     CCAGTAGGGGTTCAAGCAGACTTTGTTAACCAACAACTTTCTAAACAAACACAACTTGTT  720
LP124_cps     CCAGTAGGGGTTCAAGCAGACTTTGTTAACCAACAACTTTCTAAACAAACACAACTTGTT  720
LP99_cps      CCAGTAGGGGTTCAAGCAGACTTTGTTAACCAACAACTTTCTAAACAAACACAACTTGTT  720
LP48_cps      CCAGTAGGGGTTCAAGCAGACTTTGTTAACCAACAACTTTCTAAACAAACACAACTTGTT  720
LP125_cps     CCAGTAGGGGTTCAAGCAGACTTTGTTAACCAACAACTTTCTAAACAAACACAACTTGTT  720
P100_cps      CCAGTAGGGGTTCAAGCAGACTTTGTTAACCAACAACTTTCTAAACAAACACAGCTTGTT  720
LP40_cps      CCAGTAGGGGTTCAAGCAGACTTTGTTAACCAACAACTTTCTAAACAAACACAACTTGTT  720
              ***************************************************** ******
```

FIGURE 26 (continued)

```
LP143_cps    CGCGATAACGGAAACAACGTAAGCGTTGGTTTCAACATCCAAGGTTTCCATTCAGCTCGT  777
A511_cps     CGCGATAACGGAAACAACGTAAGCGTTGGTTTCAACATCCAAGGTTTCCATTCAGCTCGT  777
LP101_cps    CGCGATAACGGAAACAACGTAAGCGTTGGTTTCAACATCCAAGGTTTCCATTCAGCTCGT  780
LP124_cps    CGCGATAACGGAAACAACGTAAGCGTTGGTTTCAACATCCAAGGTTTCCATTCAGCTCGT  780
LP99_cps     CGCGATAACGGAAACAACGTAAGCGTTGGTTTCAACATCCAAGGTTTCCATTCAGCTCGT  780
LP48_cps     CGCGATAACGGAAACAACGTAAGCGTTGGTTTCAACATCCAAGGTTTCCATTCAGCTCGT  780
LP125_cps    CGTGATAACGGAAACAACGTAAGCGTTGGTTTCAACATCCAAGGTTTCCATTCAGCTCGT  780
P100_cps     CGTGATAACGGAAACAACGTAAGCGTTGGTTTCAACATCCAAGGTTTCCATTCAGCTCGT  780
LP40_cps     CGCGATAACGGAAACAACGTAAGCGTTGGTTTCAACATCCAAGGTTTCCATTCAGCTCGT  780
             ** *********************************************************

LP143_cps    GGATTTATCAAACTTCACGGTTCTACAGTAATGGAAAACGAACAAATCTTAGATGAACGT  837
A511_cps     GGATTTATCAAACTTCACGGTTCTACAGTAATGGAAAACGAACAAATCTTAGATGAACGT  837
LP101_cps    GGATTTATCAAACTTCACGGTTCTACAGTAATGGAAAACGAACAAATCTTAGATGAACGT  840
LP124_cps    GGATTTATCAAACTTCACGGTTCTACAGTAATGGAAAACGAACAAATCTTAGATGAACGT  840
LP99_cps     GGATTTATCAAACTTCACGGTTCTACAGTAATGGAAAACGAACAAATCTTAGATGAACGT  840
LP48_cps     GGATTTATCAAACTTCACGGTTCTACAGTAATGGAAAACGAACAAATCTTAGATGAACGT  840
LP125_cps    GGATTTATCAAACTTCACGGTTCTACAGTAATGGAAAACGAACAAATCTTAGATGAACGT  840
P100_cps     GGATTTATCAAACTTCACGGTTCTACAGTAATGGAAAACGAACAAATCTTAGATGAACGT  840
LP40_cps     GGATTTATCAAACTTCACGGTTCTACAGTAATGGAAAACGAACAAATCTTAGATGAACGT  840
             ************************************************************

LP143_cps    ATTCTTGCTTTACCAACAGCTCCACAACCAGCTAAGGTAACTGCAACACAAGAAGCAGGT  897
A511_cps     ATTCTTGCTTTACCAACAGCTCCACAACCAGCTAAGGTAACTGCAACACAAGAAGCAGGT  897
LP101_cps    ATTCTTGCTTTACCAACAGCTCCACAACCAGCTAAGGTAACTGCAACACAAGAAGCAGGT  900
LP124_cps    ATTCTTGCTTTACCAACAGCTCCACAACCAGCTAAGGTAACTGCAACACAAGAAGCAGGT  900
LP99_cps     ATTCTTGCTTTACCAACAGCTCCACAACCAGCTAAGGTAACTGCAACACAAGAAGCAGGT  900
LP48_cps     ATTCTTGCTTTACCAACAGCTCCACAACCAGCTAAGGTAACTGCAACACAAGAAGCAGGT  900
LP125_cps    ATTCTTGCTTTACCAACAGCTCCACAACCAGCTAAGGTAACTGCAACACAAGAAGCAGGT  900
P100_cps     ATTCTTGCTTTACCAACAGCTCCACAACCAGCTAAGGTAACTGCAACACAAGAAGCAGGT  900
LP40_cps     ATTCTTGCTTTACCAACAGCTCCACAACCAGCTAAGGTAACTGCAACACAAGAAGCAGGT  900
             ************************************************************

LP143_cps    AAAAAAGGACAATTTAGAGCAGAAGATTTAGCAGCACATGAATATAAAGTTGTTGTAAGT  957
A511_cps     AAAAAAGGACAATTTAGAGCAGAAGATTTAGCAGCACATGAATATAAAGTTGTTGTAAGT  957
LP101_cps    AAAAAAGGACAATTTAGAGCAGAAGATTTAGCAGCACATGAATATAAAGTTGTTGTAAGT  960
LP124_cps    AAAAAAGGACAATTTAGAGCAGAAGATTTAGCAGCACATGAATATAAAGTTGTTGTAAGT  960
LP99_cps     AAAAAAGGACAATTTAGAGCAGAAGATTTAGCAGCACATGAATATAAAGTTGTTGTAAGT  960
LP48_cps     AAAAAAGGACAATTTAGAGCAGAAGATTTAGCAGCACATGAATATAAAGTTGTTGTAAGT  960
LP125_cps    AAAAAAGGACAATTTAGAGCAGAAGATTTAGCAGCACATGAATATAAAGTTGTTGTAAGT  960
P100_cps     AAAAAAGGACAATTTAGAGCAGAAGACTTAGCAGCACACGAATACAAAGTTGTTGTAAGT  960
LP40_cps     AAAAAAGGACAATTTAGAGCAGAAGATTTAGCAGCACATGAATATAAAGTTGTTGTAAGT  960
             ************************** *********** ***** ***************

LP143_cps    TCTGACGATGCAGAGTCTATTGCAAGTGAAGTGGCTACAGCTACAGTTACTGCAAAAGAT  1017
A511_cps     TCTGACGATGCAGAGTCTATTGCAAGTGAAGTGGCTACAGCTACAGTTACTGCAAAAGAT  1017
LP101_cps    TCTGACGATGCAGAGTCTATTGCAAGTGAAGTGGCTACAGCTACAGTTACTGCAAAAGAT  1020
LP124_cps    TCTGACGATGCAGAGTCTATTGCAAGTGAAGTGGCTACAGCTACAGTTACTGCAAAAGAT  1020
LP99_cps     TCTGACGATGCAGAGTCTATTGCAAGTGAAGTGGCTACAGCTACAGTTACTGCAAAAGAT  1020
LP48_cps     TCTGACGATGCAGAGTCTATTGCAAGTGAAGTGGCTACAGCTACAGTTACTGCAAAAGAT  1020
LP125_cps    TCTGACGATGCAGAGTCTATTGCAAGTGAAGTGGCTACAGCTACAGTTACTGCAAAAGAT  1020
P100_cps     TCTGACGATGCAGAGTCTATTGCAAGTGAAGTGGCTACAGCTACAGTTACTGCAAAAGAT  1020
LP40_cps     TCTGACGATGCAGAGTCTATTGCAAGTGAAGTGGCTACAGCTACAGTTACTGCAAAAGAT  1020
             ************************************************************

LP143_cps    GACGGCGTTAAACTAGAAATCGAATTAGCTCCAATGTATAGCTCTCGTCCACAATTCGTT  1077
A511_cps     GACGGCGTTAAACTAGAAATCGAATTAGCTCCAATGTATAGCTCTCGTCCACAATTCGTT  1077
LP101_cps    GACGGCGTTAAACTAGAAATCGAATTAGCTCCAATGTATAGCTCTCGTCCACAATTCGTT  1080
LP124_cps    GACGGCGTTAAACTAGAAATCGAATTAGCTCCAATGTATAGCTCTCGTCCACAATTCGTT  1080
LP99_cps     GACGGCGTTAAACTAGAAATCGAATTAGCTCCAATGTATAGCTCTCGTCCACAATTCGTT  1080
LP48_cps     GACGGCGTTAAACTAGAAATCGAATTAGCTCCAATGTATAGCTCTCGTCCACAATTCGTT  1080
LP125_cps    GACGGCGTTAAACTAGAAATCGAATTAGCTCCAATGTATAGCTCTCGTCCACAATTCGTT  1080
P100_cps     GACGGCGTTAAACTAGAAATCGAGTTAGCTCCAATGTACAGCTCCCGTCCACAATTCGTT  1080
LP40_cps     GACGGCGTTAAACTAGAAATCGAATTAGCTCCAATGTATAGCTCTCGTCCACAATTCGTT  1080
             *********************** ************** ***** ***************
```

FIGURE 26 (continued)

```
LP143_cps     TCAATCTATAGAAAAGGTGCAGAAACAGGTTTATTCTACCTAATCGCTCGTGTACCTGCT 1137
A511_cps      TCAATCTATAGAAAAGGTGCAGAAACAGGTTTATTCTACCTAATCGCTCGTGTACCTGCT 1137
LP101_cps     TCAATCTATAGAAAAGGTGCAGAAACAGGTTTATTCTACCTAATCGCTCGTGTACCTGCT 1140
LP124_cps     TCAATCTATAGAAAAGGTGCAGAAACAGGTTTATTCTACCTAATCGCTCGTGTACCTGCT 1140
LP99_cps      TCAATCTATAGAAAAGGTGCAGAAACAGGTTTATTCTACCTAATCGCTCGTGTACCTGCT 1140
LP48_cps      TCAATCTATAGAAAAGGTGCAGAAACAGGTTTATTCTACCTAATCGCTCGTGTACCTGCT 1140
LP125_cps     TCAATCTATAGAAAAGGTGCAGAAACAGGTTTATTCTACCTAATCGCTCGTGTACCTGCT 1140
P100_cps      TCAATCTATAGAAAAGGTGCAGAAACAGGTTTATTCTACCTAATCGCTCGTGTACCTGCT 1140
LP40_cps      TCAATCTATAGAAAAGGTGCAGAAACAGGTTTATTCTACCTAATCGCTCGTGTACCTGCT 1140
              ************************************************************

LP143_cps     AGCAAAGCAGAGAACAACGTAATCACTTTCTACGACTTAAACGACTCTATTCCTGAAACA 1197
A511_cps      AGCAAAGCAGAGAACAACGTAATCACTTTCTACGACTTAAACGACTCTATTCCTGAAACA 1197
LP101_cps     AGCAAAGCAGAGAACAACGTAATCACTTTCTACGACTTAAACGACTCTATTCCTGAAACA 1200
LP124_cps     AGCAAAGCAGAGAACAACGTAATCACTTTCTACGACTTAAACGACTCTATTCCTGAAACA 1200
LP99_cps      AGCAAAGCAGAGAACAACGTAATCACTTTCTACGACTTAAACGACTCTATTCCTGAAACA 1200
LP48_cps      AGCAAAGCAGAGAACAACGTAATCACTTTCTACGACTTAAACGACTCTATTCCTGAAACA 1200
LP125_cps     AGCAAAGCAGAGAACAACGTAATCACTTTCTACGACTTAAACGACTCTATTCCTGAAACA 1200
P100_cps      AGCAAAGCAGAGAACAACGTAATCACTTTCTATGACTTAAACGACTCTATTCCTGAAACA 1200
LP40_cps      AGCAAAGCAGAGAACAACGTAATCACTTTCTACGACTTAAACGACTCTATTCCTGAAACA 1200
              ******************************** ***************************

LP143_cps     GTAGACGTATTCGTTGGTGAAATGTCGGCTAACGTAGTACACTTGTTTGAATTACTACCA 1257
A511_cps      GTAGACGTATTCGTTGGTGAAATGTCGGCTAACGTAGTACACTTGTTTGAATTACTACCA 1257
LP101_cps     GTAGACGTATTCGTTGGTGAAATGTCGGCTAACGTAGTACACTTGTTTGAATTACTACCA 1260
LP124_cps     GTAGACGTATTCGTTGGTGAAATGTCGGCTAACGTAGTACACTTGTTTGAATTACTACCA 1260
LP99_cps      GTAGACGTATTCGTTGGTGAAATGTCGGCTAACGTAGTACACTTGTTTGAATTACTACCA 1260
LP48_cps      GTAGACGTATTCGTTGGTGAAATGTCGGCTAACGTAGTACACTTGTTTGAATTACTACCA 1260
LP125_cps     GTAGACGTATTCGTTGGTGAAATGTCGGCTAACGTAGTACACTTGTTTGAATTACTACCA 1260
P100_cps      GTAGACGTATTCGTTGGTGAAATGTCTGCTAACGTAGTACACTTGTTTGAATTACTACCA 1260
LP40_cps      GTAGACGTATTCGTTGGTGAAATGTCGGCTAACGTAGTACACTTGTTTGAATTACTACCA 1260
              ************************** *********************************

LP143_cps     ATGATGAGATTACCTCTAGCTCAAATTAACGCATCTGTTACATTTGCAGTTTTATGGTAT 1317
A511_cps      ATGATGAGATTACCTCTAGCTCAAATTAACGCATCTGTTACATTTGCAGTTTTATGGTAT 1317
LP101_cps     ATGATGAGATTACCTCTAGCTCAAATTAACGCATCTGTTACATTTGCAGTTTTATGGTAT 1320
LP124_cps     ATGATGAGATTACCTCTAGCTCAAATTAACGCATCTGTTACATTTGCAGTTTTATGGTAT 1320
LP99_cps      ATGATGAGATTACCTCTAGCTCAAATTAACGCATCTGTTACATTTGCAGTTTTATGGTAT 1320
LP48_cps      ATGATGAGATTACCTCTAGCTCAAATTAACGCATCTGTTACATTTGCAGTTTTATGGTAT 1320
LP125_cps     ATGATGAGATTACCTCTAGCTCAAATTAACGCATCTGTTACATTTGCAGTTTTATGGTAT 1320
P100_cps      ATGATGAGATTACCTCTAGCTCAAATTAACGCATCTGTTACATTTGCAGTTTTATGGTAT 1320
LP40_cps      ATGATGAGATTACCTCTAGCTCAAATTAACGCATCTGTTACATTTGCAGTTTTATGGTAT 1320
              ************************************************************

LP143_cps     GGCGCATTAGCTCTAAGAGCACCTAAGAAATGGGTACGTATTAGAAACGTTAAATATATT 1377
A511_cps      GGCGCATTAGCTCTAAGAGCACCTAAGAAATGGGTACGTATTAGAAACGTTAAATATATT 1377
LP101_cps     GGCGCATTAGCTCTAAGAGCACCTAAGAAATGGGTACGTATTAGAAACGTTAAATATATT 1380
LP124_cps     GGCGCATTAGCTCTAAGAGCACCTAAGAAATGGGTACGTATTAGAAACGTTAAATATATT 1380
LP99_cps      GGCGCATTAGCTCTAAGAGCACCTAAGAAATGGGTACGTATTAGAAACGTTAAATATATT 1380
LP48_cps      GGCGCATTAGCTCTAAGAGCACCTAAGAAATGGGTACGTATTAGAAACGTTAAATATATT 1380
LP125_cps     GGCGCATTAGCTCTAAGAGCACCTAAGAAATGGGTACGTATTAGAAACGTTAAATATATT 1380
P100_cps      GGAGCATTAGCTCTAAGAGCACCTAAGAAATGGGTACGTATTAGAAACGTTAAATATATT 1380
LP40_cps      GGCGCATTAGCTCTAAGAGCACCTAAGAAATGGGTACGTATTAGAAACGTTAAATATATT 1380
              ** *********************************************************

LP143_cps     CCTGTAAAAAACGTTCATAGCAACTAA 1404
A511_cps      CCTGTAAAAAACGTTCATAGCAACTAA 1404
LP101_cps     CCTGTAAAAAACGTTCATAGCAACTAA 1407
LP124_cps     CCTGTAAAAAACGTTCATAGCAACTAA 1407
LP99_cps      CCTGTAAAAAACGTTCATAGCAACTAA 1407
LP48_cps      CCTGTAAAAAACGTTCATAGCAACTAA 1407
LP125_cps     CCTGTAAAAAACGTTCATAGCAACTAA 1407
P100_cps      CCTGTAAAAAACGTTCATAGCAACTAA 1407
LP40_cps      CCTGTAAAAAACGTTCATAGCAACTAA 1407
              ***************************
```

FIGURE 26 (continued)

```
LP143_cps    MPKNNK-EEVKEVNLNSVQEDALKSFTTGYGITPDTQTDAGALRREFLDDQISMLTWTEN 59
A511_cps     MPKNNK-EEVKEVNLNSVQEDALKSFTTGYGITPDTQTDAGALRREFLDDQISMLTWTEN 59
LP40_cps     MPKNNKEEEVKEVNLNSVQEDALKSFTTGYGITPDTQTDAGALRREFLDDQISMLTWTEN 60
LP48_cps     MPKNNKEEEVKEVNLNSVQEDALKSFTTGYGITPDTQTDAGALRREFLDDQISMLTWTEN 60
LP99_cps     MPKNNKEEEVKEVNLNSVQEDALKSFTTGYGITPDTQTDAGALRREFLDDQISMLTWTEN 60
LP101_cps    MPKNNKEEEVKEVNLNSVQEDALKSFTTGYGITPDTQTDAGALRREFLDDQISMLTWTEN 60
LP124_cps    MPKNNKEEEVKEVNLNSVQEDALKSFTTGYGITPDTQTDAGALRREFLDDQISMLTWTEN 60
P100_cps     MPKNNKEEEVKEVNLNSVQEDALKSFTTGYGITPDTQTDAGALRREFLDDQISMLTWTEN 60
LP125_cps    MPKNNKEEEVKEVNLNSVQEDALKSFTTGYGITPDTQTDAGALRREFLDDQISMLTWTEN 60
             ****** *****************************************************

LP143_cps    DLTFYKDIAKKPATSTVAKYDVYMQHGKVGHTRFTREIGVAPVSDPNIRQKTVNMKFASD 119
A511_cps     DLTFYKDIAKKPATSTVAKYDVYMQHGKVGHTRFTREIGVAPVSDPNIRQKTVNMKFASD 119
LP40_cps     DLTFYKDIAKKPATSTVAKYDVYMQHGKVGHTRFTREIGVAPVSDPNIRQKTVNMKFASD 120
LP48_cps     DLTFYKDIAKKPATSTVAKYDVYMQHGKVGHTRFTREIGVAPVSDPNIRQKTVNMKFASD 120
LP99_cps     DLTFYKDIAKKPATSTVAKYDVYMQHGKVGHTRFTREIGVAPVSDPNIRQKTVNMKFASD 120
LP101_cps    DLTFYKDIAKKPATSTVAKYDVYMQHGKVGHTRFTREIGVAPVSDPNIRQKTVNMKFASD 120
LP124_cps    DLTFYKDIAKKPATSTVAKYDVYMQHGKVGHTRFTREIGVAPVSDPNIRQKTVNMKFASD 120
P100_cps     DLTFYKDIAKKPATSTVAKYDVYMQHGKVGHTRFTREIGVAPVSDPNIRQKTVNMKFASD 120
LP125_cps    DLTFYKDIAKKPATSTVAKYDVYMQHGKVGHTRFTREIGVAPVSDPNIRQKTVNMKFASD 120
             ************************************************************

LP143_cps    TKNISIAAGLVNNIQDPMQILTDDAIVNIAKTIEWASFFGDSDLSDSPEPQAGLEFDGLA 179
A511_cps     TKNISIAAGLVNNIQDPMQILTDDAIVNIAKTIEWASFFGDSDLSDSPEPQAGLEFDGLA 179
LP40_cps     TKNISIAAGLVNNIQDPMQILTDDAIVNIAKTIEWASFFGDSDLSDSPEPQAGLEFDGLA 180
LP48_cps     TKNISIAAGLVNNIQDPMQILTDDAIVNIAKTIEWASFFGDSDLSDSPEPQAGLEFDGLA 180
LP99_cps     TKNISIAAGLVNNIQDPMQILTDDAIVNIAKTIEWASFFGDSDLSDSPEPQAGLEFDGLA 180
LP101_cps    TKNISIAAGLVNNIQDPMQILTDDAIVNIAKTIEWASFFGDSDLSDSPEPQAGLEFDGLA 180
LP124_cps    TKNISIAAGLVNNIQDPMQILTDDAIVNIAKTIEWASFFGDSDLSDSPEPQAGLEFDGLA 180
P100_cps     TKNISIAAGLVNNIQDPMQILTDDAIVNIAKTIEWASFFGDSDLSDSPEPQAGLEFDGLA 180
LP125_cps    TKNISIAAGLVNNIQDPMQILTDDAIVNIAKTIEWASFFGDSDLSDSPEPQAGLEFDGLA 180
             ************************************************************

LP143_cps    KLINQDNVHDARGASLTESLLNQAAVMISKGYGTPTDAYMPVGVQADFVNQQLSKQTQLV 239
A511_cps     KLINQDNVHDARGASLTESLLNQAAVMISKGYGTPTDAYMPVGVQADFVNQQLSKQTQLV 239
LP40_cps     KLINQDNVHDARGASLTESLLNQAAVMISKGYGTPTDAYMPVGVQADFVNQQLSKQTQLV 240
LP48_cps     KLINQDNVHDARGASLTESLLNQAAVMISKGYGTPTDAYMPVGVQADFVNQQLSKQTQLV 240
LP99_cps     KLINQDNVHDARGASLTESLLNQAAVMISKGYGTPTDAYMPVGVQADFVNQQLSKQTQLV 240
LP101_cps    KLINQDNVHDARGASLTESLLNQAAVMISKGYGTPTDAYMPVGVQADFVNQQLSKQTQLV 240
LP124_cps    KLINQDNVHDARGASLTESLLNQAAVMISKGYGTPTDAYMPVGVQADFVNQQLSKQTQLV 240
P100_cps     KLINQDNVHDARGASLTESLLNQAAVMISKGYGTPTDAYMPVGVQADFVNQQLSKQTQLV 240
LP125_cps    KLINQDNVHDARGASLTESLLNQAAVMISKGYGTPTDAYMPVGVQADFVNQQLSKQTQLV 240
             ************************************************************

LP143_cps    RDNGNNVSVGFNIQGFHSARGFIKLHGSTVMENEQILDERILALPTAPQPAKVTATQEAG 299
A511_cps     RDNGNNVSVGFNIQGFHSARGFIKLHGSTVMENEQILDERILALPTAPQPAKVTATQEAG 299
LP40_cps     RDNGNNVSVGFNIQGFHSARGFIKLHGSTVMENEQILDERILALPTAPQPAKVTATQEAG 300
LP48_cps     RDNGNNVSVGFNIQGFHSARGFIKLHGSTVMENEQILDERILALPTAPQPAKVTATQEAG 300
LP99_cps     RDNGNNVSVGFNIQGFHSARGFIKLHGSTVMENEQILDERILALPTAPQPAKVTATQEAG 300
LP101_cps    RDNGNNVSVGFNIQGFHSARGFIKLHGSTVMENEQILDERILALPTAPQPAKVTATQEAG 300
LP124_cps    RDNGNNVSVGFNIQGFHSARGFIKLHGSTVMENEQILDERILALPTAPQPAKVTATQEAG 300
P100_cps     RDNGNNVSVGFNIQGFHSARGFIKLHGSTVMENEQILDERILALPTAPQPAKVTATQEAG 300
LP125_cps    RDNGNNVSVGFNIQGFHSARGFIKLHGSTVMENEQILDERILALPTAPQPAKVTATQEAG 300
             ************************************************************

LP143_cps    KKGQFRAEDLAAHEYKVVVSSDDAESIASEVATATVTAKDDGVKLEIELAPMYSSRPQFV 359
A511_cps     KKGQFRAEDLAAHEYKVVVSSDDAESIASEVATATVTAKDDGVKLEIELAPMYSSRPQFV 359
LP40_cps     KKGQFRAEDLAAHEYKVVVSSDDAESIASEVATATVTAKDDGVKLEIELAPMYSSRPQFV 360
LP48_cps     KKGQFRAEDLAAHEYKVVVSSDDAESIASEVATATVTAKDDGVKLEIELAPMYSSRPQFV 360
LP99_cps     KKGQFRAEDLAAHEYKVVVSSDDAESIASEVATATVTAKDDGVKLEIELAPMYSSRPQFV 360
LP101_cps    KKGQFRAEDLAAHEYKVVVSSDDAESIASEVATATVTAKDDGVKLEIELAPMYSSRPQFV 360
LP124_cps    KKGQFRAEDLAAHEYKVVVSSDDAESIASEVATATVTAKDDGVKLEIELAPMYSSRPQFV 360
P100_cps     KKGQFRAEDLAAHEYKVVVSSDDAESIASEVATATVTAKDDGVKLEIELAPMYSSRPQFV 360
LP125_cps    KKGQFRAEDLAAHEYKVVVSSDDAESIASEVATATVTAKDDGVKLEIELAPMYSSRPQFV 360
             ************************************************************
```

FIGURE 27

```
LP143_cps    SIYRKGAETGLFYLIARVPASKAENNVITFYDLNDSIPETVDVFVGEMSANVVHLFELLP 419
A511_cps     SIYRKGAETGLFYLIARVPASKAENNVITFYDLNDSIPETVDVFVGEMSANVVHLFELLP 419
LP40_cps     SIYRKGAETGLFYLIARVPASKAENNVITFYDLNDSIPETVDVFVGEMSANVVHLFELLP 420
LP48_cps     SIYRKGAETGLFYLIARVPASKAENNVITFYDLNDSIPETVDVFVGEMSANVVHLFELLP 420
LP99_cps     SIYRKGAETGLFYLIARVPASKAENNVITFYDLNDSIPETVDVFVGEMSANVVHLFELLP 420
LP101_cps    SIYRKGAETGLFYLIARVPASKAENNVITFYDLNDSIPETVDVFVGEMSANVVHLFELLP 420
LP124_cps    SIYRKGAETGLFYLIARVPASKAENNVITFYDLNDSIPETVDVFVGEMSANVVHLFELLP 420
P100_cps     SIYRKGAETGLFYLIARVPASKAENNVITFYDLNDSIPETVDVFVGEMSANVVHLFELLP 420
LP125_cps    SIYRKGAETGLFYLIARVPASKAENNVITFYDLNDSIPETVDVFVGEMSANVVHLFELLP 420
             ************************************************************

LP143_cps    MMRLPLAQINASVTFAVLWYGALALRAPKKWVRIRNVKYIPVKNVHSN 467
A511_cps     MMRLPLAQINASVTFAVLWYGALALRAPKKWVRIRNVKYIPVKNVHSN 467
LP40_cps     MMRLPLAQINASVTFAVLWYGALALRAPKKWVRIRNVKYIPVKNVHSN 468
LP48_cps     MMRLPLAQINASVTFAVLWYGALALRAPKKWVRIRNVKYIPVKNVHSN 468
LP99_cps     MMRLPLAQINASVTFAVLWYGALALRAPKKWVRIRNVKYIPVKNVHSN 468
LP101_cps    MMRLPLAQINASVTFAVLWYGALALRAPKKWVRIRNVKYIPVKNVHSN 468
LP124_cps    MMRLPLAQINASVTFAVLWYGALALRAPKKWVRIRNVKYIPVKNVHSN 468
P100_cps     MMRLPLAQINASVTFAVLWYGALALRAPKKWVRIRNVKYIPVKNVHSN 468
LP125_cps    MMRLPLAQINASVTFAVLWYGALALRAPKKWVRIRNVKYIPVKNVHSN 468
             ************************************************
```

FIGURE 27(continued)

```
LP48___ffluc     ATGCCAAAAAATAACAAAGAAGAAGAAGTTAAAGAAGTAAACCTTAATTCAGTACAAGAG 60
LP125___ffluc    ATGCCAAAAAATAACAAAGAAGAAGAAGTTAAAGAAGTAAACCTTAATTCAGTACAAGAG 60
LP143___ffluc    ATGCCAAAAAATAACAAA---GAAGAAGTTAAAGAAGTAAACCTTAATTCAGTACAAGAG 57
A511___ffluc     ATGCCAAAAAATAACAAA---GAAGAAGTTAAAGAAGTAAACCTTAATTCAGTACAAGAG 57
LP124___ffluc    ATGCCAAAAAATAACAAAGAAGAAGAAGTTAAAGAAGTAAACCTTAATTCAGTACAAGAG 60
lp101___ffluc    ATGCCAAAAAATAACAAAGAAGAAGAAGTTAAAGAAGTAAACCTTAATTCAGTACAAGAG 60
LP99___ffluc     ATGCCAAAAAATAACAAAGAAGAAGAAGTTAAAGAAGTAAACCTTAATTCAGTACAAGAG 60
P100___ffluc     ATGCCAAAAAATAACAAAGAAGAAGAAGTTAAAGAAGTAAACCTTAATTCAGTACAAGAG 60
                 ******************   ***************************************

LP48___ffluc     GACGCGTTAAAGTCCTTTACAACTGGTTATGGTATCACACCTGATACACAAACAGATGCA 120
LP125___ffluc    GACGCGTTAAAGTCCTTTACAACTGGTTATGGTATCACACCTGATACACAAACAGATGCA 120
LP143___ffluc    GATGCGTTAAAGTCCTTTACGACTGGTTATGGTATCACACCTGATACACAAACAGATGCA 117
A511___ffluc     GATGCGTTAAAGTCCTTTACGACTGGTTATGGTATCACACCTGATACACAAACAGATGCA 117
LP124___ffluc    GACGCGTTAAAGTCCTTTACAACTGGTTATGGTATCACACCTGATACACAAACAGATGCA 120
lp101___ffluc    GACGCGTTAAAGTCCTTTACAACTGGTTATGGTATCACACCTGATACACAAACAGATGCA 120
LP99___ffluc     GACGCGTTAAAGTCCTTTACAACTGGTTATGGTATCACACCTGATACACAAACAGATGCA 120
P100___ffluc     GACGCGTTAAAGTCCTTTACAACTGGTTATGGTATCACACCTGATACACAAACAGATGCA 120
                 ** ***************** ***************************************

LP48___ffluc     GGAGCATTAAGACGTGAGTTCCTAGACGACCAAATCTCAATGCTTACTTGGACAGAGAAT 180
LP125___ffluc    GGAGCATTAAGACGTGAGTTCCTAGACGACCAAATCTCAATGCTTACTTGGACAGAGAAT 180
LP143___ffluc    GGAGCATTAAGACGTGAGTTCCTAGACGACCAAATCTCAATGCTTACTTGGACAGAGAAT 177
A511___ffluc     GGAGCATTAAGACGTGAGTTCCTAGACGACCAAATCTCAATGCTTACTTGGACAGAGAAT 177
LP124___ffluc    GGAGCATTAAGACGTGAGTTCCTAGACGACCAAATCTCAATGCTTACTTGGACAGAGAAT 180
lp101___ffluc    GGAGCATTAAGACGTGAGTTCCTAGACGACCAAATCTCAATGCTTACTTGGACAGAGAAT 180
LP99___ffluc     GGAGCATTAAGACGTGAGTTCCTAGACGACCAAATCTCAATGCTTACTTGGACAGAGAAT 180
P100___ffluc     GGAGCATTAAGACGTGAGTTCCTAGACGACCAAATCTCAATGCTTACTTGGACAGAGAAT 180
                 ************************************************************

LP48___ffluc     GATTTAACATTCTATAAAGACATCGCTAAAAAACCAGCTACATCTACAGTAGCAAAATAC 240
LP125___ffluc    GATTTAACATTCTATAAAGACATCGCTAAAAAACCAGCTACATCTACAGTAGCAAAATAC 240
LP143___ffluc    GATTTAACATTCTATAAAGACATCGCTAAAAAACCAGCTACATCTACAGTAGCAAAATAC 237
A511___ffluc     GATTTAACATTCTATAAAGACATCGCTAAAAAACCAGCTACATCTACAGTAGCAAAATAC 237
LP124___ffluc    GATTTAACATTCTATAAAGACATCGCTAAAAAACCAGCTACATCTACAGTAGCAAAATAC 240
lp101___ffluc    GATTTAACATTCTATAAAGACATCGCTAAAAAACCAGCTACATCTACAGTAGCAAAATAC 240
LP99___ffluc     GATTTAACATTCTATAAAGACATCGCTAAAAAACCAGCTACATCTACAGTAGCAAAATAC 240
P100___ffluc     GATTTAACATTCTATAAAGACATCGCTAAAAAACCAGCTACATCTACAGTAGCAAAATAC 240
                 ************************************************************
```

FIGURE 28

```
LP48___ffluc     GATGTATACATGCAACATGGTAAGGTAGGTCATACTAGATTTACTCGTGAGATTGGGGTA 300
LP125___ffluc    GATGTATACATGCAACATGGTAAGGTAGGTCATACTAGATTTACTCGTGAGATTGGGGTA 300
LP143___ffluc    GATGTATACATGCAACATGGTAAGGTAGGTCATACTAGATTTACTCGTGAGATTGGGGTA 297
A511___ffluc     GATGTATACATGCAACATGGTAAGGTAGGTCATACTAGATTTACTCGTGAGATTGGGGTA 297
LP124___ffluc    GATGTATACATGCAACATGGTAAGGTAGGTCATACTAGATTTACTCGTGAGATTGGGGTA 300
lp101___ffluc    GATGTATACATGCAACATGGTAAGGTAGGTCATACTAGATTTACTCGTGAGATTGGGGTA 300
LP99___ffluc     GATGTATACATGCAACATGGTAAGGTAGGTCATACTAGATTTACTCGTGAGATTGGGGTA 300
P100___ffluc     GATGTATACATGCAACATGGTAAGGTAGGTCATACTAGATTTACTCGTGAGATTGGGGTA 300
                 ************************************************************

LP48___ffluc     GCACCAGTAAGTGACCCTAACATCCGTCAAAAAACAGTAAACATGAAATTTGCTTCCGAT 360
LP125___ffluc    GCACCAGTAAGTGACCCTAACATCCGTCAAAAAACAGTAAACATGAAATTTGCTTCCGAT 360
LP143___ffluc    GCACCAGTAAGTGACCCTAACATCCGTCAAAAAACAGTAAATATGAAATTTGCTTCCGAT 357
A511___ffluc     GCACCAGTAAGTGACCCTAACATCCGTCAAAAAACAGTAAATATGAAATTTGCTTCCGAT 357
LP124___ffluc    GCACCAGTAAGTGACCCTAACATCCGTCAAAAAACAGTAAACATGAAATTTGCTTCCGAT 360
lp101___ffluc    GCACCAGTAAGTGACCCTAACATCCGTCAAAAAACAGTAAACATGAAATTTGCTTCCGAT 360
LP99___ffluc     GCACCAGTAAGTGACCCTAACATCCGTCAAAAAACAGTAAACATGAAATTTGCTTCCGAT 360
P100___ffluc     GCACCAGTAAGTGACCCTAACATCCGTCAAAAAACAGTAAATATGAAATTTGCTTCCGAT 360
                 ***************************************** ******************

LP48___ffluc     ACTAAAAACATCAGTATCGCAGCAGGTCTAGTAAACAACATTCAAGACCCAATGCAAATT 420
LP125___ffluc    ACTAAAAACATCAGTATCGCAGCAGGTCTAGTAAACAACATTCAAGACCCAATGCAAATT 420
LP143___ffluc    ACTAAAAACATCAGTATCGCAGCAGGTCTAGTAAACAACATTCAAGACCCAATGCAAATT 417
A511___ffluc     ACTAAAAACATCAGTATCGCAGCAGGTCTAGTAAACAACATTCAAGACCCAATGCAAATT 417
LP124___ffluc    ACTAAAAACATCAGTATCGCAGCAGGTCTAGTAAACAACATTCAAGACCCAATGCAAATT 420
lp101___ffluc    ACTAAAAACATCAGTATCGCAGCAGGTCTAGTAAACAACATTCAAGACCCAATGCAAATT 420
LP99___ffluc     ACTAAAAACATCAGTATCGCAGCAGGTCTAGTAAACAACATTCAAGACCCAATGCAAATT 420
P100___ffluc     ACTAAAAACATCAGTATCGCAGCAGGTCTAGTAAACAACATTCAAGACCCAATGCAAATT 420
                 ************************************************************

LP48___ffluc     TTGACTGACGATGCTATCGTAAATATTGCTAAAACAATTGAGTGGGCTTCATTCTTTGGA 480
LP125___ffluc    TTGACTGACGATGCTATCGTAAATATTGCTAAAACAATTGAGTGGGCTTCATTCTTTGGA 480
LP143___ffluc    TTGACTGACGATGCTATCGTAAATATTGCTAAAACAATTGAGTGGGCTTCATTCTTTGGA 477
A511___ffluc     TTGACTGACGATGCTATCGTAAATATTGCTAAAACAATTGAGTGGGCTTCATTCTTTGGA 477
LP124___ffluc    TTGACTGACGATGCTATCGTAAATATTGCTAAAACAATTGAGTGGGCTTCATTCTTTGGA 480
lp101___ffluc    TTGACTGACGATGCTATCGTAAATATTGCTAAAACAATTGAGTGGGCTTCATTCTTTGGA 480
LP99___ffluc     TTGACTGACGATGCTATCGTAAATATTGCTAAAACAATTGAGTGGGCTTCATTCTTTGGA 480
P100___ffluc     TTGACTGACGATGCTATCGTAAATATTGCTAAAACAATTGAGTGGGCTTCATTCTTTGGA 480
                 ************************************************************

LP48___ffluc     GATTCTGACTTATCAGATAGCCCAGAACCACAAGCAGGACTAGAATTTGACGGCTTGGCT 540
LP125___ffluc    GATTCTGACTTATCAGATAGCCCAGAACCACAAGCAGGACTAGAATTTGACGGCTTGGCT 540
LP143___ffluc    GATTCTGACTTATCAGATAGCCCAGAACCACAAGCAGGACTAGAATTTGACGGCTTGGCT 537
A511___ffluc     GATTCTGACTTATCAGATAGCCCAGAACCACAAGCAGGACTAGAATTTGACGGCTTGGCT 537
LP124___ffluc    GATTCTGACTTATCAGATAGCCCAGAACCACAAGCAGGACTAGAATTTGACGGCTTGGCT 540
lp101___ffluc    GATTCTGACTTATCAGATAGCCCAGAACCACAAGCAGGACTAGAATTTGACGGCTTGGCT 540
LP99___ffluc     GATTCTGACTTATCAGATAGCCCAGAACCACAAGCAGGACTAGAATTTGACGGCTTGGCT 540
P100___ffluc     GATTCTGACTTATCAGATAGCCCAGAACCACAAGCAGGACTAGAATTTGACGGCTTGGCT 540
                 ************************************************************

LP48___ffluc     AAACTTATTAACCAAGATAACGTTCATGATGCTCGTGGAGCTAGCTTGACTGAAAGCTTG 600
LP125___ffluc    AAACTTATTAACCAAGATAACGTTCATGATGCTCGTGGAGCTAGCTTGACTGAAAGCTTG 600
LP143___ffluc    AAACTTATTAACCAAGATAACGTTCATGATGCTCGTGGAGCTAGCTTGACTGAAAGCTTG 597
A511___ffluc     AAACTTATTAACCAAGATAACGTTCATGATGCTCGTGGAGCTAGCTTGACTGAAAGCTTG 597
LP124___ffluc    AAACTTATTAACCAAGATAACGTTCATGATGCTCGTGGAGCTAGCTTGACTGAAAGCTTG 600
lp101___ffluc    AAACTTATTAACCAAGATAACGTTCATGATGCTCGTGGAGCTAGCTTGACTGAAAGCTTG 600
LP99___ffluc     AAACTTATTAACCAAGATAACGTTCATGATGCTCGTGGAGCTAGCTTGACTGAAAGCTTG 600
P100___ffluc     AAACTTATTAACCAAGATAACGTTCATGATGCTCGTGGAGCTAGCTTGACTGAAAGCTTG 600
                 ************************************************************

LP48___ffluc     TTAAACCAAGCAGCAGTAATGATTAGTAAAGGTTATGGTACACCTACAGATGCTTACATG 660
LP125___ffluc    TTAAACCAAGCAGCAGTAATGATTAGTAAAGGTTATGGTACACCTACAGATGCTTACATG 660
LP143___ffluc    TTAAACCAAGCAGCAGTAATGATTAGTAAAGGTTATGGTACACCTACAGATGCTTACATG 657
A511___ffluc     TTAAACCAAGCAGCAGTAATGATTAGTAAAGGTTATGGTACACCTACAGATGCTTACATG 657
LP124___ffluc    TTAAACCAAGCAGCAGTAATGATTAGTAAAGGTTATGGTACACCTACAGATGCTTACATG 660
lp101___ffluc    TTAAACCAAGCAGCAGTAATGATTAGTAAAGGTTATGGTACACCTACAGATGCTTACATG 660
LP99___ffluc     TTAAACCAAGCAGCAGTAATGATTAGTAAAGGTTATGGTACACCTACAGATGCTTACATG 660
P100___ffluc     TTAAACCAAGCAGCAGTAATGATTAGTAAAGGTTATGGTACACCTACAGATGCTTACATG 660
                 ************************************************************
```

FIGURE 28 (continued)

```
LP48____ffluc      CCAGTAGGGGTTCAAGCAGACTTTGTTAACCAACAACTTTCTAAACAAACACAACTTGTT  720
LP125___ffluc      CCAGTAGGGGTTCAAGCAGACTTTGTTAACCAACAACTTTCTAAACAAACACAACTTGTT  720
LP143___ffluc      CCAGTAGGGGTTCAAGCAGACTTTGTTAACCAACAACTTTCTAAACAAACACAACTTGTT  717
A511___ffluc       CCAGTAGGGGTTCAAGCAGACTTTGTTAACCAACAACTTTCTAAACAAACACAACTTGTT  717
LP124___ffluc      CCAGTAGGGGTTCAAGCAGACTTTGTTAACCAACAACTTTCTAAACAAACACAACTTGTT  720
lp101____ffluc     CCAGTAGGGGTTCAAGCAGACTTTGTTAACCAACAACTTTCTAAACAAACACAACTTGTT  720
LP99___ffluc       CCAGTAGGGGTTCAAGCAGACTTTGTTAACCAACAACTTTCTAAACAAACACAACTTGTT  720
P100___ffluc       CCAGTAGGGGTTCAAGCAGACTTTGTTAACCAACAACTTTCTAAACAAACACAGCTTGTT  720
                   ***************************************************** ******

LP48___ffluc       CGCGATAACGGAAACAACGTAAGCGTTGGTTTCAACATCCAAGGTTTCCATTCAGCTCGT  780
LP125___ffluc      CGTGATAACGGAAACAACGTAAGCGTTGGTTTCAACATCCAAGGTTTCCATTCAGCTCGT  780
LP143___ffluc      CGCGATAACGGAAACAACGTAAGCGTTGGTTTCAACATCCAAGGTTTCCATTCAGCTCGT  777
A511___ffluc       CGCGATAACGGAAACAACGTAAGCGTTGGTTTCAACATCCAAGGTTTCCATTCAGCTCGT  777
LP124___ffluc      CGCGATAACGGAAACAACGTAAGCGTTGGTTTCAACATCCAAGGTTTCCATTCAGCTCGT  780
lp101___ffluc      CGCGATAACGGAAACAACGTAAGCGTTGGTTTCAACATCCAAGGTTTCCATTCAGCTCGT  780
LP99___ffluc       CGCGATAACGGAAACAACGTAAGCGTTGGTTTCAACATCCAAGGTTTCCATTCAGCTCGT  780
P100___ffluc       CGTGATAACGGAAACAACGTAAGCGTTGGTTTCAACATCCAAGGTTTCCATTCAGCTCGT  780
                   ** *********************************************************

LP48___ffluc       GGATTTATCAAACTTCACGGTTCTACAGTAATGGAAAACGAACAAATCTTAGATGAACGT  840
LP125___ffluc      GGATTTATCAAACTTCACGGTTCTACAGTAATGGAAAACGAACAAATCTTAGATGAACGT  840
LP143___ffluc      GGATTTATCAAACTTCACGGTTCTACAGTAATGGAAAACGAACAAATCTTAGATGAACGT  837
A511___ffluc       GGATTTATCAAACTTCACGGTTCTACAGTAATGGAAAACGAACAAATCTTAGATGAACGT  837
LP124___ffluc      GGATTTATCAAACTTCACGGTTCTACAGTAATGGAAAACGAACAAATCTTAGATGAACGT  840
lp101___ffluc      GGATTTATCAAACTTCACGGTTCTACAGTAATGGAAAACGAACAAATCTTAGATGAACGT  840
LP99___ffluc       GGATTTATCAAACTTCACGGTTCTACAGTAATGGAAAACGAACAAATCTTAGATGAACGT  840
P100___ffluc       GGATTTATCAAACTTCACGGTTCTACAGTAATGGAAAACGAACAAATCTTAGATGAACGT  840
                   ************************************************************

LP48___ffluc       ATTCTTGCTTTACCAACAGCTCCACAACCAGCTAAGGTAACTGCAACACAAGAAGCAGGT  900
LP125____ffluc     ATTCTTGCTTTACCAACAGCTCCACAACCAGCTAAGGTAACTGCAACACAAGAAGCAGGT  900
LP143___ffluc      ATTCTTGCTTTACCAACAGCTCCACAACCAGCTAAGGTAACTGCAACACAAGAAGCAGGT  897
A511___ffluc       ATTCTTGCTTTACCAACAGCTCCACAACCAGCTAAGGTAACTGCAACACAAGAAGCAGGT  897
LP124____ffluc     ATTCTTGCTTTACCAACAGCTCCACAACCAGCTAAGGTAACTGCAACACAAGAAGCAGGT  900
lp101___ffluc      ATTCTTGCTTTACCAACAGCTCCACAACCAGCTAAGGTAACTGCAACACAAGAAGCAGGT  900
LP99___ffluc       ATTCTTGCTTTACCAACAGCTCCACAACCAGCTAAGGTAACTGCAACACAAGAAGCAGGT  900
P100___ffluc       ATTCTTGCTTTACCAACAGCTCCACAACCAGCTAAGGTAACTGCAACACAAGAAGCAGGT  900
                   ************************************************************

LP48___ffluc       AAAAAAGGACAATTTAGAGCAGAAGATTTAGCAGCACATGAATATAAAGTTGTTGTAAGT  960
LP125____ffluc     AAAAAAGGACAATTTAGAGCAGAAGATTTAGCAGCACATGAATATAAAGTTGTTGTAAGT  960
LP143____ffluc     AAAAAAGGACAATTTAGAGCAGAAGATTTAGCAGCACATGAATATAAAGTTGTTGTAAGT  957
A511___ffluc       AAAAAAGGACAATTTAGAGCAGAAGATTTAGCAGCACATGAATATAAAGTTGTTGTAAGT  957
LP124____ffluc     AAAAAAGGACAATTTAGAGCAGAAGATTTAGCAGCACATGAATATAAAGTTGTTGTAAGT  960
lp101____ffluc     AAAAAAGGACAATTTAGAGCAGAAGATTTAGCAGCACATGAATATAAAGTTGTTGTAAGT  960
LP99___ffluc       AAAAAAGGACAATTTAGAGCAGAAGATTTAGCAGCACATGAATATAAAGTTGTTGTAAGT  960
P100___ffluc       AAAAAAGGACAATTTAGAGCAGAAGACTTAGCAGCACACGAATACAAAGTTGTTGTAAGT  960
                   ************************** *********** ***** ***************

LP48____ffluc      TCTGACGATGCAGAGTCTATTGCAAGTGAAGTGGCTACAGCTACAGTTACTGCAAAAGAT  1020
LP125___ffluc      TCTGACGATGCAGAGTCTATTGCAAGTGAAGTGGCTACAGCTACAGTTACTGCAAAAGAT  1020
LP143___ffluc      TCTGACGATGCAGAGTCTATTGCAAGTGAAGTGGCTACAGCTACAGTTACTGCAAAAGAT  1017
A511___ffluc       TCTGACGATGCAGAGTCTATTGCAAGTGAAGTGGCTACAGCTACAGTTACTGCAAAAGAT  1017
LP124___ffluc      TCTGACGATGCAGAGTCTATTGCAAGTGAAGTGGCTACAGCTACAGTTACTGCAAAAGAT  1020
lp101___ffluc      TCTGACGATGCAGAGTCTATTGCAAGTGAAGTGGCTACAGCTACAGTTACTGCAAAAGAT  1020
LP99___ffluc       TCTGACGATGCAGAGTCTATTGCAAGTGAAGTGGCTACAGCTACAGTTACTGCAAAAGAT  1020
P100___ffluc       TCTGACGATGCAGAGTCTATTGCAAGTGAAGTGGCTACAGCTACAGTTACTGCAAAAGAT  1020
                   ************************************************************

LP48___ffluc       GACGGCGTTAAACTAGAAATCGAATTAGCTCCAATGTATAGCTCTCGTCCACAATTCGTT  1080
LP125___ffluc      GACGGCGTTAAACTAGAAATCGAATTAGCTCCAATGTATAGCTCTCGTCCACAATTCGTT  1080
LP143___ffluc      GACGGCGTTAAACTAGAAATCGAATTAGCTCCAATGTATAGCTCTCGTCCACAATTCGTT  1077
A511___ffluc       GACGGCGTTAAACTAGAAATCGAATTAGCTCCAATGTATAGCTCTCGTCCACAATTCGTT  1077
LP124___ffluc      GACGGCGTTAAACTAGAAATCGAATTAGCTCCAATGTATAGCTCTCGTCCACAATTCGTT  1080
lp101___ffluc      GACGGCGTTAAACTAGAAATCGAATTAGCTCCAATGTATAGCTCTCGTCCACAATTCGTT  1080
LP99___ffluc       GACGGCGTTAAACTAGAAATCGAATTAGCTCCAATGTATAGCTCTCGTCCACAATTCGTT  1080
P100___ffluc       GACGGCGTTAAACTAGAAATCGAGTTAGCTCCAATGTACAGCTCCCGTCCACAATTCGTT  1080
                   *********************** ************** ***** ***************
```

FIGURE 28 (continued)

```
LP48___ffluc     TCAATCTATAGAAAAGGTGCAGAAACAGGTTTATTCTACCTAATCGCTCGTGTACCTGCT  1140
LP125___ffluc    TCAATCTATAGAAAAGGTGCAGAAACAGGTTTATTCTACCTAATCGCTCGTGTACCTGCT  1140
LP143___ffluc    TCAATCTATAGAAAAGGTGCAGAAACAGGTTTATTCTACCTAATCGCTCGTGTACCTGCT  1137
A511___ffluc     TCAATCTATAGAAAAGGTGCAGAAACAGGTTTATTCTACCTAATCGCTCGTGTACCTGCT  1137
LP124___ffluc    TCAATCTATAGAAAAGGTGCAGAAACAGGTTTATTCTACCTAATCGCTCGTGTACCTGCT  1140
lp101___ffluc    TCAATCTATAGAAAAGGTGCAGAAACAGGTTTATTCTACCTAATCGCTCGTGTACCTGCT  1140
LP99___ffluc     TCAATCTATAGAAAAGGTGCAGAAACAGGTTTATTCTACCTAATCGCTCGTGTACCTGCT  1140
P100___ffluc     TCAATCTATAGAAAAGGTGCAGAAACAGGTTTATTCTACCTAATCGCTCGTGTACCTGCT  1140
                 ************************************************************

LP48___ffluc     AGCAAAGCAGAGAACAACGTAATCACTTTCTACGACTTAAACGACTCTATTCCTGAAACA  1200
LP125___ffluc    AGCAAAGCAGAGAACAACGTAATCACTTTCTACGACTTAAACGACTCTATTCCTGAAACA  1200
LP143___ffluc    AGCAAAGCAGAGAACAACGTAATCACTTTCTACGACTTAAACGACTCTATTCCTGAAACA  1197
A511___ffluc     AGCAAAGCAGAGAACAACGTAATCACTTTCTACGACTTAAACGACTCTATTCCTGAAACA  1197
LP124___ffluc    AGCAAAGCAGAGAACAACGTAATCACTTTCTACGACTTAAACGACTCTATTCCTGAAACA  1200
lp101___ffluc    AGCAAAGCAGAGAACAACGTAATCACTTTCTACGACTTAAACGACTCTATTCCTGAAACA  1200
LP99___ffluc     AGCAAAGCAGAGAACAACGTAATCACTTTCTACGACTTAAACGACTCTATTCCTGAAACA  1200
P100___ffluc     AGCAAAGCAGAGAACAACGTAATCACTTTCTATGACTTAAACGACTCTATTCCTGAAACA  1200
                 ******************************** ***************************

LP48___ffluc     GTAGACGTATTCGTTGGTGAAATGTCGGCTAACGTAGTACACTTGTTTGAATTACTACCA  1260
LP125___ffluc    GTAGACGTATTCGTTGGTGAAATGTCGGCTAACGTAGTACACTTGTTTGAATTACTACCA  1260
LP143___ffluc    GTAGACGTATTCGTTGGTGAAATGTCGGCTAACGTAGTACACTTGTTTGAATTACTACCA  1257
A511___ffluc     GTAGACGTATTCGTTGGTGAAATGTCGGCTAACGTAGTACACTTGTTTGAATTACTACCA  1257
LP124___ffluc    GTAGACGTATTCGTTGGTGAAATGTCGGCTAACGTAGTACACTTGTTTGAATTACTACCA  1260
lp101___ffluc    GTAGACGTATTCGTTGGTGAAATGTCGGCTAACGTAGTACACTTGTTTGAATTACTACCA  1260
LP99___ffluc     GTAGACGTATTCGTTGGTGAAATGTCGGCTAACGTAGTACACTTGTTTGAATTACTACCA  1260
P100___ffluc     GTAGACGTATTCGTTGGTGAAATGTCTGCTAACGTAGTACACTTGTTTGAATTACTACCA  1260
                 ************************** *********************************

LP48___ffluc     ATGATGAGATTACCTCTAGCTCAAATTAACGCATCTGTTACATTTGCAGTTTTATGGTAT  1320
LP125___ffluc    ATGATGAGATTACCTCTAGCTCAAATTAACGCATCTGTTACATTTGCAGTTTTATGGTAT  1320
LP143___ffluc    ATGATGAGATTACCTCTAGCTCAAATTAACGCATCTGTTACATTTGCAGTTTTATGGTAT  1317
A511___ffluc     ATGATGAGATTACCTCTAGCTCAAATTAACGCATCTGTTACATTTGCAGTTTTATGGTAT  1317
LP124___ffluc    ATGATGAGATTACCTCTAGCTCAAATTAACGCATCTGTTACATTTGCAGTTTTATGGTAT  1320
lp101___ffluc    ATGATGAGATTACCTCTAGCTCAAATTAACGCATCTGTTACATTTGCAGTTTTATGGTAT  1320
LP99___ffluc     ATGATGAGATTACCTCTAGCTCAAATTAACGCATCTGTTACATTTGCAGTTTTATGGTAT  1320
P100___ffluc     ATGATGAGATTACCTCTAGCTCAAATTAACGCATCTGTTACATTTGCAGTTTTATGGTAT  1320
                 ************************************************************

LP48___ffluc     GGCGCATTAGCTCTAAGAGCACCTAAGAAATGGGTACGTATTAGAAACGTTAAATATATT  1380
LP125___ffluc    GGCGCATTAGCTCTAAGAGCACCTAAGAAATGGGTACGTATTAGAAACGTTAAATATATT  1380
LP143___ffluc    GGCGCATTAGCTCTAAGAGCACCTAAGAAATGGGTACGTATTAGAAACGTTAAATATATT  1377
A511___ffluc     GGCGCATTAGCTCTAAGAGCACCTAAGAAATGGGTACGTATTAGAAACGTTAAATATATT  1377
LP124___ffluc    GGCGCATTAGCTCTAAGAGCACCTAAGAAATGGGTACGTATTAGAAACGTTAAATATATT  1380
lp101___ffluc    GGCGCATTAGCTCTAAGAGCACCTAAGAAATGGGTACGTATTAGAAACGTTAAATATATT  1380
LP99___ffluc     GGCGCATTAGCTCTAAGAGCACCTAAGAAATGGGTACGTATTAGAAACGTTAAATATATT  1380
P100___ffluc     GGAGCATTAGCTCTAAGAGCACCTAAGAAATGGGTACGTATTAGAAACGTTAAATATATT  1380
                 ** *********************************************************

LP48___ffluc     CCTGTAAAAAACGTTCATAGCAACTAAGAGGAGGTAAATATATATGGAAGACGCCAAAAA  1440
LP125___ffluc    CCTGTAAAAAACGTTCATAGCAACTAAGAGGAGGTAAATATATATGGAAGACGCCAAAAA  1440
LP143___ffluc    CCTGTAAAAAACGTTCATAGCAACTAAGAGGAGGTAAATATATATGGAAGACGCCAAAAA  1437
A511___ffluc     CCTGTAAAAAACGTTCATAGCAACTAAGAGGAGGTAAATATATATGGAAGACGCCAAAAA  1437
LP124___ffluc    CCTGTAAAAAACGTTCATAGCAACTAAGAGGAGGTAAATATATATGGAAGACGCCAAAAA  1440
lp101___ffluc    CCTGTAAAAAACGTTCATAGCAACTAAGAGGAGGTAAATATATATGGAAGACGCCAAAAA  1440
LP99___ffluc     CCTGTAAAAAACGTTCATAGCAACTAAGAGGAGGTAAATATATATGGAAGACGCCAAAAA  1440
P100___ffluc     CCTGTAAAAAACGTTCATAGCAACTAAGAGGAGGTAAATATATATGGAAGACGCCAAAAA  1440
                 ************************************************************

LP48___ffluc     CATAAAGAAAGGCCCGGCGCCATTCTATCCTCTAGAGGATGGAACCGCTGGAGAGCAACT  1500
LP125___ffluc    CATAAAGAAAGGCCCGGCGCCATTCTATCCTCTAGAGGATGGAACCGCTGGAGAGCAACT  1500
LP143___ffluc    CATAAAGAAAGGCCCGGCGCCATTCTATCCTCTAGAGGATGGAACCGCTGGAGAGCAACT  1497
A511___ffluc     CATAAAGAAAGGCCCGGCGCCATTCTATCCTCTAGAGGATGGAACCGCTGGAGAGCAACT  1497
LP124___ffluc    CATAAAGAAAGGCCCGGCGCCATTCTATCCTCTAGAGGATGGAACCGCTGGAGAGCAACT  1500
lp101___ffluc    CATAAAGAAAGGCCCGGCGCCATTCTATCCTCTAGAGGATGGAACCGCTGGAGAGCAACT  1500
LP99___ffluc     CATAAAGAAAGGCCCGGCGCCATTCTATCCTCTAGAGGATGGAACCGCTGGAGAGCAACT  1500
P100___ffluc     CATAAAGAAAGGCCCGGCGCCATTCTATCCTCTAGAGGATGGAACCGCTGGAGAGCAACT  1500
                 ************************************************************
```

FIGURE 28 (continued)

```
LP48___ffluc     GCATAAGGCTATGAAGAGATACGCCCTGGTTCCTGGAACAATTGCTTTTACAGATGCACA  1560
LP125___ffluc    GCATAAGGCTATGAAGAGATACGCCCTGGTTCCTGGAACAATTGCTTTTACAGATGCACA  1560
LP143___ffluc    GCATAAGGCTATGAAGAGATACGCCCTGGTTCCTGGAACAATTGCTTTTACAGATGCACA  1557
A511___ffluc     GCATAAGGCTATGAAGAGATACGCCCTGGTTCCTGGAACAATTGCTTTTACAGATGCACA  1557
LP124___ffluc    GCATAAGGCTATGAAGAGATACGCCCTGGTTCCTGGAACAATTGCTTTTACAGATGCACA  1560
lp101___ffluc    GCATAAGGCTATGAAGAGATACGCCCTGGTTCCTGGAACAATTGCTTTTACAGATGCACA  1560
LP99___ffluc     GCATAAGGCTATGAAGAGATACGCCCTGGTTCCTGGAACAATTGCTTTTACAGATGCACA  1560
P100___ffluc     GCATAAGGCTATGAAGAGATACGCCCTGGTTCCTGGAACAATTGCTTTTACAGATGCACA  1560
                 ************************************************************

LP48___ffluc     TATCGAGGTGAACATCACGTACGCGGAATACTTCGAAATGTCCGTTCGGTTGGCAGAAGC  1620
LP125___ffluc    TATCGAGGTGAACATCACGTACGCGGAATACTTCGAAATGTCCGTTCGGTTGGCAGAAGC  1620
LP143___ffluc    TATCGAGGTGAACATCACGTACGCGGAATACTTCGAAATGTCCGTTCGGTTGGCAGAAGC  1617
A511___ffluc     TATCGAGGTGAACATCACGTACGCGGAATACTTCGAAATGTCCGTTCGGTTGGCAGAAGC  1617
LP124___ffluc    TATCGAGGTGAACATCACGTACGCGGAATACTTCGAAATGTCCGTTCGGTTGGCAGAAGC  1620
lp101___ffluc    TATCGAGGTGAACATCACGTACGCGGAATACTTCGAAATGTCCGTTCGGTTGGCAGAAGC  1620
LP99___ffluc     TATCGAGGTGAACATCACGTACGCGGAATACTTCGAAATGTCCGTTCGGTTGGCAGAAGC  1620
P100___ffluc     TATCGAGGTGAACATCACGTACGCGGAATACTTCGAAATGTCCGTTCGGTTGGCAGAAGC  1620
                 ************************************************************

LP48___ffluc     TATGAAACGATATGGGCTGAATACAAATCACAGAATCGTCGTATGCAGTGAAAACTCTCT  1680
LP125___ffluc    TATGAAACGATATGGGCTGAATACAAATCACAGAATCGTCGTATGCAGTGAAAACTCTCT  1680
LP143___ffluc    TATGAAACGATATGGGCTGAATACAAATCACAGAATCGTCGTATGCAGTGAAAACTCTCT  1677
A511___ffluc     TATGAAACGATATGGGCTGAATACAAATCACAGAATCGTCGTATGCAGTGAAAACTCTCT  1677
LP124___ffluc    TATGAAACGATATGGGCTGAATACAAATCACAGAATCGTCGTATGCAGTGAAAACTCTCT  1680
lp101___ffluc    TATGAAACGATATGGGCTGAATACAAATCACAGAATCGTCGTATGCAGTGAAAACTCTCT  1680
LP99___ffluc     TATGAAACGATATGGGCTGAATACAAATCACAGAATCGTCGTATGCAGTGAAAACTCTCT  1680
P100___ffluc     TATGAAACGATATGGGCTGAATACAAATCACAGAATCGTCGTATGCAGTGAAAACTCTCT  1680
                 ************************************************************

LP48___ffluc     TCAATTCTTTATGCCGGTGTTGGGCGCGTTATTTATCGGAGTTGCAGTTGCGCCCGCGAA  1740
LP125___ffluc    TCAATTCTTTATGCCGGTGTTGGGCGCGTTATTTATCGGAGTTGCAGTTGCGCCCGCGAA  1740
LP143___ffluc    TCAATTCTTTATGCCGGTGTTGGGCGCGTTATTTATCGGAGTTGCAGTTGCGCCCGCGAA  1737
A511___ffluc     TCAATTCTTTATGCCGGTGTTGGGCGCGTTATTTATCGGAGTTGCAGTTGCGCCCGCGAA  1737
LP124___ffluc    TCAATTCTTTATGCCGGTGTTGGGCGCGTTATTTATCGGAGTTGCAGTTGCGCCCGCGAA  1740
lp101___ffluc    TCAATTCTTTATGCCGGTGTTGGGCGCGTTATTTATCGGAGTTGCAGTTGCGCCCGCGAA  1740
LP99___ffluc     TCAATTCTTTATGCCGGTGTTGGGCGCGTTATTTATCGGAGTTGCAGTTGCGCCCGCGAA  1740
P100___ffluc     TCAATTCTTTATGCCGGTGTTGGGCGCGTTATTTATCGGAGTTGCAGTTGCGCCCGCGAA  1740
                 ************************************************************

LP48___ffluc     CGACATTTATAATGAACGTGAATTGCTCAACAGTATGAACATTTCGCAGCCTACCGTAGT  1800
LP125___ffluc    CGACATTTATAATGAACGTGAATTGCTCAACAGTATGAACATTTCGCAGCCTACCGTAGT  1800
LP143___ffluc    CGACATTTATAATGAACGTGAATTGCTCAACAGTATGAACATTTCGCAGCCTACCGTAGT  1797
A511___ffluc     CGACATTTATAATGAACGTGAATTGCTCAACAGTATGAACATTTCGCAGCCTACCGTAGT  1797
LP124___ffluc    CGACATTTATAATGAACGTGAATTGCTCAACAGTATGAACATTTCGCAGCCTACCGTAGT  1800
lp101___ffluc    CGACATTTATAATGAACGTGAATTGCTCAACAGTATGAACATTTCGCAGCCTACCGTAGT  1800
LP99___ffluc     CGACATTTATAATGAACGTGAATTGCTCAACAGTATGAACATTTCGCAGCCTACCGTAGT  1800
P100___ffluc     CGACATTTATAATGAACGTGAATTGCTCAACAGTATGAACATTTCGCAGCCTACCGTAGT  1800
                 ************************************************************

LP48___ffluc     GTTTGTTTCCAAAAAGGGGTTGCAAAAAATTTTGAACGTGCAAAAAAAATTACCAATAAT  1860
LP125___ffluc    GTTTGTTTCCAAAAAGGGGTTGCAAAAAATTTTGAACGTGCAAAAAAAATTACCAATAAT  1860
LP143___ffluc    GTTTGTTTCCAAAAAGGGGTTGCAAAAAATTTTGAACGTGCAAAAAAAATTACCAATAAT  1857
A511___ffluc     GTTTGTTTCCAAAAAGGGGTTGCAAAAAATTTTGAACGTGCAAAAAAAATTACCAATAAT  1857
LP124___ffluc    GTTTGTTTCCAAAAAGGGGTTGCAAAAAATTTTGAACGTGCAAAAAAAATTACCAATAAT  1860
lp101___ffluc    GTTTGTTTCCAAAAAGGGGTTGCAAAAAATTTTGAACGTGCAAAAAAAATTACCAATAAT  1860
LP99___ffluc     GTTTGTTTCCAAAAAGGGGTTGCAAAAAATTTTGAACGTGCAAAAAAAATTACCAATAAT  1860
P100___ffluc     GTTTGTTTCCAAAAAGGGGTTGCAAAAAATTTTGAACGTGCAAAAAAAATTACCAATAAT  1860
                 ************************************************************

LP48___ffluc     CCAGAAAATTATTATCATGGATTCTAAAACGGATTACCAGGGATTTCAGTCGATGTACAC  1920
LP125___ffluc    CCAGAAAATTATTATCATGGATTCTAAAACGGATTACCAGGGATTTCAGTCGATGTACAC  1920
LP143___ffluc    CCAGAAAATTATTATCATGGATTCTAAAACGGATTACCAGGGATTTCAGTCGATGTACAC  1917
A511___ffluc     CCAGAAAATTATTATCATGGATTCTAAAACGGATTACCAGGGATTTCAGTCGATGTACAC  1917
LP124___ffluc    CCAGAAAATTATTATCATGGATTCTAAAACGGATTACCAGGGATTTCAGTCGATGTACAC  1920
lp101___ffluc    CCAGAAAATTATTATCATGGATTCTAAAACGGATTACCAGGGATTTCAGTCGATGTACAC  1920
LP99___ffluc     CCAGAAAATTATTATCATGGATTCTAAAACGGATTACCAGGGATTTCAGTCGATGTACAC  1920
P100___ffluc     CCAGAAAATTATTATCATGGATTCTAAAACGGATTACCAGGGATTTCAGTCGATGTACAC  1920
                 ************************************************************
```

FIGURE 28 (continued)

```
LP48___ffluc     GTTCGTCACATCTCATCTACCTCCCGGTTTTAATGAATACGATTTTGTACCAGAGTCCTT  1980
LP125___ffluc    GTTCGTCACATCTCATCTACCTCCCGGTTTTAATGAATACGATTTTGTACCAGAGTCCTT  1980
LP143___ffluc    GTTCGTCACATCTCATCTACCTCCCGGTTTTAATGAATACGATTTTGTACCAGAGTCCTT  1977
A511___ffluc     GTTCGTCACATCTCATCTACCTCCCGGTTTTAATGAATACGATTTTGTACCAGAGTCCTT  1977
LP124___ffluc    GTTCGTCACATCTCATCTACCTCCCGGTTTTAATGAATACGATTTTGTACCAGAGTCCTT  1980
lp101___ffluc    GTTCGTCACATCTCATCTACCTCCCGGTTTTAATGAATACGATTTTGTACCAGAGTCCTT  1980
LP99___ffluc     GTTCGTCACATCTCATCTACCTCCCGGTTTTAATGAATACGATTTTGTACCAGAGTCCTT  1980
P100___ffluc     GTTCGTCACATCTCATCTACCTCCCGGTTTTAATGAATACGATTTTGTACCAGAGTCCTT  1980
                 ************************************************************

LP48___ffluc     TGATCGTGACAAAACAATTGCACTGATAATGAATTCCTCTGGATCTACTGGGTTACCTAA  2040
LP125___ffluc    TGATCGTGACAAAACAATTGCACTGATAATGAATTCCTCTGGATCTACTGGGTTACCTAA  2040
LP143___ffluc    TGATCGTGACAAAACAATTGCACTGATAATGAATTCCTCTGGATCTACTGGGTTACCTAA  2037
A511___ffluc     TGATCGTGACAAAACAATTGCACTGATAATGAATTCCTCTGGATCTACTGGGTTACCTAA  2037
LP124___ffluc    TGATCGTGACAAAACAATTGCACTGATAATGAATTCCTCTGGATCTACTGGGTTACCTAA  2040
lp101___ffluc    TGATCGTGACAAAACAATTGCACTGATAATGAATTCCTCTGGATCTACTGGGTTACCTAA  2040
LP99___ffluc     TGATCGTGACAAAACAATTGCACTGATAATGAATTCCTCTGGATCTACTGGGTTACCTAA  2040
P100___ffluc     TGATCGTGACAAAACAATTGCACTGATAATGAATTCCTCTGGATCTACTGGGTTACCTAA  2040
                 ************************************************************

LP48___ffluc     GGGTGTGGCCCTTCCGCATAGAACTGCCTGCGTCAGATTCTCGCATGCCAGAGATCCTAT  2100
LP125___ffluc    GGGTGTGGCCCTTCCGCATAGAACTGCCTGCGTCAGATTCTCGCATGCCAGAGATCCTAT  2100
LP143___ffluc    GGGTGTGGCCCTTCCGCATAGAACTGCCTGCGTCAGATTCTCGCATGCCAGAGATCCTAT  2097
A511___ffluc     GGGTGTGGCCCTTCCGCATAGAACTGCCTGCGTCAGATTCTCGCATGCCAGAGATCCTAT  2097
LP124___ffluc    GGGTGTGGCCCTTCCGCATAGAACTGCCTGCGTCAGATTCTCGCATGCCAGAGATCCTAT  2100
lp101___ffluc    GGGTGTGGCCCTTCCGCATAGAACTGCCTGCGTCAGATTCTCGCATGCCAGAGATCCTAT  2100
LP99___ffluc     GGGTGTGGCCCTTCCGCATAGAACTGCCTGCGTCAGATTCTCGCATGCCAGAGATCCTAT  2100
P100___ffluc     GGGTGTGGCCCTTCCGCATAGAACTGCCTGCGTCAGATTCTCGCATGCCAGAGATCCTAT  2100
                 ************************************************************

LP48___ffluc     TTTTGGCAATCAAATCATTCCGGATACTGCGATTTTAAGTGTTGTTCCATTCCATCACGG  2160
LP125___ffluc    TTTTGGCAATCAAATCATTCCGGATACTGCGATTTTAAGTGTTGTTCCATTCCATCACGG  2160
LP143___ffluc    TTTTGGCAATCAAATCATTCCGGATACTGCGATTTTAAGTGTTGTTCCATTCCATCACGG  2157
A511___ffluc     TTTTGGCAATCAAATCATTCCGGATACTGCGATTTTAAGTGTTGTTCCATTCCATCACGG  2157
LP124___ffluc    TTTTGGCAATCAAATCATTCCGGATACTGCGATTTTAAGTGTTGTTCCATTCCATCACGG  2160
lp101___ffluc    TTTTGGCAATCAAATCATTCCGGATACTGCGATTTTAAGTGTTGTTCCATTCCATCACGG  2160
LP99___ffluc     TTTTGGCAATCAAATCATTCCGGATACTGCGATTTTAAGTGTTGTTCCATTCCATCACGG  2160
P100___ffluc     TTTTGGCAATCAAATCATTCCGGATACTGCGATTTTAAGTGTTGTTCCATTCCATCACGG  2160
                 ************************************************************

LP48___ffluc     TTTTGGAATGTTTACTACACTCGGATATTTGATATGTGGATTTCGAGTCGTCTTAATGTA  2220
LP125___ffluc    TTTTGGAATGTTTACTACACTCGGATATTTGATATGTGGATTTCGAGTCGTCTTAATGTA  2220
LP143___ffluc    TTTTGGAATGTTTACTACACTCGGATATTTGATATGTGGATTTCGAGTCGTCTTAATGTA  2217
A511___ffluc     TTTTGGAATGTTTACTACACTCGGATATTTGATATGTGGATTTCGAGTCGTCTTAATGTA  2217
LP124___ffluc    TTTTGGAATGTTTACTACACTCGGATATTTGATATGTGGATTTCGAGTCGTCTTAATGTA  2220
lp101___ffluc    TTTTGGAATGTTTACTACACTCGGATATTTGATATGTGGATTTCGAGTCGTCTTAATGTA  2220
LP99___ffluc     TTTTGGAATGTTTACTACACTCGGATATTTGATATGTGGATTTCGAGTCGTCTTAATGTA  2220
P100___ffluc     TTTTGGAATGTTTACTACACTCGGATATTTGATATGTGGATTTCGAGTCGTCTTAATGTA  2220
                 ************************************************************

LP48___ffluc     TAGATTTGAAGAAGAGCTGTTTTTACGATCCCTTCAGGATTACAAAATTCAAAGTGCGTT  2280
LP125___ffluc    TAGATTTGAAGAAGAGCTGTTTTTACGATCCCTTCAGGATTACAAAATTCAAAGTGCGTT  2280
LP143___ffluc    TAGATTTGAAGAAGAGCTGTTTTTACGATCCCTTCAGGATTACAAAATTCAAAGTGCGTT  2277
A511___ffluc     TAGATTTGAAGAAGAGCTGTTTTTACGATCCCTTCAGGATTACAAAATTCAAAGTGCGTT  2277
LP124___ffluc    TAGATTTGAAGAAGAGCTGTTTTTACGATCCCTTCAGGATTACAAAATTCAAAGTGCGTT  2280
lp101___ffluc    TAGATTTGAAGAAGAGCTGTTTTTACGATCCCTTCAGGATTACAAAATTCAAAGTGCGTT  2280
LP99___ffluc     TAGATTTGAAGAAGAGCTGTTTTTACGATCCCTTCAGGATTACAAAATTCAAAGTGCGTT  2280
P100___ffluc     TAGATTTGAAGAAGAGCTGTTTTTACGATCCCTTCAGGATTACAAAATTCAAAGTGCGTT  2280
                 ************************************************************

LP48___ffluc     GCTAGTACCAACCCTATTTTCATTCTTCGCCAAAAGCACTCTGATTGACAAATACGATTT  2340
LP125___ffluc    GCTAGTACCAACCCTATTTTCATTCTTCGCCAAAAGCACTCTGATTGACAAATACGATTT  2340
LP143___ffluc    GCTAGTACCAACCCTATTTTCATTCTTCGCCAAAAGCACTCTGATTGACAAATACGATTT  2337
A511___ffluc     GCTAGTACCAACCCTATTTTCATTCTTCGCCAAAAGCACTCTGATTGACAAATACGATTT  2337
LP124___ffluc    GCTAGTACCAACCCTATTTTCATTCTTCGCCAAAAGCACTCTGATTGACAAATACGATTT  2340
lp101___ffluc    GCTAGTACCAACCCTATTTTCATTCTTCGCCAAAAGCACTCTGATTGACAAATACGATTT  2340
LP99___ffluc     GCTAGTACCAACCCTATTTTCATTCTTCGCCAAAAGCACTCTGATTGACAAATACGATTT  2340
P100___ffluc     GCTAGTACCAACCCTATTTTCATTCTTCGCCAAAAGCACTCTGATTGACAAATACGATTT  2340
                 ************************************************************
```

FIGURE 28 (continued)

```
LP48___ffluc     ATCTAATTTACACGAAATTGCTTCTGGGGGCGCACCTCTTTCGAAAGAAGTCGGGGAAGC 2400
LP125___ffluc    ATCTAATTTACACGAAATTGCTTCTGGGGGCGCACCTCTTTCGAAAGAAGTCGGGGAAGC 2400
LP143___ffluc    ATCTAATTTACACGAAATTGCTTCTGGGGGCGCACCTCTTTCGAAAGAAGTCGGGGAAGC 2397
A511___ffluc     ATCTAATTTACACGAAATTGCTTCTGGGGGCGCACCTCTTTCGAAAGAAGTCGGGGAAGC 2397
LP124___ffluc    ATCTAATTTACACGAAATTGCTTCTGGGGGCGCACCTCTTTCGAAAGAAGTCGGGGAAGC 2400
lp101___ffluc    ATCTAATTTACACGAAATTGCTTCTGGGGGCGCACCTCTTTCGAAAGAAGTCGGGGAAGC 2400
LP99___ffluc     ATCTAATTTACACGAAATTGCTTCTGGGGGCGCACCTCTTTCGAAAGAAGTCGGGGAAGC 2400
P100___ffluc     ATCTAATTTACACGAAATTGCTTCTGGGGGCGCACCTCTTTCGAAAGAAGTCGGGGAAGC 2400
                 ************************************************************

LP48___ffluc     GGTTGCAAAACGCTTCCATCTTCCAGGGATACGACAAGGATATGGGCTCACTGAGACTAC 2460
LP125___ffluc    GGTTGCAAAACGCTTCCATCTTCCAGGGATACGACAAGGATATGGGCTCACTGAGACTAC 2460
LP143___ffluc    GGTTGCAAAACGCTTCCATCTTCCAGGGATACGACAAGGATATGGGCTCACTGAGACTAC 2457
A511___ffluc     GGTTGCAAAACGCTTCCATCTTCCAGGGATACGACAAGGATATGGGCTCACTGAGACTAC 2457
LP124___ffluc    GGTTGCAAAACGCTTCCATCTTCCAGGGATACGACAAGGATATGGGCTCACTGAGACTAC 2460
lp101___ffluc    GGTTGCAAAACGCTTCCATCTTCCAGGGATACGACAAGGATATGGGCTCACTGAGACTAC 2460
LP99___ffluc     GGTTGCAAAACGCTTCCATCTTCCAGGGATACGACAAGGATATGGGCTCACTGAGACTAC 2460
P100___ffluc     GGTTGCAAAACGCTTCCATCTTCCAGGGATACGACAAGGATATGGGCTCACTGAGACTAC 2460
                 ************************************************************

LP48___ffluc     ATCAGCTATTCTGATTACACCCGAGGGGGATGATAAACCGGGCGCGGTCGGTAAAGTTGT 2520
LP125___ffluc    ATCAGCTATTCTGATTACACCCGAGGGGGATGATAAACCGGGCGCGGTCGGTAAAGTTGT 2520
LP143___ffluc    ATCAGCTATTCTGATTACACCCGAGGGGGATGATAAACCGGGCGCGGTCGGTAAAGTTGT 2517
A511___ffluc     ATCAGCTATTCTGATTACACCCGAGGGGGATGATAAACCGGGCGCGGTCGGTAAAGTTGT 2517
LP124___ffluc    ATCAGCTATTCTGATTACACCCGAGGGGGATGATAAACCGGGCGCGGTCGGTAAAGTTGT 2520
lp101___ffluc    ATCAGCTATTCTGATTACACCCGAGGGGGATGATAAACCGGGCGCGGTCGGTAAAGTTGT 2520
LP99___ffluc     ATCAGCTATTCTGATTACACCCGAGGGGGATGATAAACCGGGCGCGGTCGGTAAAGTTGT 2520
P100___ffluc     ATCAGCTATTCTGATTACACCCGAGGGGGATGATAAACCGGGCGCGGTCGGTAAAGTTGT 2520
                 ************************************************************

LP48___ffluc     TCCATTTTTTGAAGCGAAGGTTGTGGATCTGGATACCGGGAAAACGCTGGGCGTTAATCA 2580
LP125___ffluc    TCCATTTTTTGAAGCGAAGGTTGTGGATCTGGATACCGGGAAAACGCTGGGCGTTAATCA 2580
LP143___ffluc    TCCATTTTTTGAAGCGAAGGTTGTGGATCTGGATACCGGGAAAACGCTGGGCGTTAATCA 2577
A511___ffluc     TCCATTTTTTGAAGCGAAGGTTGTGGATCTGGATACCGGGAAAACGCTGGGCGTTAATCA 2577
LP124___ffluc    TCCATTTTTTGAAGCGAAGGTTGTGGATCTGGATACCGGGAAAACGCTGGGCGTTAATCA 2580
lp101___ffluc    TCCATTTTTTGAAGCGAAGGTTGTGGATCTGGATACCGGGAAAACGCTGGGCGTTAATCA 2580
LP99___ffluc     TCCATTTTTTGAAGCGAAGGTTGTGGATCTGGATACCGGGAAAACGCTGGGCGTTAATCA 2580
P100___ffluc     TCCATTTTTTGAAGCGAAGGTTGTGGATCTGGATACCGGGAAAACGCTGGGCGTTAATCA 2580
                 ************************************************************

LP48___ffluc     GAGAGGCGAATTATGTGTCAGAGGACCTATGATTATGTCCGGTTATGTAAACAATCCGGA 2640
LP125___ffluc    GAGAGGCGAATTATGTGTCAGAGGACCTATGATTATGTCCGGTTATGTAAACAATCCGGA 2640
LP143___ffluc    GAGAGGCGAATTATGTGTCAGAGGACCTATGATTATGTCCGGTTATGTAAACAATCCGGA 2637
A511___ffluc     GAGAGGCGAATTATGTGTCAGAGGACCTATGATTATGTCCGGTTATGTAAACAATCCGGA 2637
LP124___ffluc    GAGAGGCGAATTATGTGTCAGAGGACCTATGATTATGTCCGGTTATGTAAACAATCCGGA 2640
lp101___ffluc    GAGAGGCGAATTATGTGTCAGAGGACCTATGATTATGTCCGGTTATGTAAACAATCCGGA 2640
LP99___ffluc     GAGAGGCGAATTATGTGTCAGAGGACCTATGATTATGTCCGGTTATGTAAACAATCCGGA 2640
P100___ffluc     GAGAGGCGAATTATGTGTCAGAGGACCTATGATTATGTCCGGTTATGTAAACAATCCGGA 2640
                 ************************************************************

LP48___ffluc     AGCGACCAACGCCTTGATTGACAAGGATGGATGGCTACATTCTGGAGACATAGCTTACTG 2700
LP125___ffluc    AGCGACCAACGCCTTGATTGACAAGGATGGATGGCTACATTCTGGAGACATAGCTTACTG 2700
LP143___ffluc    AGCGACCAACGCCTTGATTGACAAGGATGGATGGCTACATTCTGGAGACATAGCTTACTG 2697
A511___ffluc     AGCGACCAACGCCTTGATTGACAAGGATGGATGGCTACATTCTGGAGACATAGCTTACTG 2697
LP124___ffluc    AGCGACCAACGCCTTGATTGACAAGGATGGATGGCTACATTCTGGAGACATAGCTTACTG 2700
lp101___ffluc    AGCGACCAACGCCTTGATTGACAAGGATGGATGGCTACATTCTGGAGACATAGCTTACTG 2700
LP99___ffluc     AGCGACCAACGCCTTGATTGACAAGGATGGATGGCTACATTCTGGAGACATAGCTTACTG 2700
P100___ffluc     AGCGACCAACGCCTTGATTGACAAGGATGGATGGCTACATTCTGGAGACATAGCTTACTG 2700
                 ************************************************************

LP48___ffluc     GGACGAAGACGAACACTTCTTCATAGTTGACCGCTTGAAGTCTTTAATTAAATACAAAGG 2760
LP125___ffluc    GGACGAAGACGAACACTTCTTCATAGTTGACCGCTTGAAGTCTTTAATTAAATACAAAGG 2760
LP143___ffluc    GGACGAAGACGAACACTTCTTCATAGTTGACCGCTTGAAGTCTTTAATTAAATACAAAGG 2757
A511___ffluc     GGACGAAGACGAACACTTCTTCATAGTTGACCGCTTGAAGTCTTTAATTAAATACAAAGG 2757
LP124___ffluc    GGACGAAGACGAACACTTCTTCATAGTTGACCGCTTGAAGTCTTTAATTAAATACAAAGG 2760
lp101___ffluc    GGACGAAGACGAACACTTCTTCATAGTTGACCGCTTGAAGTCTTTAATTAAATACAAAGG 2760
LP99___ffluc     GGACGAAGACGAACACTTCTTCATAGTTGACCGCTTGAAGTCTTTAATTAAATACAAAGG 2760
P100___ffluc     GGACGAAGACGAACACTTCTTCATAGTTGACCGCTTGAAGTCTTTAATTAAATACAAAGG 2760
                 ************************************************************
```

FIGURE 28(continued)

```
LP48____ffluc     ATATCAGGTGGCCCCCGCTGAATTGGAATCGATATTGTTACAACACCCCAACATCTTCGA  2820
LP125___ffluc     ATATCAGGTGGCCCCCGCTGAATTGGAATCGATATTGTTACAACACCCCAACATCTTCGA  2820
LP143___ffluc     ATATCAGGTGGCCCCCGCTGAATTGGAATCGATATTGTTACAACACCCCAACATCTTCGA  2817
A511____ffluc     ATATCAGGTGGCCCCCGCTGAATTGGAATCGATATTGTTACAACACCCCAACATCTTCGA  2817
LP124___ffluc     ATATCAGGTGGCCCCCGCTGAATTGGAATCGATATTGTTACAACACCCCAACATCTTCGA  2820
lp101___ffluc     ATATCAGGTGGCCCCCGCTGAATTGGAATCGATATTGTTACAACACCCCAACATCTTCGA  2820
LP99____ffluc     ATATCAGGTGGCCCCCGCTGAATTGGAATCGATATTGTTACAACACCCCAACATCTTCGA  2820
P100____ffluc     ATATCAGGTGGCCCCCGCTGAATTGGAATCGATATTGTTACAACACCCCAACATCTTCGA  2820
                  ************************************************************

LP48____ffluc     CGCGGGCGTGGCAGGTCTTCCCGACGATGACGCCGGTGAACTTCCAGCCGCCGTTGTTGT  2880
LP125___ffluc     CGCGGGCGTGGCAGGTCTTCCCGACGATGACGCCGGTGAACTTCCAGCCGCCGTTGTTGT  2880
LP143___ffluc     CGCGGGCGTGGCAGGTCTTCCCGACGATGACGCCGGTGAACTTCCCGCCGCCGTTGTTGT  2877
A511____ffluc     CGCGGGCGTGGCAGGTCTTCCCGACGATGACGCCGGTGAACTTCCCGCCGCCGTTGTTGT  2877
LP124___ffluc     CGCGGGCGTGGCAGGTCTTCCCGACGATGACGCCGGTGAACTTCCCGCCGCCGTTGTTGT  2880
lp101___ffluc     CGCGGGCGTGGCAGGTCTTCCCGACGATGACGCCGGTGAACTTCCCGCCGCCGTTGTTGT  2880
LP99____ffluc     CGCGGGCGTGGCAGGTCTTCCCGACGATGACGCCGGTGAACTTCCCGCCGCCGTTGTTGT  2880
P100____ffluc     CGCGGGCGTGGCAGGTCTTCCCGACGATGACGCCGGTGAACTTCCCGCCGCCGTTGTTGT  2880
                  ********************************************* **************

LP48____ffluc     TTTGGAGCACGGAAAGACGATGACGGAAAAAGAGATCGTGGATTACGTCGCCAGTCAAGT  2940
LP125___ffluc     TTTGGAGCACGGAAAGACGATGACGGAAAAAGAGATCGTGGATTACGTCGCCAGTCAAGT  2940
LP143___ffluc     TTTGGAGCACGGAAAGACGATGACGGAAAAAGAGATCGTGGATTACGTCGCCAGTCAAGT  2937
A511____ffluc     TTTGGAGCACGGAAAGACGATGACGGAAAAAGAGATCGTGGATTACGTCGCCAGTCAAGT  2937
LP124___ffluc     TTTGGAGCACGGAAAGACGATGACGGAAAAAGAGATCGTGGATTACGTCGCCAGTCAAGT  2940
lp101___ffluc     TTTGGAGCACGGAAAGACGATGACGGAAAAAGAGATCGTGGATTACGTCGCCAGTCAAGT  2940
LP99____ffluc     TTTGGAGCACGGAAAGACGATGACGGAAAAAGAGATCGTGGATTACGTCGCCAGTCAAGT  2940
P100____ffluc     TTTGGAGCACGGAAAGACGATGACGGAAAAAGAGATCGTGGATTACGTCGCCAGTCAAGT  2940
                  ************************************************************

LP48____ffluc     AACAACCGCGAAAAAGTTGCGCGGAGGAGTTGTGTTTGTGGACGAAGTACCGAAAGGTCT  3000
LP125___ffluc     AACAACCGCGAAAAAGTTGCGCGGAGGAGTTGTGTTTGTGGACGAAGTACCGAAAGGTCT  3000
LP143___ffluc     AACAACCGCGAAAAAGTTGCGCGGAGGAGTTGTGTTTGTGGACGAAGTACCGAAAGGTCT  2997
A511____ffluc     AACAACCGCGAAAAAGTTGCGCGGAGGAGTTGTGTTTGTGGACGAAGTACCGAAAGGTCT  2997
LP124___ffluc     AACAACCGCGAAAAAGTTGCGCGGAGGAGTTGTGTTTGTGGACGAAGTACCGAAAGGTCT  3000
lp101___ffluc     AACAACCGCGAAAAAGTTGCGCGGAGGAGTTGTGTTTGTGGACGAAGTACCGAAAGGTCT  3000
LP99____ffluc     AACAACCGCGAAAAAGTTGCGCGGAGGAGTTGTGTTTGTGGACGAAGTACCGAAAGGTCT  3000
P100____ffluc     AACAACCGCGAAAAAGTTGCGCGGAGGAGTTGTGTTTGTGGACGAAGTACCGAAAGGTCT  3000
                  ************************************************************

LP48____ffluc     TACCGGAAAACTCGACGCAAGAAAAATCAGAGAGATCCTCATAAAGGCCAAGAAGGGCGG  3060
LP125___ffluc     TACCGGAAAACTCGACGCAAGAAAAATCAGAGAGATCCTCATAAAGGCCAAGAAGGGCGG  3060
LP143___ffluc     TACCGGAAAACTCGACGCAAGAAAAATCAGAGAGATCCTCATAAAGGCCAAGAAGGGCGG  3057
A511____ffluc     TACCGGAAAACTCGACGCAAGAAAAATCAGAGAGATCCTCATAAAGGCCAAGAAGGGCGG  3057
LP124___ffluc     TACCGGAAAACTCGACGCAAGAAAAATCAGAGAGATCCTCATAAAGGCCAAGAAGGGCGG  3060
lp101___ffluc     TACCGGAAAACTCGACGCAAGAAAAATCAGAGAGATCCTCATAAAGGCCAAGAAGGGCGG  3060
LP99____ffluc     TACCGGAAAACTCGACGCAAGAAAAATCAGAGAGATCCTCATAAAGGCCAAGAAGGGCGG  3060
P100____ffluc     TACCGGAAAACTCGACGCAAGAAAAATCAGAGAGATCCTCATAAAGGCCAAGAAGGGCGG  3060
                  ************************************************************

LP48____ffluc     AAAGTCCAAATTGTAATAATTATAGGATAATTGAATAAAAACAGTATAGAGAGCAGATAA  3120
LP125___ffluc     AAAGTCCAAATTGTAATAATTATAGGATAATTGAATAAAAACAGTATAGAGAGCAGATAA  3120
LP143___ffluc     AAAGTCCAAATTGTAATAATTATAGGATAATTGAATAAAAACAGTATAGAGAGCAGATAA  3117
A511____ffluc     AAAGTCCAAATTGTAATAATTATAGGATAATTGAATAAAAACAGTATAGAGAGCAGATAA  3117
LP124___ffluc     AAAGTCCAAATTGTAATAATTATAGGATAATTGAATAAAAACAGTATAGAGAGCAGATAA  3120
lp101___ffluc     AAAGTCCAAATTGTAATAATTATAGGATAATTGAATAAAAACAGTATAGAGAGCAGATAA  3120
LP99____ffluc     AAAGTCCAAATTGTAATAATTATAGGATAATTGAATAAAAACAGTATAGAGAGCAGATAA  3120
P100____ffluc     AAAGTCCAAATTGTAATAATTATAGGATAATTGAATAAAAACAGTATAGAGAGCAGATAA  3120
                  ************************************************************

LP48____ffluc     ATACTGCTCTCTATTTTACTAATAAGGAGGATTTAAATTGCTAAAAAATACAAACTTAGC  3180
LP125___ffluc     ATACTGCTCTCTATTTTACTAATAAGGAGGATTTAAATTGCTAAAAAATACAAACTTAGC  3180
LP143___ffluc     ATACTGCTCTCTATTTTACTAATAAGGAGGATTTAAATTGCTAAAAAATACAAACTTAGC  3177
A511____ffluc     ATACTGCTCTCTATTTTACTAATAAGGAGGATTTAAATTGCTAAAAAATACAAACTTAGC  3177
LP124___ffluc     ATACTGCTCTCTATTTTACTAATAAGGAGGATTTAAATTGCTAAAAAATACAAACTTAGC  3180
lp101___ffluc     ATACTGCTCTCTATTTTACTAATAAGGAGGATTTAAATTGCTAAAAAATACAAACTTAGC  3180
LP99____ffluc     ATACTGCTCTCTATTTTACTAATAAGGAGGATTTAAATTGCTAAAAAATACAAACTTAGC  3180
P100____ffluc     ATACTGCTCTCTATTTTACTAATAAGGAGGATTTAAATTGCTAAAAAATACAAACTTAGC  3180
                  ************************************************************
```

FIGURE 28 (continued)

```
LP48___ffluc     TAATTATAAAAAAGTGAATACACGGTTTGGAAATCTTAGTTTTGACGACAAAGGTATTTC 3240
LP125___ffluc    TAATTATAAAAAAGTGAATACACGGTTTGGAAATCTTAGTTTTGACGACAAAGGTATTTC 3240
LP143___ffluc    TAATTATAAAAAAGTGAATACACGGTTTGGAAATCTTAGTTTTGACGACAAAGGTATTTC 3237
A511___ffluc     TAATTATAAAAAAGTGAATACACGGTTTGGAAATCTTAGTTTTGACGACAAAGGTATTTC 3237
LP124___ffluc    TAATTATAAAAAAGTGAATACACGGTTTGGAAATCTTAGTTTTGACGACAAAGGTATTTC 3240
lp101___ffluc    TAATTATAAAAAAGTGAATACACGGTTTGGAAATCTTAGTTTTGACGACAAAGGTATTTC 3240
LP99___ffluc     TAATTATAAAAAAGTGAATACACGGTTTGGAAATCTTAGTTTTGACGACAAAGGTATTTC 3240
P100___ffluc     TAATTATAAAAAAGTGAATACACGATTTGGAAATCTTAGTTTTGATGATAAAGGTATTTC 3240
                 ************************ ******************** ** ***********

LP48___ffluc     TAATGACTTAACGGAAGAACAGCAAAAAGAATTAGGTAAGCTTCGAGGATTCGAATATAT 3300
LP125___ffluc    TAATGACTTAACGGAAGAACAGCAAAAAGAATTAGGTAAGCTTCGAGGATTCGAATATAT 3300
LP143___ffluc    TAATGACTTAACGGAAGAACAGCAAAAAGAATTAGGTAAGCTTCGAGGATTCGAATATAT 3297
A511___ffluc     TAATGACTTAACGGAAGAACAGCAAAAAGAATTAGGTAAGCTTCGAGGATTCGAATATAT 3297
LP124___ffluc    TAATGACTTAACGGAAGAACAGCAAAAAGAATTAGGTAAGCTTCGAGGATTCGAATATAT 3300
lp101___ffluc    TAATGACTTAACGGAAGAACAGCAAAAAGAATTAGGTAAGCTTCGAGGATTCGAATATAT 3300
LP99___ffluc     TAATGACTTAACGGAAGAACAGCAAAAAGAATTAGGTAAGCTTCGAGGATTCGAATATAT 3300
P100___ffluc     TAATGACCTAACGGAAGAGCAGCAAAAAGAATTAGGTAAGCTTAGAGGATTCGAATATAT 3300
                 ******* ********** ************************ ****************

LP48___ffluc     TAAGACAGAACAGAAAACAAAAGAAGAACCTAAGAAAGAAGAACCTAAGAAAGAA----- 3355
LP125___ffluc    TAAGACAGAACAGAAAACAAAAGAAGAACCTAAGAAAGAAGAACCTAAGAAAGAA----- 3355
LP143___ffluc    TAAGACAGAACAGAAAACAAAAGAAGAACCTAAGAAAGAAGAACCTAAGAAAGAAGAACC 3357
A511___ffluc     TAAGACAGAACAGAAAACAAAAGAAGAACCTAAGAAAGAAGAACCTAAGAAAGAAGAACC 3357
LP124___ffluc    TAAGACAGAACAGAAAACAAAAGAAGAACCTAAGAAAGAAGAACCTAAGAAAGAAGAACC 3360
lp101___ffluc    TAAGACAGAACAGAAAACAAAAGAAGAACCTAAGAAAGAAGAACCTAAGAAAGAAGAACC 3360
LP99___ffluc     TAAGACAGAACAGAAAACAAAAGAAGAACCTAAGAAAGAAGAACCTAAGAAAGAAGAACC 3360
P100___ffluc     TAAGACAGAACAGAAAACGAAAGAAGAACCTAAGAAAGAAGAACCTAAGAAAGAA----- 3355
                 ****************** ************************************

LP48___ffluc     -------------------------------------------------------AGTAC 3360
LP125___ffluc    -------------------------------------------------------AGTAC 3360
LP143___ffluc    TAAGAAAGAAGAACCTAAGAAAGAAGAACCTAAGAAAGAAGAACCTAAGAAAGAAAGTAC 3417
A511___ffluc     TAAGAAAGAAGAACCTAAGAAAGAAGAACCTAAGAAAGAAGAACCTAAGAAAGAAAGTAC 3417
LP124___ffluc    TAAGAAAGAAGAACCTAAGAAAGAAGAACCTAAGAAAGAAGAACCTAAGAAAGAAAGTAC 3420
lp101___ffluc    TAAGAAAGAAGAACCTAAGAAAGAAGAACCTAAGAAAGAAGAACCTAAGAAAGAAAGTAC 3420
LP99___ffluc     TAAGAAAGAAGAACCTAAGAAAGAAGAACCTAAGAAAGAAGAACCTAAGAAAGAAAGTAC 3420
P100___ffluc     -------------------------------------------------------AGTAC 3360
                                                                        *****

LP48___ffluc     AGAAAATGAATTAGACAGCTTCTTAGCTAAAGAGCCTTCAATCAAAGAATTAAAAGAATT 3420
LP125___ffluc    AGAAAATGAATTAGACAGCTTCTTAGCTAAAGAGCCTTCAATCAAAGAATTAAAAGAATT 3420
LP143___ffluc    AGAAAATGAATTAGACAGCTTCTTAGCTAAAGAGCCTTCAATCAAAGAATTAAAAGAATT 3477
A511___ffluc     AGAAAATGAATTAGACAGCTTCTTAGCTAAAGAGCCTTCAATCAAAGAATTAAAAGAATT 3477
LP124___ffluc    AGAAAATGAATTAGACAGCTTCTTAGCTAAAGAGCCTTCAATCAAAGAATTAAAAGAATT 3480
lp101___ffluc    AGAAAATGAATTAGACAGCTTCTTAGCTAAAGAGCCTTCAATCAAAGAATTAAAAGAATT 3480
LP99___ffluc     AGAAAATGAATTAGACAGCTTCTTAGCTAAAGAGCCTTCAATCAAAGAATTAAAAGAATT 3480
P100___ffluc     AGAAAATGAATTAGACAGCTTCTTAGCTAAAGAACCTTCAATCAAAGAATTAAAAGAATT 3420
                 ********************************* **************************

LP48___ffluc     TGCGAGTAAAAAAGGCATTAAAATTGAAAAAACTAAGAAAAATGATATAATTGAAGAACT 3480
LP125___ffluc    TGCGAGTAAAAAAGGCATTAAAATTGAAAAAACTAAGAAAAATGATATAATTGAAGAACT 3480
LP143___ffluc    TGCGAGTAAAAAAGGCATTAAAATTGAAAAAACTAAGAAAAATGATATAATTGAAGAACT 3537
A511___ffluc     TGCGAGTAAAAAAGGCATTAAAATTGAAAAAACTAAGAAAAATGATATAATTGAAGAACT 3537
LP124___ffluc    TGCGAGTAAAAAAGGCATTAAAATTGAAAAAACTAAGAAAAATGATATAATTGAAGAACT 3540
lp101___ffluc    TGCGAGTAAAAAAGGCATTAAAATTGAAAAAACTAAGAAAAATGATATAATTGAAGAACT 3540
LP99___ffluc     TGCGAGTAAAAAAGGCATTAAAATTGAAAAAACTAAGAAAAATGATATAATTGAAGAACT 3540
P100___ffluc     TGCGAGTAAAAAAGGCATTAAAATTGAAAAAACTAAGAAAAATGATATAATTGAAGAACT 3480
                 ************************************************************

LP48___ffluc     AAAGAGAGGGTAATGTATAATGTATGGAGGTTATGAAGGACAAGATTCTTACGAATACCC 3540
LP125___ffluc    AAAGAGAGGGTAATGTATAATGTATGGAGGTTATGAAGGACAAGATTCTTACGAATACCC 3540
LP143___ffluc    AAAGAGAGGGTAATGTATAATGTATGGAGGTTATGAAGGACAAGATTCTTACGAATACCC 3597
A511___ffluc     AAAGAGAGGGTAATGTATAATGTATGGAGGTTATGAAGGACAAGATTCTTACGAATACCC 3597
LP124___ffluc    AAAGAGAGGGTAATGTATAATGTATGGAGGTTATGAAGGACAAGATTCTTACGAATACCC 3600
lp101___ffluc    AAAGAGAGGGTAATGTATAATGTATGGAGGTTATGAAGGACAAGATTCTTACGAATACCC 3600
LP99___ffluc     AAAGAGAGGGTAATGTATAATGTATGGAGGTTATGAAGGACAAGATTCTTACGAATACCC 3600
P100___ffluc     AAAGAGAGGGTAATGTACAATGTATGGAGGTTATGAAGGACAAGATTCTTACGAATACCC 3540
                 ***************** ******************************************
```

FIGURE 28 (continued)

```
LP48___ffluc     TTACTCACATGGGAACCCTAAGCATGTAGAGCCAGAAAAAGTTGACGAATATGTTCTTTC  3600
LP125___ffluc    TTACTCACATGGGAACCCTAAGCATGTAGAGCCAGAAAAAGTTGACGAATATGTTCTTTC  3600
LP143___ffluc    TTACTCACATGGGAACCCTAAGCATGTAGAGCCAGAAAAAGTTGACGAATATGTTCTTTC  3657
A511___ffluc     TTACTCACATGGGAACCCTAAGCATGTAGAGCCAGAAAAAGTTGACGAATATGTTCTTTC  3657
LP124___ffluc    TTACTCACATGGGAACCCTAAGCATGTAGAGCCAGAAAAAGTTGACGAATATGTTCTTTC  3660
lp101___ffluc    TTACTCACATGGGAACCCTAAGCATGTAGAGCCAGAAAAAGTTGACGAATATGTTCTTTC  3660
LP99___ffluc     TTACTCACATGGGAACCCTAAGCATGTAGAGCCAGAAAAAGTTGACGAATATGTTCTTTC  3660
P100___ffluc     TTACTCACACGGGAACCCTAAGCATGTAGAGCCAGAAAAAGTTGACGAATATGTTCTTTC  3600
                 ********* **************************************************

LP48___ffluc     TGATTATGGTTGGACTGCGGAAACAATTAAAGCATACATGTATGGTGTTCGTGTAGTAGA  3660
LP125___ffluc    TGATTATGGTTGGACTGCGGAAACAATTAAAGCATACATGTATGGTGTTCGTGTAGTAGA  3660
LP143___ffluc    TGATTATGGTTGGACTGCGGAAACAATTAAAGCATACATGTATGGTGTTCGTGTAGTAGA  3717
A511___ffluc     TGATTATGGTTGGACTGCGGAAACAATTAAAGCATACATGTATGGTGTTCGTGTAGTAGA  3717
LP124___ffluc    TGATTATGGTTGGACTGCGGAAACAATTAAAGCATACATGTATGGTGTTCGTGTAGTAGA  3720
lp101___ffluc    TGATTATGGTTGGACTGCGGAAACAATTAAAGCATACATGTATGGTGTTCGTGTAGTAGA  3720
LP99___ffluc     TGATTATGGTTGGACTGCGGAAACAATTAAAGCATACATGTATGGTGTTCGTGTAGTAGA  3720
P100___ffluc     TGATTATGGCTGGACTGCGGAAACAATTAAAGCATACATGTATGGTGTTCGTGTAGTAGA  3660
                 ********* **************************************************

LP48___ffluc     CCCTGAAACAGGAGAGGAAATGGGAGACACCTTCTACAATCATATTATAGAGGTTGCCGT  3720
LP125___ffluc    CCCTGAAACAGGAGAGGAAATGGGAGACACCTTCTACAATCATATTATAGAGGTTGCCGT  3720
LP143___ffluc    CCCTGAAACAGGAGAGGAAATGGGAGACACCTTCTACAATCATATTATAGAGGTTGCCGT  3777
A511___ffluc     CCCTGAAACAGGAGAGGAAATGGGAGACACCTTCTACAATCATATTATAGAGGTTGCCGT  3777
LP124___ffluc    CCCTGAAACAGGAGAGGAAATGGGAGACACCTTCTACAATCATATTATAGAGGTTGCCGT  3780
lp101___ffluc    CCCTGAAACAGGAGAGGAAATGGGAGACACCTTCTACAATCATATTATAGAGGTTGCCGT  3780
LP99___ffluc     CCCTGAAACAGGAGAGGAAATGGGAGACACCTTCTACAATCATATTATAGAGGTTGCCGT  3780
P100___ffluc     CCCTGAAACAGGAGAGGAAATGGGAGACACCTTCTACAATCATATTATAGAGGTTGCCGT  3720
                 ************************************************************

LP48___ffluc     TGATAAGGC  3729
LP125___ffluc    TGATAAGGC  3729
LP143___ffluc    TGATAAGGC  3786
A511___ffluc     TGATAAGGC  3786
LP124___ffluc    TGATAAGGC  3789
lp101___ffluc    TGATAAGGC  3789
LP99___ffluc     TGATAAGGC  3789
P100___ffluc     TGATAAGGC  3729
                 *********
```

FIGURE 28 (continued)

```
LP124___nluc    ATGCCAAAAAATAACAAAGAAGAAGAAGTTAAAGAAGTAAACCTTAATTCAGTACAAGAG 60
A511___nluc     ATGCCAAAAAATAACAAA---GAAGAAGTTAAAGAAGTAAACCTTAATTCAGTACAAGAG 57
LP125___nluc    ATGCCAAAAAATAACAAAGAAGAAGAAGTTAAAGAAGTAAACCTTAATTCAGTACAAGAG 60
LP40___nluc     ATGCCAAAAAATAACAAAGAAGAAGAAGTTAAAGAAGTAAACCTTAATTCAGTACAAGAG 60
P100___nluc     ATGCCAAAAAATAACAAAGAAGAAGAAGTTAAAGAAGTAAACCTTAATTCAGTACAAGAG 60
                ******************   ***************************************

LP124___nluc    GACGCGTTAAAGTCCTTTACAACTGGTTATGGTATCACACCTGATACACAAACAGATGCA 120
A511___nluc     GATGCGTTAAAGTCCTTTACGACTGGTTATGGTATCACACCTGATACACAAACAGATGCA 117
LP125___nluc    GACGCGTTAAAGTCCTTTACAACTGGTTATGGTATCACACCTGATACACAAACAGATGCA 120
LP40___nluc     GATGCGTTAAAGTCCTTTACAACTGGTTATGGTATCACACCTGATACACAAACAGATGCA 120
P100___nluc     GACGCGTTAAAGTCCTTTACAACTGGTTATGGTATCACACCTGATACACAAACAGATGCA 120
                ** ***************** ***************************************

LP124___nluc    GGAGCATTAAGACGTGAGTTCCTAGACGACCAAATCTCAATGCTTACTTGGACAGAGAAT 180
A511___nluc     GGAGCATTAAGACGTGAGTTCCTAGACGACCAAATCTCAATGCTTACTTGGACAGAGAAT 177
LP125___nluc    GGAGCATTAAGACGTGAGTTCCTAGACGACCAAATCTCAATGCTTACTTGGACAGAGAAT 180
LP40___nluc     GGGGCACTAAGACGTGAGTTCCTAGACGACCAAATCTCAATGCTTACTTGGACAGAAAAT 180
P100___nluc     GGAGCATTAAGACGTGAGTTCCTAGACGACCAAATCTCAATGCTTACTTGGACAGAGAAT 180
                ** *** ************************************************* ***

LP124___nluc    GATTTAACATTCTATAAAGACATCGCTAAAAAACCAGCTACATCTACAGTAGCAAAATAC 240
A511___nluc     GATTTAACATTCTATAAAGACATCGCTAAAAAACCAGCTACATCTACAGTAGCAAAATAC 237
LP125___nluc    GATTTAACATTCTATAAAGACATCGCTAAAAAACCAGCTACATCTACAGTAGCAAAATAC 240
LP40___nluc     GATTTAACATTCTACAAAGACATCGCTAAAAAACCAGCTACATCTACAGTAGCAAAATAC 240
P100___nluc     GATTTAACATTCTATAAAGACATCGCTAAAAAACCAGCTACATCTACAGTAGCAAAATAC 240
                ************** *********************************************

LP124___nluc    GATGTATACATGCAACATGGTAAGGTAGGTCATACTAGATTTACTCGTGAGATTGGGGTA 300
A511___nluc     GATGTATACATGCAACATGGTAAGGTAGGTCATACTAGATTTACTCGTGAGATTGGGGTA 297
LP125___nluc    GATGTATACATGCAACATGGTAAGGTAGGTCATACTAGATTTACTCGTGAGATTGGGGTA 300
LP40___nluc     GATGTGTACATGCAACACGGTAAAGTAGGTCATACTAGATTTACTCGTGAGATTGGGGTA 300
P100___nluc     GATGTATACATGCAACATGGTAAGGTAGGTCATACTAGATTTACTCGTGAGATTGGGGTA 300
                ***** *********** ***** ************************************

LP124___nluc    GCACCAGTAAGTGACCCTAACATCCGTCAAAAAACAGTAAACATGAAATTTGCTTCCGAT 360
A511___nluc     GCACCAGTAAGTGACCCTAACATCCGTCAAAAAACAGTAAATATGAAATTTGCTTCCGAT 357
LP125___nluc    GCACCAGTAAGTGACCCTAACATCCGTCAAAAAACAGTAAACATGAAATTTGCTTCCGAT 360
LP40___nluc     GCACCAGTAAGTGACCCTAACATCCGTCAAAAAACAGTAAACATGAAATTTGCTTCTGAT 360
P100___nluc     GCACCAGTAAGTGACCCTAACATCCGTCAAAAAACAGTAAATATGAAATTTGCTTCCGAT 360
                ***************************************** ************** ***

LP124___nluc    ACTAAAAACATCAGTATCGCAGCAGGTCTAGTAAACAACATTCAAGACCCAATGCAAATT 420
A511___nluc     ACTAAAAACATCAGTATCGCAGCAGGTCTAGTAAACAACATTCAAGACCCAATGCAAATT 417
LP125___nluc    ACTAAAAACATCAGTATCGCAGCAGGTCTAGTAAACAACATTCAAGACCCAATGCAAATT 420
LP40___nluc     ACTAAAAATATTAGTATCGCAGCAGGTCTAGTAAACAACATTCAAGACCCTATGCAAATT 420
P100___nluc     ACTAAAAACATCAGTATCGCAGCAGGTCTAGTAAACAACATTCAAGACCCAATGCAAATT 420
                ******** ** ************************************** *********

LP124___nluc    TTGACTGACGATGCTATCGTAAATATTGCTAAAACAATTGAGTGGGCTTCATTCTTTGGA 480
A511___nluc     TTGACTGACGATGCTATCGTAAATATTGCTAAAACAATTGAGTGGGCTTCATTCTTTGGA 477
LP125___nluc    TTGACTGACGATGCTATCGTAAATATTGCTAAAACAATTGAGTGGGCTTCATTCTTTGGA 480
LP40___nluc     TTGACTGATGATGCTATCGTAAATATCGCTAAAACAATTGAGTGGGCTTCATTCTTTGGA 480
P100___nluc     TTGACTGACGATGCTATCGTAAATATTGCTAAAACAATTGAGTGGGCTTCATTCTTTGGA 480
                ******** ***************** *********************************

LP124___nluc    GATTCTGACTTATCAGATAGCCCAGAACCACAAGCAGGACTAGAATTTGACGGCTTGGCT 540
A511___nluc     GATTCTGACTTATCAGATAGCCCAGAACCACAAGCAGGACTAGAATTTGACGGCTTGGCT 537
LP125___nluc    GATTCTGACTTATCAGATAGCCCAGAACCACAAGCAGGACTAGAATTTGACGGCTTGGCT 540
LP40___nluc     GATTCTGACTTATCAGATAGCCCAGAACCACAAGCAGGATTAGAATTTGATGGCTTGGCT 540
P100___nluc     GATTCTGACTTATCAGATAGCCCAGAACCACAAGCAGGACTAGAATTTGACGGCTTGGCT 540
                *************************************** ********** *********
```

FIGURE 29

```
LP124___nluc    AAACTTATTAACCAAGATAACGTTCATGATGCTCGTGGAGCTAGCTTGACTGAAAGCTTG  600
A511___nluc     AAACTTATTAACCAAGATAACGTTCATGATGCTCGTGGAGCTAGCTTGACTGAAAGCTTG  597
LP125___nluc    AAACTTATTAACCAAGATAACGTTCATGATGCTCGTGGAGCTAGCTTGACTGAAAGCTTG  600
LP40___nluc     AAACTTATTAACCAAGATAACGTTCATGATGCTCGTGGAGCTAGCTTGACTGAAAGCTTG  600
P100___nluc     AAACTTATTAACCAAGATAACGTTCATGATGCTCGTGGAGCTAGCTTGACTGAAAGCTTG  600
                ************************************************************

LP124___nluc    TTAAACCAAGCAGCAGTAATGATTAGTAAAGGTTATGGTACACCTACAGATGCTTACATG  660
A511___nluc     TTAAACCAAGCAGCAGTAATGATTAGTAAAGGTTATGGTACACCTACAGATGCTTACATG  657
LP125___nluc    TTAAACCAAGCAGCAGTAATGATTAGTAAAGGTTATGGTACACCTACAGATGCTTACATG  660
LP40___nluc     TTAAACCAAGCAGCAGTAATGATTAGTAAAGGTTATGGTACACCTACAGATGCTTACATG  660
P100___nluc     TTAAACCAAGCAGCAGTAATGATTAGTAAAGGTTATGGTACACCTACAGATGCTTACATG  660
                ************************************************************

LP124___nluc    CCAGTAGGGGTTCAAGCAGACTTTGTTAACCAACAACTTTCTAAACAAACACAACTTGTT  720
A511___nluc     CCAGTAGGGGTTCAAGCAGACTTTGTTAACCAACAACTTTCTAAACAAACACAACTTGTT  717
LP125___nluc    CCAGTAGGGGTTCAAGCAGACTTTGTTAACCAACAACTTTCTAAACAAACACAACTTGTT  720
LP40___nluc     CCAGTAGGGGTTCAAGCAGACTTTGTTAACCAACAACTTTCTAAACAAACACAACTTGTT  720
P100___nluc     CCAGTAGGGGTTCAAGCAGACTTTGTTAACCAACAACTTTCTAAACAAACACAGCTTGTT  720
                ***************************************************** ******

LP124___nluc    CGCGATAACGGAAACAACGTAAGCGTTGGTTTCAACATCCAAGGTTTCCATTCAGCTCGT  780
A511___nluc     CGCGATAACGGAAACAACGTAAGCGTTGGTTTCAACATCCAAGGTTTCCATTCAGCTCGT  777
LP125___nluc    CGTGATAACGGAAACAACGTAAGCGTTGGTTTCAACATCCAAGGTTTCCATTCAGCTCGT  780
LP40___nluc     CGCGATAACGGAAACAACGTAAGCGTTGGTTTCAACATCCAAGGTTTCCATTCAGCTCGT  780
P100___nluc     CGTGATAACGGAAACAACGTAAGCGTTGGTTTCAACATCCAAGGTTTCCATTCAGCTCGT  780
                ** *********************************************************

LP124___nluc    GGATTTATCAAACTTCACGGTTCTACAGTAATGGAAAACGAACAAATCTTAGATGAACGT  840
A511___nluc     GGATTTATCAAACTTCACGGTTCTACAGTAATGGAAAACGAACAAATCTTAGATGAACGT  837
LP125___nluc    GGATTTATCAAACTTCACGGTTCTACAGTAATGGAAAACGAACAAATCTTAGATGAACGT  840
LP40___nluc     GGATTTATCAAACTTCACGGTTCTACAGTAATGGAAAACGAACAAATCTTAGATGAACGT  840
P100___nluc     GGATTTATCAAACTTCACGGTTCTACAGTAATGGAAAACGAACAAATCTTAGATGAACGT  840
                ************************************************************

LP124___nluc    ATTCTTGCTTTACCAACAGCTCCACAACCAGCTAAGGTAACTGCAACACAAGAAGCAGGT  900
A511___nluc     ATTCTTGCTTTACCAACAGCTCCACAACCAGCTAAGGTAACTGCAACACAAGAAGCAGGT  897
LP125___nluc    ATTCTTGCTTTACCAACAGCTCCACAACCAGCTAAGGTAACTGCAACACAAGAAGCAGGT  900
LP40___nluc     ATTCTTGCTTTACCAACAGCTCCACAACCAGCTAAGGTAACTGCAACACAAGAAGCAGGT  900
P100___nluc     ATTCTTGCTTTACCAACAGCTCCACAACCAGCTAAGGTAACTGCAACACAAGAAGCAGGT  900
                ************************************************************

LP124___nluc    AAAAAAGGACAATTTAGAGCAGAAGATTTAGCAGCACATGAATATAAAGTTGTTGTAAGT  960
A511___nluc     AAAAAAGGACAATTTAGAGCAGAAGATTTAGCAGCACATGAATATAAAGTTGTTGTAAGT  957
LP125___nluc    AAAAAAGGACAATTTAGAGCAGAAGATTTAGCAGCACATGAATATAAAGTTGTTGTAAGT  960
LP40___nluc     AAAAAAGGACAATTTAGAGCAGAAGATTTAGCAGCACATGAATATAAAGTTGTTGTAAGT  960
P100___nluc     AAAAAAGGACAATTTAGAGCAGAAGACTTAGCAGCACACGAATACAAAGTTGTTGTAAGT  960
                ************************** *********** ***** ***************

LP124___nluc    TCTGACGATGCAGAGTCTATTGCAAGTGAAGTGGCTACAGCTACAGTTACTGCAAAAGAT  1020
A511___nluc     TCTGACGATGCAGAGTCTATTGCAAGTGAAGTGGCTACAGCTACAGTTACTGCAAAAGAT  1017
LP125___nluc    TCTGACGATGCAGAGTCTATTGCAAGTGAAGTGGCTACAGCTACAGTTACTGCAAAAGAT  1020
LP40___nluc     TCTGACGATGCAGAGTCTATTGCAAGTGAAGTGGCTACAGCTACAGTTACTGCAAAAGAT  1020
P100___nluc     TCTGACGATGCAGAGTCTATTGCAAGTGAAGTGGCTACAGCTACAGTTACTGCAAAAGAT  1020
                ************************************************************

LP124___nluc    GACGGCGTTAAACTAGAAATCGAATTAGCTCCAATGTATAGCTCTCGTCCACAATTCGTT  1080
A511___nluc     GACGGCGTTAAACTAGAAATCGAATTAGCTCCAATGTATAGCTCTCGTCCACAATTCGTT  1077
LP125___nluc    GACGGCGTTAAACTAGAAATCGAATTAGCTCCAATGTATAGCTCTCGTCCACAATTCGTT  1080
LP40___nluc     GACGGCGTTAAACTAGAAATCGAATTAGCTCCAATGTATAGCTCTCGTCCACAATTCGTT  1080
P100___nluc     GACGGCGTTAAACTAGAAATCGAGTTAGCTCCAATGTACAGCTCCCGTCCACAATTCGTT  1080
                ********************** *************** ***** ***************

LP124___nluc    TCAATCTATAGAAAAGGTGCAGAAACAGGTTTATTCTACCTAATCGCTCGTGTACCTGCT  1140
A511___nluc     TCAATCTATAGAAAAGGTGCAGAAACAGGTTTATTCTACCTAATCGCTCGTGTACCTGCT  1137
LP125___nluc    TCAATCTATAGAAAAGGTGCAGAAACAGGTTTATTCTACCTAATCGCTCGTGTACCTGCT  1140
LP40___nluc     TCAATCTATAGAAAAGGTGCAGAAACAGGTTTATTCTACCTAATCGCTCGTGTACCTGCT  1140
P100___nluc     TCAATCTATAGAAAAGGTGCAGAAACAGGTTTATTCTACCTAATCGCTCGTGTACCTGCT  1140
                ************************************************************
```

FIGURE 29 (continued)

```
LP124___nluc    AGCAAAGCAGAGAACAACGTAATCACTTTCTACGACTTAAACGACTCTATTCCTGAAACA  1200
A511___nluc     AGCAAAGCAGAGAACAACGTAATCACTTTCTACGACTTAAACGACTCTATTCCTGAAACA  1197
LP125___nluc    AGCAAAGCAGAGAACAACGTAATCACTTTCTACGACTTAAACGACTCTATTCCTGAAACA  1200
LP40___nluc     AGCAAAGCAGAGAACAACGTAATCACTTTCTACGACTTAAACGACTCTATTCCTGAAACA  1200
P100___nluc     AGCAAAGCAGAGAACAACGTAATCACTTTCTATGACTTAAACGACTCTATTCCTGAAACA  1200
                ******************************** ***************************

LP124___nluc    GTAGACGTATTCGTTGGTGAAATGTCGGCTAACGTAGTACACTTGTTTGAATTACTACCA  1260
A511___nluc     GTAGACGTATTCGTTGGTGAAATGTCGGCTAACGTAGTACACTTGTTTGAATTACTACCA  1257
LP125___nluc    GTAGACGTATTCGTTGGTGAAATGTCGGCTAACGTAGTACACTTGTTTGAATTACTACCA  1260
LP40___nluc     GTAGACGTATTCGTTGGTGAAATGTCGGCTAACGTAGTACACTTGTTTGAATTACTACCA  1260
P100___nluc     GTAGACGTATTCGTTGGTGAAATGTCTGCTAACGTAGTACACTTGTTTGAATTACTACCA  1260
                ************************** *********************************

LP124___nluc    ATGATGAGATTACCTCTAGCTCAAATTAACGCATCTGTTACATTTGCAGTTTTATGGTAT  1320
A511___nluc     ATGATGAGATTACCTCTAGCTCAAATTAACGCATCTGTTACATTTGCAGTTTTATGGTAT  1317
LP125___nluc    ATGATGAGATTACCTCTAGCTCAAATTAACGCATCTGTTACATTTGCAGTTTTATGGTAT  1320
LP40___nluc     ATGATGAGATTACCTCTAGCTCAAATTAACGCATCTGTTACATTTGCAGTTTTATGGTAT  1320
P100___nluc     ATGATGAGATTACCTCTAGCTCAAATTAACGCATCTGTTACATTTGCAGTTTTATGGTAT  1320
                ************************************************************

LP124___nluc    GGCGCATTAGCTCTAAGAGCACCTAAGAAATGGGTACGTATTAGAAACGTTAAATATATT  1380
A511___nluc     GGCGCATTAGCTCTAAGAGCACCTAAGAAATGGGTACGTATTAGAAACGTTAAATATATT  1377
LP125___nluc    GGCGCATTAGCTCTAAGAGCACCTAAGAAATGGGTACGTATTAGAAACGTTAAATATATT  1380
LP40___nluc     GGCGCATTAGCTCTAAGAGCACCTAAGAAATGGGTACGTATTAGAAACGTTAAATATATT  1380
P100___nluc     GGAGCATTAGCTCTAAGAGCACCTAAGAAATGGGTACGTATTAGAAACGTTAAATATATT  1380
                ** *********************************************************

LP124___nluc    CCTGTAAAAAACGTTCATAGCAACTAATAATAAGAGGAGGTAAATATATATGGTCTTCAC  1440
A511___nluc     CCTGTAAAAAACGTTCATAGCAACTAA------GAGGAGGTAAATATATATGGTCTTCAC  1431
LP125___nluc    CCTGTAAAAAACGTTCATAGCAACTAATAATAAGAGGAGGTAAATATATATGGTCTTCAC  1440
LP40___nluc     CCTGTAAAAAACGTTCATAGCAACTAATAATAAGAGGAGGTAAATATATATGGTCTTCAC  1440
P100___nluc     CCTGTAAAAAACGTTCATAGCAACTAA------GAGGAGGTAAATATATATGGTCTTCAC  1434
                ***************************      ***************************

LP124___nluc    ACTCGAAGATTTCGTTGGGGACTGGCGACAGACAGCCGGCTACAACCTGGACCAAGTCCT  1500
A511___nluc     ACTCGAAGATTTCGTTGGGGACTGGCGACAGACAGCCGGCTACAACCTGGACCAAGTCCT  1491
LP125___nluc    ACTCGAAGATTTCGTTGGGGACTGGCGACAGACAGCCGGCTACAACCTGGACCAAGTCCT  1500
LP40___nluc     ACTCGAAGATTTCGTTGGGGACTGGCGACAGACAGCCGGCTACAACCTGGACCAAGTCCT  1500
P100___nluc     ACTCGAAGATTTCGTTGGGGACTGGCGACAGACAGCCGGCTACAACCTGGACCAAGTCCT  1494
                ************************************************************

LP124___nluc    TGAACAGGGAGGTGTGTCCAGTTTGTTTCAGAATCTCGGGGTGTCCGTAACTCCGATCCA  1560
A511___nluc     TGAACAGGGAGGTGTGTCCAGTTTGTTTCAGAATCTCGGGGTGTCCGTAACTCCGATCCA  1551
LP125___nluc    TGAACAGGGAGGTGTGTCCAGTTTGTTTCAGAATCTCGGGGTGTCCGTAACTCCGATCCA  1560
LP40___nluc     TGAACAGGGAGGTGTGTCCAGTTTGTTTCAGAATCTCGGGGTGTCCGTAACTCCGATCCA  1560
P100___nluc     TGAACAGGGAGGTGTGTCCAGTTTGTTTCAGAATCTCGGGGTGTCCGTAACTCCGATCCA  1554
                ************************************************************

LP124___nluc    AAGGATTGTCCTGAGCGGTGAAAATGGGCTGAAGATCGACATCCATGTCATCATCCCGTA  1620
A511___nluc     AAGGATTGTCCTGAGCGGTGAAAATGGGCTGAAGATCGACATCCATGTAATCATCCCGTA  1611
LP125___nluc    AAGGATTGTCCTGAGCGGTGAAAATGGGCTGAAGATCGACATCCATGTCATCATCCCGTA  1620
LP40___nluc     AAGGATTGTCCTGAGCGGTGAAAATGGGCTGAAGATCGACATCCATGTCATCATCCCGTA  1620
P100___nluc     AAGGATTGTCCTGAGCGGTGAAAATGGGCTGAAGATCGACATCCATGTCATCATCCCGTA  1614
                ************************************************ ***********

LP124___nluc    TGAAGGTCTGAGCGGCGACCAAATGGGCCAGATCGAAAAAATTTTTAAGGTGGTGTACCC  1680
A511___nluc     TGAAGGTCTGAGCGGCGACCAAATGGGCCAGATCGAAAAAATTTTTAAGGTGGTGTACCC  1671
LP125___nluc    TGAAGGTCTGAGCGGCGACCAAATGGGCCAGATCGAAAAAATTTTTAAGGTGGTGTACCC  1680
LP40___nluc     TGAAGGTCTGAGCGGCGACCAAATGGGCCAGATCGAAAAAATTTTTAAGGTGGTGTACCC  1680
P100___nluc     TGAAGGTCTGAGCGGCGACCAAATGGGCCAGATCGAAAAAATTTTTAAGGTGGTGTACCC  1674
                ************************************************************

LP124___nluc    TGTGGATGATCATCACTTTAAGGTGATCCTGCACTATGGCACACTGGTAATCGACGGGGT  1740
A511___nluc     TGTGGATGATCATCACTTTAAGGTGATCCTGCACTATGGCACACTGGTAATCGACGGGGT  1731
LP125___nluc    TGTGGATGATCATCACTTTAAGGTGATCCTGCACTATGGCACACTGGTAATCGACGGGGT  1740
LP40___nluc     TGTGGATGATCATCACTTTAAGGTGATCCTGCACTATGGCACACTGGTAATCGACGGGGT  1740
P100___nluc     TGTGGATGATCATCACTTTAAGGTGATCCTGCACTATGGCACACTGGTAATCGACGGGGT  1734
                ************************************************************
```

FIGURE 29 (continued)

```
LP124___nluc    TACGCCGAACATGATCGACTATTTCGGACGGCCGTATGAAGGCATCGCCGTGTTCGACGG  1800
A511___nluc     TACGCCGAACATGATCGACTATTTCGGACGGCCGTATGAAGGCATCGCCGTGTTCGACGG  1791
LP125___nluc    TACGCCGAACATGATCGACTATTTCGGACGGCCGTATGAAGGCATCGCCGTGTTCGACGG  1800
LP40___nluc     TACGCCGAACATGATCGACTATTTCGGACGGCCGTATGAAGGCATCGCCGTGTTCGACGG  1800
P100___nluc     TACGCCGAACATGATCGACTATTTCGGACGGCCGTATGAAGGCATCGCCGTGTTCGACGG  1794
                ************************************************************

LP124___nluc    CAAAAAGATCACTGTAACAGGGACCCTGTGGAACGGCAACAAAATTATCGACGAGCGCCT  1860
A511___nluc     CAAAAAGATCACTGTAACAGGGACCCTGTGGAACGGCAACAAAATTATCGACGAGCGCCT  1851
LP125___nluc    CAAAAAGATCACTGTAACAGGGACCCTGTGGAACGGCAACAAAATTATCGACGAGCGCCT  1860
LP40___nluc     CAAAAAGATCACTGTAACAGGGACCCTGTGGAACGGCAACAAAATTATCGACGAGCGCCT  1860
P100___nluc     CAAAAAGATCACTGTAACAGGGACCCTGTGGAACGGCAACAAAATTATCGACGAGCGCCT  1854
                ************************************************************

LP124___nluc    GATCAACCCCGACGGCTCCCTGCTGTTCCGAGTAACCATCAACGGAGTGACCGGCTGGCG  1920
A511___nluc     GATCAACCCCGACGGCTCCCTGCTGTTCCGAGTAACCATCAACGGAGTGACCGGCTGGCG  1911
LP125___nluc    GATCAACCCCGACGGCTCCCTGCTGTTCCGAGTAACCATCAACGGAGTGACCGGCTGGCG  1920
LP40___nluc     GATCAACCCCGACGGCTCCCTGCTGTTCCGAGTAACCATCAACGGAGTGACCGGCTGGCG  1920
P100___nluc     GATCAACCCCGACGGCTCCCTGCTGTTCCGAGTAACCATCAACGGAGTGACCGGCTGGCG  1914
                ************************************************************

LP124___nluc    GCTGTGCGAACGCATTCTGGCGTAATAATTATAGGATAATTGAATAAAAACAGTATAGAG  1980
A511___nluc     GCTGTGCGAACGCATTCTGGCGTAATAATTATAGGATAATTGAATAAAAACAGTATAGAG  1971
LP125___nluc    GCTGTGCGAACGCATTCTGGCGTAATAATTATAGGATAATTGAATAAAAACAGTATAGAG  1980
LP40___nluc     GCTGTGCGAACGCATTCTGGCGTAATAATTATAGGATAATTGAATAAAAACAGTATAGAG  1980
P100___nluc     GCTGTGCGAACGCATTCTGGCGTAATAATTATAGGATAATTGAATAAAAACAGTATAGAG  1974
                ************************************************************

LP124___nluc    AGCAGATAAATACTGCTCTCTATTTTACTAATAAGGAGGATTTAAATTGCTAAAAAATAC  2040
A511___nluc     AGCAGATAAATACTGCTCTCTATTTTACTAATAAGGAGGATTTAAATTGCTAAAAAATAC  2031
LP125___nluc    AGCAGATAAATACTGCTCTCTATTTTACTAATAAGGAGGATTTAAATTGCTAAAAAATAC  2040
LP40___nluc     AGCAGATAAATACTGCTCTCTATTTTACTAATAAGGAGGATTTAAATTGCTAAAAAATAC  2040
P100___nluc     AGCAGATAAATACTGCTCTCTATTTTACTAATAAGGAGGATTTAAATTGCTAAAAAATAC  2034
                ************************************************************

LP124___nluc    AAACTTAGCTAATTATAAAAAAGTGAATACACGGTTTGGAAATCTTAGTTTTGACGACAA  2100
A511___nluc     AAACTTAGCTAATTATAAAAAAGTGAATACACGGTTTGGAAATCTTAGTTTTGACGACAA  2091
LP125___nluc    AAACTTAGCTAATTATAAAAAAGTGAATACACGGTTTGGAAATCTTAGTTTTGACGACAA  2100
LP40___nluc     AAACTTAGCTAATTATAAAAAAGTGAATACACGGTTTGGAAATCTTAGTTTTGACGACAA  2100
P100___nluc     AAACTTAGCTAATTATAAAAAAGTGAATACACGATTTGGAAATCTTAGTTTTGATGATAA  2094
                ********************************* ******************** ** **

LP124___nluc    AGGTATTTCTAATGACTTAACGGAAGAACAGCAAAAAGAATTAGGTAAGCTTCGAGGATT  2160
A511___nluc     AGGTATTTCTAATGACTTAACGGAAGAACAGCAAAAAGAATTAGGTAAGCTTCGAGGATT  2151
LP125___nluc    AGGTATTTCTAATGACTTAACGGAAGAACAGCAAAAAGAATTAGGTAAGCTTCGAGGATT  2160
LP40___nluc     AGGTATTTCTAATGACTTAACGGAAGAACAGCAAAAAGAATTAGGTAAGCTTCGAGGATT  2160
P100___nluc     AGGTATTTCTAATGACCTAACGGAAGAGCAGCAAAAAGAATTAGGTAAGCTTAGAGGATT  2154
                **************** ********** ************************ *******

LP124___nluc    CGAATATATTAAGACAGAACAGAAAACAAAGAAGAACCTAAGAAAGAAGAACCTAAGAA  2220
A511___nluc     CGAATATATTAAGACAGAACAGAAAACAAAGAAGAACCTAAGAAAGAAGAACCTAAGAA  2211
LP125___nluc    CGAATATATTAAGACAGAACAGAAAACAAAGAAGAACCTAAGAAAGAAGAACCTAAGAA  2220
LP40___nluc     CGAATATATTAAGACAGAACAGAAAACAAAGAAGAACCTAAGAAAGAAGAACCTAAGAA  2220
P100___nluc     CGAATATATTAAGACAGAACAGAAAACGAAAGAAGAACCTAAGAAAGAAGAACCTAAGAA  2214
                *************************** ********************************

LP124___nluc    AGAAGAACCTAAGAAAGAAGAACCTAAGAAAGAAGAACCTAAGAAAGAAGAACCTAAGAA  2280
A511___nluc     AGAAGAACCTAAGAAAGAAGAACCTAAGAAAGAAGAACCTAAGAAAGAAGAACCTAAGAA  2271
LP125___nluc    AGAA--------------------------------------------------------  2224
LP40___nluc     AGAA---------------------------------------------GAACCTAAGAA  2235
P100___nluc     AGAA--------------------------------------------------------  2218
                ****

LP124___nluc    AGAAAGTACAGAAAATGAATTAGACAGCTTCTTAGCTAAAGAGCCTTCAATCAAAGAATT  2340
A511___nluc     AGAAAGTACAGAAAATGAATTAGACAGCTTCTTAGCTAAAGAGCCTTCAATCAAAGAATT  2331
LP125___nluc    ----AGTACAGAAAATGAATTAGACAGCTTCTTAGCTAAAGAGCCTTCAATCAAAGAATT  2280
LP40___nluc     AGAAAGTACAGAAAATGAATTAGACAGCTTCTTAGCTAAAGAGCCTTCAATCAAAGAATT  2295
P100___nluc     ----AGTACAGAAAATGAATTAGACAGCTTCTTAGCTAAAGAACCTTCAATCAAAGAATT  2274
                    ************************************** *****************
```

FIGURE 29 (continued)

```
LP124___nluc    AAAAGAATTTGCGAGTAAAAAAGGCATTAAAATTGAAAAAACTAAGAAAAATGATATAAT  2400
A511___nluc     AAAAGAATTTGCGAGTAAAAAAGGCATTAAAATTGAAAAAACTAAGAAAAATGATATAAT  2391
LP125___nluc    AAAAGAATTTGCGAGTAAAAAAGGCATTAAAATTGAAAAAACTAAGAAAAATGATATAAT  2340
LP40___nluc     AAAAGAATTTGCGAGTAAAAAAGGCATTAAAATTGAAAAAACTAAGAAAAACGATATAAT  2355
P100___nluc     AAAAGAATTTGCGAGTAAAAAAGGCATTAAAATTGAAAAAACTAAGAAAAATGATATAAT  2334
                *************************************************** ********

LP124___nluc    TGAAGAACTAAAGAGAGGGTAATGTATAATGTATGGAGGTTATGAAGGACAAGATTCTTA  2460
A511___nluc     TGAAGAACTAAAGAGAGGGTAATGTATAATGTATGGAGGTTATGAAGGACAAGATTCTTA  2451
LP125___nluc    TGAAGAACTAAAGAGAGGGTAATGTATAATGTATGGAGGTTATGAAGGACAAGATTCTTA  2400
LP40___nluc     TGAAGAACTAAAGAGAGGGTAATGTATAATGTATGGAGGTTATGAAGGACAAGATTCTTA  2415
P100___nluc     TGAAGAACTAAAGAGAGGGTAATGTACAATGTATGGAGGTTATGAAGGACAAGATTCTTA  2394
                ************************** *********************************

LP124___nluc    CGAATACCCTTACTCACATGGGAACCCTAAGCATGTAGAGCCAGAAAAAGTTGACGAATA  2520
A511___nluc     CGAATACCCTTACTCACATGGGAACCCTAAGCATGTAGAGCCAGAAAAAGTTGACGAATA  2511
LP125___nluc    CGAATACCCTTACTCACATGGGAACCCTAAGCATGTAGAGCCAGAAAAAGTTGACGAATA  2460
LP40___nluc     CGAATACCCTTACTCACATGGGAACCCTAAGCATGTAGAGCCAGAAAAAGTTGACGAATA  2475
P100___nluc     CGAATACCCTTACTCACACGGGAACCCTAAGCATGTAGAGCCAGAAAAAGTTGACGAATA  2454
                ***************** ******************************************

LP124___nluc    TGTTCTTTCTGATTATGGTTGGACTGCGGAAACAATTAAAGCATACATGTATGGTGTTCG  2580
A511___nluc     TGTTCTTTCTGATTATGGTTGGACTGCGGAAACAATTAAAGCATACATGTATGGTGTTCG  2571
LP125___nluc    TGTTCTTTCTGATTATGGTTGGACTGCGGAAACAATTAAAGCATACATGTATGGTGTTCG  2520
LP40___nluc     TGTTCTTTCTGATTATGGTTGGACTGCGGAAACAATTAAAGCATACATGTATGGTGTTCG  2535
P100___nluc     TGTTCTTTCTGATTATGGCTGGACTGCGGAAACAATTAAAGCATACATGTATGGTGTTCG  2514
                ****************** *****************************************

LP124___nluc    TGTAGTAGACCCTGAAACAGGAGAGGAAATGGGAGACACCTTCTACAATCATATTATAGA  2640
A511___nluc     TGTAGTAGACCCTGAAACAGGAGAGGAAATGGGAGACACCTTCTACAATCATATTATAGA  2631
LP125___nluc    TGTAGTAGACCCTGAAACAGGAGAGGAAATGGGAGACACCTTCTACAATCATATTATAGA  2580
LP40___nluc     TGTAGTAGACCCTGAAACAGGAGAGGAAATGGGAGACACCTTCTACAATCATATTATAGA  2595
P100___nluc     TGTAGTAGACCCTGAAACAGGAGAGGAAATGGGAGACACCTTCTACAATCATATTATAGA  2574
                ************************************************************

LP124___nluc    GGTTGCCGTTGATAAGGC  2658
A511___nluc     GGTTGCCGTTGATAAGGC  2649
LP125___nluc    GGTTGCCGTTGATAAGGC  2598
LP40___nluc     GGTTGCCGTTGATAAGGC  2613
P100___nluc     GGTTGCCGTTGATAAGGC  2592
                ******************
```

FIGURE 29 (continued)

TABLE 19

| NP # | A511 Plate | P100 Plate | Avg A511 | Avg P100 | A511/P100 Cocktail |
|---|---|---|---|---|---|
| NP1900 | | 0.00 | 0.09 | 1.03 | 0.29 |
| NP1901 | 0.75 | 0.17 | 0.15 | 0.10 | 0.10 |
| NP1902 | | | 0.10 | 1.04 | 0.30 |
| NP1903 | 0.75 | 0.03 | 0.09 | 0.11 | 0.10 |
| NP1904 | | | 0.09 | 0.11 | 0.11 |
| NP1905 | | | 0.16 | 0.12 | 0.12 |
| NP1906 | | | 0.10 | 1.08 | 0.79 |
| NP1907 | | 0.00 | 0.09 | 1.05 | 0.30 |
| NP1908 | 0.45 | 0.17 | 0.19 | 0.10 | 0.11 |
| NP1909 | | 0.00 | 0.09 | 1.00 | 0.10 |
| NP1912 | | 0.00 | 0.10 | 0.93 | 0.28 |
| NP1959 | 0.28 | 0.20 | 0.09 | 0.09 | 0.10 |
| NP1960 | 0.00 | 0.00 | 0.09 | 0.91 | 0.15 |
| NP1961 | | 0.20 | 0.11 | 0.10 | 0.12 |
| NP1962 | | 0.00 | 0.09 | 0.91 | 0.34 |
| NP1963 | 0.12 | 0.90 | 0.09 | 0.09 | 0.12 |
| NP1964 | 0.80 | 1.40 | 0.09 | 0.09 | 0.10 |
| NP1965 | 0.20 | 0.30 | 0.09 | 0.09 | 0.10 |
| NP1966 | | 0.20 | 0.09 | 0.10 | 0.11 |
| NP1967 | 1.40 | 0.50 | 0.10 | 0.09 | 0.10 |
| NP1915 | 0.10 | | 0.77 | 0.10 | 0.11 |
| NP1997 | 0.05 | 0.00 | 0.09 | 0.11 | 0.11 |
| NP1998 | 0.10 | | 0.09 | 0.10 | 0.11 |
| NP1999 | 0.10 | 0.70 | 0.09 | 0.14 | 0.11 |
| NP2000 | 0.10 | 0.00 | 0.09 | 0.10 | 0.11 |
| NP2001 | 0.05 | 1.00 | 0.10 | 0.11 | 0.11 |
| NP2002 | | | 0.10 | 0.98 | 0.28 |
| NP2003 | | 0.00 | 0.16 | 1.03 | 0.09 |
| NP2004 | | 0.00 | 0.13 | 1.00 | 0.10 |
| NP2005 | | 0.00 | 0.31 | 0.89 | 0.13 |
| NP1916 | | 0.00 | 0.41 | 0.90 | 1.01 |
| NP2006 | | 0.00 | 0.12 | 0.77 | 0.09 |
| NP2007 | 0.06 | 10.00 | 0.09 | 0.09 | 0.11 |
| NP2008 | 0.10 | 1.00 | 0.09 | 0.09 | 0.11 |

FIGURE 30

| | | | | | |
|---|---|---|---|---|---|
| NP2009 | 0.25 | 0.90 | 0.09 | 0.11 | 0.11 |
| NP2010 | | 0.00 | 0.29 | 0.76 | 0.09 |
| NP2011 | | 0.00 | 0.45 | 0.78 | 1.00 |
| NP2012 | 0.00 | 0.00 | 0.57 | 1.04 | 1.04 |
| NP2013 | 0.00 | 0.00 | 0.49 | 1.00 | 1.04 |
| NP2014 | | 0.00 | 0.39 | 0.84 | 0.10 |
| NP1869 | 0.10 | 1.71 | 0.13 | 0.21 | 0.13 |
| NP1840 | | | 1.02 | 1.17 | 1.05 |
| NP1839 | 1.00 | 1.00 | 0.24 | 0.35 | 0.14 |
| NP2024 | 4.00 | 0.50 | 0.10 | 0.10 | 0.11 |
| NP2025 | 1.20 | 0.33 | 0.09 | 0.09 | 0.11 |
| NP2026 | 1.10 | 0.33 | 0.56 | 0.57 | 0.26 |
| NP2027 | 0.00 | 0.27 | 0.10 | 0.12 | 0.12 |
| NP2028 | 1.00 | 0.33 | 0.09 | 0.09 | 0.12 |
| NP2029 | | | 0.21 | 0.98 | 0.12 |
| NP2030 | 0.00 | 1.33 | 0.10 | 0.09 | 0.12 |
| NP2031 | 0.10 | 0.27 | 0.09 | 0.09 | 0.11 |
| NP2032 | 1.00 | 0.33 | 0.08 | 0.09 | 0.12 |
| NP1879 | 0.20 | 0.50 | 1.05 | 0.13 | 0.20 |
| NP2033 | 1.00 | 0.67 | 0.10 | 0.11 | 0.10 |
| NP2034 | 0.90 | 3.33 | 0.10 | 0.11 | 0.11 |
| NP2035 | 2.00 | 0.30 | 0.10 | 0.11 | 0.11 |
| NP2036 | 1.00 | 0.33 | 0.09 | 0.09 | 0.12 |
| NP2037 | 1.00 | 0.33 | 0.10 | 0.11 | 0.11 |
| NP2038 | | 1.00 | 1.04 | 0.11 | 0.23 |
| NP2039 | | 0.33 | 0.99 | 0.10 | 0.24 |
| NP2040 | | 0.33 | 0.89 | 0.10 | 0.23 |
| NP2041 | 1.50 | 0.33 | 0.10 | 0.12 | 0.12 |
| NP2042 | | 0.17 | 0.15 | 0.09 | 0.13 |
| NP2043 | | 1.33 | 0.09 | 0.09 | 0.10 |
| NP2044 | | 0.00 | 0.09 | 0.09 | 0.26 |
| NP2045 | | 3.33 | 0.20 | 0.20 | 0.11 |
| NP2046 | 0.00 | 0.07 | 0.09 | 0.09 | 0.11 |
| NP2047 | | 0.17 | 0.10 | 0.10 | 0.13 |
| NP2048 | | 0.33 | 0.13 | 0.10 | 0.17 |
| NP2049 | | 0.33 | 0.10 | 0.09 | 0.21 |
| NP2050 | | 0.27 | 0.10 | 0.09 | 0.12 |
| NP1880 | 0.00 | 0.00 | 1.01 | 1.07 | 1.07 |

FIGURE 30 (continued)

| | | | | | |
|---|---|---|---|---|---|
| NP2051 | | 0.33 | 0.90 | 0.09 | 0.19 |
| NP2052 | 1.00 | 0.07 | 0.09 | 0.09 | 0.10 |
| NP2053 | 0.30 | 0.33 | 0.09 | 0.09 | 0.12 |
| NP2054 | 0.30 | 0.07 | 0.09 | 0.09 | 0.16 |
| NP2055 | 2.00 | 0.43 | 0.09 | 0.09 | 0.10 |
| NP2056 | 1.20 | 0.10 | 0.09 | 0.09 | 0.12 |
| NP2057 | | 0.33 | 0.97 | 0.09 | 0.28 |
| NP2058 | | 0.10 | 0.97 | 0.10 | 0.25 |
| NP2059 | 0.09 | 0.17 | 0.12 | 0.13 | 0.14 |
| NP1881 | 0.00 | 0.00 | 0.17 | 1.05 | 0.20 |
| NP2060 | 0.00 | | 0.44 | 0.95 | 0.98 |
| NP2061 | | | 0.12 | 0.89 | 0.12 |
| NP2062 | | | 0.12 | 0.90 | 0.13 |
| NP2063 | | | 0.96 | 1.03 | 1.25 |
| NP2064 | | 0.01 | 0.09 | 0.09 | 0.25 |
| NP2065 | | | 0.11 | 0.97 | 0.09 |
| NP2066 | | | 0.49 | 1.02 | 0.96 |
| NP2067 | 0.00 | 0.00 | 1.06 | 1.08 | 0.93 |
| NP2068 | | | 1.12 | 1.11 | 1.05 |
| NP2069 | | | 0.19 | 1.04 | 0.17 |
| NP2070 | | 0.27 | 0.45 | 0.10 | 0.11 |
| NP2071 | 0.00 | 0.00 | 1.14 | 1.14 | 1.21 |
| NP2072 | 0.60 | 0.33 | 0.10 | 0.11 | 0.12 |
| NP2073 | | | 0.63 | 1.12 | 1.07 |
| NP2074 | 0.10 | 0.33 | 0.18 | 0.11 | 0.16 |
| NP2075 | | 0.03 | 0.12 | 0.91 | 0.79 |
| NP2076 | 1.20 | 0.27 | 0.09 | 0.10 | 0.11 |
| NP2077 | 0.00 | 0.17 | 0.14 | 0.10 | 0.11 |
| NP1882 | 0.95 | 0.58 | 0.93 | 0.11 | 0.12 |
| NP2078 | | | 0.11 | 0.77 | 0.17 |
| NP2079 | | | 1.04 | 1.07 | 1.04 |
| NP2080 | 0.00 | 0.00 | 1.04 | 1.05 | 1.02 |
| NP2081 | 0.00 | 0.00 | 1.00 | 0.98 | 1.01 |
| NP2082 | 0.00 | 0.00 | 1.07 | 1.06 | 1.02 |
| NP2083 | | | 0.13 | 0.36 | 0.89 |
| NP2084 | | | 0.14 | 1.00 | 0.17 |
| NP2085 | 0.00 | 0.00 | 1.01 | 1.00 | 0.95 |
| NP2086 | | | 0.19 | 1.06 | 0.17 |

FIGURE 30 (continued)

| | | | | | |
|---|---|---|---|---|---|
| NP2087 | 0.00 | 0.00 | 0.96 | 0.96 | 1.16 |
| NP2088 | 0.20 | 0.60 | 0.11 | 0.11 | 0.15 |
| NP2089 | 0.00 | 0.00 | 0.90 | 1.00 | 1.06 |
| NP2090 | 0.50 | 0.40 | 0.12 | 0.12 | 0.17 |
| NP2091 | 0.01 | 0.01 | 0.10 | 0.16 | 0.49 |
| NP2092 | 0.50 | 1.00 | 0.09 | 0.09 | 0.10 |
| NP2093 | | 1.00 | 0.25 | 0.09 | 0.10 |
| NP2094 | | 1.00 | 0.09 | 0.09 | 0.10 |
| NP2095 | 1.00 | 0.20 | 0.14 | 0.18 | 0.22 |
| NP2096 | | 0.30 | 0.13 | 0.09 | 0.10 |
| NP2097 | 0.00 | 0.70 | 0.12 | 0.10 | 0.11 |
| NP2098 | | 0.00 | 0.12 | 0.09 | 0.13 |
| NP2099 | 0.00 | 0.20 | 0.12 | 0.09 | 0.11 |
| NP2100 | 0.00 | 0.00 | 0.97 | 1.00 | 0.99 |
| NP2101 | | 0.00 | 0.91 | 1.02 | 1.04 |
| NP2102 | | 0.00 | 0.98 | 1.02 | 1.01 |
| NP2103 | 0.00 | 0.00 | 1.02 | 1.01 | 0.98 |
| NP2104 | | 0.00 | 0.98 | 1.02 | 1.03 |
| NP1883 | 0.00 | 0.00 | 0.40 | 0.94 | 1.00 |
| NP2105 | 0.00 | 0.00 | 1.05 | 1.03 | 1.02 |
| NP2106 | | | 0.79 | 1.04 | 1.01 |
| NP2107 | 0.00 | 0.00 | 1.07 | 1.12 | 1.03 |
| NP2108 | 0.00 | 0.00 | 1.05 | 1.11 | 1.01 |
| NP2109 | | | 0.10 | 1.09 | 0.10 |
| NP2110 | 0.00 | 0.00 | 0.92 | 0.84 | 1.06 |
| NP2111 | | | 0.71 | 0.92 | 1.12 |
| NP2112 | 0.00 | 0.00 | 1.00 | 0.92 | 1.05 |
| NP2113 | 2.00 | 0.30 | 0.09 | 0.09 | 0.10 |
| NP1884 | 0.00 | | 0.10 | 1.09 | 0.20 |
| NP2114 | | | 0.09 | 0.48 | 0.09 |
| NP2115 | | | 0.09 | 0.97 | 0.09 |
| NP2116 | | | 0.09 | 1.03 | 0.09 |
| NP2117 | | | 0.10 | 0.88 | 0.10 |
| NP2118 | | | 0.10 | 1.01 | 0.10 |
| NP2119 | | | 0.09 | 0.86 | 0.09 |
| NP2120 | | 0.00 | 0.11 | 1.06 | 0.11 |
| NP2121 | | | 0.09 | 0.98 | 0.09 |
| NP2122 | | | 0.09 | 0.88 | 0.09 |

FIGURE 30 (continued)

| | | | | | |
|---|---|---|---|---|---|
| NP1885 | 1.50 | 0.50 | 0.94 | 0.11 | 0.12 |
| NP2123 | 0.10 | 0.20 | 0.09 | 0.09 | 0.11 |
| NP2124 | 0.60 | 1.00 | 0.09 | 0.09 | 0.11 |
| NP2125 | | 2.00 | 0.09 | 0.09 | 0.10 |
| NP2126 | | 1.00 | 0.52 | 0.10 | 0.22 |
| NP2127 | | | 0.93 | 1.06 | 1.08 |
| NP2128 | 0.09 | 0.10 | 0.09 | 0.09 | 0.10 |
| NP2129 | 0.20 | 0.03 | 0.09 | 0.09 | 0.10 |
| NP2130 | 0.60 | 0.10 | 0.09 | 0.09 | 0.10 |
| NP2131 | 0.00 | 0.11 | 0.09 | 0.09 | 0.10 |
| NP1886 | 0.00 | 0.00 | 0.47 | 0.96 | 1.04 |
| NP2132 | 0.00 | 0.00 | 1.03 | 1.02 | 1.03 |
| NP1887 | | 0.00 | 1.02 | 0.99 | 1.00 |
| NP2133 | | 0.40 | 1.07 | 0.09 | 0.12 |
| NP2134 | | 0.00 | 1.06 | 1.12 | 1.16 |
| NP2135 | 0.00 | 0.30 | 0.12 | 0.08 | 0.18 |
| NP2136 | | 0.20 | 0.86 | 0.09 | 0.10 |
| NP2137 | | 0.20 | 0.85 | 0.09 | 0.10 |
| NP2138 | | 0.00 | 0.98 | 1.01 | 1.00 |
| NP2139 | 0.10 | 0.10 | 0.09 | 0.10 | 0.12 |
| NP2140 | | | 0.96 | 0.97 | 1.08 |
| NP2141 | | | 0.14 | 0.10 | 0.18 |
| NP2142 | | | 0.71 | 1.06 | 1.02 |
| NP2143 | | | 0.90 | 1.05 | 1.03 |
| NP2144 | 0.00 | 0.00 | 0.10 | 0.10 | 0.11 |
| NP2145 | 0.00 | 0.00 | 0.09 | 0.10 | 0.11 |
| NP2146 | 0.40 | 0.20 | 0.94 | 0.94 | 1.12 |
| NP2147 | | 0.00 | 0.09 | 0.09 | 0.15 |
| NP2148 | 0.00 | 0.30 | 0.10 | 0.10 | 0.10 |
| NP2149 | 0.00 | 0.00 | 1.12 | 1.18 | 1.01 |
| NP2150 | 0.00 | 0.00 | 0.73 | 1.12 | 1.11 |
| NP1888 | | | 0.09 | 0.97 | 0.19 |
| NP2151 | 0.00 | 0.00 | 1.13 | 1.07 | 1.04 |
| NP2152 | | 1.00 | 0.10 | 0.10 | 0.14 |
| NP2153 | | 0.00 | 0.81 | 1.01 | 1.05 |
| NP2154 | | 0.00 | 1.06 | 1.00 | 1.09 |
| NP2155 | 0.00 | 0.00 | 0.74 | 1.00 | 1.10 |
| NP2156 | 0.20 | 0.20 | 0.11 | 0.10 | 0.13 |

FIGURE 30 (continued)

| | | | | | |
|---|---|---|---|---|---|
| NP2157 | 0.40 | 6.00 | 0.10 | 0.10 | 0.10 |
| NP2158 | 0.00 | 0.50 | 0.13 | 0.12 | 0.12 |
| NP2159 | 0.00 | 0.00 | 1.11 | 1.10 | 1.23 |
| NP1889 | 0.80 | 0.17 | 1.02 | 0.10 | 0.10 |
| NP2160 | 0.20 | 0.00 | 0.11 | 0.11 | 0.14 |
| NP2161 | 0.20 | 1.50 | 0.10 | 0.10 | 0.17 |
| NP2162 | 0.40 | 1.00 | 0.10 | 0.10 | 0.12 |
| NP2163 | 0.30 | 1.00 | 0.10 | 0.10 | 0.16 |
| NP2164 | 0.14 | 1.00 | 1.05 | 1.11 | 0.96 |
| NP2165 | | 1.10 | 0.44 | 0.95 | 1.16 |
| NP2166 | 0.00 | 0.00 | 0.09 | 0.09 | 0.13 |
| NP2167 | 0.12 | 1.60 | 0.10 | 0.11 | 0.16 |
| NP2168 | 0.80 | 1.30 | 0.11 | 0.11 | 0.14 |
| NP1890 | 0.00 | 0.00 | 0.89 | 1.02 | 1.04 |
| NP2169 | 0.04 | 1.00 | 0.10 | 0.10 | 0.14 |
| NP2170 | 0.30 | 0.70 | 0.10 | 0.10 | 0.13 |
| NP2171 | 0.60 | 0.60 | 0.09 | 0.10 | 0.11 |
| NP2172 | 0.22 | 0.10 | 0.09 | 0.10 | 0.11 |
| NP2173 | 0.40 | 0.10 | 0.10 | 0.10 | 0.11 |
| NP2174 | 0.20 | 3.00 | 0.09 | 0.09 | 0.11 |
| NP2175 | 0.00 | 0.00 | 1.08 | 1.05 | 1.05 |
| NP2176 | 0.00 | 0.00 | 1.07 | 1.06 | 1.08 |
| NP2177 | | | 1.08 | 1.06 | 0.91 |
| NP1878 | | | 0.11 | 0.12 | 0.12 |
| NP1911 | 0.00 | | 0.15 | 0.54 | 0.15 |
| NP1950 | 0.30 | 2.00 | 0.09 | 0.11 | 0.09 |
| NP1951 | 0.20 | 1.40 | 0.10 | 0.10 | 0.23 |
| NP1952 | 0.05 | 1.20 | 0.09 | 0.10 | 0.10 |
| NP1953 | | | 0.10 | 0.10 | 0.10 |
| NP1954 | 0.10 | 2.00 | 0.09 | 0.10 | 0.10 |
| NP1955 | | 1.30 | 0.14 | 0.09 | 0.10 |
| NP1956 | | 0.00 | 0.09 | 1.03 | 0.27 |
| NP1957 | 0.00 | 0.70 | 0.10 | 0.09 | 0.10 |
| NP1958 | 0.20 | 3.00 | 0.08 | 0.10 | 0.10 |
| NP1913 | | 0.00 | 0.09 | 0.78 | 0.15 |
| NP1968 | 0.40 | 2.00 | 0.10 | 0.10 | 0.09 |
| NP1969 | 1.00 | 2.00 | 0.09 | 0.10 | 0.09 |
| NP1970 | 0.08 | 0.50 | 0.10 | 0.10 | 0.08 |

FIGURE 30 (continued)

| | | | | | |
|---|---|---|---|---|---|
| NP1971 | 0.40 | 0.60 | 0.12 | 0.10 | 0.09 |
| NP1972 | 0.00 | 0.00 | 1.11 | 1.22 | 0.92 |
| NP1973 | | 0.00 | 0.22 | 0.73 | 0.21 |
| NP1974 | | 0.00 | 0.23 | 0.70 | 0.31 |
| NP1975 | | | 0.95 | 1.03 | 1.12 |
| NP1976 | 0.50 | 1.00 | 0.10 | 0.10 | 0.11 |
| NP1891 | 0.00 | 0.00 | 0.99 | 1.03 | 0.95 |
| NP1892 | 0.00 | 0.00 | 1.01 | 1.04 | 0.96 |
| NP1893 | 0.00 | 0.00 | 1.00 | 1.04 | 0.97 |
| NP1894 | 0.00 | 0.00 | 0.10 | 0.99 | 0.20 |
| NP1895 | 3.00 | 0.67 | 0.16 | 0.11 | 0.12 |
| NP1896 | 1.00 | 0.33 | 0.10 | 0.16 | 0.12 |
| NP1897 | 1.00 | 0.25 | 0.09 | 0.10 | 0.10 |
| NP1898 | 5.00 | 16.70 | 0.99 | 0.09 | 0.10 |
| NP1899 | 0.00 | 0.00 | 0.12 | 1.04 | 0.40 |
| NP1990 | | 0.00 | 0.10 | 1.07 | 0.59 |
| NP1991 | | 0.00 | 0.10 | 1.03 | 0.09 |
| NP1992 | | 0.00 | 0.10 | 1.07 | 0.10 |
| NP1993 | | 0.00 | 0.10 | 1.04 | 0.10 |
| NP1994 | | 0.00 | 0.09 | 0.99 | 0.16 |
| NP1995 | | 0.00 | 0.10 | 0.93 | 0.13 |
| NP1996 | 0.05 | 12.00 | 0.09 | 0.10 | 0.10 |
| NP1910 | 0.55 | | 0.09 | 0.09 | 0.11 |
| NP1945 | 0.10 | 0.60 | 0.14 | 0.10 | 0.10 |
| NP1946 | 0.00 | 1.90 | 0.12 | 0.10 | 0.17 |
| NP1947 | 0.00 | 0.70 | 0.14 | 0.10 | 0.12 |
| NP1948 | 0.00 | 0.20 | 0.09 | 0.14 | 0.47 |
| NP1949 | 0.10 | 20.00 | 0.10 | 0.10 | 0.11 |
| NP1977 | 0.06 | 2.00 | 0.09 | 0.09 | 0.11 |
| NP1978 | | 0.00 | 0.44 | 1.04 | 1.10 |
| NP1979 | 0.00 | 0.00 | 0.52 | 1.01 | 1.04 |
| NP1980 | | | 0.27 | 1.04 | 0.20 |
| NP1981 | | 0.00 | 0.39 | 0.84 | 0.39 |
| NP1982 | | 0.00 | 0.38 | 0.87 | 0.13 |
| NP1983 | | 0.20 | 0.11 | 0.10 | 0.10 |
| NP1984 | 0.00 | 0.00 | 0.27 | 0.95 | 0.21 |
| NP1985 | | 0.00 | 0.63 | 1.05 | 1.01 |
| NP1914 | | 0.25 | 0.09 | 0.10 | 0.11 |

FIGURE 30 (continued)

| | | | | | |
|---|---|---|---|---|---|
| NP1986 | | 0.70 | 0.09 | 0.10 | 0.11 |
| NP1987 | | 0.60 | 0.09 | 0.10 | 0.11 |
| NP1988 | 0.00 | 0.40 | 0.10 | 0.10 | 0.11 |
| NP1989 | 0.00 | 1.00 | 0.83 | 0.09 | 0.21 |
| NP1917 | | 0.00 | 0.10 | 1.00 | 0.20 |
| NP2015 | 0.00 | 0.00 | 0.17 | 0.20 | 0.10 |
| NP2016 | 0.00 | 0.00 | 0.12 | 0.20 | 0.12 |
| NP2017 | | | 0.13 | 0.20 | 0.26 |
| NP2018 | | 0.00 | 0.10 | 0.25 | 0.25 |
| NP2019 | | | 0.10 | 0.24 | 0.24 |
| NP2020 | 0.00 | 0.20 | 0.12 | 0.27 | 0.83 |
| NP2021 | 0.00 | 0.00 | 0.26 | 1.06 | 0.39 |
| NP2022 | | 0.00 | 0.30 | 1.07 | 0.13 |
| NP2023 | | 0.00 | 0.44 | 0.98 | 1.03 |

FIGURE 30(continued)

TABLE 20

| NP # | LP14 | LP20 | LP30 | LP34 | LP39 | LP40 | LP44 |
|---|---|---|---|---|---|---|---|
| 1900 | 1.18 | 0.09 | 1.01 | 1.14 | 1.14 | 0.52 | 0.24 |
| 1901 | 1.11 | 0.18 | 1.00 | 0.12 | 1.14 | 0.98 | 0.09 |
| 1902 | 1.10 | 0.13 | 0.99 | 0.22 | 1.15 | 0.95 | 0.09 |
| 1903 | 1.10 | 0.11 | 1.01 | 0.13 | 1.13 | 0.95 | 0.09 |
| 1904 | 1.11 | 0.10 | 1.02 | 0.11 | 1.13 | 0.85 | 0.14 |
| 1905 | 1.12 | 0.10 | 1.01 | 0.19 | 1.12 | 0.87 | 0.13 |
| 1906 | 1.08 | 0.16 | 0.99 | 0.10 | 1.08 | 0.91 | 0.09 |
| 1907 | 1.14 | 0.10 | 1.02 | 1.11 | 1.12 | 0.22 | 0.25 |
| 1908 | 1.03 | 0.12 | 1.05 | 0.11 | 1.03 | 0.89 | 0.09 |
| 1909 | 1.08 | 0.09 | 0.95 | 1.05 | 1.07 | 0.21 | 0.16 |
| 1912 | 1.23 | 0.10 | 0.98 | 1.31 | 1.21 | 0.24 | 0.17 |
| 1959 | 1.02 | 0.22 | 1.04 | 0.10 | 0.99 | 0.97 | 0.22 |
| 1960 | 0.11 | 0.18 | 0.76 | 0.11 | 1.04 | 0.93 | 0.09 |
| 1961 | 0.94 | 0.09 | 0.88 | 0.12 | 1.25 | 0.87 | 0.10 |
| 1962 | 1.08 | 0.09 | 1.09 | 1.30 | 1.30 | 0.19 | 0.25 |
| 1963 | 0.97 | 0.09 | 1.02 | 0.13 | 1.22 | 0.78 | 0.23 |
| 1964 | 1.04 | 0.10 | 1.11 | 0.10 | 1.11 | 0.93 | 0.30 |
| 1965 | 1.04 | 0.11 | 0.97 | 0.10 | 1.13 | 0.87 | 0.23 |
| 1966 | 1.09 | 0.22 | 0.98 | 0.11 | 1.19 | 1.02 | 0.28 |
| 1967 | 1.00 | 0.42 | 1.16 | 0.11 | 1.16 | 0.95 | 0.18 |
| 1915 | 1.15 | 0.09 | 0.70 | 0.22 | 1.12 | 0.89 | 0.16 |
| 1997 | 1.08 | 0.09 | 0.11 | 0.10 | 1.06 | 0.93 | 0.18 |
| 1998 | 1.07 | 0.09 | 0.11 | 0.10 | 1.07 | 0.88 | 0.18 |
| 1999 | 1.06 | 0.09 | 0.16 | 0.10 | 1.05 | 0.91 | 0.25 |
| 2000 | 1.07 | 0.09 | 0.11 | 0.10 | 1.05 | 0.94 | 0.33 |
| 2001 | 1.08 | 0.10 | 0.14 | 0.11 | 1.06 | 0.89 | 0.19 |
| 2002 | 1.04 | 1.10 | 1.03 | 0.14 | 1.06 | 0.72 | 0.13 |
| 2003 | 1.05 | 0.09 | 0.73 | 0.10 | 1.05 | 0.80 | 0.22 |
| 2004 | 1.03 | 0.09 | 0.20 | 0.12 | 1.00 | 1.10 | 0.16 |
| 2005 | 1.05 | 0.10 | 0.16 | 0.11 | 1.04 | 0.98 | 0.21 |
| 1916 | 1.17 | 0.47 | 1.02 | 0.14 | 1.04 | 0.44 | 0.18 |
| 2006 | 1.08 | 0.25 | 1.04 | 0.11 | 0.90 | 0.31 | 0.23 |
| 2007 | 0.10 | 0.27 | 0.11 | 0.13 | 1.00 | 0.47 | 0.09 |
| 2008 | 0.10 | 0.16 | 0.11 | 0.09 | 1.01 | 0.45 | 0.10 |
| 2009 | 1.08 | 0.40 | 0.10 | 0.10 | 1.07 | 0.86 | 0.09 |

FIGURE 31

| | | | | | | | |
|---|---|---|---|---|---|---|---|
| **2010** | 1.01 | 0.18 | 1.16 | 0.10 | 0.91 | 0.26 | 0.20 |
| **2011** | 1.04 | 0.31 | 0.97 | 0.11 | 0.92 | 0.40 | 0.22 |
| **2012** | 1.06 | 0.34 | 0.99 | 1.02 | 1.07 | 0.61 | 0.32 |
| **2013** | 1.06 | 0.36 | 0.98 | 1.05 | 1.07 | 0.67 | 0.30 |
| **2014** | 1.04 | 0.33 | 0.98 | 0.11 | 0.96 | 0.42 | 0.27 |
| **1869** | 0.83 | 0.22 | 1.01 | 0.21 | 0.15 | 0.13 | 0.13 |
| **1840** | 1.04 | 0.38 | 0.14 | 0.24 | 1.09 | 0.41 | 0.32 |
| **1839** | 1.16 | 1.56 | 1.02 | 1.12 | 0.16 | 0.21 | 0.95 |
| **2024** | 1.00 | 1.16 | 0.20 | 0.95 | 0.10 | 0.08 | 1.02 |
| **2025** | 1.04 | 1.13 | 0.20 | 1.02 | 0.33 | 0.08 | 1.05 |
| **2026** | 1.05 | 1.35 | 0.52 | 0.17 | 0.21 | 0.44 | 1.05 |
| **2027** | 1.04 | 1.06 | 0.63 | 1.01 | 0.27 | 0.08 | 1.01 |
| **2028** | 0.98 | 1.12 | 0.16 | 0.99 | 0.19 | 0.10 | 0.99 |
| **2029** | 1.10 | 1.17 | 0.97 | 1.09 | 0.16 | 0.10 | 0.94 |
| **2030** | 1.03 | 1.22 | 0.25 | 0.90 | 0.12 | 0.09 | 0.84 |
| **2031** | 1.00 | 1.06 | 0.94 | 1.03 | 0.11 | 0.08 | 0.89 |
| **2032** | 0.26 | 1.12 | 0.15 | 1.04 | 0.10 | 0.08 | 0.96 |
| **1878** | 1.15 | 1.18 | 1.08 | 1.15 | 0.15 | 0.08 | 1.03 |
| **2033** | 1.01 | 1.21 | 0.18 | 0.98 | 0.20 | 0.09 | 1.01 |
| **2034** | 1.04 | 1.10 | 0.16 | 1.06 | 0.15 | 0.09 | 0.96 |
| **2035** | 1.02 | 1.19 | 0.14 | 1.02 | 0.16 | 0.09 | 0.97 |
| **2036** | 1.01 | 1.11 | 0.23 | 1.02 | 0.12 | 0.09 | 0.98 |
| **2037** | 0.99 | 1.09 | 0.17 | 1.05 | 0.13 | 0.09 | 0.92 |
| **2038** | 1.02 | 1.07 | 1.08 | 1.05 | 0.19 | 0.11 | 0.94 |
| **2039** | 1.06 | 1.02 | 1.03 | 1.03 | 0.22 | 0.10 | 0.93 |
| **2040** | 0.99 | 1.09 | 1.02 | 1.25 | 0.23 | 0.11 | 0.91 |
| **2041** | 1.13 | 1.10 | 0.20 | 1.15 | 0.12 | 0.11 | 1.01 |
| **2042** | 1.08 | 0.94 | 0.10 | 1.03 | 1.04 | 0.81 | 0.12 |
| **2043** | 1.05 | 1.09 | 0.83 | 1.08 | 1.05 | 0.65 | 0.11 |
| **2044** | 1.08 | 1.00 | 0.28 | 1.10 | 1.08 | 0.48 | 0.10 |
| **2045** | 1.03 | 0.45 | 0.10 | 0.19 | 1.04 | 0.26 | 0.09 |
| **2046** | 1.03 | 0.75 | 0.10 | 0.27 | 1.03 | 0.35 | 0.09 |
| **2047** | 1.00 | 1.12 | 0.10 | 1.07 | 1.00 | 0.44 | 0.09 |
| **2048** | 1.01 | 0.32 | 0.23 | 0.12 | 1.01 | 0.23 | 0.23 |
| **2049** | 1.07 | 0.97 | 1.06 | 1.14 | 1.12 | 0.58 | 0.12 |
| **2050** | 1.04 | 0.86 | 0.99 | 1.13 | 1.08 | 0.43 | 0.09 |
| **1880** | 1.15 | 1.05 | 1.08 | 1.15 | 1.15 | 0.09 | 1.03 |
| **2051** | 1.05 | 1.10 | 1.00 | 1.13 | 0.16 | 0.09 | 0.93 |

FIGURE 31(continued)

| | | | | | | | |
|---|---|---|---|---|---|---|---|
| **2052** | 1.06 | 1.15 | 0.18 | 1.08 | 0.15 | 0.10 | 0.94 |
| **2053** | 1.00 | 1.15 | 0.23 | 1.04 | 0.45 | 0.11 | 1.04 |
| **2054** | 1.11 | 1.14 | 0.77 | 1.17 | 0.18 | 0.11 | 0.96 |
| **2055** | 0.98 | 1.09 | 0.18 | 1.06 | 0.19 | 0.09 | 0.97 |
| **2056** | 1.21 | 1.07 | 0.25 | 1.21 | 0.12 | 0.10 | 0.99 |
| **2057** | 1.17 | 1.04 | 1.03 | 1.06 | 0.13 | 0.10 | 1.02 |
| **2058** | 1.16 | 1.14 | 1.01 | 1.12 | 0.16 | 0.10 | 0.95 |
| **2059** | 0.92 | 1.08 | 0.17 | 1.00 | 0.11 | 0.10 | 1.11 |
| **1881** | 1.15 | 1.24 | 1.13 | 1.09 | 1.13 | 0.08 | 1.01 |
| **2060** | 1.13 | 1.14 | 1.06 | 1.08 | 0.16 | 0.11 | 1.06 |
| **2061** | 1.15 | 1.32 | 1.08 | 1.09 | 0.20 | 0.10 | 1.04 |
| **2062** | 1.14 | 1.10 | 0.98 | 1.06 | 0.11 | 0.10 | 1.06 |
| **2063** | 1.06 | 1.06 | 1.02 | 1.11 | 0.21 | 0.10 | 1.08 |
| **2064** | 0.95 | 1.09 | 1.03 | 1.21 | 0.17 | 0.09 | 1.00 |
| **2065** | 0.98 | 1.12 | 1.04 | 1.01 | 0.13 | 0.11 | 1.04 |
| **2066** | 0.88 | 1.19 | 1.07 | 0.95 | 0.12 | 0.10 | 0.96 |
| **2067** | 0.89 | 1.09 | 0.99 | 0.94 | 0.91 | 0.90 | 1.00 |
| **2068** | 0.88 | 1.06 | 1.08 | 0.97 | 0.93 | 0.10 | 1.03 |
| **2069** | 0.90 | 1.07 | 1.13 | 1.07 | 0.96 | 0.12 | 1.05 |
| **2070** | 0.93 | 1.19 | 1.20 | 1.08 | 0.12 | 0.10 | 1.06 |
| **2071** | 0.92 | 1.18 | 1.09 | 1.03 | 1.09 | 0.95 | 1.01 |
| **2072** | 0.96 | 1.18 | 0.32 | 1.09 | 0.14 | 0.11 | 1.08 |
| **2073** | 1.04 | 1.21 | 1.04 | 1.09 | 0.29 | 0.11 | 1.06 |
| **2074** | 1.11 | 1.10 | 1.00 | 1.01 | 0.16 | 0.11 | 0.49 |
| **2075** | 1.01 | 1.30 | 1.03 | 1.20 | 0.17 | 0.11 | 1.04 |
| **2076** | 1.07 | 1.05 | 0.24 | 0.77 | 0.12 | 0.10 | 1.01 |
| **2077** | 1.13 | 1.11 | 1.08 | 1.17 | 0.13 | 0.09 | 1.02 |
| **1882** | 1.06 | 1.04 | 1.03 | 1.02 | 0.12 | 0.09 | 1.00 |
| **2078** | 1.08 | 1.05 | 1.06 | 1.11 | 0.14 | 0.09 | 1.03 |
| **2079** | 1.04 | 1.10 | 1.09 | 1.07 | 1.00 | 0.09 | 1.03 |
| **2080** | 1.05 | 1.05 | 1.08 | 1.09 | 0.16 | 0.10 | 1.06 |
| **2081** | 1.05 | 1.06 | 1.08 | 1.11 | 1.02 | 1.10 | 1.08 |
| **2082** | 1.02 | 1.08 | 1.06 | 1.07 | 0.98 | 1.17 | 1.06 |
| **2083** | 1.02 | 1.08 | 1.04 | 1.07 | 0.25 | 0.10 | 1.04 |
| **2084** | 0.97 | 1.09 | 1.06 | 1.01 | 0.14 | 0.09 | 1.05 |
| **2085** | 1.04 | 1.07 | 1.08 | 1.06 | 0.12 | 0.10 | 1.10 |
| **2086** | 1.06 | 0.97 | 1.07 | 0.96 | 0.12 | 0.11 | 1.08 |
| **2087** | 1.03 | 1.21 | 1.22 | 1.05 | 1.12 | 1.12 | 1.03 |

FIGURE 31(continued)

| | | | | | | | |
|---|---|---|---|---|---|---|---|
| 2088 | 1.02 | 1.00 | 0.22 | 0.72 | 0.81 | 0.35 | 0.10 |
| 2089 | 1.05 | 1.03 | 1.22 | 1.02 | 0.91 | 0.98 | 1.04 |
| 2090 | 1.13 | 1.04 | 0.72 | 0.99 | 1.07 | 0.37 | 0.11 |
| 2091 | 1.07 | 1.09 | 1.10 | 1.04 | 0.16 | 0.11 | 1.05 |
| 2092 | 0.89 | 1.01 | 0.18 | 0.11 | 0.99 | 0.58 | 0.10 |
| 2093 | 1.05 | 0.98 | 1.05 | 1.08 | 1.01 | 0.82 | 0.09 |
| 2094 | 1.08 | 1.00 | 0.87 | 1.03 | 0.95 | 0.78 | 0.09 |
| 2095 | 1.09 | 1.08 | 0.24 | 1.08 | 1.02 | 0.11 | 1.07 |
| 2096 | 1.09 | 1.10 | 1.08 | 1.05 | 0.24 | 0.09 | 1.06 |
| 2097 | 0.93 | 1.04 | 1.11 | 1.05 | 0.12 | 0.10 | 1.04 |
| 2098 | 1.13 | 1.05 | 1.07 | 0.94 | 0.18 | 0.10 | 1.06 |
| 2099 | 0.98 | 1.15 | 0.97 | 1.16 | 0.15 | 0.10 | 0.99 |
| 2100 | 1.06 | 1.06 | 1.13 | 1.05 | 0.12 | 0.10 | 1.04 |
| 2101 | 1.07 | 1.09 | 1.09 | 1.07 | 1.15 | 0.71 | 1.09 |
| 2102 | 1.06 | 1.08 | 1.10 | 1.04 | 1.09 | 0.70 | 1.06 |
| 2103 | 1.10 | 1.07 | 1.08 | 1.07 | 0.20 | 0.09 | 1.06 |
| 2104 | 1.06 | 1.09 | 1.10 | 1.05 | 1.16 | 0.75 | 1.07 |
| 1883 | 1.13 | 1.08 | 1.04 | 1.06 | 1.11 | 0.90 | 1.07 |
| 2105 | 1.08 | 1.12 | 1.07 | 1.06 | 1.07 | 0.10 | 1.04 |
| 2106 | 1.13 | 1.11 | 1.07 | 1.11 | 0.13 | 0.09 | 1.05 |
| 2107 | 1.06 | 1.09 | 1.07 | 1.00 | 1.00 | 0.10 | 1.05 |
| 2108 | 1.09 | 1.13 | 1.03 | 1.04 | 1.11 | 1.09 | 1.05 |
| 2109 | 1.22 | 1.23 | 1.06 | 1.04 | 1.10 | 0.13 | 0.09 |
| 2110 | 1.00 | 1.17 | 1.12 | 0.94 | 1.02 | 1.04 | 1.04 |
| 2111 | 1.00 | 1.25 | 0.98 | 1.11 | 0.24 | 0.10 | 1.00 |
| 2112 | 1.00 | 1.14 | 1.07 | 1.01 | 0.99 | 0.92 | 1.01 |
| 2113 | 0.63 | 1.16 | 0.18 | 1.03 | 0.14 | 0.09 | 1.03 |
| 1884 | 1.00 | 1.02 | 1.01 | 0.94 | 1.04 | 0.50 | 0.19 |
| 2114 | 1.03 | 1.13 | 1.07 | 0.48 | 1.02 | 0.54 | 0.09 |
| 2115 | 1.03 | 1.15 | 0.91 | 0.95 | 0.96 | 0.53 | 0.09 |
| 2116 | 1.02 | 1.11 | 1.03 | 0.92 | 1.03 | 0.70 | 0.10 |
| 2117 | 1.06 | 1.10 | 1.02 | 0.98 | 1.07 | 0.60 | 0.13 |
| 2118 | 1.03 | 1.11 | 0.96 | 0.96 | 1.05 | 0.69 | 0.11 |
| 2119 | 1.05 | 1.19 | 0.89 | 0.51 | 1.02 | 0.31 | 0.09 |
| 2120 | 1.07 | 1.12 | 1.01 | 1.08 | 1.05 | 0.12 | 0.10 |
| 2121 | 1.00 | 1.16 | 1.05 | 0.99 | 1.02 | 0.51 | 0.10 |
| 2122 | 1.11 | 1.12 | 0.97 | 0.99 | 1.00 | 0.55 | 0.09 |
| 1885 | 1.13 | 0.96 | 1.05 | 1.12 | 0.11 | 0.10 | 1.04 |

FIGURE 31 (continued)

| | | | | | | | |
|---|---|---|---|---|---|---|---|
| 2123 | 1.05 | 1.13 | 0.18 | 1.04 | 1.17 | 0.44 | 0.09 |
| 2124 | 1.08 | 1.03 | 0.15 | 0.10 | 1.05 | 0.28 | 0.09 |
| 2125 | 1.04 | 1.02 | 0.09 | 0.95 | 1.06 | 0.74 | 0.10 |
| 2126 | 1.04 | 1.12 | 1.07 | 1.08 | 0.13 | 0.10 | 1.03 |
| 2127 | 1.02 | 1.14 | 1.09 | 1.10 | 0.98 | 0.10 | 1.04 |
| 2128 | 1.07 | 1.01 | 0.10 | 1.05 | 1.08 | 0.74 | 0.09 |
| 2129 | 1.06 | 1.04 | 0.10 | 1.08 | 1.07 | 0.32 | 0.09 |
| 2130 | 1.10 | 1.03 | 0.13 | 1.12 | 1.10 | 0.26 | 0.09 |
| 2131 | 1.07 | 1.08 | 0.09 | 1.07 | 1.03 | 0.79 | 0.10 |
| 1886 | 1.02 | 1.06 | 0.95 | 1.13 | 0.17 | 0.08 | 0.92 |
| 2132 | 1.05 | 1.07 | 1.10 | 1.04 | 0.14 | 0.09 | 1.06 |
| 1887 | 0.99 | 1.20 | 1.01 | 1.05 | 0.22 | 0.08 | 0.94 |
| 2133 | 1.09 | 1.12 | 1.13 | 1.20 | 0.12 | 0.11 | 1.11 |
| 2134 | 1.11 | 1.12 | 1.18 | 0.83 | 0.84 | 0.45 | 1.15 |
| 2135 | 1.01 | 1.15 | 1.02 | 1.02 | 0.24 | 0.08 | 1.00 |
| 2136 | 0.93 | 1.02 | 1.07 | 0.95 | 0.09 | 0.10 | 1.01 |
| 2137 | 1.04 | 1.06 | 1.08 | 1.03 | 0.13 | 0.09 | 1.04 |
| 2138 | 1.15 | 1.12 | 0.98 | 1.15 | 1.07 | 1.07 | 0.96 |
| 2139 | 1.06 | 1.09 | 1.14 | 1.09 | 0.12 | 0.09 | 1.11 |
| 2140 | 1.00 | 1.06 | 1.27 | 1.00 | 1.00 | 0.10 | 1.05 |
| 2141 | 0.99 | 1.21 | 1.25 | 1.11 | 0.13 | 0.10 | 1.17 |
| 2142 | 1.08 | 1.14 | 1.19 | 1.12 | 0.14 | 0.10 | 1.11 |
| 2143 | 1.09 | 1.13 | 1.21 | 1.12 | 0.13 | 0.10 | 1.14 |
| 2148 | 1.13 | 1.10 | 0.20 | 1.09 | 0.24 | 0.10 | 1.00 |
| 2149 | 1.07 | 1.12 | 0.95 | 1.08 | 1.05 | 0.97 | 0.95 |
| 2150 | 1.13 | 1.16 | 1.11 | 1.09 | 0.17 | 0.11 | 1.11 |
| 2164 | 1.05 | 1.13 | 0.27 | 1.05 | 0.21 | 0.11 | 1.08 |
| 2165 | 1.04 | 1.12 | 0.16 | 1.11 | 0.20 | 0.10 | 1.14 |
| 2166 | 0.98 | 1.14 | 1.17 | 0.92 | 0.16 | 0.11 | 1.16 |
| 2167 | 1.12 | 1.15 | 0.31 | 1.25 | 0.17 | 0.09 | 1.03 |
| 1888 | 1.18 | 1.17 | 1.07 | 1.16 | 0.11 | 0.08 | 0.98 |
| 2151 | 1.12 | 1.24 | 1.09 | 1.06 | 0.18 | 0.11 | 1.07 |
| 2152 | 1.13 | 1.09 | 0.22 | 1.08 | 0.12 | 0.11 | 1.21 |
| 2153 | 1.12 | 1.06 | 1.03 | 1.06 | 0.17 | 0.11 | 1.01 |
| 2154 | 1.07 | 1.21 | 1.08 | 1.09 | 0.13 | 0.11 | 1.03 |
| 2155 | 1.09 | 1.11 | 0.96 | 1.05 | 0.18 | 0.11 | 1.03 |
| 2156 | 1.11 | 1.12 | 1.11 | 0.98 | 0.21 | 0.09 | 1.34 |
| 2157 | 1.16 | 1.24 | 0.14 | 1.15 | 0.12 | 0.09 | 0.94 |

FIGURE 31 (continued)

| | | | | | | | | |
|---|---|---|---|---|---|---|---|---|
| 2158 | 0.94 | 1.05 | 0.29 | 0.90 | 0.12 | 0.10 | 1.07 | |
| 2159 | 0.90 | 1.11 | 1.10 | 0.99 | 0.11 | 0.12 | 1.09 | |
| 1889 | 1.18 | 1.19 | 1.03 | 1.15 | 0.19 | 0.09 | 0.99 | |
| 2144 | 1.09 | 1.11 | 1.11 | 1.10 | 0.19 | 0.10 | 1.09 | |
| 2145 | 1.10 | 1.10 | 1.17 | 1.13 | 0.12 | 0.10 | 1.12 | |
| 2146 | 1.07 | 1.13 | 0.23 | 1.10 | 0.17 | 0.09 | 1.10 | |
| 2147 | 0.97 | 1.10 | 1.13 | 0.98 | 0.18 | 0.12 | 1.05 | |
| 2160 | 0.99 | 1.11 | 0.18 | 1.10 | 0.21 | 0.12 | 1.11 | |
| 2161 | 1.05 | 1.13 | 0.18 | 1.16 | 0.25 | 0.11 | 1.14 | |
| 2162 | 1.10 | 1.10 | 0.28 | 1.15 | 0.22 | 0.11 | 1.12 | |
| 2163 | 1.04 | 1.16 | 0.27 | 1.08 | 0.30 | 0.11 | 1.19 | |
| 2168 | 0.96 | 1.17 | 0.24 | 0.97 | 0.31 | 0.10 | 0.99 | |
| 1890 | 1.15 | 1.14 | 1.06 | 1.13 | 0.19 | 0.09 | 1.00 | |
| 2169 | 1.13 | 1.16 | 0.46 | 1.11 | 0.18 | 0.12 | 1.09 | |
| 2170 | 1.08 | 1.07 | 0.16 | 1.10 | 0.19 | 0.10 | 1.07 | |
| 2171 | 1.04 | 1.10 | 0.23 | 1.14 | 0.26 | 0.11 | 1.07 | |
| 2172 | 1.06 | 1.10 | 0.20 | 1.19 | 1.04 | 0.11 | 1.10 | |
| 2173 | 1.11 | 1.16 | 0.13 | 1.16 | 0.68 | 0.10 | 1.05 | |
| 2174 | 1.09 | 1.07 | 0.23 | 1.12 | 0.10 | 0.11 | 1.05 | |
| 2175 | 1.05 | 1.08 | 1.06 | 1.12 | 0.19 | 0.10 | 1.10 | |
| 2176 | 1.17 | 1.10 | 1.08 | 1.11 | 1.09 | 0.10 | 1.08 | |
| 2177 | 1.13 | 1.12 | 1.03 | 1.14 | 1.12 | 1.07 | 1.04 | |
| 1879 | 1.28 | 1.07 | 1.04 | 0.68 | 0.13 | 0.08 | 1.14 | |
| 1911 | 1.10 | 0.11 | 1.02 | 1.06 | 1.10 | 0.21 | 0.11 | |
| 1950 | 1.08 | 1.06 | 1.12 | 1.09 | 0.10 | 0.09 | 1.09 | |
| 1951 | 1.33 | 1.00 | 1.02 | 0.80 | 0.78 | 1.05 | 1.00 | |
| 1952 | 0.95 | 1.02 | 1.02 | 0.10 | 0.12 | 0.10 | 0.11 | |
| 1953 | 0.16 | 0.10 | 1.01 | 0.09 | 0.94 | 0.73 | 0.10 | |
| 1954 | 1.03 | 1.10 | 1.00 | 1.08 | 0.11 | 0.09 | 1.02 | |
| 1955 | 0.79 | 0.10 | 1.02 | 0.10 | 0.94 | 0.74 | 0.11 | |
| 1956 | 1.09 | 0.10 | 1.02 | 1.17 | 1.14 | 0.14 | 0.10 | |
| 1957 | 0.99 | 0.99 | 1.14 | 1.06 | 0.15 | 0.10 | 1.12 | |
| 1958 | 1.00 | 1.05 | 1.08 | 1.03 | 0.10 | 0.09 | 1.04 | |
| 1913 | 1.05 | 0.09 | 1.15 | 1.09 | 1.03 | 0.16 | 0.11 | |
| 1968 | 1.09 | 1.14 | 1.07 | 0.11 | 0.14 | 0.10 | 0.11 | |
| 1969 | 1.17 | 1.05 | 1.02 | 1.19 | 1.30 | 0.11 | 1.02 | |
| 1970 | 1.14 | 1.17 | 1.08 | 0.11 | 0.10 | 0.09 | 0.14 | |
| 1971 | 1.07 | 1.10 | 1.00 | 1.08 | 0.13 | 0.08 | 1.06 | |

FIGURE 31 (continued)

| | | | | | | | |
|---|---|---|---|---|---|---|---|
| 1972 | 1.26 | 0.09 | 0.96 | 1.07 | 1.11 | 0.15 | 0.10 |
| 1973 | 1.25 | 0.10 | 1.15 | 0.81 | 1.24 | 0.21 | 0.11 |
| 1974 | 1.16 | 0.10 | 1.05 | 0.94 | 1.10 | 0.14 | 0.10 |
| 1975 | 0.88 | 1.01 | 1.00 | 0.87 | 0.92 | 0.09 | 0.92 |
| 1976 | 0.92 | 1.02 | 0.97 | 0.97 | 0.82 | 0.09 | 1.00 |
| 1891 | 1.16 | 1.12 | 1.03 | 1.16 | 1.13 | 1.02 | 1.12 |
| 1892 | 1.12 | 1.14 | 1.06 | 1.12 | 1.12 | 1.00 | 0.99 |
| 1893 | 1.12 | 1.09 | 1.04 | 1.14 | 0.23 | 0.09 | 1.00 |
| 1894 | 1.16 | 1.02 | 1.05 | 1.15 | 1.16 | 1.04 | 1.12 |
| 1895 | 1.08 | 1.13 | 1.04 | 1.00 | 0.19 | 0.09 | 1.09 |
| 1896 | 1.09 | 1.05 | 1.02 | 1.02 | 0.18 | 0.10 | 1.03 |
| 1897 | 1.11 | 1.03 | 1.05 | 0.37 | 0.17 | 0.10 | 0.99 |
| 1898 | 0.91 | 0.94 | 1.10 | 1.04 | 0.23 | 0.09 | 0.96 |
| 1899 | 1.09 | 1.00 | 1.04 | 0.99 | 1.00 | 0.97 | 1.05 |
| 1990 | 1.00 | 0.09 | 1.05 | 0.30 | 1.00 | 0.09 | 0.09 |
| 1991 | 1.03 | 0.09 | 1.02 | 0.26 | 1.01 | 0.09 | 0.09 |
| 1992 | 1.02 | 0.09 | 1.03 | 0.38 | 1.10 | 0.09 | 0.09 |
| 1993 | 1.13 | 0.10 | 0.92 | 0.11 | 0.10 | 0.10 | 0.08 |
| 1994 | 1.06 | 0.10 | 1.08 | 0.09 | 0.12 | 0.09 | 0.09 |
| 1995 | 1.04 | 0.10 | 1.14 | 0.10 | 0.10 | 0.09 | 0.09 |
| 1996 | 1.04 | 0.09 | 0.09 | 0.09 | 1.01 | 0.09 | 0.09 |
| 1910 | 0.11 | 0.09 | 0.23 | 0.11 | 1.13 | 0.62 | 0.09 |
| 1945 | 1.14 | 1.10 | 1.05 | 0.15 | 0.20 | 0.08 | 0.90 |
| 1946 | 0.10 | 0.23 | 1.04 | 0.10 | 1.10 | 0.89 | 0.09 |
| 1947 | 0.10 | 0.29 | 0.95 | 0.15 | 1.04 | 0.72 | 0.10 |
| 1948 | 0.16 | 0.18 | 0.72 | 0.11 | 1.13 | 0.89 | 0.11 |
| 1949 | 0.17 | 0.09 | 0.22 | 0.11 | 1.09 | 0.53 | 0.09 |
| 1977 | 0.13 | 0.79 | 1.05 | 0.10 | 0.96 | 1.00 | 0.09 |
| 1978 | 0.95 | 0.75 | 1.03 | 0.96 | 1.00 | 0.80 | 0.37 |
| 1979 | 0.95 | 0.70 | 1.06 | 0.85 | 0.98 | 0.78 | 0.32 |
| 1980 | 1.01 | 0.92 | 1.09 | 1.01 | 1.04 | 0.78 | 0.82 |
| 1981 | 0.98 | 0.70 | 1.14 | 0.93 | 0.94 | 0.78 | 0.37 |
| 1982 | 1.05 | 0.90 | 1.09 | 1.03 | 1.11 | 0.94 | 0.34 |
| 1983 | 0.95 | 1.14 | 0.96 | 0.94 | 0.12 | 0.10 | 0.10 |
| 1984 | 1.05 | 0.79 | 1.03 | 1.05 | 1.04 | 0.88 | 0.27 |
| 1985 | 0.11 | 1.00 | 0.98 | 0.09 | 1.02 | 0.85 | 0.09 |
| 1914 | 1.19 | 1.05 | 1.03 | 0.11 | 1.12 | 0.86 | 0.11 |
| 1986 | 1.04 | 0.85 | 1.04 | 0.10 | 1.02 | 0.81 | 0.13 |

FIGURE 31 (continued)

| | | | | | | | |
|---|---|---|---|---|---|---|---|
| **1987** | 1.04 | 0.83 | 1.03 | 0.09 | 1.02 | 0.85 | 0.12 |
| **1988** | 1.03 | 0.58 | 1.07 | 0.09 | 1.01 | 0.88 | 0.13 |
| **1989** | 1.01 | 1.07 | 1.01 | 0.11 | 0.22 | 0.08 | 0.15 |
| **1917** | 1.14 | 0.78 | 1.05 | 1.16 | 1.16 | 0.89 | 0.68 |
| **2015** | 0.99 | 0.46 | 1.08 | 0.10 | 1.04 | 0.89 | 0.10 |
| **2016** | 0.72 | 0.46 | 1.00 | 0.10 | 0.99 | 0.77 | 0.10 |
| **2017** | 1.12 | 0.43 | 0.93 | 0.12 | 1.24 | 0.80 | 0.10 |
| **2018** | 1.10 | 0.40 | 1.07 | 0.12 | 1.19 | 0.77 | 0.11 |
| **2019** | 1.09 | 0.53 | 1.11 | 0.11 | 1.10 | 0.74 | 0.11 |
| **2020** | 1.10 | 0.65 | 1.12 | 0.11 | 1.09 | 0.87 | 0.43 |
| **2021** | 1.08 | 0.50 | 1.10 | 1.09 | 1.08 | 0.79 | 0.36 |
| **2022** | 1.05 | 0.55 | 1.08 | 1.06 | 1.06 | 0.84 | 0.36 |
| **2023** | 1.03 | 1.07 | 1.05 | 1.09 | 1.04 | 0.98 | 0.51 |

FIGURE 31 (continued)

TABLE 21

| NP # | LP48 | LP49 | LP54 | LP56 | LP95 | LP99 | LP101 |
|---|---|---|---|---|---|---|---|
| 1900 | 0.91 | 0.93 | 0.09 | 0.71 | 0.89 | 0.37 | 0.20 |
| 1901 | 0.13 | 0.95 | 0.13 | 1.01 | 0.09 | 0.09 | 0.10 |
| 1902 | 1.00 | 0.88 | 0.12 | 1.04 | 0.70 | 0.09 | 0.13 |
| 1903 | 0.13 | 0.88 | 0.10 | 1.02 | 0.10 | 0.10 | 0.10 |
| 1904 | 0.19 | 0.87 | 0.10 | 0.95 | 0.10 | 0.09 | 0.84 |
| 1905 | 0.18 | 0.94 | 0.10 | 1.01 | 0.11 | 0.09 | 0.90 |
| 1906 | 0.99 | 0.86 | 0.11 | 1.03 | 0.70 | 0.09 | 0.12 |
| 1907 | 0.94 | 0.79 | 0.10 | 0.77 | 0.98 | 0.39 | 0.15 |
| 1908 | 0.13 | 0.97 | 0.11 | 0.95 | 0.09 | 0.09 | 0.16 |
| 1909 | 0.91 | 0.82 | 0.09 | 0.72 | 0.97 | 0.40 | 0.17 |
| 1912 | 1.03 | 0.55 | 0.17 | 0.61 | 0.74 | 0.29 | 0.17 |
| 1959 | 0.14 | 1.01 | 0.22 | 0.93 | 0.09 | 0.08 | 0.10 |
| 1960 | 0.75 | 0.96 | 0.11 | 1.00 | 0.10 | 0.10 | 0.10 |
| 1961 | 0.18 | 0.97 | 0.09 | 0.89 | 0.09 | 0.09 | 0.10 |
| 1962 | 1.22 | 0.58 | 0.09 | 0.48 | 0.63 | 0.17 | 0.27 |
| 1963 | 0.12 | 0.89 | 0.09 | 0.93 | 0.08 | 0.08 | 0.09 |
| 1964 | 0.12 | 1.04 | 0.09 | 0.94 | 0.08 | 0.08 | 0.09 |
| 1965 | 0.12 | 0.92 | 0.09 | 1.02 | 0.09 | 0.08 | 0.09 |
| 1966 | 0.19 | 1.05 | 0.13 | 0.96 | 0.08 | 0.08 | 0.91 |
| 1967 | 0.17 | 1.08 | 0.18 | 1.00 | 0.09 | 0.08 | 0.49 |
| 1915 | 0.09 | 0.92 | 0.09 | 1.26 | 0.12 | 0.09 | 0.09 |
| 1997 | 0.10 | 0.95 | 0.09 | 0.99 | 0.10 | 0.09 | 0.09 |
| 1998 | 0.10 | 0.94 | 0.09 | 1.10 | 0.11 | 0.09 | 0.09 |
| 1999 | 0.11 | 0.94 | 0.09 | 1.11 | 0.10 | 0.09 | 0.10 |
| 2000 | 0.10 | 0.96 | 0.09 | 1.07 | 0.10 | 0.09 | 0.09 |
| 2001 | 0.10 | 0.97 | 0.10 | 1.04 | 0.10 | 0.09 | 0.09 |
| 2002 | 0.21 | 0.95 | 1.08 | 0.89 | 0.12 | 0.09 | 0.17 |
| 2003 | 0.83 | 0.94 | 0.09 | 1.04 | 0.22 | 0.09 | 0.09 |
| 2004 | 0.88 | 1.12 | 0.10 | 1.00 | 1.05 | 0.10 | 0.11 |
| 2005 | 0.92 | 0.90 | 0.10 | 1.07 | 1.08 | 0.12 | 0.11 |
| 1916 | 1.04 | 0.63 | 0.48 | 0.59 | 0.88 | 0.53 | 0.45 |
| 2006 | 0.94 | 0.72 | 0.13 | 0.86 | 0.95 | 0.46 | 0.22 |
| 2007 | 0.23 | 0.96 | 0.11 | 0.51 | 0.12 | 0.09 | 0.11 |
| 2008 | 0.25 | 0.89 | 0.11 | 0.65 | 0.12 | 0.10 | 0.11 |
| 2009 | 0.37 | 0.96 | 0.13 | 0.88 | 0.14 | 0.10 | 0.10 |

FIGURE 32

| | | | | | | | |
|---|---|---|---|---|---|---|---|
| 2010 | 0.82 | 0.72 | 0.12 | 0.86 | 1.24 | 0.59 | 0.20 |
| 2011 | 0.89 | 0.99 | 0.14 | 0.56 | 0.82 | 0.57 | 0.35 |
| 2012 | 0.85 | 0.96 | 0.20 | 0.87 | 0.96 | 0.41 | 0.41 |
| 2013 | 0.99 | 0.93 | 0.16 | 0.89 | 1.03 | 0.88 | 0.40 |
| 2014 | 0.95 | 0.83 | 0.14 | 0.59 | 0.70 | 0.63 | 0.44 |
| 1869 | 0.17 | 0.28 | 0.22 | 0.57 | 0.15 | 0.12 | 0.13 |
| 1840 | 1.00 | 0.99 | 0.85 | 0.85 | 1.05 | 0.48 | 0.26 |
| 1839 | 0.29 | 0.29 | 1.21 | 0.48 | 0.46 | 0.16 | 0.21 |
| 2024 | 0.09 | 0.54 | 1.10 | 0.10 | 0.10 | 0.11 | 0.08 |
| 2025 | 0.10 | 0.79 | 1.14 | 0.11 | 0.11 | 0.10 | 0.08 |
| 2026 | 0.46 | 0.50 | 1.32 | 0.60 | 0.60 | 0.32 | 0.45 |
| 2027 | 0.12 | 0.09 | 1.13 | 0.15 | 0.11 | 0.10 | 0.10 |
| 2028 | 0.10 | 0.10 | 1.07 | 0.10 | 0.09 | 0.09 | 0.11 |
| 2029 | 1.04 | 1.00 | 1.08 | 0.10 | 0.16 | 0.12 | 0.11 |
| 2030 | 0.09 | 0.49 | 1.21 | 0.10 | 0.09 | 0.10 | 0.09 |
| 2031 | 0.09 | 0.62 | 1.04 | 0.09 | 0.09 | 0.09 | 0.09 |
| 2032 | 0.10 | 0.69 | 1.11 | 0.10 | 0.09 | 0.09 | 0.08 |
| 1878 | 0.12 | 0.87 | 1.14 | 0.52 | 0.11 | 0.10 | 0.14 |
| 2033 | 0.10 | 0.72 | 1.10 | 0.10 | 0.10 | 0.11 | 0.09 |
| 2034 | 0.11 | 0.72 | 1.21 | 0.11 | 0.10 | 0.10 | 0.09 |
| 2035 | 0.10 | 0.73 | 1.09 | 0.11 | 0.10 | 0.09 | 0.09 |
| 2036 | 0.09 | 0.50 | 1.10 | 0.10 | 0.10 | 0.09 | 0.08 |
| 2037 | 0.10 | 0.77 | 1.10 | 0.11 | 0.10 | 0.10 | 0.09 |
| 2038 | 0.12 | 1.03 | 1.12 | 0.88 | 0.10 | 0.10 | 0.21 |
| 2039 | 0.11 | 0.88 | 1.03 | 0.15 | 0.10 | 0.10 | 0.12 |
| 2040 | 0.11 | 1.11 | 1.18 | 1.11 | 0.11 | 0.10 | 0.31 |
| 2041 | 0.10 | 0.52 | 1.21 | 0.11 | 0.10 | 0.10 | 0.12 |
| 2042 | 0.09 | 0.96 | 1.08 | 0.91 | 0.09 | 0.10 | 0.46 |
| 2043 | 0.09 | 0.98 | 1.01 | 0.94 | 0.10 | 0.09 | 0.33 |
| 2044 | 0.09 | 0.81 | 1.00 | 0.85 | 0.10 | 0.10 | 0.31 |
| 2045 | 0.10 | 0.86 | 0.35 | 0.57 | 0.10 | 0.10 | 0.21 |
| 2046 | 0.09 | 0.90 | 0.72 | 0.90 | 0.11 | 0.10 | 0.26 |
| 2047 | 0.11 | 1.02 | 1.11 | 0.95 | 0.11 | 0.11 | 0.26 |
| 2048 | 0.20 | 0.60 | 0.33 | 0.57 | 0.19 | 0.11 | 0.19 |
| 2049 | 0.09 | 1.07 | 1.01 | 0.97 | 0.10 | 0.10 | 0.39 |
| 2050 | 0.09 | 1.05 | 0.75 | 0.90 | 0.10 | 0.10 | 0.34 |
| 1880 | 1.13 | 0.87 | 1.16 | 1.01 | 0.73 | 0.10 | 0.94 |
| 2051 | 0.11 | 0.83 | 1.11 | 0.27 | 0.10 | 0.10 | 0.17 |

FIGURE 32 (continued)

| | | | | | | | |
|---|---|---|---|---|---|---|---|
| 2052 | 0.09 | 0.41 | 1.08 | 0.10 | 0.10 | 0.11 | 0.11 |
| 2053 | 0.10 | 0.78 | 1.17 | 1.08 | 0.10 | 0.11 | 0.31 |
| 2054 | 0.11 | 0.12 | 0.99 | 0.13 | 0.10 | 0.10 | 0.15 |
| 2055 | 0.09 | 0.60 | 1.04 | 0.10 | 0.09 | 0.09 | 0.09 |
| 2056 | 0.09 | 0.09 | 1.10 | 0.10 | 0.09 | 0.11 | 0.10 |
| 2057 | 0.10 | 0.94 | 1.09 | 0.56 | 0.10 | 0.10 | 0.21 |
| 2058 | 0.11 | 1.02 | 1.16 | 1.02 | 0.10 | 0.11 | 0.53 |
| 2059 | 0.10 | 0.51 | 1.08 | 0.11 | 0.10 | 0.10 | 0.10 |
| 1881 | 0.91 | 0.78 | 1.11 | 1.11 | 0.96 | 0.10 | 0.85 |
| 2060 | 1.05 | 1.16 | 1.12 | 0.12 | 0.13 | 0.10 | 0.13 |
| 2061 | 0.96 | 1.09 | 1.21 | 0.12 | 0.13 | 0.10 | 0.13 |
| 2062 | 1.05 | 1.03 | 1.14 | 0.12 | 0.13 | 0.11 | 0.13 |
| 2063 | 0.94 | 1.05 | 1.14 | 0.14 | 1.05 | 0.41 | 0.12 |
| 2064 | 0.22 | 0.43 | 1.13 | 0.10 | 0.09 | 0.09 | 0.09 |
| 2065 | 0.98 | 1.10 | 1.13 | 0.12 | 0.13 | 0.12 | 0.13 |
| 2066 | 1.04 | 1.03 | 1.19 | 0.13 | 0.15 | 0.13 | 0.12 |
| 2067 | 1.01 | 1.03 | 1.08 | 1.15 | 1.13 | 0.99 | 1.02 |
| 2068 | 0.90 | 1.06 | 1.16 | 1.18 | 1.17 | 0.11 | 0.96 |
| 2069 | 0.93 | 1.01 | 1.10 | 1.13 | 0.30 | 0.11 | 1.02 |
| 2070 | 0.09 | 0.93 | 1.26 | 0.12 | 0.11 | 0.10 | 0.10 |
| 2071 | 0.85 | 1.01 | 1.19 | 1.21 | 1.12 | 1.09 | 1.03 |
| 2072 | 0.10 | 0.57 | 1.14 | 0.13 | 0.11 | 0.11 | 0.11 |
| 2073 | 0.95 | 0.46 | 1.15 | 1.06 | 1.06 | 0.09 | 0.99 |
| 2074 | 0.08 | 0.69 | 0.99 | 0.11 | 0.10 | 0.12 | 0.11 |
| 2075 | 1.05 | 1.12 | 1.29 | 0.13 | 0.13 | 0.10 | 0.13 |
| 2076 | 0.10 | 0.87 | 1.11 | 1.11 | 0.11 | 0.09 | 0.99 |
| 2077 | 0.09 | 0.75 | 1.14 | 0.12 | 0.11 | 0.09 | 0.09 |
| 1882 | 0.10 | 0.48 | 1.07 | 0.11 | 0.10 | 0.09 | 0.09 |
| 2078 | 1.04 | 1.09 | 1.08 | 0.13 | 0.16 | 0.09 | 0.11 |
| 2079 | 1.07 | 0.89 | 1.14 | 1.17 | 1.16 | 0.14 | 0.89 |
| 2080 | 1.04 | 1.01 | 1.14 | 0.12 | 1.05 | 0.94 | 0.11 |
| 2081 | 1.04 | 0.96 | 1.15 | 1.13 | 1.12 | 0.99 | 0.91 |
| 2082 | 1.09 | 0.98 | 1.13 | 1.11 | 1.10 | 1.08 | 0.95 |
| 2083 | 1.07 | 0.94 | 1.05 | 0.11 | 0.12 | 0.10 | 0.10 |
| 2084 | 1.10 | 0.95 | 1.10 | 0.11 | 0.12 | 0.09 | 0.11 |
| 2085 | 1.07 | 1.03 | 1.14 | 0.12 | 1.07 | 0.98 | 0.11 |
| 2086 | 1.04 | 0.99 | 1.10 | 0.11 | 0.12 | 0.10 | 0.12 |
| 2087 | 1.01 | 0.95 | 1.20 | 0.98 | 1.00 | 1.08 | 1.17 |

FIGURE 32 (continued)

| | | | | | | | |
|---|---|---|---|---|---|---|---|
| **2088** | 0.20 | 0.97 | 0.92 | 0.76 | 0.12 | 0.11 | 0.28 |
| **2089** | 1.10 | 0.92 | 1.08 | 1.16 | 1.11 | 0.95 | 0.98 |
| **2090** | 0.19 | 0.84 | 1.01 | 0.58 | 0.12 | 0.12 | 0.31 |
| **2091** | 1.05 | 0.90 | 1.15 | 0.12 | 0.13 | 0.10 | 0.10 |
| **2092** | 0.10 | 0.92 | 1.08 | 0.92 | 0.10 | 0.09 | 0.35 |
| **2093** | 0.09 | 0.96 | 1.07 | 1.03 | 0.11 | 0.09 | 0.49 |
| **2094** | 0.10 | 0.91 | 1.13 | 1.06 | 0.11 | 0.09 | 0.42 |
| **2095** | 0.13 | 1.02 | 1.09 | 0.14 | 0.12 | 0.13 | 0.11 |
| **2096** | 0.10 | 0.94 | 1.15 | 0.12 | 0.11 | 0.09 | 0.09 |
| **2097** | 0.10 | 0.38 | 1.19 | 0.11 | 0.10 | 0.09 | 0.10 |
| **2098** | 0.09 | 0.82 | 1.14 | 0.10 | 0.10 | 0.09 | 0.11 |
| **2099** | 0.10 | 0.76 | 1.17 | 0.11 | 0.11 | 0.09 | 0.11 |
| **2100** | 1.04 | 0.99 | 1.10 | 0.13 | 1.15 | 0.96 | 0.11 |
| **2101** | 1.05 | 0.96 | 1.18 | 1.22 | 1.22 | 0.93 | 0.85 |
| **2102** | 1.07 | 1.05 | 1.08 | 1.27 | 1.16 | 0.92 | 1.10 |
| **2103** | 1.05 | 1.01 | 1.16 | 0.15 | 1.11 | 0.96 | 0.10 |
| **2104** | 1.10 | 0.83 | 1.09 | 1.25 | 1.22 | 0.96 | 0.92 |
| **1883** | 0.96 | 0.91 | 1.08 | 1.04 | 1.06 | 1.10 | 0.88 |
| **2105** | 1.04 | 1.08 | 1.19 | 1.16 | 1.11 | 0.96 | 1.00 |
| **2106** | 1.12 | 1.10 | 1.08 | 0.14 | 1.06 | 0.10 | 0.10 |
| **2107** | 1.07 | 1.01 | 1.11 | 1.05 | 1.01 | 0.97 | 0.93 |
| **2108** | 1.07 | 1.00 | 1.10 | 1.05 | 1.10 | 0.97 | 1.00 |
| **2109** | 1.05 | 0.94 | 1.23 | 0.65 | 1.09 | 0.10 | 0.11 |
| **2110** | 1.05 | 1.03 | 1.11 | 1.00 | 1.01 | 0.91 | 1.10 |
| **2111** | 0.94 | 0.95 | 1.28 | 0.11 | 0.35 | 0.09 | 0.10 |
| **2112** | 1.01 | 1.00 | 1.19 | 1.15 | 1.09 | 0.93 | 0.97 |
| **2113** | 0.09 | 0.96 | 1.17 | 0.10 | 0.10 | 0.09 | 0.09 |
| **1884** | 0.98 | 0.88 | 0.99 | 0.90 | 1.02 | 0.09 | 0.34 |
| **2114** | 1.02 | 0.97 | 1.14 | 1.01 | 1.05 | 0.09 | 0.36 |
| **2115** | 1.04 | 1.07 | 1.17 | 1.09 | 1.04 | 0.09 | 0.36 |
| **2116** | 1.02 | 1.00 | 1.19 | 1.06 | 1.04 | 0.09 | 0.50 |
| **2117** | 1.08 | 1.08 | 1.16 | 1.00 | 0.87 | 0.09 | 0.32 |
| **2118** | 1.02 | 0.99 | 1.22 | 1.00 | 1.03 | 0.09 | 0.38 |
| **2119** | 1.03 | 1.01 | 1.24 | 0.58 | 0.55 | 0.10 | 0.20 |
| **2120** | 0.97 | 1.01 | 1.16 | 0.66 | 0.99 | 0.10 | 0.11 |
| **2121** | 0.95 | 1.01 | 1.17 | 1.07 | 1.09 | 0.09 | 0.32 |
| **2122** | 0.99 | 1.00 | 1.14 | 0.95 | 1.01 | 0.09 | 0.34 |
| **1885** | 0.09 | 0.72 | 0.94 | 0.10 | 0.10 | 0.09 | 0.09 |

FIGURE 32 (continued)

| | | | | | | | |
|---|---|---|---|---|---|---|---|
| 2123 | 0.09 | 1.03 | 1.08 | 0.95 | 0.09 | 0.09 | 0.31 |
| 2124 | 0.10 | 1.02 | 1.05 | 0.84 | 0.10 | 0.09 | 0.22 |
| 2125 | 0.10 | 0.97 | 0.99 | 0.86 | 0.09 | 0.09 | 0.32 |
| 2126 | 0.11 | 0.95 | 1.14 | 0.26 | 0.10 | 0.10 | 0.16 |
| 2127 | 1.08 | 0.94 | 1.17 | 1.02 | 0.96 | 0.10 | 1.16 |
| 2128 | 0.10 | 0.96 | 0.97 | 1.04 | 0.11 | 0.09 | 0.29 |
| 2129 | 0.10 | 0.95 | 0.98 | 0.95 | 0.10 | 0.09 | 0.30 |
| 2130 | 0.10 | 1.01 | 1.12 | 0.91 | 0.11 | 0.09 | 0.25 |
| 2131 | 0.10 | 1.10 | 1.05 | 1.03 | 0.11 | 0.09 | 0.37 |
| 1886 | 1.06 | 0.97 | 1.00 | 0.11 | 0.97 | 1.06 | 0.10 |
| 2132 | 1.20 | 0.94 | 1.09 | 0.13 | 1.18 | 0.98 | 0.10 |
| 1887 | 1.12 | 0.91 | 1.08 | 0.11 | 0.31 | 0.11 | 0.09 |
| 2133 | 0.11 | 0.65 | 1.15 | 0.12 | 0.10 | 0.11 | 0.11 |
| 2134 | 1.10 | 0.91 | 1.18 | 1.00 | 1.08 | 0.85 | 1.13 |
| 2135 | 0.09 | 0.75 | 1.11 | 0.11 | 0.10 | 0.09 | 0.10 |
| 2136 | 0.09 | 0.91 | 1.15 | 0.11 | 0.10 | 0.09 | 0.10 |
| 2137 | 0.10 | 0.79 | 1.13 | 0.11 | 0.10 | 0.10 | 0.10 |
| 2138 | 0.99 | 0.92 | 1.12 | 1.11 | 1.10 | 0.97 | 1.05 |
| 2139 | 0.10 | 0.56 | 1.09 | 0.14 | 0.11 | 0.10 | 0.10 |
| 2140 | 0.94 | 0.84 | 1.04 | 1.09 | 1.07 | 0.10 | 0.97 |
| 2141 | 0.09 | 0.47 | 1.13 | 0.11 | 0.10 | 0.10 | 0.11 |
| 2142 | 0.98 | 1.00 | 1.19 | 0.12 | 0.85 | 0.10 | 0.11 |
| 2143 | 0.99 | 1.05 | 1.17 | 0.15 | 0.99 | 0.11 | 0.11 |
| 2148 | 0.10 | 0.82 | 1.06 | 0.11 | 0.09 | 0.09 | 0.10 |
| 2149 | 1.06 | 0.99 | 1.04 | 1.01 | 1.02 | 0.95 | 1.00 |
| 2150 | 1.09 | 1.01 | 1.11 | 0.12 | 0.25 | 0.09 | 0.12 |
| 2164 | 0.10 | 0.51 | 1.17 | 0.11 | 0.09 | 0.11 | 0.11 |
| 2165 | 0.10 | 0.77 | 1.21 | 0.10 | 0.09 | 0.10 | 0.11 |
| 2166 | 0.95 | 1.02 | 1.06 | 0.11 | 1.01 | 1.10 | 0.12 |
| 2167 | 0.09 | 0.87 | 1.02 | 0.11 | 0.10 | 0.08 | 0.10 |
| 1888 | 0.98 | 0.95 | 1.12 | 0.11 | 0.18 | 0.12 | 0.09 |
| 2151 | 1.08 | 1.12 | 1.22 | 0.12 | 0.20 | 0.11 | 0.12 |
| 2152 | 0.10 | 1.03 | 1.14 | 0.11 | 0.10 | 0.09 | 0.11 |
| 2153 | 1.06 | 0.90 | 1.02 | 0.11 | 0.15 | 0.12 | 0.11 |
| 2154 | 1.07 | 1.16 | 1.17 | 0.13 | 0.20 | 0.09 | 0.12 |
| 2155 | 1.14 | 1.09 | 1.21 | 0.11 | 0.15 | 0.12 | 0.11 |
| 2156 | 0.10 | 0.87 | 0.95 | 0.11 | 0.10 | 0.10 | 0.10 |
| 2157 | 0.10 | 0.96 | 1.10 | 0.10 | 0.09 | 0.09 | 0.10 |

FIGURE 32 (continued)

| | | | | | | | |
|---|---|---|---|---|---|---|---|
| 2158 | 0.09 | 0.98 | 1.06 | 0.11 | 0.10 | 0.09 | 0.11 |
| 2159 | 1.16 | 1.20 | 1.13 | 0.13 | 0.25 | 0.11 | 0.13 |
| 1889 | 0.10 | 0.63 | 1.08 | 0.10 | 0.09 | 0.11 | 0.10 |
| 2144 | 1.06 | 0.84 | 1.13 | 0.11 | 1.07 | 1.21 | 0.10 |
| 2145 | 0.77 | 0.90 | 1.14 | 1.04 | 0.94 | 0.10 | 0.94 |
| 2146 | 0.10 | 0.88 | 1.13 | 0.12 | 0.10 | 0.09 | 0.11 |
| 2147 | 0.12 | 1.03 | 1.11 | 0.14 | 0.10 | 0.10 | 0.13 |
| 2160 | 0.11 | 1.14 | 0.55 | 0.12 | 0.10 | 0.10 | 0.13 |
| 2161 | 0.10 | 1.06 | 1.17 | 0.11 | 0.10 | 0.10 | 0.11 |
| 2162 | 0.11 | 1.05 | 1.17 | 0.11 | 0.10 | 0.10 | 0.11 |
| 2163 | 0.11 | 1.00 | 1.17 | 0.11 | 0.10 | 0.10 | 0.12 |
| 2168 | 0.10 | 1.03 | 1.10 | 0.11 | 0.10 | 0.08 | 0.11 |
| 1890 | 0.90 | 0.87 | 1.10 | 0.81 | 1.00 | 1.06 | 0.19 |
| 2169 | 0.11 | 1.15 | 1.12 | 0.11 | 0.11 | 0.51 | 0.13 |
| 2170 | 0.10 | 1.01 | 1.16 | 0.38 | 0.11 | 0.09 | 0.18 |
| 2171 | 0.10 | 0.98 | 1.12 | 0.57 | 0.10 | 0.10 | 0.15 |
| 2172 | 0.11 | 0.95 | 1.16 | 1.20 | 0.11 | 0.09 | 1.07 |
| 2173 | 0.11 | 1.11 | 1.26 | 1.11 | 0.10 | 0.09 | 0.98 |
| 2174 | 0.09 | 0.88 | 1.15 | 0.11 | 0.10 | 0.30 | 0.10 |
| 2175 | 1.13 | 1.02 | 1.14 | 0.25 | 1.13 | 0.97 | 0.21 |
| 2176 | 1.09 | 1.05 | 1.15 | 1.09 | 0.75 | 0.09 | 1.05 |
| 2177 | 1.00 | 1.09 | 1.14 | 1.11 | 1.04 | 0.98 | 0.97 |
| 1879 | 0.11 | 0.66 | 1.03 | 0.10 | 0.10 | 0.10 | 0.09 |
| 1911 | 0.99 | 0.68 | 0.11 | 0.37 | 0.50 | 0.13 | 0.14 |
| 1950 | 0.10 | 1.00 | 0.98 | 0.09 | 0.09 | 0.08 | 0.09 |
| 1951 | 1.24 | 1.02 | 0.98 | 0.98 | 0.98 | 0.91 | 1.07 |
| 1952 | 0.10 | 0.97 | 1.00 | 0.09 | 0.09 | 0.09 | 0.10 |
| 1953 | 1.01 | 1.12 | 0.09 | 0.92 | 0.88 | 0.91 | 0.12 |
| 1954 | 0.09 | 0.92 | 1.05 | 0.10 | 0.10 | 0.09 | 0.09 |
| 1955 | 1.07 | 1.08 | 0.10 | 0.78 | 0.83 | 0.77 | 0.12 |
| 1956 | 1.09 | 0.62 | 0.10 | 0.38 | 0.56 | 0.11 | 0.12 |
| 1957 | 0.09 | 1.02 | 1.00 | 0.10 | 0.10 | 0.09 | 0.09 |
| 1958 | 0.09 | 0.98 | 1.07 | 0.09 | 0.09 | 0.09 | 0.09 |
| 1913 | 1.04 | 0.72 | 0.11 | 0.23 | 0.39 | 0.12 | 0.11 |
| 1968 | 0.09 | 0.96 | 1.02 | 0.09 | 0.08 | 0.09 | 0.10 |
| 1969 | 0.10 | 1.03 | 1.04 | 0.96 | 0.08 | 0.09 | 1.05 |
| 1970 | 0.09 | 0.88 | 1.05 | 0.09 | 0.09 | 0.08 | 0.09 |
| 1971 | 0.09 | 0.92 | 1.10 | 0.09 | 0.09 | 0.08 | 0.09 |

FIGURE 32 (continued)

| | | | | | | | |
|---|---|---|---|---|---|---|---|
| 1972 | 1.01 | 0.39 | 0.09 | 0.23 | 0.36 | 0.09 | 0.12 |
| 1973 | 1.20 | 0.70 | 0.09 | 0.45 | 0.40 | 0.10 | 0.19 |
| 1974 | 1.08 | 0.76 | 0.10 | 0.24 | 0.35 | 0.11 | 0.11 |
| 1975 | 0.09 | 0.87 | 1.00 | 1.14 | 0.10 | 0.12 | 0.65 |
| 1976 | 0.09 | 0.87 | 0.97 | 1.03 | 0.09 | 0.08 | 0.92 |
| 1891 | 1.03 | 0.99 | 1.07 | 1.14 | 0.95 | 1.02 | 0.88 |
| 1892 | 0.95 | 0.96 | 1.07 | 1.08 | 0.99 | 1.04 | 0.88 |
| 1893 | 0.90 | 0.90 | 1.06 | 0.11 | 1.00 | 1.04 | 0.09 |
| 1894 | 0.97 | 0.99 | 1.02 | 1.09 | 1.09 | 1.03 | 0.89 |
| 1895 | 0.11 | 0.28 | 1.02 | 0.13 | 0.14 | 0.10 | 0.10 |
| 1896 | 0.10 | 0.25 | 1.00 | 0.11 | 0.10 | 0.11 | 0.10 |
| 1897 | 0.09 | 0.32 | 0.98 | 0.09 | 0.09 | 0.09 | 0.10 |
| 1898 | 0.09 | 0.38 | 0.90 | 0.11 | 0.09 | 0.08 | 0.09 |
| 1899 | 1.00 | 0.96 | 0.98 | 1.04 | 0.94 | 1.05 | 0.96 |
| 1990 | 0.74 | 0.63 | 0.09 | 0.18 | 0.90 | 0.10 | 0.09 |
| 1991 | 0.80 | 0.32 | 0.10 | 0.15 | 0.88 | 0.10 | 0.09 |
| 1992 | 0.80 | 0.37 | 0.10 | 0.17 | 1.05 | 0.10 | 0.09 |
| 1993 | 0.94 | 0.22 | 0.09 | 0.12 | 1.14 | 0.10 | 0.10 |
| 1994 | 0.93 | 0.19 | 0.10 | 0.16 | 1.08 | 0.10 | 0.09 |
| 1995 | 0.94 | 0.27 | 0.10 | 0.14 | 1.18 | 0.10 | 0.09 |
| 1996 | 0.88 | 0.82 | 0.09 | 0.48 | 0.30 | 0.09 | 0.09 |
| 1910 | 0.24 | 0.92 | 0.10 | 1.08 | 0.12 | 0.09 | 0.09 |
| 1945 | 0.09 | 0.15 | 0.73 | 0.14 | 0.12 | 0.09 | 0.09 |
| 1946 | 0.11 | 0.98 | 0.13 | 1.24 | 0.11 | 0.09 | 0.08 |
| 1947 | 0.10 | 0.83 | 0.12 | 1.16 | 0.11 | 0.09 | 0.08 |
| 1948 | 0.92 | 0.94 | 0.30 | 1.21 | 1.28 | 0.97 | 0.09 |
| 1949 | 0.33 | 0.89 | 0.09 | 0.88 | 0.10 | 0.09 | 0.09 |
| 1977 | 0.87 | 0.91 | 0.66 | 1.05 | 0.27 | 0.19 | 0.09 |
| 1978 | 0.90 | 0.88 | 0.43 | 1.10 | 1.15 | 1.10 | 0.79 |
| 1979 | 0.95 | 0.83 | 0.49 | 0.95 | 1.00 | 0.96 | 0.80 |
| 1980 | 1.02 | 0.77 | 0.80 | 1.09 | 1.05 | 1.00 | 0.80 |
| 1981 | 1.03 | 0.85 | 0.49 | 1.03 | 1.06 | 0.92 | 0.78 |
| 1982 | 0.98 | 0.96 | 0.64 | 1.19 | 1.11 | 0.97 | 0.90 |
| 1983 | 0.10 | 0.16 | 1.09 | 0.13 | 0.11 | 0.09 | 0.11 |
| 1984 | 0.97 | 0.94 | 0.48 | 1.08 | 1.10 | 0.83 | 0.81 |
| 1985 | 0.88 | 0.88 | 0.83 | 1.15 | 1.11 | 0.93 | 0.08 |
| 1914 | 0.25 | 0.93 | 1.05 | 1.18 | 0.14 | 0.10 | 0.23 |
| 1986 | 0.27 | 0.94 | 0.53 | 1.18 | 0.15 | 0.10 | 0.28 |

FIGURE 32 (continued)

| | | | | | | | |
|---|---|---|---|---|---|---|---|
| **1987** | 0.26 | 0.94 | 0.59 | 1.13 | 0.14 | 0.10 | 0.31 |
| **1988** | 0.28 | 0.87 | 0.42 | 0.95 | 0.12 | 0.10 | 0.31 |
| **1989** | 0.10 | 0.28 | 1.05 | 0.14 | 0.11 | 0.09 | 0.09 |
| **1917** | 0.95 | 0.92 | 0.50 | 0.86 | 1.01 | 0.70 | 0.80 |
| **2015** | 0.86 | 0.95 | 0.39 | 0.88 | 0.80 | 0.21 | 0.16 |
| **2016** | 0.89 | 0.97 | 0.32 | 1.00 | 0.83 | 0.22 | 0.24 |
| **2017** | 0.97 | 0.77 | 0.29 | 0.97 | 0.85 | 0.23 | 0.19 |
| **2018** | 0.88 | 0.87 | 0.36 | 1.14 | 0.73 | 0.21 | 0.13 |
| **2019** | 1.09 | 0.79 | 0.44 | 1.10 | 0.72 | 0.19 | 0.12 |
| **2020** | 0.84 | 0.88 | 0.59 | 0.95 | 0.22 | 0.15 | 0.78 |
| **2021** | 0.94 | 0.95 | 0.34 | 1.06 | 0.93 | 0.45 | 0.69 |
| **2022** | 0.92 | 0.93 | 0.37 | 1.08 | 1.03 | 0.57 | 0.72 |
| **2023** | 1.04 | 1.05 | 0.99 | 1.15 | 1.10 | 0.18 | 0.97 |

FIGURE 32 (continued)

TABLE 22

| NP # | LP103 | LP106 | LP109 | LP114 | LP124 | LP125 |
|---|---|---|---|---|---|---|
| 1900 | 1.25 | 1.16 | 1.06 | 0.97 | 0.66 | 1.18 |
| 1901 | 0.10 | 0.16 | 0.12 | 0.09 | 0.10 | 1.14 |
| 1902 | 1.14 | 1.20 | 0.13 | 0.10 | 0.36 | 1.17 |
| 1903 | 0.10 | 0.28 | 0.12 | 0.10 | 0.11 | 1.12 |
| 1904 | 0.12 | 0.22 | 0.77 | 0.11 | 0.11 | 1.09 |
| 1905 | 0.11 | 0.23 | 0.95 | 0.11 | 0.11 | 1.14 |
| 1906 | 1.17 | 0.98 | 0.12 | 0.10 | 0.76 | 1.08 |
| 1907 | 1.22 | 1.16 | 1.02 | 0.96 | 0.76 | 1.07 |
| 1908 | 0.10 | 0.11 | 0.12 | 0.09 | 0.10 | 0.73 |
| 1909 | 1.26 | 1.05 | 0.95 | 0.88 | 0.73 | 1.00 |
| 1912 | 1.08 | 1.27 | 1.15 | 1.08 | 0.71 | 1.13 |
| 1959 | 0.09 | 0.10 | 0.09 | 1.00 | 0.09 | 1.06 |
| 1960 | 0.20 | 0.38 | 0.09 | 0.08 | 0.13 | 0.94 |
| 1961 | 0.16 | 0.16 | 0.08 | 0.95 | 0.12 | 1.00 |
| 1962 | 0.91 | 1.21 | 1.01 | 1.15 | 0.25 | 1.06 |
| 1963 | 0.08 | 0.10 | 0.09 | 1.00 | 0.09 | 1.00 |
| 1964 | 0.08 | 0.11 | 0.09 | 1.08 | 0.09 | 1.06 |
| 1965 | 0.08 | 0.10 | 0.08 | 1.03 | 0.09 | 1.01 |
| 1966 | 0.10 | 0.12 | 0.08 | 0.97 | 0.10 | 1.06 |
| 1967 | 0.09 | 0.13 | 0.10 | 1.14 | 0.10 | 1.03 |
| 1915 | 0.09 | 0.23 | 0.09 | 0.12 | 0.10 | 0.10 |
| 1997 | 0.09 | 0.10 | 0.09 | 1.03 | 0.09 | 0.10 |
| 1998 | 0.09 | 0.11 | 0.09 | 1.03 | 0.10 | 0.10 |
| 1999 | 0.09 | 0.10 | 0.09 | 1.00 | 0.09 | 0.11 |
| 2000 | 0.09 | 0.10 | 0.09 | 1.02 | 0.09 | 0.09 |
| 2001 | 0.09 | 0.23 | 0.09 | 1.02 | 0.10 | 0.10 |
| 2002 | 0.10 | 0.12 | 0.09 | 0.97 | 0.10 | 0.77 |
| 2003 | 0.97 | 1.04 | 0.09 | 1.10 | 0.09 | 1.10 |
| 2004 | 1.06 | 1.06 | 0.09 | 0.96 | 0.09 | 1.06 |
| 2005 | 1.12 | 1.17 | 0.09 | 1.10 | 0.10 | 1.02 |
| 1916 | 1.08 | 1.04 | 1.14 | 1.11 | 0.73 | 1.07 |
| 2006 | 0.97 | 0.99 | 0.77 | 1.00 | 0.59 | 1.18 |
| 2007 | 0.14 | 0.23 | 0.10 | 0.10 | 0.11 | 1.11 |
| 2008 | 0.18 | 0.20 | 0.10 | 0.10 | 0.11 | 1.08 |
| 2009 | 0.28 | 0.45 | 0.09 | 0.09 | 0.14 | 1.05 |

FIGURE 33

| | | | | | | |
|---|---|---|---|---|---|---|
| 2010 | 1.24 | 0.84 | 0.74 | 0.98 | 0.57 | 1.13 |
| 2011 | 0.94 | 0.86 | 0.88 | 1.02 | 0.59 | 1.14 |
| 2012 | 1.06 | 1.04 | 0.94 | 1.01 | 0.91 | 1.03 |
| 2013 | 1.06 | 1.04 | 0.92 | 0.98 | 0.89 | 1.03 |
| 2014 | 1.01 | 0.89 | 0.78 | 1.01 | 0.63 | 1.08 |
| 1869 | 0.13 | 0.14 | 0.13 | 0.13 | 0.22 | 0.62 |
| 1840 | 1.19 | 1.08 | 0.16 | 0.13 | 1.02 | 1.10 |
| 1839 | 0.17 | 0.15 | 1.07 | 1.23 | 0.21 | 0.17 |
| 2024 | 0.09 | 0.10 | 1.00 | 1.09 | 0.10 | 0.09 |
| 2025 | 0.09 | 0.18 | 1.04 | 1.14 | 0.09 | 0.09 |
| 2026 | 0.30 | 0.16 | 0.97 | 1.05 | 0.26 | 0.32 |
| 2027 | 0.10 | 0.20 | 1.09 | 1.11 | 0.09 | 0.09 |
| 2028 | 0.09 | 0.15 | 0.97 | 0.95 | 0.09 | 0.09 |
| 2029 | 0.47 | 0.29 | 1.11 | 0.99 | 0.15 | 0.11 |
| 2030 | 0.09 | 0.24 | 0.90 | 0.96 | 0.10 | 0.10 |
| 2031 | 0.08 | 0.11 | 0.92 | 0.91 | 0.10 | 0.10 |
| 2032 | 0.09 | 0.19 | 1.05 | 0.93 | 0.09 | 0.10 |
| 1878 | 0.10 | 0.11 | 0.95 | 0.98 | 0.11 | 0.11 |
| 2033 | 0.10 | 0.10 | 1.15 | 0.97 | 0.10 | 0.10 |
| 2034 | 0.09 | 0.15 | 0.95 | 0.99 | 0.10 | 0.12 |
| 2035 | 0.09 | 0.12 | 1.08 | 0.93 | 0.10 | 0.11 |
| 2036 | 0.09 | 0.15 | 1.14 | 0.95 | 0.09 | 0.11 |
| 2037 | 0.09 | 0.10 | 1.09 | 0.94 | 0.10 | 0.10 |
| 2038 | 0.09 | 0.28 | 0.96 | 0.91 | 0.09 | 0.10 |
| 2039 | 0.09 | 0.23 | 1.07 | 0.94 | 0.09 | 0.10 |
| 2040 | 0.09 | 0.12 | 0.90 | 1.07 | 0.10 | 0.11 |
| 2041 | 0.10 | 0.16 | 1.14 | 0.99 | 0.10 | 0.10 |
| 2042 | 0.09 | 0.16 | 0.91 | 0.98 | 0.10 | 0.10 |
| 2043 | 0.09 | 0.10 | 0.89 | 0.99 | 0.09 | 0.09 |
| 2044 | 0.09 | 0.14 | 1.01 | 1.03 | 0.09 | 0.10 |
| 2045 | 0.10 | 0.11 | 0.75 | 0.93 | 0.13 | 0.10 |
| 2046 | 0.09 | 0.10 | 0.94 | 1.08 | 0.10 | 0.09 |
| 2047 | 0.11 | 0.11 | 0.96 | 0.91 | 0.11 | 0.12 |
| 2048 | 0.10 | 0.10 | 0.30 | 0.95 | 0.13 | 0.12 |
| 2049 | 0.09 | 0.15 | 1.03 | 0.93 | 0.09 | 0.09 |
| 2050 | 0.10 | 0.13 | 0.98 | 0.90 | 0.10 | 0.10 |
| 1880 | 1.26 | 1.16 | 0.98 | 1.03 | 1.07 | 1.12 |
| 2051 | 0.10 | 0.11 | 0.98 | 0.91 | 0.10 | 0.10 |

FIGURE 33 (continued)

| | | | | | | |
|---|---|---|---|---|---|---|
| 2052 | 0.10 | 0.24 | 0.98 | 0.86 | 0.10 | 0.10 |
| 2053 | 0.11 | 0.34 | 1.12 | 1.07 | 0.10 | 0.10 |
| 2054 | 0.10 | 0.13 | 1.07 | 1.10 | 0.11 | 0.11 |
| 2055 | 0.09 | 0.23 | 1.02 | 1.15 | 0.09 | 0.09 |
| 2056 | 0.10 | 0.17 | 1.03 | 0.99 | 0.09 | 0.10 |
| 2057 | 0.10 | 0.11 | 1.03 | 0.98 | 0.09 | 0.10 |
| 2058 | 0.11 | 0.11 | 1.00 | 0.96 | 0.10 | 0.10 |
| 2059 | 0.10 | 0.16 | 1.10 | 1.09 | 0.10 | 0.22 |
| 1881 | 1.23 | 1.16 | 0.93 | 0.97 | 1.06 | 1.20 |
| 2060 | 0.51 | 0.19 | 1.07 | 1.04 | 0.14 | 0.11 |
| 2061 | 0.25 | 0.23 | 1.08 | 1.03 | 0.14 | 0.26 |
| 2062 | 0.28 | 0.18 | 1.06 | 1.25 | 0.13 | 0.12 |
| 2063 | 0.99 | 0.87 | 1.05 | 1.16 | 1.06 | 0.96 |
| 2064 | 0.14 | 0.30 | 1.05 | 1.24 | 0.09 | 0.09 |
| 2065 | 0.42 | 0.15 | 1.07 | 1.02 | 0.14 | 0.11 |
| 2066 | 0.38 | 0.11 | 1.00 | 1.11 | 0.17 | 0.10 |
| 2067 | 1.14 | 1.08 | 0.96 | 1.10 | 1.10 | 0.94 |
| 2068 | 0.98 | 1.17 | 1.03 | 1.12 | 1.17 | 0.97 |
| 2069 | 0.70 | 0.25 | 1.08 | 1.33 | 0.36 | 0.11 |
| 2070 | 0.09 | 0.20 | 1.12 | 1.21 | 0.11 | 0.11 |
| 2071 | 0.93 | 0.92 | 1.06 | 0.94 | 1.05 | 0.97 |
| 2072 | 0.11 | 0.16 | 1.07 | 0.96 | 0.11 | 0.10 |
| 2073 | 0.90 | 0.20 | 1.14 | 0.89 | 1.09 | 0.31 |
| 2074 | 0.11 | 0.12 | 1.13 | 0.57 | 0.09 | 0.11 |
| 2075 | 0.23 | 0.24 | 1.13 | 1.14 | 0.15 | 0.13 |
| 2076 | 0.08 | 0.21 | 0.96 | 1.04 | 0.09 | 0.10 |
| 2077 | 0.09 | 0.11 | 0.97 | 1.01 | 0.10 | 0.10 |
| 1882 | 0.09 | 0.10 | 0.99 | 0.97 | 0.10 | 0.10 |
| 2078 | 0.19 | 0.16 | 1.10 | 1.02 | 0.15 | 0.13 |
| 2079 | 0.94 | 1.03 | 1.02 | 1.08 | 1.11 | 1.07 |
| 2080 | 0.93 | 1.03 | 1.04 | 1.06 | 1.03 | 1.07 |
| 2081 | 0.96 | 1.02 | 0.94 | 0.99 | 1.02 | 1.02 |
| 2082 | 1.03 | 0.99 | 1.01 | 1.07 | 1.09 | 0.98 |
| 2083 | 0.15 | 0.12 | 1.05 | 1.09 | 0.13 | 0.09 |
| 2084 | 0.16 | 0.10 | 1.05 | 1.04 | 0.13 | 0.14 |
| 2085 | 1.00 | 1.09 | 1.09 | 1.20 | 1.10 | 0.97 |
| 2086 | 0.17 | 0.14 | 1.12 | 1.19 | 0.11 | 0.21 |
| 2087 | 1.16 | 1.11 | 1.13 | 1.18 | 1.08 | 0.11 |

FIGURE 33 (continued)

| | | | | | | |
|---|---|---|---|---|---|---|
| **2088** | 0.12 | 0.16 | 0.96 | 1.07 | 0.13 | 0.17 |
| **2089** | 1.03 | 0.95 | 0.97 | 1.09 | 1.12 | 1.01 |
| **2090** | 0.12 | 0.14 | 1.10 | 1.04 | 0.12 | 0.12 |
| **2091** | 0.13 | 0.23 | 1.02 | 1.06 | 0.15 | 0.10 |
| **2092** | 0.08 | 0.10 | 1.04 | 1.07 | 0.09 | 0.10 |
| **2093** | 0.08 | 0.09 | 0.94 | 1.05 | 0.09 | 0.10 |
| **2094** | 0.08 | 0.09 | 1.01 | 1.05 | 0.09 | 0.09 |
| **2095** | 0.11 | 0.86 | 1.05 | 1.05 | 0.11 | 0.10 |
| **2096** | 0.09 | 0.19 | 1.05 | 1.19 | 0.09 | 0.09 |
| **2097** | 0.09 | 0.13 | 1.09 | 1.07 | 0.09 | 0.09 |
| **2098** | 0.09 | 0.12 | 1.12 | 1.13 | 0.09 | 0.10 |
| **2099** | 0.09 | 0.28 | 1.12 | 1.07 | 0.10 | 0.09 |
| **2100** | 1.07 | 1.07 | 1.08 | 1.08 | 1.10 | 1.09 |
| **2101** | 0.97 | 1.07 | 1.02 | 1.14 | 1.06 | 1.10 |
| **2102** | 0.97 | 0.97 | 0.96 | 1.07 | 1.11 | 1.02 |
| **2103** | 1.00 | 1.04 | 1.11 | 1.07 | 1.12 | 0.99 |
| **2104** | 0.99 | 1.03 | 0.95 | 1.15 | 1.14 | 1.08 |
| **1883** | 1.22 | 1.13 | 1.00 | 0.96 | 1.02 | 1.06 |
| **2105** | 1.02 | 1.06 | 0.99 | 1.15 | 1.18 | 0.94 |
| **2106** | 1.00 | 0.67 | 1.14 | 1.15 | 1.00 | 0.12 |
| **2107** | 0.98 | 1.02 | 1.02 | 1.25 | 1.11 | 0.92 |
| **2108** | 1.12 | 1.03 | 0.96 | 1.15 | 1.05 | 1.10 |
| **2109** | 0.92 | 1.04 | 1.06 | 1.16 | 1.10 | 0.93 |
| **2110** | 0.97 | 1.14 | 1.17 | 1.15 | 1.11 | 0.94 |
| **2111** | 1.05 | 0.37 | 1.05 | 1.12 | 0.34 | 0.12 |
| **2112** | 1.02 | 0.99 | 1.13 | 1.14 | 1.12 | 1.15 |
| **2113** | 0.08 | 0.09 | 1.07 | 1.10 | 0.10 | 0.10 |
| **1884** | 1.12 | 1.01 | 1.12 | 0.93 | 0.98 | 1.05 |
| **2114** | 0.97 | 0.92 | 1.01 | 1.20 | 1.06 | 1.09 |
| **2115** | 0.98 | 0.99 | 1.12 | 1.18 | 1.08 | 1.09 |
| **2116** | 1.13 | 0.87 | 1.00 | 1.15 | 1.10 | 1.14 |
| **2117** | 1.03 | 1.01 | 0.96 | 1.12 | 1.03 | 1.04 |
| **2118** | 1.06 | 1.05 | 1.03 | 1.11 | 1.13 | 1.01 |
| **2119** | 1.11 | 1.00 | 1.07 | 1.10 | 1.15 | 0.97 |
| **2120** | 0.99 | 1.05 | 1.02 | 1.18 | 1.04 | 0.95 |
| **2121** | 0.97 | 0.96 | 1.02 | 1.09 | 1.11 | 1.03 |
| **2122** | 0.86 | 1.09 | 1.21 | 1.13 | 1.12 | 0.92 |
| **1885** | 0.10 | 0.16 | 1.06 | 0.96 | 0.09 | 0.09 |

FIGURE 33 (continued)

| | | | | | | |
|---|---|---|---|---|---|---|
| 2123 | 0.09 | 0.12 | 1.01 | 0.98 | 0.09 | 0.09 |
| 2124 | 0.09 | 0.10 | 1.03 | 1.17 | 0.09 | 0.10 |
| 2125 | 0.09 | 0.09 | 1.03 | 0.15 | 0.09 | 0.10 |
| 2126 | 0.09 | 0.15 | 1.04 | 1.13 | 0.10 | 0.09 |
| 2127 | 1.03 | 1.03 | 1.03 | 1.14 | 1.01 | 0.97 |
| 2128 | 0.09 | 0.09 | 1.00 | 0.14 | 0.09 | 0.09 |
| 2129 | 0.09 | 0.14 | 1.01 | 0.17 | 0.09 | 0.11 |
| 2130 | 0.09 | 0.19 | 1.00 | 1.16 | 0.10 | 0.11 |
| 2131 | 0.09 | 0.13 | 1.02 | 0.14 | 0.09 | 0.10 |
| 1886 | 0.98 | 1.14 | 0.94 | 1.13 | 1.00 | 1.05 |
| 2132 | 0.92 | 1.05 | 1.04 | 1.10 | 1.01 | 1.04 |
| 1887 | 1.14 | 0.12 | 0.93 | 0.92 | 0.36 | 0.10 |
| 2133 | 0.10 | 0.18 | 1.02 | 1.03 | 0.10 | 0.09 |
| 2134 | 0.88 | 0.85 | 1.01 | 1.26 | 1.11 | 0.89 |
| 2135 | 0.09 | 0.16 | 1.05 | 1.15 | 0.09 | 0.09 |
| 2136 | 0.09 | 0.13 | 0.11 | 1.02 | 0.09 | 0.08 |
| 2137 | 0.09 | 0.16 | 1.21 | 1.20 | 0.10 | 0.09 |
| 2138 | 0.97 | 1.14 | 1.04 | 1.20 | 1.03 | 0.97 |
| 2139 | 0.10 | 0.27 | 1.03 | 1.17 | 0.10 | 0.09 |
| 2140 | 0.86 | 0.18 | 1.08 | 1.09 | 0.54 | 0.17 |
| 2141 | 0.09 | 0.16 | 1.18 | 1.25 | 0.10 | 0.09 |
| 2142 | 1.00 | 0.13 | 1.05 | 1.19 | 1.03 | 0.10 |
| 2143 | 1.06 | 0.50 | 1.03 | 1.32 | 0.98 | 0.15 |
| 2148 | 0.09 | 0.23 | 1.13 | 1.09 | 0.10 | 0.10 |
| 2149 | 0.92 | 1.07 | 1.08 | 1.00 | 0.96 | 1.06 |
| 2150 | 0.78 | 0.32 | 0.99 | 1.11 | 0.60 | 0.19 |
| 2164 | 0.10 | 0.20 | 1.07 | 1.20 | 0.10 | 0.09 |
| 2165 | 0.10 | 0.15 | 0.97 | 1.27 | 0.10 | 0.08 |
| 2166 | 1.12 | 0.93 | 1.03 | 1.37 | 1.06 | 1.03 |
| 2167 | 0.08 | 0.11 | 1.04 | 1.09 | 0.10 | 0.10 |
| 1888 | 1.13 | 0.12 | 1.02 | 0.97 | 0.19 | 0.11 |
| 2151 | 0.92 | 0.15 | 1.15 | 1.09 | 0.54 | 0.11 |
| 2152 | 0.09 | 0.11 | 1.11 | 1.18 | 0.10 | 0.11 |
| 2153 | 0.44 | 0.23 | 1.22 | 1.07 | 0.14 | 0.10 |
| 2154 | 0.90 | 0.25 | 1.39 | 1.12 | 0.22 | 0.11 |
| 2155 | 0.44 | 0.13 | 1.20 | 1.05 | 0.15 | 0.12 |
| 2156 | 0.10 | 0.12 | 1.16 | 1.06 | 0.09 | 0.09 |
| 2157 | 0.09 | 0.11 | 1.17 | 1.20 | 0.09 | 0.09 |

FIGURE 33 (continued)

| | | | | | | |
|---|---|---|---|---|---|---|
| 2158 | 0.09 | 0.14 | 1.22 | 1.17 | 0.09 | 0.09 |
| 2159 | 1.05 | 0.20 | 1.00 | 1.09 | 0.21 | 0.13 |
| 1889 | 0.10 | 0.18 | 0.99 | 0.97 | 0.10 | 0.11 |
| 2144 | 1.18 | 1.14 | 1.22 | 1.21 | 1.11 | 0.99 |
| 2145 | 0.11 | 0.85 | 1.02 | 1.26 | 0.71 | 0.10 |
| 2146 | 0.09 | 0.14 | 1.15 | 1.16 | 0.10 | 0.09 |
| 2147 | 0.11 | 0.23 | 1.10 | 1.15 | 0.10 | 0.11 |
| 2160 | 0.11 | 0.18 | 1.05 | 1.08 | 0.10 | 0.09 |
| 2161 | 0.10 | 0.28 | 1.05 | 1.15 | 0.10 | 0.10 |
| 2162 | 0.10 | 0.23 | 1.03 | 1.20 | 0.10 | 0.09 |
| 2163 | 0.10 | 0.19 | 1.07 | 1.22 | 0.10 | 0.10 |
| 2168 | 0.08 | 0.41 | 1.05 | 1.06 | 0.10 | 0.09 |
| 1890 | 1.20 | 1.10 | 1.00 | 0.97 | 1.04 | 1.13 |
| 2169 | 0.50 | 0.11 | 1.64 | 1.19 | 0.10 | 0.10 |
| 2170 | 0.08 | 0.16 | 1.09 | 1.08 | 0.10 | 0.09 |
| 2171 | 0.10 | 0.30 | 1.13 | 1.12 | 0.10 | 0.09 |
| 2172 | 0.10 | 0.13 | 1.12 | 1.06 | 0.10 | 0.09 |
| 2173 | 0.09 | 0.11 | 1.06 | 1.04 | 0.11 | 0.09 |
| 2174 | 0.31 | 0.13 | 1.04 | 1.02 | 0.09 | 0.09 |
| 2175 | 0.90 | 1.21 | 1.04 | 1.15 | 1.14 | 0.89 |
| 2176 | 0.84 | 0.43 | 1.15 | 1.13 | 0.65 | 0.14 |
| 2177 | 1.00 | 1.14 | 1.02 | 1.03 | 1.12 | 0.95 |
| 1879 | 0.10 | 0.43 | 0.99 | 1.01 | 0.10 | 0.12 |
| 1911 | 1.18 | 1.03 | 1.06 | 1.09 | 0.27 | 1.13 |
| 1950 | 0.08 | 0.15 | 1.01 | 1.18 | 0.09 | 0.08 |
| 1951 | 0.89 | 0.91 | 1.00 | 1.02 | 1.07 | 0.09 |
| 1952 | 0.09 | 0.12 | 0.38 | 0.17 | 0.09 | 0.09 |
| 1953 | 1.11 | 1.00 | 0.14 | 0.09 | 0.76 | 0.97 |
| 1954 | 0.09 | 0.14 | 0.92 | 0.98 | 0.09 | 0.09 |
| 1955 | 1.09 | 0.10 | 0.14 | 0.09 | 0.74 | 1.01 |
| 1956 | 1.10 | 0.95 | 0.90 | 1.02 | 0.16 | 0.98 |
| 1957 | 0.09 | 0.23 | 1.18 | 1.04 | 0.09 | 0.09 |
| 1958 | 0.09 | 0.14 | 1.03 | 1.07 | 0.09 | 0.09 |
| 1913 | 1.23 | 0.98 | 0.91 | 1.07 | 0.45 | 1.00 |
| 1968 | 0.09 | 0.14 | 0.26 | 0.15 | 0.09 | 0.10 |
| 1969 | 0.09 | 0.14 | 1.16 | 1.02 | 0.10 | 0.10 |
| 1970 | 0.08 | 0.15 | 0.12 | 0.17 | 0.09 | 0.10 |
| 1971 | 0.07 | 0.13 | 1.16 | 0.98 | 0.09 | 0.09 |

FIGURE 33 (continued)

| | | | | | | |
|---|---|---|---|---|---|---|
| 1972 | 0.89 | 0.34 | 0.93 | 0.94 | 0.13 | 1.00 |
| 1973 | 1.14 | 0.30 | 0.65 | 1.02 | 0.17 | 1.01 |
| 1974 | 0.98 | 0.96 | 0.76 | 0.82 | 0.15 | 1.05 |
| 1975 | 0.11 | 0.13 | 0.95 | 0.85 | 0.09 | 0.10 |
| 1976 | 0.08 | 0.27 | 0.83 | 0.85 | 0.09 | 0.10 |
| 1891 | 1.07 | 1.13 | 1.02 | 1.06 | 1.04 | 1.12 |
| 1892 | 1.12 | 1.13 | 1.17 | 1.02 | 1.03 | 1.06 |
| 1893 | 1.11 | 1.11 | 1.19 | 0.96 | 1.02 | 1.12 |
| 1894 | 1.13 | 1.14 | 1.04 | 1.01 | 1.05 | 1.03 |
| 1895 | 0.10 | 0.15 | 1.09 | 1.00 | 0.11 | 0.11 |
| 1896 | 0.11 | 0.14 | 1.13 | 1.03 | 0.11 | 0.10 |
| 1897 | 0.08 | 0.12 | 1.01 | 1.04 | 0.09 | 0.09 |
| 1898 | 0.08 | 0.23 | 0.97 | 1.00 | 0.08 | 0.10 |
| 1899 | 1.14 | 1.03 | 1.00 | 0.99 | 0.97 | 1.20 |
| 1990 | 0.94 | 1.01 | 0.95 | 0.90 | 0.46 | 1.00 |
| 1991 | 0.96 | 0.97 | 0.99 | 0.91 | 0.40 | 1.03 |
| 1992 | 0.92 | 1.08 | 0.82 | 0.94 | 0.36 | 1.03 |
| 1993 | 1.02 | 1.11 | 0.86 | 1.01 | 0.11 | 0.95 |
| 1994 | 1.13 | 0.98 | 1.05 | 0.98 | 0.10 | 1.08 |
| 1995 | 1.10 | 1.03 | 0.84 | 0.97 | 0.10 | 1.09 |
| 1996 | 0.76 | 0.14 | 0.09 | 0.09 | 0.20 | 1.07 |
| 1910 | 0.14 | 0.36 | 0.09 | 0.09 | 0.09 | 1.14 |
| 1945 | 0.09 | 0.19 | 0.97 | 1.04 | 0.09 | 0.10 |
| 1946 | 0.10 | 0.13 | 0.09 | 0.09 | 0.09 | 1.14 |
| 1947 | 0.09 | 0.10 | 0.10 | 0.10 | 0.10 | 1.14 |
| 1948 | 1.09 | 1.19 | 0.09 | 0.09 | 0.59 | 1.07 |
| 1949 | 0.15 | 0.70 | 0.09 | 0.09 | 0.11 | 1.07 |
| 1977 | 0.89 | 0.56 | 0.69 | 0.09 | 0.34 | 1.04 |
| 1978 | 1.12 | 1.15 | 0.99 | 0.90 | 1.03 | 1.06 |
| 1979 | 1.11 | 1.09 | 1.01 | 0.85 | 0.99 | 1.05 |
| 1980 | 1.00 | 1.18 | 0.94 | 1.01 | 1.01 | 1.08 |
| 1981 | 0.95 | 1.09 | 1.08 | 1.12 | 0.96 | 0.98 |
| 1982 | 1.07 | 1.19 | 1.08 | 1.10 | 1.08 | 1.02 |
| 1983 | 0.09 | 0.14 | 0.88 | 0.11 | 0.09 | 0.10 |
| 1984 | 1.05 | 1.07 | 0.83 | 1.02 | 0.98 | 1.03 |
| 1985 | 1.04 | 1.04 | 0.34 | 0.09 | 1.02 | 1.03 |
| 1914 | 0.17 | 0.16 | 0.09 | 0.12 | 0.16 | 1.16 |
| 1986 | 0.16 | 0.11 | 0.09 | 0.12 | 0.14 | 1.03 |

FIGURE 33 (continued)

| | | | | | | |
|---|---|---|---|---|---|---|
| 1987 | 0.15 | 0.12 | 0.09 | 0.11 | 0.12 | 1.06 |
| 1988 | 0.16 | 0.11 | 0.09 | 0.12 | 0.12 | 1.01 |
| 1989 | 0.09 | 0.15 | 0.12 | 0.31 | 0.10 | 0.09 |
| 1917 | 1.17 | 1.15 | 1.02 | 1.03 | 1.03 | 1.04 |
| 2015 | 0.98 | 0.98 | 0.12 | 0.10 | 0.83 | 1.02 |
| 2016 | 1.00 | 0.96 | 0.13 | 0.10 | 0.83 | 1.05 |
| 2017 | 0.97 | 1.11 | 0.14 | 0.10 | 0.81 | 0.98 |
| 2018 | 1.01 | 1.25 | 0.15 | 0.11 | 0.85 | 0.98 |
| 2019 | 1.05 | 1.05 | 0.13 | 0.11 | 0.94 | 0.98 |
| 2020 | 0.69 | 0.78 | 1.09 | 1.21 | 0.30 | 0.99 |
| 2021 | 1.05 | 1.10 | 1.05 | 1.19 | 0.96 | 1.06 |
| 2022 | 1.10 | 1.06 | 1.06 | 1.14 | 0.96 | 0.98 |
| 2023 | 1.10 | 1.03 | 1.01 | 0.99 | 1.11 | 0.95 |

FIGURE 33(continued)

TABLE 23

| NP # | LP128 | LP129 | LP141 | LP143 | LP177 |
|---|---|---|---|---|---|
| 1900 | 0.54 | 1.01 | 1.10 | 0.30 | 0.79 |
| 1901 | 0.10 | 0.09 | 0.10 | 0.10 | 0.09 |
| 1902 | 0.10 | 0.09 | 0.10 | 0.36 | 0.55 |
| 1903 | 0.10 | 0.09 | 0.11 | 0.10 | 0.10 |
| 1904 | 0.10 | 0.10 | 0.10 | 0.11 | 0.10 |
| 1905 | 0.10 | 0.10 | 0.11 | 0.10 | 0.10 |
| 1906 | 0.09 | 0.10 | 0.10 | 0.20 | 0.48 |
| 1907 | 0.55 | 1.11 | 1.02 | 0.28 | 0.64 |
| 1908 | 0.09 | 0.09 | 0.11 | 0.11 | 0.09 |
| 1909 | 0.53 | 1.26 | 1.11 | 0.17 | 0.76 |
| 1912 | 0.56 | 0.75 | 1.10 | 0.62 | 0.61 |
| 1959 | 0.60 | 0.96 | 0.84 | 0.09 | 0.09 |
| 1960 | 0.09 | 0.09 | 0.10 | 0.11 | 0.10 |
| 1961 | 0.48 | 0.96 | 0.95 | 0.12 | 0.09 |
| 1962 | 0.44 | 0.62 | 0.85 | 0.12 | 0.52 |
| 1963 | 0.61 | 0.91 | 0.86 | 0.09 | 0.08 |
| 1964 | 0.72 | 0.97 | 0.95 | 0.09 | 0.08 |
| 1965 | 0.47 | 0.92 | 0.93 | 0.09 | 0.08 |
| 1966 | 0.63 | 0.79 | 0.98 | 0.09 | 0.08 |
| 1967 | 0.45 | 0.95 | 0.89 | 0.09 | 0.09 |
| 1915 | 0.67 | 0.75 | 1.04 | 0.09 | 0.12 |
| 1997 | 0.64 | 0.84 | 1.07 | 0.09 | 0.10 |
| 1998 | 0.76 | 0.95 | 0.74 | 0.09 | 0.11 |
| 1999 | 0.98 | 0.90 | 0.95 | 0.09 | 0.10 |
| 2000 | 0.77 | 1.02 | 0.94 | 0.09 | 0.10 |
| 2001 | 0.59 | 0.85 | 0.97 | 0.10 | 0.11 |
| 2002 | 0.59 | 1.07 | 1.14 | 0.11 | 0.11 |
| 2003 | 0.57 | 1.00 | 1.04 | 0.10 | 1.01 |
| 2004 | 0.54 | 0.36 | 1.16 | 0.10 | 0.23 |
| 2005 | 0.45 | 0.99 | 1.18 | 0.11 | 1.08 |
| 1916 | 0.16 | 0.65 | 0.16 | 0.68 | 0.72 |
| 2006 | 0.20 | 0.53 | 0.29 | 0.39 | 0.78 |
| 2007 | 0.11 | 0.09 | 0.10 | 0.11 | 0.13 |
| 2008 | 0.11 | 0.09 | 0.10 | 0.11 | 0.13 |
| 2009 | 0.10 | 0.09 | 0.28 | 0.12 | 0.13 |

FIGURE 34

| | | | | | |
|---|---|---|---|---|---|
| 2010 | 0.20 | 0.79 | 0.66 | 0.30 | 0.90 |
| 2011 | 0.14 | 0.65 | 0.46 | 0.44 | 0.56 |
| 2012 | 0.79 | 1.11 | 1.14 | 0.43 | 0.81 |
| 2013 | 0.86 | 1.02 | 1.10 | 0.44 | 0.89 |
| 2014 | 0.13 | 0.84 | 0.25 | 0.43 | 0.51 |
| 1869 | 0.15 | 0.12 | 0.13 | 0.22 | 0.14 |
| 1840 | 0.10 | 0.10 | 0.11 | 1.06 | 1.10 |
| 1839 | 1.21 | 0.98 | 1.28 | 0.18 | 0.47 |
| 2024 | 1.06 | 1.09 | 1.07 | 0.10 | 0.10 |
| 2025 | 1.13 | 1.18 | 1.07 | 0.09 | 0.11 |
| 2026 | 1.10 | 0.72 | 1.02 | 0.28 | 0.61 |
| 2027 | 1.09 | 1.09 | 1.06 | 0.10 | 0.11 |
| 2028 | 1.02 | 1.01 | 1.02 | 0.10 | 0.09 |
| 2029 | 1.04 | 1.11 | 1.12 | 0.20 | 0.14 |
| 2030 | 1.01 | 1.01 | 1.06 | 0.10 | 0.09 |
| 2031 | 1.00 | 1.02 | 1.01 | 0.10 | 0.09 |
| 2032 | 1.01 | 0.99 | 1.13 | 0.10 | 0.09 |
| 1878 | 1.14 | 1.22 | 1.20 | 0.11 | 0.11 |
| 2033 | 1.10 | 1.02 | 1.03 | 0.10 | 0.10 |
| 2034 | 1.09 | 0.98 | 1.01 | 0.10 | 0.10 |
| 2035 | 1.10 | 0.96 | 1.00 | 0.10 | 0.10 |
| 2036 | 1.07 | 0.95 | 1.09 | 0.09 | 0.10 |
| 2037 | 1.10 | 1.04 | 1.16 | 0.10 | 0.10 |
| 2038 | 1.09 | 0.98 | 1.00 | 0.09 | 0.10 |
| 2039 | 1.13 | 0.93 | 1.10 | 0.09 | 0.10 |
| 2040 | 1.27 | 0.96 | 1.02 | 0.10 | 0.11 |
| 2041 | 1.09 | 1.03 | 1.09 | 0.10 | 0.10 |
| 2042 | 0.24 | 1.07 | 1.09 | 0.10 | 0.09 |
| 2043 | 0.23 | 1.12 | 1.10 | 0.09 | 0.10 |
| 2044 | 0.29 | 1.24 | 1.17 | 0.09 | 0.11 |
| 2045 | 0.19 | 0.85 | 1.18 | 0.14 | 0.10 |
| 2046 | 0.18 | 1.09 | 1.20 | 0.10 | 0.10 |
| 2047 | 0.25 | 1.01 | 1.24 | 0.11 | 0.11 |
| 2048 | 0.23 | 0.44 | 0.95 | 0.14 | 0.19 |
| 2049 | 0.28 | 1.04 | 1.05 | 0.09 | 0.10 |
| 2050 | 0.20 | 1.07 | 1.05 | 0.10 | 0.10 |
| 1880 | 1.02 | 1.10 | 1.17 | 1.06 | 0.84 |
| 2051 | 1.11 | 1.03 | 0.98 | 0.10 | 0.10 |

FIGURE 34 (continued)

| | | | | | |
|---|---|---|---|---|---|
| 2052 | 1.12 | 1.05 | 1.24 | 0.10 | 0.10 |
| 2053 | 1.07 | 1.11 | 1.21 | 0.10 | 0.10 |
| 2054 | 1.03 | 0.98 | 1.11 | 0.12 | 0.09 |
| 2055 | 1.02 | 1.02 | 1.17 | 0.09 | 0.09 |
| 2056 | 1.03 | 1.08 | 1.34 | 0.10 | 0.09 |
| 2057 | 1.00 | 1.05 | 1.13 | 0.10 | 0.10 |
| 2058 | 1.02 | 1.18 | 1.07 | 0.10 | 0.10 |
| 2059 | 1.09 | 1.00 | 1.05 | 0.10 | 0.10 |
| 1881 | 1.13 | 1.20 | 1.00 | 1.07 | 1.02 |
| 2060 | 1.07 | 0.97 | 1.10 | 0.30 | 0.11 |
| 2061 | 1.07 | 1.02 | 0.97 | 0.18 | 0.11 |
| 2062 | 1.09 | 0.99 | 0.93 | 0.18 | 0.12 |
| 2063 | 0.95 | 0.93 | 0.92 | 1.17 | 1.06 |
| 2064 | 0.99 | 0.82 | 1.00 | 0.09 | 0.09 |
| 2065 | 1.03 | 1.06 | 1.07 | 0.16 | 0.11 |
| 2066 | 1.00 | 0.99 | 1.04 | 0.18 | 0.13 |
| 2067 | 1.15 | 1.01 | 1.08 | 1.05 | 1.21 |
| 2068 | 1.14 | 1.07 | 1.02 | 1.27 | 1.21 |
| 2069 | 1.13 | 0.92 | 1.04 | 0.52 | 0.25 |
| 2070 | 1.13 | 1.02 | 0.93 | 0.11 | 0.11 |
| 2071 | 1.17 | 1.22 | 1.03 | 1.18 | 1.17 |
| 2072 | 1.11 | 1.32 | 1.03 | 0.10 | 0.12 |
| 2073 | 1.06 | 0.98 | 0.92 | 1.26 | 1.04 |
| 2074 | 1.08 | 1.03 | 1.48 | 0.09 | 0.10 |
| 2075 | 0.99 | 1.07 | 1.05 | 0.18 | 0.12 |
| 2076 | 1.06 | 0.97 | 1.02 | 0.10 | 0.10 |
| 2077 | 1.16 | 1.06 | 1.04 | 0.09 | 0.11 |
| 1882 | 1.07 | 1.22 | 0.99 | 0.10 | 0.10 |
| 2078 | 1.07 | 0.94 | 0.97 | 0.14 | 0.14 |
| 2079 | 1.21 | 0.84 | 0.98 | 1.09 | 1.14 |
| 2080 | 1.08 | 0.84 | 0.96 | 1.13 | 1.09 |
| 2081 | 1.26 | 0.99 | 1.03 | 1.06 | 1.23 |
| 2082 | 1.11 | 1.05 | 1.04 | 1.07 | 1.14 |
| 2083 | 1.05 | 1.18 | 1.02 | 0.13 | 0.12 |
| 2084 | 1.07 | 1.03 | 0.99 | 0.13 | 0.12 |
| 2085 | 1.09 | 1.02 | 0.99 | 1.17 | 1.12 |
| 2086 | 1.09 | 1.14 | 1.06 | 0.11 | 0.12 |
| 2087 | 0.92 | 1.02 | 0.95 | 1.22 | 1.00 |

FIGURE 34 (continued)

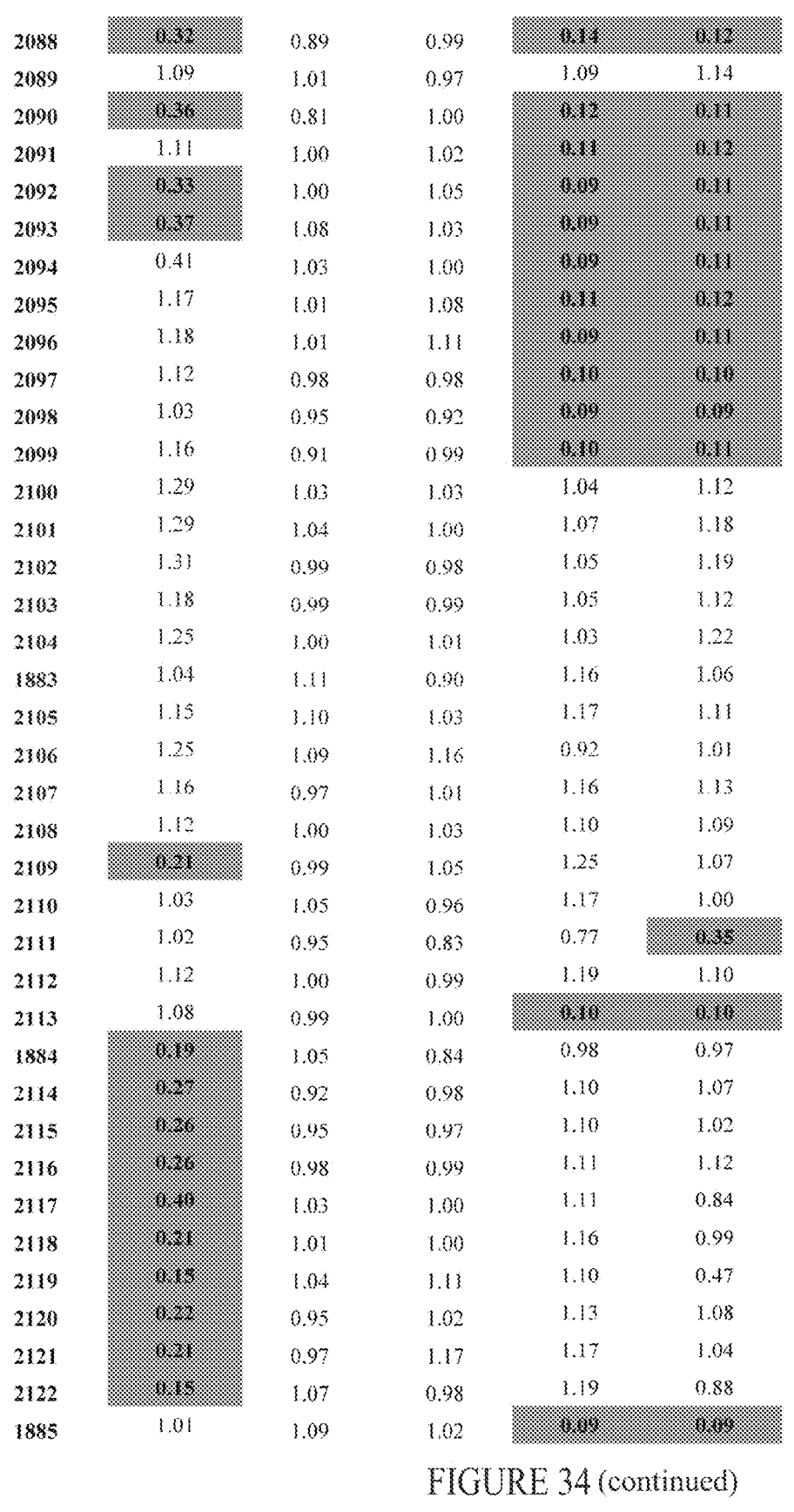

| | | | | | |
|---|---|---|---|---|---|
| 2088 | 0.32 | 0.89 | 0.99 | 0.14 | 0.12 |
| 2089 | 1.09 | 1.01 | 0.97 | 1.09 | 1.14 |
| 2090 | 0.36 | 0.81 | 1.00 | 0.12 | 0.11 |
| 2091 | 1.11 | 1.00 | 1.02 | 0.11 | 0.12 |
| 2092 | 0.33 | 1.00 | 1.05 | 0.09 | 0.11 |
| 2093 | 0.37 | 1.08 | 1.03 | 0.09 | 0.11 |
| 2094 | 0.41 | 1.03 | 1.00 | 0.09 | 0.11 |
| 2095 | 1.17 | 1.01 | 1.08 | 0.11 | 0.12 |
| 2096 | 1.18 | 1.01 | 1.11 | 0.09 | 0.11 |
| 2097 | 1.12 | 0.98 | 0.98 | 0.10 | 0.10 |
| 2098 | 1.03 | 0.95 | 0.92 | 0.09 | 0.09 |
| 2099 | 1.16 | 0.91 | 0.99 | 0.10 | 0.11 |
| 2100 | 1.29 | 1.03 | 1.03 | 1.04 | 1.12 |
| 2101 | 1.29 | 1.04 | 1.00 | 1.07 | 1.18 |
| 2102 | 1.31 | 0.99 | 0.98 | 1.05 | 1.19 |
| 2103 | 1.18 | 0.99 | 0.99 | 1.05 | 1.12 |
| 2104 | 1.25 | 1.00 | 1.01 | 1.03 | 1.22 |
| 1883 | 1.04 | 1.11 | 0.90 | 1.16 | 1.06 |
| 2105 | 1.15 | 1.10 | 1.03 | 1.17 | 1.11 |
| 2106 | 1.25 | 1.09 | 1.16 | 0.92 | 1.01 |
| 2107 | 1.16 | 0.97 | 1.01 | 1.16 | 1.13 |
| 2108 | 1.12 | 1.00 | 1.03 | 1.10 | 1.09 |
| 2109 | 0.21 | 0.99 | 1.05 | 1.25 | 1.07 |
| 2110 | 1.03 | 1.05 | 0.96 | 1.17 | 1.00 |
| 2111 | 1.02 | 0.95 | 0.83 | 0.77 | 0.35 |
| 2112 | 1.12 | 1.00 | 0.99 | 1.19 | 1.10 |
| 2113 | 1.08 | 0.99 | 1.00 | 0.10 | 0.10 |
| 1884 | 0.19 | 1.05 | 0.84 | 0.98 | 0.97 |
| 2114 | 0.27 | 0.92 | 0.98 | 1.10 | 1.07 |
| 2115 | 0.26 | 0.95 | 0.97 | 1.10 | 1.02 |
| 2116 | 0.26 | 0.98 | 0.99 | 1.11 | 1.12 |
| 2117 | 0.40 | 1.03 | 1.00 | 1.11 | 0.84 |
| 2118 | 0.21 | 1.01 | 1.00 | 1.16 | 0.99 |
| 2119 | 0.15 | 1.04 | 1.11 | 1.10 | 0.47 |
| 2120 | 0.22 | 0.95 | 1.02 | 1.13 | 1.08 |
| 2121 | 0.21 | 0.97 | 1.17 | 1.17 | 1.04 |
| 2122 | 0.15 | 1.07 | 0.98 | 1.19 | 0.88 |
| 1885 | 1.01 | 1.09 | 1.02 | 0.09 | 0.09 |

FIGURE 34 (continued)

| | | | | | |
|---|---|---|---|---|---|
| 2123 | 0.10 | 0.14 | 1.04 | 0.09 | 0.09 |
| 2124 | 0.16 | 0.86 | 1.09 | 0.09 | 0.10 |
| 2125 | 0.10 | 0.13 | 0.32 | 0.09 | 0.09 |
| 2126 | 1.14 | 1.10 | 1.20 | 0.10 | 0.11 |
| 2127 | 1.08 | 0.97 | 1.06 | 1.09 | 1.03 |
| 2128 | 0.11 | 0.12 | 0.31 | 0.09 | 0.11 |
| 2129 | 0.11 | 0.13 | 0.49 | 0.09 | 0.10 |
| 2130 | 0.25 | 0.85 | 1.15 | 0.10 | 0.11 |
| 2131 | 0.12 | 0.12 | 0.32 | 0.09 | 0.11 |
| 1886 | 1.01 | 0.98 | 0.95 | 1.01 | 0.99 |
| 2132 | 1.25 | 0.96 | 1.11 | 1.03 | 1.17 |
| 1887 | 1.08 | 1.04 | 0.99 | 1.17 | 0.12 |
| 2133 | 1.10 | 1.00 | 1.10 | 0.10 | 0.10 |
| 2134 | 1.00 | 0.94 | 1.03 | 1.24 | 1.07 |
| 2135 | 1.02 | 1.14 | 1.00 | 0.09 | 0.09 |
| 2136 | 1.05 | 1.10 | 0.97 | 0.09 | 0.10 |
| 2137 | 1.07 | 1.13 | 0.97 | 0.09 | 0.10 |
| 2138 | 1.09 | 1.03 | 0.84 | 1.08 | 1.09 |
| 2139 | 1.10 | 1.03 | 1.11 | 0.09 | 0.10 |
| 2140 | 1.08 | 1.00 | 0.93 | 0.88 | 1.08 |
| 2141 | 1.03 | 0.96 | 0.96 | 0.11 | 0.10 |
| 2142 | 1.08 | 1.05 | 1.18 | 0.83 | 0.96 |
| 2143 | 1.11 | 1.07 | 1.00 | 1.03 | 1.07 |
| 2148 | 1.08 | 1.08 | 1.00 | 0.09 | 0.10 |
| 2149 | 1.02 | 1.18 | 0.96 | 1.06 | 1.17 |
| 2150 | 1.10 | 1.00 | 0.86 | 0.71 | 0.31 |
| 2164 | 1.06 | 1.06 | 0.98 | 0.10 | 0.09 |
| 2165 | 1.04 | 1.03 | 0.97 | 0.10 | 0.09 |
| 2166 | 1.02 | 1.15 | 1.24 | 1.09 | 0.97 |
| 2167 | 1.07 | 0.80 | 0.92 | 0.10 | 0.10 |
| 1888 | 1.08 | 1.14 | 1.09 | 0.22 | 0.19 |
| 2151 | 1.15 | 0.94 | 0.90 | 0.36 | 0.28 |
| 2152 | 1.10 | 0.97 | 1.05 | 0.10 | 0.10 |
| 2153 | 1.09 | 1.03 | 0.95 | 0.16 | 0.15 |
| 2154 | 1.11 | 0.95 | 0.85 | 0.29 | 0.30 |
| 2155 | 1.06 | 1.07 | 1.18 | 0.19 | 0.17 |
| 2156 | 0.99 | 0.95 | 1.02 | 0.09 | 0.10 |
| 2157 | 1.01 | 1.07 | 0.99 | 0.09 | 0.09 |

FIGURE 34 (continued)

| | | | | | |
|---|---|---|---|---|---|
| 2158 | 0.97 | 0.81 | 0.91 | 0.09 | 0.10 |
| 2159 | 1.06 | 0.93 | 1.09 | 0.40 | 0.35 |
| 1889 | 1.03 | 1.09 | 1.09 | 0.10 | 0.09 |
| 2144 | 1.10 | 1.11 | 1.04 | 1.07 | 1.08 |
| 2145 | 1.03 | 1.07 | 1.06 | 0.64 | 0.94 |
| 2146 | 1.05 | 1.04 | 1.05 | 0.10 | 0.10 |
| 2147 | 1.06 | 0.98 | 0.99 | 0.10 | 0.10 |
| 2160 | 1.01 | 0.89 | 1.05 | 0.10 | 0.10 |
| 2161 | 1.06 | 0.95 | 1.08 | 0.10 | 0.10 |
| 2162 | 1.02 | 0.96 | 1.05 | 0.10 | 0.09 |
| 2163 | 0.98 | 0.92 | 0.97 | 0.10 | 0.10 |
| 2168 | 1.13 | 0.93 | 0.93 | 0.10 | 0.10 |
| 1890 | 1.06 | 1.12 | 1.07 | 1.03 | 1.01 |
| 2169 | 1.12 | 0.90 | 1.11 | 0.10 | 0.10 |
| 2170 | 1.12 | 0.82 | 0.94 | 0.10 | 0.11 |
| 2171 | 1.10 | 0.86 | 0.91 | 0.11 | 0.11 |
| 2172 | 1.15 | 0.83 | 1.07 | 0.10 | 0.12 |
| 2173 | 1.03 | 0.84 | 0.95 | 0.11 | 0.10 |
| 2174 | 1.09 | 3.35 | 3.43 | 0.10 | 0.10 |
| 2175 | 1.14 | 0.91 | 0.97 | 1.11 | 1.11 |
| 2176 | 0.98 | 0.95 | 0.97 | 0.58 | 0.89 |
| 2177 | 1.02 | 1.01 | 1.08 | 1.18 | 1.05 |
| 1879 | 0.99 | 1.30 | 1.20 | 0.10 | 0.09 |
| 1911 | 0.18 | 0.94 | 1.23 | 0.14 | 0.30 |
| 1950 | 0.91 | 1.08 | 1.07 | 0.09 | 0.09 |
| 1951 | 0.98 | 0.89 | 0.98 | 1.00 | 0.98 |
| 1952 | 0.10 | 0.11 | 0.98 | 0.09 | 0.09 |
| 1953 | 0.10 | 0.09 | 0.11 | 0.27 | 0.79 |
| 1954 | 1.02 | 1.06 | 1.05 | 0.09 | 0.10 |
| 1955 | 0.09 | 0.09 | 0.11 | 0.27 | 0.81 |
| 1956 | 0.19 | 0.96 | 1.00 | 0.10 | 0.28 |
| 1957 | 1.09 | 0.92 | 0.96 | 0.09 | 0.09 |
| 1958 | 1.02 | 0.99 | 0.92 | 0.09 | 0.09 |
| 1913 | 0.17 | 0.97 | 1.18 | 0.35 | 0.20 |
| 1968 | 0.09 | 0.11 | 0.99 | 0.09 | 0.08 |
| 1969 | 0.92 | 0.99 | 0.86 | 0.10 | 0.08 |
| 1970 | 0.11 | 0.20 | 0.97 | 0.09 | 0.08 |
| 1971 | 0.98 | 0.84 | 0.87 | 0.08 | 0.09 |

FIGURE 34 (continued)

| | | | | | |
|---|---|---|---|---|---|
| 1972 | 0.17 | 0.21 | 0.95 | 0.11 | 0.20 |
| 1973 | 0.24 | 0.79 | 0.95 | 0.11 | 0.27 |
| 1974 | 0.18 | 0.81 | 0.95 | 0.11 | 0.20 |
| 1975 | 1.14 | 1.26 | 1.27 | 0.09 | 0.19 |
| 1976 | 1.03 | 1.00 | 0.89 | 0.09 | 0.09 |
| 1891 | 1.07 | 1.06 | 1.02 | 1.06 | 1.14 |
| 1892 | 1.15 | 1.13 | 1.00 | 1.04 | 1.11 |
| 1893 | 1.09 | 1.11 | 0.95 | 1.13 | 1.09 |
| 1894 | 1.15 | 1.05 | 0.92 | 1.02 | 1.14 |
| 1895 | 1.11 | 1.08 | 0.95 | 0.11 | 0.11 |
| 1896 | 0.99 | 0.95 | 0.91 | 0.09 | 0.10 |
| 1897 | 0.98 | 1.01 | 0.97 | 0.09 | 0.09 |
| 1898 | 1.07 | 0.96 | 0.85 | 0.08 | 0.09 |
| 1899 | 0.99 | 0.99 | 1.07 | 1.00 | 1.03 |
| 1990 | 0.12 | 0.27 | 1.11 | 0.09 | 0.20 |
| 1991 | 0.12 | 0.31 | 1.12 | 0.10 | 0.19 |
| 1992 | 0.13 | 0.28 | 1.07 | 0.09 | 0.22 |
| 1993 | 0.11 | 0.21 | 1.16 | 0.10 | 0.58 |
| 1994 | 0.11 | 0.28 | 1.08 | 0.09 | 1.16 |
| 1995 | 0.13 | 0.22 | 1.05 | 0.10 | 0.71 |
| 1996 | 0.11 | 0.09 | 0.10 | 0.09 | 0.33 |
| 1910 | 0.11 | 0.09 | 0.10 | 0.09 | 0.12 |
| 1945 | 0.35 | 0.81 | 0.99 | 0.09 | 0.12 |
| 1946 | 0.11 | 0.09 | 0.09 | 0.09 | 0.11 |
| 1947 | 0.11 | 0.09 | 0.09 | 0.09 | 0.11 |
| 1948 | 0.11 | 0.09 | 0.09 | 0.31 | 1.04 |
| 1949 | 0.09 | 0.09 | 0.09 | 0.10 | 0.10 |
| 1977 | 0.09 | 0.10 | 0.10 | 0.31 | 0.26 |
| 1978 | 1.10 | 1.10 | 1.17 | 1.00 | 1.06 |
| 1979 | 0.95 | 1.10 | 0.97 | 0.87 | 0.85 |
| 1980 | 1.08 | 1.06 | 0.98 | 0.99 | 0.98 |
| 1981 | 1.01 | 0.97 | 0.93 | 0.87 | 0.93 |
| 1982 | 0.97 | 1.06 | 0.93 | 1.10 | 1.13 |
| 1983 | 0.11 | 1.02 | 0.91 | 0.10 | 0.11 |
| 1984 | 0.95 | 1.05 | 1.04 | 0.94 | 1.00 |
| 1985 | 0.10 | 0.08 | 0.09 | 1.00 | 1.01 |
| 1914 | 0.11 | 0.10 | 0.11 | 0.15 | 0.14 |
| 1986 | 0.11 | 0.09 | 0.13 | 0.14 | 0.15 |

FIGURE 34 (continued)

| | | | | | |
|---|---|---|---|---|---|
| 1987 | 0.11 | 0.09 | 0.12 | 0.14 | 0.14 |
| 1988 | 0.10 | 0.09 | 0.11 | 0.13 | 0.12 |
| 1989 | 0.13 | 0.98 | 1.04 | 0.10 | 0.11 |
| 1917 | 0.81 | 1.20 | 0.90 | 1.05 | 0.71 |
| 2015 | 0.10 | 0.11 | 0.22 | 0.67 | 0.55 |
| 2016 | 0.11 | 0.11 | 0.21 | 0.61 | 0.58 |
| 2017 | 0.10 | 0.11 | 0.22 | 0.58 | 0.56 |
| 2018 | 0.11 | 0.10 | 0.27 | 0.66 | 0.70 |
| 2019 | 0.11 | 0.10 | 0.24 | 0.74 | 0.59 |
| 2020 | 0.30 | 1.11 | 0.13 | 0.25 | 0.22 |
| 2021 | 0.78 | 1.09 | 1.18 | 0.82 | 0.88 |
| 2022 | 0.82 | 1.16 | 1.11 | 0.79 | 0.96 |
| 2023 | 1.04 | 1.04 | 1.09 | 1.03 | 1.08 |

FIGURE 34 (continued)

TABLE 24

| NP # | A511:ff | P100:ff | LP48:ff | LP125:ff | A511:ff, P100:ff, LP48:ff | A511:ff, P100:ff, LP48:ff, LP125:ff |
|---|---|---|---|---|---|---|
| 1839 | 0.15 | 0.14 | 0.19 | 0.14 | 0.14 | 0.18 |
| 1840 | 1.01 | 1.03 | 1.01 | 1.06 | 1.02 | 1.04 |
| 1869 | 0.14 | 0.13 | 0.15 | 0.90 | 0.16 | 0.14 |
| 1878 | 1.02 | 0.19 | 1.01 | 1.14 | 0.26 | 0.22 |
| 1879 | 0.12 | 0.11 | 0.12 | 0.13 | 0.12 | 0.12 |
| 1880 | 1.00 | 1.05 | 0.96 | 1.06 | 1.06 | 1.02 |
| 1881 | 1.07 | 1.09 | 1.04 | 1.16 | 1.08 | 1.04 |
| 1882 | 0.76 | 0.11 | 0.22 | 0.42 | 0.14 | 0.15 |
| 1883 | 1.08 | 1.09 | 1.08 | 1.08 | 1.02 | 1.04 |
| 1884 | 1.05 | 1.03 | 1.06 | 1.07 | 1.03 | 1.01 |
| 1885 | 0.12 | 0.10 | 0.11 | 0.11 | 0.11 | 0.10 |
| 1886 | 0.99 | 1.09 | 1.00 | 1.06 | 1.09 | 1.04 |
| 1887 | 1.02 | 1.07 | 1.17 | 0.98 | 1.11 | 1.05 |
| 1888 | 0.98 | 1.05 | 1.04 | 1.02 | 1.11 | 1.01 |
| 1889 | 0.13 | 0.11 | 0.12 | 0.13 | 0.12 | 0.13 |
| 1890 | 1.04 | 1.05 | 1.07 | 1.06 | 1.13 | 1.06 |
| 1891 | 1.01 | 1.02 | 1.00 | 1.06 | 1.08 | 1.03 |
| 1892 | 0.98 | 0.97 | 0.98 | 1.06 | 1.05 | 1.01 |
| 1893 | 1.01 | 1.00 | 1.02 | 1.07 | 1.06 | 1.01 |
| 1894 | 1.03 | 1.05 | 1.02 | 1.08 | 1.06 | 1.04 |
| 1895 | 0.13 | 0.11 | 0.13 | 0.13 | 0.12 | 0.12 |
| 1896 | 0.12 | 0.11 | 0.12 | 0.17 | 0.11 | 0.12 |
| 1897 | 0.18 | 0.16 | 0.16 | 0.19 | 0.16 | 0.16 |
| 1898 | 0.10 | 0.10 | 0.10 | 0.10 | 0.10 | 0.10 |
| 1899 | 1.07 | 1.07 | 1.05 | 1.04 | 1.08 | 0.98 |
| 1900 | 1.06 | 1.07 | 1.05 | 1.03 | 1.14 | 1.00 |
| 1901 | 0.11 | 0.10 | 0.12 | 1.01 | 0.11 | 0.11 |
| 1902 | 1.02 | 1.05 | 1.03 | 1.03 | 1.05 | 0.98 |
| 1903 | 0.11 | 0.11 | 0.11 | 1.03 | 0.14 | 0.11 |
| 1904 | 0.11 | 0.12 | 0.16 | 1.04 | 0.12 | 0.12 |
| 1905 | 0.11 | 0.12 | 0.16 | 1.05 | 0.12 | 0.12 |
| 1906 | 1.04 | 1.07 | 1.04 | 1.04 | 1.04 | 0.66 |

FIGURE 35

| | | | | | | |
|---|---|---|---|---|---|---|
| 1907 | 1.04 | 1.09 | 1.03 | 1.05 | 1.05 | 0.98 |
| 1908 | 0.11 | 0.10 | 0.12 | 1.04 | 0.11 | 0.11 |
| 1909 | 0.99 | 1.01 | 1.00 | 1.01 | 1.00 | 0.94 |
| 1910 | 0.17 | 0.14 | 0.25 | 0.96 | 0.19 | 0.18 |
| 1911 | 1.06 | 1.02 | 1.06 | 1.07 | 1.20 | 1.01 |
| 1912 | 1.04 | 0.97 | 1.02 | 1.02 | 1.13 | 1.05 |
| 1913 | 0.99 | 0.98 | 0.96 | 0.95 | 1.13 | 0.96 |
| 1914 | 0.92 | 0.13 | 0.56 | 1.14 | 0.27 | 0.20 |
| 1915 | 0.14 | 0.11 | 0.11 | 0.13 | 0.12 | 0.12 |
| 1916 | 1.07 | 1.06 | 1.05 | 1.32 | 1.23 | 1.02 |
| 1917 | 1.02 | 0.99 | 1.06 | 1.09 | 1.09 | 1.02 |
| 1945 | 0.12 | 0.10 | 0.11 | 0.16 | 0.10 | 0.10 |
| 1946 | 0.75 | 0.14 | 0.85 | 1.09 | 0.20 | 0.24 |
| 1947 | 0.85 | 0.15 | 0.87 | 1.15 | 0.21 | 0.20 |
| 1948 | 0.43 | 0.99 | 1.05 | 1.04 | 0.43 | 0.85 |
| 1949 | 0.13 | 0.13 | 0.17 | 1.07 | 0.14 | 0.12 |
| 1950 | 0.09 | 0.09 | 0.09 | 0.09 | 0.10 | 0.09 |
| 1951 | 1.02 | 1.00 | 1.00 | 1.00 | 1.00 | 1.00 |
| 1952 | 0.11 | 0.09 | 0.09 | 0.09 | 0.10 | 0.09 |
| 1953 | 0.11 | 0.10 | 0.98 | 1.08 | 0.13 | 0.12 |
| 1954 | 0.09 | 0.09 | 0.09 | 0.09 | 0.09 | 0.09 |
| 1955 | 0.11 | 0.10 | 0.97 | 1.10 | 0.12 | 0.12 |
| 1956 | 0.97 | 0.87 | 0.97 | 1.02 | 0.98 | 0.94 |
| 1957 | 0.13 | 0.10 | 0.66 | 0.17 | 0.10 | 0.10 |
| 1958 | 0.09 | 0.09 | 0.09 | 0.10 | 0.09 | 0.09 |
| 1959 | 0.10 | 0.10 | 0.12 | 1.03 | 0.10 | 0.10 |
| 1960 | 0.14 | 0.93 | 0.19 | 1.00 | 0.19 | 0.18 |
| 1961 | 0.12 | 0.16 | 1.01 | 1.25 | 0.12 | 0.12 |
| 1962 | 1.10 | 1.17 | 1.13 | 1.21 | 1.17 | 1.10 |
| 1963 | 0.13 | 0.10 | 0.13 | 1.09 | 0.12 | 0.12 |
| 1964 | 0.11 | 0.10 | 0.13 | 1.09 | 0.12 | 0.12 |
| 1965 | 0.12 | 0.10 | 0.13 | 1.13 | 0.12 | 0.12 |
| 1966 | 0.11 | 0.10 | 0.16 | 1.00 | 0.11 | 0.11 |
| 1967 | 0.12 | 0.10 | 0.23 | 1.05 | 0.12 | 0.12 |
| 1968 | 0.11 | 0.10 | 0.10 | 0.10 | 0.10 | 0.10 |
| 1969 | 0.12 | 0.10 | 0.10 | 0.10 | 0.10 | 0.10 |
| 1970 | 0.09 | 0.08 | 0.08 | 0.09 | 0.09 | 0.08 |
| 1971 | 0.09 | 0.08 | 0.09 | 0.09 | 0.08 | 0.08 |

FIGURE 35 (continued)

| | | | | | | |
|---|---|---|---|---|---|---|
| 1972 | 1.08 | 1.02 | 1.10 | 1.46 | 1.10 | 1.14 |
| 1973 | 1.10 | 1.08 | 1.08 | 1.11 | 1.31 | 1.11 |
| 1974 | 1.14 | 1.15 | 1.15 | 1.14 | 1.27 | 1.14 |
| 1975 | 0.97 | 0.96 | 0.97 | 0.98 | 0.58 | 0.99 |
| 1976 | 0.12 | 0.10 | 0.10 | 0.10 | 0.10 | 0.10 |
| 1977 | 0.13 | 0.11 | 0.90 | 1.03 | 0.15 | 0.15 |
| 1978 | 1.10 | 1.04 | 1.08 | 1.08 | 1.17 | 1.15 |
| 1979 | 1.14 | 1.12 | 1.11 | 1.16 | 1.26 | 1.21 |
| 1980 | 1.01 | 1.09 | 1.04 | 1.12 | 1.11 | 1.08 |
| 1981 | 1.16 | 1.21 | 1.09 | 1.14 | 1.18 | 1.15 |
| 1982 | 1.01 | 1.08 | 0.94 | 1.03 | 1.04 | 1.00 |
| 1983 | 0.43 | 0.14 | 0.39 | 0.34 | 0.18 | 0.16 |
| 1984 | 1.06 | 1.03 | 1.05 | 1.05 | 1.06 | 1.06 |
| 1985 | 1.00 | 1.03 | 1.02 | 1.01 | 1.04 | 1.02 |
| 1986 | 0.86 | 0.12 | 0.60 | 1.06 | 0.14 | 0.14 |
| 1987 | 0.81 | 0.12 | 0.61 | 1.02 | 0.13 | 0.15 |
| 1988 | 0.81 | 0.12 | 0.42 | 1.06 | 0.14 | 0.15 |
| 1989 | 0.96 | 0.17 | 0.76 | 0.71 | 0.22 | 0.26 |
| 1990 | 1.07 | 1.04 | 1.04 | 1.10 | 1.06 | 1.03 |
| 1991 | 1.03 | 1.03 | 1.00 | 1.06 | 1.01 | 0.98 |
| 1992 | 0.98 | 1.02 | 0.99 | 1.04 | 1.04 | 0.96 |
| 1993 | 1.00 | 1.02 | 1.12 | 1.20 | 1.36 | 1.04 |
| 1994 | 1.02 | 1.06 | 0.96 | 0.98 | 1.14 | 0.98 |
| 1995 | 1.03 | 1.00 | 1.02 | 1.02 | 1.07 | 1.01 |
| 1996 | 0.10 | 0.09 | 0.87 | 1.05 | 0.09 | 0.09 |
| 1997 | 0.12 | 0.10 | 0.10 | 0.12 | 0.10 | 0.11 |
| 1998 | 0.12 | 0.10 | 0.10 | 0.11 | 0.10 | 0.10 |
| 1999 | 0.13 | 0.13 | 0.10 | 0.51 | 0.11 | 0.12 |
| 2000 | 0.13 | 0.10 | 0.10 | 0.12 | 0.11 | 0.11 |
| 2001 | 0.12 | 0.10 | 0.10 | 0.12 | 0.11 | 0.11 |
| 2002 | 0.30 | 1.03 | 1.03 | 1.04 | 0.80 | 0.72 |
| 2003 | 1.00 | 1.01 | 1.01 | 1.03 | 1.01 | 0.95 |
| 2004 | 1.02 | 1.04 | 1.03 | 1.03 | 1.01 | 0.98 |
| 2005 | 0.98 | 1.00 | 1.02 | 1.00 | 1.12 | 1.00 |
| 2006 | 1.07 | 1.11 | 0.94 | 1.03 | 1.12 | 0.94 |
| 2007 | 0.12 | 0.13 | 0.18 | 1.01 | 0.13 | 0.12 |
| 2008 | 0.12 | 0.13 | 0.19 | 1.03 | 0.13 | 0.12 |
| 2009 | 0.11 | 0.13 | 0.21 | 0.98 | 0.12 | 0.11 |

FIGURE 35 (continued)

| | | | | | | |
|---|---|---|---|---|---|---|
| 2010 | 0.96 | 1.07 | 0.98 | 1.12 | 1.20 | 0.92 |
| 2011 | 0.97 | 1.01 | 0.95 | 0.98 | 1.09 | 0.90 |
| 2012 | 1.02 | 1.02 | 1.05 | 1.01 | 1.05 | 0.99 |
| 2013 | 0.96 | 1.01 | 1.01 | 0.97 | 1.02 | 0.95 |
| 2014 | 0.94 | 1.07 | 1.00 | 1.05 | 1.15 | 0.90 |
| 2015 | 0.98 | 1.03 | 1.03 | 1.01 | 0.99 | 0.96 |
| 2016 | 1.00 | 1.02 | 1.03 | 1.06 | 1.02 | 0.99 |
| 2017 | 0.95 | 0.93 | 0.98 | 0.99 | 1.04 | 0.96 |
| 2018 | 0.89 | 0.93 | 0.87 | 0.93 | 0.91 | 0.86 |
| 2019 | 1.00 | 0.99 | 0.97 | 1.03 | 1.06 | 0.98 |
| 2020 | 1.03 | 0.89 | 0.97 | 1.07 | 0.96 | 0.89 |
| 2021 | 0.98 | 1.01 | 0.98 | 1.01 | 1.04 | 0.98 |
| 2022 | 1.02 | 1.04 | 1.00 | 1.05 | 1.06 | 1.01 |
| 2023 | 1.12 | 1.05 | 1.03 | 1.06 | 1.10 | 1.11 |
| 2024 | 0.11 | 0.10 | 0.10 | 0.11 | 0.10 | 0.10 |
| 2025 | 0.12 | 0.11 | 0.11 | 0.11 | 0.11 | 0.11 |
| 2026 | 0.55 | 0.55 | 0.55 | 0.56 | 0.55 | 0.55 |
| 2027 | 0.13 | 0.11 | 0.13 | 0.15 | 0.13 | 0.13 |
| 2028 | 0.11 | 0.10 | 0.10 | 0.10 | 0.10 | 0.10 |
| 2029 | 0.98 | 0.91 | 1.06 | 1.02 | 1.07 | 1.04 |
| 2030 | 0.12 | 0.09 | 0.10 | 0.10 | 0.10 | 0.10 |
| 2031 | 0.21 | 0.10 | 0.16 | 0.23 | 0.11 | 0.12 |
| 2032 | 0.11 | 0.10 | 0.11 | 0.10 | 0.10 | 0.10 |
| 2033 | 0.11 | 0.10 | 0.10 | 0.10 | 0.11 | 0.10 |
| 2034 | 0.11 | 0.10 | 0.11 | 0.10 | 0.10 | 0.10 |
| 2035 | 0.10 | 0.09 | 0.10 | 0.10 | 0.10 | 0.10 |
| 2036 | 0.11 | 0.10 | 0.10 | 0.10 | 0.10 | 0.10 |
| 2037 | 0.10 | 0.10 | 0.10 | 0.10 | 0.10 | 0.10 |
| 2038 | 0.99 | 0.18 | 1.04 | 0.86 | 0.22 | 0.19 |
| 2039 | 1.04 | 0.18 | 0.96 | 0.75 | 0.23 | 0.23 |
| 2040 | 1.01 | 0.15 | 1.07 | 1.09 | 0.25 | 0.24 |
| 2041 | 0.11 | 0.10 | 0.11 | 0.11 | 0.11 | 0.10 |
| 2042 | 0.60 | 0.10 | 0.78 | 0.96 | 0.25 | 0.20 |
| 2043 | 1.02 | 0.10 | 0.65 | 0.95 | 0.11 | 0.10 |
| 2044 | 1.03 | 0.11 | 0.82 | 1.04 | 0.19 | 0.13 |
| 2045 | 1.00 | 0.10 | 0.16 | 1.01 | 0.11 | 0.11 |
| 2046 | 1.12 | 0.11 | 0.66 | 1.07 | 0.12 | 0.12 |
| 2047 | 0.99 | 0.12 | 0.84 | 0.99 | 0.14 | 0.13 |

FIGURE 35 (continued)

| | | | | | | |
|---|---|---|---|---|---|---|
| 2048 | 1.21 | 0.22 | 1.08 | 1.36 | 0.25 | 0.27 |
| 2049 | 0.97 | 0.10 | 0.79 | 1.00 | 0.12 | 0.12 |
| 2050 | 1.14 | 0.11 | 0.99 | 1.16 | 0.12 | 0.13 |
| 2051 | 0.99 | 0.19 | 1.02 | 0.90 | 0.23 | 0.23 |
| 2052 | 0.12 | 0.10 | 0.11 | 0.10 | 0.10 | 0.10 |
| 2053 | 0.10 | 0.10 | 0.10 | 0.11 | 0.11 | 0.10 |
| 2054 | 0.14 | 0.13 | 0.14 | 0.16 | 0.14 | 0.14 |
| 2055 | 0.11 | 0.09 | 0.11 | 0.10 | 0.10 | 0.10 |
| 2056 | 0.13 | 0.11 | 0.12 | 0.12 | 0.12 | 0.12 |
| 2057 | 1.06 | 0.20 | 1.07 | 1.07 | 0.32 | 0.29 |
| 2058 | 1.00 | 0.24 | 1.12 | 1.04 | 0.28 | 0.29 |
| 2059 | 0.11 | 0.10 | 0.11 | 0.12 | 0.10 | 0.10 |
| 2060 | 1.19 | 1.18 | 1.26 | 1.19 | 1.28 | 1.28 |
| 2061 | 1.03 | 0.91 | 1.07 | 0.98 | 1.01 | 0.95 |
| 2062 | 1.13 | 1.08 | 1.15 | 1.07 | 1.12 | 1.08 |
| 2063 | 1.00 | 1.00 | 1.06 | 1.04 | 1.17 | 1.04 |
| 2064 | 1.09 | 0.87 | 1.15 | 1.24 | 1.13 | 1.24 |
| 2065 | 0.96 | 0.97 | 0.94 | 0.86 | 0.93 | 0.96 |
| 2066 | 1.00 | 1.08 | 1.09 | 1.18 | 1.16 | 1.13 |
| 2067 | 1.14 | 1.09 | 1.18 | 1.18 | 1.13 | 1.15 |
| 2068 | 1.10 | 1.02 | 1.05 | 1.11 | 1.08 | 1.09 |
| 2069 | 1.11 | 1.13 | 1.08 | 1.26 | 1.09 | 1.16 |
| 2070 | 0.99 | 0.10 | 0.20 | 0.21 | 0.11 | 0.11 |
| 2071 | 1.13 | 1.12 | 1.03 | 1.20 | 1.21 | 1.15 |
| 2072 | 0.14 | 0.12 | 0.13 | 0.12 | 0.12 | 0.12 |
| 2073 | 1.01 | 0.99 | 0.98 | 1.11 | 1.08 | 1.05 |
| 2074 | 1.04 | 0.12 | 0.80 | 0.87 | 0.14 | 0.15 |
| 2075 | 1.00 | 1.00 | 1.04 | 1.17 | 1.04 | 1.07 |
| 2076 | 0.11 | 0.10 | 0.11 | 0.10 | 0.10 | 0.10 |
| 2077 | 0.34 | 0.11 | 0.27 | 0.22 | 0.12 | 0.12 |
| 2078 | 0.97 | 0.97 | 0.97 | 0.98 | 0.99 | 1.01 |
| 2079 | 1.06 | 1.06 | 1.07 | 1.07 | 1.04 | 1.06 |
| 2080 | 1.01 | 1.02 | 1.02 | 1.03 | 1.02 | 1.05 |
| 2081 | 1.03 | 1.03 | 1.07 | 1.05 | 1.02 | 1.04 |
| 2082 | 1.05 | 1.06 | 1.07 | 1.03 | 1.02 | 1.06 |
| 2083 | 1.08 | 1.07 | 1.05 | 1.04 | 1.03 | 1.09 |
| 2084 | 1.00 | 1.03 | 1.02 | 1.03 | 1.05 | 1.05 |
| 2085 | 1.09 | 1.06 | 1.02 | 1.09 | 0.97 | 1.11 |

FIGURE 35 (continued)

| | | | | | | |
|---|---|---|---|---|---|---|
| 2086 | 1.06 | 1.07 | 1.10 | 1.13 | 1.18 | 1.11 |
| 2087 | 1.01 | 1.30 | 0.94 | 0.97 | 1.08 | 1.01 |
| 2088 | 0.18 | 0.13 | 0.53 | 0.87 | 0.16 | 0.16 |
| 2089 | 1.09 | 1.19 | 1.12 | 1.08 | 1.11 | 1.07 |
| 2090 | 0.15 | 0.11 | 0.34 | 0.74 | 0.13 | 0.14 |
| 2091 | 1.04 | 1.06 | 1.06 | 1.04 | 1.06 | 1.03 |
| 2092 | 0.11 | 0.09 | 0.11 | 0.16 | 0.10 | 0.10 |
| 2093 | 0.80 | 0.09 | 0.82 | 0.88 | 0.09 | 0.09 |
| 2094 | 0.77 | 0.09 | 0.78 | 0.85 | 0.09 | 0.09 |
| 2095 | 0.15 | 0.12 | 0.14 | 0.14 | 0.14 | 0.14 |
| 2096 | 0.67 | 0.09 | 0.38 | 0.67 | 0.09 | 0.09 |
| 2097 | 0.39 | 0.10 | 0.28 | 0.47 | 0.10 | 0.10 |
| 2098 | 0.57 | 0.09 | 0.43 | 0.61 | 0.09 | 0.10 |
| 2099 | 0.47 | 0.10 | 0.23 | 0.26 | 0.10 | 0.10 |
| 2100 | 1.02 | 1.03 | 1.00 | 1.03 | 1.02 | 1.01 |
| 2101 | 1.05 | 1.04 | 1.05 | 1.05 | 1.03 | 1.01 |
| 2102 | 1.00 | 0.98 | 1.00 | 0.99 | 0.99 | 0.98 |
| 2103 | 1.02 | 1.03 | 1.07 | 1.04 | 1.05 | 1.07 |
| 2104 | 0.98 | 0.99 | 0.99 | 0.98 | 0.98 | 0.99 |
| 2105 | 1.03 | 1.06 | 1.02 | 1.07 | 1.01 | 0.99 |
| 2106 | 1.00 | 0.98 | 1.01 | 1.00 | 1.00 | 1.02 |
| 2107 | 1.01 | 1.00 | 0.99 | 1.00 | 0.98 | 0.98 |
| 2108 | 1.00 | 0.98 | 1.01 | 0.96 | 1.01 | 1.01 |
| 2109 | 1.00 | 1.00 | 1.02 | 0.99 | 0.99 | 1.02 |
| 2110 | 1.01 | 0.96 | 1.02 | 0.98 | 1.04 | 1.00 |
| 2111 | 1.02 | 1.07 | 0.98 | 1.05 | 1.05 | 1.04 |
| 2112 | 1.00 | 1.03 | 1.06 | 1.03 | 1.01 | 1.04 |
| 2113 | 0.12 | 0.10 | 0.10 | 0.10 | 0.10 | 0.10 |
| 2114 | 0.98 | 0.99 | 1.00 | 1.01 | 0.98 | 1.02 |
| 2115 | 1.00 | 1.06 | 1.03 | 1.06 | 1.01 | 1.03 |
| 2116 | 0.98 | 0.97 | 0.98 | 0.98 | 0.95 | 1.01 |
| 2117 | 0.99 | 1.04 | 1.05 | 1.02 | 1.01 | 0.92 |
| 2118 | 0.93 | 0.97 | 1.00 | 0.96 | 0.95 | 1.02 |
| 2119 | 1.08 | 1.05 | 1.07 | 1.06 | 1.03 | 0.95 |
| 2120 | 0.92 | 0.95 | 0.98 | 0.98 | 0.95 | 1.01 |
| 2121 | 1.13 | 1.16 | 1.18 | 1.22 | 1.12 | 1.20 |
| 2122 | 1.03 | 0.97 | 1.02 | 1.03 | 1.08 | 1.01 |
| 2123 | 0.10 | 0.10 | 0.10 | 0.10 | 0.10 | 0.10 |

FIGURE 35 (continued)

| | | | | | | |
|---|---|---|---|---|---|---|
| 2124 | 0.11 | 0.09 | 0.10 | 0.10 | 0.10 | 0.10 |
| 2125 | 0.10 | 0.10 | 0.10 | 0.10 | 0.10 | 0.10 |
| 2126 | 1.00 | 0.17 | 1.06 | 0.86 | 0.22 | 0.21 |
| 2127 | 1.07 | 1.13 | 1.10 | 1.06 | 1.08 | 1.05 |
| 2128 | 0.09 | 0.09 | 0.09 | 0.09 | 0.09 | 0.09 |
| 2129 | 0.10 | 0.10 | 0.10 | 0.10 | 0.09 | 0.10 |
| 2130 | 0.09 | 0.09 | 0.10 | 0.10 | 0.09 | 0.09 |
| 2131 | 0.10 | 0.10 | 0.09 | 0.24 | 0.09 | 0.10 |
| 2132 | 0.93 | 1.00 | 1.00 | 0.95 | 1.00 | 0.98 |
| 2133 | 1.07 | 0.12 | 0.14 | 0.14 | 0.13 | 0.14 |
| 2134 | 1.09 | 0.96 | 0.97 | 0.99 | 1.06 | 0.98 |
| 2135 | 0.57 | 0.15 | 0.96 | 1.09 | 0.16 | 0.23 |
| 2136 | 1.07 | 0.10 | 0.11 | 0.12 | 0.10 | 0.11 |
| 2137 | 1.14 | 0.11 | 0.12 | 0.13 | 0.11 | 0.11 |
| 2138 | 1.11 | 1.06 | 1.02 | 1.04 | 1.05 | 1.04 |
| 2139 | 0.75 | 0.11 | 0.24 | 0.14 | 0.13 | 0.13 |
| 2140 | 1.02 | 1.05 | 1.05 | 1.05 | 0.98 | 1.05 |
| 2141 | 0.84 | 0.14 | 1.04 | 0.99 | 0.16 | 0.16 |
| 2142 | 0.99 | 1.02 | 1.06 | 1.03 | 0.94 | 0.95 |
| 2143 | 1.16 | 1.14 | 1.21 | 1.15 | 1.11 | 1.10 |
| 2164 | 0.10 | 0.10 | 0.11 | 0.11 | 0.10 | 0.10 |
| 2165 | 0.13 | 0.12 | 0.14 | 0.14 | 0.13 | 0.13 |
| 2166 | 1.04 | 1.00 | 1.09 | 1.09 | 1.10 | 1.08 |
| 2167 | 0.15 | 0.11 | 0.11 | 0.11 | 0.11 | 0.13 |
| 2148 | 0.11 | 0.10 | 0.11 | 0.12 | 0.10 | 0.10 |
| 2149 | 0.96 | 1.13 | 0.97 | 1.07 | 1.06 | 1.00 |
| 2150 | 0.93 | 1.05 | 0.95 | 1.03 | 1.02 | 1.04 |
| 2151 | 0.93 | 0.94 | 0.97 | 1.02 | 1.01 | 1.01 |
| 2152 | 0.10 | 0.09 | 0.09 | 0.10 | 0.10 | 0.09 |
| 2153 | 1.03 | 1.10 | 1.12 | 1.11 | 1.09 | 1.10 |
| 2154 | 0.93 | 1.03 | 1.12 | 1.02 | 1.01 | 1.10 |
| 2155 | 0.98 | 1.11 | 1.07 | 1.13 | 1.11 | 1.10 |
| 2156 | 0.12 | 0.09 | 0.09 | 0.10 | 0.09 | 0.09 |
| 2157 | 0.45 | 0.44 | 0.45 | 0.46 | 0.44 | 0.45 |
| 2158 | 0.12 | 0.10 | 0.11 | 0.11 | 0.10 | 0.11 |
| 2159 | 1.02 | 1.10 | 1.09 | 1.13 | 1.21 | 1.16 |
| 2160 | 0.17 | 0.12 | 0.13 | 0.14 | 0.13 | 0.13 |
| 2161 | 0.14 | 0.10 | 0.11 | 0.11 | 0.11 | 0.11 |

FIGURE 35 (continued)

| | | | | | | |
|---|---|---|---|---|---|---|
| 2162 | 0.14 | 0.10 | 0.11 | 0.11 | 0.12 | 0.11 |
| 2163 | 0.13 | 0.11 | 0.10 | 0.11 | 0.11 | 0.11 |
| 2144 | 1.03 | 1.00 | 1.03 | 1.07 | 1.13 | 1.14 |
| 2145 | 1.05 | 1.09 | 1.05 | 1.12 | 1.17 | 1.18 |
| 2146 | 0.12 | 0.10 | 0.11 | 0.11 | 0.10 | 0.10 |
| 2147 | 1.09 | 0.13 | 0.18 | 1.04 | 0.17 | 0.17 |
| 2168 | 0.13 | 0.12 | 0.13 | 0.13 | 0.12 | 0.11 |
| 2169 | 0.13 | 0.13 | 0.13 | 0.12 | 0.13 | 0.12 |
| 2170 | 0.11 | 0.09 | 0.11 | 0.10 | 0.10 | 0.11 |
| 2171 | 0.12 | 0.12 | 0.13 | 0.12 | 0.12 | 0.11 |
| 2172 | 0.11 | 0.13 | 0.21 | 0.20 | 0.12 | 0.12 |
| 2173 | 0.12 | 0.12 | 0.17 | 0.26 | 0.11 | 0.11 |
| 2174 | 0.11 | 0.10 | 0.11 | 0.11 | 0.11 | 0.10 |
| 2175 | 0.97 | 0.97 | 1.01 | 1.01 | 0.97 | 0.94 |
| 2176 | 1.03 | 1.01 | 1.00 | 1.02 | 1.00 | 1.00 |
| 2177 | 0.98 | 0.90 | 0.95 | 0.99 | 0.95 | 0.89 |

FIGURE 35 (continued)

TABLE 25

| NP # | P100 and A511:nluc | LP124:nluc | A511, P100, 124:nluc | LP124:nluc RLU |
|---|---|---|---|---|
| 1839 | 0.14 | 0.27 | 0.31 | 4.14E+08 |
| 1840 | 1.05 | 1.11 | 1.04 | 5.68E+02 |
| 1869 | 0.13 | 0.20 | 0.17 | 4.63E+08 |
| 1878 | 0.20 | 0.55 | 0.65 | 2.43E+08 |
| 1879 | 0.12 | 0.10 | 0.10 | |
| 1880 | 1.07 | 1.01 | 1.09 | 1.16E+06 |
| 1881 | 1.00 | 0.96 | 1.08 | 2.41E+06 |
| 1882 | 0.12 | 0.20 | 0.23 | 8.90E+05 |
| 1883 | 1.00 | 1.12 | 1.03 | 8.22E+02 |
| 1884 | 1.05 | 1.04 | 1.01 | 1.14E+04 |
| 1885 | 0.12 | 0.09 | 0.09 | 9.07E+08 |
| 1886 | 1.04 | 1.02 | 0.96 | 4.83E+02 |
| 1887 | 1.00 | 0.94 | 1.08 | 5.87E+05 |
| 1888 | 0.94 | 0.88 | 1.00 | 3.72E+06 |
| 1889 | 0.10 | 0.10 | 0.10 | 7.50E+08 |
| 1890 | 1.04 | 0.96 | 1.01 | 1.32E+03 |
| 1891 | 0.95 | 0.90 | 1.13 | 4.48E+02 |
| 1892 | 0.96 | 1.00 | 1.04 | 5.21E+02 |
| 1893 | 0.97 | 1.03 | 1.07 | 5.34E+02 |
| 1894 | 0.96 | 0.90 | 1.05 | 4.04E+02 |
| 1895 | 0.12 | 0.11 | 0.15 | 1.18E+09 |
| 1896 | 0.12 | 0.10 | 0.15 | 1.18E+09 |
| 1897 | 0.10 | 0.11 | 0.10 | 1.20E+09 |
| 1898 | 0.10 | 0.13 | 0.10 | 1.18E+09 |
| 1899 | 0.98 | 1.16 | 1.09 | 7.88E+02 |
| 1900 | 0.94 | 0.88 | 1.06 | 6.40E+02 |
| 1901 | 0.10 | 0.09 | 0.10 | 5.17E+08 |
| 1902 | 1.02 | 1.00 | 0.57 | 2.88E+06 |
| 1903 | 0.10 | 0.11 | 0.10 | 4.89E+08 |
| 1904 | 0.11 | 0.13 | 0.10 | 1.03E+08 |
| 1905 | 0.12 | 0.16 | 0.11 | 1.12E+08 |
| 1906 | 0.79 | 0.91 | 1.06 | 3.11E+06 |

FIGURE 36

| | | | | |
|---|---|---|---|---|
| 1907 | 0.98 | 0.98 | 1.07 | 6.91E+02 |
| 1908 | 0.11 | 0.11 | 0.12 | 4.99E+08 |
| 1909 | 1.10 | 0.98 | 1.02 | 6.89E+02 |
| 1910 | 0.11 | 0.11 | 0.13 | 1.36E+09 |
| 1911 | 1.05 | 0.92 | 1.10 | 4.16E+05 |
| 1912 | 1.08 | 1.07 | 1.11 | 4.00E+02 |
| 1913 | 1.15 | 1.59 | 0.97 | 6.22E+02 |
| 1914 | 0.11 | 0.17 | 0.11 | 3.71E+08 |
| 1915 | 0.11 | 0.10 | 0.11 | 2.25E+08 |
| 1916 | 1.01 | 0.89 | 0.99 | 1.88E+04 |
| 1917 | 1.10 | 0.89 | 1.05 | 1.18E+06 |
| 1945 | 0.10 | 0.12 | 0.09 | 1.07E+09 |
| 1946 | 0.17 | 0.30 | 0.79 | 8.28E+04 |
| 1947 | 0.12 | 0.31 | 0.54 | 1.08E+05 |
| 1948 | 0.47 | 0.79 | 0.56 | 1.68E+04 |
| 1949 | 0.11 | 0.14 | 0.13 | 9.51E+08 |
| 1950 | 0.09 | 0.11 | 0.12 | 1.14E+09 |
| 1951 | 1.02 | 1.00 | 1.02 | 8.32E+02 |
| 1952 | 0.10 | 0.14 | 0.10 | 1.26E+09 |
| 1953 | 0.10 | 1.22 | 0.10 | 1.31E+08 |
| 1954 | 0.10 | 0.13 | 0.11 | 7.70E+08 |
| 1955 | 0.10 | 1.04 | 0.10 | 1.15E+08 |
| 1956 | 1.07 | 1.08 | 1.01 | 1.50E+06 |
| 1957 | 0.10 | 0.14 | 0.10 | 3.15E+07 |
| 1958 | 0.10 | 0.13 | 0.11 | 8.58E+08 |
| 1959 | 0.10 | 0.12 | 0.11 | 4.59E+08 |
| 1960 | 0.15 | 0.14 | 0.14 | 6.09E+08 |
| 1961 | 0.12 | 0.12 | 0.13 | 1.49E+08 |
| 1962 | 1.04 | 0.97 | 1.41 | 9.90E+02 |
| 1963 | 0.12 | 0.10 | 0.11 | 1.13E+09 |
| 1964 | 0.10 | 0.10 | 0.11 | 1.24E+09 |
| 1965 | 0.10 | 0.10 | 0.09 | 1.31E+09 |
| 1966 | 0.11 | 0.09 | 0.10 | 8.83E+08 |
| 1967 | 0.10 | 0.10 | 0.10 | 5.14E+08 |
| 1968 | 0.09 | 0.12 | 0.12 | 1.08E+09 |
| 1969 | 0.09 | 0.12 | 0.12 | 1.19E+09 |
| 1970 | 0.08 | 0.09 | 0.10 | 9.52E+08 |
| 1971 | 0.09 | 0.10 | 0.10 | 1.17E+09 |

FIGURE 36 (continued)

| | | | | |
|---|---|---|---|---|
| 1972 | 0.92 | 0.75 | 1.68 | 2.46E+06 |
| 1973 | 1.10 | 1.02 | 1.80 | 1.27E+03 |
| 1974 | 1.11 | 0.96 | 1.08 | 5.58E+02 |
| 1975 | 1.12 | 0.10 | 0.12 | 2.05E+09 |
| 1976 | 0.11 | 0.11 | 0.12 | 1.01E+09 |
| 1977 | 0.11 | 0.78 | 0.13 | 9.36E+08 |
| 1978 | 1.10 | 1.04 | 1.17 | 4.25E+03 |
| 1979 | 1.04 | 0.90 | 1.08 | 8.68E+02 |
| 1980 | 0.99 | 0.93 | 1.14 | 1.01E+06 |
| 1981 | 1.59 | 0.78 | 1.18 | 8.87E+02 |
| 1982 | 1.03 | 1.02 | 0.98 | 2.26E+04 |
| 1983 | 0.16 | 0.26 | 0.25 | 1.10E+05 |
| 1984 | 1.01 | 1.14 | 0.99 | 5.70E+05 |
| 1985 | 1.01 | 1.07 | 1.00 | 3.71E+05 |
| 1986 | 0.11 | 0.17 | 0.11 | 4.42E+08 |
| 1987 | 0.11 | 0.16 | 0.11 | 4.19E+08 |
| 1988 | 0.11 | 0.16 | 0.12 | 5.10E+08 |
| 1989 | 0.21 | 0.35 | 0.70 | 7.94E+03 |
| 1990 | 0.59 | 1.05 | 1.03 | 5.21E+02 |
| 1991 | 0.97 | 1.08 | 0.97 | 7.81E+02 |
| 1992 | 0.98 | 1.06 | 0.98 | 5.54E+02 |
| 1993 | 1.10 | 1.05 | 1.08 | 5.49E+02 |
| 1994 | 0.99 | 1.12 | 1.05 | 6.11E+02 |
| 1995 | 1.05 | 1.07 | 1.07 | 6.58E+02 |
| 1996 | 0.10 | 0.40 | 0.09 | 9.57E+08 |
| 1997 | 0.11 | 0.10 | 0.11 | 1.03E+09 |
| 1998 | 0.11 | 0.10 | 0.11 | 7.04E+08 |
| 1999 | 0.11 | 0.10 | 0.13 | 7.03E+08 |
| 2000 | 0.11 | 0.12 | 0.12 | 7.44E+08 |
| 2001 | 0.11 | 0.85 | 0.20 | 7.40E+08 |
| 2002 | 0.28 | 0.14 | 0.55 | 2.40E+08 |
| 2003 | 1.06 | 1.08 | 1.07 | 2.97E+06 |
| 2004 | 1.06 | 1.00 | 1.12 | 2.48E+06 |
| 2005 | 1.09 | 1.02 | 1.07 | 1.91E+06 |
| 2006 | 1.01 | 1.39 | 1.08 | 2.27E+03 |
| 2007 | 0.11 | 0.15 | 0.11 | 1.03E+09 |
| 2008 | 0.11 | 0.15 | 0.12 | 1.49E+09 |
| 2009 | 0.11 | 0.14 | 0.10 | 7.14E+08 |

FIGURE 36 (continued)

| | | | | |
|---|---|---|---|---|
| **2010** | 1.00 | 1.16 | 1.15 | 1.41E+05 |
| **2011** | 1.00 | 1.18 | 1.18 | 9.53E+04 |
| **2012** | 1.04 | 1.06 | 1.04 | 1.96E+03 |
| **2013** | 1.04 | 1.05 | 1.05 | 4.57E+03 |
| **2014** | 0.95 | 1.18 | 1.18 | 6.58E+04 |
| **2015** | 0.98 | 1.04 | 1.00 | 9.04E+04 |
| **2016** | 1.01 | 1.17 | 0.93 | 1.18E+05 |
| **2017** | 1.05 | 0.91 | 1.32 | 1.27E+05 |
| **2018** | 1.12 | 1.15 | 0.99 | 1.63E+05 |
| **2019** | 1.00 | 1.15 | 1.02 | 5.09E+04 |
| **2020** | 0.83 | 0.67 | 0.74 | 1.33E+08 |
| **2021** | 1.05 | 1.05 | 1.04 | 8.08E+03 |
| **2022** | 1.04 | 1.12 | 1.05 | 1.60E+04 |
| **2023** | 1.03 | 1.06 | 0.96 | 2.05E+05 |
| **2024** | 0.11 | 0.10 | 0.09 | 2.00E+09 |
| **2025** | 0.11 | 0.10 | 0.10 | 9.29E+08 |
| **2026** | 0.26 | 0.42 | 0.41 | 8.12E+07 |
| **2027** | 0.12 | 0.13 | 0.10 | 2.18E+09 |
| **2028** | 0.12 | 0.10 | 0.09 | 5.25E+08 |
| **2029** | 1.12 | 1.06 | 0.98 | 8.97E+05 |
| **2030** | 0.12 | 0.11 | 0.10 | 4.29E+06 |
| **2031** | 0.11 | 0.18 | 0.20 | 3.22E+05 |
| **2032** | 0.12 | 0.11 | 0.09 | 8.40E+08 |
| **2033** | 0.10 | 0.10 | 0.09 | 8.34E+08 |
| **2034** | 0.11 | 0.10 | 0.09 | 9.17E+08 |
| **2035** | 0.11 | 0.09 | 0.09 | 1.02E+09 |
| **2036** | 0.12 | 0.10 | 0.09 | 1.25E+09 |
| **2037** | 0.11 | 0.10 | 0.09 | 8.85E+08 |
| **2038** | 0.23 | 0.57 | 0.26 | 8.38E+03 |
| **2039** | 0.24 | 0.57 | 0.37 | 1.71E+04 |
| **2040** | 0.23 | 0.38 | 0.56 | 2.20E+04 |
| **2041** | 0.12 | 0.10 | 0.10 | 7.90E+08 |
| **2042** | 0.13 | 0.29 | 0.56 | 2.60E+06 |
| **2043** | 0.10 | 0.15 | 0.25 | 1.51E+06 |
| **2044** | 0.26 | 0.15 | 0.31 | 1.54E+06 |
| **2045** | 0.11 | 0.71 | 0.38 | 1.85E+06 |
| **2046** | 0.11 | 0.19 | 0.34 | 3.69E+05 |
| **2047** | 0.13 | 0.16 | 0.29 | 5.60E+05 |

FIGURE 36 (continued)

| | | | | |
|---|---|---|---|---|
| 2048 | 0.17 | 0.91 | 0.73 | 5.59E+03 |
| 2049 | 0.21 | 0.13 | 0.33 | 5.39E+05 |
| 2050 | 0.12 | 0.16 | 0.28 | 6.97E+05 |
| 2051 | 0.19 | 0.52 | 0.48 | 2.43E+04 |
| 2052 | 0.10 | 0.10 | 0.10 | 5.51E+08 |
| 2053 | 0.12 | 0.12 | 0.11 | 2.63E+08 |
| 2054 | 0.16 | 0.13 | 0.11 | 2.25E+09 |
| 2055 | 0.10 | 0.10 | 0.10 | 1.79E+09 |
| 2056 | 0.12 | 0.09 | 0.10 | 1.24E+09 |
| 2057 | 0.28 | 0.53 | 0.54 | 1.38E+04 |
| 2058 | 0.25 | 0.69 | 0.65 | 2.17E+04 |
| 2059 | 0.14 | 0.10 | 0.10 | 1.94E+09 |
| 2060 | 0.98 | 0.88 | 0.97 | 1.62E+06 |
| 2061 | 1.00 | 0.69 | 0.93 | 2.51E+06 |
| 2062 | 1.03 | 0.39 | 1.01 | 3.04E+06 |
| 2063 | 1.25 | 0.96 | 0.99 | 8.85E+05 |
| 2064 | 0.25 | 0.12 | 0.13 | 1.21E+09 |
| 2065 | 0.90 | 0.35 | 0.95 | 2.52E+06 |
| 2066 | 0.96 | 0.19 | 1.12 | 1.77E+06 |
| 2067 | 0.93 | 1.48 | 1.42 | 5.81E+02 |
| 2068 | 1.05 | 1.02 | 1.07 | 1.34E+06 |
| 2069 | 0.92 | 0.95 | 1.15 | 1.63E+06 |
| 2070 | 0.11 | 0.13 | 0.16 | 6.71E+08 |
| 2071 | 1.21 | 1.40 | 1.07 | 2.29E+03 |
| 2072 | 0.12 | 0.12 | 0.11 | 8.04E+08 |
| 2073 | 1.07 | 0.94 | 1.13 | 1.32E+09 |
| 2074 | 0.16 | 0.22 | 0.51 | 7.06E+06 |
| 2075 | 0.79 | 0.40 | 0.51 | 3.07E+06 |
| 2076 | 0.11 | 0.09 | 0.10 | 2.65E+09 |
| 2077 | 0.11 | 0.19 | 0.41 | 7.24E+05 |
| 2078 | 1.01 | 0.39 | 1.05 | 4.00E+08 |
| 2079 | 1.04 | 1.06 | 1.09 | 2.89E+04 |
| 2080 | 1.02 | 1.02 | 1.11 | 6.69E+02 |
| 2081 | 1.01 | 1.15 | 1.58 | 5.28E+02 |
| 2082 | 1.02 | 1.05 | 1.11 | 5.89E+02 |
| 2083 | 0.89 | 0.18 | 0.99 | 1.30E+09 |
| 2084 | 1.02 | 0.49 | 1.04 | 8.76E+08 |
| 2085 | 0.95 | 1.11 | 0.98 | 4.66E+03 |

FIGURE 36 (continued)

| | | | | |
|---|---|---|---|---|
| 2086 | 1.17 | 0.25 | 0.99 | 1.15E+09 |
| 2087 | 1.16 | 1.13 | 1.09 | 9.13E+02 |
| 2088 | 0.15 | 0.19 | 0.15 | 1.93E+09 |
| 2089 | 1.06 | 1.15 | 1.08 | 1.55E+04 |
| 2090 | 0.17 | 0.24 | 0.14 | 2.09E+09 |
| 2091 | 0.49 | 0.19 | 0.68 | 7.86E+08 |
| 2092 | 0.10 | 0.10 | 0.10 | 1.93E+09 |
| 2093 | 0.10 | 0.42 | 0.54 | 5.39E+05 |
| 2094 | 0.10 | 0.43 | 0.64 | 6.93E+04 |
| 2095 | 0.22 | 0.13 | 0.10 | 7.54E+08 |
| 2096 | 0.10 | 0.21 | 0.30 | 2.01E+05 |
| 2097 | 0.11 | 0.23 | 0.20 | 5.42E+06 |
| 2098 | 0.13 | 0.30 | 0.24 | 1.89E+05 |
| 2099 | 0.11 | 0.24 | 0.41 | 1.80E+04 |
| 2100 | 0.99 | 1.13 | 1.06 | 9.19E+02 |
| 2101 | 1.04 | 1.05 | 1.06 | 2.03E+03 |
| 2102 | 1.01 | 1.09 | 1.03 | 7.52E+03 |
| 2103 | 0.98 | 1.26 | 1.07 | 1.80E+03 |
| 2104 | 1.03 | 1.02 | 1.06 | 2.07E+03 |
| 2105 | 1.02 | 1.09 | 1.02 | 8.50E+02 |
| 2106 | 1.01 | 1.19 | 1.03 | 7.00E+06 |
| 2107 | 1.03 | 1.34 | 1.02 | 1.20E+03 |
| 2108 | 1.01 | 1.09 | 0.98 | 7.31E+02 |
| 2109 | 1.04 | 1.15 | 1.06 | 1.35E+03 |
| 2110 | 1.06 | 0.99 | 1.05 | 1.23E+03 |
| 2111 | 1.12 | 0.99 | 1.05 | 4.33E+05 |
| 2112 | 1.05 | 1.09 | 1.01 | 9.46E+02 |
| 2113 | 0.10 | 0.09 | 0.09 | 8.06E+08 |
| 2114 | 1.06 | 0.94 | 1.02 | 3.13E+04 |
| 2115 | 1.08 | 0.99 | 0.94 | 9.25E+03 |
| 2116 | 1.04 | 1.01 | 1.05 | 1.23E+04 |
| 2117 | 1.04 | 0.78 | 1.03 | 3.64E+04 |
| 2118 | 1.05 | 1.00 | 1.02 | 1.31E+04 |
| 2119 | 1.08 | 0.48 | 0.72 | 2.41E+05 |
| 2120 | 1.05 | 0.48 | 0.78 | 1.13E+04 |
| 2121 | 1.03 | 0.62 | 1.04 | 6.97E+03 |
| 2122 | 1.10 | 0.39 | 1.05 | 7.79E+03 |
| 2123 | 0.11 | 0.09 | 0.10 | 1.19E+09 |

FIGURE 36 (continued)

| | | | | |
|---|---|---|---|---|
| 2124 | 0.11 | 0.09 | 0.10 | 1.84E+09 |
| 2125 | 0.10 | 0.10 | 0.09 | 1.04E+09 |
| 2126 | 0.22 | 0.50 | 0.66 | 1.52E+05 |
| 2127 | 1.08 | 1.05 | 1.08 | 1.40E+06 |
| 2128 | 0.10 | 0.10 | 0.09 | 9.27E+08 |
| 2129 | 0.10 | 0.10 | 0.09 | 9.59E+08 |
| 2130 | 0.10 | 0.10 | 0.09 | 1.10E+09 |
| 2131 | 0.10 | 0.10 | 0.09 | 8.76E+08 |
| 2132 | 1.03 | 1.21 | 1.01 | 8.98E+03 |
| 2133 | 0.12 | 0.12 | 0.10 | 7.24E+08 |
| 2134 | 1.16 | 1.07 | 1.10 | 4.11E+03 |
| 2135 | 0.18 | 0.33 | 0.32 | 6.59E+05 |
| 2136 | 0.10 | 0.09 | 0.09 | 1.73E+09 |
| 2137 | 0.10 | 0.09 | 0.09 | 1.13E+09 |
| 2138 | 1.00 | 1.16 | 0.99 | 2.04E+04 |
| 2139 | 0.12 | 0.09 | 0.10 | 7.09E+08 |
| 2140 | 1.08 | 0.85 | 1.02 | 8.74E+04 |
| 2141 | 0.18 | 0.19 | 0.72 | 2.03E+04 |
| 2142 | 1.02 | 0.88 | 1.01 | 1.19E+06 |
| 2143 | 1.03 | 0.54 | 1.02 | 2.61E+06 |
| 2164 | 0.11 | 0.11 | 0.09 | 3.17E+08 |
| 2165 | 0.11 | 0.11 | 0.09 | 3.67E+08 |
| 2166 | 1.12 | 0.56 | 1.04 | 2.34E+04 |
| 2167 | 0.15 | 0.13 | 0.10 | 9.74E+08 |
| 2148 | 0.10 | 0.12 | 0.10 | 2.01E+09 |
| 2149 | 1.01 | 1.06 | 1.12 | 9.57E+03 |
| 2150 | 1.11 | 1.09 | 1.06 | 8.18E+05 |
| 2151 | 1.04 | 1.07 | 1.05 | 8.33E+05 |
| 2152 | 0.14 | 0.09 | 0.10 | 6.38E+08 |
| 2153 | 1.05 | 0.85 | 1.06 | 1.12E+06 |
| 2154 | 1.09 | 0.98 | 1.09 | 1.31E+06 |
| 2155 | 1.10 | 0.50 | 1.12 | 9.99E+05 |
| 2156 | 0.13 | 0.11 | 0.09 | 9.04E+08 |
| 2157 | 0.10 | 0.37 | 0.17 | 7.10E+07 |
| 2158 | 0.12 | 0.10 | 0.10 | 6.65E+08 |
| 2159 | 1.23 | 0.87 | 1.10 | 1.01E+06 |
| 2160 | 0.14 | 0.12 | 0.13 | 6.33E+08 |
| 2161 | 0.17 | 0.15 | 0.11 | 3.43E+08 |

FIGURE 36 (continued)

| | | | | |
|---|---|---|---|---|
| 2162 | 0.12 | 0.12 | 0.11 | 6.64E+08 |
| 2163 | 0.16 | 0.10 | 0.12 | 1.23E+09 |
| 2144 | 0.96 | 1.09 | 1.13 | 8.40E+03 |
| 2145 | 1.16 | 0.55 | 1.17 | 1.41E+07 |
| 2146 | 0.13 | 0.11 | 0.11 | 1.48E+09 |
| 2147 | 0.16 | 0.15 | 0.17 | 1.08E+09 |
| 2168 | 0.14 | 0.09 | 0.11 | 7.92E+08 |
| 2169 | 0.14 | 0.11 | 0.12 | 1.49E+09 |
| 2170 | 0.13 | 0.10 | 0.11 | 2.46E+09 |
| 2171 | 0.11 | 0.09 | 0.11 | 1.83E+09 |
| 2172 | 0.11 | 0.10 | 0.24 | 1.23E+09 |
| 2173 | 0.11 | 0.10 | 0.11 | 1.68E+09 |
| 2174 | 0.11 | 0.09 | 0.10 | 1.48E+09 |
| 2175 | 1.05 | 1.04 | 1.08 | 1.44E+04 |
| 2176 | 1.08 | 0.97 | 1.03 | 1.51E+06 |
| 2177 | 0.91 | 1.30 | 1.02 | 1.31E+03 |

FIGURE 36 (continued)

TABLE 26

| NP # | LP124:nluc clearance | LP124:nluc RLU |
|---|---|---|
| 1839 | 0.27 | 4.14E+08 |
| 1840 | 1.11 | 5.68E+02 |
| 1869 | 0.20 | 4.63E+08 |
| 1878 | 0.10 | 2.43E+08 |
| 1879 | 0.55 | |
| 1880 | 1.01 | 1.16E+06 |
| 1881 | 0.96 | 2.41E+06 |
| 1882 | 0.20 | 8.90E+05 |
| 1883 | 1.12 | 8.22E+02 |
| 1884 | 1.04 | 1.14E+04 |
| 1885 | 0.09 | 9.07E+08 |
| 1886 | 1.02 | 4.83E+02 |
| 1887 | 0.94 | 5.87E+05 |
| 1888 | 0.88 | 3.72E+06 |
| 1889 | 0.10 | 7.50E+08 |
| 1890 | 0.96 | 1.32E+03 |
| 1891 | 0.90 | 4.48E+02 |
| 1892 | 1.00 | 5.21E+02 |
| 1893 | 1.03 | 5.34E+02 |
| 1894 | 0.90 | 4.04E+02 |
| 1895 | 0.11 | 1.18E+09 |
| 1896 | 0.10 | 1.18E+09 |
| 1897 | 0.11 | 1.20E+09 |
| 1898 | 0.13 | 1.18E+09 |
| 1899 | 1.16 | 7.88E+02 |
| 1900 | 0.88 | 6.40E+02 |
| 1901 | 0.09 | 5.17E+08 |
| 1902 | 1.00 | 2.88E+06 |
| 1903 | 0.11 | 4.89E+08 |
| 1904 | 0.13 | 1.03E+08 |
| 1905 | 0.16 | 1.12E+08 |
| 1906 | 0.91 | 3.11E+06 |
| 1907 | 0.98 | 6.91E+02 |
| 1908 | 0.11 | 4.99E+08 |

FIGURE 37

| | | |
|---|---|---|
| 1909 | 0.98 | 6.89E+02 |
| 1910 | 0.11 | 1.36E+09 |
| 1911 | 0.92 | 4.16E+05 |
| 1912 | 1.07 | 4.00E+02 |
| 1913 | 1.59 | 6.22E+02 |
| 1914 | 0.17 | 3.71E+08 |
| 1915 | 0.10 | 2.25E+08 |
| 1916 | 0.89 | 1.88E+04 |
| 1917 | 0.89 | 1.18E+06 |
| 1945 | 0.12 | 1.07E+09 |
| 1946 | 0.30 | 8.28E+04 |
| 1947 | 0.31 | 1.08E+05 |
| 1948 | 0.79 | 1.68E+04 |
| 1949 | 0.14 | 9.51E+08 |
| 1950 | 0.11 | 1.14E+09 |
| 1951 | 1.00 | 8.32E+02 |
| 1952 | 0.14 | 1.26E+09 |
| 1953 | 1.22 | 1.31E+08 |
| 1954 | 0.13 | 7.70E+08 |
| 1955 | 1.04 | 1.15E+08 |
| 1956 | 1.08 | 1.50E+06 |
| 1957 | 0.14 | 3.15E+07 |
| 1958 | 0.13 | 8.58E+08 |
| 1959 | 0.12 | 4.59E+08 |
| 1960 | 0.14 | 6.09E+08 |
| 1961 | 0.12 | 1.49E+08 |
| 1962 | 0.97 | 9.90E+02 |
| 1963 | 0.10 | 1.13E+09 |
| 1964 | 0.10 | 1.24E+09 |
| 1965 | 0.10 | 1.31E+09 |
| 1966 | 0.09 | 8.83E+08 |
| 1967 | 0.10 | 5.14E+08 |
| 1968 | 0.12 | 1.08E+09 |
| 1969 | 0.12 | 1.19E+09 |
| 1970 | 0.09 | 9.52E+08 |
| 1971 | 0.10 | 1.17E+09 |
| 1972 | 0.75 | 2.46E+06 |
| 1973 | 1.02 | 1.27E+03 |

FIGURE 37 (continued)

| | | |
|---|---|---|
| 1974 | 0.96 | 5.58E+02 |
| 1975 | 0.10 | 2.05E+09 |
| 1976 | 0.11 | 1.01E+09 |
| 1977 | 0.78 | 9.36E+08 |
| 1978 | 1.04 | 4.25E+03 |
| 1979 | 0.90 | 8.68E+02 |
| 1980 | 0.93 | 1.01E+06 |
| 1981 | 0.78 | 8.87E+02 |
| 1982 | 1.02 | 2.26E+04 |
| 1983 | 0.26 | 1.10E+05 |
| 1984 | 1.14 | 5.70E+05 |
| 1985 | 1.07 | 3.71E+05 |
| 1986 | 0.17 | 4.42E+08 |
| 1987 | 0.16 | 4.19E+08 |
| 1988 | 0.16 | 5.10E+08 |
| 1989 | 0.35 | 7.94E+03 |
| 1990 | 1.05 | 5.21E+02 |
| 1991 | 1.08 | 7.81E+02 |
| 1992 | 1.06 | 5.54E+02 |
| 1993 | 1.05 | 5.49E+02 |
| 1994 | 1.12 | 6.11E+02 |
| 1995 | 1.07 | 6.58E+02 |
| 1996 | 0.40 | 9.57E+08 |
| 1997 | 0.10 | 1.03E+09 |
| 1998 | 0.10 | 7.04E+08 |
| 1999 | 0.10 | 7.03E+08 |
| 2000 | 0.12 | 7.44E+08 |
| 2001 | 0.85 | 7.40E+08 |
| 2002 | 0.14 | 2.40E+08 |
| 2003 | 1.08 | 2.97E+06 |
| 2004 | 1.00 | 2.48E+06 |
| 2005 | 1.02 | 1.91E+06 |
| 2006 | 1.39 | 2.27E+03 |
| 2007 | 0.15 | 1.03E+09 |
| 2008 | 0.15 | 1.49E+09 |
| 2009 | 0.14 | 7.14E+08 |
| 2010 | 1.16 | 1.41E+05 |
| 2011 | 1.18 | 9.53E+04 |

FIGURE 37 (continued)

| | | |
|---|---|---|
| 2012 | 1.06 | 1.96E+03 |
| 2013 | 1.05 | 4.57E+03 |
| 2014 | 1.18 | 6.58E+04 |
| 2015 | 1.04 | 9.04E+04 |
| 2016 | 1.17 | 1.18E+05 |
| 2017 | 0.91 | 1.27E+05 |
| 2018 | 1.15 | 1.63E+05 |
| 2019 | 1.15 | 5.09E+04 |
| 2020 | 0.67 | 1.33E+08 |
| 2021 | 1.05 | 8.08E+03 |
| 2022 | 1.12 | 1.60E+04 |
| 2023 | 1.06 | 2.05E+05 |
| 2024 | 0.10 | 2.00E+09 |
| 2025 | 0.10 | 9.29E+08 |
| 2026 | 0.42 | 8.12E+07 |
| 2027 | 0.13 | 2.18E+09 |
| 2028 | 0.10 | 5.25E+08 |
| 2029 | 1.06 | 8.97E+05 |
| 2030 | 0.11 | 4.29E+06 |
| 2031 | 0.15 | 3.22E+05 |
| 2032 | 0.11 | 8.40E+08 |
| 2033 | 0.10 | 8.34E+08 |
| 2034 | 0.10 | 9.17E+08 |
| 2035 | 0.09 | 1.02E+09 |
| 2036 | 0.10 | 1.25E+09 |
| 2037 | 0.10 | 8.85E+08 |
| 2038 | 0.57 | 8.38E+03 |
| 2039 | 0.57 | 1.71E+04 |
| 2040 | 0.38 | 2.20E+04 |
| 2041 | 0.10 | 7.90E+08 |
| 2042 | 0.29 | 2.60E+06 |
| 2043 | 0.15 | 1.51E+06 |
| 2044 | 0.15 | 1.54E+06 |
| 2045 | 0.71 | 1.85E+06 |
| 2046 | 0.19 | 3.69E+05 |
| 2047 | 0.16 | 5.60E+05 |
| 2048 | 0.91 | 5.59E+03 |
| 2049 | 0.13 | 5.39E+05 |

FIGURE 37 (continued)

| | | |
|---|---|---|
| 2050 | 0.16 | 6.97E+05 |
| 2051 | 0.52 | 2.43E+04 |
| 2052 | 0.10 | 5.51E+08 |
| 2053 | 0.12 | 2.63E+08 |
| 2054 | 0.13 | 2.25E+09 |
| 2055 | 0.10 | 1.79E+09 |
| 2056 | 0.09 | 1.24E+09 |
| 2057 | 0.53 | 1.38E+04 |
| 2058 | 0.69 | 2.17E+04 |
| 2059 | 0.10 | 1.94E+09 |
| 2060 | 0.88 | 1.62E+06 |
| 2061 | 0.69 | 2.51E+06 |
| 2062 | 0.39 | 3.04E+06 |
| 2063 | 0.96 | 8.85E+05 |
| 2064 | 0.12 | 1.21E+09 |
| 2065 | 0.35 | 2.52E+06 |
| 2066 | 0.19 | 1.77E+06 |
| 2067 | 1.48 | 5.81E+02 |
| 2068 | 1.02 | 1.34E+06 |
| 2069 | 0.95 | 1.63E+06 |
| 2070 | 0.13 | 6.71E+08 |
| 2071 | 1.40 | 2.29E+03 |
| 2072 | 0.12 | 8.04E+08 |
| 2073 | 0.94 | 1.32E+09 |
| 2074 | 0.22 | 7.06E+06 |
| 2075 | 0.40 | 3.07E+06 |
| 2076 | 0.09 | 2.65E+09 |
| 2077 | 0.19 | 7.24E+05 |
| 2078 | 0.39 | 4.00E+08 |
| 2079 | 1.06 | 2.89E+04 |
| 2080 | 1.02 | 6.69E+02 |
| 2081 | 1.15 | 5.28E+02 |
| 2082 | 1.05 | 5.89E+02 |
| 2083 | 0.18 | 1.30E+09 |
| 2084 | 0.49 | 8.76E+08 |
| 2085 | 1.11 | 4.66E+03 |
| 2086 | 0.25 | 1.15E+09 |
| 2087 | 1.13 | 9.13E+02 |

FIGURE 37 (continued)

| | | |
|---|---|---|
| 2088 | 0.19 | 1.93E+09 |
| 2089 | 1.15 | 1.55E+04 |
| 2090 | 0.24 | 2.09E+09 |
| 2091 | 0.19 | 7.86E+08 |
| 2092 | 0.10 | 1.93E+09 |
| 2093 | 0.42 | 5.39E+05 |
| 2094 | 0.43 | 6.93E+04 |
| 2095 | 0.13 | 7.54E+08 |
| 2096 | 0.21 | 2.01E+05 |
| 2097 | 0.23 | 5.42E+06 |
| 2098 | 0.30 | 1.89E+05 |
| 2099 | 0.24 | 1.80E+04 |
| 2100 | 1.13 | 9.19E+02 |
| 2101 | 1.05 | 2.03E+03 |
| 2102 | 1.09 | 7.52E+03 |
| 2103 | 1.26 | 1.80E+03 |
| 2104 | 1.02 | 2.07E+03 |
| 2105 | 1.09 | 8.50E+02 |
| 2106 | 1.19 | 7.00E+06 |
| 2107 | 1.34 | 1.20E+03 |
| 2108 | 1.09 | 7.31E+02 |
| 2109 | 1.15 | 1.35E+03 |
| 2110 | 0.99 | 1.23E+03 |
| 2111 | 0.99 | 4.33E+05 |
| 2112 | 1.09 | 9.46E+02 |
| 2113 | 0.09 | 8.06E+08 |
| 2114 | 0.94 | 3.13E+04 |
| 2115 | 0.99 | 9.25E+03 |
| 2116 | 1.01 | 1.23E+04 |
| 2117 | 0.78 | 3.64E+04 |
| 2118 | 1.00 | 1.31E+04 |
| 2119 | 0.48 | 2.41E+05 |
| 2120 | 0.48 | 1.13E+04 |
| 2121 | 0.62 | 6.97E+03 |
| 2122 | 0.39 | 7.79E+03 |
| 2123 | 0.09 | 1.19E+09 |
| 2124 | 0.09 | 1.84E+09 |
| 2125 | 0.10 | 1.04E+09 |

FIGURE 37 (continued)

| | | |
|---|---|---|
| 2126 | 0.50 | 1.52E+05 |
| 2127 | 1.05 | 1.40E+06 |
| 2128 | 0.10 | 9.27E+08 |
| 2129 | 0.10 | 9.59E+08 |
| 2130 | 0.10 | 1.10E+09 |
| 2131 | 0.10 | 8.76E+08 |
| 2132 | 1.21 | 8.98E+03 |
| 2133 | 0.12 | 7.24E+08 |
| 2134 | 1.07 | 4.11E+03 |
| 2135 | 0.33 | 6.59E+05 |
| 2136 | 0.09 | 1.73E+09 |
| 2137 | 0.09 | 1.13E+09 |
| 2138 | 1.16 | 2.04E+04 |
| 2139 | 0.09 | 7.09E+08 |
| 2140 | 0.85 | 8.74E+04 |
| 2141 | 0.19 | 2.03E+04 |
| 2142 | 0.88 | 1.19E+06 |
| 2143 | 0.54 | 2.61E+06 |
| 2164 | 0.11 | 3.17E+08 |
| 2165 | 0.11 | 3.67E+08 |
| 2166 | 0.56 | 2.34E+04 |
| 2167 | 0.13 | 9.74E+08 |
| 2148 | 0.12 | 2.01E+09 |
| 2149 | 1.06 | 9.57E+03 |
| 2150 | 1.09 | 8.18E+05 |
| 2151 | 1.07 | 8.33E+05 |
| 2152 | 0.09 | 6.38E+08 |
| 2153 | 0.85 | 1.12E+06 |
| 2154 | 0.98 | 1.31E+06 |
| 2155 | 0.50 | 9.99E+05 |
| 2156 | 0.11 | 9.04E+08 |
| 2157 | 0.37 | 7.10E+07 |
| 2158 | 0.10 | 6.65E+08 |
| 2159 | 0.87 | 1.01E+06 |
| 2160 | 0.12 | 6.33E+08 |
| 2161 | 0.15 | 3.43E+08 |
| 2162 | 0.12 | 6.64E+08 |
| 2163 | 0.10 | 1.23E+09 |

FIGURE 37 (continued)

| | | |
|---|---|---|
| **2144** | 1.09 | 8.40E+03 |
| **2145** | 0.55 | 1.41E+07 |
| **2146** | 0.11 | 1.48E+09 |
| **2147** | 0.15 | 1.08E+09 |
| **2168** | 0.09 | 7.92E+08 |
| **2169** | 0.11 | 1.49E+09 |
| **2170** | 0.10 | 2.46E+09 |
| **2171** | 0.09 | 1.83E+09 |
| **2172** | 0.10 | 1.23E+09 |
| **2173** | 0.10 | 1.68E+09 |
| **2174** | 0.09 | 1.48E+09 |
| **2175** | 1.04 | 1.44E+04 |
| **2176** | 0.97 | 1.51E+06 |
| **2177** | 1.30 | 1.31E+03 |
| **2178** | 0.85 | 3.67E+04 |

FIGURE 37(continued)

TABLE 29

| NP # | A511: nluc | LP124:nluc | LP124/A511 RLU output |
|---|---|---|---|
| 1997 | 5.13E+05 | 1.03E+09 | 2.01E+03 |
| 1998 | 4.47E+05 | 7.04E+08 | 1.58E+03 |
| 1999 | 4.15E+05 | 7.03E+08 | 1.69E+03 |
| 2000 | 4.60E+05 | 7.44E+08 | 1.62E+03 |
| 2001 | 3.76E+05 | 7.40E+08 | 1.97E+03 |
| 2002 | 4.39E+05 | 2.40E+08 | 5.47E+02 |
| 2003 | 1.25E+02 | 2.97E+06 | 2.38E+04 |
| 2004 | 1.69E+02 | 2.48E+06 | 1.47E+04 |
| 2005 | 8.90E+01 | 1.91E+06 | 2.15E+04 |
| 2006 | 1.90E+01 | 2.27E+03 | 1.20E+02 |
| 2007 | 4.55E+06 | 1.03E+09 | 2.27E+02 |
| 2008 | 4.69E+06 | 1.49E+09 | 3.18E+02 |
| 2009 | 8.22E+06 | 7.14E+08 | 8.68E+01 |
| 2010 | 5.70E+01 | 1.41E+05 | 2.48E+03 |
| 2011 | 1.20E+01 | 9.53E+04 | 7.94E+03 |
| 2012 | 1.50E+01 | 1.96E+03 | 1.31E+02 |
| 2013 | 1.20E+01 | 4.57E+03 | 3.81E+02 |
| 2014 | 9.00E+00 | 6.58E+04 | 7.31E+03 |
| 1869 | 6.15E+06 | 4.63E+08 | 7.52E+01 |
| 1840 | 4.20E+01 | 5.68E+02 | 1.35E+01 |
| 1839 | 4.84E+06 | 4.14E+08 | 8.54E+01 |
| 2024 | 7.74E+06 | 2.00E+09 | 2.58E+02 |
| 2025 | 2.50E+06 | 9.29E+08 | 3.71E+02 |
| 2026 | 9.99E+05 | 8.12E+07 | 8.13E+01 |
| 2027 | 1.74E+06 | 2.18E+09 | 1.25E+03 |
| 2028 | 5.89E+06 | 5.25E+08 | 8.91E+01 |
| 2029 | 3.46E+02 | 8.97E+05 | 2.59E+03 |
| 2030 | 9.18E+06 | 4.29E+06 | 4.68E-01 |
| 2031 | 3.36E+03 | 3.22E+05 | 9.57E+01 |
| 2032 | 5.53E+06 | 8.40E+08 | 1.52E+02 |
| 2033 | 5.22E+06 | 8.34E+08 | 1.60E+02 |
| 2034 | 4.50E+06 | 9.17E+08 | 2.04E+02 |
| 2035 | 3.66E+06 | 1.02E+09 | 2.78E+02 |

FIGURE 38

| | | | |
|---|---|---|---|
| 2036 | 6.27E+06 | 1.25E+09 | 2.00E+02 |
| 2037 | 3.65E+06 | 8.85E+08 | 2.42E+02 |
| 2038 | 4.60E+01 | 8.38E+03 | 1.82E+02 |
| 2039 | 3.10E+01 | 1.71E+04 | 5.50E+02 |
| 2040 | 4.40E+01 | 2.20E+04 | 4.99E+02 |
| 2041 | 6.25E+06 | 7.90E+08 | 1.26E+02 |
| 2042 | 1.38E+03 | 2.60E+06 | 1.89E+03 |
| 2043 | 3.65E+02 | 1.51E+06 | 4.13E+03 |
| 2044 | 7.03E+02 | 1.54E+06 | 2.19E+03 |
| 2045 | 4.52E+02 | 1.85E+06 | 4.10E+03 |
| 2046 | 7.35E+02 | 3.69E+05 | 5.02E+02 |
| 2047 | 2.18E+02 | 5.60E+05 | 2.57E+03 |
| 2048 | 2.01E+02 | 5.59E+03 | 2.78E+01 |
| 2049 | 3.10E+02 | 5.39E+05 | 1.74E+03 |
| 2050 | 5.27E+02 | 6.97E+05 | 1.32E+03 |
| 2051 | 7.00E+00 | 2.43E+04 | 3.47E+03 |
| 2052 | 8.15E+06 | 5.51E+08 | 6.76E+01 |
| 2053 | 6.19E+06 | 2.63E+08 | 4.25E+01 |
| 2054 | 2.47E+06 | 2.25E+09 | 9.13E+02 |
| 2055 | 1.06E+07 | 1.79E+09 | 1.69E+02 |
| 2056 | 3.54E+06 | 1.24E+09 | 3.52E+02 |
| 2057 | 4.40E+01 | 1.38E+04 | 3.14E+02 |
| 2058 | 8.00E+00 | 2.17E+04 | 2.72E+03 |
| 2059 | 8.19E+06 | 1.94E+09 | 2.37E+02 |
| 2060 | 1.13E+03 | 1.62E+06 | 1.43E+03 |
| 2061 | 1.20E+03 | 2.51E+06 | 2.08E+03 |
| 2062 | 8.02E+02 | 3.04E+06 | 3.79E+03 |
| 2063 | 1.49E+03 | 8.85E+05 | 5.96E+02 |
| 2064 | 1.02E+04 | 1.21E+09 | 1.19E+05 |
| 2065 | 1.01E+03 | 2.52E+06 | 2.50E+03 |
| 1973 | 4.40E+01 | 1.27E+03 | 2.88E+01 |
| 1974 | 9.00E+00 | 5.58E+02 | 6.20E+01 |
| 1975 | 1.40E+01 | 2.05E+09 | 1.47E+08 |
| 1976 | 1.16E+07 | 1.01E+09 | 8.72E+01 |
| 1990 | 1.40E+01 | 5.21E+02 | 3.72E+01 |
| 1991 | 6.00E+00 | 7.81E+02 | 1.30E+02 |
| 1992 | 1.00E+01 | 5.54E+02 | 5.54E+01 |
| 1993 | 8.00E+00 | 5.49E+02 | 6.86E+01 |

FIGURE 38 (continued)

| | | | |
|---|---|---|---|
| **1994** | 9.00E+00 | 6.11E+02 | 6.79E+01 |
| **1995** | 8.00E+00 | 6.58E+02 | 8.23E+01 |
| **1996** | 5.07E+06 | 9.57E+08 | 1.89E+02 |
| **1977** | 6.55E+06 | 9.36E+08 | 1.43E+02 |
| **1978** | 2.00E+01 | 4.25E+03 | 2.12E+02 |
| **1979** | 8.00E+00 | 8.68E+02 | 1.09E+02 |
| **1980** | 1.45E+03 | 1.01E+06 | 7.00E+02 |
| **1981** | 1.00E+01 | 8.87E+02 | 8.87E+01 |
| **1982** | 3.30E+01 | 2.26E+04 | 6.85E+02 |
| **1983** | 1.47E+03 | 1.10E+05 | 7.52E+01 |
| **1984** | 2.07E+02 | 5.70E+05 | 2.75E+03 |
| **1985** | 5.78E+02 | 3.71E+05 | 6.42E+02 |
| **1986** | 1.27E+06 | 4.42E+08 | 3.49E+02 |
| **1987** | 1.13E+06 | 4.19E+08 | 3.72E+02 |
| **1988** | 1.32E+06 | 5.10E+08 | 3.87E+02 |
| **1989** | 5.02E+02 | 7.94E+03 | 1.58E+01 |
| **2015** | 1.00E+02 | 9.04E+04 | 9.04E+02 |
| **2016** | 1.49E+02 | 1.18E+05 | 7.90E+02 |
| **2017** | 1.18E+02 | 1.27E+05 | 1.08E+03 |
| **2018** | 1.34E+02 | 1.63E+05 | 1.22E+03 |
| **2019** | 1.46E+02 | 5.09E+04 | 3.48E+02 |
| **2020** | 1.40E+02 | 1.33E+08 | 9.48E+05 |
| **2021** | 8.20E+01 | 8.08E+03 | 9.86E+01 |
| **2022** | 3.60E+01 | 1.60E+04 | 4.45E+02 |
| **2023** | 4.40E+01 | 2.05E+05 | 4.67E+03 |

FIGURE 38 (continued)

TABLE 31

| NP # | A511/LP124 Clearance | A511/LP124 RLU |
|---|---|---|
| 2180 | 0.51 | 9425355 |
| 2181 | 0.91 | 4829460 |
| 2182 | 0.97 | 22478532 |
| 2183 | 0.21 | 1178748672 |
| 2184 | 0.95 | 8949 |
| 2185 | 1.08 | 3540 |
| 2186 | 0.93 | 13285696 |
| 2187 | 0.87 | 1446053376 |
| 2188 | 0.11 | 1317144704 |
| 2189 | 0.15 | 1227835136 |
| 2190 | 0.60 | 11299 |
| 2191 | 0.09 | 1444555264 |
| 2192 | 0.69 | 5535 |
| 2193 | 0.75 | 1314372736 |
| 2194 | 0.95 | 33425 |
| 2195 | 0.63 | 483384224 |
| 2196 | 0.11 | 1402767616 |
| 2197 | 0.97 | 12005105 |
| 2198 | 1.00 | 4624066 |
| 2199 | 1.05 | 13923259 |
| 2201 | 1.04 | 17701700 |
| 2200 | 1.09 | 13959437 |
| 2202 | 1.01 | 18058374 |
| 2203 | 1.19 | 15579639 |
| 2204 | 0.93 | 1058 |
| 2217 | 1.08 | 738479 |
| 2218 | 0.60 | 3828983 |
| 2222 | 0.89 | 3141 |
| 2234 | 1.47 | 111 |
| 2235 | 1.00 | 553 |

FIGURE 39

| | | |
|---|---|---|
| 2236 | 1.18 | 1656 |
| 2237 | 0.12 | 624961 |
| 2238 | 0.56 | 25193 |
| 2239 | 0.97 | 39008 |
| 2242 | 0.96 | 152481 |
| 2243 | 0.97 | 1249 |
| 2244 | 0.10 | 1478536320 |
| 2246 | 0.93 | 12594 |
| 2248 | 0.43 | 36580156 |
| 2249 | 0.17 | 43955716 |
| 2250 | 0.60 | 236283 |
| 2251 | 1.02 | 1681 |
| 2253 | 1.05 | 31609824 |
| 2254 | 0.98 | 1130 |
| 2256 | 0.98 | 30291 |
| 2257 | 1.06 | 134811 |
| 2258 | 1.00 | 1072 |
| 2260 | 0.17 | 38230588 |
| 2262 | 1.03 | 6718 |
| 2263 | 0.67 | 152658896 |
| 2265 | 0.89 | 1923 |
| 2267 | 0.92 | 86490696 |
| 2269 | 0.15 | 239873472 |
| 2270 | 0.13 | 1182304128 |
| 2271 | 0.98 | 9737881 |
| 2272 | 0.34 | 28609152 |
| 2275 | 0.91 | 22955124 |
| 2278 | 0.16 | 36394420 |
| 2281 | 1.17 | 8376739 |
| 2282 | 0.13 | 187224464 |
| 2283 | 0.79 | 4552574 |
| 2284 | 0.33 | 400019616 |

FIGURE 39 (continued)

| | | |
|---|---|---|
| 2287 | 0.12 | 334971200 |
| 2290 | 0.14 | 83818688 |
| 2291 | 0.45 | 11715284 |
| 2293 | 1.05 | 457 |
| 2295 | 0.97 | 45340 |
| 2296 | 0.91 | 13112 |
| 2298 | 0.66 | 153830 |
| 2299 | 1.01 | 586 |
| 2301 | 1.13 | 567 |
| 2302 | 0.56 | 3343962 |
| 2303 | 0.37 | 3420569 |
| 2305 | 0.15 | 331570720 |
| 2306 | 1.12 | 1588 |
| 2307 | 1.10 | 12765 |
| 2308 | 1.10 | 4390 |
| 2309 | 1.17 | 6388 |
| 2310 | 1.20 | 3387 |
| 2311 | 1.06 | 33898140 |
| 2312 | 0.19 | 19504462 |
| 2313 | 1.12 | 1712 |
| 2314 | 1.04 | 6168 |
| 2316 | 0.11 | 71091864 |
| 2318 | 0.11 | 337684704 |
| 2319 | 0.11 | 476671232 |
| 2320 | 0.99 | 5048 |
| 2321 | 1.02 | 4614 |
| 2323 | 0.60 | 10705072 |
| 2325 | 0.79 | 10092227 |
| 2327 | 0.90 | 175424880 |
| 2330 | 1.07 | 236237904 |
| 2331 | 0.92 | 3027250 |
| 2333 | 1.06 | 19965 |

FIGURE 39 (continued)

| | | |
|---|---|---|
| 2334 | 1.03 | 11160 |
| 2335 | 0.13 | 8174093 |
| 2336 | 0.61 | 38853036 |
| 2337 | 0.75 | 17568558 |
| 2340 | 0.16 | 92967936 |
| 2341 | 0.69 | 11054598 |

FIGURE 39 (continued)

Table 32

| | Phage | | | | | | Aqueous Solution | |
|---|---|---|---|---|---|---|---|---|
| Embodiments | A511::COP2 | LP124::COP2 | LP40::COP2 | A511::COP3 | LP124::COP3 | LP40::COP3 | Aqueous Solution composition comprising Tryptic Soy Broth, LiCl, nalidixic acid, yeast extract, glucose, MgSO4, pyruvate, HEPES | Aqueous Solution composition comprising Tryptic Soy Broth, LiCl, nalidixic acid, yeast extract, glucose, MgSO4, pyruvate, HEPES, TWEEN®-80, lecithin, and potassium phosphate |
| 1 | X | | | | | | | |
| 2 | | X | | | | | | |
| 3 | | | X | | | | | |
| 4 | | | | X | | | | |
| 5 | | | | | X | | | |
| 6 | | | | | | X | | |
| 7 | X | X | | | | | | |
| 8 | X | | X | | | | | |
| 9 | X | | | X | | | | |
| 10 | X | | | | X | | | |
| 11 | X | | | | | X | | |

FIGURE 40

| | | | | | | | | |
|---|---|---|---|---|---|---|---|---|
| 12 | X | | | | | | X | |
| 13 | X | | | | | | | X |
| 14 | | X | X | | | | | |
| 15 | | X | | X | | | | |
| 16 | | X | | | X | | | |
| 17 | | X | | | | X | | |
| 18 | | X | | | | | X | |
| 19 | | X | | | | | | X |
| 20 | | | X | X | | | | |
| 21 | | | X | | X | | | |
| 22 | | | X | | | X | | |
| 23 | | | X | | | | X | |
| 24 | | | X | | | | | X |
| 25 | | | | X | X | | | |
| 26 | | | | X | | X | | |
| 27 | | | | X | | | X | |
| 28 | | | | X | | | | X |
| 29 | | | | | X | X | | |
| 30 | | | | | X | | X | |
| 31 | | | | | X | | | X |
| 32 | | | | | | X | X | |
| 33 | | | | | | X | | X |
| 34 | X | X | X | | | | | |
| 35 | X | X | | X | | | | |
| 36 | X | X | | | X | | | |
| 37 | X | X | | | | X | | |
| 38 | X | X | | | | | X | |
| 39 | X | X | | | | | | X |
| 40 | X | | X | X | | | | |
| 41 | X | | X | | X | | | |

FIGURE 40 (continued)

| | | | | | | | | |
|---|---|---|---|---|---|---|---|---|
| 42 | X | | X | | | X | | |
| 43 | X | | X | | | | X | |
| 44 | X | | X | | | | | X |
| 45 | X | | | X | X | | | |
| 46 | X | | | X | | X | | |
| 47 | X | | | X | | | X | |
| 48 | X | | | X | | | | X |
| 49 | X | | | | X | X | | |
| 50 | X | | | | X | | X | |
| 51 | X | | | | X | | | X |
| 52 | X | | | | | X | X | |
| 53 | X | | | | | X | | X |
| 54 | | X | X | X | | | | |
| 55 | | X | X | | X | | | |
| 56 | | X | X | | | X | | |
| 57 | | X | X | | | | X | |
| 58 | | X | X | | | | | X |
| 59 | | X | | X | X | | | |
| 60 | | X | | X | | X | | |
| 61 | | X | | X | | | X | |
| 62 | | X | | X | | | | X |
| 63 | | X | | | X | X | | |
| 64 | | X | | | X | | X | |
| 65 | | X | | | X | | | X |
| 66 | | X | | | | X | X | |
| 67 | | X | | | | X | | X |
| 68 | | | X | X | X | | | |
| 69 | | | X | X | | X | | |
| 70 | | | X | X | | | X | |
| 71 | | | X | X | | | | X |

FIGURE 40 (continued)

| | | | | | | | | |
|---|---|---|---|---|---|---|---|---|
| 72 | | | X | | X | X | | |
| 73 | | | X | | X | | X | |
| 74 | | | X | | X | | | X |
| 75 | | | X | | | X | X | |
| 76 | | | X | | | X | | X |
| 77 | | | | X | X | X | | |
| 78 | | | | X | X | | X | |
| 79 | | | | X | X | | | X |
| 80 | | | | X | | X | X | |
| 81 | | | | X | | X | | X |
| 82 | | | | | X | X | X | |
| 83 | | | | | X | X | | X |
| 84 | X | X | X | X | | | | |
| 85 | X | X | X | | X | | | |
| 86 | X | X | X | | | X | | |
| 87 | X | X | X | | | | X | |
| 88 | X | X | X | | | | | X |
| 89 | X | X | | X | X | | | |
| 90 | X | X | | X | | X | | |
| 91 | X | X | | X | | | X | |
| 92 | X | X | | X | | | | X |
| 93 | X | X | | | X | X | | |
| 94 | X | X | | | X | | X | |
| 95 | X | X | | | X | | | X |
| 96 | X | X | | | | X | X | |
| 97 | X | X | | | | X | | X |
| 98 | X | | X | X | X | | | |
| 99 | X | | X | X | | X | | |
| 100 | X | | X | X | | | X | |
| 101 | X | | X | X | | | | X |

FIGURE 40 (continued)

| | | | | | | | | |
|---|---|---|---|---|---|---|---|---|
| 102 | X | | X | | X | X | | |
| 103 | X | | X | | X | | X | |
| 104 | X | | X | | X | | | X |
| 105 | X | | X | | | X | X | |
| 106 | X | | X | | | X | | X |
| 107 | X | | | X | X | X | | |
| 108 | X | | | X | X | | X | |
| 109 | X | | | X | X | | | X |
| 110 | X | | | X | | X | X | |
| 111 | X | | | X | | X | | X |
| 112 | X | | | | X | X | X | |
| 113 | X | | | | X | X | | X |
| 114 | | X | X | X | X | | | |
| 115 | | X | X | X | | X | | |
| 116 | | X | X | X | | | X | |
| 117 | | X | X | X | | | | X |
| 118 | | X | X | | X | X | | |
| 119 | | X | X | | X | | X | |
| 120 | | X | X | | X | | | X |
| 121 | | X | X | | | X | X | |
| 122 | | X | X | | | X | | X |
| 123 | | X | | X | X | X | | |
| 124 | | X | | X | X | | X | |
| 125 | | X | | X | X | | | X |
| 126 | | X | | X | | X | X | |
| 127 | | X | | X | | X | | X |
| 128 | | X | | | X | X | X | |
| 129 | | X | | | X | X | | X |
| 130 | | X | | | X | | | X |
| 131 | | | X | X | X | X | | |

FIGURE 40 (continued)

| | | | | | | | | |
|---|---|---|---|---|---|---|---|---|
| 132 | | | X | X | X | | X | |
| 133 | | | X | X | X | | | X |
| 134 | | | X | X | | X | X | |
| 135 | | | X | X | | X | | X |
| 136 | | | X | | X | X | X | |
| 137 | | | X | | X | X | | X |
| 138 | | | | X | X | X | X | |
| 139 | | | | X | X | X | | X |
| 140 | X | X | X | X | X | | | |
| 141 | X | X | X | X | | X | | |
| 142 | X | X | X | X | | | X | |
| 143 | X | X | X | X | | | | X |
| 144 | X | X | X | | X | X | | |
| 145 | X | X | X | | X | | X | |
| 146 | X | X | X | | X | | | X |
| 147 | X | X | X | | | X | X | |
| 148 | X | X | X | | | X | | X |
| 149 | X | X | | X | X | X | | |
| 150 | X | X | | X | X | | X | |
| 151 | X | X | | X | X | | | X |
| 152 | X | X | | X | | X | X | |
| 153 | X | X | | X | | X | | X |
| 154 | X | X | | X | | | X | |
| 155 | X | X | | | X | X | X | |
| 156 | X | X | | | X | X | | X |
| 157 | X | | X | X | X | X | | |
| 158 | X | | X | X | X | | X | |
| 159 | X | | X | X | X | | | X |
| 160 | X | | X | X | | X | X | |
| 161 | X | | X | X | | X | | X |

FIGURE 40 (continued)

| | | | | | | | | |
|---|---|---|---|---|---|---|---|---|
| 162 | X | | X | X | | | X | |
| 163 | X | | X | | X | X | X | |
| 164 | X | | X | | X | X | | X |
| 165 | X | | X | | X | X | | |
| 166 | X | | | X | X | X | X | |
| 167 | X | | | X | X | X | | X |
| 168 | X | | | X | X | | X | |
| 169 | | X | X | X | X | X | | |
| 170 | | X | X | X | X | | X | |
| 171 | | X | X | X | X | | | X |
| 172 | | X | X | X | | X | X | |
| 173 | | X | X | X | | X | | X |
| 174 | | X | X | | X | X | X | |
| 175 | | X | X | | X | X | | X |
| 176 | | X | | X | X | X | X | |
| 177 | | X | | X | X | X | | X |
| 178 | | | X | X | X | X | X | |
| 179 | | | X | X | X | X | | X |
| 180 | X | X | X | X | X | X | | |
| 181 | X | X | X | X | X | | X | |
| 182 | X | X | X | X | X | | | X |
| 183 | X | X | X | | X | X | X | |
| 184 | X | X | X | | X | X | | X |
| 185 | X | X | | X | X | X | X | |
| 186 | X | X | | X | X | X | | X |
| 187 | X | | X | X | X | X | X | |
| 188 | X | | X | X | X | X | | X |
| 189 | | X | X | X | X | X | X | |
| 190 | | X | X | X | X | X | | X |

FIGURE 40 (continued)

CODON OPTIMIZED RECOMBINANT PHAGE AND METHODS OF USING SAME

RELATED APPLICATIONS

This application claims priority to, and the benefit of U.S. Provisional Application No. 61/991,132 filed on May 9, 2014, U.S. Provisional Application No. 62/044,082 filed on Aug. 29, 2014, U.S. Provisional Application No. 62/053,481 filed on Sep. 22, 2014, and U.S. Provisional Application No. 62/086,445 filed Dec. 2, 2014, the contents of each of which are incorporated herein by reference in their entireties.

FIELD OF THE DISCLOSURE

This disclosure generally relates to the detection of microbes through the use of codon-optimized recombinant phage.

INCORPORATION OF SEQUENCE LISTING

The contents of the text file named "SAM6-017 SEQ Listing_ST25.txt", which was created on May 7, 2015 and is 155 KB in size, are hereby incorporated by reference in their entirety.

BACKGROUND

Bacterial contamination and infection is a significant problem to public health and in many other areas. Bacterial food borne diseases pose a significant threat to human health, estimated to cause as many as about 76 million illnesses, 325,000 hospitalizations, and 5,000 deaths in the US annually.

For example, in 1996, juice that was contaminated with *Escherichia coli* was released into the public by a juice maker and resulted in one death and 66 illnesses. The company paid a $1.5 million fine, and the recall alone cost the company $6.5 million. In 2006, an *E. coli* O157:H7 outbreak from contaminated spinach originating from California resulted in 205 illnesses and 3 deaths. In 2011 a listeriosis outbreak from cantaloupes from Colorado in July, August and September resulted in 30 deaths. That is the second deadliest recorded U.S. outbreak in terms of the number of deaths since the Centers for Disease Control and Prevention began tracking outbreaks in the 1970s. Another recall of cantaloupes in 2012 suggests that the food supply is still not safe and highlights the general and pervasive need for additional methods and reagents for testing the food supply to identify contamination.

Another example is bovine mastitis, an infection caused by bacterial cells that results in the inflammation of the bovine breast, reduction in milk yield and a decrease in milk quality. This condition is caused by the bacteria *Staphylococcus aureus* and *Staphylococcus agalactiae*. This reduction in milk yields and quality in the western world alone have been suggested to cause annual financial losses of $3.7 billion.

Another example is bovine tuberculosis (*Mycobacterium bovis*), a bacteria that causes financial loses worldwide. In 2005, for example, 12 of a herd of 55 cattle in a small Michigan farm tested positive for bovine tuberculosis. The farm was forced to destroy the entire herd of cattle, along with an entire herd of hogs. Tuberculosis testing in cattle requires the animal to be held for 2 days, and tests are false positive 5 percent of the time. Often entire herds have to be quarantined or destroyed. The annual worldwide financial losses have been estimated at $3 billion.

Tuberculosis is a leading cause of death worldwide. One third of the world's population is infected with *Mycobacterium tuberculosis*, the bacterium that causes tuberculosis. Every day 25,000 people are infected and 5,000 people die from the disease. Furthermore, due primarily to poor diagnosis, multidrug resistant strains of *M. tuberculosis* are emerging and the reemergence of tuberculosis as a worldwide epidemic has become a real threat. The worldwide annual market for tuberculosis diagnostics has been estimated at $1.8 billion.

MRSA is a drug-resistant version of the common *Staphylococcus aureus* bacteria and is contagious, due to the nature of the MRSA bacterium. The bacteria are highly contagious and spread by touch. Approximately 86% of all infections occur within hospitals, and these infections carry a 20% mortality rate. This bacterium costs an average of $21,000 over the standard costs to treat, and kills approximately 19,000 people in the US annually.

*Listeria monocytogenes* is an intracellular pathogen that can cause invasive disease in humans and animals. Approximately 99% of human listeriosis infections appear to be food borne. While *L. monocytogenes* has been isolated from a variety of raw and ready-to-eat foods, most human listeriosis infections appear to be caused by consumption of RTE foods that permit postcontamination growth of this pathogen. Listeriosis is estimated to be responsible for about 500 deaths per year in the United States, accounting for 28% of annual deaths attributable to known food-borne patho-gens, second only to deaths due to *Salmonella* infections.

Methods and systems exist for detecting microbial contamination. Such methods and systems suffer from a number of drawbacks, including the need in most cases to remove a potentially contaminated sample from the environment where it is collected and transferring it to a laboratory environment, where the sample is placed in a culture environment for enrichment and growth over a long period of time, ranging from many hours to days. Additionally, because these labs are frequently offsite there is often a delay in the shipping of a sample to a laboratory. Once enriched, samples are typically analyzed using expensive equipment, traditional culturing methods, PCR and other methods. Thus, current processes often comprise a large time lag between sampling and a result, during which time the sampled conditions may have changed and the results of the assay cannot be utilized to diagnose an infection in a patient or to act on contamination in a lot of manufactured food, for example. Accordingly, new composition, methods, and kits for detecting microbial contamination are needed. Compositions and methods of the present disclosure address these needs.

SUMMARY

Compositions and methods of the disclosure address the long-felt need in the art for compositions and methods of immediate detection of bacterial infection by a non-technical or layperson at the site of potential contamination.

Compositions and methods of the disclosure may be used to detect a target microbe within minutes of contacting a recombinant phage of the disclosure to a target microbe. This important feature of the compositions and methods of the disclosure enables the user to not only identify sources of contamination on-site, but also, to contain the target microbe before it can spread. This advantage stands in sharp contrast to existing methods of detecting microbial infections, in which a sample of a potentially contaminated item must be sent to a laboratory to be analyzed using time-intensive and expensive techniques that require specialized scientific training to perform.

Compositions and methods of the disclosure may be used by a non-technical or layperson. Compositions and kits of the disclosure include at least one recombinant phage, an aqueous solution to contain the recombinant phage and facilitate infection of the target microbe, a substrate for the marker, and an aqueous solution to contain the substrate for the marker. In a preferred embodiment, each component of the kits of the disclosure are provided in the kit in separate containers. To initiate contact between a recombinant phage and target microbe of the disclosure, the user need only combine the contents of the kit with the target microbe, either directly onto a surface or item of interest or by taking a sample of the surface or item and mixing the test sample in a container with the compositions of the kit. When a recombinant phage of the disclosure contacts the target microbe, a signal is produced that may be detected by visual inspection alone. For example, when the codon-optimized marker of the recombinant phage is luciferase, upon contact with the target microbe in the presence of a marker substrate (e.g. luciferin), visible light will be emitted from the resultant mixture. Enhancement of the signal may be accomplished by decreasing the intensity of light sources in proximity to the resultant mixture.

Compositions and methods of the disclosure may be used to detect a target microbe at the site of potential contamination. For example, compositions and methods of the disclosure may be used to detect a target microbe in food or an environment containing food and/or other agricultural products at any point along a food supply chain ranging including a location of harvesting or import; a processing or distribution facility; a storage facility; a transportation vehicle; a market, restaurant or point of sale to a consumer; or any point in between. Moreover, compositions and methods of the disclosure may be used to detect bacterial infection in the context of medical treatment, including a field hospital, emergency medical tent, refuge center, clinic, physician office, hospital or any other location at which subjects are at risk of contracting an infection. Government regulatory agencies may also use the compositions and methods of the disclosure to test for contamination of imported products, bodies of water (and in particular, supplies of drinking water), public facilities, and security checkpoints (in the interest of identifying biological hazards and/or weapons).

Compositions of the disclosure include at least one recombinant phage capable of infecting a target microbe, wherein the recombinant phage contains a codon-optimized marker that, upon contact with the target microbe, produces a detectable signal. Preferred embodiments of the recombinant phages of the disclosure contain a nucleic acid sequence encoding a codon-optimized luciferase enzyme. Codon optimization of the sequence encoding a marker provides the recombinant phage with increased sensitivity and specificity to the target microbe. For example, when used to detect bacterial contamination in a food sample, distinguishing between those bacteria in the sample that mediate infection (and subsequent illness in animals or humans) from those bacteria that do not cause infection is a significant challenge. Codon optimization of the sequence encoding a the marker of the recombinant phage is a feature that enables the recombinant phage described herein to specifically identify target microbes among bacterial populations that are not harmful.

Compositions and methods of the disclosure include at least one recombinant phage containing a sequence that encodes a codon-optimized marker to detect microbes. Compositions and methods of the disclosure may also include an optimized aqueous formulation for the detection of microbes in unfavorable conditions or environments. Exemplary unfavorable conditions include, but are not limited to, those conditions or environments in which traces of sanitizing solutions are present that, without the inclusion of the optimized aqueous formulation, may otherwise impede the activity of the recombinant phage of the disclosure.

Compositions of the disclosure include at least one recombinant phage capable of infecting a target microbe, the phage containing at least a capsid protein sequence, a ribosome binding site, and a codon-optimized marker. In certain embodiments, a composition includes at least two, three, four, five, or six recombinant phages capable of infecting a target microbe, wherein each of the phage includes at least a capsid protein sequence, a ribosome binding site, and a codon-optimized marker. Compositions of the disclosure may include greater than six recombinant phages capable of infecting a target microbe, wherein each of the phage includes at least a capsid protein sequence, a ribosome binding site, and a codon-optimized marker.

Compositions and methods of the disclosure may be used to contact and/or detect a target microbe located on any surface or material. For example, the target microbe may be located in a liquid, solid or gel. The target microbe may be located on any material, including, but not limited to, glass, metal, brick, concrete, slab, tile, stone, or rug. By way of non-limiting example, the target microbe may be located in or on an agriculture product as well as in or on any surface or portion of an environment in proximity to an agricultural product (e.g. on a floor, sink, or wall). Recombinant phages of the disclosure contain a ribosome binding site. When a composition includes more than one recombinant phage, the ribosome binding site of each phage may be distinct or identical to the ribosome binding sites in the other phages of the composition. In certain embodiments, the ribosome binding site of each phage is SEQ ID NO: 54. In a related embodiment, the ribosome binding site is 70% identical to SEQ ID NO: 54.

Recombinant phages of the disclosure contain a codon-optimized marker. In certain embodiments, the codon-optimized marker is luciferase. In a related embodiment, the codon-optimized marker is SEQ ID NO: 36 (also referred to as COP2). Alternatively, the codon-optimized marker is SEQ ID NO: 37 (also referred to as COP3). In another embodiment, the codon-optimized marker further includes an affinity tag. The affinity tag may be a HIS tag.

In certain embodiments, compositions of the disclosure contain at least one recombinant phage of the composition selected from the group consisting of LP143, A511, LP101, LP124, LP99, LP48, LP125, P100, and LP40. Exemplary compositions of the disclosure include at least one recombinant phage of the composition, wherein the recombinant phage is A511, LP40 or LP124. Alternatively, compositions of the disclosure include A511, LP40 and LP124. In another embodiment, the at least one recombinant phage is A511. In another embodiment, the at least one recombinant phage is LP40. In another embodiment, the at least one recombinant phage is LP124.

Target microbes of the disclosure include, but are not limited to, coliform bacteria, *Escherichia, Shigella, Listeria, Clostridium, Vibrio*, Enterobacteriacae, Cronobacter, *Mycobacterium, Staphylococcus, Bacillus, Campylobacter,*

*Pseudomonas, Streptococcus, Acinetobacter, Klebsiella, Campylobacter*, and *Yersinia*.

A target microbe of the disclosure may belong to the genus *Listeria*. Exemplary species of *Listeria* include, but are not limited to, *Listeria* selected from the group consisting of *Listeria innocua, Listeria monocytogenes, Listeria seeligeri, Listeria ivanovii, Listeria grayi, Listeria marthii, Listeria rocourti, Listeria welshimeri, Listeria floridensis, Listeria aquatic, Listeria cornellensis, Listeria riparia, Listeria weihenstephanensis, Listeria flieschmannii*, and *Listeria grandensis*.

In another embodiment of the disclosure, the target microbe is *Listeria monocytogenes*.

Compositions of the disclosure include at least one recombinant phage and an aqueous solution, wherein the aqueous solution includes: a) at least one nutrient; b) at least one selective agent suitable to inhibit growth of at least one non-target microbe in an environmental sample or an agricultural sample; c) at least one vitamin; d) at least one divalent metal; and e) at least one buffering agent capable of maintaining the composition at pH 7.0-7.5. Compositions of the disclosure include at least one recombinant phage and an aqueous solution, wherein the aqueous solution includes: a) at least one nutrient; b) at least one selective agent suitable to inhibit growth of at least one non-target microbe in an environmental sample or an agricultural sample; c) at least one vitamin; d) at least one divalent metal ion; and e) at least one buffering agent capable of maintaining the composition at pH 7.0-7.5. In certain embodiments of the aqueous solution, the at least one nutrient is a culture medium, alcohol, sugar, sugar derivatives, or a combination thereof.

In certain embodiments of the aqueous solution, the at least one nutrient is Brain Heart Infusion medium, Tryptic Soy Broth, glucose, glycerol, pyruvate, or a combination thereof.

In certain embodiments of the aqueous solution, the at least one selective agent suitable to inhibit growth of a non-target microbe is LiCl, acriflavine, nalidixic acid, cycloheximide, or a combination thereof.

In certain embodiments of the aqueous solution, the at least one vitamin comprises yeast extract.

In certain embodiments of the aqueous solution, the at least one divalent metal or divalent metal ion is $CaCl_2$, MgSO4, or a combination thereof.

In certain embodiments of the aqueous solution, the at least one buffering agent includes HEPES buffer.

In a preferred embodiment, the aqueous solution includes Tryptic Soy Broth, LiCl, nalidixic acid, yeast extract, glucose, $MgSO_4$, pyruvate, and HEPES. For example, the aqueous solution consists of Tryptic Soy Broth, LiCl, nalidixic acid, yeast extract, glucose, $MgSO_4$, pyruvate, and HEPES (and may be referred to herein as NIB12).

In another preferred embodiment, the aqueous solution includes Tryptic Soy Broth, LiCl, nalidixic acid, yeast extract, glucose, $MgSO_4$, pyruvate, HEPES, TWEEN®-80, lecithin, and potassium phosphate. For example, the aqueous solution consists of Tryptic Soy Broth, LiCl, nalidixic acid, yeast extract, glucose, $MgSO_4$, pyruvate, HEPES, TWEEN®, lecithin, and potassium phosphate (and may be referred to herein as NIB14).

Compositions of the disclosure may include at least one agent to prevent the decomposition of a marker. For example, compositions of the disclosure may include at least one recombinant phage capable of infecting a target microbe, an aqueous solution, and at least one agent to prevent the decomposition of a marker.

Exemplary compounds prevent decomposition of the marker until after the recombinant phage contacts a target microbe and the marker produces a detectable signal. Exemplary compounds may prevent decomposition of the marker during manufacture, during storage in a kit, during combination with one or more components of a kit, during contact and/or reaction with a substrate in the presence of a target microbe, and/or during production of a signal indicating the presence of a target microbe. For example, following combination of the marker with one or more components of a kit, including a recombinant phage, an aqueous solution, and/or a marker substrate, the compound prevents decomposition of the marker for an hour, 5 hours, 5 to 10 hours, greater than 10 hours or any duration in between. In certain embodiments, the compound prevents decomposition of the marker for less than 5 hours, for between 5 and 10 hours, or for greater than 10 hours.

In a related embodiment, the compound to prevent the decomposition of a marker substrate prevents decomposition of luciferin.

In another embodiment, the at least one agent to prevent decomposition of the marker substrate, including those embodiments in which the marker substrate is luciferin, is selected from the group consisting of non-ionic detergents, oxygen scavengers and emulsifiers.

In another embodiment, the at least one agent to prevent decomposition of the marker substrate, including those embodiments in which the marker substrate is luciferin, is selected from the group consisting of: sodium metabisulfite, sodium thiosulfate, TWEEN®-80, HEPES and lecithin.

In another embodiment, the composition further includes at least one agent suitable to neutralize a sanitizer present in an environmental sample. Exemplary agents suitable to neutralize a sanitizer include, but are not limited to, sodium metabisulfite, sodium thiosulfate, TWEEN®-80, HEPES and lecithin.

Compositions of the disclosure may include a substrate for the codon-optimized marker. In certain embodiments, the codon-optimized marker is luciferase. When the codon-optimized marker is luciferase, the substrate includes luciferin.

Compositions of the disclosure may include a buffer to facilitate a light reaction. For example, compositions of the disclosure include at least one recombinant phage containing a sequence encoding a codon-optimized marker, wherein the marker is a codon-optimized luciferase, the composition includes luciferin as a substrate for the marker, and the composition includes a buffer to facilitate a light reaction.

The disclosure provides a kit, wherein the kit includes a composition that includes at least one recombinant phage capable of infecting a target microbe, the at least one recombinant phage containing at least a capsid protein sequence, a ribosome binding site, and a codon-optimized marker. The composition may include at least one recombinant phage of the disclosure and an aqueous solution of the disclosure. The composition may include at least one recombinant phage of the disclosure, an aqueous solution of the disclosure, and a marker substrate. The composition may include at least one recombinant phage of the disclosure, an aqueous solution of the disclosure, a marker substrate, and a buffer composition to facilitate a light reaction. In certain embodiments of a kit of the disclosure, each of the at least one recombinant phage of the disclosure, an aqueous solution of the disclosure, a marker substrate, and a buffer composition to facilitate a light reaction are stored in separate containers. Kits of the disclosure may optionally include an instrument for obtaining a sample of microbes for testing and/or a sterile container for combining one or more of the compositions of the kit with the target microbe.

In a preferred embodiment, a kit includes: a first container including at least one recombinant phage capable of infecting a target microbe, said phage containing at least a capsid protein sequence, a ribosome binding site, and a codon-optimized marker; a second container including an aqueous solution composition containing Tryptic Soy Broth, LiCl, nalidixic acid, yeast extract, glucose, $MgSO_4$, pyruvate, HEPES, TWEEN®-80, lecithin, and potassium phosphate; a third container containing a marker substrate; and a fourth container containing a buffer to optimize light detection. In certain embodiments of this kit, the kit further includes a swab and/or a sterile container for mixing the contents of the kit with a target microbe.

This kit may further include a container for facilitating detection of light.

The disclosure provides methods of determining the presence or absence of a target microbe in an environmental sample, an agricultural sample or both, including: a) contacting an environmental sample, an agricultural sample, or both with a composition of the disclosure to form a test sample; and b) detecting the presence or absence of light thereby determining the presence or absence of a target microbe in an environmental sample and/or an agricultural sample.

In certain embodiments of the methods of the disclosure, the environmental sample may include a fixed feature of an environment that is not removed from its context within the environment but, rather, is tested in situ. For example, in the environment of a building, the floor may be an environmental sample when the compositions, kits, and methods described herein are applied to a portion of the floor without isolating or removing any portion of the floor for testing. Alternatively, the environmental sample may include a portable feature of an environment that may be removed from its context for testing. For example, in the environment of a building, an individual floor file may be isolated or removed from the surrounding tiles for application of the compositions, kits, and methods of the disclosure. Non-limiting examples of environmental samples include a surface, a container, or a machine or part thereof. Exemplary environments and/or environmental samples also include a processing plant, a storage facility, a health care facility, an educational institution, a loading dock, a cargo hold, a vehicle, an airport, and a customs facility.

In certain embodiments, the environmental sample is from a health care facility.

Exemplary the health care facilities include a clinic, an emergency medical services location, a hospice, a hospital ship, a hospital train, a hospital, a military medical installation, a doctor's office, a long term care facility, respite care facility, and a quarantine station.

Environmental samples of the disclosure may include or be obtained from a food production facility. Exemplary food production facilities include, but are not limited to, a farm, a boat, a food distribution facility, a food processing plant, a food retail location, a home, or a restaurant.

In certain embodiments of the methods of the disclosure, the agricultural sample includes stock feed or food supply. Agricultural samples may be intended for use by animals (including research subjects and those animals raised for butchering or entering the food supply) as well as humans. The term food supply includes plant and animal matter, including but not limited to, a dairy product, a fruit product, a grain product, a sweet, a vegetable product, a meat product, or any combination thereof. Agricultural and food products may either solid, liquid, or a mixture thereof.

Exemplary dairy products include food products derived from milk, butter, yogurt, cheese, ice cream, queso fresco, or any combination thereof Exemplary fruit products include apples, oranges, bananas, berries, lemons, or any combination thereof.

Exemplary grain products includes wheat, rice, oats, barley, bread, pasta, or any combination thereof.

Exemplary sweet products include candy, soft drinks, cake, pie, or any combination thereof.

Exemplary vegetable products include spinach, carrots, onions, peppers, avocado, broccoli, or any combination thereof. The vegetable product may include guacamole.

Exemplary meat products include any portion of a chicken, fish, turkey, pork, beef, or any combination thereof. Meat products may include whole muscle meat, ground meats, or any combination thereof.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present disclosure, and be protected by the accompanying claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a map of the insertion site in the A511:COP2 engineered phage.

FIG. 2 is a map of the insertion site in the LP124::COP2 engineered phage.

FIG. 3 is a map of the insertion site in the LP40::COP2 engineered phage.

FIG. 17A depicts the effects of using either buffer in the presence of various concentrations of F29 on phage infection activity. FIG. 17B depicts the effects of using either buffer in the presence of various concentrations of F29 on enzymatic activity. FIG. 17C depicts the effects of using either buffer during exposure of the NanoGlo luciferin to various concentrations of the F29 solution. FIG. 17D depicts a table with a summary of the results obtained from this series of experiments. When graphs are depicted, the y-axis represents percentage activity compared to no addition of F29.

FIG. 22A-M is a series of graphs that depict the time course of *L. innocua* and *L. monocytogenes* detection in various food samples. *L. innocua* or *L. monocytogenes* was added to the food samples for defined amounts of time, followed by infection with a recombinant, luciferase encoding phage and subsequent detection of the luciferin signal. The food samples used in the assays included potato salad (FIGS. 22A, 22B, 22H, and 22I), smoked salmon (FIGS.

Figure 22E:
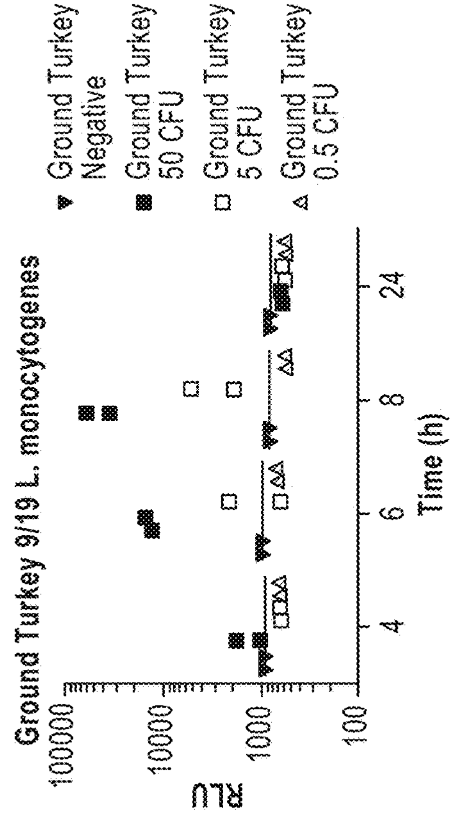
Figure 22F:
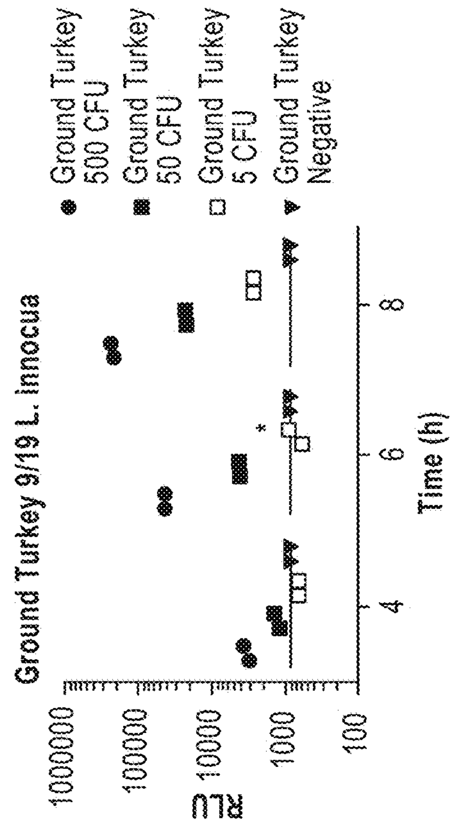
Figure 22G:
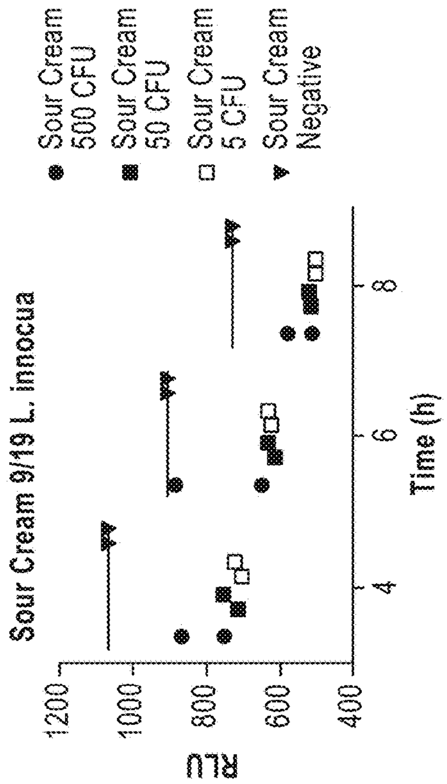
Figure 22H:
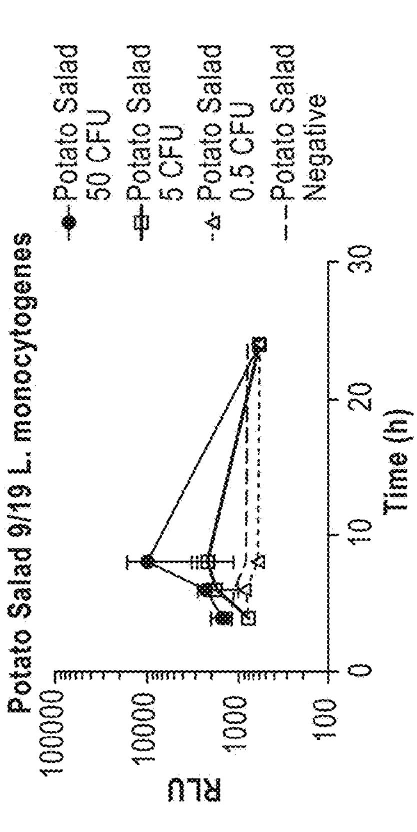
Figure 22I:
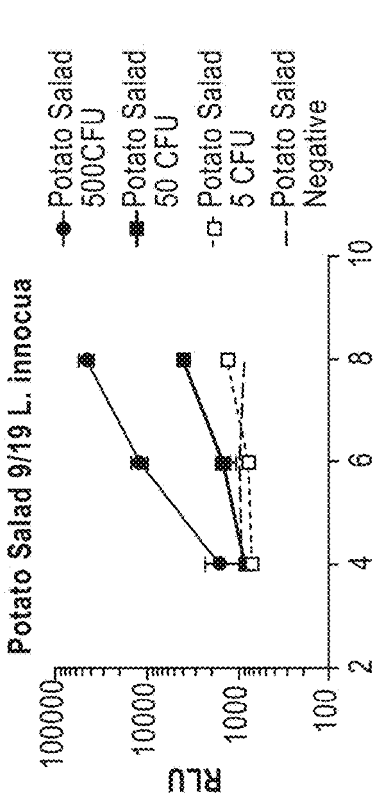
Figure 22J:
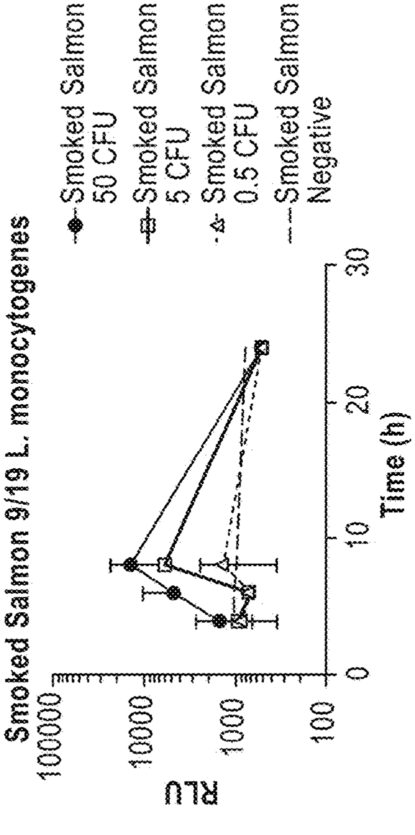
Figure 22K:
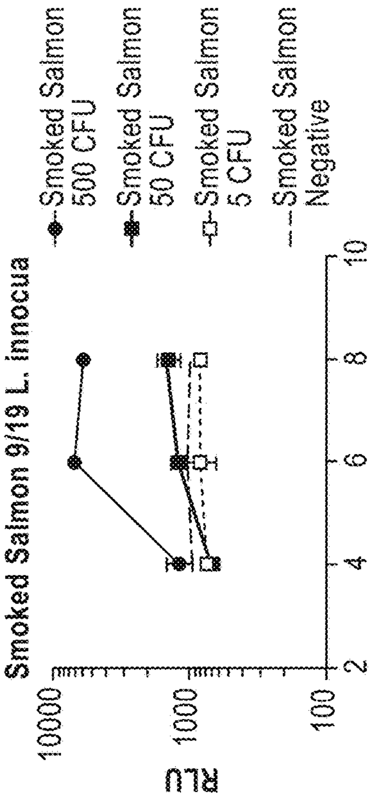
Figure 22L:
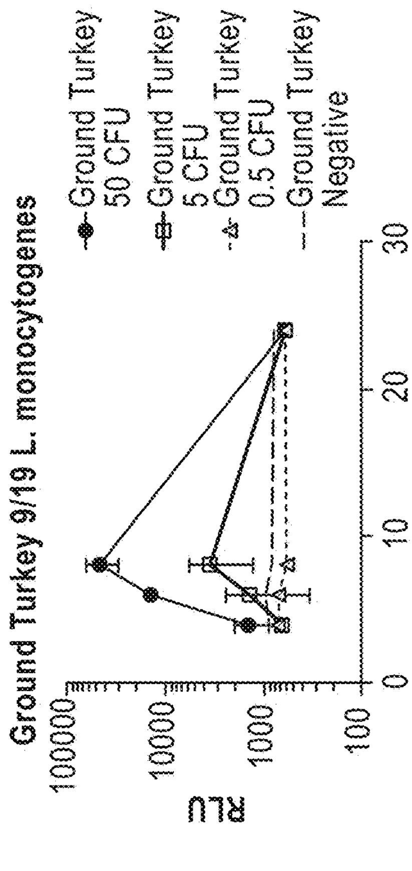
Figure 22M:
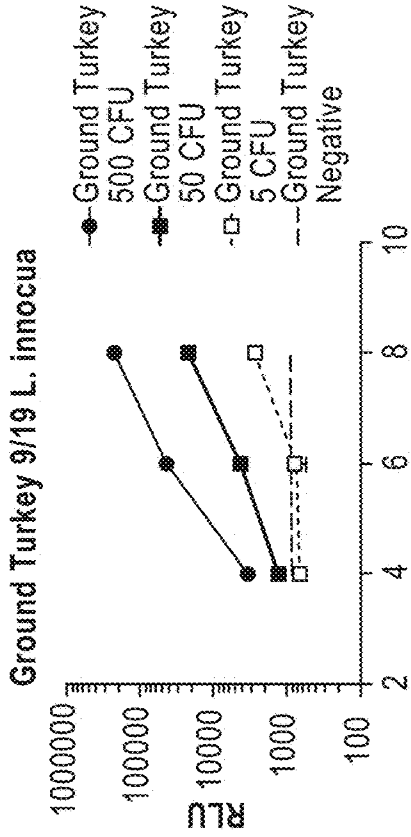

22C, 22D, 22J and 22K), ground turkey (FIGS. 22E, 22F, 22L and 22M) and sour cream (FIG. 22G). RLU values are on the y axis.

Figure 23A:
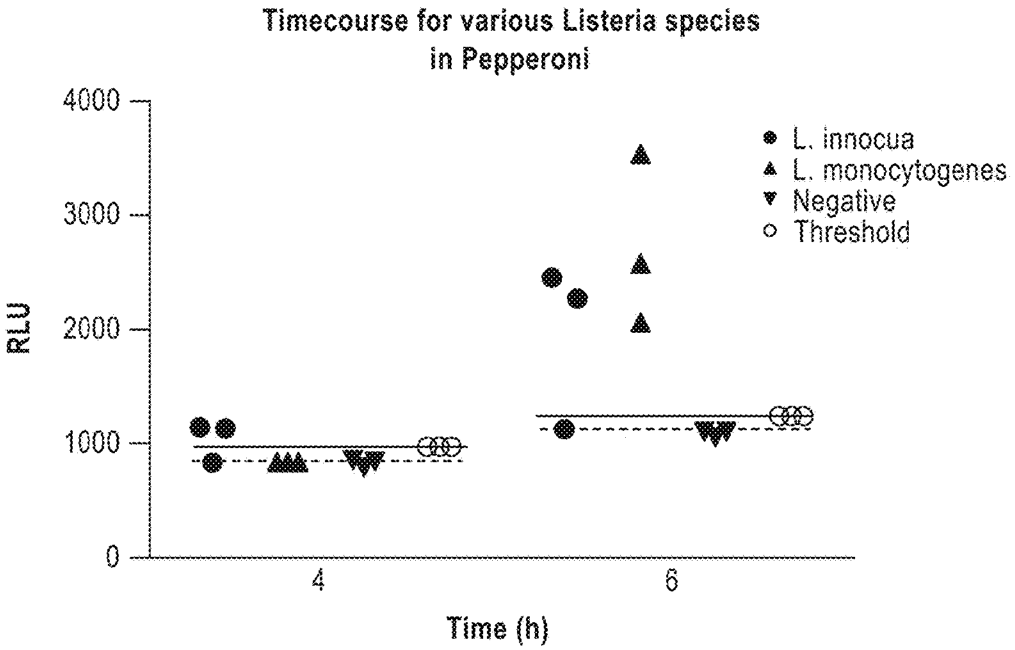
Figure 23B:
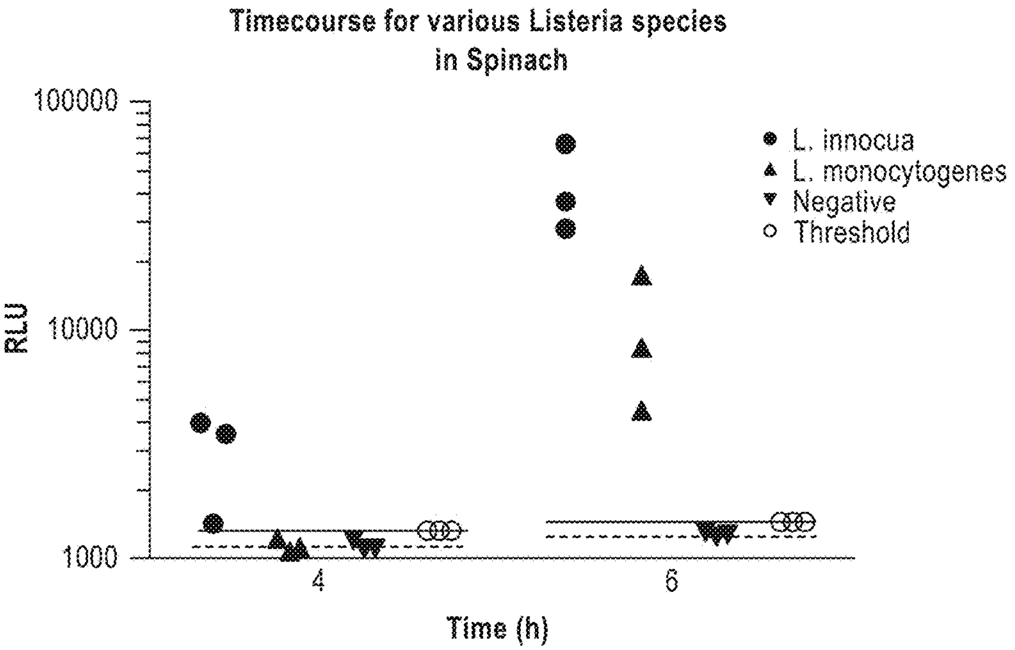

FIG. 23A-B is a series of graphs that depict the time course of *L. innocua* and *monocytogenes* detection in either pepperoni or spinach.

Figure 24A:
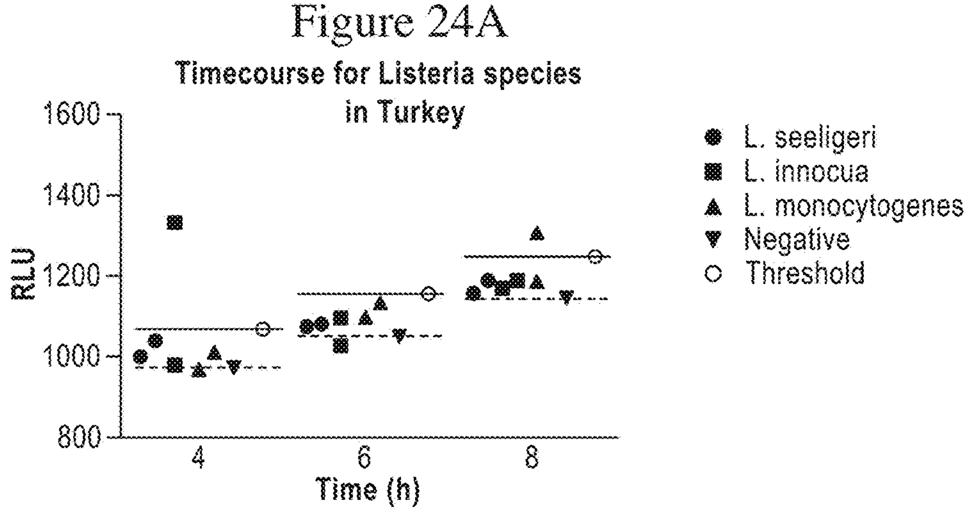
Figure 24B:
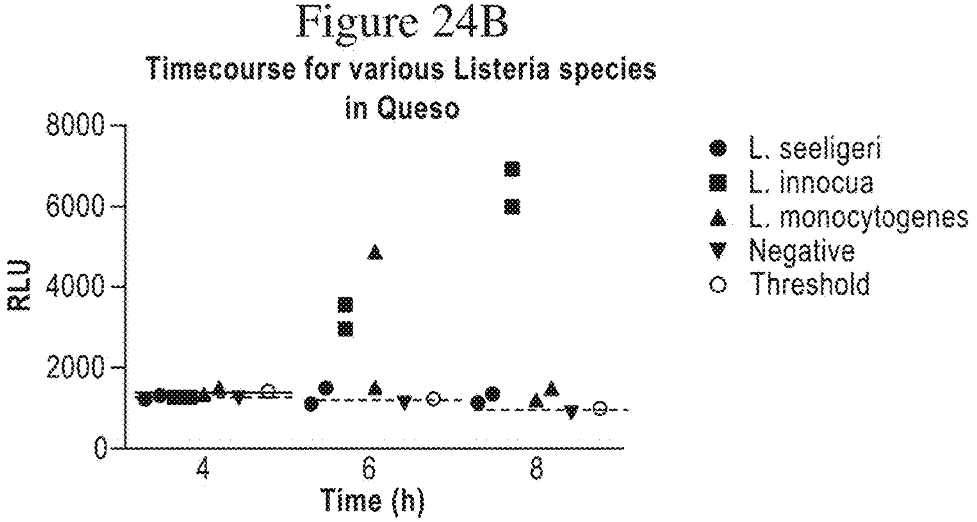
Figure 24C:
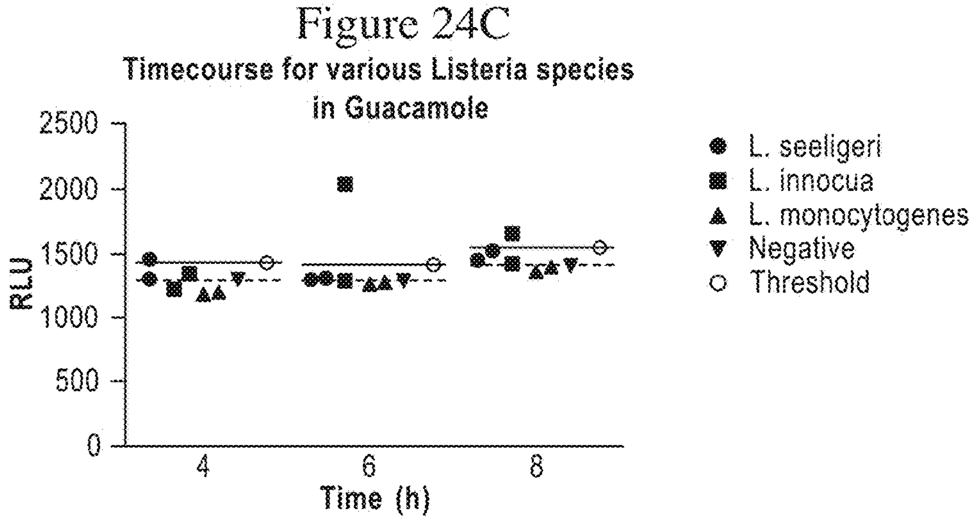
Figure 25A:
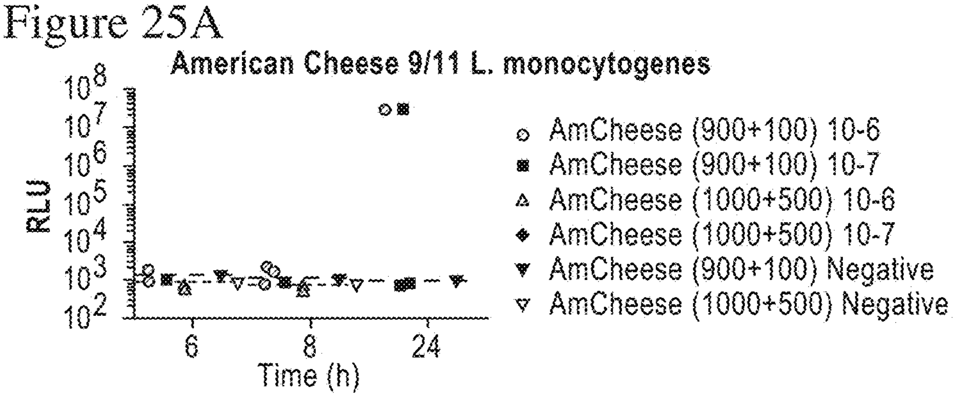
Figure 25B:
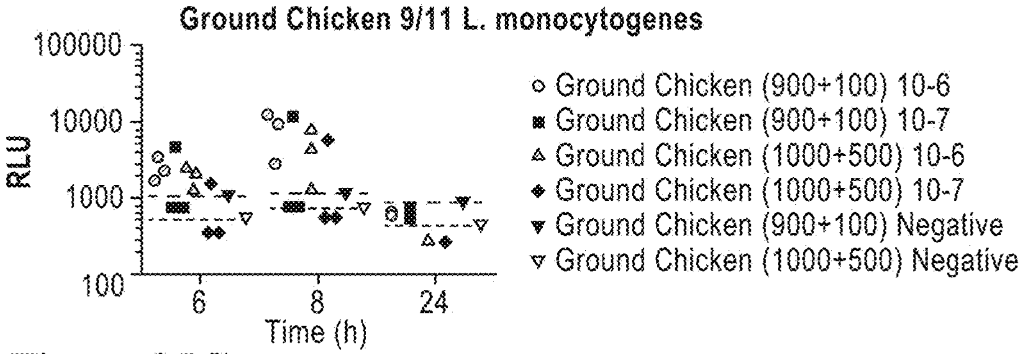
Figure 25C:
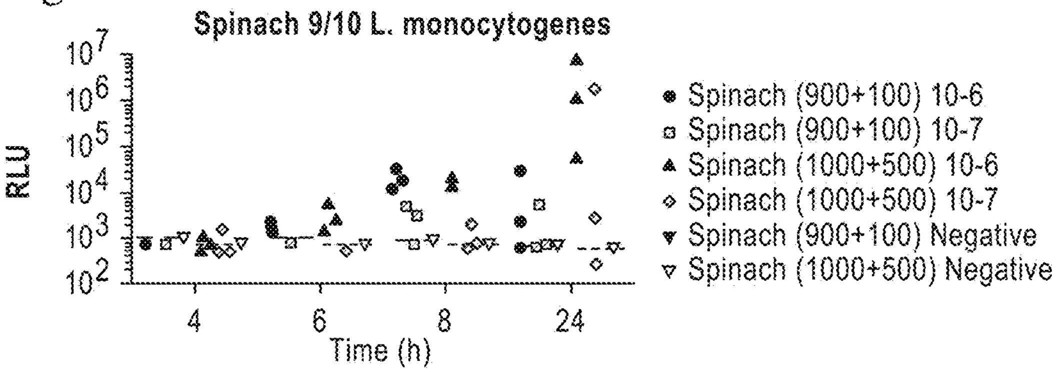
Figure 25D:
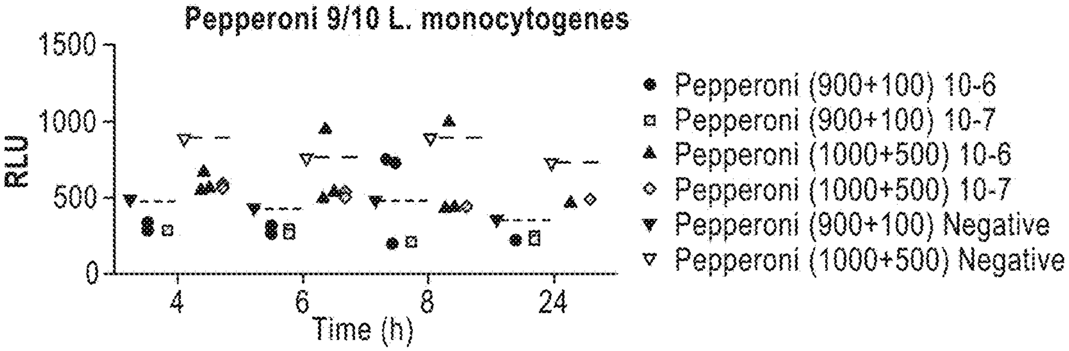

FIG. 24A-C is a series of graphs that depict the time course of detection of *L. seeligeri, L. innocua*, and *L. monocytogenes* in turkey, queso, and in guacamole.

FIG. 25A-D is a series of graphs that depict the detection of *L. monocytogenes* in various food types when the assay is performed utilizing various dilution of food matrix to incubation buffer.

FIG. 26 is a sequence alignment of the CPS open reading frame of LP143 (SEQ ID NO: 17), A511 (SEQ ID NO: 19), LP101 (SEQ ID NO: 11), LP124 (SEQ ID NO: 13), LP99 (SEQ ID NO: 9), LP48 (SEQ ID NO: 7), LP125 (SEQ ID NO: 15), P100 (SEQ ID NO: 21) and LP40 (SEQ ID NO: 5) phage.

FIG. 27 is an amino acid alignment of LP143 (SEQ ID NO: 18), A511 (SEQ ID NO: 20), LP101 (SEQ ID NO: 12), LP124 (SEQ ID NO: 14), LP99 (SEQ ID NO: 10), LP48 (SEQ ID NO: 8), LP125 (SEQ ID NO: 16), P100 (SEQ ID NO: 22) and LP40 (SEQ ID NO: 6) phage.

FIG. 28 is a sequence alignment of recombinant LP143 (SEQ ID NO: 28), A511 (SEQ ID NO: 29), LP101 (SEQ ID NO: 25), LP124 (SEQ ID NO: 26), LP99 (SEQ ID NO: 24), LP48 (SEQ ID NO: 23), LP125 (SEQ ID NO: 27) and P100 (SEQ ID NO: 30) phage engineered with firefly luciferase.

FIG. 29 is a sequence alignment of recombinant A511 (SEQ ID NO: 33), LP124 (SEQ ID NO: 31), LP125 (SEQ ID NO: 32), P100 (SEQ ID NO: 34) and LP40 (SEQ ID NO: 35) phage with nanoluc luciferase.

FIG. 30 shows Table 19.

FIG. 31 shows Table 20.

FIG. 32 shows Table 21.

FIG. 33 shows Table 22.

FIG. 34 shows Table 23.

FIG. 35 shows Table 24.

FIG. 36 shows Table 25.

FIG. 37 shows Table 26.

FIG. 38 shows Table 29.

FIG. 39 shows Table 31.

FIG. 40 shows Table 32.

DETAILED DESCRIPTION

Compositions, methods, and kits are presented herein for the detection of target microbes through the use of codon-optimized recombinant phage. This disclosure provides recombinant phage with sequence encoding a codon optimized marker, aqueous solutions that enable robust signal detection following contact with the target microbes in a sample. The compositions and methods of the disclosure provide broad detection coverage of a microbe genus, species or a combination of species.

The composition and buffer components necessary for robust signal detection following infection by codon optimized phage is dependent on the sampled area. For example, at least one recombinant phage is provided in combination with an aqueous solution, that, together, provide optimal for the detection of microbes in an agricultural facility. A particular challenge of detection of microbes in an agricultural facility is the potential for the presence of trace sanitation solutions that may interfere with signal detection. Another embodiment relates to the use of recombinant phage for the detection of microbes in agricultural products themselves, such as, for example, food stuffs intended for human or animal consumption. Detection of microbes in an agricultural sample presents unique challenges in that components of the agricultural sample may contain substances that interfere with signal detection. The aqueous solutions presented herein are formulated to minimize such interference.

The methods and compositions presented herein are optimized in order to allow the propagation of microbes from a test sample, infection of the microbes with a recombinant phage that encodes a detectable marker, and the quantification of the amounts of the microbes from the sample by way of detection of the recombinant phage marker.

Methods of Making Recombinant Phage

Any method known in the art can be used to make genetically modified phage from starting phage. For example, U.S. Pat. No. 5,824,468 discloses methods of making genetically modified phage. Alternative methods are disclosed in co-pending application Ser. No. 13/627,060, filed Sep. 26, 2012, which is hereby incorporated herein by reference.

Phage infective engineering (PIE) is used herein to make recombinant phage. PIE methodology is disclosed in U.S. patent application Ser. No. 14/226,889, which is hereby incorporated herein in its entirety by reference. This method is sometimes referred to herein as phage infective engineering (PIE). This method allows insertion of a heterologous nucleic acid sequence into any desired location of a phage genome. The PIE method utilizes a phage targeting vector (PTV) that is transformed into a phage host cell. The PTV comprises a heterologous nucleic acid sequence (such as an open reading frame encoding a marker) for insertion into a phage genome. The heterologous nucleic acid sequence is flanked by upstream and downstream homology regions, which are located adjacent to the desired insertion site. In some embodiments the homology regions in the vector are directly adjacent in a starting phage genome. Such embodiments allow insertion of the heterologous nucleic acid sequence into the phage genome without a loss of endogenous phage sequence. In some embodiments the homology regions in the vector flank a region of the starting phage genome that is not included in the vector. Such embodiments allow insertion of the heterologous nucleic acid sequence into the phage genome while deleting a region of the starting phage genome at the site of insertion. Such embodiments allow, for example, the replacement of an endogenous phage sequence with a replacement sequence. In some embodiments the starting sequence that is deleted and the replacement sequence display sequence homology, such as homology of at least 50%, 60%, 70%, 80%, 90%, 95%, 96%, 97%, 98%, 99% or higher.

The upstream homology region, downstream homology region, and heterologous nucleic acid sequence are combined in a vector to make a PTV. One example of a suitable vector is pMK4; however, skilled artisans are aware of many suitable vectors that may be used for this purpose. The plasmid may be isolated in any suitable host, such as *E. coli*. Upon verification, the plasmid is then transformed into a phage host cell. One example of such a cell useful for many *Listeria* phage is the *L. monocytogenes* strain EGD-e.

Once the PTV is successfully transformed into the phage host, the initial recombination was performed by incubating the transformed phage host cell with starting phage.

To assess whether recombination has occurred, the infection is assayed using any suitable method to identify recombinant phage that comprise the heterologous nucleic acid sequence. PCR is one method that may be used. Alternatively, if the heterologous nucleic acid sequence comprises an open reading frame the presence of transcripts encoded by that open reading frame, the presence of the encoded gene product, or functional readouts of the encoded gene product may be screened for in cultures of cells infected with the resultant phage to identify recombinant phage.

Codon Optimized Phage

The disclosure provides recombinant phage comprising a heterologous nucleic acid sequence encoding a codon optimized marker. The phage can be LP40, LP48, LP99, LP101, LP124, LP125, LP143, A511, or P100. The marker can be any detectable marker. In one embodiment the marker is luciferase.

The design of codon optimized phages should take into account a variety of factors, including the frequency of codon usage in a host organism, nearest neighbor frequencies, RNA stability, the potential for secondary structure formation, the route of synthesis and the intended future DNA manipulations of that gene.

The degeneracy of the genetic code permits the same amino acid sequence to be encoded and translated in many different ways. For example, leucine, serine and arginine are each encoded by six different codons, while valine, proline, threonine, alanine and glycine are each encoded by four different codons.

However, the frequency of use of such synonymous codons varies from genome to genome among kingdoms and phyla. For example, synonymous codon-choice patterns among mammals are very similar, while evolutionarily distant organisms such as yeast (*S. cerevisiae*), bacteria (such as *E. coli*) and insects (such as *D. melanogaster*) reveal a clearly different pattern of genomic codon use frequencies. In reference to phage codon optimization, codon selection may vary with the species, strain or ribotype of the host to be infected by a particular phage. Additionally, codon usage may vary with the environment in which the host exists, depending on factors such as temperature, pH, pressure, and other external parameters. Further, codon usage may vary with the state of growth in which the host exists, e.g. depending on rapid division vs. non-division, or within a healthy or an injured cellular state.

These differences in codon-choice patterns appear to contribute to the overall expression levels of individual genes by modulating translation initiation rates, as well as peptide elongation rates. Experimental evidence supports this argument; the rate of polypeptide synthesis depends on the character of the codons being translated, as well as the initial kinetics for transfer RNA ("tRNA") ternary complex formation.

The preferred codon usage frequencies for a recombinant phage should reflect the codon usages of genes derived from the genome of the intended host organism.

In some embodiments, a gene can be optimized by replacing codons of the origin species with known preferred codons from a host organism encoding the same amino acid. In some embodiments, a host organism is *Listeria*. In some embodiments, software can be utilized which applies an algorithm to a genetic sequence which will codon optimize the sequence for a specific host organism. In some embodiments, software from DNA 2.0™ can be used to codon optimize a genetic sequence for a specific host organism. Example algorithms for codon optimization in silico have been described (see Villalobos et al. BMC Bioinformatics. *Gene Designer: a synthetic biology tool for constructing artificial DNA segments. PLoS ONE.* 2011 6:e19912.; U.S. Pat. No. 8,635,029; U.S. Pat. No. 8,401,708; U.S. Pat. No. 8,126,653; U.S. Pat. No. 8,005,620; U.S. Pat. No. 7,805,252; U.S. Pat. No. 7,561,973; U.S. Pat. No. 7,561,72.)

In some embodiments, codon optimization allows for increased expression of phage encoded proteins in a host organism. In some embodiments, the host organism is a bacterium. In some embodiments, codon optimization allows for increased expression of reporter proteins or polypeptides encoded by a recombinant phage in a host organism. In some embodiments, codon optimization of recombinant phage allows for increased expression of a luciferase reported by *Listeria.*

In some embodiments, *Listeria* phages used for recombination may be selected from A511, LP124, and LP40. In some embodiments, recombinant phages comprise the entirety of the original phage genome. In some embodiments, recombinant phages comprise deletions to the original phage genome and addition of heterologous nucleic acid sequences. In some embodiments, recombinant phages comprise added stop codons. In some embodiments, recombinant phages comprise added ribosome binding sites. In some embodiments, recombinant phages comprise a codon optimized reporter gene. In some embodiments, a reporter gene is a sequence encoding luciferase. In some embodiments, the luciferase reporter gene is a codon optimized NanoLuc sequence optimized for expression in *Listeria*. In some embodiments, a recombinant phage is an A511 phage comprising added stop codons, an added ribosome binding site, and an added codon optimized NanoLuc sequence. In some embodiments, a recombinant phage is a LP124 phage comprising added stop codons, an added ribosome binding site, and an added codon optimized NanoLuc sequence. In some embodiments, a recombinant phage is a LP40 phage comprising added stop codons, an added ribosome binding site and added codon optimized NanoLuc sequence.

Optimized Assay Aqueous Solution for Microbial Detection

The disclosure provides formulations of an aqueous solution which effectively enable bacteria isolated from a test site to be productively infected by recombinant phage. Furthermore, the aqueous solution is capable of preserving the enzymatic activity used in the phage based detection system. A major difficulty encountered in the detection of bacteria using phage based recombinant markers is the potential interactions between sanitation reagents found in the sample and the test reagent compounds that are used to quantify bacterial presence or absence. This problem is augmented given the propensity of facilities to use amounts of disinfectants in excess of the recommended guidelines presented by the Federal Drug Administration (FDA), United States Department of Agriculture (USDA), and Centers for Disease Control (CDC). Overuse of these sanitization agents may lead to obfuscation of true positive or true negative results due to (i) decreasing enzymatic activity required for the phage-based detection system, (ii) lowering the ability of phage to infect bacteria collected from the test site, or (iii) disrupting the bacterial cells to a degree that they are not detectable.

Collection and processing of a an environmental sample from a test site follows a stepwise process that includes: (a) collection of the sample by way of swabbing the surface with a sponge, followed by immediate placement of the sponge into an isolated container; (b) processing the sample begins with the addition of an aqueous solution (infection buffer), and the addition of a marker encoding phage to the sample collecting sponge; (c) incubation of the solution impregnated sponge at an appropriate temperature range; (d) isolation of the liquid from the sponge by way of centrifugation; and (e) detection of a signal in the liquid with an instrument (e.g. luciferase presence with a luminometer). The solution added to the sponge is a buffer that contains reagents that minimize the interaction with components of commonly used sanitization solutions that have been found to reduce signal detection ability (e.g. by either reducing phage infection or by reducing enzymatic activity, or by affecting the luciferin substrate). The purposes of the buffer include recovery of the isolated stressed and injured bacteria in order to optimize phage infection and to optimize downstream signal detection. The marker used for signal detection can be any detectable marker. Preferred detection signal systems include luciferase based assays.

Ideal formulations of the disclosure would allow for high amounts of signal following phage infection, high amount of signal stability, and the ability to effectively neutralize various components found in sterilization solutions without the loss of either signal or stability. The formulations presented herein make use of additives that serve as neutralizers to overcome these challenges. Commonly found sanitation chemicals that may have the ability to interfere with environmental sample test results include chlorine, quaternary ammonium salts, organic acids and peracids, iodophors, and detergents. Formulations presented herein contain remedies to overcome these agents including, for example, sodium metabisulfite, sodium thiosulfate, lecithin, TWEEN®-80, HEPES and buffering salts.

Bacterial cells collected from the environment present many additional challenges to the downstream processing required for adequate signal detection. Many of these challenges relate to the health of the cells upon collection. The collected cells may be starved, osmotically stressed, and have underlying oxidative stress. Formulations have been developed, and described herein, to overcome these challenges encountered following the collection of the cells. For example, detailed herein, and specifically in the Examples section, are formulations to overcome osmotic stress (e.g. via addition of glycerol), cell starvation (e.g. via addition of nutrients including carbon, nitrogen source, sugars and vitamins), and oxidative stress (e.g. via the addition of vitamins including those contained in yeast extract). Interaction with non-target biologicals also poses a challenge in the downstream signal detection methods. Formulations presented herein have been optimized to overcome non-target biological interactions via the addition of either nalidixic acid and/or lithium salts.

The Examples detail various formulations that work well at preserving signal and signal stability (See Examples 6-12). A base aqueous solution of the disclosure is Formulation-1 (Table 1). A variation of the base aqueous solution Formulation-1, Forumulation-1A, makes use of additives (i.e. 0.08% $MgSO_4$, and 0.1% pyruvate) that further aid in preservation of signal intensity and phage infection (Table 2).

TABLE 1

Base Infection Buffer Formulation (Formulation 1)

| Components | Group | Function |
|---|---|---|
| 1x Tryptic Soy Broth | Media (nutrients) | Support recovery and growth of stressed cells (provide hydrolyzed amino acids, sugars, minerals) |
| 0.25% LiCl | Selective agents | Prevent or limit growth of competing biologicals |
| 0.002% nalidixic acid | Selective agents | Prevent or limit growth of competing biologicals |

TABLE 1-continued

Base Infection Buffer Formulation (Formulation 1)

| Components | Group | Function |
|---|---|---|
| 0.5% yeast extract | Vitamins (B complex) | Prevent oxidative stress |
| 0.25% glucose | Carbon Source | Nutrient |

TABLE 2

Base Infection Formulation (Formulation 1-A)

| Components | Group | Function |
|---|---|---|
| 1x Tryptic Soy Broth | Media (nutrients) | Support recovery and growth of stressed cells (provide hydrolyzed amino acids, sugars, minerals) |
| 0.25% LiCl | Selective agents | Prevent or limit growth of competing biologicals |
| 0.002% nalidixic acid | Selective agents | Prevent or limit growth of competing biologicals |
| 0.5% yeast extract | Vitamins (B complex) | Prevent oxidative stress |
| 0.25% glucose | Carbon Source | Nutrient |
| 0.08% $MgSO_4$ | Ions | Increases infection ability |
| 0.1% sodium pyruvate | Carbon Source | Nutrient |

A preferred embodiment of the aqueous solutions of the disclosure is Formulation-2 (also referred to herein as "NIB-12") (Table 3). As detailed in the Example section, the addition of 20 mM HEPES increases enzyme activity and stability, and increases the buffering capacity against pH extremes (See Example 7).

Another preferred embodiment of the aqueous solutions of the disclosure is formulation NIB-14 (Table 4). NIB-14 contains lecithin, TWEEN®-80 and potassium phosphate added to the base components of NIB-12. NIB-14 allows for greater phage infection ability and increased enzymatic activity compared with a base medium (BHI), and also allows for greater neutralization of remnant sanitizer chemicals in comparison to other aqueous solutions tested (See Examples 8 and 11).

TABLE 3

Infection Formulation 2 (NIB-12)

| Components | Group | Function |
|---|---|---|
| 1x Tryptic Soy Broth | Media (nutrients) | Support recovery and growth of stressed cells (provide hydrolyzed amino acids, sugars, minerals) |
| 0.25% LiCl | Selective agents | Prevent or limit growth of competing biologicals |
| 0.002% nalidixic acid | Selective agents | Prevent or limit growth of competing biologicals |
| 0.5% yeast extract | Vitamins (B complex) | Prevent oxidative stress |
| 0.25% glucose | Carbon Source | Nutrient |
| 0.08% $MgSO_4$ | Ions | Increases infection ability |
| 0.1% sodium pyruvate | Carbon Source | Nutrient |
| 20 mM HEPES, pH 7.5 | Buffering agents | Neutralize environmental pH extremes |

TABLE 4

| Infection Formulation NIB-14 | | |
|---|---|---|
| Components | Group | Function |
| 1x Tryptic Soy Broth | Media (nutrients) | Support recovery and growth of stressed cells (provide hydrolyzed amino acids, sugars, minerals) |
| 0.25% LiCl | Selective agents | Prevent or limit growth of competing biologicals |
| 0.002% nalidixic acid | Selective agents | Prevent or limit growth of competing biologicals |
| 0.5% yeast extract | Vitamins (B complex) | Prevent oxidative stress |
| 0.25% glucose | Carbon Source | Nutrient |
| 0.08% $MgSO_4$ | Ions | Increases phage infection ability |
| 0.1% sodium pyruvate | Carbon Source | Nutrient |
| 20 mM HEPES, pH 7.5 | Buffering agents | Neutralize environmental pH extremes |

TABLE 4-continued

| Infection Formulation NIB-14 | | |
|---|---|---|
| Components | Group | Function |
| Tween-80 1.5% | Neutralizer of sanitizers, Non-ionic detergent | Neutralize biguanides (chlorhexidine), bis-phenols (hexachlorophene), phenolic compounds, cresols, formalin, to some extent quaternary ammonium compounds, organic acids, parabens, alcohols |
| Lecithin 0.22% | Nutrient and Neutralizer | Nutrient and Neutralizer |
| 0.02% Potassium Phosphate, pH 7.4 | Buffering agents | Neutralize environmental pH extremes |

Table 5 lists the groups and category of the reagents that are included in the aqueous solutions disclosed herein, and the affect that each of these components has on *Listeria* detection.

TABLE 5

| Reagents in Aqueous Solution and Influence on *Listeria* Detection | | | | |
|---|---|---|---|---|
| Group | Category | Components tested | Function | Effect on *Listeria* Detection |
| Nutrients | Carbohydrates | Glucose | | positive |
| | | Glycerol | Energy source for stressed cells | neutral |
| | | Mannose | | |
| | | Fructose | | |
| | | Sucrose | | neutral |
| | Meat and plant extracts | Beef extract | Nutrient source | |
| | | Pancreatic digest of casein | Nitrogen source | |
| | | Papaic digest of soybean meal | Nutrient source | |
| | | Proteose peptone | Nitrogen source | |
| | | Sodium succinate | Energy source | |
| | Carbon sources | Sodium acetate | | |
| | | Acetoin | | |
| | | Sodium pyruvate | | positive |
| | | Alpha-ketoglutarate | | negative |
| | | Sodium malonate | | negative |
| | | Sodium citrate | | negative |
| | | Ferric ammonium citrate | | neutral |
| | Minerals | Ferric citrate | Iron source, growth enhancer | neutral |
| | | Ferric sulfate | | neutral |
| | | Sodium glutamate | | |
| | Nitrogen sources | Ammonium nitrate | | |
| | | Ammonium sulfate | | |
| | | Urea | | |
| | Amino acids | Sodium glutamate | Energy source for stressed cells | neutral |
| | | Branched-chain amino acids (leucine, isoleucine, valine) | Conversion of cells in stationary phase into growing phase | neutral |
| | | Proline | | |
| | | Cysteine | | |
| | | Methionine | | |
| | Media | Brain Heart Infusion | Support recovery and growth of stressed cells by providing variety of nutrients(provide hydrolyzed amino acids, sugars, minerals) | positive |
| | | Tryptic Soy Broth | | positive |
| | | Buffered Peptone Water | | positive |
| | | LPT-6F (BioMerieux) | | negative |
| | | Moxalactam | Prevent or limit growth of competing biologicals | neutral |

TABLE 5-continued

Reagents in Aqueous Solution and Influence on *Listeria* Detection

| Group | Category | Components tested | Function | Effect on *Listeria* Detection |
|---|---|---|---|---|
| Selective agents | Antibiotics | Nalidixic acid | | positive |
| | | Polymyxin B | | |
| | | Ceftazidime | | positive |
| | | Acriflavin | | negative |
| | | Carbenicillin | | |
| | | Erythromycin | | |
| | | Mitomycin C | | |
| | | Penicillin G | | |
| | | Streptomycin | | |
| | | Tetracycline | | positive |
| | | Nitrofurantoin | | |
| | Growth inhibitors | Lithium chloride | Prevent or limit growth of competing biologicals | optimized for positive |
| | Yeast growth inhibitor | Cycloheximide | Antifungal agent | neutral |
| Vitamins | B complex | Yeast extract | Prevent oxidative stress | positive |
| | | Biotin | | |
| | | Riboflavin | | |
| | | Nicotinamide | | |
| | | Calcium panthotenate | | |
| | | Cyanocobalamine | | |
| | | Pyridoxine | | |
| | | Thiamine | | neutral |
| | | Lipoic acid | | |
| Divalent metals | | Magnesium sulphate | Support enzymatic functions of cells, support phage activity | positive |
| | | Magnesium chloride | | |
| | | Ferrous sulphate | | negative |
| | | Calcium chloride | | neutral |
| | | Zinc sulfate | | |
| Buffering agents | pH buffers | Sodium monobasic/ sodium dibasic phosphates, pH 7.2 | Neutralize environmental pH extremes | |
| | | HEPES, pH 7.4 | | positive |
| | | MOPS, pH 7.2 | | positive |
| Neutralizer of sanitizers | Oxygen scavenger | Sodium metabisulfite | Scavenge peroxides, neutralize glutaraldehyde, formaldehyde | positive |
| | | Catalase | Neutralize peroxides | |
| | | Sodium pyruvate | Scavenges peroxides | positive |
| | Halogens neutralizer | Sodium thiosulfate | Neutralize halogens (iodine, chlorine, sodium hypochlorite, chlorine dioxide, also peroxides, peroxyacids) | negative |
| | Mercury neutralizer | Sodium thioglycollate | | negative |
| | Non-ionic detergent/ surfactant | Polysorbate 80 | Neutralize biguanides (chlorhexidine), bis-phenols (hexachlorophene), phenolic compounds, cresols, formalin, to some extent quaternary ammonium compounds, organic acids, parabens, alcohols | positive |
| | | Polysorbate 20 | | negative |
| | | Triton X-100 | | negative |
| | Emulsifier | Soy based lecithin | Neutralize quaternary ammonium compounds, parabens | positive |
| | | Soy based hydroxylated lecithin | | negative |
| | | Phosphocholine chloride | | negative |
| | | O-octophosphorylcholine | | negative |

Detection of Microbes in Agricultural Products

The detection of microbes in agricultural products is essential to maintain food safety. The disclosure provides methods and compositions to rapidly detect microbes in or on agricultural products with high sensitivity and within a timeframe that is relevant to enabling reaction within a work shirt (less than 8-10 hours). Compositions and methods of the disclosure are particularly beneficial in comparison to currently used methods of microbial detection in that the present invention, (i) has minimal sample preparation, (ii) is capable of detecting microbes in undiluted or minimally diluted matrix of certain foods resulting in less operator and cross-contamination risk, smaller volumes (less cost) and less waste, (iii) has high sensitivity and specificity, and (iv) has a total time to result of less than 8-10 hours.

Compositions and methods of the disclosure, as described in the Examples section (see Examples 13-14), incorporate the use of marker encoding phage, infection buffer/media, and a quantification of the amounts of phage marker present following phage infection of a sample in order to identify microbial presence in food samples. Preferred embodiments of the compositions and methods of the disclosure enable the detection of microbes in various food sources, including fatty foods, such as for example, whole milk, ice cream, queso fresco, and guacamole; salty foods, such as for example, deli turkey; and other foods, such as for example, beef. Preferred, although not limiting, microbial target species for the current invention include species of *Listeria*.

Unlike all other methods of microbial detection available today, the compositions and methods of the disclosure are capable of detecting target microbes in an undiluted food matrix. These properties contribute to the minimal sample preparation steps and associated rapid processing associated with the use of the present methods and compositions. Unlike other microbial detection methods, the use of the recombinant phage containing the codon-optimized marker sequence in the compositions and methods of the disclosure enables the rapid detection of extremely low numbers of microbes (e.g. *Listeria monocytogenes* in various foods, see Example 13), and the detection of microbes in lower limit of detection assays (also referred to herein as "LLOD") of down to 1 CFU in certain foods (see Example 14). For example, in LLOD assays from whole milk samples, *Listeria monocytogenes* was detected in quantities as low as 50 cells in 50 mL of sample utilizing the recombinant phage based microbe detection system within a two hour period. (See Example 8). The detection of *S. enterica* was also assessed in various kinds of foods and was found to have a sensitivity of 1 CFU as well. Both LLOD and time course to detection assays revealed that using the compositions and methods of the disclosure enables the rapid detection of *S. enterica* with no enrichment (See Examples 13 and 14).

Recombinant Phage

The phage LP40, LP48, LP99, LP101, LP124, LP125, LP143, and A511 were selected for engineering. The examples describe making recombinant versions of the phage LP40, LP48, LP99, LP101, LP124, LP125, LP143, A511, and P100, comprising a heterologous nucleic acid sequence encoding a marker. As demonstrated in the examples, those phage are useful, for example, to detect target bacteria, as further disclosed throughout this application.

Accordingly, this disclosure provides recombinant *Listeria* phage comprising a heterologous nucleic acid sequence encoding a marker. In some embodiments the recombinant phage comprises a genome comprising a region of at least 1 kb that comprises substantial homology to a region of at least 1 kb of the genome of at least one phage selected from LP40, LP48, LP99, LP101, LP124, LP125, LP143, A511, and P100. In some embodiments the region of homology comprises at least 2 kb, at least 3 kb, at least 4 kb, at least 5 kb, at least 6 kb, at least 7 kb, at least 8 kb, at least 9 kb, at least 10 kb, or more. In some embodiments the region of homology is the entire genome of the recombinant *Listeria* phage. In some embodiments the substantial homology is nucleotide sequence identity of at least 50%, 60%, 70%, 80%, 85%, 90%, 91%, 92%, 93%, 94%, 95%, 96%, 97%, 98% or 99% across the region of homology.

This disclosure provides the amino acid sequences of the cps gene of the phage LP40 (SEQ ID NO: 6), LP48 (SEQ ID NO: 8), LP99 (SEQ ID NO: 10), LP101 (SEQ ID NO: 12), LP124 (SEQ ID NO: 14), LP125 (SEQ ID NO: 16), LP143 (SEQ ID NO: 18), A511 (SEQ ID NO: 20), and P100 (SEQ ID NO: 22). Accordingly, in some embodiments this disclosure provides recombinant *Listeria* phage comprising a heterologous nucleic acid sequence encoding a marker, wherein the recombinant *Listeria* phage comprises a nucleic acid sequence that encodes a protein selected from SEQ ID NOS: 6, 8, 10, 12, 14, 16, 18, 20, and 22, and muteins thereof.

This disclosure also provides the nucleotide sequences of the open reading frames of the cps gene of the phage LP40 (SEQ ID NO: 5), LP48 (SEQ ID NO: 7), LP99 (SEQ ID NO: 9), LP101 (SEQ ID NO: 11), LP124 (SEQ ID NO: 13), LP125 (SEQ ID NO: 15), LP143 (SEQ ID NO: 17), A511 (SEQ ID NO: 19), and P100 (SEQ ID NO: 21). Accordingly, in some embodiments this disclosure provides recombinant *Listeria* phage comprising a heterologous nucleic acid sequence encoding a marker, wherein the recombinant *Listeria* phage comprises a nucleic acid sequence selected from SEQ ID NOS: 5, 7, 9, 11, 13, 15, 17, 19, and 21, and nucleic acid sequences comprising substantial homology thereto.

In some embodiments the recombinant *Listeria* phage comprising a heterologous nucleic acid sequence encoding a marker comprises a screenable marker. In some embodiments the marker is a luciferase. In some embodiments the luciferase is at least 70%, at least 80%, at least 90%, at least 91%, at least 92%, at least 93%, at least 94%, at least 95%, at least 96%, at least 97%, at least 98% or at least 99% identical to SEQ ID NO: 2. In some embodiments the luciferase is encoded by a nucleic acid sequence comprising SEQ ID NO: 1 or a nucleic acid sequence comprising substantial homology to SEQ ID NO: 1 capable of encoding a luciferase that is at least 70%, at least 80%, at least 90%, at least 91%, at least 92%, at least 93%, at least 94%, at least 95%, at least 96%, at least 97%, at least 98%, or at least 99 identical to SEQ ID NO: 2. In some embodiments the recombinant *Listeria* phage is selected from LP48::ffluc, LP99::ffluc, LP101::ffluc, LP124::ffluc, LP125::ffluc, LP143::ffluc, A511::ffluc, P100::ffluc, LP48::COP2, LP48::COP2, LP48::COP2, LP48::COP2, LP48::COP2, LP48::COP2, LP48::COP2, P100::COP2, LP48::COP3, LP48::COP3, LP48::COP3, LP48::COP3, LP48::COP3, LP48::COP3, LP48::COP3, and P100::COP3. In some embodiments the recombinant *Listeria* phage is selected from phage comprising genomes comprising substantial homology to at least one phage selected from LP48::ffluc, LP99::ffluc, LP101::ffluc, LP124::ffluc, LP125::ffluc, LP143::ffluc, A511::ffluc, P100::ffluc, LP48::COP2, LP48::COP2, LP48::COP2, LP48::COP2, LP48::COP2, LP48::COP2, LP48::COP2, P100::COP2, LP48::COP3, LP48::COP3, LP48::COP3, LP48::COP3, LP48::COP3, LP48::COP3, LP48::COP3, and P100::COP3.

In some embodiments the luciferase is at least 70%, at least 80%, at least 90%, at least 91%, at least 92%, at least 93%, at least 94%, at least 95%, at least 96%, at least 97%, at least 98% or at least 99% identical to SEQ ID NO: 4. In some embodiments the luciferase is encoded by a nucleic acid sequence comprising SEQ ID NO: 3 or a nucleic acid sequence comprising substantial homology to SEQ ID NO: 3 capable of encoding a luciferase that is at least 70%, at least 80%, at least 90%, at least 91%, at least 92%, at least 93%, at least 94%, at least 95%, at least 96%, at least 97%, at least 98%, or at least 99 identical to SEQ ID NO: 4. In some embodiments the recombinant *Listeria* phage is selected from LP040::nluc, LP124::nluc, LP125::nluc, A511::nluc, P100::nluc, LP040::COP2, LP124::COP2, LP125::COP2, A511::COP2, P100::COP2, LP040::COP3, LP124::COP3, LP125::COP3, A511::COP3, P100::COP3. In some embodiments the recombinant *Listeria* phage is selected from phage comprising genomes comprising substantial homology to at least one phage selected from LP040::nluc, LP124::nluc, LP125::nluc, A511::nluc, P100::nluc, LP040::COP2, LP124::COP2, LP125::COP2, A511::COP2, P100::COP2, LP040::COP3, LP124::COP3, LP125::COP3, A511::COP3, P100::COP3.

In some embodiments the heterologous nucleic acid sequence encoding a marker is operatively linked in the recombinant phage genome to at least one regulatory element that is also heterologous to the phage genome. In some embodiments expression of the heterologous nucleic acid sequence encoding a marker in target bacteria is controlled exclusively by regulatory elements that are heterologous to the phage genome.

In some embodiments the heterologous nucleic acid sequence encoding a marker is operatively linked in the recombinant phage genome to at least one regulatory element that is endogenous to the phage genome. In other words, the heterologous nucleic acid sequence encoding a marker is operatively linked to the endogenous regulatory element by virtue of the location in the starting phage genome where the heterologous nucleic acid sequence encoding a marker is placed. In some embodiments expression of the heterologous nucleic acid sequence encoding a marker in target bacteria is controlled exclusively by regulatory elements that are endogenous to the phage genome. In some embodiments expression of the heterologous nucleic acid sequence encoding a marker in target bacteria is controlled in part by regulatory elements that are endogenous to the phage genome and in part by regulatory elements that are heterologous to the phage genome.

In some embodiments the recombinant *Listeria* phage comprising a heterologous nucleic acid sequence encoding a marker comprises more than one heterologous nucleic acid sequence encoding a marker. In some embodiments the recombinant phage comprises multiple copies of the same nucleic acid sequence encoding a marker (i.e., copy encodes the same marker). In some embodiments the recombinant phage comprises copies of more than one type of nucleic acid sequence encoding a marker (i.e., at least two copies encode different markers). In some embodiments the more than one copy are positioned at adjacent locations in the recombinant phage genome. In other embodiments at least one (up to all) of the more than one copy are located at non-adjacent locations in the recombinant phage genome.

In some embodiments the length of the heterologous nucleic acid sequence is at least 100 bases, at least 200 based, at least 300 bases, at least 400 bases, at least 500 bases, at least 600 bases, at least 700 bases, at least 800 bases, at least 900 bases, at least 1.0 kilobase (kb), at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2.0 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3.0 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4.0 kb, at least 4.5 kb, at least 5.0 kb, at least 5.5 kb, at least 5.5 kb, at least 6.0 kb, at least 6.5 kb, at least 7.0 kb, at least 7.5 kb, at least 8.0 kb, at least 8.5 kb, at least 9.0 kb, at least 9.5 kb, at least 10 kb, or more. In some embodiments the length of the heterologous nucleic acid sequence is 500 bases or less, 1.0 kb or less, 1.5 kb or less, 2.0 kb or less, 2.5 kb or less, 3.0 kb or less, 3.5 kb or less, 4.0 kb or less, 4.5 kb or less, 5.0 kb or less, 5.5 kb or less, 6.0 kb or less, 6.5 kb or less, 7.0 kb or less, 7.5 kb or less, 8.0 kb or less, 8.5 kb or less, 9.0 kb or less, 9.5 kb or less, or 10.0 kb or less. In some such embodiments the heterologous nucleic acid sequence comprises a length that is less than the maximum length of heterologous nucleic acid sequence that can be packaged into a phage particle encoded by the phage genome and comprising the phage genome.

In some embodiments the length of the heterologous nucleic acid sequence is from 100 to 500 bases, from 200 to 1,000 bases, from 500 to 1,000 bases, from 500 to 1,500 bases, from 1 kb to 2 kb, from 1.5 kb to 2.5 kb, from 2.0 kb to 3.0 kb, from 2.5 kb to 3.5 kb, from 3.0 kb to 4.0 kb, from 3.5 kb to 4.5 kb, from 4.0 kb to 5.0 kb, from 4.5 kb to 5.5 kb, from 5.0 kb to 6.0 kb, from 5.5 kb to 6.5 kb, from 6.0 kb to 7.0 kb, from 6.5 kb to 7.5 kb, from 7.0 kb to 8.0 kb, from 7.5 kb to 8.5 kb, from 8.0 kb to 9.0 kb, from 8.5 kb to 9.5 kb, or from 9.0 kb to 10.0 kb.

In some embodiments the ratio of the length of the heterologous nucleic acid sequence to the total length of the genome of the recombinant phage is at least 0.05, at least 0.10, at least 0.15, at least 0.20, or at least 0.25. In some embodiments the ratio of the length of the genome of the recombinant phage to the length of the genome of the corresponding starting phage is at least 1.05, at least 1.10, at least 1.15, at least 1.20, or at least 1.25.

In some embodiments the heterologous nucleic acid sequence is inserted into the starting phage genome with no loss of endogenous starting phage genome sequence. In some embodiments the inserted heterologous nucleic acid sequence replaces endogenous starting phage genome sequence. In some such embodiments the heterologous nucleic acid sequence replaces an amount of endogenous genomic sequence that is less than the length of the heterologous nucleic acid sequence. Thus, in such embodiments the length of the recombinant phage genome is longer than the length of the starting phage genome. In some such embodiments the heterologous nucleic acid sequence replaces an amount of endogenous genomic sequence that is greater than the length of the heterologous nucleic acid sequence. Thus, in such embodiments the length of the recombinant phage genome is shorter than the length of the starting phage genome. In some such embodiments the heterologous nucleic acid sequence replaces an amount of endogenous genomic sequence that is equal to the length of the heterologous nucleic acid sequence.

In some embodiments the protein or polypeptide encoded by a heterologous open reading frame is modified to reduce cleavage by proteases present in phage host cells. For example, computational algorithms can be used to identify known protease cleavage sites and the sequence of the open reading frame may be modified using conservative substitutions to remove these sites. Alternatively, directed mutagenesis is used to evolve the open reading frame sequence to encode a product that has an increased resistance to at least one protease present in a phage host cell or in the culture of a phage host cell.

This disclosure also provides isolated nucleic acids obtainable from a recombinant phage of this disclosure. In some embodiments the isolated nucleic acid is an isolated genome of a recombinant phage of this disclosure. In some embodiments the isolated nucleic acid comprises a fragment of less than the total genome of recombinant phage of this disclosure, the fragment comprising at least 10%, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98% or at least 99% of the genome of the recombinant phage. In some embodiments the isolated nucleic acid comprises a fragment of less than the total genome of recombinant phage of this disclosure, the fragment comprising at least 20 bp, at least 50 bp, at least 100 bp, at least 500 bp, at least 1 kb, at least 2 kb, at least 3 kb, at least 4 kb, or at least 5 kb of the phage genome. In some embodiments the isolated nucleic acid comprises a fragment that is homologous to a fragment disclosed in this paragraph.

Phage Target Bacteria

The recombinant phage of this disclosure may be used to detect the presence of bacteria. Detection of target bacteria is based on the ability of the recombinant phage to bind to target bacteria, transfer of the phage genome into the target bacteria, and express the heterologous nucleic acid sequence encoding a marker by the bacteria. Accordingly, the specificity of a method of detecting target bacteria using recombinant phage comprising a heterologous nucleic acid sequence encoding a marker is based on the range of bacterial types that support expression of the marker following exposure to the phage. Sometimes the range of bacterial types that support expression of the marker following exposure to the phage is referred to herein as the "host range" of the phage. The set of bacterial types that make up the host range of the phage is sometimes referred to herein as "target bacteria" for the phage.

This disclosure provides novel methods of assessing phage host range and thus of defining target bacteria for a phage. In certain embodiments the methods comprise exposing a candidate type of bacteria to a phage in a liquid culture. The ability of the phage to cause clearing of the culture, which reflects infection and lysis of bacteria in the culture by the phage, is an indication that the bacteria in the culture are target bacteria of the phage. As demonstrated in the examples this method is surprisingly more accurate in assessing the true phage host range for a phage than prior art plate-based plaque assays. In some embodiments herein, the "host range" of a phage or the "target bacteria" of a phage are defined based on a set of bacteria that a phage can clear in a liquid culture-based assay.

While the liquid culture method is an improvement over prior methods and is very useful for many purposes, it does embody all aspects of methods of using a recombinant phage to detect target bacteria. Such methods rely on the ability of the recombinant phage to bind to target bacteria, transfer of the phage genome into the target bacteria, and expression of the heterologous nucleic acid sequence encoding a marker by the bacteria. Accordingly, even if a phage is unable to lyse a liquid culture of a particular bacterial cell type the phage may nonetheless be able to bind to the bacteria type, transfer the phage genome into the target bacteria, and thus cause expression of a heterologous nucleic acid sequence encoding a marker by the bacteria. Indeed, as demonstrated by the examples, assays that detect the presence of the marker in a type of bacteria following exposure to a recombinant phage are in some embodiments more sensitive even than liquid based host range assays. Accordingly, in some embodiments herein, the "host range" of a phage or the "target bacteria" of a phage are defined by a process that comprises 1) providing a recombinant phage comprising a heterologous nucleic acid sequence encoding a marker; 2) exposing a sample to the phage; and 3) assaying for the presence of the marker in the exposed sample. This type of assay is sometimes referred to herein generally as a "marker host range assay." In some embodiments assaying for the presence of the marker in the exposed sample is by a method comprising detection of an mRNA. In some embodiments assaying for the presence of the marker in the exposed sample is by a method comprising direct detection of marker protein, such as using an antibody. In some embodiments assaying for the presence of the marker in the exposed sample is by a method comprising functional detection of marker protein. For example, if the marker protein is a luciferase the exposed sample may be exposed to luciferin and production of light may be assayed. This method may be adapted to any type of marker disclosed herein and skilled artisans are aware that many variations on the detection method of the marker may be used.

Certain variables may modify the host range of phage under certain conditions. Conditions that sustain constant bacterial growth and therefore maximal bacteriophage infectivity are seldom found in environments where methods of detecting bacteria are useful. Oligotrophic environments and competition among microorganisms force bacteria to be able to adapt quickly to rough and changing situations. A particular lifestyle composed of continuous cycles of growth and starvation is commonly referred to as feast and famine. Bacteria have developed many different mechanisms to survive in nutrient-depleted and harsh environments, varying from producing a more resistant vegetative cell to complex developmental programs. As a consequence of prolonged starvation, certain bacterial species enter a dynamic non-proliferative state in which continuous cycles of growth and death occur until 'better times' come, a.k.a. restoration of favorable growth conditions and with them the favorable infective condition.

The infectivity of bacteriophages is determined in part not only by the specificity of their encoded tail fiber recognition proteins, but also by the environmental conditions that are present. That includes but is not limited to the metabolic state of the bacterium the bacteriophage is capable of recognizing. Furthermore, it includes the chemical and physical composition of the environment that the bacteriophage and the bacterium experience when the phage contacts a bacterium. Environmental factors of the solution such as but not limited to pH, osmolarity, temperature, rheological properties and others all may impact the ability of a bacteriophage to infect a bacterium.

To account for these variables, the step of exposing a sample of bacteria to a phage in the liquid clearing host-range assay and the marker host range assay may be conducted under defined conditions. The defined conditions may comprise at least one of: a defined time duration, a defined temperature, and the presence of at least one of a) at least one compound selected from carbohydrates and related compounds, b) at least compound selected from nitrogen containing compounds, c) at least compound selected from nucleic acids and related compounds, d) at least compound selected from lipid, e) at least one inorganic compound, and f) at least one organic compound.

In some embodiments the carbohydrates and related compounds are selected from sugars such as glucose, mannose, and maltose. In some embodiments the carbohydrates and related compounds are selected from carboxy sugars that are degraded by the pentose phosphate pathway, which may but need not generate more moles of NADPH per mole consumed as compared to glucose. In some embodiments the carbohydrates and related compounds are selected from compounds feeding into central metabolism, such as but not limited to a ketoglutarate, D-malic acid, or pyruvic acid. In some embodiments the carbohydrates and related compounds are selected from glycerol and other carbohydrate (or other) osmoprotectants that may but need not provide osmotic support to cells that exist in a potentially weakened or damaged state in the environment. In some embodiments glycerol functions as a volume excluder that increases the efficiency of phage infection. In some embodiments the carbohydrates and related compounds are selected from sugar alcohols, such as aminoethanol.

In some embodiments the nitrogen containing compounds are selected from ammonium, other amino acid building blocks, and free amino acids. The free amino acid may be any genome encoded standard amino acid or any non-standard amino acid. In some embodiments the amino acid is selected from glutamic acid and glutamine. In some embodiments the amino acid is selected from branched chain amino acids. In some embodiments the nitrogen containing compounds are selected from degradation products of branched amino acids such as propionic acid.

In some embodiments the nucleic acids and related compounds are selected from nucleotides, nucleosides, deoxynucleotides, and deoxynucleosides. In some embodiments the nucleic acids and related compounds are selected from metabolites of the nucleotide generation pathways such as inosine.

In some embodiments the lipid compounds are selected from fatty acids and related compounds. TWEEN® 20, 40, and 80 are converted to fatty acids upon ester hydrolysis and can also be used. In some embodiments the lipid compounds are selected from lecithin and related compounds.

In some embodiments the inorganic compounds are selected from salts, such as for example thiosulfate.

In some embodiments the organic compounds are selected from aliphatics, aromatics, heterocyclics, and non-biogenic polymers.

In some embodiments the at least one compound is selected from:

| Compound | CAS # |
|---|---|
| 1,2-Propanediol | 57-55-6 |
| 2-Aminoethanol | 141-43-5 |
| Glucuronamide | 3789-97-7 |
| Tyramine | 60-19-5 |
| b-Phenylethylamine | 156-28-5 |
| L-Aspartic Acid | 3792-50-5 |
| L-Proline | 147-85-3 |
| D-Alanine | 338-69-2 |
| D-Serine | 312-84-5 |
| L-Glutamic Acid | 6106-04-3 |
| L-Asparagine | 70-47-3 |
| D-Aspartic Acid | 1783-96-6 |
| L-Glutamine | 56-85-9 |
| Gly-Asp | |
| D-Threonine | 632-20-2 |
| Gly-Glu | 7412-78-4 |
| L-Serine | 56-45-1 |
| L-Threonine | 72-19-5 |
| L-Alanine | 56-41-7 |
| Ala-Gly | 687-69-4 |
| Gly-Pro | 704-15-4 |
| L-Arabinose | 87-72-9 |
| N-Acetyl-D-Glucosamine | 7512-17-6 |
| D-Galactose | 59-23-4 |
| D-Trehalose | 99-20-7 |
| D-Mannose | 3458-28-4 |
| Dulcitol | 608-66-2 |
| D-Sorbitol | 50-70-4 |
| Glycerol | 56-81-5 |
| L-Fucose | 2438-80-4 |
| D,L-a-Glycerol Phosphate | 3325-00-6 |

-continued

| Compound | CAS # |
|---|---|
| D-Xylose | 58-86-6 |
| D-Mannitol | 69-65-8 |
| D-Glucose-6-Phosphate | 3671-99-6 |
| D-Ribose | 50-69-1 |
| L-Rhamnose | 3615-41-6 |
| D-Fructose | 57-48-7 |
| a-D-Glucose | 50-99-7 |
| Maltose | 69-79-4 |
| D-Melibiose | 585-99-9 |
| Thymidine | 50-89-5 |
| a-Methyl-D-Galactoside | 3396-99-4 |
| a-D-Lactose | 63-42-3 |
| Lactulose | 4618-18-2 |
| Sucrose | 57-50-1 |
| Uridine | 58-96-8 |
| D-Glucose-1-Phosphate | 56401-20-8 |
| D-Fructose-6-Phosphate | 26177-86-637250-85-4 |
| b-Methyl-D-Glucoside | 709-50-2 |
| Adonitol | 488-81-3 |
| Maltotriose | 1109-28-0 |
| 2'-Deoxyadenosine | 16373-93-6 |
| Adenosine | 58-61-7 |
| m-Inositol | 87-89-8 |
| D-Cellobiose | 528-50-7 |
| Inosine | 58-63-9 |
| N-Acetyl-D-Mannosamine | 7772-94-3 |
| D-Psicose | 551-68-8 |
| L-Lyxose | 1949-78-6 |
| D-Saccharic Acid | 576-42-1 |
| Succinic Acid | 6106-21-4 |
| D-Glucuronic Acid | 14984-34-0 |
| D-Gluconic Acid | 527-07-1 |
| D,L-Lactic Acid | 312-85-6 |
| Formic Acid | 141-53-7 |
| D-Galactonic Acid-g-Lactone | 2782-07-2 |
| D,L-Malic Acid | 6915-15-7 |
| Acetic Acid | 127-09-3 |
| D-Glucosaminic Acid | 3646-68-2 |
| a-Ketoglutaric Acid | 22202-68-2 |
| a-Ketobutyric Acid | 2013-26-5 |
| m-Tartaric Acid | 147-73-9 |
| a-Hydroxyglutaric Acid-g-Lactone | 21461-84-7 |
| a-Hydroxybutyric Acid | 19054-57-0 |
| Citric Acid | 6132-04-3 |
| Fumaric Acid | 17013-01-3 |
| Bromosuccinic Acid | 923-06-8 |
| Propionic Acid | 137-40-6 |
| Mucic Acid | 526-99-8 |
| Glycolic Acid | 79-14-1 |
| Glyoxylic Acid | 563-96-2 |
| Tricarballylic Acid | 99-14-9 |
| Acetoacetic Acid | 3483-11-2 |
| Mono-Methylsuccinate | 3878-55-5 |
| D-Malic Acid | 636-61-3 |
| L-Malic Acid | 138-09-0 |
| p-Hydroxyphenyl Acetic Acid | 156-38-7 |
| m-Hydroxyphenyl Acetic Acid | 621-37-4 |
| Pyruvic Acid | 113-24-6 |
| L-Galactonic Acid-g-Lactone | 1668-08-2 |
| D-Galacturonic Acid | 91510-62-2 |
| Methylpyruvate | 600-22-6 |
| Tween 20 | 9005-64-5 |
| Tween 40 | 9005-66-7 |
| Tween 80 | 9005-65-6 |

Another approach to modify the host range detected in a host range assay is to pretreat bacteria before exposing the bacterial samples to the phage. This allows for a decoupling of steps designed to modify the state of a bacterial cell (and possibly its susceptibility to phage infection) from conditions used for the infection itself. For example the metabolic rate may be increased during a pre-incubation step, which in turn may increase at least one of the replicative, transcriptive, and translative functions that influence clearing or production of a marker following infection of a bacterial cell by a phage. Furthermore, it is possible that such an incubation period also changes the surface receptor expression, or changes the composition of the cell wall of the bacterium, which may also modify whether a phage can productively infect the bacteria.

Accordingly, in some embodiments samples of bacteria are incubated in metabolic stimulation conditions before exposure to the phage for the phage host range assay. In some embodiments exposure of the cells to metabolic stimulation conditions stimulates cell division in the cells. In some embodiments exposure of the cells to metabolic stimulation conditions does not stimulate cell division in the cells. In some embodiments, exposure of the cells to metabolic stimulation conditions stimulates at least one of the replicative, transcriptive, and translative functions that influence clearing or production of a marker following infection of a bacterial cell by a phage.

As used herein, "metabolic stimulation conditions" are conditions that promote development of a microorganism metabolic state in which the microorganism is permissive to infection and maintenance of a phage life cycle and/or infection followed by expression of a marker gene produce encoded by a heterologous nucleic acid sequence in the genome of the phage. In some embodiments the microorganism prior to exposure to the metabolic stimulation conditions is not permissive to infection and maintenance of a phage life cycle. In other embodiments the microorganism prior to exposure to the metabolic stimulation conditions is in a metabolic state that reduces its susceptibility to infection and maintenance of a phage life cycle compared to a comparable microorganism grown under log phase conditions. In such embodiments exposure of the microorganism to the metabolic stimulation conditions increases the susceptibility of the microorganism to infection and maintenance of a phage life cycle. In some embodiments metabolic stimulation conditions comprise at least one of a permissive temperature, pH, $Po_2$, and nutrient combination. In some embodiments the target microbe undergoes at least one cell division under metabolic stimulation conditions. In some embodiments the target microbe does not undergo at least one cell division under metabolic stimulation conditions.

In some embodiments the sample is exposed to metabolic stimulation conditions before the sample is contacted with a phage. In some such embodiments the sample is then removed from metabolic stimulation conditions prior to contacting with a phage while in other embodiments the sample is maintained under metabolic stimulation conditions when contacted by a phage. In some embodiments the sample is exposed to a first set of metabolic stimulation conditions for a first period of time and then transferred to a second set of metabolic stimulation conditions. In some embodiments the recombinant phage is exposed to the sample while the sample is maintained under the second set of metabolic stimulation conditions. In some embodiments the sample is exposed to metabolic stimulation conditions for from 5 minutes to 24 hours before the sample is contacted by a phage. In some embodiments the sample is exposed to metabolic stimulation conditions for from 5 minutes to 6 hours before the sample is contacted by a phage. In some embodiments the sample is exposed to metabolic stimulation conditions for from 10 minutes to 6 hours before the sample is contacted by a phage. In some embodiments the sample is exposed to metabolic stimulation conditions for from 20 minutes to 6 hours before the sample is contacted by a phage. In some embodiments the sample is exposed to metabolic stimulation conditions for from 30 minutes to 6 hours before the sample is contacted by a phage. In some embodiments the sample is exposed to metabolic stimulation conditions for from 1 to 6 hours before the sample is contacted by a phage. In some embodiments the sample is exposed to metabolic stimulation conditions for from 2 to 6 hours before the sample is contacted by a phage. In some embodiments the sample is exposed to metabolic stimulation conditions for from 2 to 12 hours before the sample is contacted by a phage. In some embodiments the sample is exposed to metabolic stimulation conditions for from 3 to 12 hours before the sample is contacted by a phage. In some embodiments the sample is exposed to metabolic stimulation conditions for from 6 to 12 hours before the sample is contacted by a phage. In some embodiments the sample is exposed to metabolic stimulation conditions for from 12 to 24 hours before the sample is contacted by a phage. In some embodiments the sample is exposed to metabolic stimulation conditions for at least 10 minutes, at least 20 minutes, at least 30 minutes, at least 40 minutes, at least 50 minutes, at least 1 hour, at least 1.5 hours, or at least 2 hours.

By conducting a host range analysis under at least one embodiment of conditions described in this section it is possible to define conditions that provide a useful level of sensitivity and/or selectivity for a method of detecting target bacteria. In some embodiments the conditions used for the host range analysis are also used for methods of detecting target bacteria using the phage when those phage are used to detect target bacteria in other contexts (i.e., when testing environmental samples).

Methods of Detecting Target Bacteria

The recombinant phage are useful to detect target microbes. This disclosure provides exemplary recombinant phage and methods of making further recombinant phage. This disclosure also defines the target bacteria of certain disclosed recombinant phage and provides methods of identifying the target bacteria of any phage, including any recombinant phage. Accordingly, this disclosure enables methods of detecting target microbes using recombinant phage. By, among other things, enabling a detailed characterization of the target bacteria of the recombinant phage this disclosure in certain embodiments provides useful methods not available in the prior art.

The methods are broadly applicable and in view of the teachings of this disclosure skilled artisans will understand how to apply the methods to detect any type of archaea and/or bacteria. In some embodiments the archaea is a Euryarcheota. In some embodiments the archaea is a Crenarcheota. In some embodiments the bacteria is a member of a phyla selected from Actinobacteria, Aquificae, Armatimonadetes, Bacteroidetes, Caldiserica, Chlamydiae, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Nitrospirae, Planctomycetes, Proteobacteria, Spirochaetes, Synergistets, Tenericutes, Thermodesulfobacteria, Thermotogae. In some embodiments the bacteria is at least one Firmicutes selected from *Bacillus, Listeria, Staphylococcus*. In some embodiments the bacteria is at least one Proteobacteria selected from Acidobacillus, *Aeromonas, Burkholderia, Neisseria, Shewanella, Citrobacter, Enterobacter, Erwinia, Escherichia, Klebsiella, Kluyvera, Morganella, Shigella, Yersinia, Coxiella, Rickettsia, Legionella, Avibacterium, Haemophilus, Pasteurella, Acinetobacter, Moraxella, Pseudomonas, Vibrio, Xanthomonas*. In some embodiments the bacteria is at least one Tenericutes selected from *Mycoplasma*, Spiroplasma, and *Ureaplasma*.

Common bacterial contaminates of food that are detected using the phage and methods disclosed herein include, without limitation, *E. coli* (including without limitation pathogenic *E. coli, E. coli* O157:H7, Shiga-toxin producing *E. coli, E. coli* 026, *E. coli* 111, *E. coli* 0103, *E. coli* 0121, *E. coli* 045 and *E. coli* 0145), coliform bacteria (which include without limitation, *Citrobacter, Enterobacter, Hafnia, Klebsiella, Serratia*), *Shigella, Listeria, Clostridium* (including *Clostridium botulinum* and *Clostridium perfringens*), *Vibrio* (including *Vibrio cholera* and *Vibrio vulnificus*), Enterobacteriacae, *Staphylococcus* (including *Staphylococcus aureus* and *Staphylococcus epidermis*), *Bacillus* (including *Bacillus cereus*), *Campylobacter* (including *Campylobacter jejuni*), *Pseudomonas, Streptococcus, Acinetobacter, Klebsiella, Campylobacter*, and *Yersinia*.

The methods comprise providing a sample; exposing the sample to at least a first type of recombinant phage capable of infecting at least a first set of target bacteria, comprising a heterologous nucleic acid sequence encoding at least a first marker and assay for the at least one first marker in the exposed sample. Preferably, the first type of recombinant phage comprises a heterologous nucleic acid sequence; a codon optimized at least first markers. In some embodiments, detection of the first marker in the sample indicates the presence of bacteria of the first set of target bacteria in the sample.

In certain embodiments the methods comprise providing a sample; exposing the sample to a first type of phage capable of infecting a first set of target bacteria and comprising a heterologous nucleic acid sequence encoding a first marker; exposing the sample to a second type of phage capable of infecting a second set of target bacteria and comprising a heterologous nucleic acid sequence encoding a second marker; and assaying for the presence of the first marker and the second marker in the exposed sample. In some embodiments, detection of the first marker in the sample indicates the presence of bacteria of the first set of target bacteria in the sample. In some embodiments, detection of the second marker in the sample indicates the presence of bacteria of the second set of target bacteria in the sample. In some embodiments the first marker and the second marker are the same, and detection of the marker in the sample indicates the presence of bacteria of at least one of the first set of target bacteria and the second set of target bacteria in the sample.

In some embodiments, the first set of target bacteria and the second set of target bacteria independently comprise at least two species of a single genus of bacteria. In some embodiments, the first set of target bacteria and the second set of target bacteria independently comprise at least three species of a single genus of bacteria. In some embodiments, the first set of target bacteria and the second set of target bacteria independently comprise at least four species of a single genus of bacteria. In some embodiments, the single genus of bacteria is *Listeria*. In some embodiments, the first set of target bacteria and the second set of target bacteria comprise at least one species of bacteria in common. In some embodiments, the first set of target bacteria and the second set of target bacteria comprise at least two species of bacteria in common. In some embodiments, the first set of target bacteria and the second set of target bacteria comprise at least three species of bacteria in common. In some embodiments, the first set of target bacteria and the second set of target bacteria comprise at least four species of bacteria in common. In some embodiments, the species of *Listeria* are selected from *Listeria innocua, Listeria monocytogenes, Listeria seeligeri, Listeria ivanovii, Listeria marthii, Listeria* rocourti and *Listeria* welshimeri. In some embodiments, the species of *Listeria* are selected from *Listeria innocua, Listeria monocytogenes, Listeria seeligeri*, and *Listeria* welshimeri.

In some embodiments, the target bacteria comprise at least one sig B allelotype of *Listeria innocua* selected from 11, 22, 37, and 56. In some embodiments, the target bacteria comprise at least four allelotypes of *Listeria innocua*. In some embodiments, the at least four allelotypes of *Listeria innocua* are 11, 22, 37, and 56.

In some embodiments, the target bacteria comprise at least one ribotype of *Listeria monocytogenes* selected from DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D. In some embodiments, the target bacteria comprise at least nineteen ribotypes of *Listeria monocytogenes*. In some embodiments, the at least nineteen ribotypes of *Listeria monocytogenes* are DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D.

In some embodiments, the target bacteria comprise at least one sig B allelotype of *Listeria* seeligeri selected from 3, 20, 24, and 35. In some embodiments, the target bacteria comprise at least four allelotypes of *Listeria* seeligeri. In some embodiments, the at least four allelotypes of *Listeria* seeligeri are 3, 20, 24, and 35.

In some embodiments, the target bacteria comprise at least one sig B allelotype of *Listeria* welshimeri selected from 15, 27, 32, and 89. In some embodiments, the target bacteria comprise at least four allelotypes of *Listeria* welshimeri. In some embodiments, the at least four allelotypes of *Listeria* welshimeri are 15, 27, 32, and 89.

In some embodiments, the first set of target bacteria are all members of the same genus. In some embodiments, the second set of target bacteria are all members of the same genus. In some embodiments, all of the target bacteria are *Listeria*. In some embodiments, the target bacteria do not include at least one of *Bacillus cereus, Bacillus megaterium, Bacillus subtilis, Enterococcus durans, Enterococcus faceium, Enterococcus hirae, Kocuria varians, Kurthia gibsonii, Kurthia zopfii, Rhodococcus equi, Staphylococcus aureus, Staphylococcus epidermidis, Staphylococcus saprophyticus, Streptococcus equi, Streptococcus galloyticus, Lactobacillus casei, Lactobacillus buchneri, Lactobacillus lactus, Lactobacillus frrmentum, Micrococcus lutues, Pseudomonas protogens, Pseudomonas florescens, Aeromonas* sp, *Serratia liquefaciens, Serratia proteamaculans, Serratia liquefaciens, Bacillaceae bacterium, Serratia proteamaculans, Pseudomonas florescens, Pseudomonas poae, Pseudomonas* sp, *Pseudomonas fragi, Providencia alcalifaciens, Serratia* sp, *Serratia grimesii, Hafnia* sp., *Serratia proteamaculans, Pseudomonas florescens, Chryseobacterium* sp., *Pseudomonas fragi*, and Enterobacteriaceae. In some embodiments, the target bacteria do not include *Bacillus cereus, Bacillus megaterium, Bacillus subtilis, Enterococcus durans, Enterococcus faceium, Enterococcus hirae, Kocuria varians, Kurthia gibsonii, Kurthia zopfii, Rhodococcus equi, Staphylococcus aureus, Staphylococcus epidermidis, Staphylococcus saprophyticus, Streptococcus equi, Streptococcus galloyticus, Lactobacillus casei, Lactobacillus buchneri, Lactobacillus lactus, Lactobacillus fermentum, Micrococcus lutues, Pseudomonas protogens, Pseudomonas florescens, Aeromonas* sp, *Serratia liquefa-*

*ciens, Serratia proteamaculans, Serratia liquefaciens, Bacillaceae bacterium, Serratia proteamaculans, Pseudomonas florescens, Pseudomonas poae, Pseudomonas* sp, *Pseudomonas fragi, Providencia alcalifaciens, Serratia* sp, *Serratia grimesii, Hafnia* sp., *Serratia proteamaculans, Pseudomonas florescens, Chryseobacterium* sp., *Pseudomonas fragi*, and Enterobacteriaceae.

In some embodiments, the methods further comprise exposing the sample to a third type of phage capable of infecting a third set of target bacteria and comprising a heterologous nucleic acid sequence encoding a third marker. In some embodiments, the methods further comprise exposing the sample to a fourth type of phage capable of infecting a fourth set of target bacteria and comprising a heterologous nucleic acid sequence encoding a fourth marker. In some embodiments, the methods further comprise exposing the sample to a fifth type of phage capable of infecting a fifth set of target bacteria and comprising a heterologous nucleic acid sequence encoding a fifth marker. In some embodiments, the methods further comprise exposing the sample to a sixth type of phage capable of infecting a sixth set of target bacteria and comprising a heterologous nucleic acid sequence encoding a sixth marker. In some embodiments, the methods further comprise exposing the sample to a seventh type of phage capable of infecting a seventh set of target bacteria and comprising a heterologous nucleic acid sequence encoding a seventh marker. In some embodiments, the methods further comprise exposing the sample to an eighth type of phage capable of infecting an eighth set of target bacteria and comprising a heterologous nucleic acid sequence encoding an eighth marker. In some embodiments, the methods further comprise exposing the sample to a ninth type of phage capable of infecting a ninth set of target bacteria and comprising a heterologous nucleic acid sequence encoding a ninth marker. In some embodiments, the methods further comprise exposing the sample to ten or more types of phage capable of infecting ten or more sets of target bacteria and comprising a heterologous nucleic acid sequences encoding ten or more markers. In some embodiments that utilize three or more types of phage, all of the three or more markers are different. In some embodiments that utilize three or more types of phage, all of the three or more markers are the same. In some embodiments that utilize three or more types of phage, two, three, four, five, six, seven, eight, or nine of the markers are the same.

In some embodiments, at least one type of phage used in the method is selected from A511, P100, LP40, LP48, LP99, LP101, LP124, LP125, and LP143, and derivatives thereof. In some embodiments, every type of phage used in the method is selected from A511, P100, LP40, LP48, LP99, LP101, LP124, LP125, and LP143, and derivatives thereof.

In some embodiments, the first marker is a screenable marker. In some embodiments, the first marker is a luciferase. In some embodiments, the luciferase is at least 70%, at least 80%, at least 90%, at least 91%, at least 92%, at least 93%, at least 94%, at least 95%, at least 96%, at least 97%, at least 98%, at least 99%, at least 99.5% or at least 99.9% identical to SEQ ID NO: 2. In some embodiments, the luciferase is at least 70%, at least 80%, at least 90%, at least 91%, at least 92%, at least 93%, at least 94%, at least 95%, at least 96%, at least 97%, at least 98%, at least 99%, at least 99.5% or at least 99.9% identical to SEQ ID NO: 4.

In some embodiments, the phage is selected from LP48::ffluc, LP99::ffluc, LP101::ffluc, LP124::ffluc, LP125::ffluc, LP143::ffluc, A511::ffluc, P100::ffluc, LP48::COP2, LP99::COP2, LP101::COP2, LP124::COP2, LP125::COP2, LP143::COP2, A511::COP2, P100::COP2, LP48::COP3, LP99::COP3, LP101::COP3, LP124::COP3, LP125::COP3, LP143::COP3, A511::COP3, and P100::COP3. In some embodiments, the phage is selected from LP40::nluc, LP124::nluc, LP125::nluc, A511::nluc, P100::nluc, LP40::COP2, LP124::COP2, LP125::COP2, A511::COP2, P100::COP2, LP40::COP3, LP124::COP3, LP125::COP3, A511::COP3, P100::COP3.

In some embodiments, the sample is an environmental sample.

In some embodiments, the sample is an agricultural sample. In some embodiments the agricultural sample is stock feed or food supply. In some embodiments, the food supply is for human or non-human consumption. In some embodiments, the food supply is a plant or an animal.

In some embodiments, the agricultural sample in the composition is selected from a dairy product, a fruit product, a grain product, a sweet, a vegetable product, and a meat product. In some embodiments, the dairy product includes foods derived from milk products comprising milk, butter, yogurt, cheese, ice cream and queso fresco. In some embodiments, the fruit product comprises apple, oranges, bananas, berries and lemons. In some embodiments, the grain product comprises wheat, rice, oats, barley, bread and pasta. In some embodiments, the sweet product comprises candy, soft drinks, cake, and pie. In some embodiments, the vegetable product comprises spinach, carrots, onions, peppers, avocado and broccoli. In some embodiments, the vegetable product is guacamole. In some embodiments, the meat product comprises chicken, fish, turkey, pork and beef. In some embodiments, the meat product further comprises deli meats and ground meets, as well as deli turkey and ground beef.

In some embodiments, the food sample in the composition is selected from a dairy product, a fruit product, a grain product, a sweet, a vegetable product, and a meat product. In some embodiments, the dairy product includes foods derived from milk products comprising milk, butter, yogurt, cheese, ice cream and queso fresco. In some embodiments, the fruit product comprises apple, oranges, bananas, berries and lemons. In some embodiments, the grain product comprises wheat, rice, oats, barley, bread and pasta. In some embodiments, the sweet product comprises candy, soft drinks, cake, and pie. In some embodiments, the vegetable product comprises spinach, carrots, onions, peppers, avocado and broccoli. In some embodiments, the vegetable product is guacamole. In some embodiments, the meat product comprises chicken, fish, turkey, pork and beef. In some embodiments, the meat product further comprises deli meats and ground meets, as well as deli turkey and ground beef.

In some embodiments, the marker is detected in the sample, indicating the presence of bacteria of the first set of target bacteria in the sample.

In some embodiments, the target microbe of the method is selected from the group consisting of coliform bacteria, *Escherichia, Shigella, Listeria, Clostridium, Vibrio, Enterobactenacae, Staphylococcus, Bacillus, Campylobacter, Pseudomonas, Streptococcus, Acinetobacter, Klebsiella, Cronobacter, Mycobacterium, Campylobacter*, and *Yersinia*. In some embodiments, the target microbe is *E. coli*. In some embodiments, the target microbe is *Listeria* selected from the group consisting of *Listeria innocua, Listeria monocytogenes, Listeria seeligeri, Listeria ivanovii, Listeria grayi, Listeria marthii, Listeria rocourti, Listeria welshimeri, Listeria floridensis, Listeria aquatic, Listeria fleischmannii, Listeria weihenstephanensis, Listeria cornellensis, Listeria riparia*, and *Listeria grandensis.*

In some embodiments, the second marker is a screenable marker. In some embodiments, the second marker is a luciferase. In some embodiments, the luciferase is at least 70%, at least 80%, at least 90%, at least 91%, at least 92%, at least 93%, at least 94%, at least 95%, at least 96%, at least 97%, at least 98%, at least 99%, at least 99.5% or at least 99.9% identical to SEQ ID NO: 2. In some embodiments, the luciferase is at least 70%, at least 80%, at least 90%, at least 91%, at least 92%, at least 93%, at least 94%, at least 95%, at least 96%, at least 97%, at least 98%, at least 99%, at least 99.5% or at least 99.9% identical to SEQ ID NO:4.

In some embodiments, the second type of phage is selected from LP48::ffluc, LP99::ffluc, LP101::ffluc, LP124::ffluc, LP125::ffluc, LP143::ffluc, A511::ffluc, P100::ffluc, LP48::COP2, LP99::COP2, LP101::COP2, LP124::COP2, LP125::COP2, LP143::COP2, A511::COP2, P100::COP2, LP48::COP3, LP99::COP3, LP101::COP3, LP124::COP3, LP125::COP3, LP143::COP3, A511::COP3, P100::COP3. In some embodiments, the second type of phage is selected from LP40::nluc, LP124::nluc, LP125::nluc, A511::nluc, P100::nluc, LP40::COP2, LP124::COP2, LP125::COP2, A511::COP2, P100::COP2, LP40::COP3, LP124::COP3, LP125::COP3, A511::COP3, P100::COP3.

In some embodiments, the method comprises exposing the sample to the first type of phage and the second type of phage at the same time.

In some embodiments, the sample is an environmental sample.

In some embodiments, the first marker is detected in or on the sample, or in situ, indicating the presence of bacteria of the first set of target bacteria in or on the sample, or in situ. In some embodiments, the second marker is detected in the sample, indicating the presence of bacteria of the second set of target bacteria in the sample. In some embodiments, the first marker and the second marker are the same, and the marker is detected in or on the sample, or in situ, indicating the presence of bacteria of at least one of the first set of target bacteria and the second set of target bacteria in or on the sample, or in the in situ location.

In some embodiments, the sample is exposed to metabolic stimulation conditions before it is exposed to the phage.

In some embodiments, the methods further comprise incubating the sample under metabolic stimulation conditions for a period of time before exposing the sample to the phage capable of infecting target bacteria.

In certain embodiments the methods comprise providing a sample; exposing the sample to at least one recombinant *Listeria* phage comprising a heterologous nucleic acid sequence encoding a marker, the recombinant *Listeria* phage selected from recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof; and assaying for the presence of the marker in the exposed sample. In some embodiments, the methods further comprise exposing the sample to at least one recombinant *Listeria* phage comprising a heterologous nucleic acid sequence encoding a marker, the recombinant *Listeria* phage selected from recombinant A511 and recombinant P100. In some embodiments, detection of the marker in the sample indicates the presence of *Listeria* in the sample.

In some embodiments, target bacteria of the recombinant *Listeria* phage comprise at least one species of *Listeria* selected from *Listeria innocua, Listeria monocytogenes, Listeria seeligeri, Listeria ivanovii, Listeria marthii, Listeria rocourti*, and *Listeria* welshimeri. In some embodiments, detection of the marker in the sample indicates the presence of the at least one species of *Listeria* selected from *Listeria innocua, Listeria monocytogenes, Listeria seeligeri, Listeria ivanovii, Listeria marthii, Listeria rocourti*, and *Listeria* welshimeri in the sample.

In some embodiments, target bacteria of the *Listeria* phage comprise at least one species of *Listeria* selected from *Listeria innocua, Listeria monocytogenes, Listeria seeligeri*, and *Listeria* welshimeri. In some embodiments, detection of the marker in the sample indicates the presence of the at least one species of *Listeria* selected from *Listeria innocua, Listeria monocytogenes, Listeria seeligeri*, and *Listeria* welshimeri in the sample.

In some embodiments, target bacteria of the *Listeria* phage comprise at least one sig B allelotype of *Listeria innocua* selected from 11, 22, 37, and 56, and detection of the marker in the sample indicates the presence of at least one sig B allelotype of *Listeria innocua* selected from 11, 22, 37, and 56. In some embodiments, the at least one *Listeria* phage is capable of infecting *Listeria innocua* sig B allelotypes 11, 22, 37, and 56.

In some embodiments, target bacteria of the *Listeria* phage comprise at least one ribotype of *Listeria monocytogenes* selected from DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D; and detection of the marker in the sample indicates the presence of at least one ribotype of *Listeria monocytogenes* selected from DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D. In some embodiments, target bacteria of the *Listeria* phage comprise *Listeria monocytogenes* ribotypes DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D.

In some embodiments, target bacteria of the *Listeria* phage comprise at least one sig B allelotype of *Listeria* seeligeri selected from 3, 20, 24, and 35, and detection of the marker in the sample indicates the presence of at least one sig B allelotype of *Listeria* seeligeri selected from 3, 20, 24, and 35. In some embodiments, target bacteria of the *Listeria* phage comprise *Listeria seeligeri* sig B allelotypes 3, 20, 24, and 35.

In some embodiments, target bacteria of the *Listeria* phage comprise at least one sig B allelotype of *Listeria* welshimeri selected from 15, 27, 32, and 89, and detection of the marker in the sample indicates the presence of at least one sig B allelotype of *Listeria* welshimeri selected from 15, 27, 32, and 89. In some embodiments, target bacteria of the *Listeria* phage comprise *Listeria* welshimeri sig B allelotypes 15, 27, 32, and 89.

In some embodiments, the target bacteria comprise at least two species of *Listeria* selected from *Listeria innocua, Listeria monocytogenes, Listeria seeligeri*, and *Listeria* welshimeri. In some embodiments, the target bacteria comprise at least three species of *Listeria* selected from *Listeria innocua, Listeria monocytogenes, Listeria seeligeri*, and *Listeria* welshimeri. In some embodiments, the target bacteria comprise at least four species of *Listeria* selected from

*Listeria innocua, Listeria monocytogenes, Listeria seeligeri, Listeria ivanovii, Listeria marthii, Listeria rocourti*, and *Listeria welshimeri*. In some embodiments, the target bacteria do not include at least one of *Bacillus cereus, Bacillus megaterium, Bacillus subtilis, Enterococcus durans, Enterococcus faceium, Enterococcus hirae, Kocuria varians, Kurthia gibsonii, Kurthia zopfii, Rhodococcus equi, Staphylococcus aureus, Staphylococcus epidermidis, Staphylococcus saprophyticus, Streptococcus equi, Streptococcus galloyticus, Lactobacillus casei, Lactobacillus buchneri, Lactobacillus lactus, Lactobacillus fermentum, Micrococcus lutues, Pseudomonas protogens, Pseudomonas florescens, Aeromonas* sp, *Serratia liquefaciens, Serratia proteamaculans, Serratia liquefaciens, Bacillaceae bacterium, Serratia proteamaculans, Pseudomonas florescens, Pseudomonas poae, Pseudomonas* sp, *Pseudomonas fragi, Providencia alcalifaciens, Serratia* sp, *Serratia grimesii, Hafnia* sp., *Serratia proteamaculans, Pseudomonas florescens, Chryseobacterium* sp., *Pseudomonas fragi*, and Enterobacteriaceae. In some embodiments, the target bacteria do not include *Bacillus cereus, Bacillus megaterium, Bacillus subtilis, Enterococcus durans, Enterococcus faceium, Enterococcus hirae, Kocuria varians, Kurthia gibsonii, Kurthia zopfii, Rhodococcus equi, Staphylococcus aureus, Staphylococcus epidermidis, Staphylococcus saprophyticus, Streptococcus equi, Streptococcus galloyticus, Lactobacillus casei, Lactobacillus buchneri, Lactobacillus lactus, Lactobacillus fermentum, Micrococcus lutues, Pseudomonas protogens, Pseudomonas florescens, Aeromonas* sp, *Serratia liquefaciens, Serratia proteamaculans, Serratia liquefaciens, Bacillaceae bacterium, Serratia proteamaculans, Pseudomonas florescens, Pseudomonas poae, Pseudomonas* sp, *Pseudomonas fragi, Providencia alcalifaciens, Serratia* sp, *Serratia grimesii, Hafnia* sp., *Serratia proteamaculans, Pseudomonas florescens, Chryseobacterium* sp., *Pseudomonas fragi*, and Enterobacteriaceae.

In some embodiments the sample is exposed to the phage for a period of time before assaying for the presence of a marker in the exposed sample is conducted. In some embodiments the period of time is from 1 minute to 24 hours, from 5 minutes to 12 hours, from 5 minutes to 6 hours, from 5 minutes to 3 hours, from 5 minutes to 2 hours, from 5 minutes to 1 hour, from 5 minutes to 50 minutes, from 5 minutes to 40 minutes, from 5 minutes to 30 minutes, from 5 minutes to 20 minutes, or from 5 minutes to 10 minutes. In some embodiments the period of time is from 1 to 2 hours, from 1 to 4 hours, or from 2 to 4 hours. In some embodiments the period of time is for at least 1 minute, at least 5 minutes, at least 10 minutes, at least 20 minutes, at least 30 minutes, at least 40 minutes, at least 50 minutes, or at least 1 hour.

In some embodiments any phage and/or parts of phage in the exposed sample are substantially removed before the assaying for the presence of a marker in the exposed sample is conducted.

In some embodiments of the methods of this disclosure, the methods further comprise comparing a detected level of marker in a test sample to at least one of a positive control and a negative control. The positive and/or negative control may be used to calibrate the assay including for the purpose of defining a positive result and/or a negative result.

Compositions

The methods of assaying phage host range provided herein allow, in certain embodiments, for the characterization of the host range of phage—and thus definition of target bacteria for phage—at a resolution not previously provided. One use of the methods and of phage characterized by the methods is to identify useful combinations of phage that may be used together in a system to detect target bacteria. In some embodiments such systems provide phage separately and the phage are then mixed before or during an assay. Alternatively, such systems comprise useful mixtures of phage, such as phage provided in a buffer for use in an assay. Compositions comprising useful combinations of phage are also, necessarily, produced during the assay in several embodiments. Accordingly, this disclosure also provides compositions that comprise phage.

In some embodiments the composition comprises: at least one recombinant *Listeria* phage comprising a heterologous nucleic acid sequence encoding a marker, the recombinant *Listeria* phage selected from recombinant A511 and derivatives thereof, recombinant P100 and derivatives thereof, recombinant LP40 and derivatives thereof, recombinant LP44 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof and at least one non-phage component selected from Table 5 and/or from at least one of a) at least one compound selected from carbohydrates and related compounds, b) at least compound selected from nitrogen containing compounds, c) at least compound selected from nucleic acids and related compounds, d) at least compound selected from lipid, e) at least one inorganic compound, and f) at least one organic compound. In some embodiments the composition comprises at least one of 1,2-Propanediol, 2-Aminoethanol, Glucuronamide, Tyramine, b-Phenylethylamine, L-Aspartic Acid, L-Proline, D-Alanine, D-Serine, L-Glutamic Acid, L-Asparagine, D-Aspartic Acid, L-Glutamine, Gly-Asp, D-Threonine, Gly-Glu, L-Serine, L-Threonine, L-Alanine, Ala-Gly, Gly-Pro, L-Arabinose, N-Acetyl-D-Glucosamine, D-Galactose, D-Trehalose, D-Mannose, Dulcitol, D-Sorbitol, Glycerol, L-Fucose, D,L-a-Glycerol, Phosphate, D-Xylose, D-Mannitol, D-Glucose-6-Phosphate, D-Ribose, L-Rhamnose, D-Fructose, a-D-Glucose, Maltose, D-Melibiose, Thymidine, a-Methyl-D-Galactoside, a-D-Lactose, Lactulosem Sucrose, Uridine, D-Glucose-1-Phosphate, D-Fructose-6-Phosphate, b-Methyl-D-Glucoside, Adonitol, Maltotriose, 2'-Deoxyadenosine, Adenosine, m-Inositol, D-Cellobiose, Inosine, N-Acetyl-D-Mannosamine, D-Psicose, L-Lyxose, D-Saccharic Acid, Succinic Acid, D-Glucuronic Acid, D-Gluconic Acid, D,L-Lactic Acid, Formic Acid, D-Galactonic Acid-g-Lactone, D,L-Malic Acid, Acetic Acid, D-Glucosaminic Acid, a-Ketoglutaric Acid, a-Ketobutyric Acid, m-Tartaric Acid, a-Hydroxyglutaric Acid-g-Lactone, a-Hydroxybutyric Acid, Citric Acid, Fumaric Acid, Bromosuccinic Acid, Propionic Acid, Mucic Acid, Glycolic Acid, Glyoxylic Acid, Tricarballylic Acid, Acetoacetic Acid, Mono-Methylsuccinate, D-Malic Acid, L-Malic Acid, p-Hydroxyphenyl Acetic Acid, m-Hydroxyphenyl Acetic Acid, Pyruvic Acid, L-Galactonic Acid-g-Lactone, D-Galacturonic Acid, Methylpyruvate, TWEEN® 20, TWEEN® 40, TWEEN® 80.

In some embodiments the systems or compositions comprise at least two recombinant *Listeria* phage selected from recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof. In some embodiments the systems or compositions comprise at least three, four, five, six, seven, eight, nine, or more recombinant *Listeria* phage, selected from recombinant LP040 and derivatives thereof, recombinant LP048 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof.

Articles of Manufacture

In some embodiments the system and or composition comprising at least one recombinant *Listeria* phage comprising a heterologous nucleic acid sequence encoding a marker is provided in the form of an article of manufacture. Such an article of manufacture is useful, for example, as a means to provide the at least one recombinant *Listeria* phage comprising a heterologous nucleic acid sequence encoding a marker in combination with other components that can be used together to perform an assay to detect target bacteria. In some embodiments the article of manufacture comprises at least one container comprising the at least one recombinant *Listeria* phage comprising a heterologous nucleic acid sequence encoding a marker.

In some embodiments the article of manufacture comprises at least one container comprising at least two recombinant *Listeria* phage selected from recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof. In some embodiments the systems or compositions comprise at least three, four, five, six, seven, eight, nine, or more recombinant *Listeria* phage, selected from recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof. In some embodiments in which the article of manufacture comprises more than one phage all of the phage are provided in separate containers. In other embodiments two or more of the phage are provided in combination in a single container.

The article of manufacture comprises at least one container comprising at least one recombinant phage selected from A511, P110, LP40, LP48, LP99, LP107, LP124, LP125 and LP143, and derivatives thereof. In some embodiments, the phage comprises a heterologous nucleic acid sequence encoding a first marker. In some embodiments, the first marker is a screenable marker. In some embodiments, the first marker is a luciferase. In some embodiments, the luciferase is at least 70%, at least 80%, at least 90%, at least 91%, at least 92%, at least 93%, at least 94%, at least 95%, at least 96%, at least 97%, at least 98%, at least 99%, at least 99.5% or at least 99.9% identical to SEQ ID NO: 2. In some embodiments, the luciferase is at least 70%, at least 80%, at least 90%, at least 91%, at least 92%, at least 93%, at least 94%, at least 95%, at least 96%, at least 97%, at least 98%, at least 99%, at least 99.5% or at least 99.9% identical to SEQ ID NO: 4. In some embodiments, the luciferase is at least 70%, at least 80%, at least 90%, at least 91%, at least 92%, at least 93%, at least 94%, at least 95%, at least 96%, at least 97%, at least 98%, at least 99%, at least 99.5% or at least 99.9% identical to SEQ ID NO: 41. In some embodiments, the first type of phage is selected from LP48::ffluc, LP99::ffluc, LP101::ffluc, LP124::ffluc, LP125::ffluc, LP143::ffluc, A511::ffluc, P100::ffluc, LP48::COP2, LP99::COP2, LP101::COP2, LP124::COP2, LP125::COP2, LP143::COP2, A511::COP2, and P100::COP2, LP48::COP3, LP99::COP3, LP101::COP3, LP124::COP3, LP125::COP3, LP143::COP3, A511::COP3, and P100::COP3 and derivatives of those phage. In some embodiments, the first type of phage is selected from LP40::nluc, LP124::nluc, LP125::nluc, A511::nluc, and P100::nluc. In some embodiments, the first type of phage is selected from A511::COP2, LP124::COP2, LP40::COP2, LP125::COP2, A511::COP3, LP124::COP3, LP40::COP3, and LP125::COP3.

In some embodiments the article of manufacture further comprises an aqueous solution including one or more reagents from Table 5 and/or at least one non-phage component selected from at least one of a) at least one compound selected from carbohydrates and related compounds, b) at least compound selected from nitrogen containing compounds, c) at least compound selected from nucleic acids and related compounds, d) at least compound selected from lipid, e) at least one inorganic compound, and f) at least one organic compound. In some embodiments, the article of manufacture comprises a container comprising a solution comprising at least one of 1,2-Propanediol, 2-Aminoethanol, Glucuronamide, Tyramine, b-Phenylethylamine, L-Aspartic Acid, L-Proline, D-Alanine, D-Serine, L-Glutamic Acid, L-Asparagine, D-Aspartic Acid, L-Glutamine, Gly-Asp, D-Threonine, Gly-Glu, L-Serine, L-Threonine, L-Alanine, Ala-Gly, Gly-Pro, L-Arabinose, N-Acetyl-D-Glucosamine, D-Galactose, D-Trehalose, D-Mannose, Dulcitol, D-Sorbitol, Glycerol, L-Fucose, D,L-a-Glycerol, Phosphate, D-Xylose, D-Mannitol, D-Glucose-6-Phosphate, D-Ribose, L-Rhamnose, D-Fructose, a-D-Glucose, Maltose, D-Melibiose, Thymidine, a-Methyl-D-Galactoside, a-D-Lactose, Lactulosem Sucrose, Uridine, D-Glucose-1-Phosphate, D-Fructose-6-Phosphate, b-Methyl-D-Glucoside, Adonitol, Maltotriose, 2'-Deoxyadenosine, Adenosine, m-Inositol, D-Cellobiose, Inosine, N-Acetyl-D-Mannosamine, D-Psicose, L-Lyxose, D-Saccharic Acid, Succinic Acid, D-Glucuronic Acid, D-Gluconic Acid, D,L-Lactic Acid, Formic Acid, D-Galactonic Acid-g-Lactone, D,L-Malic Acid, Acetic Acid, D-Glucosaminic Acid, a-Ketoglutaric Acid, a-Ketobutyric Acid, m-Tartaric Acid, a-Hydroxyglutaric Acid-g-Lactone, a-Hydroxybutyric Acid, Citric Acid, Fumaric Acid, Bromosuccinic Acid, Propionic Acid, Mucic Acid, Glycolic Acid, Glyoxylic Acid, Tricarballylic Acid, Acetoacetic Acid, Mono-Methylsuccinate, D-Malic Acid, L-Malic Acid, p-Hydroxyphenyl Acetic Acid, m-Hydroxyphenyl Acetic Acid, Pyruvic Acid, L-Galactonic Acid-g-Lactone, D-Galacturonic Acid, Methylpyruvate, TWEEN® 20, TWEEN® 40, TWEEN® 80. In some embodiments at least one recombinant *Listeria* phage present in the article of manufacture is present in the aqueous solution comprising at least one non-phage component. In other embodiments the phage and solution are provided separately and may, for example, be combined by a user.

In another embodiment, the article of manufacture includes a substrate for a light reaction, or other required component for the marker to operate. By way of non-limiting example, the substrate is luciferin.

In another embodiment, the article of manufacture includes an additional aqueous solution that is optimized for a light reaction, or that provides conditions that are optimal for detection of a marker.

In some embodiments, the article of manufacture is a kit. The kit may further comprise instructions for performing one or more of the assays described herein.

Definitions

It is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The methods and techniques of the present disclosure are generally performed according to conventional methods well known in the art and as described in various general and more specific references that are cited and discussed throughout the present specification unless otherwise indicated. See, e.g., Sambrook et al., *Molecular Cloning: A Laboratory Manual,* 3d ed., Cold Spring Harbor Laboratory Press, Cold Spring Harbor, N.Y. (2001); Ausubel et al., *Current Protocols in Molecular Biology*, Greene Publishing Associates (1992, and Supplements to 2002); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); *Handbook of Biochemistry: Section A Proteins*, Vol II, CRC Press (1976); *Essentials of Glycobiology*, Cold Spring Harbor Laboratory Press (1999). Many molecular biology and genetic techniques applicable to phage are described in Clokie et al., *Bacteriophages: Methods and Protocols*, Vols. 1 and 2 (*Methods in Molecular Biology*, Vols. 501 and 502), Humana Press, New York, N.Y. (2009), which is hereby incorporated herein by reference.

This disclosure refers to sequence database entries (e.g., UniProt/SwissProt or GENBANK records) for certain amino acid and nucleic acid sequences that are published on the internet, as well as other information on the internet. The skilled artisan understands that information on the internet, including sequence database entries, is updated from time to time and that, for example, the reference number used to refer to a particular sequence can change. Where reference is made to a public database of sequence information or other information on the internet, it is understood that such changes can occur and particular embodiments of information on the internet can come and go. Because the skilled artisan can find equivalent information by searching on the internet, a reference to an internet web page address or a sequence database entry evidences the availability and public dissemination of the information in question.

The term "comprising" as used herein is synonymous with "including" or "containing", and is inclusive or open-ended and does not exclude additional, unrecited members, elements or method steps. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe). An assay that occurs at least in part in vivo within a microbe may nonetheless occur in vitro if parts of the assay occur outside of the microbe in culture, for example.

As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The term "peptide" as used herein refers to a short polypeptide, e.g., one that typically contains less than about 50 amino acids and more typically less than about 30 amino acids. The term as used herein encompasses analogs and mimetics that mimic structural and thus biological function.

The term "polypeptide" encompasses both naturally-occurring and non-naturally occurring proteins, and fragments, mutants, derivatives and analogs thereof. A polypeptide may be monomeric or polymeric. Further, a polypeptide may comprise a number of different domains each of which has one or more distinct activities. For the avoidance of doubt, a "polypeptide" may be any length greater two amino acids.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from a cell in which it was synthesized.

The term "polypeptide fragment" as used herein refers to a polypeptide that has a deletion, e.g., an amino-terminal and/or carboxy-terminal deletion compared to a full-length polypeptide, such as a naturally occurring protein. In an embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, or at least 12, 14, 16 or 18 amino, acids long, or at least 20 amino acids long, or at least 25, 30, 35, 40 or 45, amino acids, or at least 50 or 60 amino acids long, or at least 70 amino acids long.

The term "fusion protein" refers to a polypeptide comprising a polypeptide or fragment coupled to heterologous amino acid sequences. Fusion proteins are useful because they can be constructed to contain two or more desired functional elements that can be from two or more different proteins. A fusion protein comprises at least 10 contiguous amino acids from a polypeptide of interest, or at least 20 or 30 amino acids, or at least 40, 50 or 60 amino acids, or at least 75, 100 or 125 amino acids. The heterologous polypeptide included within the fusion protein is usually at least 6 amino acids in length, or at least 8 amino acids in length, or at least 15, 20, or 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, a protein has "homology" or is "homologous" to a second protein if the nucleic acid sequence that encodes the protein has a similar sequence to the nucleic acid sequence that encodes the second protein. Alternatively, a protein has homology to a second protein if the two proteins have similar amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, Methods Mol. Biol. 24:307-31 and 25:365-89.

The following six groups each contain amino acids that are conservative substitutions for one another: 1) Serine, Threonine; 2) Aspartic Acid, Glutamic Acid; 3) Asparagine, Glutamine; 4) Arginine, Lysine; 5) Isoleucine, Leucine, Methionine, Alanine, Valine, and 6) Phenylalanine, Tyrosine, Tryptophan.

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

An exemplary algorithm when comparing a particular polypeptide sequence to a database containing a large number of sequences from different organisms is the computer program BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

Exemplary parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62. The length of polypeptide sequences compared for homology will generally be at least about 16 amino acid residues, or at least about 20 residues, or at least about 24 residues, or at least about 28 residues, or more than about 35 residues. When searching a database containing sequences from a large number of different organisms, it may be useful to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, Methods Enzymol. 183:63-98 (1990). For example, percent sequence identity between amino acid sequences can be determined using FASTA with its default parameters (a word size of 2 and the PAM250 scoring matrix), as provided in GCG Version 6.1, herein incorporated by reference.

In some embodiments, polymeric molecules (e.g., a polypeptide sequence or nucleic acid sequence) are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% identical. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% similar. The term "homologous" necessarily refers to a comparison between at least two sequences (nucleotides sequences or amino acid sequences). In some embodiments, two nucleotide sequences are considered to be homologous if the polypeptides they encode are at least about 50% identical, at least about 60% identical, at least about 70% identical, at least about 80% identical, at least 90%, at least 91%, at least 92%, at least 93%, at least 94%, at least 95%, at least 96%, at least 97%, at least 98% or at least 99% identical for at least one stretch of at least about 20 amino acids. In some embodiments, homologous nucleotide sequences are characterized by the ability to encode a stretch of at least 4-5 uniquely specified amino acids. Both the identity and the approximate spacing of these amino acids relative to one another must be considered for nucleotide sequences to be considered homologous. In some embodiments of nucleotide sequences less than 60 nucleotides in length, homology is determined by the ability to encode a stretch of at least 4-5 uniquely specified amino acids. In some embodiments, two protein sequences are considered to be homologous if the proteins are at least about 50% identical, at least about 60% identical, at least about 70% identical, at least about 80% identical, at least 90%, at least 91%, at least 92%, at least 93%, at least 94%, at least 95%, at least 96%, at least 97%, at least 98% or at least 99% identical for at least one stretch of at least about 20 amino acids.

As used herein, a "modified derivative" refers to polypeptides or fragments thereof that are substantially homologous in primary structural sequence to a reference polypeptide sequence but which include, e.g., in vivo or in vitro chemical and biochemical modifications or which incorporate amino acids that are not found in the reference polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}I$, $^{32}P$, $^{35}S$, and $^{3}H$, ligands that bind to labeled antiligands (e.g., antibodies), fluorophores, chemiluminescent agents, enzymes, and antiligands that can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., Current Protocols in Molecular Biology, Greene Publishing Associates (1992, and Supplements to 2002).

As used herein, "polypeptide mutant" or "mutein" refers to a polypeptide whose sequence contains an insertion, duplication, deletion, rearrangement or substitution of one or more amino acids compared to the amino acid sequence of a reference protein or polypeptide, such as a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the reference protein, and/or truncations of the amino acid sequence at either or both the amino or carboxy termini. A mutein may have the same or a different biological activity compared to the reference protein.

In some embodiments, a mutein has, for example, at least 70% overall sequence homology to its counterpart reference polypeptide or protein. In some embodiments, a mutein has at least 75%, at least 80%, at least 85%, or at least 90% overall sequence homology to the wild-type protein or polypeptide. In other embodiments, a mutein exhibits at least 91%, at least 92%, at least 93%, at least 94%, at least 95%, at least 96%, at least 97%, at least 98%, at least 99% at least 99.5%, at least 99.9% sequence identity, or 98%, or 99%, or 99.5% or 99.9% overall sequence identity.

As used herein, "recombinant" refers to a biomolecule, e.g., a gene or protein, that (1) is not associated with all or a portion of a polynucleotide in which the gene is found in nature, (2) is operatively linked to a polynucleotide which it is not linked to in nature, or (3) does not occur in nature. Preferably, "recombinant" refers to a biomolecule that does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids. Thus, for example, a protein synthesized by a microorganism is recombinant, for example, if it is synthesized from an mRNA synthesized from a recombinant gene present in the cell. A phage is "recombinant" if it comprises a recombinant biomolecule. Preferably, a phage is "recombinant" if it comprises a recombinant biomolecule that does not occur in nature. Thus, for example and without limitation, a phage is recombinant if the genome of the phage comprises a recombinant nucleic acid sequence.

The term "polynucleotide", "nucleic acid molecule", "nucleic acid", or "nucleic acid sequence" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The nucleic acid (also referred to as polynucleotides) may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

A "synthetic" RNA, DNA or a mixed polymer is one created outside of a cell, for example one synthesized chemically.

The term "nucleic acid fragment" as used herein refers to a nucleic acid sequence that has a deletion, e.g., a 5'-terminal or 3'-terminal deletion compared to a full-length reference nucleotide sequence. In an embodiment, the nucleic acid fragment is a contiguous sequence in which the nucleotide sequence of the fragment is identical to the corresponding positions in the naturally-occurring sequence. In some embodiments, fragments are at least 10, 15, 20, or 25 nucleotides long, or at least 20, 30, 40, 50, 60, 70, 80, 90, 100, 110, 120, 130, 140, or 150 nucleotides long. In some embodiments a fragment of a nucleic acid sequence is a fragment of an open reading frame sequence. In some embodiments such a fragment encodes a polypeptide fragment (as defined herein) of the protein encoded by the open reading frame nucleotide sequence.

As used herein, an endogenous nucleic acid sequence in the genome of an organism (including a phage) (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome. With reference to a phage, a "recombinant phage genome" is a phage genome that contains an insertion, deletion or a point mutation introduced artificially, e.g., by human intervention and does not occur in nature.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32, and even more typically at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, 60%, 70%, 80%, 85%, 90%, 91%, 92%, 93%, 94%, 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y. (1989), page 9.51. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

As used herein, an "expression control sequence" refers to polynucleotide sequences that affect the expression of coding sequences to which they are operatively linked. Expression control sequences are sequences that control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences and fusion partner sequences.

As used herein, "operatively linked" or "operably linked" expression control sequences refers to a linkage in which the expression control sequence is contiguous with the gene of interest to control the gene of interest, as well as expression control sequences that act in trans or at a distance to control the gene of interest.

As used herein, a "vector" is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors").

The term "recombinant host cell" (or simply "recombinant cell" or "host cell"), as used herein, is intended to refer to a cell into which a recombinant nucleic acid such as a recombinant vector has been introduced. In some instances the word "cell" is replaced by a name specifying a type of cell. For example, a "recombinant microorganism" is a recombinant host cell that is a microorganism host cell. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "recombinant host cell," "recombinant cell," and "host cell", as used herein. A recombinant host cell may be an isolated cell or cell line grown in culture or may be a cell which resides in a living tissue or organism.

As used herein, "bacteriophage" refers to a virus that infects bacteria. Similarly, "archaeophage" refers to a virus that infects archaea. The term "phage" is used to refer to both types of viruses but in certain instances as indicated by the context may also be used as shorthand to refer to a bacteriophage or archaeophage specifically. Bacteriophage and archaeophage are obligate intracellular parasites that multiply inside bacteria/archaea by making use of some or all of the host biosynthetic machinery (i.e., viruses that infect bacteria). Though different bacteriophages and archaeophages may contain different materials, they all contain nucleic acid and protein, and can under certain circumstances be encapsulated in a lipid membrane. Depending upon the phage, the nucleic acid may be either DNA or RNA but not both and it can exist in various forms.

As used herein, "heterologous nucleic acid sequence" is any sequence placed at a location in the genome where it does not normally occur. A heterologous nucleic acid sequence may comprise a sequence that does not naturally occur in a particular bacteria/archaea and/or phage or it may comprise only sequences naturally found in the bacteria/archaea and/or phage, but placed at a non-normally occurring location in the genome. In some embodiments the heterologous nucleic acid sequence is not a natural phage sequence; in some embodiments it is a natural phage sequence, albeit from a different phage; while in still other embodiments it is a sequence that occurs naturally in the genome of the starting phage but is then moved to another site where it does not naturally occur, rendering it a heterologous sequence at that new site.

A "starting phage" or "starting phage genome" is a phage isolated from a natural or human made environment that has not been modified by genetic engineering, or the genome of such a phage.

A "recombinant phage" or "recombinant phage genome" is a phage that comprises a genome that has been genetically modified by insertion of a heterologous nucleic acid sequence into the phage, or the genome of the phage. Preferably, a "recombinant phage" or "recombinant phage genome" is a phage that does not occur in nature, i.e., does not comprise a genome that occurs in nature. In some embodiments the genome of a starting phage is modified by recombinant DNA technology to introduce a heterologous nucleic acid sequence into the genome at a defined site. In some embodiments the heterologous sequence is introduced with no corresponding loss of endogenous phage genomic nucleotides. In other words, if bases N1 and N2 are adjacent in the starting phage genome the heterologous sequence is inserted between N1 and N2. Thus, in the resulting recombinant genome the heterologous sequence is flanked by nucleotides N1 and N2. In some cases the heterologous sequence is inserted and endogenous nucleotides are removed or replaced with the exogenous sequence. For example, in some embodiments the exogenous sequence is inserted in place of some or all of the endogenous sequence which is removed. In some embodiments endogenous sequences are removed from a position in the phage genome distant from the site(s) of insertion of exogenous sequences.

A "phage host cell" is a cell that can be infected by a phage to yield progeny phage particles.

"Operatively linked" or "operably linked" expression control sequences refers to a linkage in which the expression control sequence is contiguous with coding sequences of interest to control expression of the coding sequences of interest, as well as expression control sequences that act in trans or at a distance to control expression of the coding sequence.

A "coding sequence" or "open reading frame" is a sequence of nucleotides that encodes a polypeptide or protein. The termini of the coding sequence are a start codon and a stop codon.

The term "expression control sequence" as used herein refers to polynucleotide sequences which affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

As used herein, a "phage genome" includes naturally occurring phage genomes and derivatives thereof. Generally (though not necessarily), the derivatives possess the ability to propagate in the same hosts as the parent. In some embodiments the only difference between a naturally occurring phage genome and a derivative phage genome is at least one of a deletion and an addition of nucleotides from at least one end of the phage genome if the genome is linear or at least one point in the genome if the genome is circular.

As used herein, "target microbe" includes bacteria, however, this term may also include other unicellular pathogens that cause infection in animals and/or humans. Preferred target microbes are bacteria.

As used herein, "target bacteria" are bacteria that can be infected by a phage to yield a detectable output or signal. For example, a detectable output includes cell lysis. Thus, lysis of bacterial cells by a phage indicates that the bacterial cells are "target bacteria" of that phage. Another example of a detectable output is expression of a marker following infection of a bacterial cell by a phage. Suitable markers include RNAs and polypeptides.

As used herein, a "marker" includes selectable and/or screenable markers. As used herein, a "selectable marker" is a marker that confers upon cells that possess the marker the ability to grow in the presence or absence of an agent that inhibits or stimulates, respectively, growth of similar cells that do not express the marker. Such cells can also be said to have a "selectable phenotype" by virtue of their expression of the selectable marker. For example, the ampicillin resistance gene (AmpR) confers the ability to grow in the presence of ampicillin on cells which possess and express the gene. (See Sutcliffe, J. G., *Proc Natl Acad Sci USA*. 1978 August; 75(8): 3737-3741.) Other nonlimiting examples include genes that confer resistance to chloramphenicol, kanamycin, and tetracycline. Other markers include URA3, TRP and LEU, which allow growth in the absence of said uracil, tryptophan and leucine, respectively.

As used herein, a "screenable marker" is a detectable label that that can be used as a basis to identify cells that express the marker. Such cells can also be said to have a "screenable phenotype" by virtue of their expression of the screenable marker. (In general selectable markers may also function as screenable markers in so far as the gene product of the selectable marker may be used as a basis to identify cells that express the marker independently of the function of the gene product to confer selectability on cells that express it.) Any molecule that can be differentially detected and encoded by the recombinant phage can serve as a screenable marker. A screenable marker can be a nucleic acid molecule or a portion thereof, such as an RNA or a DNA molecule that is single or double stranded. Alternatively, a screenable marker can be a protein or a portion thereof. Suitable protein markers include enzymes that catalyze formation of a detectable reaction product. An example is a chemiluminescent protein such as luciferase or variations, such as luxAB, and β-galactosidase. Another example is the horseradish peroxidase enzyme. Proteins used to generate a luminescent signal fall into two broad categories: those that generate light directly (luciferases and related proteins) and those that are used to generate light indirectly as part of a chemical cascade (horseradish peroxidase). The most common bioluminescent proteins used in biological research are aequorin and luciferase. The former protein is derived from the jellyfish *Aequorea victoria* and can be used to determine calcium concentrations in solution. The luciferase family of proteins has been adapted for a broad range of experimental purposes. Luciferases from firefly and *Renilla* are the most commonly used in biological research. These proteins have also been genetically separated into two distinct functional domains that will generate light only when the proteins are closely co-localized. A variety of emission spectrum-shifted mutant derivatives of both of these proteins have been generated over the past decade. These have been used for multi-color imaging and co-localization within a living cell. The other groups of proteins used to generate chemiluminescent signal are peroxidases and phosphatases. Peroxidases generate peroxide that oxidizes luminol in a reaction that generates light. The most widely used of these is horseradish peroxidase (HRP), which has been used extensively for detection in western blots and ELISAs. A second group of proteins that have been employed in a similar fashion are alkaline phosphatases, which remove a phosphate from a substrate molecule, destabilizing it and initiating a cascade that results in the emission of light.

Other suitable screenable markers include fluorescent proteins. Fluorescent proteins include but are not limited to blue/UV fluorescent proteins (for example, TagBFP, Azurite, EBFP2, mKalama1, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOκ, mKO2, mOrange, and mOrange2), red fluorescent proteins (for example, mRaspberry, mCherry, mStrawberry, mTangerine, tdTomato, TagRFP, TagRFP-T, mApple, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKatel, and LSS-mKate2), photoactivatible fluorescent proteins (for example, PA-GFP, PAmCherryl, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), and photoswitchable fluorescent proteins (for example, Dronpa). Several variants and alternatives to the listed examples are also well known to those of skill in the art and may be substituted in appropriate applications.

Other suitable markers include epitopes. For example, a protein comprising an epitope that can be detected with an antibody or other binding molecule is an example of a screenable marker. An antibody that recognizes the epitope can be directly linked to a signal generating moiety (such as by covalent attachment of a chemiluminescent or fluorescent protein) or it can be detected using at least one additional binding reagent such as a secondary antibody, directly linked to a signal generating moiety, for example. In some embodiments the epitope is not present in the proteins of the phage or the target microorganism so detection of the epitope in a sample indicates that the protein comprising the epitope was produced by the microorganism following infection by the recombinant phage comprising a gene encoding the protein comprising the epitope. In other embodiments the marker may be a purification tag in the context of a protein that is naturally present in the target microorganism or the phage. For example, the tag (e.g., a 6-His tag) can be used to purify the heterologous protein from other bacterial or phage proteins and the purified protein can then be detected, for example using an antibody.

As used herein, an "environmental sample" is a sample obtained from any setting other than a laboratory cell culture setting. Generally, though not necessarily, an environmental sample is obtained from a setting that comprises at least one of a) a temperature that does not support maximum growth and/or metabolism of bacterial cells, b) a nutrient profile that does not support maximum growth and/or metabolism of bacterial cells, and c) bacterial cells that are not target bacteria for a phage used in an assay. In some embodiments some or all of the bacteria present in an environmental sample are not in a metabolically active state. Without limitation, environmental samples may be obtained from industrial plants, food processing plants, veterinary sources, food, livestock, medical settings and surfaces, schools, assisted living centers, cruise ships, other confined quarters and homes. The surface may be of any material. By way of non-limiting example, the surface can be metal, glass, wood, brick, concrete, tile, rug and the like. The surface can also be on an agricultural product. The sample can also be found inside of an agricultural produce. The "environmental sample" can be in situ, in other words, the assay can be performed at the site itself, rather than removed from the site. Alternatively, the "environmental sample" can be removed for assay from a collection point, as through the use of an absorbent material, such as a cotton swab to physically collect the sample.

As used herein, "agricultural" refers to cultivated or wild plants, animals, and fungi. The term also refers to stock feed or food supply. "Food supply" encompasses food for either human or non-human animal consumption. Accordingly, an "agricultural sample" refers to a sample from of, within, or on the exterior of a plant, animal and fungi.

While the disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the disclosure. All such modifications are intended to be within the scope of the claims appended hereto.

EXAMPLES

Example 1: Design of Codon Optimized Phage

Recombinant phage were designed for increased expression of the luciferase reporter. Phages selected for recombination were A511, LP124, and LP40. The capsid (CPS) nucleotide sequences for A511 (SEQ ID NO: 19), LP124 (SEQ ID NO: 13) and LP40 (SEQ ID NO: 5) are provided herewith. The NanoLuc luciferase reporter was selected for recombination by phage optimization. Phage optimization was performed using DNA 2.0 software. The software uses an algorithm described Villalobos et al. (see Villalobos et al. BMC Bioinformatics. *Gene Designer: a synthetic biology tool for constructing artificial DNA segments. PLoS ONE.* 2011 6:e19912.) to replace synonymous codons with those preferred by a host organism, in this case *listeria.*

The codon optimized Nanoluc (COP2; SEQ ID NO: 36) was inserted into the phage CPS open reading frame following stop codons and a ribosome binding site (SEQ ID NO: 54) using methods as described in Example 19 herein. Primers used in engineering *listeria* phage include pMAK upf (SEQ ID NO: 55), dbono380 (SEQ ID NO: 56), SO472 (SEQ ID NO: 57), SO473 (SEQ ID NO: 58), 50474 (SEQ ID NO: 59) and dbono 382 (SEQ ID NO: 62) oligos. A sequence map of the insertion site for A511::COP2 recombinant phage (SEQ ID NO: 39) recombinant phage is shown in FIG. 2 indicating the location of insertion of the COP2 reporter, ribosome binding site and the flanking sequence following CPS. A sequence map of the insertion site for LP124::COP2 recombinant phage (SEQ ID NO: 39) is shown in FIG. 2 indicating the location of insertion of the COP2 reporter, ribosome binding site and the flanking sequence following CPS. A sequence map of the insertion site for LP40::COP2 recombinant phage (SEQ ID NO: 40) is shown in FIG. 3 indicating the location of insertion of the COP2 reporter, ribosome binding site and the flanking sequence following CPS.

Recombinant phage comprising the native NanoLuc luciferase was compared to recombinant phage comprising the codon optimized COP2 luciferase. Comparisons utilized a mixture of recombinant phage. The COP2 mixture comprising the A511:COP2, LP124::COP2, and LP40::COP2 phages. These experiments were done using a cocktail of A511::COP2, LP124::COP2, and LP40::COP2. The final concentration of each phage is 1.5e7 pfu/ml, the final concentration of the mixture is 4.5e7 pfu/ml. The mixture of NanoLuc phages comprised phages selected from Example 19. Protocols for the comparison assay are as follows.

On Sponge infections with NanoLuc and COP2 Phage Mixture:

3 sponges (3M spongestick w/Letheen broth) were used for each condition. The stick was removed from each sponge, and the sponges were squeezed to remove Letheen broth. ~100 CFU of *Listeria monocytogenes* CDW 1554 were spiked onto each sponge:

Healthy cells: 5 ml overnight culture (18-24 h in 0.5× BHI) diluted 1:4 into 0.5×BHI and incubated at 30° C. shaking at 180 rpm for 2 hours. 100 µl of a $1e^{-6}$ dilution was spiked into each sponge. Healthy cells, in this case, refer to an overnight culture that has reached stationary phase being back-diluted to re-enter log phase.

Sick cells: 250 µl of a CDW 1554 overnight culture diluted to ~1e7 CFU/ml in BHI+1% glucose was spread on a 4"×4" square on a stainless steel table. Cells were allowed to dry overnight (18-24 h). Cells were recovered using a cotton swab moistened with Letheen Broth, and placed in a conical tube containing 2 ml of Letheen Broth. Cells were allowed to recover for 30 minutes at 30° C. Cells were diluted in 0.5×BHI to the point where 1000 should contain ~100 CFU. 100 µl was spiked onto each sponge. The model mimics a factory condition where cells are surviving on a steel surface that may or may not have food contact. Sick cells are less metabolically active and produce less light upon phage infection than their healthy counterparts.

Conditions:

3 sponges with NanoLuc phage mixture/no cells 3 sponges with NanoLuc phage mixture/100 CFU Healthy CDW 1554

3 sponges with NanoLuc phage mixture/100 CFU Sick CDW 1554

3 sponges with COP2 phage mixture/no cells 3 sponges with COP2 phage mixture/100 CFU Healthy CDW 1554

3 sponges with COP2 phage mixture/100 CFU Sick CDW 1554

Infection:

After cells were spiked onto sponges, phage was mixed as follows:

7 ml of phage solution (9e8 pfu/ml), (NanoLuc or COP2), was added to 77 ml of NIB-10 infection buffer.

6 ml of the appropriate phage mixture was added to each sponge, with a brief massage to mix the solution into the sponge ensuring complete coverage.

Sponges were placed at 30° C. for 6 hours.

Detection:

Sponges were squeezed to separate the liquid from the sponge. 1000 μl of liquid was removed from each sponge and placed in a microcentrifuge tube. Tubes were spun at 16,000 g for 1 minute. 300 μl was transferred to an Eppendorf microcentrifuge tube. 300 μl of Nano-Glo detection reagent was added to each tube.

Samples were read in a Berthold Sirius-L luminometer using a 20 second kinetic read. RLU values across the last 16 seconds of the read were averaged resulting in the RLU value for each sample.

Figure 4:
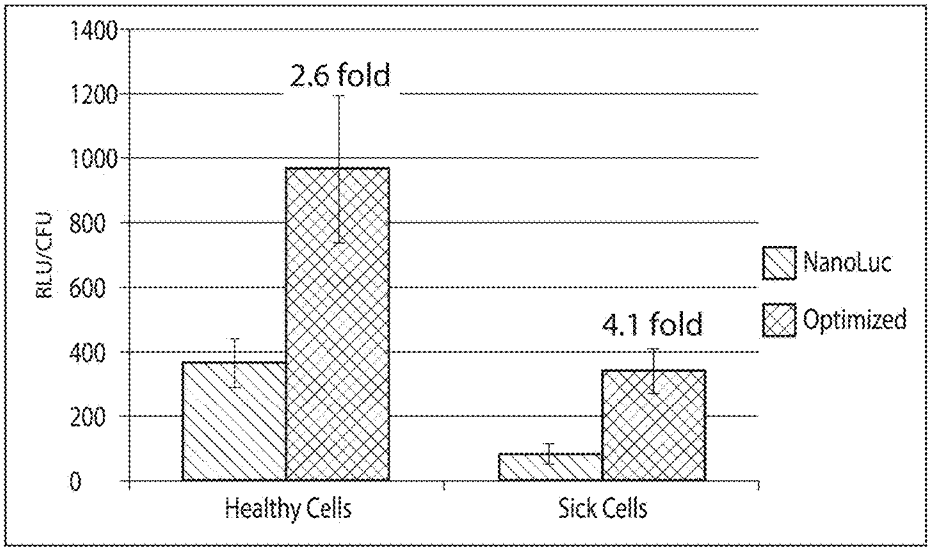
FIG. 4 is a graph comparing the relative detectable light (Relative Light Units, RLU) from healthy and sick cells infected with a mixture of A511, LP40 and LP124 engineered phage comprising either nanoluc luciferase or codon optimized COP2 luciferase.
Figure 5:
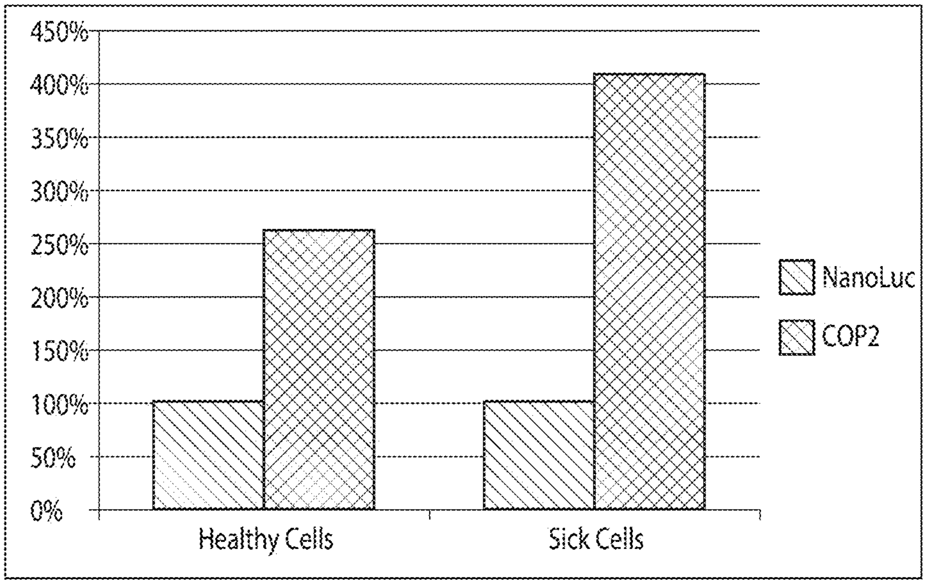
FIG. 5 is a graph comparing relative performance in healthy and sick cells of a mixture of A511, LP40 and LP124 engineered phage comprising either the nanoluc luciferase or codon optimized COP2 luciferase.

As shown in Table 6, the mixture of phages comprising codon optimized luciferase (COP2) shows a 2.6 fold increase in relative light units (RLU) per colony forming units (CFU) over recombinant phage encoding basic NanoLuc when infecting healthy *Listeria* cells. In a comparison of recombinant phage mixtures infected sick cells (e.g. cells that have dried on a counter surface, or been subjected to cleaning agents) the codon optimized COP2 encoding phage mixture shows a 4.1 fold increase in RLU/CFU over regular NanoLuc encoding phage mixtures (see FIG. 4). When normalized as an indication of performance, the codon optimized COP2 encoding phage perform at 264% of their NanoLuc encoding counterparts in healthy cells (see Table 7 and FIG. 5). In sick cells, the COP2 encoding phage perform at 409% of their NanoLuc encoding counterparts (see Table 12 and FIG. 5). This significant enhancement in the output of light from the recombinant phage encoding codon optimized COP2 improves the detectable limits of *Listeria* contamination.

TABLE 6

| | RLU/CFU Healthy | RLU/CFU Sick |
|---|---|---|
| NanoLuc | 365.50 | 83.32 |
| COP2 | 965.87 | 340.95 |

TABLE 7

| | Healthy Cells | Sick Cells |
|---|---|---|
| NanoLuc | 100% | 100% |
| COP2 | 264% | 409% |

Figure 6:
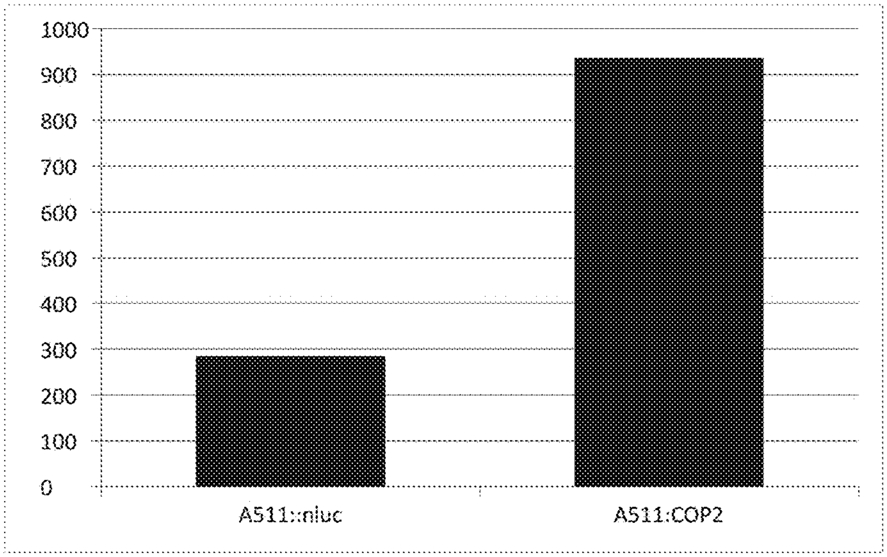
FIG. 6 is a graph comparing the relative detectable light from sick cells infected with A511 engineered phage comprising either nanoluc luciferase or codon optimized COP2 luciferase.
Figure 7:
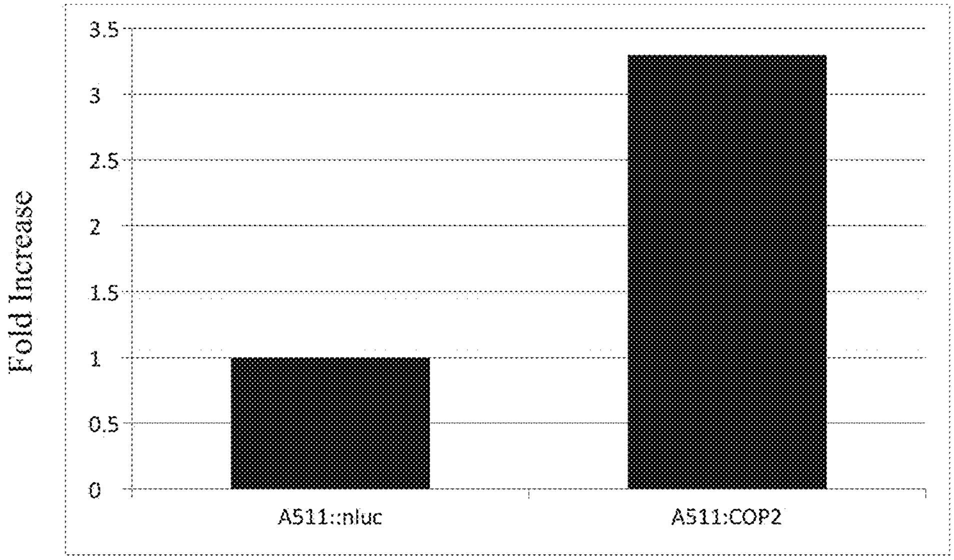
FIG. 7 is a graph comparing relative performance in sick cells of a A511 engineered phage comprising either the nanoluc luciferase or codon optimized COP2 luciferase.

Further experiments were performed using a single A511 phage engineered with COP2 to compare reporter signal in sick cells. As shown in Table 8, the A511 phage comprising codon optimized luciferase (COP2) shows a 3.3 fold increase in relative light units (RLU) per colony forming units (CFU) over recombinant A511 phage encoding basic NanoLuc when infecting sick *Listeria* cells (see FIG. 6). When normalized as an indication of performance, the codon optimized COP2 encoding A511 phage perform at 330% of their NanoLuc encoding counterparts in sick cells (see Table 9 and FIG. 7). This significant enhancement in the output of light from the recombinant phage encoding codon optimized COP2 improves the detectable limits of *Listeria* contamination and use of a single phage type in a detection assay.

TABLE 8

| | A511::nluc | A511:COP2 |
|---|---|---|
| RLU/CFU | 283.57 | 935.82 |

TABLE 9

| | A511::nluc | A511:COP2 |
|---|---|---|
| Signal | 100.00% | 330.01% |

Example 2: Design of Codon-Optimized Phage V3 (COP3)

Additional codon optimization was performed with recombinant phage in an effort to further increase the expression levels of the luciferase reporter. Phages selected for optimization were A511, LP124 and LP40. The NanoLuc luciferase reporter was selected for recombination by phage optimization. Coding sequence optimization was performed using DNA 2.0™ software. The software uses an algorithm described Villalobos et al. (see Villalobos et al. BMC Bioinformatics. *Gene Designer: a synthetic biology tool for constructing artificial DNA segments. PLoS ONE.* 2011 6:e19912.) to replace synonymous codons with those preferred by a host organism.

The purpose of this round of codon optimization was to create a custom codon optimization algorithm specific for *Listeria*. For these experiments, a set of 24 codon-optimized variants were designed and constructed by DNA 2.0™. These variants allowed for testing a variety of hypotheses concerning codon usage. The set of the new 24 codon-optimized variants (COP3) were cloned into the A511 vector. These plasmids were transformed into the *Listeria monocytogenes* strain EGD-e, and isolated using phage infective engineering (PIE) methodology described in Example 19 above.

The 24 variants of the COP3 phages were isolated and purified by ultracentrifugation. The isolated and purified COP3 phages were compared with COP2 and the non-codon optimized NanoLuc phages. The relative signal strength was generated across a subset of *Listeria* strains and normalized to COP2. These data were then traced back to specific changes in the codon usage profile. These data pointed to the improved COP3 phage herein referred to as W40_VIP_MLi178 ("VIP178") (see SEQ ID No.: 37) as the most improved variant. This version of NanoLuc was used to create three new engineered phages: A511::VIP178, LP124::VIP178, and LP40::VIP178 (also referred to herein as A511::COP3, LP124::COP3 and LP40::COP3).

The phages were engineered using the primers described herein. The primers pMAK upf (see SEQ ID No.:55) and DBONO380 (see SEQ ID No.:56) were used to amplify the upstream homology fragments for each phage. The VIP178 fragment was amplified using the SO670 (see SEQ ID No.:64) and SO671 (see SEQ ID No.:65). The downstream homology fragments were amplified using the primers SO672 (see SEQ ID No.:66) and DBONO382 (see SEQ ID No.:60).

Signal intensity levels of COP2 and COP3 phages were assessed as detailed below in Example 3.

Example 3: Signal Comparison of COP2 and COP3 Phages

In order to assess any differences in intensity or robustness of signal provided by the COP2 and COP3 phages, a screen was performed in which the signal intensity was determined by using the assay described below.

For these assays the following materials were used: Validation Plates (342 strains across *Listeria* species), Omni-Tray with 0.5×BHI agar, Deep-Well 96-well plate (Axygen), Clear flat-bottom 96-well plate (Evergreen), White flat-bottom 96-well plate (Greiner Bio-One), Plate-sealing film (breathable), 15 mL conical tubes, Letheen Broth, 0.5×BHI, NIB-14, Nano-Glo, Substrate, Nano-Glo Buffer, 200 μL multichannel pipette, 1000 μL multichannel pipette, 200 μL multichannel pipette, 96-pin replicator tool (frogger).

The detailed protocol used in these assays is described below.

Protocol

Day 0

Stamp out validation plates 1 through 3 and greatest misses plate onto 0.5×BHI agar Omni-tray plate using the 96-pin replicator tool.

Incubate plates at 35° C. overnight (18 h)

Day 1

Fill wells of 96-well DeepWell with 1 mL of 0.5×BHI

Inoculate DeepWell with colonies from stamped-out plates

Incubate plates at 30° C. for 24 h, shaking

Day 2

1. Dilute all phage variants in NIB-14 to 9E7 pfu/mL in a final volume of 20 mL a. (For lower phage concentration tests, dilute variants to 3E7 pfu/mL and/or 1E7 pfu/mL)

b. Note: GM plate is not a full plate—use the empty wells to act as negative controls for the assay 2. Add 180 μL of Letheen Broth to all wells of four (4) clear, flat-bottom 96-well plates 3. Label plates from 1E-1 through 1E-4 dilution 4. Add 900 μL of Letheen Broth to all wells of a 96-well deep-well plate a. Label deep-well plate as the 1E-5 dilution 5. Repeat previous steps 2 through 5 three additional times, one set for each plate of overnight culture a. i.e. Validation Plates 1, 2, 3, and Greatest Misses 6. For each culture, transfer 204 from every well of overnight culture to corresponding well of 1E-1 dilution plate 7. Pipette mix 10-15×

8. Repeat steps 6 and 7, transferring from 1E-1 plate to 1E-2 plate, then from 1E-2 plate to 1E-3 plate, then from 1E-3 plate to 1E-4 plate.

9. Transfer 100 μL from every well of 1E-4 dilution plate to corresponding well of 1E-5 dilution plate for a total volume of 1000 μL in each well of the deep well plate 10. Repeat previous step until there is a 1E-5 cell dilution for each phage variant being tested, plus COP2, for each overnight culture a. e.g. if testing three variants:

i. Validation plate 1—four (4) plates at 1E-5 dilution ii. Validation plate 2—four (4) plates at 1E-5 dilution iii. Validation plate 3—four (4) plates at 1E-5 dilution iv. GM Plate—four (4) plates at 1E-5 dilution 11. Dilute 1E-5 dilution of 1839 from Validation Plate 2-50 μL into 450 μL of Letheen (1:10 total dilution—1E-6 dilution from overnight culture)

12. Plate 1004 of −6 dilution onto BHI plate and incubate overnight at 35° C.

13. For each strain plate, transfer 100 μL of phage/NIB-14 mixture for each phage variant being tested 14. Start with COP2

15. Stagger each set by ≈20 minutes (or as you see fit) to allow time to read between strain plates 16. Recommended: Complete infection for all variants on Plate 1, then all variants of Plate 2, etc.

17. Incubate plates at 30° C. for 6 h

18. Mix necessary amount of Nano-glo buffer with substrate (≈5 ml/plate)

19. Transfer 404 of from each well of infection plate to corresponding wells of white, flat-bottom plate Add 40 μL of mixed Nano-Glo reagent Detect on Glomax 96

Steady Glo—0s delay, 0.5s integration

Analysis:

COPS target panel consists of strains producing between 100 RLU/CFU and 1000 RLU/CFU with COP2 assay Compare signal of target strains with COP2 phage cocktail to COP3 phage cocktail candidate Plate 100 μL of 1E-6 dilution for target strains onto BHI plate to calculate RLU/CFU of COP3 target strains for COP2 and COP3

Figure 8:
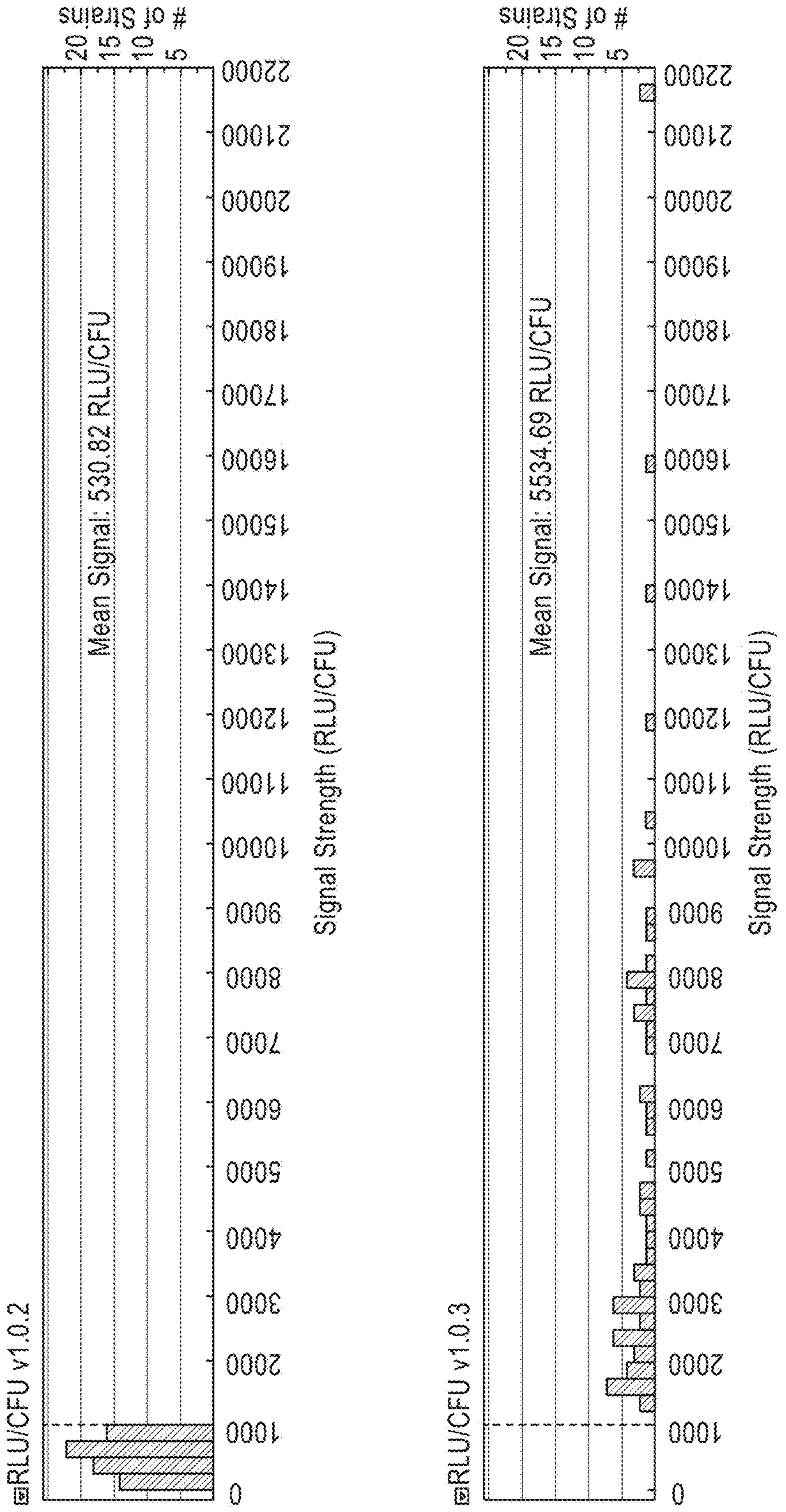
FIG. 8 is a series of graphs that depict the mean light signal detected in Relative Light Units (RLU) per colony forming units (CFU) in samples of various *Listeria* species infected with recombinant codon-optimized phage version 2 (COP2; v.1.0.2; top panel) or with recombinant optimized phage version 3 (COP3 v.1.0.3; bottom panel). The *Listeria* species used in these experiments are considered "weak signal producers" that do not typically produce strong signal following infection with recombinant luciferase-encoding phages.
Figure 9:
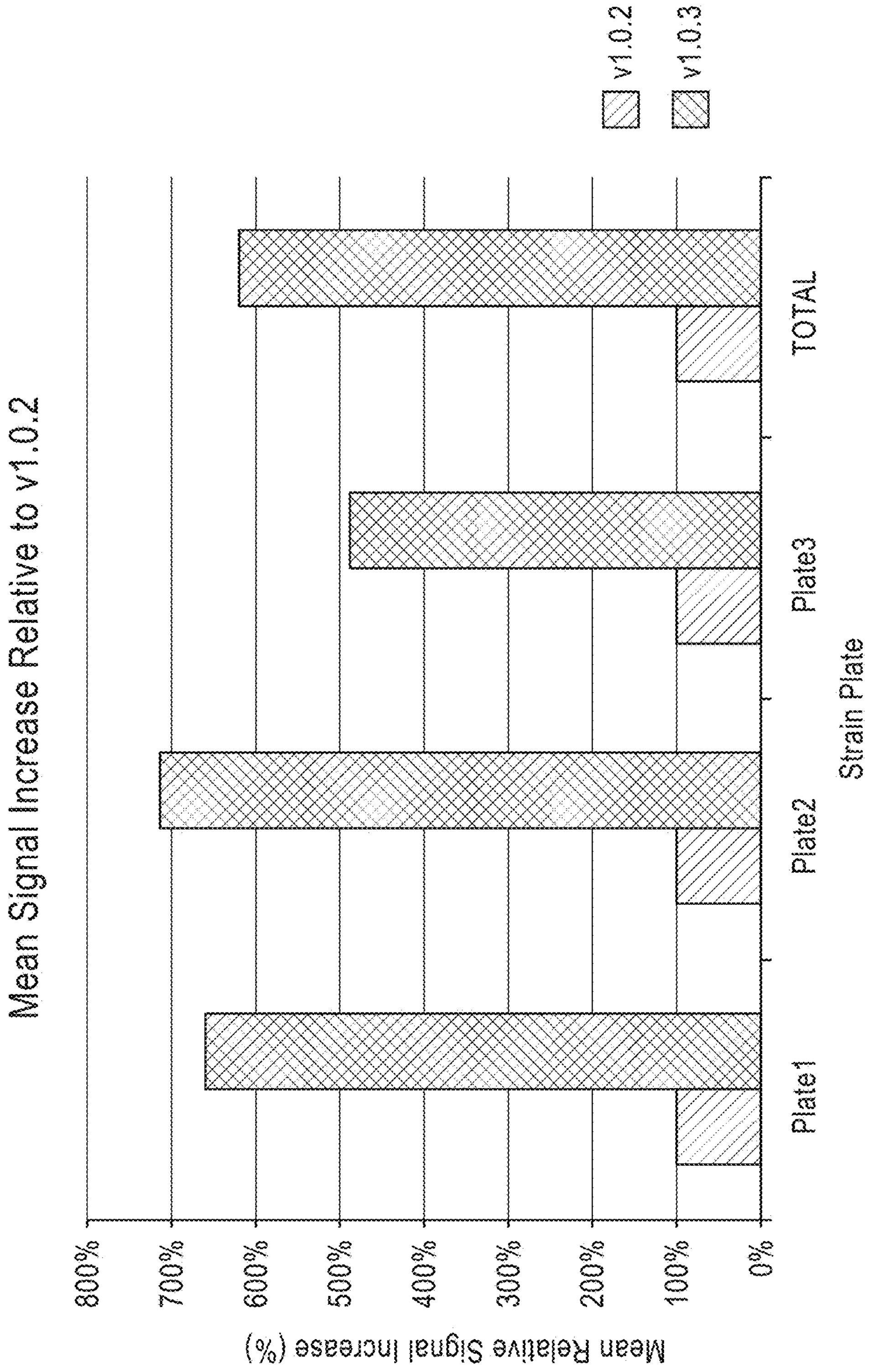
FIG. 9 is a graph that depicts a comparison of the amounts of mean light signal detected (shown as a percentage) in *Listeria* samples that were infected with either recombinant codon-optimized phage version 2 (COP2; v.1.0.2) or with recombinant optimized phage version 3 (COP3 v.1.0.3). The y-axis depicts the mean relative signal increase in percentage, and the x-axis depicts the *Listeria* strain that utilized.

Data acquired in the comparison of the COP2 and the COP3 phages are shown in FIGS. 8 and 9. The signal comparison assays demonstrate that there was a broad increase in signal intensity across tested *Listeria* species with the use of the COP3 phage in comparison with the COP2 phage. The data further indicate that there was a six time (6×) mean signal increase across all the tested conditions with the use of COP3 in comparison to COP2. The full listing of *Listeria* strains used in these studies is shown in Table 10.

TABLE 10

Full Listing of *Listeria* Strains Assessed in COP2 and COP3 Signal Intensity Assay

| Plate | NP Strain # | Strain ID | Species | Well |
|---|---|---|---|---|
| 1 | 1814 | FSL C2-010 | *Listeria ivanovii* | a1 |
| 1 | 1815 | FSL C2-011 | *Listeria ivanovii* | a2 |
| 1 | 1816 | FSL H6-011 | *Listeria seeligeri* | a3 |
| 1 | 1817 | FSL H6-169 | *Listeria seeligeri* | a4 |
| 1 | 1818 | FSL H6 017 | *Listeria welshimeri* | a5 |
| 1 | 1819 | FSL H6-105 | *Listeria welshimeri* | a6 |
| 1 | 1820 | FSL C2-008 | *Listeria innocua* | a7 |
| 1 | 1821 | FSL X1-017 | *Listeria innocua* | a8 |
| 1 | 1822 | FSL J1-023 | *Listeria innocua* (hemolytic) | a9 |
| 1 | 1823 | FSL W3-075 | *Listeria innocua* (hemolytic) | a10 |
| 1 | 1824 | FSL S4-120 | *Listeria marthii* | a11 |
| 1 | 1825 | FSL S4-965 | *Listeria marthii* | a12 |
| 1 | 1826 | FSL F6-920 | *Listeria rocourtiae* | b1 |
| 1 | 1827 | FSL C1-056 | *Listeria monocytogenes* | b2 |
| 1 | 1828 | FSL J1-177 | *Listeria monocytogenes* | b3 |
| 1 | 1829 | FSL J1-094 | *Listeria monocytogenes* | b4 |
| 1 | 1830 | FSL C1-115 | *Listeria monocytogenes* | b5 |
| 1 | 1831 | FSL J1-169 | *Listeria monocytogenes* | b6 |
| 1 | 1832 | FSL J1-049 | *Listeria monocytogenes* | b7 |
| 1 | 1833 | FSL W1-112 | *Listeria monocytogenes* | b8 |
| 1 | 1834 | FSL J1-110 | *Listeria monocytogenes* | b9 |
| 1 | 1835 | FSL J1-129 | *Listeria monocytogenes* | b10 |
| 1 | 1836 | FSL W1-110 | *Listeria monocytogenes* | b11 |

TABLE 10-continued

Full Listing of *Listeria* Strains Assessed in COP2 and COP3 Signal Intensity Assay

| Plate | NP Strain # | Strain ID | Species | Well |
|---|---|---|---|---|
| 1 | 1837 | FSL J1-107 | *Listeria monocytogenes* | b12 |
| 1 | 1838 | FSL J1-175 | *Listeria monocytogenes* | c1 |
| 1 | 1839 | FSL F6-367 (MACK) | *Listeria monocytogenes* | c2 |
| 1 | 1840 | FSL J1-208 | *Listeria monocytogenes* | c3 |
| 1 | 1869 | WSLC 3009 | *Listeria ivanovii* | c4 |
| 1 | 1879 | FSL N4-221 | *Listeria monocytogenes* | c5 |
| 1 | 1878 | EGD-e | *Listeria monocytogenes* | c6 |
| 1 | 1880 | FSL L3-159 | *Listeria monocytogenes* | c7 |
| 1 | 1881 | FSL T1-323 | *Listeria monocytogenes* | c8 |
| 1 | 1882 | FSL H5-725 | *Listeria monocytogenes* | c9 |
| 1 | 1883 | FSL T1-922 | *Listeria monocytogenes* | c10 |
| 1 | 1884 | FSL H1-251 | *Listeria monocytogenes* | c11 |
| 1 | 1885 | FSL L3-501 | *Listeria monocytogenes* | c12 |
| 1 | 1886 | FSL R2-069 | *Listeria monocytogenes* | d1 |
| 1 | 1887 | FSL H1-030 | *Listeria monocytogenes* | d2 |
| 1 | 1888 | FSL L4-019 | *Listeria monocytogenes* | d3 |
| 1 | 1889 | FSL T1-027 | *Listeria monocytogenes* | d4 |
| 1 | 1890 | FSL T1-041 | *Listeria monocytogenes* | d5 |
| 1 | 1891 | FSL R8-5241 | *Listeria seeligeri* | d6 |
| 1 | 1892 | FSL R8-5247 | *Listeria seeligeri* | d7 |
| 1 | 1893 | FSL R8-5253 | *Listeria seeligeri* | d8 |
| 1 | 1894 | FSL R8-5513 | *Listeria seeligeri* | d9 |
| 1 | 1895 | FSL R8-6629 | *Listeria seeligeri* | d10 |
| 1 | 1896 | FSL R8-6635 | *Listeria seeligeri* | d11 |
| 1 | 1897 | FSL R8-6659 | *Listeria seeligeri* | d12 |
| 1 | 1898 | FSL R8-6665 | *Listeria seeligeri* | e1 |
| 1 | 1899 | FSL R8-6852 | *Listeria seeligeri* | e2 |
| 1 | 1900 | FSL R8-5085 | *Listeria innocua* | e3 |
| 1 | 1901 | FSL R8-5091 | *Listeria innocua* | e4 |
| 1 | 1902 | FSL R8-5098 | *Listeria innocua* | e5 |
| 1 | 1903 | FSL R8-5255 | *Listeria innocua* | e6 |
| 1 | 1904 | FSL R8-5293 | *Listeria innocua* | e7 |
| 1 | 1905 | FSL R8-5295 | *Listeria innocua* | e8 |
| 1 | 1906 | FSL R8-5306 | *Listeria innocua* | e9 |
| 1 | 1907 | FSL R8-5440 | *Listeria innocua* | e10 |
| 1 | 1908 | FSL R8-5442 | *Listeria innocua* | e11 |
| 1 | 1909 | FSL R8-5448 | *Listeria innocua* | e12 |
| 1 | 1910 | FSL R8-7026 | *Listeria welshimeri* | f1 |
| 1 | 1911 | FSL R8-7641 | *Listeria seeligeri* | f2 |
| 1 | 1912 | FSL R8-7061 | *Listeria innocua* | f3 |
| 1 | 1913 | FSL R8-6826 | *Listeria seeligeri* | f4 |
| 1 | 1914 | FSL R8-7454 | *Listeria welshimeri* | f5 |
| 1 | 1915 | FSL R8-7548 | *Listeria innocua* | f6 |
| 1 | 1916 | FSL R8-6667 | *Listeria innocua* | f7 |
| 1 | 1917 | FSL R8-1903 | *Listeria welshimeri* | f8 |
| 1 | 1945 | FSL L5-079 | *Listeria welshimeri* | f9 |
| 1 | 1946 | FSL S10-1450 | *Listeria welshimeri* | f10 |
| 1 | 1947 | FSL S10-1451 | *Listeria welshimeri* | f11 |
| 1 | 1948 | FSL S4-081 | *Listeria welshimeri* | f12 |
| 1 | 1949 | FSL S4-101 | *Listeria welshimeri* | g1 |
| 1 | 1950 | FSL S10-030 | *Listeria seeligeri* | g2 |
| 1 | 1951 | FSL S10-320 | *Listeria seeligeri* | g3 |
| 1 | 1952 | FSL S10-1602 | *Listeria seeligeri* | g4 |
| 1 | 1953 | FSL L5-075 | *Listeria seeligeri* | g5 |
| 1 | 1954 | FSL L5-046 | *Listeria seeligeri* | g6 |
| 1 | 1955 | FSL L5-104 | *Listeria seeligeri* | g7 |
| 1 | 1956 | FSL R8-7575 | *Listeria seeligeri* | g8 |
| 1 | 1957 | FSL S4-178 | *Listeria seeligeri* | g9 |
| 1 | 1958 | FSL S4-135 | *Listeria seeligeri* | g10 |
| 1 | 1959 | FSL S4-158 | *Listeria innocua* | g11 |
| 1 | 1960 | FSL S10-784 | *Listeria innocua* | g12 |
| 1 | 1961 | FSL F6-1168 | *Listeria innocua* | h1 |
| 1 | 1962 | FSL R8-5961 | *Listeria innocua* | h2 |
| 1 | 1963 | FSL R8-6922 | *Listeria innocua* | h3 |
| 1 | 1964 | FSL R8-7352 | *Listeria innocua* | h4 |
| 1 | 1965 | FSL R8-5598 | *Listeria innocua* | h5 |
| 1 | 1966 | FSL R8-6733 | *Listeria innocua* | h6 |
| 1 | 1967 | FSL R8-5942 | *Listeria innocua* | h7 |
| 1 | 1968 | FSL S10-034 | *Listeria seeligeri* | h8 |
| 1 | 1969 | FSL S10-1611 | *Listeria seeligeri* | h9 |
| 1 | 1970 | FSL L5-054 | *Listeria seeligeri* | h10 |
| 1 | 1971 | FSL L5-085 | *Listeria seeligeri* | h11 |
| 1 | 1972 | FSL R8-6868 | *Listeria seeligeri* | h12 |

TABLE 10-continued

Full Listing of *Listeria* Strains Assessed in COP2 and COP3 Signal Intensity Assay

| Plate | NP Strain # | Strain ID | Species | Well |
|---|---|---|---|---|
| 2 | 1839 | FSL F6-367 (MACK) | *Listeria monocytogenes* | a1 |
| 2 | 1840 | FSL J1-208 | *Listeria monocytogenes* | a2 |
| 2 | 1869 | WSLC 3009 | *Listeria ivanovii* | a3 |
| 2 | 1973 | FSL R8-6545 | *Listeria seeligeri* | a4 |
| 2 | 1974 | FSL R8-6949 | *Listeria seeligeri* | a5 |
| 2 | 1975 | FSL S4-167 | *Listeria seeligeri* | a6 |
| 2 | 1976 | FSL S4-180 | *Listeria seeligeri* | a7 |
| 2 | 1977 | FSL N1-064 | *Listeria welshimeri* | a8 |
| 2 | 1978 | FSL R8-8163 | *Listeria welshimeri* | a9 |
| 2 | 1979 | FSL R8-7524 | *Listeria welshimeri* | a10 |
| 2 | 1980 | FSL R8-7486 | *Listeria welshimeri* | a11 |
| 2 | 1981 | FSL R8-6035 | *Listeria welshimeri* | a12 |
| 2 | 1982 | FSL R8-5807 | *Listeria welshimeri* | b1 |
| 2 | 1983 | FSL S4-182 | *Listeria welshimeri* | b2 |
| 2 | 1984 | FSL R2-630 | *Listeria welshimeri* | b3 |
| 2 | 1985 | FSL F6-1131 | *Listeria welshimeri* | b4 |
| 2 | 1986 | FSL R8-7041 | *Listeria welshimeri* | b5 |
| 2 | 1987 | FSL R8-5837 | *Listeria welshimeri* | b6 |
| 2 | 1988 | FSL R8-6136 | *Listeria welshimeri* | b7 |
| 2 | 1989 | FSL S4-289 | *Listeria welshimeri* | b8 |
| 2 | 1990 | FSL H6-027 | *Listeria seeligeri* | b9 |
| 2 | 1991 | FSL H6-079 | *Listeria seeligeri* | b10 |
| 2 | 1992 | FSL H6-185 | *Listeria seeligeri* | b11 |
| 2 | 1993 | FSL R8-6874 | *Listeria seeligeri* | b12 |
| 2 | 1994 | FSLR8-6880 | *Listeria seeligeri* | c1 |
| 2 | 1995 | FSL R8-7629 | *Listeria seeligeri* | c2 |
| 2 | 1996 | FSL S4-544 | *Listeria seeligeri* | c3 |
| 2 | 1997 | FSL R8-5764 | *Listeria innocua* | c4 |
| 2 | 1998 | FSL R8-5802 | *Listeria innocua* | c5 |
| 2 | 1999 | FSL R8-6012 | *Listeria innocua* | c6 |
| 2 | 2000 | FSL R8-6355 | *Listeria innocua* | c7 |
| 2 | 2001 | FSL R8-6369 | *Listeria innocua* | c8 |
| 2 | 2002 | FSL R8-6476 | *Listeria innocua* | c9 |
| 2 | 2003 | FSL R8-7175 | *Listeria innocua* | c10 |
| 2 | 2004 | FSL R8-6888 | *Listeria innocua* | c11 |
| 2 | 2005 | FSL R8-6672 | *Listeria innocua* | c12 |
| 2 | 2006 | FSL S10-1311 | *Listeria innocua* | d1 |
| 2 | 2007 | FSL F6-1159 | *Listeria innocua* | d2 |
| 2 | 2008 | FSL F6-1126 | *Listeria innocua* | d3 |
| 2 | 2009 | FSL S6-120 | *Listeria innocua* | d4 |
| 2 | 2010 | FSL R8-5594 | *Listeria innocua* | d5 |
| 2 | 2011 | FSL R8-7181 | *Listeria innocua* | d6 |
| 2 | 2012 | FSL R2-632 | *Listeria innocua* | d7 |
| 2 | 2013 | FSL L3-851 | *Listeria innocua* | d8 |
| 2 | 2014 | FSL S10-1377 | *Listeria innocua* | d9 |
| 2 | 2015 | FSL S10-114 | *Listeria welshimeri* | d10 |
| 2 | 2016 | FSL S10-115 | *Listeria welshimeri* | d11 |
| 2 | 2017 | FSL S10-117 | *Listeria welshimeri* | d12 |
| 2 | 2018 | FSL S10-119 | *Listeria welshimeri* | e1 |
| 2 | 2019 | FSL S10-121 | *Listeria welshimeri* | e2 |
| 2 | 2020 | FSL R8-0056 | *Listeria welshimeri* | e3 |
| 2 | 2021 | FSL R8-1198 | *Listeria welshimeri* | e4 |
| 2 | 2022 | FSL R8-7403 | *Listeria welshimeri* | e5 |
| 2 | 2023 | FSL R2-631 | *Listeria welshimeri* | e6 |
| 2 | 2024 | FSL F6-267 | *Listeria monocytogenes* | e7 |
| 2 | 2025 | FSL F6-406 | *Listeria monocytogenes* | e8 |
| 2 | 2026 | FSL H5-592 | *Listeria monocytogenes* | e9 |
| 2 | 2027 | FSL H1-219 | *Listeria monocytogenes* | e10 |
| 2 | 2028 | FSL H1-121 | *Listeria monocytogenes* | e11 |
| 2 | 2029 | FSL W3-072 | *Listeria monocytogenes* | e12 |
| 2 | 2030 | FSL N4-239 | *Listeria monocytogenes* | f1 |
| 2 | 2031 | FSL N3-293 | *Listeria monocytogenes* | f2 |
| 2 | 2032 | FSL F3-319 | *Listeria monocytogenes* | f3 |
| 2 | 2033 | FSL F2-738 | *Listeria monocytogenes* | f4 |
| 2 | 2034 | FSL N3-881 | *Listeria monocytogenes* | f5 |
| 2 | 2035 | FSL N4-048 | *Listeria monocytogenes* | f6 |
| 2 | 2036 | FSL N4-696 | *Listeria monocytogenes* | f7 |
| 2 | 2037 | FSL N4-242 | *Listeria monocytogenes* | f8 |
| 2 | 2038 | FSL H4-364 | *Listeria monocytogenes* | f9 |
| 2 | 2039 | FSL H4-147 | *Listeria monocytogenes* | f10 |
| 2 | 2040 | FSL H4-946 | *Listeria monocytogenes* | f11 |
| 2 | 2041 | FSL S4-461 | *Listeria monocytogenes* | f12 |
| 2 | 2042 | FSL F6-206 | *Listeria monocytogenes* | g1 |

TABLE 10-continued

Full Listing of *Listeria* Strains Assessed in COP2 and COP3 Signal Intensity Assay

| Plate | NP Strain # | Strain ID | Species | Well |
|---|---|---|---|---|
| 2 | 2043 | FSL F6-224 | *Listeria monocytogenes* | g2 |
| 2 | 2044 | FSL L3-739 | *Listeria monocytogenes* | g3 |
| 2 | 2045 | FSL N3-008 | *Listeria monocytogenes* | g4 |
| 2 | 2046 | FSL N3-022 | *Listeria monocytogenes* | g5 |
| 2 | 2047 | FSL J1-108 | *Listeria monocytogenes* | g6 |
| 2 | 2048 | FSL J1-119 | *Listeria monocytogenes* | g7 |
| 2 | 2049 | FSL C1-122 | *Listeria monocytogenes* | g8 |
| 2 | 2050 | FSL J1-126 | *Listeria monocytogenes* | g9 |
| 2 | 2051 | FSL F3-285 | *Listeria monocytogenes* | g10 |
| 2 | 2052 | FSL R6-288 | *Listeria monocytogenes* | g11 |
| 2 | 2053 | FSL N1-021 | *Listeria monocytogenes* | g12 |
| 2 | 2054 | FSL H1-208 | *Listeria monocytogenes* | h1 |
| 2 | 2055 | FSL N3-034 | *Listeria monocytogenes* | h2 |
| 2 | 2056 | FSL L5-072 | *Listeria monocytogenes* | h3 |
| 2 | 2057 | FSL S6-131 | *Listeria monocytogenes* | h4 |
| 2 | 2058 | FSL N3-278 | *Listeria monocytogenes* | h5 |
| 2 | 2059 | FSL R2-282 | *Listeria monocytogenes* | h6 |
| 2 | 2060 | FSL H5-770 | *Listeria monocytogenes* | h7 |
| 2 | 2061 | FSL F6-207 | *Listeria monocytogenes* | h8 |
| 2 | 2062 | FSL F6-236 | *Listeria monocytogenes* | h9 |
| 2 | 2063 | FSL H5-795 | *Listeria monocytogenes* | h10 |
| 2 | 2064 | FSL N3-246 | *Listeria monocytogenes* | h11 |
| 2 | 2065 | FSL R2-062 | *Listeria monocytogenes* | h12 |
| 3 | 1839 | FSL F6-367 (MACK) | *Listeria monocytogenes* | a1 |
| 3 | 1840 | FSL J1-208 | *Listeria monocytogenes* | a2 |
| 3 | 1869 | WSLC 3009 | *Listeria ivanovii* | a3 |
| 3 | 2066 | FSL R2-437 | *Listeria monocytogenes* | a4 |
| 3 | 2067 | FSL M1-004 | *Listeria monocytogenes* | a5 |
| 3 | 2068 | FSL L4-352 | *Listeria monocytogenes* | a6 |
| 3 | 2069 | FSL F6-605 | *Listeria monocytogenes* | a7 |
| 3 | 2070 | FSL V1-001 | *Listeria monocytogenes* | a8 |
| 3 | 2071 | FSL F6-464 | *Listeria monocytogenes* | a9 |
| 3 | 2072 | FSL R8-2748 | *Listeria monocytogenes* | a10 |
| 3 | 2073 | FSL R6-908 | *Listeria monocytogenes* | a11 |
| 3 | 2074 | FSL L3-802 | *Listeria monocytogenes* | a12 |
| 3 | 2075 | FSL F3-056 | *Listeria monocytogenes* | b1 |
| 3 | 2076 | FSL J2-020 | *Listeria monocytogenes* | b2 |
| 3 | 2077 | FSL S4-914 | *Listeria monocytogenes* | b3 |
| 3 | 2078 | FSL F6-467 | *Listeria monocytogenes* | b4 |
| 3 | 2079 | FSL F6-655 | *Listeria monocytogenes* | b5 |
| 3 | 2080 | FSL F6-352 | *Listeria monocytogenes* | b6 |
| 3 | 2081 | FSL H5-781 | *Listeria monocytogenes* | b7 |
| 3 | 2082 | FSL K2-147 | *Listeria monocytogenes* | b8 |
| 3 | 2083 | FSL V1-026 | *Listeria monocytogenes* | b9 |
| 3 | 2084 | FSL H5-572 | *Listeria monocytogenes* | b10 |
| 3 | 2085 | FSL K2-065 | *Listeria monocytogenes* | b11 |
| 3 | 2086 | FSL H4-120 | *Listeria monocytogenes* | b12 |
| 3 | 2087 | FSL F6-184 | *Listeria monocytogenes* | c1 |
| 3 | 2088 | FSL F6-191 | *Listeria monocytogenes* | c2 |
| 3 | 2089 | FSL H1-099 | *Listeria monocytogenes* | c3 |
| 3 | 2090 | FSL J1-116 | *Listeria monocytogenes* | c4 |
| 3 | 2091 | FSL R2-192 | *Listeria monocytogenes* | c5 |
| 3 | 2092 | FSL J1-225 | *Listeria monocytogenes* | c6 |
| 3 | 2093 | FSL R2-500 | *Listeria monocytogenes* | c7 |
| 3 | 2094 | FSL R2-501 | *Listeria monocytogenes* | c8 |
| 3 | 2095 | FSL E1-159 | *Listeria monocytogenes* | c9 |
| 3 | 2096 | FSL F6-355 | *Listeria monocytogenes* | c10 |
| 3 | 2097 | FSL F6-382 | *Listeria monocytogenes* | c11 |
| 3 | 2098 | FSL F3-200 | *Listeria monocytogenes* | c12 |
| 3 | 2099 | FSL K2-143 | *Listeria monocytogenes* | d1 |
| 3 | 2100 | FSL N1-176 | *Listeria monocytogenes* | d2 |
| 3 | 2101 | FSL N1-417 | *Listeria monocytogenes* | d3 |
| 3 | 2102 | FSL L3-051 | *Listeria monocytogenes* | d4 |
| 3 | 2103 | FSL T1-107 | *Listeria monocytogenes* | d5 |
| 3 | 2104 | FSL T1-408 | *Listeria monocytogenes* | d6 |
| 3 | 2105 | FSL F6-396 | *Listeria monocytogenes* | d7 |
| 3 | 2106 | FSL H5-806 | *Listeria monocytogenes* | d8 |
| 3 | 2107 | FSL F6-551 | *Listeria monocytogenes* | d9 |
| 3 | 2108 | FSL F6-446 | *Listeria monocytogenes* | d10 |
| 3 | 2109 | FSL F6-315 | *Listeria monocytogenes* | d11 |
| 3 | 2110 | FSL V1-022 | *Listeria monocytogenes* | d12 |
| 3 | 2111 | FSL R2-132 | *Listeria monocytogenes* | e1 |
| 3 | 2112 | FSL R2-273 | *Listeria monocytogenes* | e2 |
| 3 | 2113 | FSL N3-277 | *Listeria monocytogenes* | e3 |
| 3 | 2114 | FSL F6-358 | *Listeria monocytogenes* | e4 |
| 3 | 2115 | FSL F6-194 | *Listeria monocytogenes* | e5 |
| 3 | 2116 | FSL R2-763 | *Listeria monocytogenes* | e6 |
| 3 | 2117 | FSL R2-765 | *Listeria monocytogenes* | e7 |
| 3 | 2118 | FSL R2-764 | *Listeria monocytogenes* | e8 |
| 3 | 2119 | FSL N1-225 | *Listeria monocytogenes* | e9 |
| 3 | 2120 | FSL N1-227 | *Listeria monocytogenes* | e10 |
| 3 | 2121 | FSL N1-048 | *Listeria monocytogenes* | e11 |
| 3 | 2122 | FSL K2-131 | *Listeria monocytogenes* | e12 |
| 3 | 2123 | FSL F6-222 | *Listeria monocytogenes* | f1 |
| 3 | 2124 | FSL F6-249 | *Listeria monocytogenes* | f2 |
| 3 | 2125 | FSL N3-065 | *Listeria monocytogenes* | f3 |
| 3 | 2126 | FSL H4-699 | *Listeria monocytogenes* | f4 |
| 3 | 2127 | FSL L4-241 | *Listeria monocytogenes* | f5 |
| 3 | 2128 | FSL S4-643 | *Listeria monocytogenes* | f6 |
| 3 | 2129 | FSL R2-073 | *Listeria monocytogenes* | f7 |
| 3 | 2130 | FSL F3-224 | *Listeria monocytogenes* | f8 |
| 3 | 2131 | FSL N4-334 | *Listeria monocytogenes* | f9 |
| 3 | 2132 | FSL R2-070 | *Listeria monocytogenes* | f10 |
| 3 | 2133 | FSL F6-421 | *Listeria monocytogenes* | f11 |
| 3 | 2134 | FSL F6-449 | *Listeria monocytogenes* | f12 |
| 3 | 2135 | FSL J2-054 | *Listeria monocytogenes* | g1 |
| 3 | 2136 | FSL S4-024 | *Listeria monocytogenes* | g2 |
| 3 | 2137 | FSL H1-111 | *Listeria monocytogenes* | g3 |
| 3 | 2138 | FSL K2-022 | *Listeria monocytogenes* | g4 |
| 3 | 2139 | FSL S4-066 | *Listeria monocytogenes* | g5 |
| 3 | 2140 | FSL R2-067 | *Listeria monocytogenes* | g6 |
| 3 | 2141 | FSL R2-293 | *Listeria monocytogenes* | g7 |
| 3 | 2142 | FSL F6-323 | *Listeria monocytogenes* | g8 |
| 3 | 2143 | FSL F6-216 | *Listeria monocytogenes* | g9 |
| 3 | 2164 | FSL F6-360 | *Listeria monocytogenes* | g10 |
| 3 | 2165 | FSL F6-313 | *Listeria monocytogenes* | g11 |
| 3 | 2166 | FSL R2-031 | *Listeria monocytogenes* | g12 |
| 3 | 2167 | FSL R2-050 | *Listeria monocytogenes* | h1 |
| 3 | 2148 | FSL T1-313 | *Listeria monocytogenes* | h2 |
| 3 | 2149 | FSL R8-0875 | *Listeria monocytogenes* | h3 |
| 3 | 2150 | FSL R2-317 | *Listeria monocytogenes* | h4 |
| 3 | 2151 | FSL F6-335 | *Listeria monocytogenes* | h5 |
| 3 | 2152 | FSL R6-653 | *Listeria monocytogenes* | h6 |
| 3 | 2153 | FSL L3-135 | *Listeria monocytogenes* | h7 |
| 3 | 2154 | FSL L3-143 | *Listeria monocytogenes* | h8 |
| 3 | 2155 | FSL L3-167 | *Listeria monocytogenes* | h9 |
| 3 | 2156 | FSL N3-031 | *Listeria monocytogenes* | h10 |
| 3 | 2157 | FSL J1-101 | *Listeria monocytogenes* | h11 |
| 3 | 2158 | FSL F6-154 | *Listeria monocytogenes* | h12 |

Example 4: Effect of Phage Concentration on Signal Intensity

Figure 10:
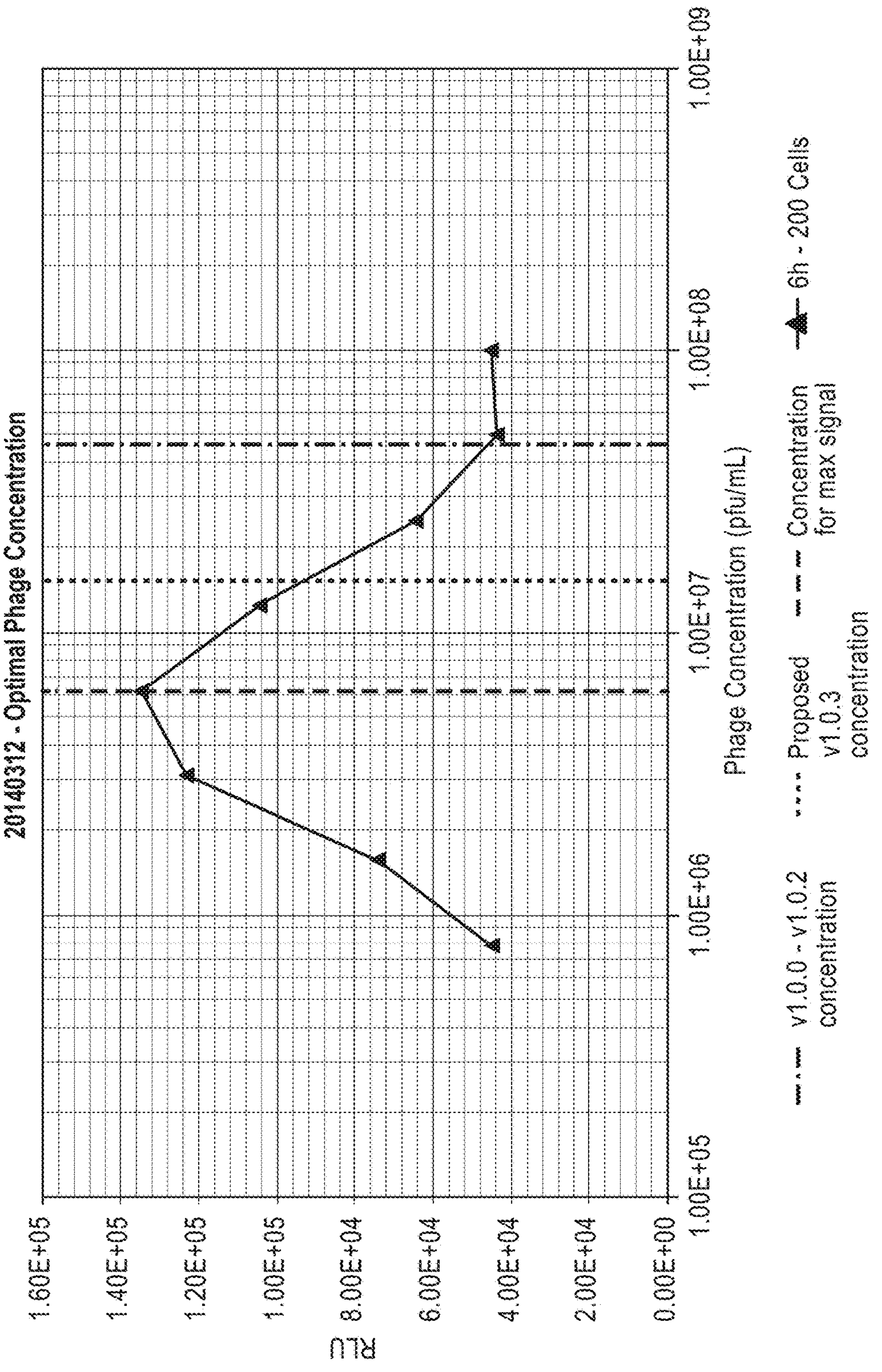
FIG. 10 is a graph that depicts optimal phage concentration using codon-optimized, luciferase encoding, recombinant phage. The y-axis depicts RLU, and the x-axis depicts phage concentration in PFU/mL.

Assays were performed to determine the effect of phage concentration on the resultant signal intensity following infection with the codon-optimized phage. See FIG. 10. For these experiments, two-fold serial dilutions of the COP2 phage (v1.0.2) cocktail were added to the infection buffer. 200 CFU of *Listeria monocytogenes* (NP#1839) were infected at various concentrations of phage. The infected samples were incubated for 6 hours at 30° C. The luciferase signal was detected using the Glomax 96 luminometer. The resultant signal intensities for the various concentrations of phage used was plotted on a graph for comparison of signal. The data from these experiments indicate that the concentration for maximum signal is approximately between $1.5\times10^6$ to $1.8\times10^6$ pfu/mL. See FIG. 10. All assays were performed minimally in triplicate.

Example 5: Alterations in the 5' UTR Results in Increased Signal Intensity

Optimization of the 5' UTR was performed by utilizing DNA 2.0™. The changes to the 5' UTR included modifications of spacer DNA and/or changes in the nucleotide sequence of the ribosome binding site (RBS). These sequences, including the original UTR sequence, can be found in the informal sequence listing at SEQ ID No.: 90-97. Multiple variants were produced, several of which resulted in greater than a 200% mean signal increase over the COP2 (v1.0.2) phage signal. See Table 11. For these assays, optimized UTR variants were linked to a modified NanoLuc construct called COPD12 (see SEQ ID No. 53).

TABLE 11

Codon-optimized 5' UTR Results in Increased Signal Intensity

| Variant | Mean Signal Increase over v1.0.2 |
| --- | --- |
| UTR2 | 264% |
| UTR4 | 289% |
| UTR7 | 232% |

The 5' UTR changes that resulted in increased signal intensity were combined with the best-performing COP3 codon-optimized variant (i.e. 40_VIP178) to assess whether this combination would result in increased signal in comparison to either the 5'UTR optimization or the COP3 variant alone. The results surprisingly show that the combined variants do not have increased signal in comparison to the COP3 variant that does not contain an altered 5' UTR sequence. See Table 12.

TABLE 12

COP3 Combined with 5'UTR Modification Does Not Result in Greater Signal Intensity

| Variant | Mean Signal Increase over v1.0.2 |
| --- | --- |
| UTR2_178 | 182% |
| UTR3_178 | 185% |
| UTR7_178 | 332% |
| 40_VIP178 | 468% |
| UTR2 | 243% |
| UTR3 | 154% |
| UTR7 | 191% |

Example 6: Selection of Base Media

Media were screened for the ability to support high infection rate and high signal intensity following infection with phage encoding a luciferase marker. Bacterial cells were purposefully stressed by way of drying for 18 hours on a stainless steel table, followed by re-suspension in brain-heart infusion medium (BHI) for 30 minutes. The recovered cells were then infected with phage containing a luciferase marker for 6 hours followed by testing of the enzymatic activity using unpurified phage lysate and NanoLuc reagent. All media tested gave similar RLU output.

BHI and TSB media were further titrated to assess whether there was an increase in RLU at different concentrations of base media. The data indicate that stressed cells recovered best in 1×TSB medium. Additional benefits of the 1×TSB medium include that the TSB does not contain animal byproducts, it contains more nutrients, and there is better consistency of the product among different lots tested.

Figure 11:
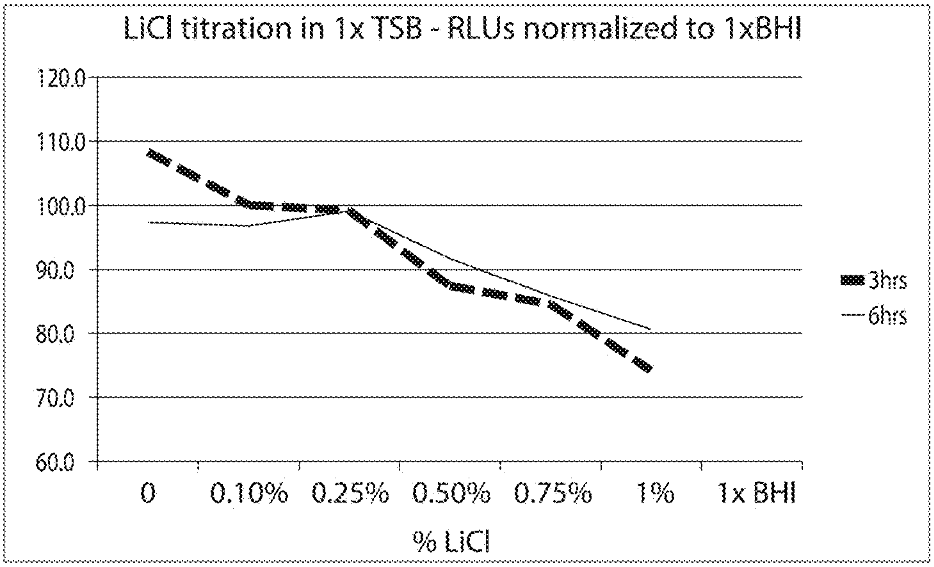
FIG. 11 is a graph that demonstrating the effect of the addition of various LiCl concentrations to the 1×TSB buffer in RLU output following infection of bacteria with luciferase encoding phage and normalized to RLU output obtained from 1×BHI buffer. A 3 hour and a 6 hour time point were assayed. The % values are shown on the y-axis.

Example 7: Selection of Media Additives—Selective Agents, Neutralizers, and Nutrients Select components were added to the media in order to remedy known stressors to cells, and to reduce the possibility for other chemicals interfering with the test results. To this end, lithium chloride was added at defined concentrations to the selected 1×TSB base medium, followed by infecting the cells with a luciferase containing phage, and lastly by assaying the RLU detectable as a function of the percentage of lithium chloride added to the media. Lithium chloride was selected as an additive in order to overcome, prevent or limit growth of competing biologicals. The data from these experiments indicate that, lithium chloride added at 0.25% resulted in the highest RLU at both 3 hours and 6 hours post-infection. (See FIG. 11).

Components selected to overcome cell starvation and oxidative stress, glucose and yeast extract, respectively, were titrated in 1×TSB, followed by infection of the bacteria with luciferase containing phage, and lastly by assaying the RLU detectable as a function of the percentage of either glucose or yeast extract. Based on the RLU levels at the 3 hour and 6 hour assay points, 0.25% glucose and 0.5% yeast extract were selected.

Antifungal agents were also added to the base medium and tested in order to determine whether there is a decrease in RLU activity, either as a result of loss of enzyme activity or because of reduced infection ability. The anti-fungal agents tested included cycloheximide solution in DMSO. Neither cycloheximide nor DMSO resulted in a decrease in the infection rate or in the enzymatic activity.

Figure 12:
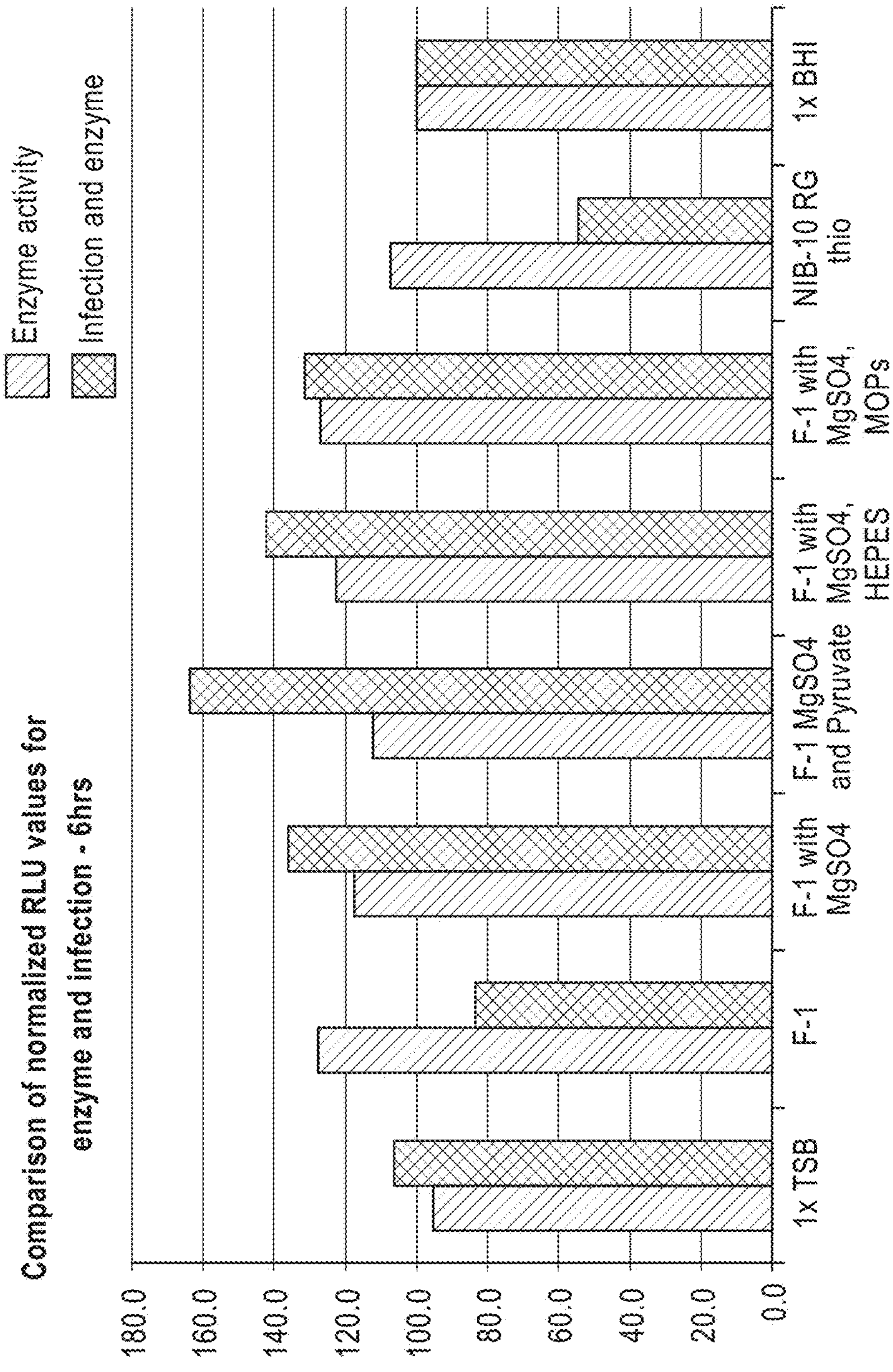
FIG. 12 is a graph that summarizes the findings with respect to enzyme activity and infection rate of bacteria exposed to luciferase encoding phage while in the presence of various iterations of the infection buffer formulations and normalized to RLU output obtained from 1×BHI buffer. The % values are shown on the y-axis.

The effect of divalent cations added to Formulation-1 was assessed. $MgSO_4$ or $CaCl_2$ was added to Formulation-1, followed by infection of bacteria with luciferase encoding phage, and assessment of resultant RLU. Addition of $MgSO_4$ to Formulation-1 resulted in a marked increase in the RLU activity in comparison to the addition of $CaCl_2$. The beneficial activity on resultant RLU activity led to the creation of Formulation-1A, which contains 0.08% $MgSO_4$. (See Table 2 and FIG. 12).

The addition of alternative carbon sources, through the addition of alpha-ketoglutarate, glutamate, malonate and citrate to Formulation-1 demonstrated that glucose sustained RLU activity more effectively.

A comparison of enzyme activity and infection ability with various media formulations indicated that a preferred embodiment of the formulation includes the base Formulation-1, with the addition of 0.08% MgSO4 and 0.1% pyruvate (also referred herein as Formulation-1A). (See FIG. 27).

Figure 13A:
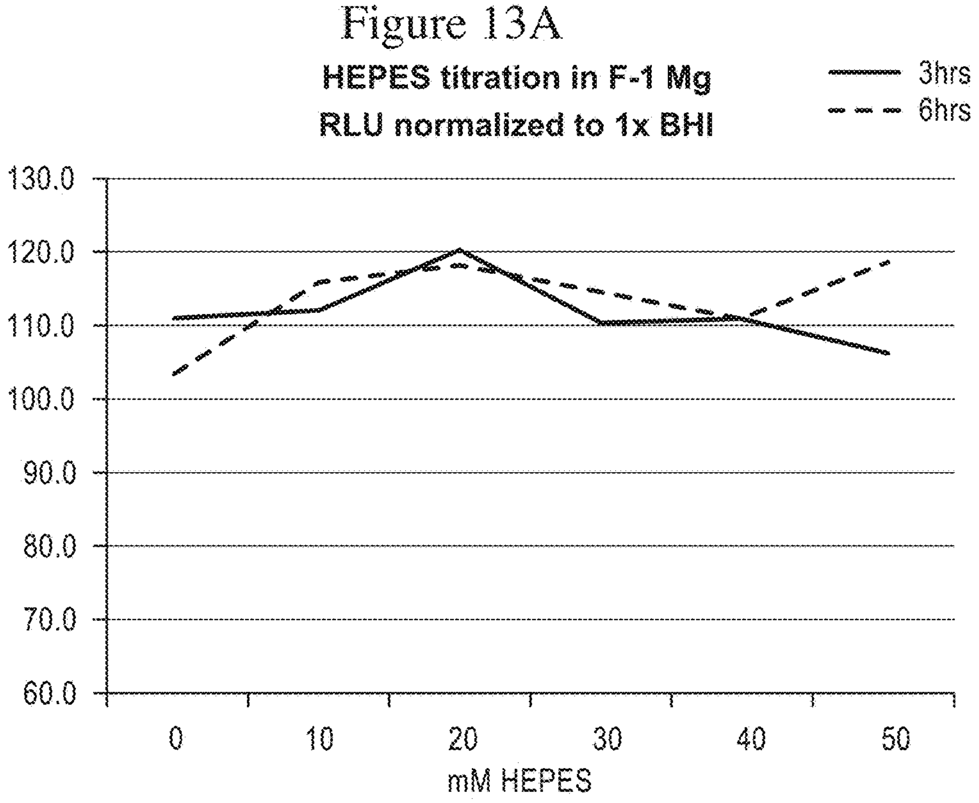
FIGS. 13A and 13B are a pair of graphs depicting the effect of the addition of HEPES buffer to the Formulation-1 infection buffer. Bacterial cells were exposed, in either Formulation-1 without HEPES or Formulation-1 with HEPES, to luciferase encoding phage, followed by assessment of RLU values normalized to RLU output obtained from 1×BHI buffer. The % values are shown on the y-axis.
Figure 13B:
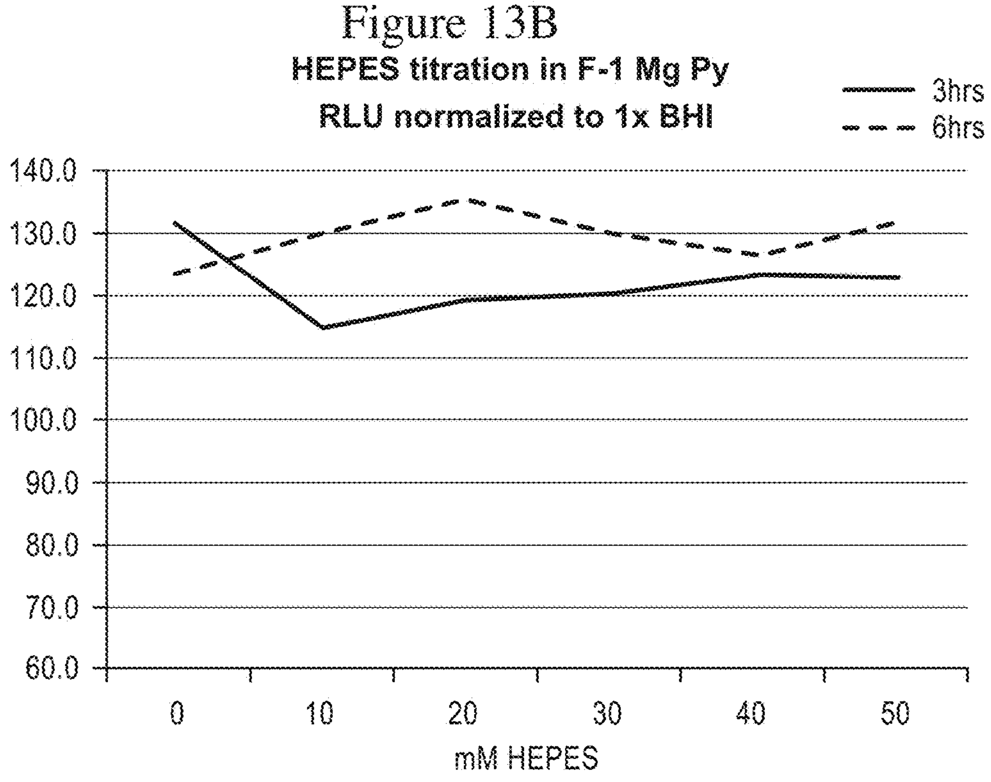

HEPES was also titrated into Formulation-1A to investigate whether addition of HEPES resulted in higher RLU activity than without the addition of the buffer. The data indicated that 20 mM HEPES was ideal in both the 3 hour and the 6 hour assay time points for high RLU activity. Furthermore, the addition of pyruvate further increased RLU activity. (See FIGS. 13A and 13B). The resultant formulation that incorporates all of the components of Formulation-1A, with the addition of HEPES, is herein referred to as Formulation-2 or as NIB-12. (See Table 3).

Example 8: Formulation NIB-14

Based on the information gleaned from the effects acquired through the addition of additives to the base TSB formulation (see Example 7 above), other components were selectively added to generate another preferred embodiment of the formulation, which is particularly well suited for resisting the negative impact of chemicals found in sanitizing solutions on both enzymatic stability and phage infection. Of particular interest are additives that are geared towards reducing the interference from quaternary ammonium salts found in various sanitizing solutions including among others: "Sani-Step," "Sani-Save," "Boost-FT," "Quorum Clear V," "Whisper V," "Sparkle QF-BH," "F29". Particularly good candidates that have the capability of reducing interference of quaternary ammonium salts are TWEEN®-80 and lecithin.

Figure 14:
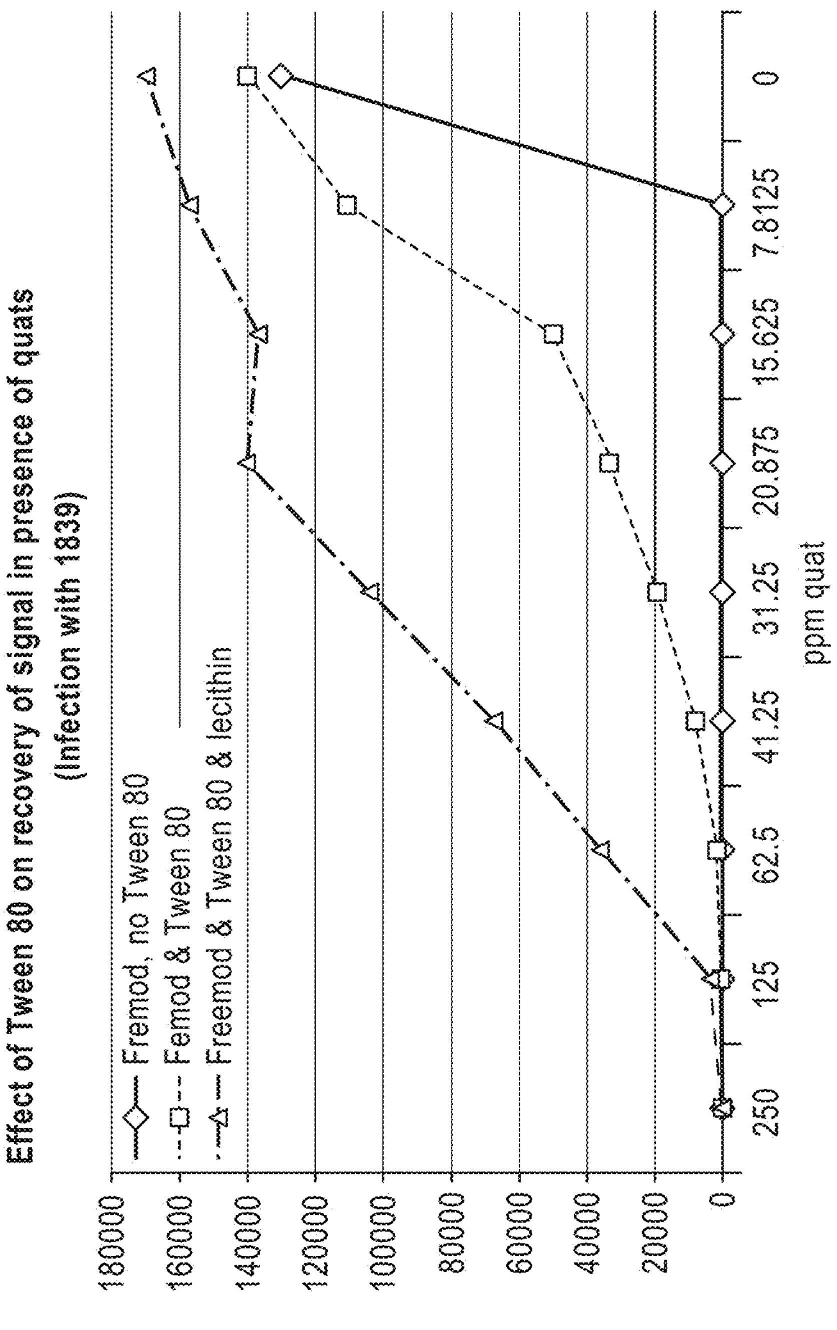
FIG. 14 is a graph that demonstrates the effects of the addition of TWEEN®-80, or TWEEN®-80 and lecithin, or the addition of neither of these components to the *Listeria* growth broth in the presence of increasing concentrations of quaternary ammonium salts. Bacterial cells were exposed to luciferase encoding phage in the following buffers, *Listeria* growth broth, *Listeria* growth broth with TWEEN®-80, or to *Listeria* growth broth with the addition of both TWEEN®-80 and lecithin. The RLU values are shown on the y-axis.

The addition of TWEEN®-80, either alone or in combination with lecithin, to the Formulation-2 (NIB-12) medium allowed for protection of the samples from interference by quaternary ammonium salts. (See FIG. 14). Without the addition of either TWEEN®-80 or of lecithin to *Listeria* Growth Broth, there was no detectable RLU when the solution contained 7.81 ppm of quaternary ammonium salts. However, the resistance to quaternary ammonium salts was also increased by the addition of TWEEN®-80 alone. In this case, there was a sustained, detectable RLU in the presence of up to 62.5 ppm quaternary ammonium salts. The amount of resistance to quaternary ammonium salts was further increased through the addition of both lecithin and TWEEN®-80. With the addition of both reagents to *Listeria* Growth Broth, there was detectable RLU up to 125 ppm quaternary ammonium salts. Another preferred embodiment of the media contains 1.5% of TWEEN®-80 and 0.22% of lecithin. This formulation is herein referred to as NIB-14, the full formulation of which is detailed in Table 4.

The stability of the NIB-14 medium was also tested at temperatures, 4° C. and 30° C., and normalized to that of the standard base medium 0.5×BHI. The data indicate that NIB-14 remains stable at both 4° C. and 30° C.

Example 9: Phage Infection and Enzyme Activity

Figure 15:
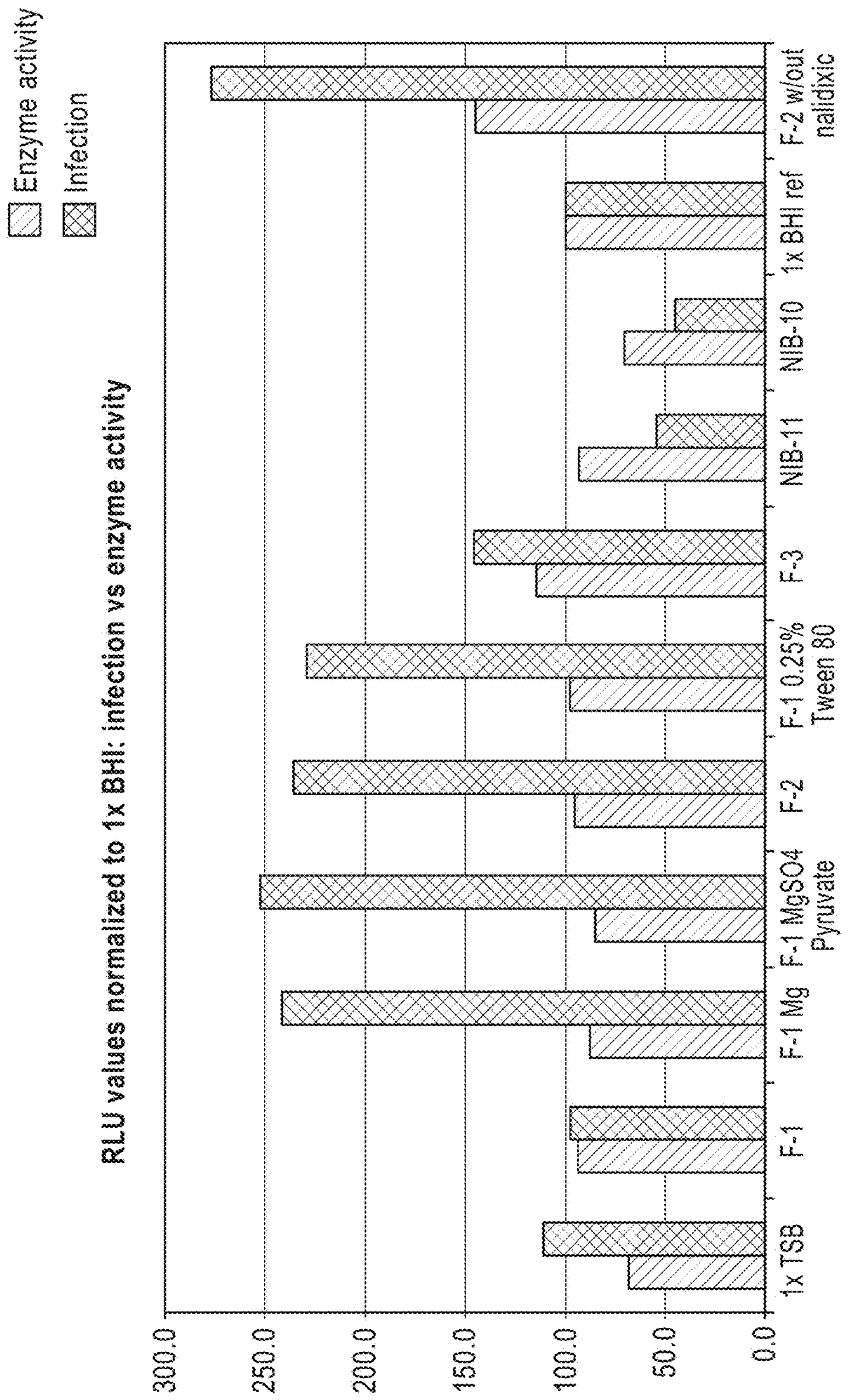
FIG. 15 is a graph that summarizes the findings with respect to enzyme activity and infection rate of bacteria exposed to luciferase encoding phage while in the presence of various iterations of the infection buffer formulations and normalized to RLU output obtained from 1×BHI buffer. The % values are shown on the y-axis.

A systematic comparison of RLU values as a function of additive component was performed on various media formulations. (See FIG. 15). The effects of different additives on both enzymatic activity, as well as infection ability, was measured and compared by way of assessing RLU across the different conditions. The data indicate that the highest infection ability was found in Formulation-1 (with Mg and pyruvate) and Formulation-2 supplemented with HEPES. Specifically, addition of Mg, pyruvate and/or 0.25% TWEEN®-80 had a large impact in increasing infection ability.

While large gains were found in the infection ability with the additions listed above, modest differences were observed with regard to promoting enzymatic activity by way of additives to the formulations.

Example 10: Effects of Media Formulation on Lower Limit of Detection Assays

Figure 16:
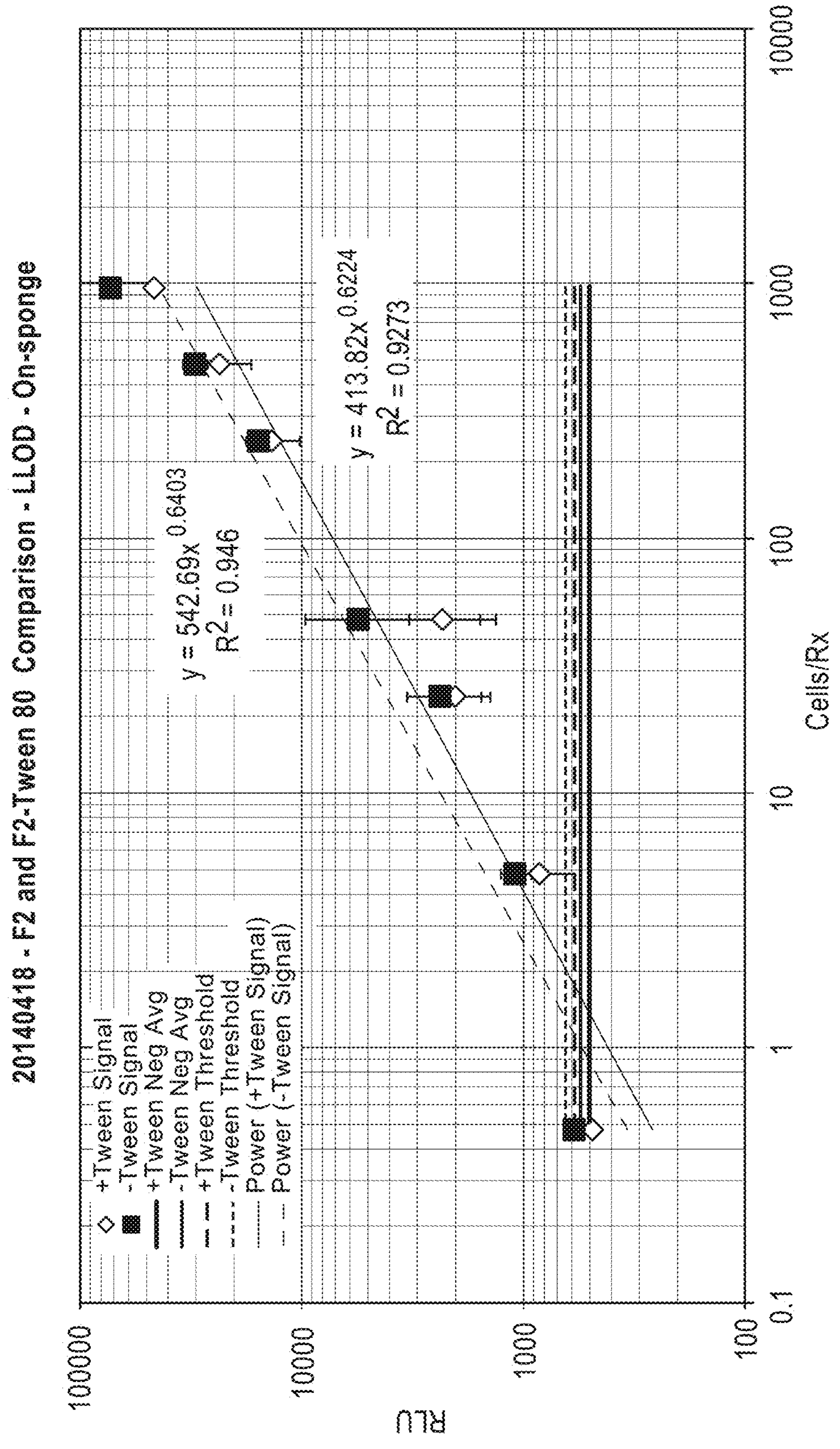
FIG. 16 is a graph that depicts the results of a lower limit of detection assay in which Formulation-2 (NIB-12) is used as the infection buffer either alone or with the addition of TWEEN®-80. The bacteria were exposed in the presence of either of these infection buffers to luciferase encoding phage, followed by detection of RLU. RLU values are shown on the y-axis.

The influence of media formulation on the ability to detect small quantities of cells was assessed by performing lower limit of detection assays (also referred to herein as "LLOD"). For these experiments, two variations of Formulation-2 were assessed (see Table 3). The two conditions tested included either the standard Formulation-2 (see Table 3), or the standard Formulation-2 containing 0.25% of TWEEN®-80. For these experiments, stressed 1554 bacterial cells were collected on sponges and incubated with the appropriate formulation medium. Cells were titrated over a range of values in order to have a graphical output in the LLOD assay ranging from 1 cell to 1000 cells. In the two conditions measured, the standard Formulation-2 (NIB-12) performed better in terms of detection sensitivity when compared with the standard formulation containing 0.25% TWEEN®-80. (See FIG. 16).

Example 11: Use of NIB-14 in the Presence of Varying Amounts of Sanitizers

The NIB-14 formulation included the use of neutralizers (e.g. TWEEN®-80 and lecithin) meant to play a role in reducing the effects of remnant amounts of sanitizers in a sample. As such, NIB-14 was shown to allow for high amounts of infection and subsequent signal stability. (See Example 8). Subsequent assays, meant to ascertain the levels of protection provided by the NIB-14 formulation towards various kinds remnant sanitizer samples were performed.

For these assays, the following were taken into account: (i) evaluation of whether the products glow on their own (i.e. in the absence of cells, phage and/or enzyme), (ii) evaluation of the effect of sanitizing chemicals on NanoGlo substrate (in the absence of cells, phage and/or enzyme), (iii) evaluation of the role that NIB-14 plays in the neutralization of remnant sanitizing chemicals by comparison of the effects obtained by the addition of NIB-14 versus those of the base bacterial growth medium, Letheen formulated to neutralize quaternary ammonium compounds. These assays incorporated the evaluation of the deleterious effects that the sanitizing compounds have at either (i) the point of phage infection, (ii) enzymatic activity, or (iii) direct effect on the NanoGlo luciferin substrate. To determine the effect of the sanitizing chemicals on phage infection, the 1893 cell-type was used at a density of 900 cells per well Bill basal medium, and further incubated with serially diluted (into either NIB-14 or Letheen buffer) sanitizing chemicals for 30 minutes. Following the 30 minute incubation period, the luciferase marker containing phage was added in BHI medium, and the samples were further allowed to incubate for an additional 3 hours at 30° C. The enzyme was then detected by the addition of the NanoGlo luciferin substrate and luminescence measurement. In another variant of this assay, meant to ascertain the remnant sanitizer chemical interaction with the enzymatic activity, the sanitizer chemicals were added to the enzyme only in either NIB-14 or in Letheen for 3 hours at 30° C. Another variant of this assay involved the direct incubation of the sterilization chemical with the NanoGlo luciferin substrate in the absence of either cells, phage or enzyme. In another version of this assay, the sanitizer chemicals were added at various time intervals (e.g. 5 min to 120 min) directly to the NIB-14 or to the Letheen, followed by the addition of cells and phage and incubated for 3 hours at 30° C.

Control assays revealed that there were no false positive luminescence signals in the absence of the NanoGlo luciferase substrate.

Figure 17A:
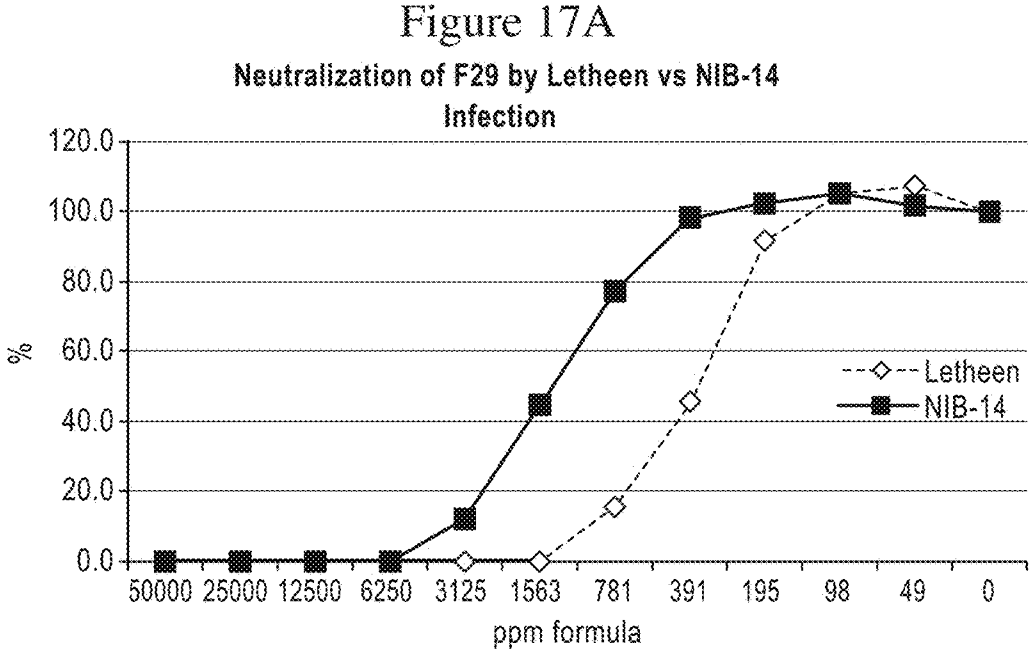
FIGS. 17A-17D are a series of graphs and a table that depict the effects of the NIB-14 infection buffer or a base buffer, Letheen, in the presence of various concentrations of the F29 sanitizing solution containing quaternary ammonium compounds. Bacteria were exposed to the different concentrations of the F29 solution for 30 minutes preceding the luciferase encoding phage infection step. The enzyme was also exposed to different concentrations of the F29 solution during the enzymatic activity test. RLU values were then collected.
Figure 17B:
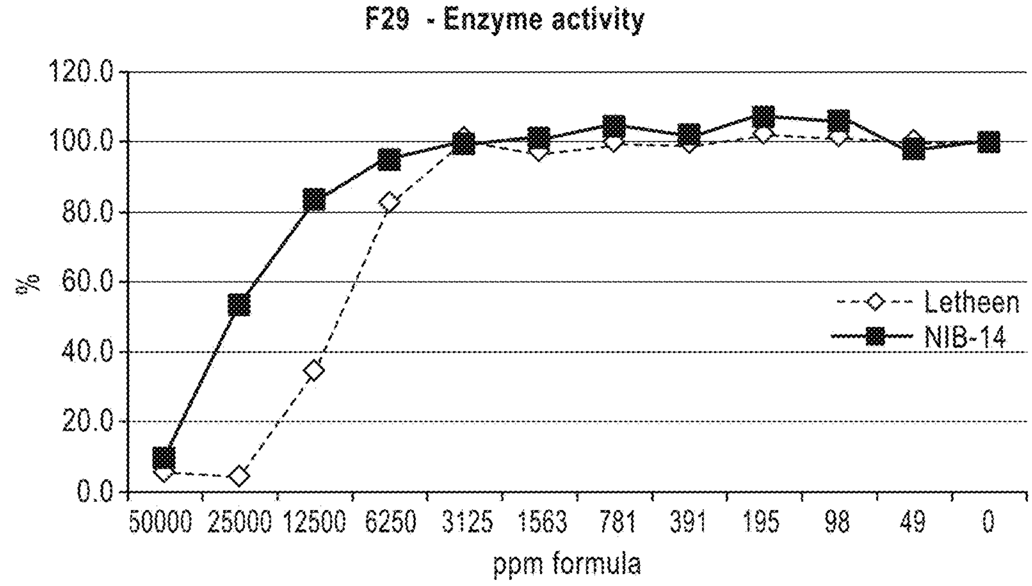
Figures 17C, 17D:
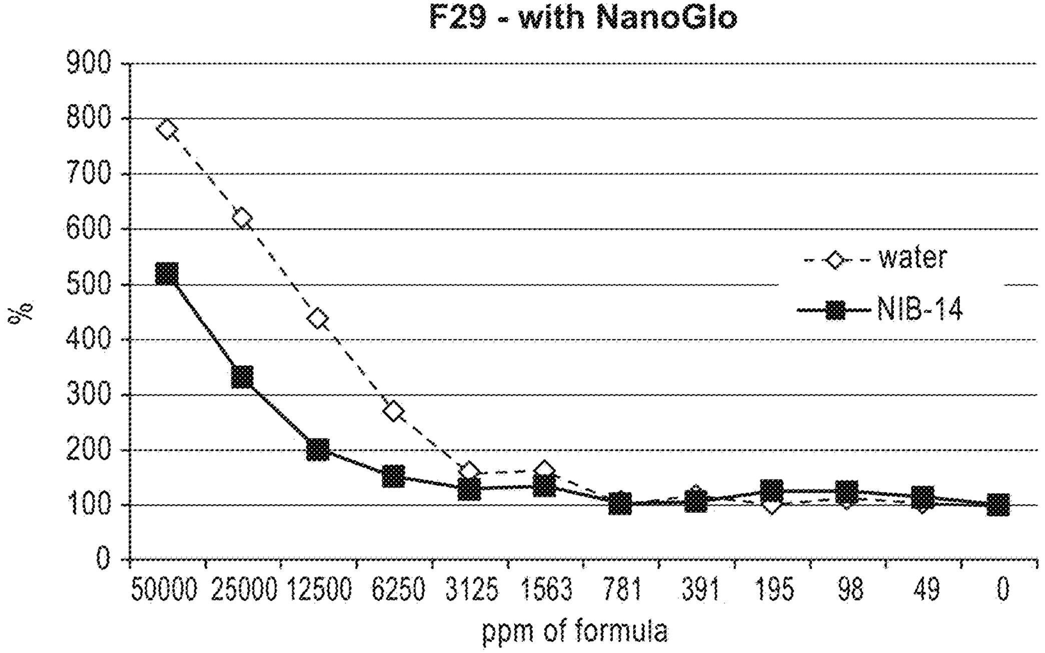

The sanitizer solution, F29, which contains quaternary ammonium salts, was diluted to a final concentration of 0.26%, for a total quaternary ammonium salt concentration of approximately 300 ppm for use in these assays. The recommended usage amounts of F29 for cleaning purposes is 150 ppm of the active ingredient for a 3 minute duration of direct contact on non-food surfaces, and 400-800 ppm in entryways. The assays indicate that both the infection ability and the enzymatic activity are protected by the use of the NIB-14 medium in comparison to the Letheen medium. (See FIGS. 17A-17D). Greater than 20% phage infection rate was retained in exposures of up to 2600 ppm of F29, and enzymatic activity of near 100% was maintained in exposures of up to 2600 ppm of F29 during incubation with the NIB-14. (See FIGS. 17A and 17B, respectively). The effect of incubating different amounts of the F29 sanitizer with the NanoGlo substrate also indicated that the addition of NIB-14 in the assays had a beneficial protective effect on preserving the NanoGlo substrate, when compared to water. (See FIG. 17C). A summary of the findings indicates that the addition of NIB-14 is beneficial at the phage infection step, the enzymatic step, and also provides protection of the NanoGlo substrate. (See FIG. 17D).

Another sanitizer used to assess the protective ability of NIB-14 was Quorum Clear. The Quorum Clear sanitizer contains quaternary ammonium salts. The recommended usage concentration for Quorum Clear is a 3% solution. Addition of the NIB-14 medium was able to preserve up to 50% phage infection ability and enzyme activity at concentrations of Quorum Clear of up to 2.0% and 3.0%, respectively. NIB-14 was also able to provide protection to the NanoGlo substrate during exposures to Quorum Clear.

Another commonly used sanitizer component that was tested in the microbial detection system assays was hydrogen peroxide ($H_2O_2$). As in the previously described assays, the protective ability of NIB-14 was determined in situations where various concentrations of the sanitizing component were added either during the phage infection step, the enzymatic activity step, or to the NanoGlo substrate. The data indicate that NIB-14 provides protection to peroxide presence in comparison to Letheen. (See FIGS. 17A, 17B and 17D). The data do not indicate protection by NIB-14 to the NanoGlo substrate. (See FIG. 17C). However, there are no deleterious effects to the NanoGlo substrate during exposure to peroxide at concentrations recommended for sanitizing (i.e. 500 ppm).

Boost FT was another sanitizer used in the microbial detection system assays to determine the protective effects of NIB-14 in the microbial detection assays. Boost FT contains a combination of quaternary ammonium salts, peroxide ($H_2O_2$), and EDTA at elevated pH. The recommended concentration of use for Boost FT is 0.7% concentration of the active ingredient. Addition of the NIB-14 medium was able to preserve up to 50% phage infection ability and enzyme activity at concentrations of Boost FT of up to 0.07% and greater than 0.7%, respectively. However, the increase noted in enzymatic activity may largely be due to oxidization of the NanoGlo substrate. The need for additional neutralization of peroxides was demonstrated.

Figure 18A:
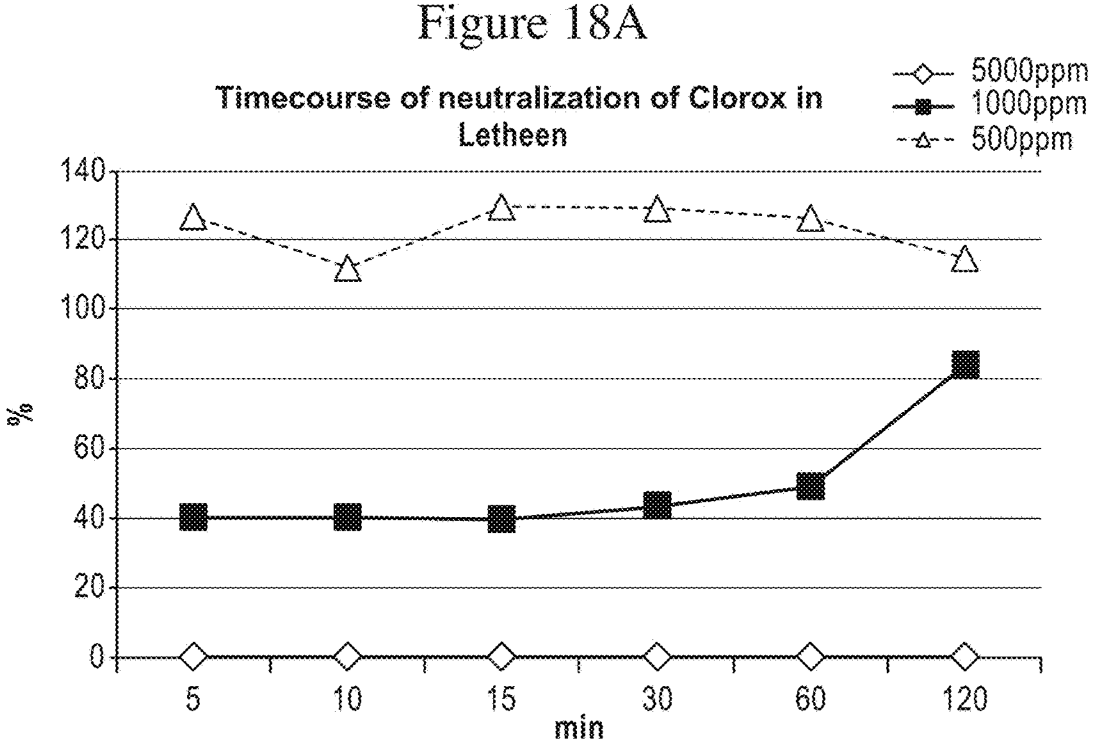
FIGS. 18A and 18B are a series of graphs that depict the effects of incubating Letheen or NIB-14 over time with the sanitizing solution, Clorox, prior to the downstream effects on the luciferase encoding phage infection assay. Assay time points for this study included 5, 10, 15, 30, 60 and 120 minutes. Three concentrations of Clorox were assessed over this time, including 500 ppm, 1000 ppm, and 5000 ppm.
Figure 18B:
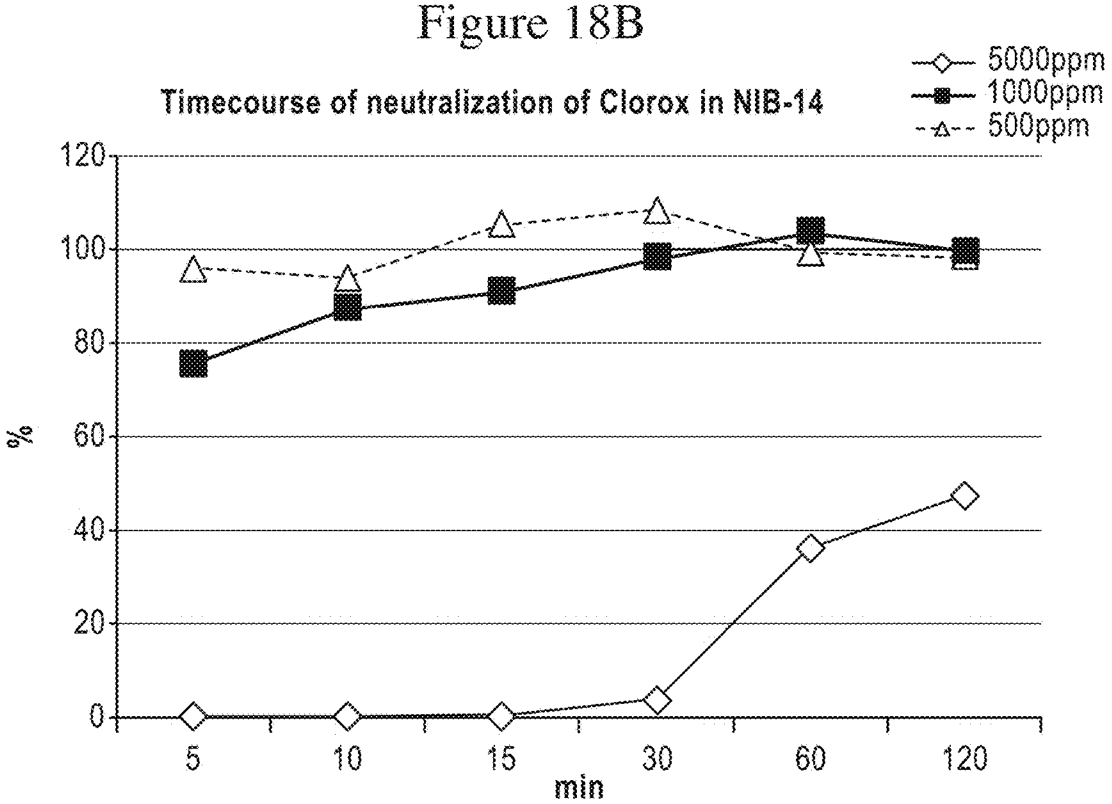

The effects of another commonly used sanitizer, Clorox, and the protective benefits of NIB-14 medium on the microbial detection system in these conditions were assayed. The data indicated that at concentrations of greater than 400 ppm of hypochlorite there was no infection signals detected. Likewise, enzymatic activity was also negatively affected in media tested, NIB-14 and Letheen. The hypochlorite concentrations that were tested did not negatively impact the NanoGlo substrate. An additional assay performed with the Clorox sanitizer was a time-course assay in which RLU was measured following incubation of Clorox for defined periods of time in either Letheen or in NIB-14, followed by addition of this solution to the microbial detection system assays. The data show that NIB-14 has a strong neutralization capacity in terms of allowing higher RLU activity with progressive time in Clorox. (See FIGS. 18A and 18B).

Further investigation into the addition of oxygen scavengers into the NIB-14 formulation was assessed. Data acquired from the microbial detection system assays demonstrated that the addition of either 2 mM sodium metabisulfite or 0.05% sodium thiosulfate reduced the oxidizing effect of peroxide in the assay. The oxidizing effect of the peroxide found in Boost FT was lowered in the assays with either neutralizer when the effect on substrate signal alone was assessed. The addition of 2 mM sodium metabisulfite was especially beneficial in lowering the signal at the highest Boost FT concentrations that were caused by peroxides when enzyme and infection activity were tested.

Example 12: Comparison of Infection Buffers in Stressed Cell Infection Assays

A direct comparison of infection and enzymatic activity using stressed cells infected with recombinant luciferase encoding phage was performed utilizing NIB buffers. These tests measured the direct performance of NIB-10*, NIB-12, and NIB-14 with regard to enhancing either enzymatic activity or infection rate. The base buffer, 1×BHI, was used as a comparison buffer for these tests. For the stressed cell assays, bacterial cells were purposefully stressed by way of drying for 18 hours on a stainless steel table followed by downstream processing. The effect of the buffers was assessed either during the infection stage or during the enzymatic processing stage. Subsequently, the RLU activity was recorded for each of the buffer conditions.

*NIB-10 is composed of: 1×BHI, 0.5% LiCl, 0.002% nalidixic acid, 0.2% yeast extract, 2 mM CaCl2, 40 mM HEPES, pH 7.4, 1 mM sodium metabisulfite, 0.1% sodium thiosulfate, 0.5% TWEEN®-80, and 0.1% lecithin.

Figure 19:
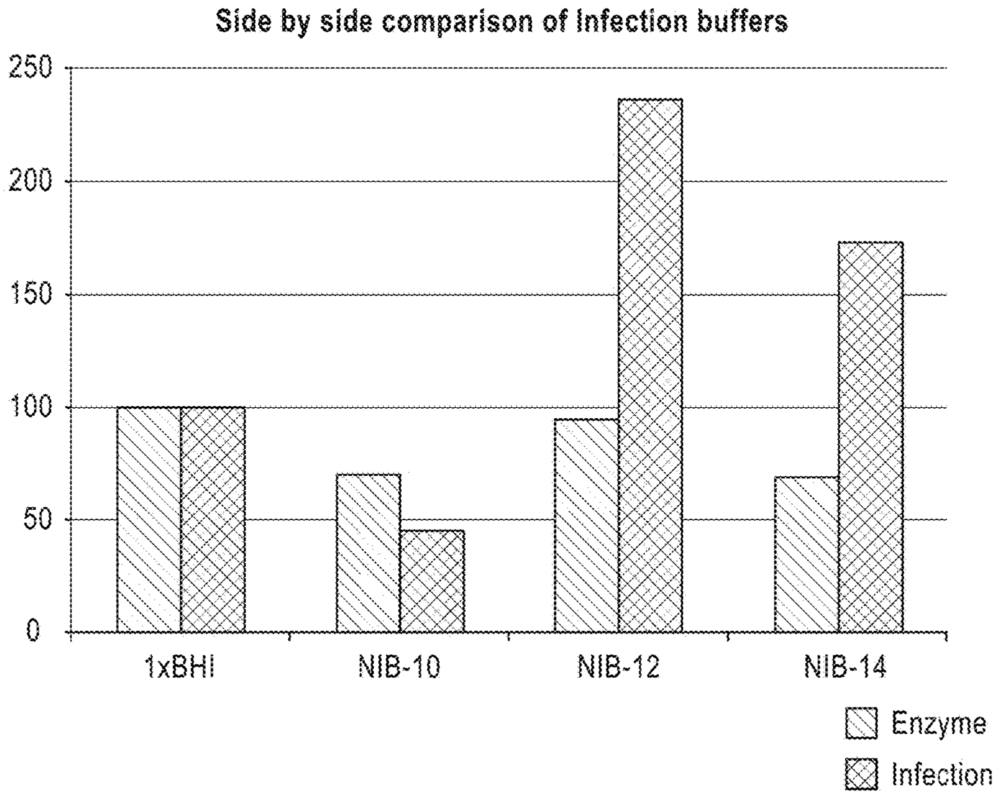
FIG. 19 is a graph that depicts the results of a series of experiments in which stressed cells (i.e. cells that were dried for 18 hours on a stainless steel table before further processing) were incubated with various NIB infection buffers, NIB-10, NIB-12 or NIB-14. As a control for the experiments, 1×BHI was used. The stressed cells were exposed in each of these buffers to luciferase encoding phage, and subsequently followed by assessing the RLU for each condition. The enzyme activity was also assessed in the presence of each buffer iteration.

The data indicate that NIB-12 (see Table 3) had the greatest beneficial effect during the infection step, as indicated by the highest RLU values among all of the buffers tested. (See FIG. 9). The second most beneficial buffer in enhancing the infection step was NIB-14. This buffer offers instead higher neutralization power against residual sanitizers. The influence of the buffers was not as pronounced during the enzymatic activity phase; however, of the NIB buffers tested, NIB-12, supported the most enzymatic activity, followed by the similar enzymatic activity rates of both NIB-10 and NIB-14 as determined by RLU output. (See FIG. 19).

Figure 20A:
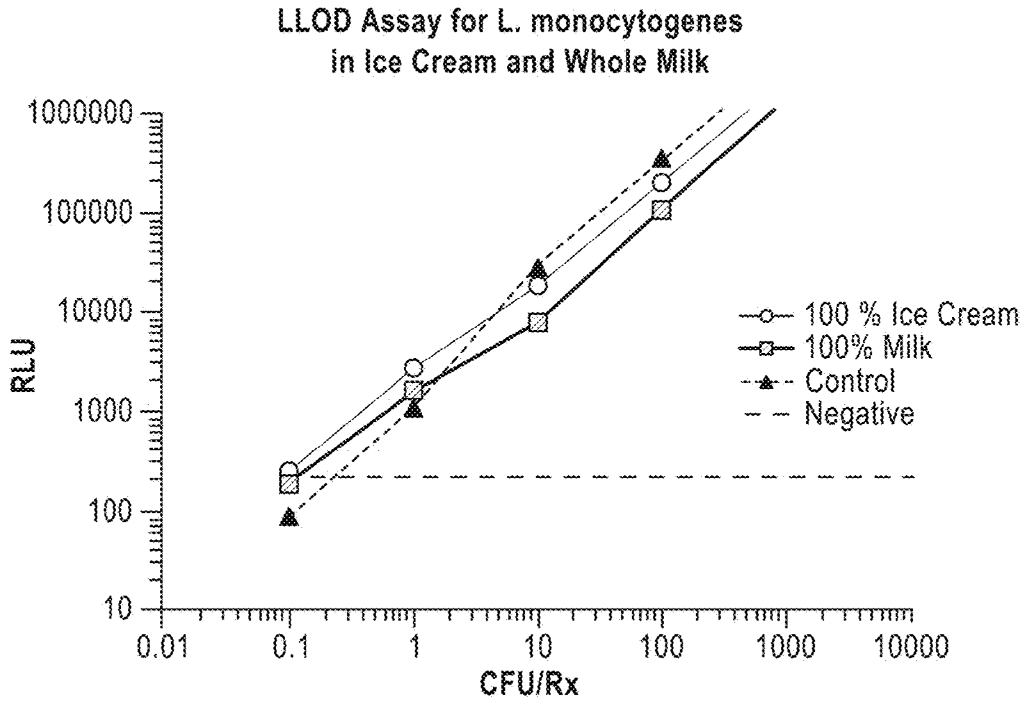
FIGS. 20A-20B are a series of graphs that depict lower limit of detection assays (also referred to herein as "LLOD") utilizing *L. monocytogenes*, incubated in various foods. LLOD assays were performed with *L. monocytogenes* incubated in 100% (full fat) ice cream and 100% (full fat) milk (FIG. 20A) or NIB-14 (as a reference), or in Demi-Fraser broth incubated at 30 C in with raw ground beef, deli turkey, guacamole and queso fresco (FIG. 20B) for 16 hours. For *L. monocytogenes* in the presence of raw ground beef, deli turkey, guacamole or queso fresco, the sample was incubated in an equal volume of NIB-14 infection buffer and luciferase encoding phage used for the infection of the microbes in the sample.

Example 13; Lower Limit of Detection Assays in the Detection of Microbes in Food Lower limit of detection assays ("LLOD") were performed with whole milk that had received a defined amount of *Listeria monocytogenes*. For these assays, 25 mL of 100% (full fat) whole milk, 25 mL of NIB-14 infection buffer (see Table 4), and $4.5\times10^7$ pfu/mL recombinant marker encoding phage were used. The recombinant phage had luciferase as the recombinant marker. The results of the LLOD assays revealed that within 2 hours of the addition of *L. monocytogenes* to the food sample there was detectable signal in the assays, wherein up to 50 cells in a 50 mL sample was detectable. (See FIG. 20A). These data indicate that up to 50 CFU of *L. monocytogenes* was detectable in the assays.

Figure 20B:
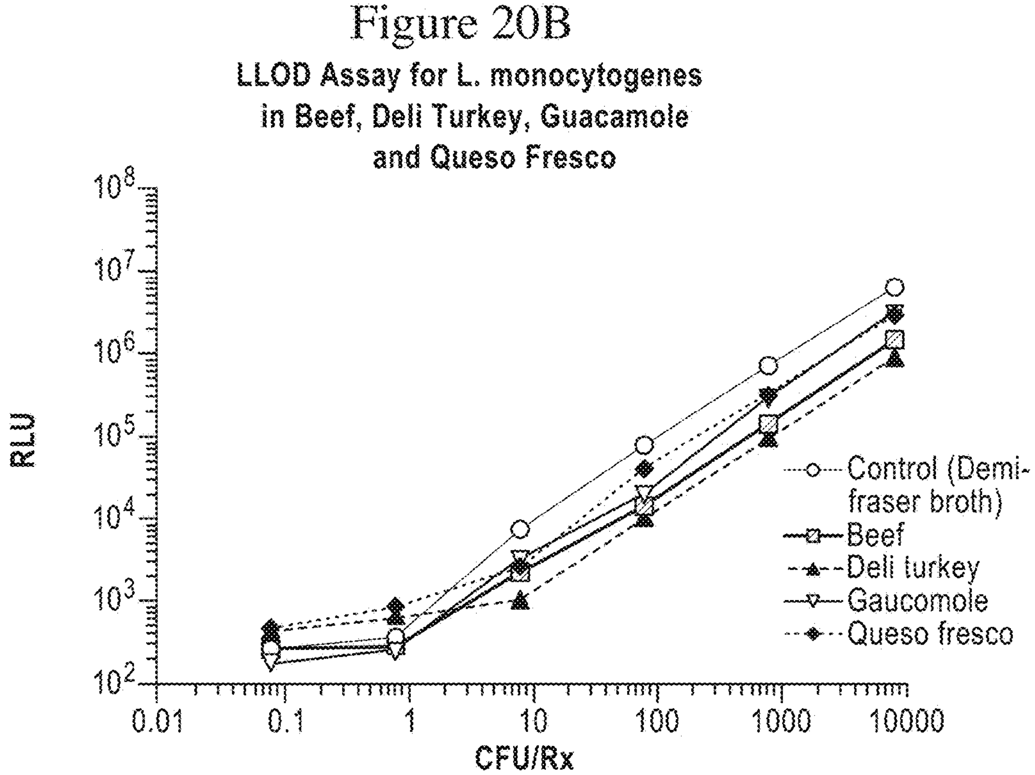

LLOD assays for the detection of *L. monocytogenes* were also performed with other foods including raw ground beef, deli turkey, guacamole and queso fresco. (See FIG. 20B). The data from the LLOD assays with these foods also indicate that the target microbe was detectable at CFUs of between 1 and 10.

Example 14: Time Course Detection Assays for Microbes in Food

Assays to establish the amount of time before the detection of defined amounts of *L. monocytogenes* is possible were performed with food samples of turkey, guacamole, queso fresco, raw ground beef, potato salad, smoked salmon, and sour cream. For these assays, *L. monocytogenes* was added to the food sample, followed by waiting for a defined amount of time prior to adding the recombinant luciferase encoding phage for at least 2 hours, and subsequent assessment of the luciferin signal in the microbial detection assay. Depending on the kind of food in the assay, different dilutions of food matrix to incubation buffer were performed. The dilutions for the different foods assessed were: guacamole 1:3, ground beef (80/20) 1:3, whole milk 1:1, ice cream 1:1, queso fresco 1:1 and deli turkey 1:3. For example, for the detection of *L. monocytogenes* in deli turkey samples, 25 g of food matrix was spiked with either 2 or 20 CFU and then incubated with 75 mL NIB-14. Following the incubation, a sample of the NIB-14 liquid was incubated with the recombinant phage for 3 hours.

Figure 21A:
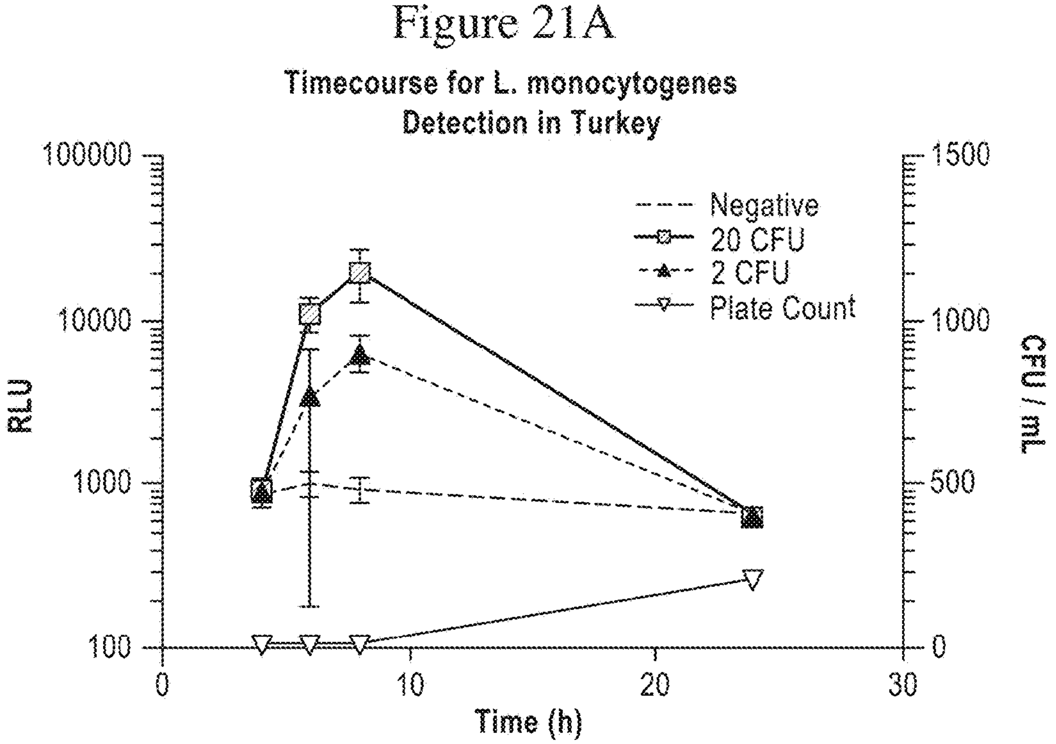
FIGS. 21A-21D are a series of graphs that depict the time course of *L. monocytogenes* detection in various food samples. *L. monocytogenes* was added to the food samples for defined amounts of time, followed by infection with a recombinant, luciferase encoding phage and subsequent detection of the luciferin signal. The food samples used in the assays included turkey (FIG. 21A), queso fresco (FIG. 21B), guacamole (FIG. 21C) and beef (FIG. 21D). RLU values are on the y axis.
Figure 21B:
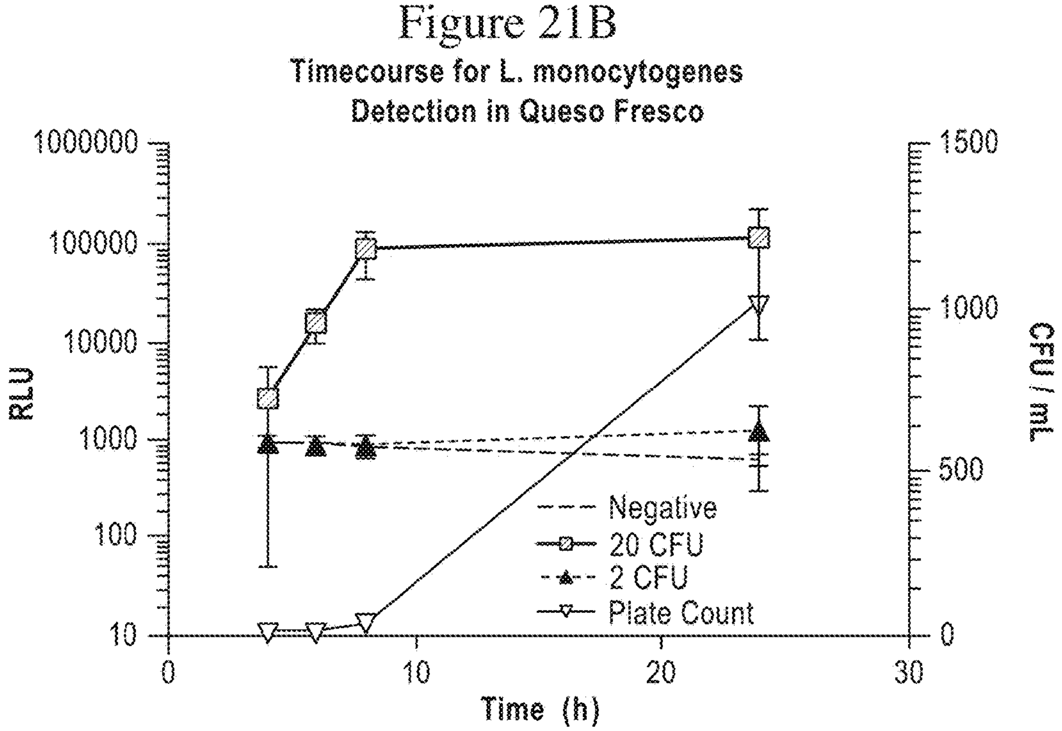
Figure 21C:
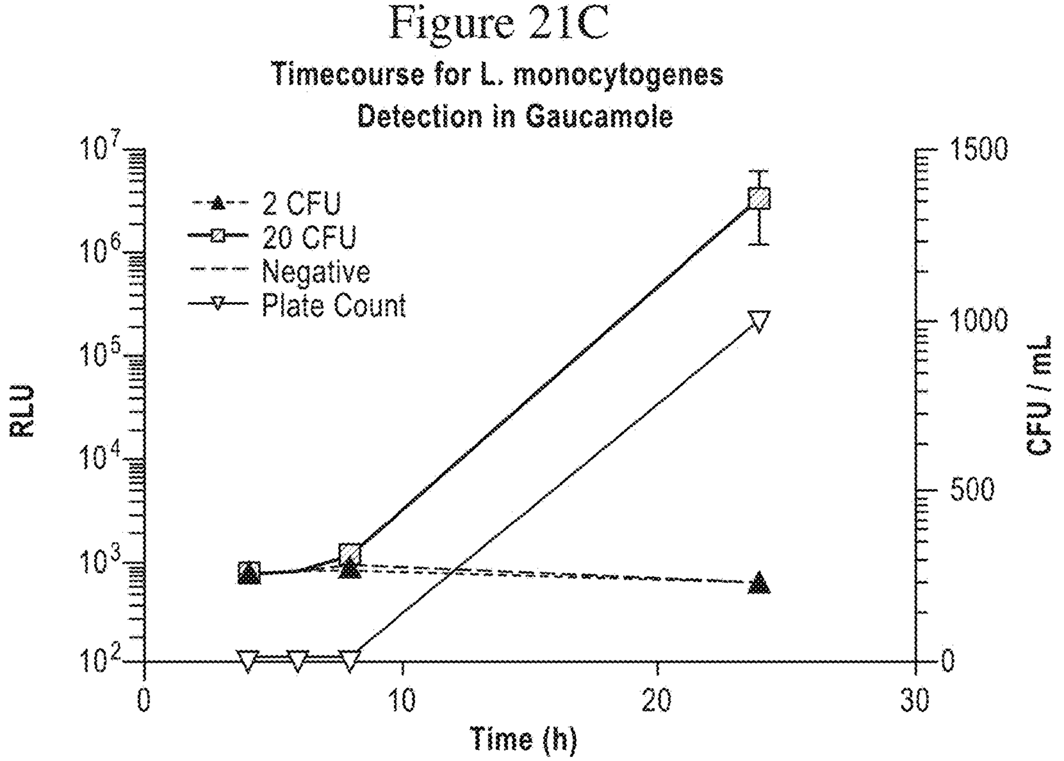
Figure 21D:
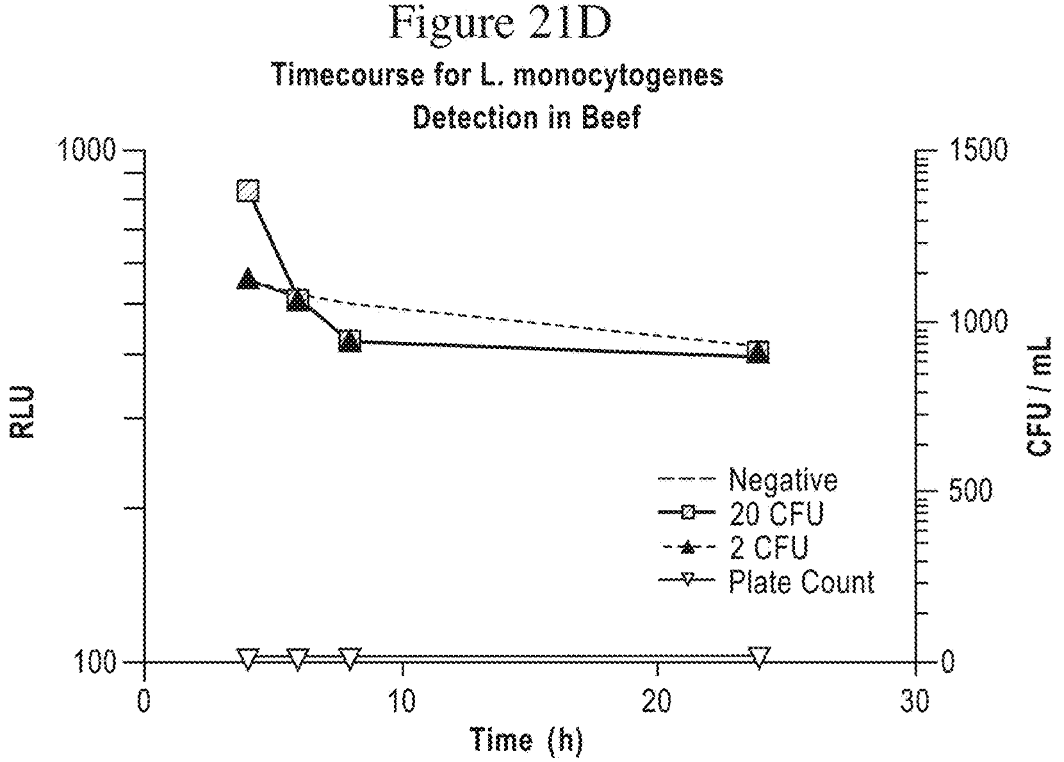

The results indicated that the detection of *L. monocytogenes* was found after 6 hours at both the 2 and 20 CFU conditions in the deli turkey food samples (FIG. 21A), after 4 hours for the 20 CFU condition and 24 hours for the 2 CFU condition in the queso fresco samples (FIG. 21B), after 8 hours in the 20 CFU condition for the guacamole samples (FIG. 21C), and there was no detectable *L. monocytogenes* found at either the 2 or the 20 CFU conditions for the beef samples (FIG. 21D). (See FIGS. 21A-D).

A comparison between the amounts of time before the detection of *L. monocytogenes* and *L. innocua* is presented in FIG. 22A-M. For these experiments a four hour resuscitation/enrichment of the bacteria was performed followed by a three hour incubation with the luciferase encoding phage. The data indicate that the detection of *L. monocytogenes* is possible at lower CFU values when compared to the detection of *L. innocua*. As is indicated by the graphs, both bacteria species are detectable with the assay system. (See FIG. 22 A-M).

Another time course to detection was performed using *L. monocytogenes* and *L. innocua* incubated in either pepperoni or spinach. (See FIG. 23A-B). For these experiments a four hour resuscitation/enrichment of the bacteria was performed followed by a three hour incubation with the luciferase encoding phage. The data indicate there are differences with regard to the time of incubation before which the bacteria are detected in either the spinach or the pepperoni. However, both bacterial species were detectable with the assay system by 6 hours of incubation.

A time course to detection assay was also performed using three species of *Listeria, L. seeligeri, L. innocua*, and *L. monocytogenes* incubated in turkey, queso, and in guacamole. (See FIG. 24A-C). The data indicate that the detection of the various species of *Listeria* is dependent on food matrix type (e.g. shorter time to detection in Turkey) and the *Listeria* species.

Another time course to detection assay was performed utilizing various dilutions of food matrix (American cheese, spinach, pepperoni and ground chicken) to incubation buffer. (See FIG. 25A-D). For these assays, *L. monocytogenes* was incubated for defined amounts of time (as illustrated in the graphs in FIG. 25A-D) with dilutions of food matrix to the incubation buffer indicated in parentheses within FIG. 25. The data indicate that food matrix, as well as the dilution of matrix to incubation buffer, has a role in the time course to detection of the *Listeria* species in these assays.

Example 15: *Listeria* Panel

A bacterial strain panel comprising a diverse combination of *Listeria* species and subspecies was selected for characterization of *Listeria* phages. The panel comprises strains that have been isolated from various geographic and environmental niches including food processing plants and food retail locations. Special consideration was given to obtain bacterial strains from food processing environments with sufficient geographic separation to maximize natural variation within the bacterial strain panel.

The panel as assembled initially contained 272 *Listeria* isolates and represents the four major species of *Listeria* (*L. monocytogenes, L. innocua, L. welshmeri* and *L. seelingri*) (Table 13). Within each species the panel comprises representative isolates of various subspecies to ensure sufficient depth of coverage to allow for meaningful extrapolation of the data to the subspecies in general. The selection of strains for the bacterial panel were based on the prevalence of particular strains within the food environment and associated with human disease. Environmental screening of retail food stores used allelotyping to identify the most commonly identified *Listeria* subspecies and identified that certain allelotypes were often highly represented among the population of species identified. (Williams, S. K. et al., J Food Prot 74, 63-77 (2011); Sauders, B. D. et al., Appl Environ Microbiol 78, 4420-4433 (2012).) Ten (10) *L. monocytogenes* strains from each of the most common ribotypes represented from isolates from food and human disease were selected for the collection. These populations are largely overlapping and have a strong correlation in prevalence and, therefore, represent the strains most useful to identify in food processing plants. When looking at breadth of coverage of *L. monocytogenes* strains based on ribotypes isolated in human disease and food processing plants, the panel as constructed represents ~86% and 91% coverage, respectively. The purpose for selecting 10 strains of each *L. monocytogenes* ribotype was to allow for the identification of natural variation within a group to ensure a reasonably complete coverage of the *L. monocytogenes* species.

To expand beyond *L. monocytogenes* and cover other species within the genus additional species and subspecies variation was considered to select further strains for the panel. Again, focus was placed on the species and subspecies that are commonly identified in food processing plants. Ten (10) isolates representing each of the most common allelotypes of *L. welshmeri, L. innocua* and *L. selelingri* were selected. The panel as constructed covers 96% of the *L. innocua,* 98% of the *L. selelingri*, and 100% of the *L. welshmeri* ribotypes identified by Saunders et al. and provides an accurate representation of the *Listeria* genus. The *Listeria* host panel as assembled thus serves as a tool for the analysis of the host range of any bacteriophage against the *Listeria* genus. Accordingly, this panel can be used to define target bacteria of any given phage.

The genus, species, and subspecies of the members of the panel are provided in Table 13.

TABLE 13

| Identifier | Strain Name | Genus/Species | Subspecies |
|---|---|---|---|
| NP1900 | FSL R8-5085 | *Listeria innocua* | sig B allelotype 11 |
| NP1901 | FSL R8-5091 | *Listeria innocua* | sig B allelotype 11 |
| NP1902 | FSL R8-5098 | *Listeria innocua* | sig B allelotype 11 |
| NP1903 | FSL R8-5255 | *Listeria innocua* | sig B allelotype 11 |
| NP1904 | FSL R8-5293 | *Listeria innocua* | sig B allelotype 11 |
| NP1905 | FSL R8-5295 | *Listeria innocua* | sig B allelotype 11 |
| NP1906 | FSL R8-5306 | *Listeria innocua* | sig B allelotype 11 |
| NP1907 | FSL R8-5440 | *Listeria innocua* | sig B allelotype 11 |
| NP1908 | FSL R8-5442 | *Listeria innocua* | sig B allelotype 11 |
| NP1909 | FSL R8-5448 | *Listeria innocua* | sig B allelotype 11 |

TABLE 13-continued

| Identifier | Strain Name | Genus/Species | Subspecies |
|---|---|---|---|
| NP1912 | FSL R8-7061 | *Listeria innocua* | sig B allelotype 22 |
| NP1959 | FSL S4-158 | *Listeria innocua* | sig B allelotype 22 |
| NP1960 | FSL S10-784 | *Listeria innocua* | sig B allelotype 22 |
| NP1961 | FSL F6-1168 | *Listeria innocua* | sig B allelotype 22 |
| NP1962 | FSL R8-5961 | *Listeria innocua* | sig B allelotype 22 |
| NP1963 | FSL R8-6922 | *Listeria innocua* | sig B allelotype 22 |
| NP1964 | FSL R8-7352 | *Listeria innocua* | sig B allelotype 22 |
| NP1965 | FSL R8-5598 | *Listeria innocua* | sig B allelotype 22 |
| NP1966 | FSL R8-6733 | *Listeria innocua* | sig B allelotype 22 |
| NP1967 | FSL R8-5942 | *Listeria innocua* | sig B allelotype 22 |
| NP1915 | FSL R8-7548 | *Listeria innocua* | sig B allelotype 37 |
| NP1997 | FSL R8-5764 | *Listeria innocua* | sig B allelotype 37 |
| NP1998 | FSL R8-5802 | *Listeria innocua* | sig B allelotype 37 |
| NP1999 | FSL R8-6012 | *Listeria innocua* | sig B allelotype 37 |
| NP2000 | FSL R8-6355 | *Listeria innocua* | sig B allelotype 37 |
| NP2001 | FSL R8-6369 | *Listeria innocua* | sig B allelotype 37 |
| NP2002 | FSL R8-6476 | *Listeria innocua* | sig B allelotype 37 |
| NP2003 | FSL R8-7175 | *Listeria innocua* | sig B allelotype 37 |
| NP2004 | FSL R8-6888 | *Listeria innocua* | sig B allelotype 37 |
| NP2005 | FSL R8-6672 | *Listeria innocua* | sig B allelotype 37 |
| NP1916 | FSL R8-6667 | *Listeria innocua* | sig B allelotype 56 |
| NP2006 | FSL S10-1311 | *Listeria innocua* | sig B allelotype 56 |
| NP2007 | FSL F6-1159 | *Listeria innocua* | sig B allelotype 56 |
| NP2008 | FSL F6-1126 | *Listeria innocua* | sig B allelotype 56 |
| NP2009 | FSL S6-120 | *Listeria innocua* | sig B allelotype 56 |
| NP2010 | FSL R8-5594 | *Listeria innocua* | sig B allelotype 56 |
| NP2011 | FSL R8-7181 | *Listeria innocua* | sig B allelotype 56 |
| NP2012 | FSL R2-632 | *Listeria innocua* | sig B allelotype 56 |
| NP2013 | FSL L3-851 | *Listeria innocua* | sig B allelotype 56 |
| NP2014 | FSL S10-1377 | *Listeria innocua* | sig B allelotype 56 |
| NP 1869 | WSLC 3009 | *Listeria ivanovii* | sig B allelotype 73 |
| NP 1840 | FSL J1-208 | *Listeria monocytogenes* | ribotype DUP-10142 |
| NP 1839 | FSL F6-367 | *Listeria monocytogenes* | ribotype DUP-1030A |
| NP2024 | FSL F6-267 | *Listeria monocytogenes* | ribotype DUP-1030A |
| NP2025 | FSL F6-406 | *Listeria monocytogenes* | ribotype DUP-1030A |
| NP2026 | FSL H5-592 | *Listeria monocytogenes* | ribotype DUP-1030A |
| NP2027 | FSL H1-219 | *Listeria monocytogenes* | ribotype DUP-1030A |
| NP2028 | FSL H1-121 | *Listeria monocytogenes* | ribotype DUP-1030A |
| NP2029 | FSL W3-072 | *Listeria monocytogenes* | ribotype DUP-1030A |
| NP2030 | FSL N4-239 | *Listeria monocytogenes* | ribotype DUP-1030A |
| NP2031 | FSL N3-293 | *Listeria monocytogenes* | ribotype DUP-1030A |
| NP2032 | FSL F3-319 | *Listeria monocytogenes* | ribotype DUP-1030A |
| NP1879 | FSL N4-221 | *Listeria monocytogenes* | ribotype DUP-1030B |
| NP2033 | FSL F2-738 | *Listeria monocytogenes* | ribotype DUP-1030B |
| NP2034 | FSL N3-881 | *Listeria monocytogenes* | ribotype DUP-1030B |
| NP2035 | FSL N4-048 | *Listeria monocytogenes* | ribotype DUP-1030B |
| NP2036 | FSL N4-696 | *Listeria monocytogenes* | ribotype DUP-1030B |
| NP2037 | FSL N4-242 | *Listeria monocytogenes* | ribotype DUP-1030B |
| NP2038 | FSL H4-364 | *Listeria monocytogenes* | ribotype DUP-1030B |
| NP2039 | FSL H4-147 | *Listeria monocytogenes* | ribotype DUP-1030B |
| NP2040 | FSL H4-946 | *Listeria monocytogenes* | ribotype DUP-1030B |
| NP2041 | FSL S4-461 | *Listeria monocytogenes* | ribotype DUP-1030B |
| NP2042 | FSL F6-206 | *Listeria monocytogenes* | ribotype DUP-1038B |
| NP2043 | FSL F6-224 | *Listeria monocytogenes* | ribotype DUP-1038B |

TABLE 13-continued

| Identifier | Strain Name | Genus/Species | Subspecies |
|---|---|---|---|
| NP2044 | FSL L3-739 | *Listeria monocytogenes* | ribotype DUP-1038B |
| NP2045 | FSL N3-008 | *Listeria monocytogenes* | ribotype DUP-1038B |
| NP2046 | FSL N3-022 | *Listeria monocytogenes* | ribotype DUP-1038B |
| NP2047 | FSL J1-108 | *Listeria monocytogenes* | ribotype DUP-1038B |
| NP2048 | FSL J1-119 | *Listeria monocytogenes* | ribotype DUP-1038B |
| NP2049 | FSL C1-122 | *Listeria monocytogenes* | ribotype DUP-1038B |
| NP2050 | FSL J1-126 | *Listeria monocytogenes* | ribotype DUP-1038B |
| NP1880 | FSL L3-159 | *Listeria monocytogenes* | ribotype DUP-1039A |
| NP2051 | FSL F3-285 | *Listeria monocytogenes* | ribotype DUP-1039A |
| NP2052 | FSL R6-288 | *Listeria monocytogenes* | ribotype DUP-1039A |
| NP2053 | FSL N1-021 | *Listeria monocytogenes* | ribotype DUP-1039A |
| NP2054 | FSL H1-208 | *Listeria monocytogenes* | ribotype DUP-1039A |
| NP2055 | FSL N3-034 | *Listeria monocytogenes* | ribotype DUP-1039A |
| NP2056 | FSL L5-072 | *Listeria monocytogenes* | ribotype DUP-1039A |
| NP2057 | FSL S6-131 | *Listeria monocytogenes* | ribotype DUP-1039A |
| NP2058 | FSL N3-278 | *Listeria monocytogenes* | ribotype DUP-1039A |
| NP2059 | FSL R2-282 | *Listeria monocytogenes* | ribotype DUP-1039A |
| NP1881 | FSL T1-323 | *Listeria monocytogenes* | ribotype DUP-1039B |
| NP2060 | FSL H5-770 | *Listeria monocytogenes* | ribotype DUP-1039B |
| NP2061 | FSL F6-207 | *Listeria monocytogenes* | ribotype DUP-1039B |
| NP2062 | FSL F6-236 | *Listeria monocytogenes* | ribotype DUP-1039B |
| NP2063 | FSL H5-795 | *Listeria monocytogenes* | ribotype DUP-1039B |
| NP2064 | FSL N3-246 | *Listeria monocytogenes* | ribotype DUP-1039B |
| NP2065 | FSL R2-062 | *Listeria monocytogenes* | ribotype DUP-1039B |
| NP2066 | FSL R2-437 | *Listeria monocytogenes* | ribotype DUP-1039B |
| NP2067 | FSL M1-004 | *Listeria monocytogenes* | ribotype DUP-1039B |
| NP2068 | FSL L4-352 | *Listeria monocytogenes* | ribotype DUP-1039B |
| NP2069 | FSL F6-605 | *Listeria monocytogenes* | ribotype DUP-1039C |
| NP2070 | FSL V1-001 | *Listeria monocytogenes* | ribotype DUP-1039C |
| NP2071 | FSL F6-464 | *Listeria monocytogenes* | ribotype DUP-1039C |
| NP2072 | FSL R8-2748 | *Listeria monocytogenes* | ribotype DUP-1039C |
| NP2073 | FSL R6-908 | *Listeria monocytogenes* | ribotype DUP-1039C |
| NP2074 | FSL L3-802 | *Listeria monocytogenes* | ribotype DUP-1039C |
| NP2075 | FSL F3-056 | *Listeria monocytogenes* | ribotype DUP-1039C |
| NP2076 | FSL J2-020 | *Listeria monocytogenes* | ribotype DUP-1039C |
| NP2077 | FSL S4-914 | *Listeria monocytogenes* | ribotype DUP-1039C |
| NP1882 | FSL H5-725 | *Listeria monocytogenes* | ribotype DUP-1042A |
| NP2078 | FSL F6-467 | *Listeria monocytogenes* | ribotype DUP-1042A |
| NP2079 | FSL F6-655 | *Listeria monocytogenes* | ribotype DUP-1042A |

TABLE 13-continued

| Identifier | Strain Name | Genus/Species | Subspecies |
|---|---|---|---|
| NP2080 | FSL F6-352 | *Listeria monocytogenes* | ribotype DUP-1042A |
| NP2081 | FSL H5-781 | *Listeria monocytogenes* | ribotype DUP-1042A |
| NP2082 | FSL K2-147 | *Listeria monocytogenes* | ribotype DUP-1042A |
| NP2083 | FSL V1-026 | *Listeria monocytogenes* | ribotype DUP-1042A |
| NP2084 | FSL H5-572 | *Listeria monocytogenes* | ribotype DUP-1042A |
| NP2085 | FSL K2-065 | *Listeria monocytogenes* | ribotype DUP-1042A |
| NP2086 | FSL H4-120 | *Listeria monocytogenes* | ribotype DUP-1042A |
| NP2087 | FSL F6-184 | *Listeria monocytogenes* | ribotype DUP-1042B |
| NP2088 | FSL F6-191 | *Listeria monocytogenes* | ribotype DUP-1042B |
| NP2089 | FSL H1-099 | *Listeria monocytogenes* | ribotype DUP-1042B |
| NP2090 | FSL J1-116 | *Listeria monocytogenes* | ribotype DUP-1042B |
| NP2091 | FSL R2-192 | *Listeria monocytogenes* | ribotype DUP-1042B |
| NP2092 | FSL J1-225 | *Listeria monocytogenes* | ribotype DUP-1042B |
| NP2093 | FSL R2-500 | *Listeria monocytogenes* | ribotype DUP-1042B |
| NP2094 | FSL R2-501 | *Listeria monocytogenes* | ribotype DUP-1042B |
| NP2095 | FSL E1-159 | *Listeria monocytogenes* | ribotype DUP-1042B |
| NP2096 | FSL F6-355 | *Listeria monocytogenes* | ribotype DUP-1042C |
| NP2097 | FSL F6-382 | *Listeria monocytogenes* | ribotype DUP-1042C |
| NP2098 | FSL F3-200 | *Listeria monocytogenes* | ribotype DUP-1042C |
| NP2099 | FSL K2-143 | *Listeria monocytogenes* | ribotype DUP-1042C |
| NP2100 | FSL N1-176 | *Listeria monocytogenes* | ribotype DUP-1042C |
| NP2101 | FSL N1-417 | *Listeria monocytogenes* | ribotype DUP-1042C |
| NP2102 | FSL L3-051 | *Listeria monocytogenes* | ribotype DUP-1042C |
| NP2103 | FSL T1-107 | *Listeria monocytogenes* | ribotype DUP-1042C |
| NP2104 | FSL T1-408 | *Listeria monocytogenes* | ribotype DUP-1042C |
| NP1883 | FSL T1-922 | *Listeria monocytogenes* | ribotype DUP-1043A |
| NP2105 | FSL F6-396 | *Listeria monocytogenes* | ribotype DUP-1043A |
| NP2106 | FSL H5-806 | *Listeria monocytogenes* | ribotype DUP-1043A |
| NP2107 | FSL F6-551 | *Listeria monocytogenes* | ribotype DUP-1043A |
| NP2108 | FSL F6-446 | *Listeria monocytogenes* | ribotype DUP-1043A |
| NP2109 | FSL F6-315 | *Listeria monocytogenes* | ribotype DUP-1043A |
| NP2110 | FSL V1-022 | *Listeria monocytogenes* | ribotype DUP-1043A |
| NP2111 | FSL R2-132 | *Listeria monocytogenes* | ribotype DUP-1043A |
| NP2112 | FSL R2-273 | *Listeria monocytogenes* | ribotype DUP-1043A |
| NP2113 | FSL N3-277 | *Listeria monocytogenes* | ribotype DUP-1043A |
| NP1884 | FSL H1-251 | *Listeria monocytogenes* | ribotype DUP-1044A |
| NP2114 | FSL F6-358 | *Listeria monocytogenes* | ribotype DUP-1044A |
| NP2115 | FSL F6-194 | *Listeria monocytogenes* | ribotype DUP-1044A |
| NP2116 | FSL R2-763 | *Listeria monocytogenes* | ribotype DUP-1044A |

TABLE 13-continued

| Identifier | Strain Name | Genus/Species | Subspecies |
|---|---|---|---|
| NP2117 | FSL R2-765 | *Listeria monocytogenes* | ribotype DUP-1044A |
| NP2118 | FSL R2-764 | *Listeria monocytogenes* | ribotype DUP-1044A |
| NP2119 | FSL N1-225 | *Listeria monocytogenes* | ribotype DUP-1044A |
| NP2120 | FSL N1-227 | *Listeria monocytogenes* | ribotype DUP-1044A |
| NP2121 | FSL N1-048 | *Listeria monocytogenes* | ribotype DUP-1044A |
| NP2122 | FSL K2-131 | *Listeria monocytogenes* | ribotype DUP-1044A |
| NP1885 | FSL L3-501 | *Listeria monocytogenes* | ribotype DUP-1044B |
| NP2123 | FSL F6-222 | *Listeria monocytogenes* | ribotype DUP-1044B |
| NP2124 | FSL F6-249 | *Listeria monocytogenes* | ribotype DUP-1044B |
| NP2125 | FSL N3-065 | *Listeria monocytogenes* | ribotype DUP-1044B |
| NP2126 | FSL H4-699 | *Listeria monocytogenes* | ribotype DUP-1044B |
| NP2127 | FSL L4-241 | *Listeria monocytogenes* | ribotype DUP-1044B |
| NP2128 | FSL S4-643 | *Listeria monocytogenes* | ribotype DUP-1044B |
| NP2129 | FSL R2-073 | *Listeria monocytogenes* | ribotype DUP-1044B |
| NP2130 | FSL F3-224 | *Listeria monocytogenes* | ribotype DUP-1044B |
| NP2131 | FSL N4-334 | *Listeria monocytogenes* | ribotype DUP-1044B |
| NP1886 | FSL R2-069 | *Listeria monocytogenes* | ribotype DUP-1044E |
| NP2132 | FSL R2-070 | *Listeria monocytogenes* | ribotype DUP-1044E |
| NP1887 | FSL H1-030 | *Listeria monocytogenes* | ribotype DUP-1045B |
| NP2133 | FSL F6-421 | *Listeria monocytogenes* | ribotype DUP-1045B |
| NP2134 | FSL F6-449 | *Listeria monocytogenes* | ribotype DUP-1045B |
| NP2135 | FSL J2-054 | *Listeria monocytogenes* | ribotype DUP-1045B |
| NP2136 | FSL S4-024 | *Listeria monocytogenes* | ribotype DUP-1045B |
| NP2137 | FSL H1-111 | *Listeria monocytogenes* | ribotype DUP-1045B |
| NP2138 | FSL K2-022 | *Listeria monocytogenes* | ribotype DUP-1045B |
| NP2139 | FSL S4-066 | *Listeria monocytogenes* | ribotype DUP-1045B |
| NP2140 | FSL R2-067 | *Listeria monocytogenes* | ribotype DUP-1045B |
| NP2141 | FSL R2-293 | *Listeria monocytogenes* | ribotype DUP-1045B |
| NP2142 | FSL F6-323 | *Listeria monocytogenes* | ribotype DUP-1052A |
| NP2143 | FSL F6-216 | *Listeria monocytogenes* | ribotype DUP-1052A |
| NP2144 | FSL F6-321 | *Listeria monocytogenes* | ribotype DUP-1052A |
| NP2145 | FSL V1-117 | *Listeria monocytogenes* | ribotype DUP-1052A |
| NP2146 | FSL H5-846 | *Listeria monocytogenes* | ribotype DUP-1052A |
| NP2147 | FSL L3-055 | *Listeria monocytogenes* | ribotype DUP-1052A |
| NP2148 | FSL T1-313 | *Listeria monocytogenes* | ribotype DUP-1052A |
| NP2149 | FSL R8-0875 | *Listeria monocytogenes* | ribotype DUP-1052A |
| NP2150 | FSL R2-317 | *Listeria monocytogenes* | ribotype DUP-1052A |
| NP1888 | FSL L4-019 | *Listeria monocytogenes* | ribotype DUP-1053A |
| NP2151 | FSL F6-335 | *Listeria monocytogenes* | ribotype DUP-1053A |

TABLE 13-continued

| Identifier | Strain Name | Genus/Species | Subspecies |
|---|---|---|---|
| NP2152 | FSL R6-653 | *Listeria monocytogenes* | ribotype DUP-1053A |
| NP2153 | FSL L3-135 | *Listeria monocytogenes* | ribotype DUP-1053A |
| NP2154 | FSL L3-143 | *Listeria monocytogenes* | ribotype DUP-1053A |
| NP2155 | FSL L3-167 | *Listeria monocytogenes* | ribotype DUP-1053A |
| NP2156 | FSL N3-031 | *Listeria monocytogenes* | ribotype DUP-1053A |
| NP2157 | FSL J1-101 | *Listeria monocytogenes* | ribotype DUP-1053A |
| NP2158 | FSL F6-154 | *Listeria monocytogenes* | ribotype DUP-1053A |
| NP2159 | FSL R2-499 | *Listeria monocytogenes* | ribotype DUP-1053A |
| NP1889 | FSL T1-027 | *Listeria monocytogenes* | ribotype DUP-1062A |
| NP2160 | FSL F6-325 | *Listeria monocytogenes* | ribotype DUP-1062A |
| NP2161 | FSL F6-220 | *Listeria monocytogenes* | ribotype DUP-1062A |
| NP2162 | FSL F6-319 | *Listeria monocytogenes* | ribotype DUP-1062A |
| NP2163 | FSL F6-365 | *Listeria monocytogenes* | ribotype DUP-1062A |
| NP2164 | FSL F6-360 | *Listeria monocytogenes* | ribotype DUP-1062A |
| NP2165 | FSL F6-313 | *Listeria monocytogenes* | ribotype DUP-1062A |
| NP2166 | FSL R2-031 | *Listeria monocytogenes* | ribotype DUP-1062A |
| NP2167 | FSL R2-050 | *Listeria monocytogenes* | ribotype DUP-1062A |
| NP2168 | FSL R2-078 | *Listeria monocytogenes* | ribotype DUP-1062A |
| NP1890 | FSL T1-041 | *Listeria monocytogenes* | ribotype DUP-1062D |
| NP2169 | FSL F6-264 | *Listeria monocytogenes* | ribotype DUP-1062D |
| NP2170 | FSL F3-146 | *Listeria monocytogenes* | ribotype DUP-1062D |
| NP2171 | FSL F3-194 | *Listeria monocytogenes* | ribotype DUP-1062D |
| NP2172 | FSL H4-122 | *Listeria monocytogenes* | ribotype DUP-1062D |
| NP2173 | FSL H4-286 | *Listeria monocytogenes* | ribotype DUP-1062D |
| NP2174 | FSL R6-646 | *Listeria monocytogenes* | ribotype DUP-1062D |
| NP2175 | FSL T1-041 | *Listeria monocytogenes* | ribotype DUP-1062D |
| NP2176 | FSL F7-002 | *Listeria monocytogenes* | ribotype DUP-1062D |
| NP2177 | FSL X1-005 | *Listeria monocytogenes* | ribotype DUP-1062D |
| NP 1878 | EGD-e | *Listeria monocytogenes* | |
| NP1911 | FSL R8-7641 | *Listeria seeligeri* | sig B allelotype 20 |
| NP1950 | FSL S10-030 | *Listeria seeligeri* | sig B allelotype 20 |
| NP1951 | FSL S10-320 | *Listeria seeligeri* | sig B allelotype 20 |
| NP1952 | FSL S10-1602 | *Listeria seeligeri* | sig B allelotype 20 |
| NP1953 | FSL L5-075 | *Listeria seeligeri* | sig B allelotype 20 |
| NP1954 | FSL L5-046 | *Listeria seeligeri* | sig B allelotype 20 |
| NP1955 | FSL L5-104 | *Listeria seeligeri* | sig B allelotype 20 |
| NP1956 | FSL R8-7575 | *Listeria seeligeri* | sig B allelotype 20 |
| NP1957 | FSL S4-178 | *Listeria seeligeri* | sig B allelotype 20 |
| NP1958 | FSL S4-135 | *Listeria seeligeri* | sig B allelotype 20 |
| NP1913 | FSL R8-6826 | *Listeria seeligeri* | sig B allelotype 24 |
| NP1968 | FSL S10-034 | *Listeria seeligeri* | sig B allelotype 24 |
| NP1969 | FSL S10-1611 | *Listeria seeligeri* | sig B allelotype 24 |
| NP1970 | FSL L5-054 | *Listeria seeligeri* | sig B allelotype 24 |
| NP1971 | FSL L5-085 | *Listeria seeligeri* | sig B allelotype 24 |
| NP1972 | FSL R8-6868 | *Listeria seeligeri* | sig B allelotype 24 |
| NP1973 | FSL R8-6545 | *Listeria seeligeri* | sig B allelotype 24 |
| NP1974 | FSL R8-6949 | *Listeria seeligeri* | sig B allelotype 24 |
| NP1975 | FSL S4-167 | *Listeria seeligeri* | sig B allelotype 24 |
| NP1976 | FSL S4-180 | *Listeria seeligeri* | sig B allelotype 24 |

TABLE 13-continued

| Identifier | Strain Name | Genus/Species | Subspecies |
|---|---|---|---|
| NP1891 | FSL R8-5241 | *Listeria seeligeri* | sig B allelotype 3 |
| NP1892 | FSL R8-5247 | *Listeria seeligeri* | sig B allelotype 3 |
| NP1893 | FSL R8-5253 | *Listeria seeligeri* | sig B allelotype 3 |
| NP1894 | FSL R8-5513 | *Listeria seeligeri* | sig B allelotype 3 |
| NP1895 | FSL R8-6629 | *Listeria seeligeri* | sig B allelotype 3 |
| NP1896 | FSL R8-6635 | *Listeria seeligeri* | sig B allelotype 3 |
| NP1897 | FSL R8-6659 | *Listeria seeligeri* | sig B allelotype 3 |
| NP1898 | FSL R8-6665 | *Listeria seeligeri* | sig B allelotype 3 |
| NP1899 | FSL R8-6852 | *Listeria seeligeri* | sig B allelotype 3 |
| NP1990 | FSL H6-027 | *Listeria seeligeri* | sig B allelotype 35 |
| NP1991 | FSL H6-079 | *Listeria seeligeri* | sig B allelotype 35 |
| NP1992 | FSL H6-185 | *Listeria seeligeri* | sig B allelotype 35 |
| NP1993 | FSL R8-6874 | *Listeria seeligeri* | sig B allelotype 35 |
| NP1994 | FSL R8-6880 | *Listeria seeligeri* | sig B allelotype 35 |
| NP1995 | FSL R8-7629 | *Listeria seeligeri* | sig B allelotype 35 |
| NP1996 | FSL S4-544 | *Listeria seeligeri* | sig B allelotype 35 |
| NP1910 | FSL R8-7026 | *Listeria welshimeri* | sig B allelotype 15 |
| NP1945 | FSL L5-079 | *Listeria welshimeri* | sig B allelotype 15 |
| NP1946 | FSL S10-1450 | *Listeria welshimeri* | sig B allelotype 15 |
| NP1947 | FSL S10-1451 | *Listeria welshimeri* | sig B allelotype 15 |
| NP1948 | FSL S4-081 | *Listeria welshimeri* | sig B allelotype 15 |
| NP1949 | FSL S4-101 | *Listeria welshimeri* | sig B allelotype 15 |
| NP1977 | FSL N1-064 | *Listeria welshimeri* | sig B allelotype 27 |
| NP1978 | FSL R8-8163 | *Listeria welshimeri* | sig B allelotype 27 |
| NP1979 | FSL R8-7524 | *Listeria welshimeri* | sig B allelotype 27 |
| NP1980 | FSL R8-7486 | *Listeria welshimeri* | sig B allelotype 27 |
| NP1981 | FSL R8-6035 | *Listeria welshimeri* | sig B allelotype 27 |
| NP1982 | FSL R8-5807 | *Listeria welshimeri* | sig B allelotype 27 |
| NP1983 | FSL S4-182 | *Listeria welshimeri* | sig B allelotype 27 |
| NP1984 | FSL R2-630 | *Listeria welshimeri* | sig B allelotype 27 |
| NP1985 | FSL F6-1131 | *Listeria welshimeri* | sig B allelotype 27 |
| NP1914 | FSL R8-7454 | *Listeria welshimeri* | sig B allelotype 32 |
| NP1986 | FSL R8-7041 | *Listeria welshimeri* | sig B allelotype 32 |
| NP1987 | FSL R8-5837 | *Listeria welshimeri* | sig B allelotype 32 |
| NP1988 | FSL R8-6136 | *Listeria welshimeri* | sig B allelotype 32 |
| NP1989 | FSL S4-289 | *Listeria welshimeri* | sig B allelotype 32 |
| NP1917 | FSL R8-1903 | *Listeria welshimeri* | sig B allelotype 89 |
| NP2015 | FSL S10-114 | *Listeria welshimeri* | sig B allelotype 89 |
| NP2016 | FSL S10-115 | *Listeria welshimeri* | sig B allelotype 89 |
| NP2017 | FSL S10-117 | *Listeria welshimeri* | sig B allelotype 89 |
| NP2018 | FSL S10-119 | *Listeria welshimeri* | sig B allelotype 89 |
| NP2019 | FSL S10-121 | *Listeria welshimeri* | sig B allelotype 89 |
| NP2020 | FSL R8-0056 | *Listeria welshimeri* | sig B allelotype 89 |
| NP2021 | FSL R8-1198 | *Listeria welshimeri* | sig B allelotype 89 |
| NP2022 | FSL R8-7403 | *Listeria welshimeri* | sig B allelotype 89 |
| NP2023 | FSL R2-631 | *Listeria welshimeri* | sig B allelotype 89 |

Example 16: Plate-Based Phage Host Range Assay

In order to quantify the host range a given bacteriophage the plaque forming efficiency of the bacteriophage on a given isolate was standardized to a reference strain for the bacteriophage, normally the strain used for bacteriophage production. To determine the plaque forming efficiency a dilution series for the phage is generated and titered on each host. Before the work reported herein, this was the standard method of phage host range analysis. See, e.g., Sambrook et al., Molecular Cloning: A Laboratory Manual, 3d ed., Cold Spring Harbor Laboratory Press, Cold Spring Harbor, N.Y. (2001).

The *Listeria* bacterial strain panel was used to determine the host range for a particular bacteriophage. To do this a culture of each *Listeria* strain to be tested was started in 5 ml of LBL1 and grown overnight at 30 C in an orbital shaker and allowed to grow for 16 hours. For each bacterial host strain 30 μl of the 16-hour culture was mixed with 270 μl of fresh LBL1 medium. To each cell dilution, 4 ml of LBL1 soft agar was added and overlayed onto LBL1 agar in 100 mm petri dish. The soft agar overlay was allowed to cool and solidify at room temperature. Additionally, a reference strain (FSL F6-367 for A511 and P100) was treated in a similar manner to the host range isolates. A 10-fold dilution series of the bacteriophage in LBL1 medium was prepared from $10^{-1}$ to $10^{-8}$. 5 μl of each dilution of the bacteriophage was spotted onto the soft agar overlay and the liquid was allowed to adsorb and then the plate was incubated at 30 C for 16 hours. After incubation the plaques present at each dilution series were counted and compared to the reference strain to provide an efficiency of plaquing for each host range isolate. The host range was represented as a percentage of the titer observed on the experimental host compared to the reference strain. Bacterial strains that showed a plaquing efficiency greater than 10% (FIG. 30 (Table 19), dark gray shading) of the reference strain were considered to be within the host range. Bacterial strains that showed a plaquing efficiency less than 10% but greater than 0.01% (FIG. 30 (Table 19), light gray shade) of the reference strain were considered to be weakly susceptible to the phage. Bacterial strains that showed a plaquing efficiency less than 0.01% (FIG. 30 (Table 19), unshaded) of the reference strain were considered to be outside of the host range for a phage. A phenomenon that was seen for many of the bacterial strains tested was what has been described in the literature and art as "extracellular killing" (ECK) (FIG. 30 (Table 19), black), see e.g. Shaw et al. (J Immunol Methods. 1983; 56(1):75-83). A strain was defined as demonstrating ECK for a particular phage when at high phage concentration completely cleared the lawn, however, subsequent dilutions did not produce clearing.

The plate-based host range determination allowed for a rough approximation of the host range of A511 and P100 against the *Listeria* isolate library. Of the 272 strains tested in the bacterial strain library 67 and 120 strains supported plaque formation by A511 and P100, respectively (FIG. 30 (Table 19)). The greatest limitations of this method were the length of time needed to process the entire library for a give bacteriophage and the inability to determine the entire host range due to the ECK phenomenon. For the bacteriophage A511 and P100, of the 272 bacterial strains in the host range panel tested, 117 and 42, respectively, showed ECK and hence provided no information about the host range for these strains. Additionally, in view of the ECK phenomenon and because of the general differences between bacteria growing on a plate and bacteria growing in a liquid culture, it was hypothesized that the plate-based method for determining host range may not represent the host range for a liquid-based application.

Example 17: A Liquid Culture Phage Host Range Assay

The prevalence of the extra-cellular killing (ECK) phenomenon demonstrated by both A511 and P100 in the plate-based host range method demonstrates that the plate based is not as useful as it could be for determining the host range for either phage. To overcome those deficiencies a novel liquid-based host range assay was developed. The liquid-based host range assay is an end point assay where the ability of a phage to infect a particular bacterial isolate is determined by comparing the optical density of a culture with or without bacteriophage.

The *Listeria* host panel strain collection (Table 13) was struck out on Brain Heart Infusion (BHI) agar plates and single colonies were inoculated in 1 ml BHI liquid in a 2-ml 96-deep well dish, covered with a sterile breathable sterile membrane and grown at 30 C for 16 hours. Each of the 16-hour cultures from the 96-well plates were diluted 1:10,000 in 198 μl of LBL1 in a 300 μl flat-bottom optical 96-well plate and then either $1\times10^5$ pfu of the bacteriophage or an equivalent volume of LBL1 was added to each well of the 96-well plate. This concentration of bacteriophage and bacterial cell dilutions was to approximate a multiplicity of infection (MOI) of 1 in each well. After addition of the phage or control, the plates were incubated at 26 C with shaking at 50 rpm for 16-hours. Plates were placed in a 96-well plate reader (Biotek Eon Microplate Reader) and agitated for 3 seconds with orbital shaking to resuspend cells that had settled out of culture. After the agitation, the optical density of each well was measure at 600 nm (OD600) wavelength light. The ratio of OD600 of the bacterial isolate in the presence of bacteriophage to the uninfected bacterial isolate culture was used as a metric to determine the efficiency of infection for a bacterial strain. A bacterial strain with a ratio of less than or equal to 0.4 (Table 2, dark gray shade) was considered to be sensitive to infection by the bacteriophage.

The liquid-based host range assay identified 192 and 153 bacterial strains sensitive to A511 and P100, respectively, of the 272 strains in the bacterial strain panel (FIG. 30 (Table 19)). This data shows that A511 is capable of infecting approximately 70% and P100 is capable of infecting approximately 58% of the host range panel. In comparison to the liquid-based host range, the plate-based host range method identified 62 and 120 bacterial strains that demonstrated a plaquing-efficiency for A511 and P100, respectively. Of the strains identified in the plate-based host range methods, only 8 A511-sensitive bacterial strains and 3 P100-sensitive bacterial strains did not show clearance in the liquid-based clearance assay. Because the liquid-based assay is an endpoint assay and represents a kinetic interaction between bacteriophage infection and bacterial cell growth certain bacterial strains with increased cell growth rates may be able to saturate a culture even though the strain is susceptible to infection and this may explain the reason why a small number of strains identified in the plaque-based assay were not identified in the liquid assay.

The additional strains identified by the liquid-based host range assay were due to the ability to collect data on strains that demonstrated an ECK phenotype in the plate-based host range assay. The large number of strains that demonstrated this phenotype created a large amount of unknown information regarding the host range for A511 and P100. The liquid-based assay eliminated the ECK phenomenon, one of the large drawbacks of the plate-based host range method. Two factors contributed to the lack of ECK. First the concentration of phages used in the liquid-based assay is a set concentration that is lower than the concentrations of phage that demonstrated ECK in the plate-based host range assay. Second, the delocalized concentration of bacteriophage within the liquid infection and the low MOI decreases the number of interactions between the bacterial cells and bacteriophage. The limited interaction decreases the possibility of non-productive encounters and lowers super-infection, or infection by multiple bacteriophages of a cell. By eliminating ECK, the sensitivity for measuring susceptibility of a particular bacterial cell to a bacteriophage was increased substantially and provided a more accurate representation of the host range of a bacteriophage across the *Listeria* species.

The liquid-based host range assay showed substantial advances over the prior method of using a plate-based system for determining host range of a bacteriophage. Previous literature did not report the ability of growing these bacteriophages in a format other than a plate-based method. The liquid format is also useful because the speed with which the liquid-based host range assay can be performed increases the speed of determining the host range of a bacteriophage from 7-10 days for the panel as it was assembled to several hours of hands on labor. Additionally, the high-throughput nature of the scoring of host susceptibility allowed for multiple bacteriophage host ranges to be determined concurrently, a possibility that did not exist previously. The ability to process multiple bacteriophages concurrently allowed for a more direct comparison of bacteriophages by minimizing variation between bacterial culture physiology and media lots. Together, the increased speed and direct bacteriophage characterizations allowed for rapid processing of multiple phages and prioritization for bacteriophage engineering described herein. Moreover, the liquid-based host range assay allowed for a more accurate representation of the functional determination of a potential bacteriophage in a predicted product compared to a plate-based host range assay. The combination of the increased speed, ability for more direct comparison and ability to assess functionality of a bacteriophage in a more direct method to the final product makes the liquid-based host range assay significantly more useful than the plate-based host range method in most contexts.

The efficacy of a cocktail of a P100 and A511 bacteriophage can be determined by the ability of each of the bacteriophages to infect a particular strain. Infections of the host panel with a cocktail of P100 and A511 show the additive host range expected from the extrapolation of the individual host ranges. Based on observations regarding the bacteriophage concentration required for optimum luciferase production during the course of infection, the concentration of bacteriophage added was maintained at a constant total phage concentration of $1\times10^7$ whether a single bacteriophage or multiple phage cocktail was used for infections. The cocktail of A511 and P100 shows coverage of 74% of the panel constructed, while the individual bacteriophages show 70% and 55% coverage, respectively. (FIG. 30 (Table 19)) This increased coverage of the panel arises from the face that while the phages have largely overlapping coverage the subset of strains susceptible to P100 infection is not full encompassed within the A511 strains. The ability to extrapolate function of a bacteriophage cocktail from the individual liquid-based host range provides as a powerful tool to identify and prioritize new bacteriophages for engineering to build a more complete cocktail.

The function of a bacteriophage cocktail of P100 and A511 on samples collected from environmental samples cannot be strictly inferred from the host panel assembled. The sites sampled in environmental testing represent diverse populations of bacteria and often have more than one species or subspecies of *Listeria* present at an individual location. Environmental sampling at food processing plants with geographic and source diversity identified 31 samples that have been confirmed positive for *Listeria* using a culture based method of detection at a third-party laboratory. Of these 31 positive samples, 10 samples contained multiple *Listeria* species or subspecies. The A511 and P100 cocktail was capable of detecting 24 of the 31 (77%) of the positive samples. The correlation between the liquid-based host range results and the environmental samples collected allows for further iterations on the bacteriophage cocktail to be made in order to gain more complete coverage of the *Listeria* genus and validated the usefulness of the liquid-based host range method.

Example 18: Host Range Characterization of Additional *Listeria* Phages

Construction of a *Listeria* host strain panel and development of a rapid liquid-based host range assay allowed for the rapid screening of additional bacteriophages to identify those bacteriophages that would increase the breadth of coverage of the *Listeria* genus. Twenty five additional bacteriophages were screened against the host panel in the liquid-based host range assay and analyzed for host susceptibility based on clearance versus an uninfected control. The data are presented in FIGS. 32-34 (Tables 21-23, respectively). Strains were considered within host range if they demonstrated a ratio of 0.4 or less (shaded dark gray). During the determination of the OD600 of the cultures there was no correction for the absorbance of the growth medium or culture plate, therefore, a ratio of 0.09 constituted a completely cleared culture by infection. Because of variations in the maximum OD600 obtained by different *Listeria* strains a conservative ratio of 0.4 was chosen to denote *Listeria* strains that were sensitive to a given bacteriophage. Strains that had an OD600 ratio of greater than 0.4 were considered to be outside of host range (FIGS. 32-34 (Tables 21-23, respectively), unshaded). From these twenty five bacteriophages assayed, seven (7) bacteriophages were selected to proceed into engineering based on the criteria that they provided useful host panel coverage, had genome sequence availability for development of phage targeting vectors and were capable of infecting *L. monocytogenes* strain EGD-e, the strain of *Listeria* most amenable to transformation.

The seven bacteriophages selected in addition to A511 and P100 were LP44, LP40, LP48, LP99, LP101, LP124, LP125, and LP143. No individual phage assayed covers more than 78% of the *Listeria* host strain panel. In combination, the bacteriophages cover approximately 92% of the host strain panel as assayed by liquid-based host range assay (FIGS. 31-34 (Tables 20-23, respectively). This combinatorial approach allows for the construction of a bacteriophage cocktail that provides the necessary coverage of the *Listeria* species to provide a reliable determination of the presence of *Listeria* in environmental sample collection.

After engineering the genome of the phages with two different genetic payloads, Firefly Luciferase and Nanoluciferase, the host range of these phages was retested to ensure that the genome modifications did not affect the fitness of the phages or compromise their ability to infect the target bacteria. To examine the result of combining bacteriophages in an infection the liquid-based host range assay was used to test the combinatorial effects of phage infection. For these infections the final concentration of phage was maintained at a constant $1\times10^5$ pfu consisting of equal amounts of each of the phage within the cocktail (i.e.—a two phage cocktail would consist of $5\times10^4$ pfu of each of the two component phages.

Example 19: Engineering *Listeria* Phage

A novel phage engineering method was developed to create recombinant phage. This method is sometimes referred to herein as Phage Infective Engineering (PIE). This method allows insertion of a heterologous nucleic acid sequence into any desired location of a phage genome. The initial site chosen for insertion was that used in Loessner, et al. (Appl. Environ Microbiol., 62:1133-1140), downstream of the major capsid protein gene cps. The coding sequence (SEQ ID NO: 1) for the firefly luciferase (SEQ ID NO: 2) or the coding sequence (SEQ ID NO: 3) for the nanoluc luciferase (SEQ ID NO: 4) was inserted at this location.

The PIE method uses Phage Targeting Vectors PTVs which include the luciferase gene sequence flanked by ~1 KB of phage sequence directly upstream and downstream of the desired insertion site (referred to as an upstream homology region (UHR) and downstream homology region (DHR)). Each of these inserts was created using PCR primers that would amplify the desired amplicon, while adding 20 bp of homology to facilitate assembly. Plasmids were assembled using the GeneArt Seamless Assembly Kit (Life Technologies). The 3 inserts (UHR, luc, DHR) were assembled into the gram positive/gram negative shuttle vector pMK4, which was restriction-digested with SmaI and PstI (NEB).

The A511 phage genome sequence is available in Genbank (NC_009811). A511 phage may be obtained from ATCC (PTA-4608™).

The PIE method was used to insert the firefly luciferase gene (SEQ ID NO: 1) directly after the stop codon of the cps gene of A511, between bases 46,695 and 46,696 of the genomic sequence. No sequence was deleted from the phage genome. A 16 bp sequence containing a ribosome-binding site (GAGGAGGTAAATATAT) (SEQ ID NO: 67) was placed before the start (ATG) of the firefly luciferase gene.

To engineer phage A511, 1276 bases of the cps gene were amplified using oligos "pMAK upf" and "pMAK upr", forming the fragment "A511 UHR". The luciferase gene was amplified using primers "pMAK lucf" and "pMAK lucr", creating the fragment "A511 luc". The primer "pMAK lucf" also added a ribosome binding site (Shine-Dalgarno) upstream of the luciferase gene. The 1140 bp immediately after the cps stop codon was amplified using "pMAK dnf" and "pMAK dnr", named "A511 DHR".

These 3 amplicons were recombineered into pMK4 which had been restriction digested with SmaI/PstI using the GeneArt Seamless Assembly Kit, according to the manufacturer's instructions. Once isolated in *E. coli*, the plasmid was sequenced to verify correct amplification and assembly. Upon verification, the plasmid was transformed into the *L. monocytogenes* strain EGD-e and selected on BHI-chloramphenicol (10 μg/ml) agar plates.

Once the PTV was successfully transformed into EGD-e, the initial recombination was performed: An overnight culture of the A511::FF PTV-containing EGD-e was diluted 1:100 and allowed to grow to an OD600 of 0.1. This culture was then diluted back to an OD600 of 0.02 and mixed with 1e5 pfu/ml of wild-type A511 phage in a 2 ml volume. This infection was cultured at 30° C., shaken at 50 rpm overnight.

To assess whether recombination had occurred, the infection was assayed on the following day. First, the lysate was mixed with chloroform to kill any remaining cells, and to destroy the background luciferase made by the PTV. The phage is chloroform-resistant, which is a common trait in bacteriophages. 4% v/v CHCl3 was added to the lysate, vortexed, spun down, and the supernatant was recovered. A test infection was done, adding a 1:10 dilution of an overnight culture of EGD-e was mixed with the recombinant lysate (90 μl cell dilution, 100 phage lysate). A control infection was set up without cells. The infections were incubated statically at 30° C. for 3 hr, then assayed for luminescence on the Glomax 20/20. 20 μl of the infection was mixed with 100 μl of Promega Luciferase Assay Reagent (20 μl of lysate and 20 μl of NanoGlo for the NanoLuc phages), then read using a 10 second integration (1s for NanoGlo). The recombinant lysate produced light, indicating that there were recombinant phage in the lysate.

In order to enrich and isolate the recombinant phage, it needed to be separated away from the wild-type phages present in the recombinant lysate. Successive rounds of dilution and division were employed. Lysates were made with 10-fold dilutions of input phages, and screened for the presence of recombinant phage by assaying the lysates for luciferase activity.

The recombination efficiency was estimated to be 1:1e5 to 1:1e6. In order to isolate a pure recombinant lysate, the methods described in (Appl. Environ Microbiol. 62:1133-1140) were modified as follows. The initial recombinant lysate was titered. 20 1-ml lysates were set up each with 1e6, 1e5, and 1e4 pfu/ml of the recombinant lysate: 1 ml EGD-e @ OD 0.02, 1 eX phages; O/N, 30 C, 50 rpm. On the following day, the CHCl3 treatment was done, as described above, for each lysate. The lysates were used to set up infections as above. Each lysate was assayed on the Glomax 20/20 (20 μl infection, 100 μl Reagent for FF, 20 μl infection, 20 μl NanoGlo for nluc). The goal was to locate the lysate that was made with the fewest number of phages that exhibits luminescence upon infection. Once this lysate was identified, it was titered and used to set up lysates with 1 e3, 1 e2 and 1 e1 pfu/ml. Once a luminescent lysate was isolated that had been made with 1e2 phages, this lysate was plated for single plaques. Plaques were picked into SM buffer. These "soakates" were diluted 1:10 in dH2O and assayed by PCR using "DBONO360" and "DBONO361" to look for the presence of recombinant junctions between the luciferase gene and phage sequence.

The P100 phage genomic sequence is available in Genbank (DQ004855). P100 may be obtained from ATCC (PTA-4383™).

The luciferase insertion site for P100 was also downstream of the same cps gene. The location of the firefly luciferase insertion in P100 is between base 13,196 and 13,197 of the P100 genomic sequence.

P100 was engineered in the same manner as A511 with the following exceptions: the "P100 DHR" fragment was amplified using the primers "pMAK dnf" and "pMAK dnr P100". The single recombinant plaque was identified by picking the plaque into 100 μl SM buffer. 10 μl of this soakate was mixed with 50 μl of luciferin and luminescence was seen on the luminometer. This method of identifying positives was utilized in subsequent recombinant phage isolation.

The following phages were engineered using the firefly luciferase gene and the methods described for A511::ffluc: LP48, LP124, LP125, LP99, LP101, LP143.

The following phages were engineered using the NanoLuc gene: A511, P100, LP40, LP124 and LP125.

The PTV for A511::nluc was constructed by amplifying the following PCR fragments: Using an A511 lysate as the template, the UHR fragment was generated using oligos pMAK upf and DBONO356; the DHR fragment was amplified using oligos DBONO359 and pMAK dnr. Using the Promega plasmid pNL1.1 as a template, the NanoLuc fragment was amplified using oligos DBONO357 and DBONO358. The assembly and subsequent PIE methods were similar to those described.

The PTV and engineering for P100::nluc was performed in the same way as for A511::nluc, with the exception that the DHR fragment was amplified using the oligo pMAK dnr P100 rather than pMAK dnr.

The PTVs for LP124, LP125, and LP40 were constructed in the same way as A511::nluc, with the following changes. The DHR fragment amplified was shorter to allow for more efficient assembly of the plasmid, using oligos DBONO359 and DBONO382. Also, the insertion site was modified by adding two additional stop codons (TAATAA) directly downstream of the cps gene of these phages. These 6 bases were added by creating additional primers DBONO379 and DBONO380. The UHR fragments for these phages were amplified using oligos pMAK upf and DBONO380. The NanoLuc fragments were amplified using oligos DBONO379 and DBONO358.

The following oligonucleotides were used in the PIE methods:

```
pMAK upf:
                                         (SEQ ID NO: 55)
TTACGCCAAGCTTGGCTGCAACGTGAGTTCCTAGACGACC

pMAK upr:
                                         (SEQ ID NO: 68)
ATGTTTTTGGCGTCTTCCATATATATTTACCTCCTCTTAGTTGCTATGAA

CGTTTT

pMAK lucf:
                                         (SEQ ID NO: 69)
AAAACGTTCATAGCAACTAAGAGGAGGTAAATATATATGGAAGACGCCAA

AAACAT

pMAK lucr:
                                         (SEQ ID NO: 70)
ATTCAATTATCCTATAATTATTACAATTTGGACTTTCCGC

pMAK dnf:
                                         (SEQ ID NO: 71)
GCGGAAAGTCCAAATTGTAATAATTATAGGATAATTGAAT

pMAK dnr:
                                         (SEQ ID NO: 72)
ACGACGGCCAGTGAATTCCCAGTTACTAACTGCTCTAATG

pMAK dnr P100:
                                         (SEQ ID NO: 73)
ACGACGGCCAGTGAATTCCCAGTTACTAACTGTTCTAATG

DBONO360:
                                         (SEQ ID NO: 74)
CCTCTAGCTCAAATTAACGCATCTGT

DBONO361:
                                         (SEQ ID NO: 75)
TGGCTCTACATGCTTAGGGTTCC

DBONO356:
                                         (SEQ ID NO: 76)
TCTTCGAGTGTGAAGACCATATATATTTACCTCCTCTTAGTTGC

DBONO357:
                                         (SEQ ID NO: 77)
CTAAGAGGAGGTAAATATATATGGTCTTCACACTCGAAGATTT

DBONO358:
                                         (SEQ ID NO: 78)
ATTCAATTATCCTATAATTATTACGCCAGAATGCGTTCGC

DBONO359:
                                         (SEQ ID NO: 79)
GCGAACGCATTCTGGCGTAATAATTATAGGATAATTGAATAAA

DBONO379:
                                         (SEQ ID NO: 80)
AAAACGTTCATAGCAACTAATAATAAGAGGAGGTAAATATATATGGTCTT

CACACTCGAAGATTT

DBONO380:
                                         (SEQ ID NO: 81)
ATATTTACCTCCTCTTATTATTAGTTGCTATGAACGTTTTTTACAGG

DBONO382:
                                         (SEQ ID NO: 60)
ACGACGGCCAGTGAATTCCCTCGTGGTGTTCTGACTCCCG.
```

In subsequent experiments some modifications were made to the method. During PTV construction it was discovered that the DHR fragment was often missing from the assembled plasmid. This was overcome by shortening the length of the fragment used, utilizing oligo DBONO382.

In a modified approach, following determining the titer of the recombinant lysate, the enrichment process was sometimes conducted as follows and was used to make the nanoluc phages.

96-well microtiter plates were used to grow the PIE lysates at a 200 μl volume. For the FF lysates, the initial step was making 96 lysates at 1 e6 pfu/lysate (5e6 pfu/ml), 96 at 1 e5, and 96 at 1 e4. For the NanoLuc phages, it was found that the recombination efficiency of the recombinant lysate was significantly higher, and that dilutions down to 1e0 pfu/lysate could be used. These lysates were made by incubating at 30° C., shaking at 50 rpm overnight. The lysates were assayed using the appropriate luciferase assay system (ff or nanoglo). Instead of using the lysates to infect fresh cells, it was found that the background signal of the lysate itself was an indication of the presence of recombinant phage.

Upon identification of a lysate made from the fewest number of phages, that lysate was used to set up new 96-well lysates using fewer phages. Once an approximate recombinant frequency of 1:10-1:100 was reached, the phages were plated on agar plates to isolate single plaques as described above.

These methods were used to create recombinant phage comprising either a heterologous open reading frame encoding the ff luciferase or an open reading frame encoding the nanoluc luciferase. In order to confirm the integrity of the inserted payload and the surrounding sequence in the recombinant phages, a fragment was amplified by PCR and sequenced. This fragment spanned the inserted sequence, beginning in the cps gene, crossing through the firefly or nanoluc gene, and crossing into the downstream sequence. The full cps gene was also PCR amplified using oligos DBONO398 and pMAK upr

```
                                         (SEQ ID NO: 82)
DBONO398: TGCTATATTATAGGAACATGGGAA.
```

The gene was sequenced using oligos DBONO273, DBONO398, and pMAK upr.

The PCR fragment was amplified using primers:

```
DBONO273:
                                         (SEQ ID NO: 83)
TGCTTACATGCCAGTAGGGGT;
and

DBONO382:
                                         (SEQ ID NO: 60)
ACGACGGCCAGTGAATTCCCTCGTGGTGTTCTGACTCCCG
```

The nanoluc phages were sequenced using oligos:

```
DBONO273;
DBONO382;
DBONO361:
                                         (SEQ ID NO: 75)
TGGCTCTACATGCTTAGGGTTCC;

DBONO360:
                                         (SEQ ID NO: 74)
CCTCTAGCTCAAATTAACGCATCTGT;
```

-continued

```
DBONO362:
                                   (SEQ ID NO: 84)
GTATGAAGGTCTGAGCGGCG
and

DBONO363:
                                   (SEQ ID NO: 85)
GATCTGGCCCATTTGGTCGC.
```

The firefly phages were sequenced using oligos:

```
DBONO273;
DBONO382;
DBONO360;
DBONO361;
DBONO274:
                                   (SEQ ID NO: 86)
CGCATAGAACTGCCTGCGTC;

DBONO151:
                                   (SEQ ID NO: 87)
CACCCCAACATCTTCGACGC;
and

DBONO152:
                                   (SEQ ID NO: 88)
GCGCAACTGCAACTCCGATA
```

Sequencing was performed by Genewiz, Inc. Using the Geneious software package, alignments were made and a consensus sequence was generated for each phage.

The following recombinant phages have been created and the insertion site regions sequenced as described above:

Phages containing an inserted firefly luciferase:
LP48::ffluc (SEQ ID NO: 23);
LP99::ffluc (SEQ ID NO: 24);
LP101::ffluc (SEQ ID NO: 25);
LP124::ffluc (SEQ ID NO: 26);
LP125::ffluc (SEQ ID NO: 27);
LP143::ffluc (SEQ ID NO: 28);
A511::ffluc (SEQ ID NO: 29); and
P100::ffluc (SEQ ID NO: 30).

Phages containing an inserted nanoluc luciferase:
LP124::nluc (SEQ ID NO: 31);
LP125::nluc (SEQ ID NO: 32);
A511::nluc (SEQ ID NO: 33);
P100::nluc (SEQ ID NO: 34); and
LP40::nluc (SEQ ID NO: 35).

The insertion site regions of the phages comprising an inserted firefly luciferase coding sequence are aligned in FIG. 28. The insertion site regions of the phages comprising an inserted firefly luciferase coding sequence contain the following parts as indicated in Table 14.

TABLE 14

| | LP48 | LP99 | LP101 | LP124 | LP125 | LP143 | A511 | P100 |
|---|---|---|---|---|---|---|---|---|
| cps gene | 1-1407 | 1-1407 | 1-1407 | 1-1407 | 1-1407 | 1-1404 | 1-1404 | 1-1407 |
| RBS (inserted) | 1408-1423 | 1408-1423 | 1408-1423 | 1408-1423 | 1408-1423 | 1405-1420 | 1405-1420 | 1408-1423 |
| Firefly Luciferase | 1424-3076 | 1424-3076 | 1424-3076 | 1424-3076 | 1424-3076 | 1421-3073 | 1421-3073 | 1424-3076 |
| Downstream genes | 3077-3729 | 3077-3789 | 3077-3789 | 3077-3789 | 3077-3729 | 3074-3786 | 3074-3786 | 3077-3729 |

The insertion site regions of the phages comprising an inserted nanoluc luciferase coding sequence are aligned in FIG. 29. The insertion site regions of the phages comprising an inserted nanoluc luciferase coding sequence contain the following parts as indicated in Table 15.

TABLE 15

| | LP124::nluc | LP125::nluc | A511::nluc | P100::nluc | LP40::nluc |
|---|---|---|---|---|---|
| cps gene | 1-1407 | 1-1407 | 1-1404 | 1-1407 | 1-1407 |
| additional stop codons (inserted) | 1408-1413 | 1408-1413 | n/a | n/a | 1408-1413 |
| RBS (inserted) | 1414-1429 | 1414-1429 | 1405-1420 | 1408-1423 | 1414-1429 |
| NanoLuc | 1430-1945 | 1430-1945 | 1421-1936 | 1424-1939 | 1430-1945 |
| Downstream genes | 1946-2658 | 1946-2598 | 1937-2649 | 1940-2592 | 1946-2613 |

The cps open reading frames and encoded proteins for each phage are listed in Table 16.

TABLE 16

| Phage | Cps Gene Sequence | Cps Protein Sequence |
|---|---|---|
| LP40 | 5 | 6 |
| LP48 | 7 | 8 |
| LP99 | 9 | 10 |
| LP101 | 11 | 12 |
| LP124 | 13 | 14 |
| LP125 | 15 | 16 |
| LP143 | 17 | 18 |
| A511 | 19 | 20 |
| P100 | 21 | 22 |

The cps gene sequences are aligned in FIG. 26 and the protein sequences in

FIG. 27. The cps genes of the engineered phage display a relatively high degree of homology.

All of the above phages were engineered using the methods described above. Partial genome sequences showed that the primers used for A511 could be used to create PTVs for LP48, LP124, and LP125. No genome sequence was available at the time for LP99, LP101 or LP143. Using the A511 PTV primers, it was possible to amplify the appropriate fragments for PTV construction in the same manner as A511. This reflects homology between the cps gene regions across those phages. The luciferase gene insertion site was at the same location (after the cps gene stop codon TAA) as in A511::ffluc.

Engineering of HIS-Tagged Phages

To allow for the concentration of signal produced by the infection of *listeria* by recombinant phages, alternate versions of recombinant phage were produced that included a HIS tag. The 6×HIS tag (SEQ ID NO: 89) is a commonly used affinity tag for concentrating and purifying recombinant proteins.

HIS tags are commonly placed at the N-terminus or C-terminus of a protein, as it is often unknown a priori which location is optimal. Depending on the structure of the protein being tagged, as well as interactions with substrates, the tag sequence can interfere with, inhibit, or enhance enzyme function. For this reason phages were engineered with the HIS tag at either the N- or C-terminus.

Further, often times a spacer sequence comprising a small number of amino acid residues is place between the HIS tag and the gene being tagged. The size, charge, and other characteristics of this spacer can effect interactions with the enzyme, substrate, or HIS-binding beads/resins/antibodies. For this reason 2 different spacer were used between the HIS tag and the Nanoluc protein.

The HIS-tagged nanoluc versions of A511, LP124, and LP40 were constructed using the same methods as the untagged phages. The HIS tag and spacer were introduced during PTV construction by adding sequence to the oligos used to amplify the various DNA fragments. The oligos used in constructing the PTVs for A511, LP124 and LP40 are common to all 3 phages.

4 versions of each phage were constructed:

C-terminal long spacer

C-terminal short spacer

N-terminal long spacer

N-terminal short spacer

Oligos used to construct C-terminal long spacer PTV:

UHR fragment: pMAK upf and DBONO380

NLUC fragment: DBONO379 and DBONO400

DHR fragment: DBONO401 and DBONO382

Oligos used to construct C-terminal short spacer PTV:

UHR fragment: pMAK upf and DBONO380

NLUC fragment: DBONO379 and DBONO402

DHR fragment: DBONO401 and DBONO382

Oligos used to construct N-terminal long spacer PTV:

UHR fragment: pMAK upf and DBONO380

NLUC fragment: DBONO403 and DBONO358

DHR fragment: DBONO359 and DBONO382

Oligos used to construct N-terminal short spacer PTV:

UHR fragment: pMAK upf and DBONO380

NLUC fragment: DBONO404 and DBONO358

DHR fragment: DBONO359 and DBONO382

Once PTVs were constructed and verified, the rest of the PIE process was carried out as described above.

Oligo Sequences:

DBONO400:
(SEQ ID NO: 90)
ATTCAATTATCCTATAATTATTAATGGTGATGGTGATGATGACCTCCACC
TGCTGCCGCCAGAATGCGTTCGCACA

DBONO401:
(SEQ ID NO: 91)
ATCATCACCATCACCATTAATAATTATAGGATAATTGAATAAAAAC

DBONO402:
(SEQ ID NO: 92)
ATTCAATTATCCTATAATTATTAATGGTGATGGTGATGATGTGCTGCCGC
CAGAATGCGTTCGCACA

DBONO403:
(SEQ ID NO: 93)
TAATAAGAGGAGGTAAATATATATGCATCATCACCATCACCATGGTGGAG
GTGCAGCAGTCTTCACACTCGAAGATTTCG

DBONO404:
(SEQ ID NO: 94)
AGCAACTAATAATAAGAGGAGGTAAATATATATGCATCATCACCATCACC
ATGCAGCAGTCTTCACACTCGAAGATTTCG

HIS tag amino acid sequence: HHHHHH (SEQ ID NO: 89)

HIS tag DNA sequence: CATCATCACCATCACCAT (SEQ ID NO: 95)

C-terminal HIS with long spacer amino acid sequence: AAGGGHHHHHH (SEQ ID NO: 96)

C-terminal HIS with long spacer DNA sequence:

(SEQ ID NO: 97)
GCAGCAGGTGGAGGTCATCATCACCATCACCAT

C-terminal HIS with short spacer amino acid sequence: AAHHHHHH (SEQ ID NO: 98)

C-terminal HIS with short spacer DNA sequence:

GCAGCACATCATCACCATCACCAT (SEQ ID NO: 99)

N-terminal HIS with long spacer amino acid sequence: HHHHHHGGGAA (SEQ ID NO: 100)

N-terminal HIS with long spacer DNA sequence:

(SEQ ID NO: 101)
CATCATCACCATCACCATGGTGGAGGTGCAGCA

N-terminal HIS with short spacer amino acid sequence: HHHHHHAA (SEQ ID NO: 102)

N-terminal HIS with short spacer DNA sequence:

CATCATCACCATCACCATGCAGCA (SEQ ID NO: 103)

The insertion locations for each of the twelve tagged enzymes are provided in Table D. The numbering is the same as in the preceding tables in this example.

TABLE D

| Phage | Tag Location | Spacer | Inserted between bases |
|---|---|---|---|
| A511 | C-terminal | Long | 1933-1934 |
| LP124 | C-terminal | Long | 1941-1942 |
| LP40 | C-terminal | Long | 1941-1942 |
| A511 | C-terminal | Short | 1933-1934 |
| LP124 | C-terminal | Short | 1941-1942 |
| LP40 | C-terminal | Short | 1941-1942 |
| A511 | N-terminal | Long | 1423-1424 |
| LP124 | N-terminal | Long | 1432-1433 |
| LP40 | N-terminal | Long | 1432-1433 |
| A511 | N-terminal | Short | 1423-1424 |
| LP124 | N-terminal | Short | 1432-1433 |
| LP40 | N-terminal | Short | 1432-1433 |

The recombinant phage described in this example were deposited on May 16, 2013, with the American Type Culture Collection (ATCC®). The deposits were made under the terms of the Budapest Treaty on the International Recognition of the Deposit of Microorganisms for the Purposes of Patent Procedure. The ATCC® Patent Deposit Designations for the deposits are provided in Table E.

TABLE E

| Phage | ATCC Patent Deposit Designation |
|---|---|
| LP48::ffluc | PTA-120333 |
| LP125::ffluc | PTA-120334 |
| LP40::nluc | PTA-120335 |
| A511::nluc | PTA-120336 |
| P100::ffluc | PTA-120337 |
| LP124::nluc | PTA-120338 |
| LP101::ffluc | PTA-120339 |
| LP99::ffluc | PTA-120340 |
| LP143::ffluc | PTA-120341 |
| A511::ffluc | PTA-120342 |
| P100::nluc | PTA-120343 |
| LP124:ffluc | PTA-120344 |
| LP125::nluc | PTA-120345 |

Example 20: Host Range Characterization of Combinations of *Listeria* Phages

After engineering the genome of the phages with two different genetic payloads, Firefly Luciferase and Nanoluciferase, the host range of these phages was retested to ensure that the genome modifications did not affect the fitness of the phages or compromise their ability to provide coverage across the *Listeria* strain host panel. Engineered phages were tested in the liquid-based host range assay and compared to non-modified bacteriophages. The engineered bacteriophages did not show a change in their host range compared to the non-modified wild-type versions (FIGS. 35-36 (Tables 24-25, respectively).

The identification of bacteriophages that, when their individual host range profiles were combined, provided the necessary coverage of the *Listeria* genus raised the question of whether the phages when used in a combinatorial infection would provide the additive coverage expected or whether the presence of additional bacteriophages in an infection would diminish the ability of a single bacteriophage to infect a susceptible strain. To test this, combinations of bacteriophages (cocktails) were tested for the ability of a bacteriophage cocktail to provide clearance in the liquid-based host range assay. For these infections the final concentration of phage was maintained at a constant $1\times10^5$ pfu consisting of equal amounts of each of the phage within the cocktail (i.e.—a two phage cocktail would consist of $5\times10^4$ pfu of each of the two component phages). The combination of bacteriophages in a cocktail (either a two, three or four bacteriophage cocktail) did not cause a loss of host range and provided the expected additive effects of the host range of the individual bacteriophages (FIGS. 35-36 (Tables 24-25, respectively). The additive effect of the bacteriophages was independent of the genomic modifications as neither the engineered Firefly luciferase and Nanoluc luciferase expressing bacteriophages had an altered liquid-based host range compared to the unengineered bacteriophages.

Example 21: Comparison of Liquid-Based Host Range Versus Marker-Based Host Range The ability of a bacteriophage to clear an actively growing culture is determined by a number of factors including the rate of growth of a particular strain and the rate of bacteriophage replication, in addition to the ability of the bacteriophage to infect a specific strain. Therefore, the output of culture clearance measure used in the liquid culture method disclosed herein is potentially more restrictive than the host range that could be determined by exposing bacterial strains to an recombinant phage comprising a heterologous nucleic acid sequence encoding a marker and assaying for marker production. One example of such a marker is luciferase. Therefore, the host range was determined for phage LP124: nluc by both the liquid-based host range assay and by an infection based luciferase detection assay. To carry out the infection based assay, the *Listeria* host panel strain collection was struck out on Brain Heart Infusion (BHI) agar plates and single colonies were inoculated in 1 ml BHI liquid in a 2-ml 96-deep well dish, covered with a sterile breathable sterile membrane and grown at 30 C for 16 hours. Each of the 16-hour cultures from the 96-well plates were diluted 1:10,000 in 198 μl of BHI. For the infection, 12.5 μl of the culture dilution were mixed added to 12.5 μl of LP124:nluc at a concentration of $1\times10^7$ pfu/ml in an opaque luminescence reader plate and incubated at 30 C for 3 hours. After three hours the level of luminescence was detected using a Promega Glomax 96-well plate reader using Promega Nano-Glo reaction following manufacturer's recommendations.

Table 5 shows the host range determined by the two methods. A strain was considered to be within host range for the clearance assay if the ratio of infected culture OD600 to the uninfected culture OD600 was less than 0.4. For the luciferase detection-based host range assay strains were stratified in three categories, high RLU strains (FIG. 37 (Table 26), dark gray shading,), medium RLU strains (FIG. 37 (Table 26), light gray shading), and low RLU strains (FIG. 37 (Table 26), unshaded). Based on the performance of the assay a strain was considered to be within the host range of the bacteriophage if the RLU measurement was greater than 10,000 Random Light Units (RLU) (FIG. 37 (Table 26), light gray shading). This luciferase activity cut-off was used because it characterizes a useful level of sensitivity in bacterial assays. Based on these criteria the liquid-based host range clearance, LP124 shows a broad host range by clearing 50.5% (140 of 276) of the *Listeria* strains tested. By the luciferase detection assay, 78.2% (216 of 276) of the *Listeria* strains tested showed high RLU levels.

The comparison between the ability of LP124::nluc to clear cultures of the *Listeria* host-panel to the RLU output shows that the host range measured using marker expression is greater than that defined using the liquid-based host range. This could be for several reasons. First, a bacterial strain that is not cleared by the infection but that produces light may have a growth rate that outpaces the ability of the bacteriophage to infect and replicate. In this case, the strain would never succumb completely to bacteriophage because the number of uninfected cells would outpace the bacteriophage in the culture. Second, the bacteriophage may be able to carry out the initial steps of infection (i.e. attachment, injection of DNA and translation of viral proteins) but be unable to complete the infection process (i.e. virion assembly, release from the cell). Because the bacteriophage lifecycle can be separated into discrete steps, a bacteriophage is capable to produce phage encoded proteins, in this case luciferase, without clearance of the culture or producing additional bacteriophage. While additional strains that produce luciferase without producing bacteriophage would not fall within the classical definition of host range for a bacteriophage, the strains do meet inclusion in the host range definition for the purpose of this disclosure because the host range that matters in methods of detecting target bacteria using a phage comprising a heterologous nucleic acid sequence encoding a marker is the types of bacteria that support marker production. This increased host-range observed when using the engineered bacteriophage is an advantageous byproduct of the engineering process and could not be determined a priori for the *Listeria* host panel.

One possible concern raised by the ability of a bacteriophage to produce light in a bacterial strain that it could not clear from a liquid-based culture is that other off-target bacterial genera may also produce luciferase in the presence of engineered phages. These bacterial species would not have been considered to be in host range of these phages because of an inability to produce bacteriophage in response to bacteriophage infections. However, the increased sensitivity for detecting early stages of infection with the engineered phages could, at least theoretically, result in production of marker (in this case luciferase-assayed by light production) in strains of bacteria not identified as hosts using the liquid culture method, for example. To address this issue, a panel of bacterial species closely related to *Listeria* was assembled (Table 27). This panel consisted of other Gram-positive organisms phylogenetically similar to *Listeria*. To determine if these strains were able to produce light in the presence of the engineered bacteriophage each of the species were grown for 16 hours under appropriate growth conditions (Table 27). The strains were diluted to a concentration of $10^5$ cfu/ml and then 90 μl of cells were mixed with 10 μl of a bacteriophage cocktail at $1\times10^7$ pfu/ml and incubated for 3 hours at 30 C. The reactions were then measured for the presence of luciferase using the standard protocol. None of the bacterial species tested had detectable levels of RLU (Table 27) demonstrating that the ability of the bacteriophages to show RLUs in strains that they do not clear is not a strictly off-target effect that will decrease the accuracy of a bacteriophage reporter based assay.

A second question was whether these bacteria species that were phylogenetically similar to *Listeria* would decrease the sensitivity of the engineered bacteriophages to detect *Listeria* when the *Listeria* and non-*Listeria* bacteria species were present together in an assay. To examine this possibility the related bacterial species were grown as above and diluted to a concentration of $10^5$ cfu/ml. A *Listeria* strain was struck out on Brain Heart Infusion (BHI) agar plates and single colonies were inoculated in 5 ml BHI liquid and grown at 30 C for 16 hours. The overnight culture was diluter 1:5 in fresh 0.5×BHI medium and grown for 2 hours at 30 C shaking at 200 rpm in an orbital shaker. After two hours a 10-fold serial dilution of the culture was made. To perform the test 10 μl of the *Listeria* serial dilution that should represent ~10 cfu total was mixed with 20 μl of the potentially inhibitory bacterial species and 10 μl of the bacteriophage cocktail (A511::nluc/LP124::nluc/P100::nluc) and the mixture was incubated for 3 hours at 30 C. After the incubation the reaction was assayed for the presence of luciferase using the Promega Glomax 20/20 luminometer and Promega NanoGlo reaction as suggested. These assays showed that there was no decrease in the ability to detect *Listeria* in the presence of $10^4$ greater numbers of competing bacteria (Table 27) demonstrating the sensitivity of the assay is not affected by the presence of non-target bacteria in samples.

This selection of bacteria was a limited set and did not represent all of the bacteria that could be present during environmental sampling. To generate a more exhaustive sample of bacterial species that may decrease the sensitivity and accuracy of the bacteriophage cocktail, environmental samples were collected from food processing plants and bacterial species were isolated from environmental swabs to determine the effect of these species on performance of the assay. To isolate bacterial species that were present, environmental samples were plated onto both Brain Heart Infusion Agar or R2A agar and grown overnight at 30 C. Bacteria that were present on the plates were identified based on colony morphology and struck to purity on BHI agar plates. Pure cultures of the bacterial species were grown in BHI medium at 30 C for 16 hours. The cultures were diluted to a concentration of $10^5$ cfu/ml and tested for both the production of luciferase in the presence of the bacteriophage cocktail and inhibition of *Listeria* infection by the bacteriophage cocktail as above. None of the bacterial species, consisting of both Gram-positive and Gram-negative bacteria, showed any luciferase production in the presence of the bacteriophage (Table 28). Additionally, incubation of *Listeria* in the presence of the collected samples failed to show any decrease in the production of luciferase, demonstrating that the environmentally collected bacteria do not decrease the sensitivity or accuracy of the assay.

Example 22: Design of Phage Compositions

The increased host range observed by the RLU-based luciferase detection assay compared to the liquid-based host range assay identified a novel method for distinguishing differences between the host range of bacteriophages. Additionally, the RLU-based luciferase detection assay as a means to assess phage host range allows for a highly accurate assessment of the target bacteria identified by an engineered bacteriophage under conditions similar to those of methods of detecting target bacteria. One way this information may be used is to identify useful combinations of phage that can be combined to make a combination of phage having a useful cumulative host range.

To determine the additive effect of including LP124::nluc in a bacteriophage cocktail a RLU-based luciferase detection assay was compared between A511::nluc and LP124::nluc for a portion of the *Listeria* host range panel. LP124::nluc had a larger RLU-based host range (detects 77 of 96 strains, 80.2%) compared to A511:nluc (detects 37 of 96 strains, 38.5%) (FIG. 38 (Table 29)). Moreover, LP124:nluc produces greater than 100-times higher RLU values compared to A511:nluc in 73 of 96 strains (76%). This increased RLU output from LP124:nluc infections predicts that a bacteriophage cocktail that contains both A511 and LP124:nluc would have greater sensitivity and accuracy over a A511:nluc alone.

To test whether LP124::nluc would increase the levels of RLU produced in the presence of A511 and P100 the RLU values were compared between samples infected with both a two-phage cocktail (A511::nluc/P100::nluc) and a three-phage cocktail (A511::nluc/P100::nluc/LP124::nluc). To test this, 1 ml of complex environmental samples grown in UVM medium were pelleted by centrifugation. The supernatant was removed and the cells were resuspended in 100 μl of either the two-phage or three-phage cocktail at a total bacteriophage concentration of $1\times10^7$ and incubated at 30 C. RLU levels were measured by using Promega NanoGlo reagent and the Promega 20/20 luminometer. As for the *Listeria* host panel, the environmental samples showed higher levels of RLU in the presence of the three-phage cocktail than the two-phage cocktail (Table 30). This increase in the RLU output of the infection demonstrates a clear advantage from having LP124::nluc present over P100::nluc and A511::nluc alone.

The increased host range and RLU output of the three-phage compared to the two-phage cocktail suggested that a cocktail of A511::nluc and LP124::nluc would provide useful coverage against environmental samples. To determine the ability of the cocktail to identify *Listeria* relevant to food processing plants environmental sampling was conducted in various food processing plants in the United States. These food processing plants represented seafood, dairy, meat and produce processing plants and were geographically diverse in their location. After environmental collection was performed, *Listeria* that were present in the environmental samples were isolated using a modified USDA isolation method. The *Listeria* were struck out on BHI agar plates and a single colony was used to inoculate 1 ml of 0.5×BHI medium in a 2 ml deep well dish and covered with a sterile breathable membrane and incubated for 16 hours at 30 C. Each of the 16-hour cultures from the 96-well plated were diluted 1:10,000 in 198 μl of BHI. For the infection, 12.5 μl of the culture dilution were mixed added to 12.5 μl of a bacteriophage cocktail containing A511::nluc and LP124::nluc at a total bacteriophage concentration of $1\times10^7$ pfu/ml in an opaque luminescence reader plate and incubated at 30 C for 3 hours. After three hours the level of luminescence was detected using a Promega Glomax 96-well plate reader using Promega NanoGlo reaction following manufacturer's recommendations. Concurrently, a liquid-based host range assay was performed to compare the RLU output to culture clearance.

Based on the liquid-based host range assay the bacteriophage cocktail was able to clear the bacterial culture in 25 of 100 strains (25%). This decreased level of clearance is due to a greater growth rate for the environmentally isolated strains compared to common lab isolates tested in the *Listeria* host range panel. The RLU based host range assay identified 75 of 100 strains (75%) (FIG. 39 (Table 31)). These environmental samples represented complex microbiological communities and had multiple *Listeria* isolates per environmental sample. The presence of multiple strains of *Listeria* within these microbiological communities improves the sensitivity of the assay. In this example the environmental samples were collected using sponges and the sponges were incubated for up to 24 h with media, after which an aliquot was removed and assayed for the presence or absence of the bacterial population to be detected. Based on the ability of the bacteriophage cocktail to identify individual *Listeria* strains identified from the same environmental samples it would have been predicted that the bacteriophage cocktail of A511 and LP124:nluc would be able to detect 48 of 57 (84.2%) *Listeria* positive sponges. When the environmental sponge was incubated in a growth medium and a sample of the enriched sample is tested using the assay the bacteriophage cocktail containing A511 and LP124:nluc was able to detect 49 of 57 (85.9%) *Listeria*-positive sponges. This increased sensitivity demonstrates that the presence of multiple *Listeria* strains, including those out of host range for the bacteriophage cocktail, does not diminish the sensitivity of the assay to detect *Listeria* strains that are sensitive to the bacteriophage cocktail.

TABLE 27

| Species | Growth Medium | Growth Temperature | $10^5$ negative cfu | $10^1$ *Listeria*/$10^5$ negative cfu |
|---|---|---|---|---|
| *Bacillus cereus* | Nutrient Broth | 30 C. | 53 | 3756 |
| *Bacillus megaterium* | Nutrient Broth | 30 C. | 74 | 4814 |
| *Bacillus subtilis* | Nutrient Broth | 30 C. | 56 | 1982 |
| *Enterococcus durans* | Brain Heart Infusion | 37 C. | 57 | 3507 |
| *Enterococcus faceium* | Brain Heart Infusion | 37 C. | 55 | 8735 |
| *Enterococcus hirae* | Brain Heart Infusion | 37 C. | 57 | 6145 |
| *Kocuria varians* | Nutrient Broth | 30 C. | 52 | 6283 |
| *Kurthia gibsonii* | Brain Heart Infusion | 30 C. | 44 | 4420 |
| *Kurthia zopfii* | Nutrient Broth | 26 C. | 54 | 7226 |
| *Rhodococcus equi* | Brain Heart Infusion | 37 C. | 61 | 4367 |
| *Staphylococcus aureus* | Tryptic Soy Broth | 37 C. | 55 | 3575 |
| *Staphylococcus epidermidis* | Tryptic Soy Broth | 37 C. | 51 | 4544 |
| *Staphylococcus saprophyticus* | Nutrient Broth | 37 C. | 59 | 4434 |
| *Streptococcus equi* | Brain Heart Infusion | 37 C. | 63 | 3368 |
| *Streptococcus galloyticus* | Brain Heart Infusion | 37 C. | 64 | 5287 |
| *Lactobacillus casei* | MRS | 37 C., 5% $CO_2$ | 59 | 5320 |
| *Lactobacillus buchneri* | MRS | 37 C., 5% $CO_3$ | 53 | 6331 |
| *Lactobacillus lactus* | MRS | 37 C., 5% $CO_4$ | 67 | 5065 |
| *Lactobacillus fermentum* | MRS | 37 C., 5% $CO_5$ | 67 | 4318 |
| *Micrococcus lutues* | Tryptic Soy Broth | 30 C. | 79 | 3322 |

TABLE 28

| Sample # | Species | $10^5$ negative cfu | $10^1$ *Listeria*/$10^5$ negative cfu |
|---|---|---|---|
| 2501-1 | *Pseudomonas protogens* | 253 | 3513 |
| 250-2 | *Pseudomonas florescens* | 285 | 1737 |
| 251(2)-1 | *Pseudomonas florescens* | 236 | 2903 |
| 251(2)-2 | *Aeromonas* sp | 240 | 1790 |
| 261(1)-1 | *Serratia liquefaciens* | 318 | 6165 |
| 261(1)-2 | *Serratia proteamaculans* | 260 | 4614 |
| 261(2)-1 | *Serratia liquefaciens* | 296 | 2421 |
| 261(2)-2 | Bacillaceae bacterium | 320 | 5289 |
| 289-1 | *Serratia proteamaculans* | 273 | 3487 |

TABLE 28-continued

| Sample # | Species | $10^5$ negative cfu | $10^1$ *Listeria*/$10^5$ negative cfu |
|---|---|---|---|
| 289-2 | *Pseudomonas florescens* | 279 | 5161 |
| 289-3 | *Pseudomonas poae* | 241 | 1922 |
| 290(1)-1 | *Pseudomonas* sp | 241 | 1965 |
| 290(1)-2 | *Pseudomonas* sp | 271 | 2178 |
| 290(2)-1 | *Pseudomonas* fragi | 223 | 3052 |
| 290(3)-1 | *Pseudomonas* sp | 272 | 2560 |
| 291(1)-1 | *Providencia alcalifaciens* | 262 | 4963 |
| 291(1)-2 | *Serratia* sp | 272 | 3827 |
| 291(2)-1 | *Serratia grimesii* | 240 | 3302 |
| 291(2)-2 | *Serratia* sp | 213 | 3086 |
| 291-1 | *Serratia* sp | 270 | 2430 |
| 293-1 | *Serratia* sp, *Hafnia* sp. | 243 | 2989 |
| 293-2 | *Serratia proteamaculans* | 259 | 3254 |
| 296-4 | *Serratia proteamaculans* | 304 | 2314 |
| 304-1 | *Pseudomonas florescens* | 272 | 2639 |
| 304-2 | *Chryseobacterium* sp. | 269 | 2911 |
| 306-1 | *Pseudomonas fragi* | 266 | 3212 |
| 306-2 | Enterobacteriaceae | 273 | 4358 |

TABLE 30

| Sample # | A511/P100 cocktail RLU | A511/P100/LP124 cocktail RLU | Signal Ratio of 3-phage/2-phage |
|---|---|---|---|
| 398 | 1164 | 2212 | 1.9 |
| 399 | 11459 | 27183 | 2.4 |
| 401 | 2100 | 3058 | 1.5 |
| 402 | 113103 | 217389 | 1.9 |
| 403 | 46219 | 58768 | 1.3 |
| 405 | 9988 | 24151 | 2.4 |
| 407 | 2732 | 5329 | 2.0 |
| 426 | 64717 | 444121 | 6.9 |
| 427 | 75896 | 613358 | 8.1 |

INFORMAL SEQUENCE LISTING

SEQ ID NO: 1 - FF luc open reading frame

```
ATGGAAGACGCCAAAAACATAAAGAAAGGCCCGGCGCCATTCTATCCTCTAGAGGATGGAACCGCTGGAGA

GCAACTGCATAAGGCTATGAAGAGATACGCCCTGGTTCCTGGAACAATTGCTTTTACAGATGCACATATCG

AGGTGAACATCACGTACGCGGAATACTTCGAAATGTCCGTTCGGTTGGCAGAAGCTATGAAACGATATGGG

CTGAATACAAATCACAGAATCGTCGTATGCAGTGAAAACTCTCTTCAATTCTTTATGCCGGTGTTGGGCGC

GTTATTTATCGGAGTTGCAGTTGCGCCCGCGAACGACATTTATAATGAACGTGAATTGCTCAACAGTATGA

ACATTTCGCAGCCTACCGTAGTGTTTGTTTCCAAAAAGGGGTTGCAAAAAATTTTGAACGTGCAAAAAAAA

TTACCAATAATCCAGAAAATTATTATCATGGATTCTAAAACGGATTACCAGGGATTTCAGTCGATGTACAC

GTTCGTCACATCTCATCTACCTCCCGGTTTTAATGAATACGATTTTGTACCAGAGTCCTTTGATCGTGACA

AAACAATTGCACTGATAATGAATTCCTCTGGATCTACTGGGTTACCTAAGGGTGTGGCCCTTCCGCATAGA

ACTGCCTGCGTCAGATTCTCGCATGCCAGAGATCCTATTTTTGGCAATCAAATCATTCCGGATACTGCGAT

TTTAAGTGTTGTTCCATTCCATCACGGTTTTGGAATGTTTACTACACTCGGATATTTGATATGTGGATTTC

GAGTCGTCTTAATGTATAGATTTGAAGAAGAGCTGTTTTTACGATCCCTTCAGGATTACAAAATTCAAAGT

GCGTTGCTAGTACCAACCCTATTTTCATTCTTCGCCAAAAGCACTCTGATTGACAAATACGATTTATCTAA

TTTACACGAAATTGCTTCTGGGGGCGCACCTCTTTCGAAAGAAGTCGGGGAAGCGGTTGCAAAACGCTTCC

ATCTTCCAGGGATACGACAAGGATATGGGCTCACTGAGACTACATCAGCTATTCTGATTACACCCGAGGGG

GATGATAAACCGGGCGCGGTCGGTAAAGTTGTTCCATTTTTTGAAGCGAAGGTTGTGGATCTGGATACCGG

GAAAACGCTGGGCGTTAATCAGAGAGGCGAATTATGTGTCAGAGGACCTATGATTATGTCCGGTTATGTAA

ACAATCCGGAAGCGACCAACGCCTTGATTGACAAGGATGGATGGCTACATTCTGGAGACATAGCTTACTGG

GACGAAGACGAACACTTCTTCATAGTTGACCGCTTGAAGTCTTTAATTAAATACAAAGGATATCAGGTGGC

CCCCGCTGAATTGGAATCGATATTGTTACAACACCCCAACATCTTCGACGCGGGCGTGGCAGGTCTTCCCG

ACGATGACGCCGGTGAACTTCCCGCCGCCGTTGTTGTTTTGGAGCACGGAAAGACGATGACGGAAAAAGAG

ATCGTGGATTACGTCGCCAGTCAAGTAACAACCGCGAAAAAGTTGCGCGGAGGAGTTGTGTTTGTGGACGA

AGTACCGAAAGGTCTTACCGGAAAACTCGACGCAAGAAAAATCAGAGAGATCCTCATAAAGGCCAAGAAGG

GCGGAAAGTCCAAATTGTAA
```

-continued

SEQ ID NO: 2 - FF luc amino acid sequence
MEDAKNIKKGPAPFYPLEDGTAGEQLHKAMKRYALVPGTIAFTDAHIEVNITYAEYFEMSVRLAEAMKRYG

LNTNHRIVVCSENSLQFFMPVLGALFIGVAVAPANDIYNERELLNSMNISQPTVVFVSKKGLQKILNVQKK

LPIIQKIIIMDSKTDYQGFQSMYTFVTSHLPPGFNEYDFVPESFDRDKTIALIMNSSGSTGLPKGVALPHR

TACVRFSHARDPIFGNQIIPDTAILSVVPFHHGFGMFTTLGYLICGFRVVLMYRFEEELFLRSLQDYKIQS

ALLVPTLFSFFAKSTLIDKYDLSNLHEIASGGAPLSKEVGEAVAKRFHLPGIRQGYGLTETTSAILITPEG

DDKPGAVGKVVPFFEAKVVDLDTGKTLGVNQRGELCVRGPMIMSGYVNNPEATNALIDKDGWLHSGDIAYW

DEDEHFFIVDRLKSLIKYKGYQVAPAELESILLQHPNIFDAGVAGLPDDDAGELPAAVVVLEHGKTMTEKE

IVDYVASQVTTAKKLRGGVVFVDEVPKGLTGKLDARKIREILIKAKKGGKSKL

SEQ ID NO: 3 - Nano luc open reading frame
ATGGTCTTCACACTCGAAGATTTCGTTGGGGACTGGCGACAGACAGCCGGCTACAACCTGGACCAAGTCCT

TGAACAGGGAGGTGTGTCCAGTTTGTTTCAGAATCTCGGGGTGTCCGTAACTCCGATCCAAAGGATTGTCC

TGAGCGGTGAAAATGGGCTGAAGATCGACATCCATGTCATCATCCCGTATGAAGGTCTGAGCGGCGACCAA

ATGGGCCAGATCGAAAAAATTTTTAAGGTGGTGTACCCTGTGGATGATCATCACTTTAAGGTGATCCTGCA

CTATGGCACACTGGTAATCGACGGGGTTACGCCGAACATGATCGACTATTTCGGACGGCCGTATGAAGGCA

TCGCCGTGTTCGACGGCAAAAAGATCACTGTAACAGGGACCCTGTGGAACGGCAACAAAATTATCGACGAG

CGCCTGATCAACCCCGACGGCTCCCTGCTGTTCCGAGTAACCATCAACGGAGTGACCGGCTGGCGGCTGTG

CGAACGCATTCTGGCGTAA

SEQ ID NO: 4 - Nano luc amino acid sequence
MVFTLEDFVGDWRQTAGYNLDQVLEQGGVSSLFQNLGVSVTPIQRIVLSGENGLKIDIHVIIPYEGLSGDQ

MGQIEKIFKVVYPVDDHHFKVILHYGTLVIDGVTPNMIDYFGRPYEGIAVFDGKKITVTGTLWNGNKIIDE

RLINPDGSLLFRVTINGVTGWRLCERILA

SEQ ID NO: 5 - LP040 Cps open reading frame
ATGCCAAAAAATAACAAAGAAGAAGAAGTTAAAGAAGTAAACCTTAATTCAGTACAAGAGGATGCGTTAAA

GTCCTTTACAACTGGTTATGGTATCACACCTGATACACAAACAGATGCAGGGGCACTAAGACGTGAGTTCC

TAGACGACCAAATCTCAATGCTTACTTGGACAGAAAATGATTTAACATTCTACAAAGACATCGCTAAAAAA

CCAGCTACATCTACAGTAGCAAAATACGATGTGTACATGCAACACGGTAAAGTAGGTCATACTAGATTTAC

TCGTGAGATTGGGGTAGCACCAGTAAGTGACCCTAACATCCGTCAAAAAACAGTAAACATGAAATTTGCTT

CTGATACTAAAAATATTAGTATCGCAGCAGGTCTAGTAAACAACATTCAAGACCCTATGCAAATTTTGACT

GATGATGCTATCGTAAATATCGCTAAAACAATTGAGTGGGCTTCATTCTTTGGAGATTCTGACTTATCAGA

TAGCCCAGAACCACAAGCAGGATTAGAATTTGATGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAA

-continued

SEQ ID NO: 6 - LP40 Cps protein
MPKNNKEEEVKEVNLNSVQEDALKSFTTGYGITPDTQTDAGALRREFLDDQISMLTWTENDLTFYKDIAKK

PATSTVAKYDVYMQHGKVGHTRFTREIGVAPVSDPNIRQKTVNMKFASDTKNISIAAGLVNNIQDPMQILT

DDAIVNIAKTIEWASFFGDSDLSDSPEPQAGLEFDGLAKLINQDNVHDARGASLTESLLNQAAVMISKGYG

TPTDAYMPVGVQADFVNQQLSKQTQLVRDNGNNVSVGFNIQGFHSARGFIKLHGSTVMENEQILDERILAL

PTAPQPAKVTATQEAGKKGQFRAEDLAAHEYKVVVSSDDAESIASEVATATVTAKDDGVKLEIELAPMYSS

RPQFVSIYRKGAETGLFYLIARVPASKAENNVITFYDLNDSIPETVDVFVGEMSANVVHLFELLPMMRLPL

AQINASVTFAVLWYGALALRAPKKWVRIRNVKYIPVKNVHSN

SEQ ID NO: 7 - LP48 Cps open reading frame
ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAACATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAA

SEQ ID NO: 8 - LP48 protein
MPKNNKEEEVKEVNLNSVQEDALKSFTTGYGITPDTQTDAGALRREFLDDQISMLTWTENDLTFYKDIAKK

PATSTVAKYDVYMQHGKVGHTRFTREIGVAPVSDPNIRQKTVNMKFASDTKNISIAAGLVNNIQDPMQILT

DDAIVNIAKTIEWASFFGDSDLSDSPEPQAGLEFDGLAKLINQDNVHDARGASLTESLLNQAAVMISKGYG

TPTDAYMPVGVQADFVNQQLSKQTQLVRDNGNNVSVGFNIQGFHSARGFIKLHGSTVMENEQILDERILAL

PTAPQPAKVTATQEAGKKGQFRAEDLAAHEYKVVVSSDDAESIASEVATATVTAKDDGVKLEIELAPMYSS

RPQFVSIYRKGAETGLFYLIARVPASKAENNVITFYDLNDSIPETVDVFVGEMSANVVHLFELLPMMRLPL

AQINASVTFAVLWYGALALRAPKKWVRIRNVKYIPVKNVHSN

SEQ ID NO: 9 - LP099 Cps open reading frame
ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

-continued

TCGTGAGATTGGGGTAGCACCAGTAAGTGACCCTAACATCCGTCAAAAAACAGTAAACATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAA

SEQ ID NO: 10 - LP099 Cps protein
MPKNNKEEEVKEVNLNSVQEDALKSFTTGYGITPDTQTDAGALRREFLDDQISMLTWTENDLTFYKDIAKK

PATSTVAKYDVYMQHGKVGHTRFTREIGVAPVSDPNIRQKTVNMKFASDTKNISIAAGLVNNIQDPMQILT

DDAIVNIAKTIEWASFFGDSDLSDSPEPQAGLEFDGLAKLINQDNVHDARGASLTESLLNQAAVMISKGYG

TPTDAYMPVGVQADFVNQQLSKQTQLVRDNGNNVSVGFNIQGFHSARGFIKLHGSTVMENEQILDERILAL

PTAPQPAKVTATQEAGKKGQFRAEDLAAHEYKVVVSSDDAESIASEVATATVTAKDDGVKLEIELAPMYSS

RPQFVSIYRKGAETGLFYLIARVPASKAENNVITFYDLNDSIPETVDVFVGEMSANVVHLFELLPMMRLPL

AQINASVTFAVLWYGALALRAPKKWVRIRNVKYIPVKNVHSN

SEQ ID NO: 11 - LP101 Cps open reading frame
ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAACATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

-continued

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAA

SEQ ID NO: 12 - LP101 Cps protein
MPKNNKEEEVKEVNLNSVQEDALKSFTTGYGITPDTQTDAGALRREFLDDQISMLTWTENDLTFYKDIAKK

PATSTVAKYDVYMQHGKVGHTRFTREIGVAPVSDPNIRQKTVNMKFASDTKNISIAAGLVNNIQDPMQILT

DDAIVNIAKTIEWASFFGDSDLSDSPEPQAGLEFDGLAKLINQDNVHDARGASLTESLLNQAAVMISKGYG

TPTDAYMPVGVQADFVNQQLSKQTQLVRDNGNNVSVGFNIQGFHSARGFIKLHGSTVMENEQILDERILAL

PTAPQPAKVTATQEAGKKGQFRAEDLAAHEYKVVVSSDDAESIASEVATATVTAKDDGVKLEIELAPMYSS

RPQFVSIYRKGAETGLFYLIARVPASKAENNVITFYDLNDSIPETVDVFVGEMSANVVHLFELLPMMRLPL

AQINASVTFAVLWYGALALRAPKKWVRIRNVKYIPVKNVHSN

SEQ ID NO: 13 - LP124 Cps open reading frame
ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAACATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAA

SEQ ID NO: 14 - LP124 Cps protein
MPKNNKEEEVKEVNLNSVQEDALKSFTTGYGITPDTQTDAGALRREFLDDQISMLTWTENDLTFYKDIAKK

PATSTVAKYDVYMQHGKVGHTRFTREIGVAPVSDPNIRQKTVNMKFASDTKNISIAAGLVNNIQDPMQILT

DDAIVNIAKTIEWASFFGDSDLSDSPEPQAGLEFDGLAKLINQDNVHDARGASLTESLLNQAAVMISKGYG

TPTDAYMPVGVQADFVNQQLSKQTQLVRDNGNNVSVGFNIQGFHSARGFIKLHGSTVMENEQILDERILAL

PTAPQPAKVTATQEAGKKGQFRAEDLAAHEYKVVVSSDDAESIASEVATATVTAKDDGVKLEIELAPMYSS

RPQFVSIYRKGAETGLFYLIARVPASKAENNVITFYDLNDSIPETVDVFVGEMSANVVHLFELLPMMRLPL

AQINASVTFAVLWYGALALRAPKKWVRIRNVKYIPVKNVHSN

-continued

SEQ ID NO: 15 - LP125 Cps open reading frame
ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAACATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGTGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAA

SEQ ID NO: 16 - LP125 Cps protein
MPKNNKEEEVKEVNLNSVQEDALKSFTTGYGITPDTQTDAGALRREFLDDQISMLTWTENDLTFYKDIAKK

PATSTVAKYDVYMQHGKVGHTRFTREIGVAPVSDPNIRQKTVNMKFASDTKNISIAAGLVNNIQDPMQILT

DDAIVNIAKTIEWASFFGDSDLSDSPEPQAGLEFDGLAKLINQDNVHDARGASLTESLLNQAAVMISKGYG

TPTDAYMPVGVQADFVNQQLSKQTQLVRDNGNNVSVGFNIQGFHSARGFIKLHGSTVMENEQILDERILAL

PTAPQPAKVTATQEAGKKGQFRAEDLAAHEYKVVVSSDDAESIASEVATATVTAKDDGVKLEIELAPMYSS

RPQFVSIYRKGAETGLFYLIARVPASKAENNVITFYDLNDSIPETVDVFVGEMSANVVHLFELLPMMRLPL

AQINASVTFAVLWYGALALRAPKKWVRIRNVKYIPVKNVHSN

SEQ ID NO: 17 - LP143 Cps open reading frame
ATGCCAAAAAATAACAAAGAAGAAGTTAAAGAAGTAAACCTTAATTCAGTACAAGAGGATGCGTTAAAGTC

CTTTACGACTGGTTATGGTATCACACCTGATACACAAACAGATGCAGGAGCATTAAGACGTGAGTTCCTAG

ACGACCAAATCTCAATGCTTACTTGGACAGAGAATGATTTAACATTCTATAAAGACATCGCTAAAAAACCA

GCTACATCTACAGTAGCAAAATACGATGTATACATGCAACATGGTAAGGTAGGTCATACTAGATTTACTCG

TGAGATTGGGGTAGCACCAGTAAGTGACCCTAACATCCGTCAAAAAACAGTAAATATGAAATTTGCTTCCG

ATACTAAAAACATCAGTATCGCAGCAGGTCTAGTAAACAACATTCAAGACCCAATGCAAATTTTGACTGAC

GATGCTATCGTAAATATTGCTAAAACAATTGAGTGGGCTTCATTCTTTGGAGATTCTGACTTATCAGATAG

CCCAGAACCACAAGCAGGACTAGAATTTGACGGCTTGGCTAAACTTATTAACCAAGATAACGTTCATGATG

CTCGTGGAGCTAGCTTGACTGAAAGCTTGTTAAACCAAGCAGCAGTAATGATTAGTAAAGGTTATGGTACA

CCTACAGATGCTTACATGCCAGTAGGGGTTCAAGCAGACTTTGTTAACCAACAACTTTCTAAACAAACACA

ACTTGTTCGCGATAACGGAAACAACGTAAGCGTTGGTTTCAACATCCAAGGTTTCCATTCAGCTCGTGGAT

TTATCAAACTTCACGGTTCTACAGTAATGGAAAACGAACAAATCTTAGATGAACGTATTCTTGCTTTACCA

-continued

ACAGCTCCACAACCAGCTAAGGTAACTGCAACACAAGAAGCAGGTAAAAAAGGACAATTTAGAGCAGAAGA

TTTAGCAGCACATGAATATAAAGTTGTTGTAAGTTCTGACGATGCAGAGTCTATTGCAAGTGAAGTGGCTA

CAGCTACAGTTACTGCAAAAGATGACGGCGTTAAACTAGAAATCGAATTAGCTCCAATGTATAGCTCTCGT

CCACAATTCGTTTCAATCTATAGAAAAGGTGCAGAAACAGGTTTATTCTACCTAATCGCTCGTGTACCTGC

TAGCAAAGCAGAGAACAACGTAATCACTTTCTACGACTTAAACGACTCTATTCCTGAAACAGTAGACGTAT

TCGTTGGTGAAATGTCGGCTAACGTAGTACACTTGTTTGAATTACTACCAATGATGAGATTACCTCTAGCT

CAAATTAACGCATCTGTTACATTTGCAGTTTTATGGTATGGCGCATTAGCTCTAAGAGCACCTAAGAAATG

GGTACGTATTAGAAACGTTAAATATATTCCTGTAAAAAACGTTCATAGCAACTAA

SEQ ID NO: 18 - LP143 Cps protein
MPKNNKEEVKEVNLNSVQEDALKSFTTGYGITPDTQTDAGALRREFLDDQISMLTWTENDLTFYKDIAKKP

ATSTVAKYDVYMQHGKVGHTRFTREIGVAPVSDPNIRQKTVNMKFASDTKNISIAAGLVNNIQDPMQILTD

DAIVNIAKTIEWASFFGDSDLSDSPEPQAGLEFDGLAKLINQDNVHDARGASLTESLLNQAAVMISKGYGT

PTDAYMPVGVQADFVNQQLSKQTQLVRDNGNNVSVGFNIQGFHSARGFIKLHGSTVMENEQILDERILALP

TAPQPAKVTATQEAGKKGQFRAEDLAAHEYKVVVSSDDAESIASEVATATVTAKDDGVKLEIELAPMYSSR

PQFVSIYRKGAETGLFYLIARVPASKAENNVITFYDLNDSIPETVDVFVGEMSANVVHLFELLPMMRLPLA

QINASVTFAVLWYGALALRAPKKWVRIRNVKYIPVKNVHSN

SEQ ID NO: 19 - A511 Cps open reading frame
ATGCCAAAAAATAACAAAGAAGAAGTTAAAGAAGTAAACCTTAATTCAGTACAAGAGGATGCGTTAAAGTC

CTTTACGACTGGTTATGGTATCACACCTGATACACAAACAGATGCAGGAGCATTAAGACGTGAGTTCCTAG

ACGACCAAATCTCAATGCTTACTTGGACAGAGAATGATTTAACATTCTATAAAGACATCGCTAAAAAACCA

GCTACATCTACAGTAGCAAAATACGATGTATACATGCAACATGGTAAGGTAGGTCATACTAGATTTACTCG

TGAGATTGGGGTAGCACCAGTAAGTGACCCTAACATCCGTCAAAAAACAGTAAATATGAAATTTGCTTCCG

ATACTAAAAACATCAGTATCGCAGCAGGTCTAGTAAACAACATTCAAGACCCAATGCAAATTTTGACTGAC

GATGCTATCGTAAATATTGCTAAAACAATTGAGTGGGCTTCATTCTTTGGAGATTCTGACTTATCAGATAG

CCCAGAACCACAAGCAGGACTAGAATTTGACGGCTTGGCTAAACTTATTAACCAAGATAACGTTCATGATG

CTCGTGGAGCTAGCTTGACTGAAAGCTTGTTAAACCAAGCAGCAGTAATGATTAGTAAAGGTTATGGTACA

CCTACAGATGCTTACATGCCAGTAGGGGTTCAAGCAGACTTTGTTAACCAACAACTTTCTAAACAAACACA

ACTTGTTCGCGATAACGGAAACAACGTAAGCGTTGGTTTCAACATCCAAGGTTTCCATTCAGCTCGTGGAT

TTATCAAACTTCACGGTTCTACAGTAATGGAAAACGAACAAATCTTAGATGAACGTATTCTTGCTTTACCA

ACAGCTCCACAACCAGCTAAGGTAACTGCAACACAAGAAGCAGGTAAAAAAGGACAATTTAGAGCAGAAGA

TTTAGCAGCACATGAATATAAAGTTGTTGTAAGTTCTGACGATGCAGAGTCTATTGCAAGTGAAGTGGCTA

CAGCTACAGTTACTGCAAAAGATGACGGCGTTAAACTAGAAATCGAATTAGCTCCAATGTATAGCTCTCGT

CCACAATTCGTTTCAATCTATAGAAAAGGTGCAGAAACAGGTTTATTCTACCTAATCGCTCGTGTACCTGC

TAGCAAAGCAGAGAACAACGTAATCACTTTCTACGACTTAAACGACTCTATTCCTGAAACAGTAGACGTAT

TCGTTGGTGAAATGTCGGCTAACGTAGTACACTTGTTTGAATTACTACCAATGATGAGATTACCTCTAGCT

CAAATTAACGCATCTGTTACATTTGCAGTTTTATGGTATGGCGCATTAGCTCTAAGAGCACCTAAGAAATG

GGTACGTATTAGAAACGTTAAATATATTCCTGTAAAAAACGTTCATAGCAACTAA

SEQ ID NO: 20 - A511 Cps protein
MPKNNKEEVKEVNLNSVQEDALKSFTTGYGITPDTQTDAGALRREFLDDQISMLTWTENDLTFYKDIAKKP

ATSTVAKYDVYMQHGKVGHTRFTREIGVAPVSDPNIRQKTVNMKFASDTKNISIAAGLVNNIQDPMQILTD

DAIVNIAKTIEWASFFGDSDLSDSPEPQAGLEFDGLAKLINQDNVHDARGASLTESLLNQAAVMISKGYGT

PTDAYMPVGVQADFVNQQLSKQTQLVRDNGNNVSVGFNIQGFHSARGFIKLHGSTVMENEQILDERILALP

-continued

TAPQPAKVTATQEAGKKGQFRAEDLAAHEYKVVVSSDDAESIASEVATATVTAKDDGVKLEIELAPMYSSR

PQFVSIYRKGAETGLFYLIARVPASKAENNVITFYDLNDSIPETVDVFVGEMSANVVHLFELLPMMRLPLA

QINASVTFAVLWYGALALRAPKKWVRIRNVKYIPVKNVHSN

SEQ ID NO: 21 - P100 Cps open reading frame
ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAATATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAGCTTGTTCGTGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGACTTAGCAGCACACGAATACAAAGTTGTTGTAAGTTCTGACGATGCAGAGTCTATTGCAAGTGAAGTGG

CTACAGCTACAGTTACTGCAAAAGATGACGGCGTTAAACTAGAAATCGAGTTAGCTCCAATGTACAGCTCC

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTATGACTTAAACGACTCTATTCCTGAAACAGTAGACG

TATTCGTTGGTGAAATGTCTGCTAACGTAGTACACTTGTTTGAATTACTACCAATGATGAGATTACCTCTA

GCTCAAATTAACGCATCTGTTACATTTGCAGTTTTATGGTATGGAGCATTAGCTCTAAGAGCACCTAAGAA

ATGGGTACGTATTAGAAACGTTAAATATATTCCTGTAAAAAACGTTCATAGCAACTAA

SEQ ID NO: 22 - P100 Cps protein
MPKNNKEEEVKEVNLNSVQEDALKSFTTGYGITPDTQTDAGALRREFLDDQISMLTWTENDLTFYKDIAKK

PATSTVAKYDVYMQHGKVGHTRFTREIGVAPVSDPNIRQKTVNMKFASDTKNISIAAGLVNNIQDPMQILT

DDAIVNIAKTIEWASFFGDSDLSDSPEPQAGLEFDGLAKLINQDNVHDARGASLTESLLNQAAVMISKGYG

TPTDAYMPVGVQADFVNQQLSKQTQLVRDNGNNVSVGFNIQGFHSARGFIKLHGSTVMENEQILDERILAL

PTAPQPAKVTATQEAGKKGQFRAEDLAAHEYKVVVSSDDAESIASEVATATVTAKDDGVKLEIELAPMYSS

RPQFVSIYRKGAETGLFYLIARVPASKAENNVITFYDLNDSIPETVDVFVGEMSANVVHLFELLPMMRLPL

AQINASVTFAVLWYGALALRAPKKWVRIRNVKYIPVKNVHSN

SEQ ID NO: 23 - LP48::ffluc
ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAACATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

-continued

ACACCTACAGATGCTTACATGCCAGTAGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAAGAGGAGGTAAATA

TATATGGAAGACGCCAAAAACATAAAGAAAGGCCCGGCGCCATTCTATCCTCTAGAGGATGGAACCGCTGG

AGAGCAACTGCATAAGGCTATGAAGAGATACGCCCTGGTTCCTGGAACAATTGCTTTTACAGATGCACATA

TCGAGGTGAACATCACGTACGCGGAATACTTCGAAATGTCCGTTCGGTTGGCAGAAGCTATGAAACGATAT

GGGCTGAATACAAATCACAGAATCGTCGTATGCAGTGAAAACTCTCTTCAATTCTTTATGCCGGTGTTGGG

CGCGTTATTTATCGGAGTTGCAGTTGCGCCCGCGAACGACATTTATAATGAACGTGAATTGCTCAACAGTA

TGAACATTTCGCAGCCTACCGTAGTGTTTGTTTCCAAAAAGGGGTTGCAAAAAATTTTGAACGTGCAAAAA

AAATTACCAATAATCCAGAAAATTATTATCATGGATTCTAAAACGGATTACCAGGGATTTCAGTCGATGTA

CACGTTCGTCACATCTCATCTACCTCCCGGTTTTAATGAATACGATTTTGTACCAGAGTCCTTTGATCGTG

ACAAAACAATTGCACTGATAATGAATTCCTCTGGATCTACTGGGTTACCTAAGGGTGTGGCCCTTCCGCAT

AGAACTGCCTGCGTCAGATTCTCGCATGCCAGAGATCCTATTTTTGGCAATCAAATCATTCCGGATACTGC

GATTTTAAGTGTTGTTCCATTCCATCACGGTTTTGGAATGTTTACTACACTCGGATATTTGATATGTGGAT

TTCGAGTCGTCTTAATGTATAGATTTGAAGAAGAGCTGTTTTTACGATCCCTTCAGGATTACAAAATTCAA

AGTGCGTTGCTAGTACCAACCCTATTTTCATTCTTCGCCAAAAGCACTCTGATTGACAAATACGATTTATC

TAATTTACACGAAATTGCTTCTGGGGGCGCACCTCTTTCGAAAGAAGTCGGGGAAGCGGTTGCAAAACGCT

TCCATCTTCCAGGGATACGACAAGGATATGGGCTCACTGAGACTACATCAGCTATTCTGATTACACCCGAG

GGGGATGATAAACCGGGCGCGGTCGGTAAAGTTGTTCCATTTTTTGAAGCGAAGGTTGTGGATCTGGATAC

CGGGAAAACGCTGGGCGTTAATCAGAGAGGCGAATTATGTGTCAGAGGACCTATGATTATGTCCGGTTATG

TAAACAATCCGGAAGCGACCAACGCCTTGATTGACAAGGATGGATGGCTACATTCTGGAGACATAGCTTAC

TGGGACGAAGACGAACACTTCTTCATAGTTGACCGCTTGAAGTCTTTAATTAAATACAAAGGATATCAGGT

GGCCCCCGCTGAATTGGAATCGATATTGTTACAACACCCCAACATCTTCGACGCGGGCGTGGCAGGTCTTC

CCGACGATGACGCCGGTGAACTTCCAGCCGCCGTTGTTGTTTTGGAGCACGGAAAGACGATGACGGAAAAA

GAGATCGTGGATTACGTCGCCAGTCAAGTAACAACCGCGAAAAAGTTGCGCGGAGGAGTTGTGTTTGTGGA

CGAAGTACCGAAAGGTCTTACCGGAAAACTCGACGCAAGAAAAATCAGAGAGATCCTCATAAAGGCCAAGA

AGGGCGGAAAGTCCAAATTGTAATAATTATAGGATAATTGAATAAAAACAGTATAGAGAGCAGATAAATAC

TGCTCTCTATTTTACTAATAAGGAGGATTTAAATTGCTAAAAAATACAAACTTAGCTAATTATAAAAAAGT

GAATACACGGTTTGGAAATCTTAGTTTTGACGACAAAGGTATTTCTAATGACTTAACGGAAGAACAGCAAA

AAGAATTAGGTAAGCTTCGAGGATTCGAATATATTAAGACAGAACAGAAAACAAAAGAAGAACCTAAGAAA

GAAGAACCTAAGAAAGAAAGTACAGAAAATGAATTAGACAGCTTCTTAGCTAAAGAGCCTTCAATCAAAGA

ATTAAAAGAATTTGCGAGTAAAAAAGGCATTAAAATTGAAAAAACTAAGAAAAATGATATAATTGAAGAAC

TAAAGAGAGGGTAATGTATAATGTATGGAGGTTATGAAGGACAAGATTCTTACGAATACCCTTACTCACAT

-continued

GGGAACCCTAAGCATGTAGAGCCAGAAAAAGTTGACGAATATGTTCTTTCTGATTATGGTTGGACTGCGGA

AACAATTAAAGCATACATGTATGGTGTTCGTGTAGTAGACCCTGAAACAGGAGAGGAAATGGGAGACACCT

TCTACAATCATATTATAGAGGTTGCCGTTGATAAGGC

SEQ ID NO: 24 - LP99::ffluc
ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAACATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAAGAGGAGGTAAATA

TATATGGAAGACGCCAAAAACATAAAGAAAGGCCCGGCGCCATTCTATCCTCTAGAGGATGGAACCGCTGG

AGAGCAACTGCATAAGGCTATGAAGAGATACGCCCTGGTTCCTGGAACAATTGCTTTTACAGATGCACATA

TCGAGGTGAACATCACGTACGCGGAATACTTCGAAATGTCCGTTCGGTTGGCAGAAGCTATGAAACGATAT

GGGCTGAATACAAATCACAGAATCGTCGTATGCAGTGAAAACTCTCTTCAATTCTTTATGCCGGTGTTGGG

CGCGTTATTTATCGGAGTTGCAGTTGCGCCCGCGAACGACATTTATAATGAACGTGAATTGCTCAACAGTA

TGAACATTTCGCAGCCTACCGTAGTGTTTGTTTCCAAAAAGGGGTTGCAAAAAATTTTGAACGTGCAAAAA

AAATTACCAATAATCCAGAAAATTATTATCATGGATTCTAAAACGGATTACCAGGGATTTCAGTCGATGTA

CACGTTCGTCACATCTCATCTACCTCCCGGTTTTAATGAATACGATTTTGTACCAGAGTCCTTTGATCGTG

ACAAAACAATTGCACTGATAATGAATTCCTCTGGATCTACTGGGTTACCTAAGGGTGTGGCCCTTCCGCAT

AGAACTGCCTGCGTCAGATTCTCGCATGCCAGAGATCCTATTTTTGGCAATCAAATCATTCCGGATACTGC

GATTTTAAGTGTTGTTCCATTCCATCACGGTTTTGGAATGTTTACTACACTCGGATATTTGATATGTGGAT

TTCGAGTCGTCTTAATGTATAGATTTGAAGAAGAGCTGTTTTTACGATCCCTTCAGGATTACAAAATTCAA

AGTGCGTTGCTAGTACCAACCCTATTTTCATTCTTCGCCAAAAGCACTCTGATTGACAAATACGATTTATC

TAATTTACACGAAATTGCTTCTGGGGGCGCACCTCTTTCGAAAGAAGTCGGGGAAGCGGTTGCAAAACGCT

TCCATCTTCCAGGGATACGACAAGGATATGGGCTCACTGAGACTACATCAGCTATTCTGATTACACCCGAG

GGGGATGATAAACCGGGCGCGGTCGGTAAAGTTGTTCCATTTTTTGAAGCGAAGGTTGTGGATCTGGATAC

CGGGAAAACGCTGGGCGTTAATCAGAGAGGCGAATTATGTGTCAGAGGACCTATGATTATGTCCGGTTATG

-continued

TAAACAATCCGGAAGCGACCAACGCCTTGATTGACAAGGATGGATGGCTACATTCTGGAGACATAGCTTAC

TGGGACGAAGACGAACACTTCTTCATAGTTGACCGCTTGAAGTCTTTAATTAAATACAAAGGATATCAGGT

GGCCCCCGCTGAATTGGAATCGATATTGTTACAACACCCCAACATCTTCGACGCGGGCGTGGCAGGTCTTC

CCGACGATGACGCCGGTGAACTTCCCGCCGCCGTTGTTGTTTTGGAGCACGGAAAGACGATGACGGAAAAA

GAGATCGTGGATTACGTCGCCAGTCAAGTAACAACCGCGAAAAAGTTGCGCGGAGGAGTTGTGTTTGTGGA

CGAAGTACCGAAAGGTCTTACCGGAAAACTCGACGCAAGAAAAATCAGAGAGATCCTCATAAAGGCCAAGA

AGGGCGGAAAGTCCAAATTGTAATAATTATAGGATAATTGAATAAAAACAGTATAGAGAGCAGATAAATAC

TGCTCTCTATTTTACTAATAAGGAGGATTTAAATTGCTAAAAAATACAAACTTAGCTAATTATAAAAAGT

GAATACACGGTTTGGAAATCTTAGTTTTGACGACAAAGGTATTTCTAATGACTTAACGGAAGAACAGCAAA

AAGAATTAGGTAAGCTTCGAGGATTCGAATATATTAAGACAGAACAGAAAACAAAAGAAGAACCTAAGAAA

GAAGAACCTAAGAAAGAAGAACCTAAGAAAGAAGAACCTAAGAAAGAAGAACCTAAGAAAGAAGAACCTAA

GAAAGAAAGTACAGAAAATGAATTAGACAGCTTCTTAGCTAAAGAGCCTTCAATCAAAGAATTAAAAGAAT

TTGCGAGTAAAAAAGGCATTAAAATTGAAAAAACTAAGAAAAATGATATAATTGAAGAACTAAAGAGAGGG

TAATGTATAATGTATGGAGGTTATGAAGGACAAGATTCTTACGAATACCCTTACTCACATGGGAACCCTAA

GCATGTAGAGCCAGAAAAAGTTGACGAATATGTTCTTTCTGATTATGGTTGGACTGCGGAAACAATTAAAG

CATACATGTATGGTGTTCGTGTAGTAGACCCTGAAACAGGAGAGGAAATGGGAGACACCTTCTACAATCAT

ATTATAGAGGTTGCCGTTGATAAGGC

SEQ ID NO: 25 - LP101::ffluc
ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAACATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAAGAGGAGGTAAATA

TATATGGAAGACGCCAAAAACATAAAGAAAGGCCCGGCGCCATTCTATCCTCTAGAGGATGGAACCGCTGG

AGAGCAACTGCATAAGGCTATGAAGAGATACGCCCTGGTTCCTGGAACAATTGCTTTTACAGATGCACATA

TCGAGGTGAACATCACGTACGCGGAATACTTCGAAATGTCCGTTCGGTTGGCAGAAGCTATGAAACGATAT

-continued

GGGCTGAATACAAATCACAGAATCGTCGTATGCAGTGAAAACTCTCTTCAATTCTTTATGCCGGTGTTGGG

CGCGTTATTTATCGGAGTTGCAGTTGCGCCCGCGAACGACATTTATAATGAACGTGAATTGCTCAACAGTA

TGAACATTTCGCAGCCTACCGTAGTGTTTGTTTCCAAAAAGGGGTTGCAAAAAATTTTGAACGTGCAAAAA

AAATTACCAATAATCCAGAAAATTATTATCATGGATTCTAAAACGGATTACCAGGGATTTCAGTCGATGTA

CACGTTCGTCACATCTCATCTACCTCCCGGTTTTAATGAATACGATTTTGTACCAGAGTCCTTTGATCGTG

ACAAAACAATTGCACTGATAATGAATTCCTCTGGATCTACTGGGTTACCTAAGGGTGTGGCCCTTCCGCAT

AGAACTGCCTGCGTCAGATTCTCGCATGCCAGAGATCCTATTTTTGGCAATCAAATCATTCCGGATACTGC

GATTTTAAGTGTTGTTCCATTCCATCACGGTTTTGGAATGTTTACTACACTCGGATATTTGATATGTGGAT

TTCGAGTCGTCTTAATGTATAGATTTGAAGAAGAGCTGTTTTTACGATCCCTTCAGGATTACAAAATTCAA

AGTGCGTTGCTAGTACCAACCCTATTTTCATTCTTCGCCAAAAGCACTCTGATTGACAAATACGATTTATC

TAATTTACACGAAATTGCTTCTGGGGGCGCACCTCTTTCGAAAGAAGTCGGGGAAGCGGTTGCAAAACGCT

TCCATCTTCCAGGGATACGACAAGGATATGGGCTCACTGAGACTACATCAGCTATTCTGATTACACCCGAG

GGGGATGATAAACCGGGCGCGGTCGGTAAAGTTGTTCCATTTTTTGAAGCGAAGGTTGTGGATCTGGATAC

CGGGAAAACGCTGGGCGTTAATCAGAGAGGCGAATTATGTGTCAGAGGACCTATGATTATGTCCGGTTATG

TAAACAATCCGGAAGCGACCAACGCCTTGATTGACAAGGATGGATGGCTACATTCTGGAGACATAGCTTAC

TGGGACGAAGACGAACACTTCTTCATAGTTGACCGCTTGAAGTCTTTAATTAAATACAAAGGATATCAGGT

GGCCCCCGCTGAATTGGAATCGATATTGTTACAACACCCCAACATCTTCGACGCGGGCGTGGCAGGTCTTC

CCGACGATGACGCCGGTGAACTTCCCGCCGCCGTTGTTGTTTTGGAGCACGGAAAGACGATGACGGAAAAA

GAGATCGTGGATTACGTCGCCAGTCAAGTAACAACCGCGAAAAAGTTGCGCGGAGGAGTTGTGTTTGTGGA

CGAAGTACCGAAAGGTCTTACCGGAAAACTCGACGCAAGAAAAATCAGAGAGATCCTCATAAAGGCCAAGA

AGGGCGGAAAGTCCAAATTGTAATAATTATAGGATAATTGAATAAAAACAGTATAGAGAGCAGATAAATAC

TGCTCTCTATTTTACTAATAAGGAGGATTTAAATTGCTAAAAAATACAAACTTAGCTAATTATAAAAAAGT

GAATACACGGTTTGGAAATCTTAGTTTTGACGACAAAGGTATTTCTAATGACTTAACGGAAGAACAGCAAA

AAGAATTAGGTAAGCTTCGAGGATTCGAATATATTAAGACAGAACAGAAAACAAAAGAAGAACCTAAGAAA

GAAGAACCTAAGAAAGAAGAACCTAAGAAAGAAGAACCTAAGAAAGAAGAACCTAAGAAAGAAGAACCTAA

GAAAGAAAGTACAGAAAATGAATTAGACAGCTTCTTAGCTAAAGAGCCTTCAATCAAAGAATTAAAAGAAT

TTGCGAGTAAAAAAGGCATTAAAATTGAAAAAACTAAGAAAAATGATATAATTGAAGAACTAAAGAGAGGG

TAATGTATAATGTATGGAGGTTATGAAGGACAAGATTCTTACGAATACCCTTACTCACATGGGAACCCTAA

GCATGTAGAGCCAGAAAAAGTTGACGAATATGTTCTTTCTGATTATGGTTGGACTGCGGAAACAATTAAAG

CATACATGTATGGTGTTCGTGTAGTAGACCCTGAAACAGGAGAGGAAATGGGAGACACCTTCTACAATCAT

ATTATAGAGGTTGCCGTTGATAAGGC

SEQ ID NO: 26 - LP124::ffluc
ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAACATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

-continued

ACACCTACAGATGCTTACATGCCAGTAGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAAGAGGAGGTAAATA

TATATGGAAGACGCCAAAAACATAAAGAAAGGCCCGGCGCCATTCTATCCTCTAGAGGATGGAACCGCTGG

AGAGCAACTGCATAAGGCTATGAAGAGATACGCCCTGGTTCCTGGAACAATTGCTTTTACAGATGCACATA

TCGAGGTGAACATCACGTACGCGGAATACTTCGAAATGTCCGTTCGGTTGGCAGAAGCTATGAAACGATAT

GGGCTGAATACAAATCACAGAATCGTCGTATGCAGTGAAAACTCTCTTCAATTCTTTATGCCGGTGTTGGG

CGCGTTATTTATCGGAGTTGCAGTTGCGCCCGCGAACGACATTTATAATGAACGTGAATTGCTCAACAGTA

TGAACATTTCGCAGCCTACCGTAGTGTTTGTTTCCAAAAAGGGGTTGCAAAAAATTTTGAACGTGCAAAAA

AAATTACCAATAATCCAGAAAATTATTATCATGGATTCTAAAACGGATTACCAGGGATTTCAGTCGATGTA

CACGTTCGTCACATCTCATCTACCTCCCGGTTTTAATGAATACGATTTTGTACCAGAGTCCTTTGATCGTG

ACAAAACAATTGCACTGATAATGAATTCCTCTGGATCTACTGGGTTACCTAAGGGTGTGGCCCTTCCGCAT

AGAACTGCCTGCGTCAGATTCTCGCATGCCAGAGATCCTATTTTTGGCAATCAAATCATTCCGGATACTGC

GATTTTAAGTGTTGTTCCATTCCATCACGGTTTTGGAATGTTTACTACACTCGGATATTTGATATGTGGAT

TTCGAGTCGTCTTAATGTATAGATTTGAAGAAGAGCTGTTTTTACGATCCCTTCAGGATTACAAAATTCAA

AGTGCGTTGCTAGTACCAACCCTATTTTCATTCTTCGCCAAAAGCACTCTGATTGACAAATACGATTTATC

TAATTTACACGAAATTGCTTCTGGGGGCGCACCTCTTTCGAAAGAAGTCGGGGAAGCGGTTGCAAAACGCT

TCCATCTTCCAGGGATACGACAAGGATATGGGCTCACTGAGACTACATCAGCTATTCTGATTACACCCGAG

GGGGATGATAAACCGGGCGCGGTCGGTAAAGTTGTTCCATTTTTTGAAGCGAAGGTTGTGGATCTGGATAC

CGGGAAAACGCTGGGCGTTAATCAGAGAGGCGAATTATGTGTCAGAGGACCTATGATTATGTCCGGTTATG

TAAACAATCCGGAAGCGACCAACGCCTTGATTGACAAGGATGGATGGCTACATTCTGGAGACATAGCTTAC

TGGGACGAAGACGAACACTTCTTCATAGTTGACCGCTTGAAGTCTTTAATTAAATACAAAGGATATCAGGT

GGCCCCCGCTGAATTGGAATCGATATTGTTACAACACCCCAACATCTTCGACGCGGGCGTGGCAGGTCTTC

CCGACGATGACGCCGGTGAACTTCCCGCCGCCGTTGTTGTTTTGGAGCACGGAAAGACGATGACGGAAAAA

GAGATCGTGGATTACGTCGCCAGTCAAGTAACAACCGCGAAAAAGTTGCGCGGAGGAGTTGTGTTTGTGGA

CGAAGTACCGAAAGGTCTTACCGGAAAACTCGACGCAAGAAAAATCAGAGAGATCCTCATAAAGGCCAAGA

AGGGCGGAAAGTCCAAATTGTAATAATTATAGGATAATTGAATAAAAACAGTATAGAGAGCAGATAAATAC

TGCTCTCTATTTTACTAATAAGGAGGATTTAAATTGCTAAAAAATACAAACTTAGCTAATTATAAAAAAGT

GAATACACGGTTTGGAAATCTTAGTTTTGACGACAAAGGTATTTCTAATGACTTAACGGAAGAACAGCAAA

AAGAATTAGGTAAGCTTCGAGGATTCGAATATATTAAGACAGAACAGAAAACAAAAGAAGAACCTAAGAAA

GAAGAACCTAAGAAAGAAGAACCTAAGAAAGAAGAACCTAAGAAAGAAGAACCTAAGAAAGAAGAACCTAA

GAAAGAAAGTACAGAAAATGAATTAGACAGCTTCTTAGCTAAAGAGCCTTCAATCAAAGAATTAAAAGAAT

-continued

TTGCGAGTAAAAAAGGCATTAAAATTGAAAAAACTAAGAAAAATGATATAATTGAAGAACTAAAGAGAGGG

TAATGTATAATGTATGGAGGTTATGAAGGACAAGATTCTTACGAATACCCTTACTCACATGGGAACCCTAA

GCATGTAGAGCCAGAAAAAGTTGACGAATATGTTCTTTCTGATTATGGTTGGACTGCGGAAACAATTAAAG

CATACATGTATGGTGTTCGTGTAGTAGACCCTGAAACAGGAGAGGAAATGGGAGACACCTTCTACAATCAT

ATTATAGAGGTTGCCGTTGATAAGGC

SEQ ID NO: 27 - LP125::ffluc

ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAACATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGTGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAAGAGGAGGTAAATA

TATATGGAAGACGCCAAAAACATAAAGAAAGGCCCGGCGCCATTCTATCCTCTAGAGGATGGAACCGCTGG

AGAGCAACTGCATAAGGCTATGAAGAGATACGCCCTGGTTCCTGGAACAATTGCTTTTACAGATGCACATA

TCGAGGTGAACATCACGTACGCGGAATACTTCGAAATGTCCGTTCGGTTGGCAGAAGCTATGAAACGATAT

GGGCTGAATACAAATCACAGAATCGTCGTATGCAGTGAAAACTCTCTTCAATTCTTTATGCCGGTGTTGGG

CGCGTTATTTATCGGAGTTGCAGTTGCGCCCGCGAACGACATTTATAATGAACGTGAATTGCTCAACAGTA

TGAACATTTCGCAGCCTACCGTAGTGTTTGTTTCCAAAAAGGGGTTGCAAAAAATTTTGAACGTGCAAAAA

AAATTACCAATAATCCAGAAAATTATTATCATGGATTCTAAAACGGATTACCAGGGATTTCAGTCGATGTA

CACGTTCGTCACATCTCATCTACCTCCCGGTTTTAATGAATACGATTTTGTACCAGAGTCCTTTGATCGTG

ACAAAACAATTGCACTGATAATGAATTCCTCTGGATCTACTGGGTTACCTAAGGGTGTGGCCCTTCCGCAT

AGAACTGCCTGCGTCAGATTCTCGCATGCCAGAGATCCTATTTTTGGCAATCAAATCATTCCGGATACTGC

GATTTTAAGTGTTGTTCCATTCCATCACGGTTTTGGAATGTTTACTACACTCGGATATTTGATATGTGGAT

TTCGAGTCGTCTTAATGTATAGATTTGAAGAAGAGCTGTTTTTACGATCCCTTCAGGATTACAAAATTCAA

AGTGCGTTGCTAGTACCAACCCTATTTTCATTCTTCGCCAAAAGCACTCTGATTGACAAATACGATTTATC

TAATTTACACGAAATTGCTTCTGGGGGCGCACCTCTTTCGAAAGAAGTCGGGGAAGCGGTTGCAAAACGCT

TCCATCTTCCAGGGATACGACAAGGATATGGGCTCACTGAGACTACATCAGCTATTCTGATTACACCCGAG

-continued

GGGGATGATAAACCGGGCGCGGTCGGTAAAGTTGTTCCATTTTTTGAAGCGAAGGTTGTGGATCTGGATAC

CGGGAAAACGCTGGGCGTTAATCAGAGAGGCGAATTATGTGTCAGAGGACCTATGATTATGTCCGGTTATG

TAAACAATCCGGAAGCGACCAACGCCTTGATTGACAAGGATGGATGGCTACATTCTGGAGACATAGCTTAC

TGGGACGAAGACGAACACTTCTTCATAGTTGACCGCTTGAAGTCTTTAATTAAATACAAAGGATATCAGGT

GGCCCCCGCTGAATTGGAATCGATATTGTTACAACACCCCAACATCTTCGACGCGGGCGTGGCAGGTCTTC

CCGACGATGACGCCGGTGAACTTCCAGCCGCCGTTGTTGTTTTGGAGCACGGAAAGACGATGACGGAAAAA

GAGATCGTGGATTACGTCGCCAGTCAAGTAACAACCGCGAAAAAGTTGCGCGGAGGAGTTGTGTTTGTGGA

CGAAGTACCGAAAGGTCTTACCGGAAAACTCGACGCAAGAAAAATCAGAGAGATCCTCATAAAGGCCAAGA

AGGGCGGAAAGTCCAAATTGTAATAATTATAGGATAATTGAATAAAAACAGTATAGAGAGCAGATAAATAC

TGCTCTCTATTTTACTAATAAGGAGGATTTAAATTGCTAAAAAATACAAACTTAGCTAATTATAAAAAAGT

GAATACACGGTTTGGAAATCTTAGTTTTGACGACAAAGGTATTTCTAATGACTTAACGGAAGAACAGCAAA

AAGAATTAGGTAAGCTTCGAGGATTCGAATATATTAAGACAGAACAGAAAACAAAAGAAGAACCTAAGAAA

GAAGAACCTAAGAAAGAAAGTACAGAAAATGAATTAGACAGCTTCTTAGCTAAAGAGCCTTCAATCAAAGA

ATTAAAAGAATTTGCGAGTAAAAAAGGCATTAAAATTGAAAAAACTAAGAAAAATGATATAATTGAAGAAC

TAAAGAGAGGGTAATGTATAATGTATGGAGGTTATGAAGGACAAGATTCTTACGAATACCCTTACTCACAT

GGGAACCCTAAGCATGTAGAGCCAGAAAAAGTTGACGAATATGTTCTTTCTGATTATGGTTGGACTGCGGA

AACAATTAAAGCATACATGTATGGTGTTCGTGTAGTAGACCCTGAAACAGGAGAGGAAATGGGAGACACCT

TCTACAATCATATTATAGAGGTTGCCGTTGATAAGGC

SEQ ID NO: 28 - LP143::ffluc
ATGCCAAAAAATAACAAAGAAGAAGTTAAAGAAGTAAACCTTAATTCAGTACAAGAGGATGCGTTAAAGTC

CTTTACGACTGGTTATGGTATCACACCTGATACACAAACAGATGCAGGAGCATTAAGACGTGAGTTCCTAG

ACGACCAAATCTCAATGCTTACTTGGACAGAGAATGATTTAACATTCTATAAAGACATCGCTAAAAAACCA

GCTACATCTACAGTAGCAAAATACGATGTATACATGCAACATGGTAAGGTAGGTCATACTAGATTTACTCG

TGAGATTGGGGTAGCACCAGTAAGTGACCCTAACATCCGTCAAAAAACAGTAAATATGAAATTTGCTTCCG

ATACTAAAAACATCAGTATCGCAGCAGGTCTAGTAAACAACATTCAAGACCCAATGCAAATTTTGACTGAC

GATGCTATCGTAAATATTGCTAAAACAATTGAGTGGGCTTCATTCTTTGGAGATTCTGACTTATCAGATAG

CCCAGAACCACAAGCAGGACTAGAATTTGACGGCTTGGCTAAACTTATTAACCAAGATAACGTTCATGATG

CTCGTGGAGCTAGCTTGACTGAAAGCTTGTTAAACCAAGCAGCAGTAATGATTAGTAAAGGTTATGGTACA

CCTACAGATGCTTACATGCCAGTAGGGGTTCAAGCAGACTTTGTTAACCAACAACTTTCTAAACAAACACA

ACTTGTTCGCGATAACGGAAACAACGTAAGCGTTGGTTTCAACATCCAAGGTTTCCATTCAGCTCGTGGAT

TTATCAAACTTCACGGTTCTACAGTAATGGAAAACGAACAAATCTTAGATGAACGTATTCTTGCTTTACCA

ACAGCTCCACAACCAGCTAAGGTAACTGCAACACAAGAAGCAGGTAAAAAAGGACAATTTAGAGCAGAAGA

TTTAGCAGCACATGAATATAAAGTTGTTGTAAGTTCTGACGATGCAGAGTCTATTGCAAGTGAAGTGGCTA

CAGCTACAGTTACTGCAAAAGATGACGGCGTTAAACTAGAAATCGAATTAGCTCCAATGTATAGCTCTCGT

CCACAATTCGTTTCAATCTATAGAAAAGGTGCAGAAACAGGTTTATTCTACCTAATCGCTCGTGTACCTGC

TAGCAAAGCAGAGAACAACGTAATCACTTTCTACGACTTAAACGACTCTATTCCTGAAACAGTAGACGTAT

TCGTTGGTGAAATGTCGGCTAACGTAGTACACTTGTTTGAATTACTACCAATGATGAGATTACCTCTAGCT

CAAATTAACGCATCTGTTACATTTGCAGTTTTATGGTATGGCGCATTAGCTCTAAGAGCACCTAAGAAATG

GGTACGTATTAGAAACGTTAAATATATTCCTGTAAAAAACGTTCATAGCAACTAAGAGGAGGTAAATATAT

ATGGAAGACGCCAAAAACATAAAGAAAGGCCCGGCGCCATTCTATCCTCTAGAGGATGGAACCGCTGGAGA

GCAACTGCATAAGGCTATGAAGAGATACGCCCTGGTTCCTGGAACAATTGCTTTTACAGATGCACATATCG

-continued

AGGTGAACATCACGTACGCGGAATACTTCGAAATGTCCGTTCGGTTGGCAGAAGCTATGAAACGATATGGG

CTGAATACAAATCACAGAATCGTCGTATGCAGTGAAAACTCTCTTCAATTCTTTATGCCGGTGTTGGGCGC

GTTATTTATCGGAGTTGCAGTTGCGCCCGCGAACGACATTTATAATGAACGTGAATTGCTCAACAGTATGA

ACATTTCGCAGCCTACCGTAGTGTTTGTTTCCAAAAAGGGGTTGCAAAAAATTTTGAACGTGCAAAAAAAA

TTACCAATAATCCAGAAAATTATTATCATGGATTCTAAAACGGATTACCAGGGATTTCAGTCGATGTACAC

GTTCGTCACATCTCATCTACCTCCCGGTTTTAATGAATACGATTTTGTACCAGAGTCCTTTGATCGTGACA

AAACAATTGCACTGATAATGAATTCCTCTGGATCTACTGGGTTACCTAAGGGTGTGGCCCTTCCGCATAGA

ACTGCCTGCGTCAGATTCTCGCATGCCAGAGATCCTATTTTTGGCAATCAAATCATTCCGGATACTGCGAT

TTTAAGTGTTGTTCCATTCCATCACGGTTTTGGAATGTTTACTACACTCGGATATTTGATATGTGGATTTC

GAGTCGTCTTAATGTATAGATTTGAAGAAGAGCTGTTTTTACGATCCCTTCAGGATTACAAAATTCAAAGT

GCGTTGCTAGTACCAACCCTATTTTCATTCTTCGCCAAAAGCACTCTGATTGACAAATACGATTTATCTAA

TTTACACGAAATTGCTTCTGGGGGCGCACCTCTTTCGAAAGAAGTCGGGGAAGCGGTTGCAAAACGCTTCC

ATCTTCCAGGGATACGACAAGGATATGGGCTCACTGAGACTACATCAGCTATTCTGATTACACCCGAGGGG

GATGATAAACCGGGCGCGGTCGGTAAAGTTGTTCCATTTTTTGAAGCGAAGGTTGTGGATCTGGATACCGG

GAAAACGCTGGGCGTTAATCAGAGAGGCGAATTATGTGTCAGAGGACCTATGATTATGTCCGGTTATGTAA

ACAATCCGGAAGCGACCAACGCCTTGATTGACAAGGATGGATGGCTACATTCTGGAGACATAGCTTACTGG

GACGAAGACGAACACTTCTTCATAGTTGACCGCTTGAAGTCTTTAATTAAATACAAAGGATATCAGGTGGC

CCCCGCTGAATTGGAATCGATATTGTTACAACACCCCAACATCTTCGACGCGGGCGTGGCAGGTCTTCCCG

ACGATGACGCCGGTGAACTTCCCGCCGCCGTTGTTGTTTTGGAGCACGGAAAGACGATGACGGAAAAAGAG

ATCGTGGATTACGTCGCCAGTCAAGTAACAACCGCGAAAAAGTTGCGCGGAGGAGTTGTGTTTGTGGACGA

AGTACCGAAAGGTCTTACCGGAAAACTCGACGCAAGAAAAATCAGAGAGATCCTCATAAAGGCCAAGAAGG

GCGGAAAGTCCAAATTGTAATAATTATAGGATAATTGAATAAAAACAGTATAGAGAGCAGATAAATACTGC

TCTCTATTTTACTAATAAGGAGGATTTAAATTGCTAAAAAATACAAACTTAGCTAATTATAAAAAAGTGAA

TACACGGTTTGGAAATCTTAGTTTTGACGACAAAGGTATTTCTAATGACTTAACGGAAGAACAGCAAAAAG

AATTAGGTAAGCTTCGAGGATTCGAATATATTAAGACAGAACAGAAAACAAAAGAAGAACCTAAGAAAGAA

GAACCTAAGAAAGAAGAACCTAAGAAAGAAGAACCTAAGAAAGAAGAACCTAAGAAAGAAGAACCTAAGAA

AGAAAGTACAGAAAATGAATTAGACAGCTTCTTAGCTAAAGAGCCTTCAATCAAAGAATTAAAAGAATTTG

CGAGTAAAAAAGGCATTAAAATTGAAAAAACTAAGAAAAATGATATAATTGAAGAACTAAAGAGAGGGTAA

TGTATAATGTATGGAGGTTATGAAGGACAAGATTCTTACGAATACCCTTACTCACATGGGAACCCTAAGCA

TGTAGAGCCAGAAAAAGTTGACGAATATGTTCTTTCTGATTATGGTTGGACTGCGGAAACAATTAAAGCAT

ACATGTATGGTGTTCGTGTAGTAGACCCTGAAACAGGAGAGGAAATGGGAGACACCTTCTACAATCATATT

ATAGAGGTTGCCGTTGATAAGGC

SEQ ID NO: 29 - A511::ffluc
ATGCCAAAAAATAACAAAGAAGAAGTTAAAGAAGTAAACCTTAATTCAGTACAAGAGGATGCGTTAAAGTC

CTTTACGACTGGTTATGGTATCACACCTGATACACAAACAGATGCAGGAGCATTAAGACGTGAGTTCCTAG

ACGACCAAATCTCAATGCTTACTTGGACAGAGAATGATTTAACATTCTATAAAGACATCGCTAAAAAACCA

GCTACATCTACAGTAGCAAAATACGATGTATACATGCAACATGGTAAGGTAGGTCATACTAGATTTACTCG

TGAGATTGGGGTAGCACCAGTAAGTGACCCTAACATCCGTCAAAAAACAGTAAATATGAAATTTGCTTCCG

ATACTAAAAACATCAGTATCGCAGCAGGTCTAGTAAACAACATTCAAGACCCAATGCAAATTTTGACTGAC

GATGCTATCGTAAATATTGCTAAAACAATTGAGTGGGCTTCATTCTTTGGAGATTCTGACTTATCAGATAG

CCCAGAACCACAAGCAGGACTAGAATTTGACGGCTTGGCTAAACTTATTAACCAAGATAACGTTCATGATG

-continued

CTCGTGGAGCTAGCTTGACTGAAAGCTTGTTAAACCAAGCAGCAGTAATGATTAGTAAAGGTTATGGTACA

CCTACAGATGCTTACATGCCAGTAGGGGTTCAAGCAGACTTTGTTAACCAACAACTTTCTAAACAAACACA

ACTTGTTCGCGATAACGGAAACAACGTAAGCGTTGGTTTCAACATCCAAGGTTTCCATTCAGCTCGTGGAT

TTATCAAACTTCACGGTTCTACAGTAATGGAAAACGAACAAATCTTAGATGAACGTATTCTTGCTTTACCA

ACAGCTCCACAACCAGCTAAGGTAACTGCAACACAAGAAGCAGGTAAAAAAGGACAATTTAGAGCAGAAGA

TTTAGCAGCACATGAATATAAAGTTGTTGTAAGTTCTGACGATGCAGAGTCTATTGCAAGTGAAGTGGCTA

CAGCTACAGTTACTGCAAAAGATGACGGCGTTAAACTAGAAATCGAATTAGCTCCAATGTATAGCTCTCGT

CCACAATTCGTTTCAATCTATAGAAAAGGTGCAGAAACAGGTTTATTCTACCTAATCGCTCGTGTACCTGC

TAGCAAAGCAGAGAACAACGTAATCACTTTCTACGACTTAAACGACTCTATTCCTGAAACAGTAGACGTAT

TCGTTGGTGAAATGTCGGCTAACGTAGTACACTTGTTTGAATTACTACCAATGATGAGATTACCTCTAGCT

CAAATTAACGCATCTGTTACATTTGCAGTTTTATGGTATGGCGCATTAGCTCTAAGAGCACCTAAGAAATG

GGTACGTATTAGAAACGTTAAATATATTCCTGTAAAAAACGTTCATAGCAACTAAGAGGAGGTAAATATAT

ATGGAAGACGCCAAAAACATAAAGAAAGGCCCGGCGCCATTCTATCCTCTAGAGGATGGAACCGCTGGAGA

GCAACTGCATAAGGCTATGAAGAGATACGCCCTGGTTCCTGGAACAATTGCTTTTACAGATGCACATATCG

AGGTGAACATCACGTACGCGGAATACTTCGAAATGTCCGTTCGGTTGGCAGAAGCTATGAAACGATATGGG

CTGAATACAAATCACAGAATCGTCGTATGCAGTGAAAACTCTCTTCAATTCTTTATGCCGGTGTTGGGCGC

GTTATTTATCGGAGTTGCAGTTGCGCCCGCGAACGACATTTATAATGAACGTGAATTGCTCAACAGTATGA

ACATTTCGCAGCCTACCGTAGTGTTTGTTTCCAAAAAGGGGTTGCAAAAAATTTTGAACGTGCAAAAAAAA

TTACCAATAATCCAGAAAATTATTATCATGGATTCTAAAACGGATTACCAGGGATTTCAGTCGATGTACAC

GTTCGTCACATCTCATCTACCTCCCGGTTTTAATGAATACGATTTTGTACCAGAGTCCTTTGATCGTGACA

AAACAATTGCACTGATAATGAATTCCTCTGGATCTACTGGGTTACCTAAGGGTGTGGCCCTTCCGCATAGA

ACTGCCTGCGTCAGATTCTCGCATGCCAGAGATCCTATTTTTGGCAATCAAATCATTCCGGATACTGCGAT

TTTAAGTGTTGTTCCATTCCATCACGGTTTTGGAATGTTTACTACACTCGGATATTTGATATGTGGATTTC

GAGTCGTCTTAATGTATAGATTTGAAGAAGAGCTGTTTTTACGATCCCTTCAGGATTACAAAATTCAAAGT

GCGTTGCTAGTACCAACCCTATTTTCATTCTTCGCCAAAAGCACTCTGATTGACAAATACGATTTATCTAA

TTTACACGAAATTGCTTCTGGGGGCGCACCTCTTTCGAAAGAAGTCGGGGAAGCGGTTGCAAAACGCTTCC

ATCTTCCAGGGATACGACAAGGATATGGGCTCACTGAGACTACATCAGCTATTCTGATTACACCCGAGGGG

GATGATAAACCGGGCGCGGTCGGTAAAGTTGTTCCATTTTTTGAAGCGAAGGTTGTGGATCTGGATACCGG

GAAAACGCTGGGCGTTAATCAGAGAGGCGAATTATGTGTCAGAGGACCTATGATTATGTCCGGTTATGTAA

ACAATCCGGAAGCGACCAACGCCTTGATTGACAAGGATGGATGGCTACATTCTGGAGACATAGCTTACTGG

GACGAAGACGAACACTTCTTCATAGTTGACCGCTTGAAGTCTTTAATTAAATACAAAGGATATCAGGTGGC

CCCCGCTGAATTGGAATCGATATTGTTACAACACCCCAACATCTTCGACGCGGGCGTGGCAGGTCTTCCCG

ACGATGACGCCGGTGAACTTCCCGCCGCCGTTGTTGTTTTGGAGCACGGAAAGACGATGACGGAAAAAGAG

ATCGTGGATTACGTCGCCAGTCAAGTAACAACCGCGAAAAAGTTGCGCGGAGGAGTTGTGTTTGTGGACGA

AGTACCGAAAGGTCTTACCGGAAAACTCGACGCAAGAAAAATCAGAGAGATCCTCATAAAGGCCAAGAAGG

GCGGAAAGTCCAAATTGTAATAATTATAGGATAATTGAATAAAAACAGTATAGAGAGCAGATAAATACTGC

TCTCTATTTTACTAATAAGGAGGATTTAAATTGCTAAAAAATACAAACTTAGCTAATTATAAAAAAGTGAA

TACACGGTTTGGAAATCTTAGTTTTGACGACAAAGGTATTTCTAATGACTTAACGGAAGAACAGCAAAAAG

AATTAGGTAAGCTTCGAGGATTCGAATATATTAAGACAGAACAGAAAACAAAGAAGAACCTAAGAAAGAA

GAACCTAAGAAAGAAGAACCTAAGAAAGAAGAACCTAAGAAAGAAGAACCTAAGAAAGAAGAACCTAAGAA

AGAAAGTACAGAAAATGAATTAGACAGCTTCTTAGCTAAAGAGCCTTCAATCAAAGAATTAAAAGAATTTG

-continued

CGAGTAAAAAAGGCATTAAAATTGAAAAAACTAAGAAAAATGATATAATTGAAGAACTAAAGAGAGGGTAA

TGTATAATGTATGGAGGTTATGAAGGACAAGATTCTTACGAATACCCTTACTCACATGGGAACCCTAAGCA

TGTAGAGCCAGAAAAAGTTGACGAATATGTTCTTTCTGATTATGGTTGGACTGCGGAAACAATTAAAGCAT

ACATGTATGGTGTTCGTGTAGTAGACCCTGAAACAGGAGAGGAAATGGGAGACACCTTCTACAATCATATT

ATAGAGGTTGCCGTTGATAAGGC

SEQ ID NO: 30 - P100::ffluc
ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAATATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAGCTTGTTCGTGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGACTTAGCAGCACACGAATACAAAGTTGTTGTAAGTTCTGACGATGCAGAGTCTATTGCAAGTGAAGTGG

CTACAGCTACAGTTACTGCAAAAGATGACGGCGTTAAACTAGAAATCGAGTTAGCTCCAATGTACAGCTCC

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTATGACTTAAACGACTCTATTCCTGAAACAGTAGACG

TATTCGTTGGTGAAATGTCTGCTAACGTAGTACACTTGTTTGAATTACTACCAATGATGAGATTACCTCTA

GCTCAAATTAACGCATCTGTTACATTTGCAGTTTTATGGTATGGAGCATTAGCTCTAAGAGCACCTAAGAA

ATGGGTACGTATTAGAAACGTTAAATATATTCCTGTAAAAAACGTTCATAGCAACTAAGAGGAGGTAAATA

TATATGGAAGACGCCAAAAACATAAAGAAAGGCCCGGCGCCATTCTATCCTCTAGAGGATGGAACCGCTGG

AGAGCAACTGCATAAGGCTATGAAGAGATACGCCCTGGTTCCTGGAACAATTGCTTTTACAGATGCACATA

TCGAGGTGAACATCACGTACGCGGAATACTTCGAAATGTCCGTTCGGTTGGCAGAAGCTATGAAACGATAT

GGGCTGAATACAAATCACAGAATCGTCGTATGCAGTGAAAACTCTCTTCAATTCTTTATGCCGGTGTTGGG

CGCGTTATTTATCGGAGTTGCAGTTGCGCCCGCGAACGACATTTATAATGAACGTGAATTGCTCAACAGTA

TGAACATTTCGCAGCCTACCGTAGTGTTTGTTTCCAAAAAGGGGTTGCAAAAAATTTTGAACGTGCAAAAA

AAATTACCAATAATCCAGAAAATTATTATCATGGATTCTAAAACGGATTACCAGGGATTTCAGTCGATGTA

CACGTTCGTCACATCTCATCTACCTCCCGGTTTTAATGAATACGATTTTGTACCAGAGTCCTTTGATCGTG

ACAAAACAATTGCACTGATAATGAATTCCTCTGGATCTACTGGGTTACCTAAGGGTGTGGCCCTTCCGCAT

AGAACTGCCTGCGTCAGATTCTCGCATGCCAGAGATCCTATTTTTGGCAATCAAATCATTCCGGATACTGC

GATTTTAAGTGTTGTTCCATTCCATCACGGTTTTGGAATGTTTACTACACTCGGATATTTGATATGTGGAT

TTCGAGTCGTCTTAATGTATAGATTTGAAGAAGAGCTGTTTTTACGATCCCTTCAGGATTACAAAATTCAA

AGTGCGTTGCTAGTACCAACCCTATTTTCATTCTTCGCCAAAAGCACTCTGATTGACAAATACGATTTATC

TAATTTACACGAAATTGCTTCTGGGGGCGCACCTCTTTCGAAAGAAGTCGGGGAAGCGGTTGCAAAACGCT

TCCATCTTCCAGGGATACGACAAGGATATGGGCTCACTGAGACTACATCAGCTATTCTGATTACACCCGAG

-continued

GGGGATGATAAACCGGGCGCGGTCGGTAAAGTTGTTCCATTTTTTGAAGCGAAGGTTGTGGATCTGGATAC

CGGGAAAACGCTGGGCGTTAATCAGAGAGGCGAATTATGTGTCAGAGGACCTATGATTATGTCCGGTTATG

TAAACAATCCGGAAGCGACCAACGCCTTGATTGACAAGGATGGATGGCTACATTCTGGAGACATAGCTTAC

TGGGACGAAGACGAACACTTCTTCATAGTTGACCGCTTGAAGTCTTTAATTAAATACAAAGGATATCAGGT

GGCCCCCGCTGAATTGGAATCGATATTGTTACAACACCCCAACATCTTCGACGCGGGCGTGGCAGGTCTTC

CCGACGATGACGCCGGTGAACTTCCCGCCGCCGTTGTTGTTTTGGAGCACGGAAAGACGATGACGGAAAAA

GAGATCGTGGATTACGTCGCCAGTCAAGTAACAACCGCGAAAAAGTTGCGCGGAGGAGTTGTGTTTGTGGA

CGAAGTACCGAAAGGTCTTACCGGAAAACTCGACGCAAGAAAAATCAGAGAGATCCTCATAAAGGCCAAGA

AGGGCGGAAAGTCCAAATTGTAATAATTATAGGATAATTGAATAAAAACAGTATAGAGAGCAGATAAATAC

TGCTCTCTATTTTACTAATAAGGAGGATTTAAATTGCTAAAAAATACAAACTTAGCTAATTATAAAAAAGT

GAATACACGATTTGGAAATCTTAGTTTTGATGATAAAGGTATTTCTAATGACCTAACGGAAGAGCAGCAAA

AAGAATTAGGTAAGCTTAGAGGATTCGAATATATTAAGACAGAACAGAAAACGAAAGAAGAACCTAAGAAA

GAAGAACCTAAGAAAGAAAGTACAGAAAATGAATTAGACAGCTTCTTAGCTAAAGAACCTTCAATCAAAGA

ATTAAAAGAATTTGCGAGTAAAAAAGGCATTAAAATTGAAAAAACTAAGAAAAATGATATAATTGAAGAAC

TAAAGAGAGGGTAATGTACAATGTATGGAGGTTATGAAGGACAAGATTCTTACGAATACCCTTACTCACAC

GGGAACCCTAAGCATGTAGAGCCAGAAAAAGTTGACGAATATGTTCTTTCTGATTATGGCTGGACTGCGGA

AACAATTAAAGCATACATGTATGGTGTTCGTGTAGTAGACCCTGAAACAGGAGAGGAAATGGGAGACACCT

TCTACAATCATATTATAGAGGTTGCCGTTGATAAGGC

SEQ ID NO: 31 - LP124::nluc
ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAACATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAATAATAAGAGGAGG

TAAATATATATGGTCTTCACACTCGAAGATTTCGTTGGGGACTGGCGACAGACAGCCGGCTACAACCTGGA

CCAAGTCCTTGAACAGGGAGGTGTGTCCAGTTTGTTTCAGAATCTCGGGGTGTCCGTAACTCCGATCCAAA

-continued

GGATTGTCCTGAGCGGTGAAAATGGGCTGAAGATCGACATCCATGTCATCATCCCGTATGAAGGTCTGAGC

GGCGACCAAATGGGCCAGATCGAAAAAATTTTTAAGGTGGTGTACCCTGTGGATGATCATCACTTTAAGGT

GATCCTGCACTATGGCACACTGGTAATCGACGGGGTTACGCCGAACATGATCGACTATTTCGGACGGCCGT

ATGAAGGCATCGCCGTGTTCGACGGCAAAAAGATCACTGTAACAGGGACCCTGTGGAACGGCAACAAAATT

ATCGACGAGCGCCTGATCAACCCCGACGGCTCCCTGCTGTTCCGAGTAACCATCAACGGAGTGACCGGCTG

GCGGCTGTGCGAACGCATTCTGGCGTAATAATTATAGGATAATTGAATAAAAACAGTATAGAGAGCAGATA

AATACTGCTCTCTATTTTACTAATAAGGAGGATTTAAATTGCTAAAAAATACAAACTTAGCTAATTATAAA

AAAGTGAATACACGGTTTGGAAATCTTAGTTTTGACGACAAAGGTATTTCTAATGACTTAACGGAAGAACA

GCAAAAAGAATTAGGTAAGCTTCGAGGATTCGAATATATTAAGACAGAACAGAAAACAAAAGAAGAACCTA

AGAAAGAAGAACCTAAGAAAGAAGAACCTAAGAAAGAAGAACCTAAGAAAGAAGAACCTAAGAAAGAAGAA

CCTAAGAAAGAAAGTACAGAAAATGAATTAGACAGCTTCTTAGCTAAAGAGCCTTCAATCAAAGAATTAAA

AGAATTTGCGAGTAAAAAAGGCATTAAAATTGAAAAAACTAAGAAAAATGATATAATTGAAGAACTAAAGA

GAGGGTAATGTATAATGTATGGAGGTTATGAAGGACAAGATTCTTACGAATACCCTTACTCACATGGGAAC

CCTAAGCATGTAGAGCCAGAAAAAGTTGACGAATATGTTCTTTCTGATTATGGTTGGACTGCGGAAACAAT

TAAAGCATACATGTATGGTGTTCGTGTAGTAGACCCTGAAACAGGAGAGGAAATGGGAGACACCTTCTACA

ATCATATTATAGAGGTTGCCGTTGATAAGGC

SEQ ID NO: 32 - LP125::nluc
ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAACATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGTGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAATAATAAGAGGAGG

TAAATATATATGGTCTTCACACTCGAAGATTTCGTTGGGGACTGGCGACAGACAGCCGGCTACAACCTGGA

CCAAGTCCTTGAACAGGGAGGTGTGTCCAGTTTGTTTCAGAATCTCGGGGTGTCCGTAACTCCGATCCAAA

GGATTGTCCTGAGCGGTGAAAATGGGCTGAAGATCGACATCCATGTCATCATCCCGTATGAAGGTCTGAGC

GGCGACCAAATGGGCCAGATCGAAAAAATTTTTAAGGTGGTGTACCCTGTGGATGATCATCACTTTAAGGT

-continued

GATCCTGCACTATGGCACACTGGTAATCGACGGGGTTACGCCGAACATGATCGACTATTTCGGACGGCCGT

ATGAAGGCATCGCCGTGTTCGACGGCAAAAAGATCACTGTAACAGGGACCCTGTGGAACGGCAACAAAATT

ATCGACGAGCGCCTGATCAACCCCGACGGCTCCCTGCTGTTCCGAGTAACCATCAACGGAGTGACCGGCTG

GCGGCTGTGCGAACGCATTCTGGCGTAATAATTATAGGATAATTGAATAAAAACAGTATAGAGAGCAGATA

AATACTGCTCTCTATTTTACTAATAAGGAGGATTTAAATTGCTAAAAAATACAAACTTAGCTAATTATAAA

AAAGTGAATACACGGTTTGGAAATCTTAGTTTTGACGACAAAGGTATTTCTAATGACTTAACGGAAGAACA

GCAAAAAGAATTAGGTAAGCTTCGAGGATTCGAATATATTAAGACAGAACAGAAAACAAAAGAAGAACCTA

AGAAAGAAGAACCTAAGAAAGAAAGTACAGAAAATGAATTAGACAGCTTCTTAGCTAAAGAGCCTTCAATC

AAAGAATTAAAAGAATTTGCGAGTAAAAAAGGCATTAAAATTGAAAAAACTAAGAAAAATGATATAATTGA

AGAACTAAAGAGAGGGTAATGTATAATGTATGGAGGTTATGAAGGACAAGATTCTTACGAATACCCTTACT

CACATGGGAACCCTAAGCATGTAGAGCCAGAAAAAGTTGACGAATATGTTCTTTCTGATTATGGTTGGACT

GCGGAAACAATTAAAGCATACATGTATGGTGTTCGTGTAGTAGACCCTGAAACAGGAGAGGAAATGGGAGA

CACCTTCTACAATCATATTATAGAGGTTGCCGTTGATAAGGC

SEQ ID NO: 33 - A511::nluc

ATGCCAAAAAATAACAAAGAAGAAGTTAAAGAAGTAAACCTTAATTCAGTACAAGAGGATGCGTTAAAGTC

CTTTACGACTGGTTATGGTATCACACCTGATACACAAACAGATGCAGGAGCATTAAGACGTGAGTTCCTAG

ACGACCAAATCTCAATGCTTACTTGGACAGAGAATGATTTAACATTCTATAAAGACATCGCTAAAAAACCA

GCTACATCTACAGTAGCAAAATACGATGTATACATGCAACATGGTAAGGTAGGTCATACTAGATTTACTCG

TGAGATTGGGGTAGCACCAGTAAGTGACCCTAACATCCGTCAAAAAACAGTAAATATGAAATTTGCTTCCG

ATACTAAAAACATCAGTATCGCAGCAGGTCTAGTAAACAACATTCAAGACCCAATGCAAATTTTGACTGAC

GATGCTATCGTAAATATTGCTAAAACAATTGAGTGGGCTTCATTCTTTGGAGATTCTGACTTATCAGATAG

CCCAGAACCACAAGCAGGACTAGAATTTGACGGCTTGGCTAAACTTATTAACCAAGATAACGTTCATGATG

CTCGTGGAGCTAGCTTGACTGAAAGCTTGTTAAACCAAGCAGCAGTAATGATTAGTAAAGGTTATGGTACA

CCTACAGATGCTTACATGCCAGTAGGGGTTCAAGCAGACTTTGTTAACCAACAACTTTCTAAACAAACACA

ACTTGTTCGCGATAACGGAAACAACGTAAGCGTTGGTTTCAACATCCAAGGTTTCCATTCAGCTCGTGGAT

TTATCAAACTTCACGGTTCTACAGTAATGGAAAACGAACAAATCTTAGATGAACGTATTCTTGCTTTACCA

ACAGCTCCACAACCAGCTAAGGTAACTGCAACACAAGAAGCAGGTAAAAAAGGACAATTTAGAGCAGAAGA

TTTAGCAGCACATGAATATAAAGTTGTTGTAAGTTCTGACGATGCAGAGTCTATTGCAAGTGAAGTGGCTA

CAGCTACAGTTACTGCAAAAGATGACGGCGTTAAACTAGAAATCGAATTAGCTCCAATGTATAGCTCTCGT

CCACAATTCGTTTCAATCTATAGAAAAGGTGCAGAAACAGGTTTATTCTACCTAATCGCTCGTGTACCTGC

TAGCAAAGCAGAGAACAACGTAATCACTTTCTACGACTTAAACGACTCTATTCCTGAAACAGTAGACGTAT

TCGTTGGTGAAATGTCGGCTAACGTAGTACACTTGTTTGAATTACTACCAATGATGAGATTACCTCTAGCT

CAAATTAACGCATCTGTTACATTTGCAGTTTTATGGTATGGCGCATTAGCTCTAAGAGCACCTAAGAAATG

GGTACGTATTAGAAACGTTAAATATATTCCTGTAAAAAACGTTCATAGCAACTAAGAGGAGGTAAATATAT

ATGGTCTTCACACTCGAAGATTTCGTTGGGGACTGGCGACAGACAGCCGGCTACAACCTGGACCAAGTCCT

TGAACAGGGAGGTGTGTCCAGTTTGTTTCAGAATCTCGGGGTGTCCGTAACTCCGATCCAAAGGATTGTCC

TGAGCGGTGAAAATGGGCTGAAGATCGACATCCATGTAATCATCCCGTATGAAGGTCTGAGCGGCGACCAA

ATGGGCCAGATCGAAAAAATTTTTAAGGTGGTGTACCCTGTGGATGATCATCACTTTAAGGTGATCCTGCA

CTATGGCACACTGGTAATCGACGGGGTTACGCCGAACATGATCGACTATTTCGGACGGCCGTATGAAGGCA

TCGCCGTGTTCGACGGCAAAAAGATCACTGTAACAGGGACCCTGTGGAACGGCAACAAAATTATCGACGAG

CGCCTGATCAACCCCGACGGCTCCCTGCTGTTCCGAGTAACCATCAACGGAGTGACCGGCTGGCGGCTGTG

-continued

CGAACGCATTCTGGCGTAATAATTATAGGATAATTGAATAAAAACAGTATAGAGAGCAGATAAATACTGCT

CTCTATTTTACTAATAAGGAGGATTTAAATTGCTAAAAAATACAAACTTAGCTAATTATAAAAAAGTGAAT

ACACGGTTTGGAAATCTTAGTTTTGACGACAAAGGTATTTCTAATGACTTAACGGAAGAACAGCAAAAAGA

ATTAGGTAAGCTTCGAGGATTCGAATATATTAAGACAGAACAGAAAACAAAAGAAGAACCTAAGAAAGAAG

AACCTAAGAAAGAAGAACCTAAGAAAGAAGAACCTAAGAAAGAAGAACCTAAGAAAGAAGAACCTAAGAAA

GAAAGTACAGAAAATGAATTAGACAGCTTCTTAGCTAAAGAGCCTTCAATCAAAGAATTAAAAGAATTTGC

GAGTAAAAAAGGCATTAAAATTGAAAAAACTAAGAAAAATGATATAATTGAAGAACTAAAGAGAGGGTAAT

GTATAATGTATGGAGGTTATGAAGGACAAGATTCTTACGAATACCCTTACTCACATGGGAACCCTAAGCAT

GTAGAGCCAGAAAAAGTTGACGAATATGTTCTTTCTGATTATGGTTGGACTGCGGAAACAATTAAAGCATA

CATGTATGGTGTTCGTGTAGTAGACCCTGAAACAGGAGAGGAAATGGGAGACACCTTCTACAATCATATTA

TAGAGGTTGCCGTTGATAAGGC

SEQ ID NO: 34 - P100::nluc
ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAATATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAGCTTGTTCGTGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGACTTAGCAGCACACGAATACAAAGTTGTTGTAAGTTCTGACGATGCAGAGTCTATTGCAAGTGAAGTGG

CTACAGCTACAGTTACTGCAAAAGATGACGGCGTTAAACTAGAAATCGAGTTAGCTCCAATGTACAGCTCC

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTATGACTTAAACGACTCTATTCCTGAAACAGTAGACG

TATTCGTTGGTGAAATGTCTGCTAACGTAGTACACTTGTTTGAATTACTACCAATGATGAGATTACCTCTA

GCTCAAATTAACGCATCTGTTACATTTGCAGTTTTATGGTATGGAGCATTAGCTCTAAGAGCACCTAAGAA

ATGGGTACGTATTAGAAACGTTAAATATATTCCTGTAAAAAACGTTCATAGCAACTAAGAGGAGGTAAATA

TATATGGTCTTCACACTCGAAGATTTCGTTGGGGACTGGCGACAGACAGCCGGCTACAACCTGGACCAAGT

CCTTGAACAGGGAGGTGTGTCCAGTTTGTTTCAGAATCTCGGGGTGTCCGTAACTCCGATCCAAAGGATTG

TCCTGAGCGGTGAAAATGGGCTGAAGATCGACATCCATGTCATCATCCCGTATGAAGGTCTGAGCGGCGAC

CAAATGGGCCAGATCGAAAAAATTTTTAAGGTGGTGTACCCTGTGGATGATCATCACTTTAAGGTGATCCT

GCACTATGGCACACTGGTAATCGACGGGGTTACGCCGAACATGATCGACTATTTCGGACGGCCGTATGAAG

GCATCGCCGTGTTCGACGGCAAAAAGATCACTGTAACAGGGACCCTGTGGAACGGCAACAAAATTATCGAC

GAGCGCCTGATCAACCCCGACGGCTCCCTGCTGTTCCGAGTAACCATCAACGGAGTGACCGGCTGGCGGCT

GTGCGAACGCATTCTGGCGTAATAATTATAGGATAATTGAATAAAAACAGTATAGAGAGCAGATAAATACT

GCTCTCTATTTTACTAATAAGGAGGATTTAAATTGCTAAAAAATACAAACTTAGCTAATTATAAAAAAGTG

-continued

AATACACGATTTGGAAATCTTAGTTTTGATGATAAAGGTATTTCTAATGACCTAACGGAAGAGCAGCAAAA

AGAATTAGGTAAGCTTAGAGGATTCGAATATATTAAGACAGAACAGAAAACGAAAGAAGAACCTAAGAAAG

AAGAACCTAAGAAAGAAAGTACAGAAAATGAATTAGACAGCTTCTTAGCTAAAGAACCTTCAATCAAAGAA

TTAAAAGAATTTGCGAGTAAAAAAGGCATTAAAATTGAAAAAACTAAGAAAAAATGATATAATTGAAGAACT

AAAGAGAGGGTAATGTACAATGTATGGAGGTTATGAAGGACAAGATTCTTACGAATACCCTTACTCACACG

GGAACCCTAAGCATGTAGAGCCAGAAAAAGTTGACGAATATGTTCTTTCTGATTATGGCTGGACTGCGGAA

ACAATTAAAGCATACATGTATGGTGTTCGTGTAGTAGACCCTGAAACAGGAGAGGAAATGGGAGACACCTT

CTACAATCATATTATAGAGGTTGCCGTTGATAAGGC

SEQ ID NO: 35 - LP40::nluc
ATGCCAAAAAATAACAAAGAAGAAGAAGTTAAAGAAGTAAACCTTAATTCAGTACAAGAGGATGCGTTAAA

GTCCTTTACAACTGGTTATGGTATCACACCTGATACACAAACAGATGCAGGGGCACTAAGACGTGAGTTCC

TAGACGACCAAATCTCAATGCTTACTTGGACAGAAAATGATTTAACATTCTACAAAGACATCGCTAAAAAA

CCAGCTACATCTACAGTAGCAAAATACGATGTGTACATGCAACACGGTAAAGTAGGTCATACTAGATTTAC

TCGTGAGATTGGGGTAGCACCAGTAAGTGACCCTAACATCCGTCAAAAAACAGTAAACATGAAATTTGCTT

CTGATACTAAAAATATTAGTATCGCAGCAGGTCTAGTAAACAACATTCAAGACCCTATGCAAATTTTGACT

GATGATGCTATCGTAAATATCGCTAAAACAATTGAGTGGGCTTCATTCTTTGGAGATTCTGACTTATCAGA

TAGCCCAGAACCACAAGCAGGATTAGAATTTGATGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAATAATAAGAGGAGG

TAAATATATATGGTCTTCACACTCGAAGATTTCGTTGGGGACTGGCGACAGACAGCCGGCTACAACCTGGA

CCAAGTCCTTGAACAGGGAGGTGTGTCCAGTTTGTTTCAGAATCTCGGGGTGTCCGTAACTCCGATCCAAA

GGATTGTCCTGAGCGGTGAAAATGGGCTGAAGATCGACATCCATGTCATCATCCCGTATGAAGGTCTGAGC

GGCGACCAAATGGGCCAGATCGAAAAAATTTTTAAGGTGGTGTACCCTGTGGATGATCATCACTTTAAGGT

GATCCTGCACTATGGCACACTGGTAATCGACGGGGTTACGCCGAACATGATCGACTATTTCGGACGGCCGT

ATGAAGGCATCGCCGTGTTCGACGGCAAAAAGATCACTGTAACAGGGACCCTGTGGAACGGCAACAAAATT

ATCGACGAGCGCCTGATCAACCCCGACGGCTCCCTGCTGTTCCGAGTAACCATCAACGGAGTGACCGGCTG

GCGGCTGTGCGAACGCATTCTGGCGTAATAATTATAGGATAATTGAATAAAAACAGTATAGAGAGCAGATA

AATACTGCTCTCTATTTTACTAATAAGGAGGATTTAAATTGCTAAAAAATACAAACTTAGCTAATTATAAA

AAAGTGAATACACGGTTTGGAAATCTTAGTTTTGACGACAAAGGTATTTCTAATGACTTAACGGAAGAACA

GCAAAAAGAATTAGGTAAGCTTCGAGGATTCGAATATATTAAGACAGAACAGAAAACAAAAGAAGAACCTA

AGAAAGAAGAACCTAAGAAAGAAGAACCTAAGAAAGAAAGTACAGAAAATGAATTAGACAGCTTCTTAGCT

-continued

AAAGAGCCTTCAATCAAAGAATTAAAAGAATTTGCGAGTAAAAAAGGCATTAAAATTGAAAAAACTAAGAA

AAACGATATAATTGAAGAACTAAAGAGAGGGTAATGTATAATGTATGGAGGTTATGAAGGACAAGATTCTT

ACGAATACCCTTACTCACATGGGAACCCTAAGCATGTAGAGCCAGAAAAAGTTGACGAATATGTTCTTTCT

GATTATGGTTGGACTGCGGAAACAATTAAAGCATACATGTATGGTGTTCGTGTAGTAGACCCTGAAACAGG

AGAGGAAATGGGAGACACCTTCTACAATCATATTATAGAGGTTGCCGTTGATAAGGC

SEQ ID NO: 36 - COP2 NanoLuc
GAGGAGGTAAATATATATGGTATTCACATTAGAAGATTTTGTAGGGGATTGGCGACAAACAGCGGGATATA

ACTTAGATCAAGTTTTGGAACAGGGTGGAGTCTCAAGCCTCTTTCAAAATCTTGGAGTGAGTGTTACTCCT

ATTCAAAGAATTGTACTATCTGGTGAAAATGGCTTAAAGATTGATATACATGTTATCATTCCATACGAAGG

CTTATCGGGTGATCAAATGGGTCAAATTGAGAAAATCTTTAAAGTAGTGTATCCTGTAGACGATCATCATT

TCAAAGTTATTCTTCACTATGGTACGCTTGTGATAGACGGGGTTACACCAAATATGATTGATTACTTTGGT

CGGCCGTATGAAGGCATTGCTGTTTTTGACGGGAAAAAAATCACCGTCACTGGAACTTTATGGAATGGTAA

CAAAATCATTGATGAACGTTTGATAAATCCAGATGGATCCTTACTTTTCCGCGTGACAATCAACGGAGTAA

CGGGCTGGAGATTATGTGAACGTATTCTAGCATAA

SEQ ID NO: 37-W40_VIP_MLi178 (COP3)
ATGGTATTCACATTGGAAGATTTTGTGGGGGATTGGAGACAGACAGCTGGATATAACTTAGACCAAGTATT

AGAACAGGGTGGAGTGTCAAGCTTATTTCAAAACTTAGGTGTGTCAGTGACTCCAATTCAACGTATTGTGT

TAAGTGGAGAAAACGGTTTAAAAATAGACATTCATGTGATTATTCCGTACGAAGGCCTCAGTGGTGACCAA

ATGGGACAAATAGAGAAAATCTTTAAAGTAGTGTACCCTGTGGACGACCATCACTTTAAAGTAATCTTACA

CTATGGTACGTTAGTAATTGATGGCGTAACGCCAAACATGATAGACTACTTTGGGCGTCCTTATGAAGGCA

TTGCCGTGTTTGACGGCAAAAAGATCACCGTGACAGGTACTCTATGGAATGGAAACAAAATCATTGACGAG

CGTTTAATCAACCCAGACGGCTCTTTACTATTTCGGGTAACAATTAACGGCGTGACCGGATGGCGATTATG

CGAGCGCATTTTAGCCTAA

SEQ ID NO: 38 - A511::COP2
ATGCCAAAAAATAACAAAGAAGAAGTTAAAGAAGTAAACCTTAATTCAGTACAAGAGGATGCGTTAAAGTC

CTTTACGACTGGTTATGGTATCACACCTGATACACAAACAGATGCAGGAGCATTAAGACGTGAGTTCCTAG

ACGACCAAATCTCAATGCTTACTTGGACAGAGAATGATTTAACATTCTATAAAGACATCGCTAAAAAACCA

GCTACATCTACAGTAGCAAAATACGATGTATACATGCAACATGGTAAGGTAGGTCATACTAGATTTACTCG

TGAGATTGGGGTAGCACCAGTAAGTGACCCTAACATCCGTCAAAAAACAGTAAATATGAAATTTGCTTCCG

ATACTAAAAACATCAGTATCGCAGCAGGTCTAGTAAACAACATTCAAGACCCAATGCAAATTTTGACTGAC

GATGCTATCGTAAATATTGCTAAAACAATTGAGTGGGCTTCATTCTTTGGAGATTCTGACTTATCAGATAG

CCCAGAACCACAAGCAGGACTAGAATTTGACGGCTTGGCTAAACTTATTAACCAAGATAACGTTCATGATG

CTCGTGGAGCTAGCTTGACTGAAAGCTTGTTAAACCAAGCAGCAGTAATGATTAGTAAAGGTTATGGTACA

CCTACAGATGCTTACATGCCAGTAGGGGTTCAAGCAGACTTTGTTAACCAACAACTTTCTAAACAAACACA

ACTTGTTCGCGATAACGGAAACAACGTAAGCGTTGGTTTCAACATCCAAGGTTTCCATTCAGCTCGTGGAT

TTATCAAACTTCACGGTTCTACAGTAATGGAAAACGAACAAATCTTAGATGAACGTATTCTTGCTTTACCA

ACAGCTCCACAACCAGCTAAGGTAACTGCAACACAAGAAGCAGGTAAAAAAGGACAATTTAGAGCAGAAGA

TTTAGCAGCACATGAATATAAAGTTGTTGTAAGTTCTGACGATGCAGAGTCTATTGCAAGTGAAGTGGCTA

CAGCTACAGTTACTGCAAAAGATGACGGCGTTAAACTAGAAATCGAATTAGCTCCAATGTATAGCTCTCGT

CCACAATTCGTTTCAATCTATAGAAAAGGTGCAGAAACAGGTTTATTCTACCTAATCGCTCGTGTACCTGC

TAGCAAAGCAGAGAACAACGTAATCACTTTCTACGACTTAAACGACTCTATTCCTGAAACAGTAGACGTAT

TCGTTGGTGAAATGTCGGCTAACGTAGTACACTTGTTTGAATTACTACCAATGATGAGATTACCTCTAGCT

-continued

CAAATTAACGCATCTGTTACATTTGCAGTTTTATGGTATGGCGCATTAGCTCTAAGAGCACCTAAGAAATG

GGTACGTATTAGAAACGTTAAATATATTCCTGTAAAAAACGTTCATAGCAACTAATAATAAGAGGAGGTAA

ATATATATGGTATTCACATTAGAAGATTTTGTAGGGGATTGGCGACAAACAGCGGGATATAACTTAGATCA

AGTTTTGGAACAGGGTGGAGTCTCAAGCCTCTTTCAAAATCTTGGAGTGAGTGTTACTCCTATTCAAAGAA

TTGTACTATCTGGTGAAAATGGCTTAAAGATTGATATACATGTTATCATTCCATACGAAGGCTTATCGGGT

GATCAAATGGGTCAAATTGAGAAAATCTTTAAAGTAGTGTATCCTGTAGACGATCATCATTTCAAAGTTAT

TCTTCACTATGGTACGCTTGTGATAGACGGGGTTACACCAAATATGATTGATTACTTTGGTCGGCCGTATG

AAGGCATTGCTGTTTTTGACGGGAAAAAAATCACCGTCACTGGAACTTTATGGAATGGTAACAAAATCATT

GATGAACGTTTGATAAATCCAGATGGATCCTTACTTTTCCGCGTGACAATCAACGGAGTAACGGGCTGGAG

ATTATGTGAACGTATTCTAGCATAATAATTATAGGATAATTGAATAAAAACAGTATAGAGAGCAGATAAAT

ACTGCTCTCTATTTTACTAATAAGGAGGATTTAAATTGCTAAAAAATACAAACTTAGCTAATTATAAAAAA

GTGAATACACGGTTTGGAAATCTTAGTTTTGACGACAAAGGTATTTCTAATGACTTAACGGAAGAACAGCA

AAAAGAATTAGGTAAGCTTCGAGGATTCGAATATATTAAGACAGAACAGAAAACAAAAGAAGAACCTAAGA

AAGAAGAACCTAAGAAAGAAGAACCTAAGAAAGAAGAACCTAAGAAAGAAGAACCTAAGAAAGAAGAACCT

AAGAAAGAAAGTACAGAAAATGAATTAGACAGCTTCTTAGCTAAAGAGCCTTCAATCAAAGAATTAAAAGA

ATTTGCGAGTAAAAAAGGCATTAAAATTGAAAAAACTAAGAAAAATGATATAATTGAAGAACTAAAGAGAG

GGTAATGTATAATGTATGGAGGTTATGA

SEQ ID NO: 39 - LP124::COP2

ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAACATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAATAATAAGAGGAGG

TAAATATATATGGTATTCACATTAGAAGATTTTGTAGGGGATTGGCGACAAACAGCGGGATATAACTTAGA

TCAAGTTTTGGAACAGGGTGGAGTCTCAAGCCTCTTTCAAAATCTTGGAGTGAGTGTTACTCCTATTCAAA

GAATTGTACTATCTGGTGAAAATGGCTTAAAGATTGATATACATGTTATCATTCCATACGAAGGCTTATCG

-continued

GGTGATCAAATGGGTCAAATTGAGAAAATCTTTAAAGTAGTGTATCCTGTAGACGATCATCATTTCAAAGT

TATTCTTCACTATGGTACGCTTGTGATAGACGGGGTTACACCAAATATGATTGATTACTTTGGTCGGCCGT

ATGAAGGCATTGCTGTTTTTGACGGGAAAAAAATCACCGTCACTGGAACTTTATGGAATGGTAACAAAATC

ATTGATGAACGTTTGATAAATCCAGATGGATCCTTACTTTTCCGCGTGACAATCAACGGAGTAACGGGCTG

GAGATTATGTGAACGTATTCTAGCATAATAATTATAGGATAATTGAATAAAAACAGTATAGAGAGCAGATA

AATACTGCTCTCTATTTTACTAATAAGGAGGATTTAAATTGCTAAAAAATACAAACTTAGCTAATTATAAA

AAAGTGAATACACGGTTTGGAAATCTTAGTTTTGACGACAAAGGTATTTCTAATGACTTAACGGAAGAACA

GCAAAAAGAATTAGGTAAGCTTCGAGGATTCGAATATATTAAGACAGAACAGAAAACAAAAGAAGAACCTA

AGAAAGAAGAACCTAAGAAAGAAGAACCTAAGAAAGAAGAACCTAAGAAAGAAGAACCTAAGAAAGAAGAA

CCTAAGAAAGAAAGTACAGAAAATGAATTAGACAGCTTCTTAGCTAAAGAGCCTTCAATCAAAGAATTAAA

AGAATTTGCGAGTAAAAAAGGCATTAAAATTGAAAAAACTAAGAAAAATGATATAATTGAAGAACTAAAGA

GAGGGTAATGTATAATGTATGGAGGTTATGA

SEQ ID NO: 40 - LP40::COP2
ATGCCAAAAAATAACAAAGAAGAAGAAGTTAAAGAAGTAAACCTTAATTCAGTACAAGAGGATGCGTTAAA

GTCCTTTACAACTGGTTATGGTATCACACCTGATACACAAACAGATGCAGGGGCACTAAGACGTGAGTTCC

TAGACGACCAAATCTCAATGCTTACTTGGACAGAAAATGATTTAACATTCTACAAAGACATCGCTAAAAAA

CCAGCTACATCTACAGTAGCAAAATACGATGTGTACATGCAACACGGTAAAGTAGGTCATACTAGATTTAC

TCGTGAGATTGGGGTAGCACCAGTAAGTGACCCTAACATCCGTCAAAAAACAGTAAACATGAAATTTGCTT

CTGATACTAAAAATATTAGTATCGCAGCAGGTCTAGTAAACAACATTCAAGACCCTATGCAAATTTTGACT

GATGATGCTATCGTAAATATCGCTAAAACAATTGAGTGGGCTTCATTCTTTGGAGATTCTGACTTATCAGA

TAGCCCAGAACCACAAGCAGGATTAGAATTTGATGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAATAATAAGAGGAGG

TAAATATATATGGTATTCACATTAGAAGATTTTGTAGGGGATTGGCGACAAACAGCGGGATATAACTTAGA

TCAAGTTTTGGAACAGGGTGGAGTCTCAAGCCTCTTTCAAAATCTTGGAGTGAGTGTTACTCCTATTCAAA

GAATTGTACTATCTGGTGAAAATGGCTTAAAGATTGATATACATGTTATCATTCCATACGAAGGCTTATCG

GGTGATCAAATGGGTCAAATTGAGAAAATCTTTAAAGTAGTGTATCCTGTAGACGATCATCATTTCAAAGT

TATTCTTCACTATGGTACGCTTGTGATAGACGGGGTTACACCAAATATGATTGATTACTTTGGTCGGCCGT

ATGAAGGCATTGCTGTTTTTGACGGGAAAAAAATCACCGTCACTGGAACTTTATGGAATGGTAACAAAATC

ATTGATGAACGTTTGATAAATCCAGATGGATCCTTACTTTTCCGCGTGACAATCAACGGAGTAACGGGCTG

GAGATTATGTGAACGTATTCTAGCATAATAATTATAGGATAATTGAATAAAAACAGTATAGAGAGCAGATA

-continued

AATACTGCTCTCTATTTTACTAATAAGGAGGATTTAAATTGCTAAAAAATACAAACTTAGCTAATTATAAA

AAAGTGAATACACGGTTTGGAAATCTTAGTTTTGACGACAAAGGTATTTCTAATGACTTAACGGAAGAACA

GCAAAAAGAATTAGGTAAGCTTCGAGGATTCGAATATATTAAGACAGAACAGAAAACAAAAGAAGAACCTA

AGAAAGAAGAACCTAAGAAAGAAGAACCTAAGAAAGAAAGTACAGAAAATGAATTAGACAGCTTCTTAGCT

AAAGAGCCTTCAATCAAAGAATTAAAAGAATTTGCGAGTAAAAAAGGCATTAAAATTGAAAAAACTAAGAA

AAACGATATAATTGAAGAACTAAAGAGAGGGTAATGTATAATGTATGGAGGTTATGAAGGACAAGATTCTT

ACGAATACCCTTACTCACATGGGAACCCTAA

SEQ ID NO: 41 - COP2 NanoLuc
GAGGAGGTAAATATATATGGTATTCACATTAGAAGATTTTGTAGGGGATTGGCGACAAACAGCGGGATATA

ACTTAGATCAAGTTTTGGAACAGGGTGGAGTCTCAAGCCTCTTTCAAAATCTTGGAGTGAGTGTTACTCCT

ATTCAAAGAATTGTACTATCTGGTGAAAATGGCTTAAAGATTGATATACATGTTATCATTCCATACGAAGG

CTTATCGGGTGATCAAATGGGTCAAATTGAGAAAATCTTTAAAGTAGTGTATCCTGTAGACGATCATCATT

TCAAAGTTATTCTTCACTATGGTACGCTTGTGATAGACGGGGTTACACCAAATATGATTGATTACTTTGGT

CGGCCGTATGAAGGCATTGCTGTTTTTGACGGGAAAAAAATCACCGTCACTGGAACTTTATGGAATGGTAA

CAAAATCATTGATGAACGTTTGATAAATCCAGATGGATCCTTACTTTTCCGCGTGACAATCAACGGAGTAA

CGGGCTGGAGATTATGTGAACGTATTCTAGCATAA

SEQ ID NO: 42--A511::COP3
ATGCCAAAAAATAACAAAGAAGAAGTTAAAGAAGTAAACCTTAATTCAGTACAAGAGGATGCGTTAAAGTC

CTTTACGACTGGTTATGGTATCACACCTGATACACAAACAGATGCAGGAGCATTAAGACGTGAGTTCCTAG

ACGACCAAATCTCAATGCTTACTTGGACAGAGAATGATTTAACATTCTATAAAGACATCGCTAAAAAACCA

GCTACATCTACAGTAGCAAAATACGATGTATACATGCAACATGGTAAGGTAGGTCATACTAGATTTACTCG

TGAGATTGGGGTAGCACCAGTAAGTGACCCTAACATCCGTCAAAAAACAGTAAATATGAAATTTGCTTCCG

ATACTAAAAACATCAGTATCGCAGCAGGTCTAGTAAACAACATTCAAGACCCAATGCAAATTTTGACTGAC

GATGCTATCGTAAATATTGCTAAAACAATTGAGTGGGCTTCATTCTTTGGAGATTCTGACTTATCAGATAG

CCCAGAACCACAAGCAGGACTAGAATTTGACGGCTTGGCTAAACTTATTAACCAAGATAACGTTCATGATG

CTCGTGGAGCTAGCTTGACTGAAAGCTTGTTAAACCAAGCAGCAGTAATGATTAGTAAAGGTTATGGTACA

CCTACAGATGCTTACATGCCAGTAGGGGTTCAAGCAGACTTTGTTAACCAACAACTTTCTAAACAAACACA

ACTTGTTCGCGATAACGGAAACAACGTAAGCGTTGGTTTCAACATCCAAGGTTTCCATTCAGCTCGTGGAT

TTATCAAACTTCACGGTTCTACAGTAATGGAAAACGAACAAATCTTAGATGAACGTATTCTTGCTTTACCA

ACAGCTCCACAACCAGCTAAGGTAACTGCAACACAAGAAGCAGGTAAAAAAGGACAATTTAGAGCAGAAGA

TTTAGCAGCACATGAATATAAAGTTGTTGTAAGTTCTGACGATGCAGAGTCTATTGCAAGTGAAGTGGCTA

CAGCTACAGTTACTGCAAAAGATGACGGCGTTAAACTAGAAATCGAATTAGCTCCAATGTATAGCTCTCGT

CCACAATTCGTTTCAATCTATAGAAAAGGTGCAGAAACAGGTTTATTCTACCTAATCGCTCGTGTACCTGC

TAGCAAAGCAGAGAACAACGTAATCACTTTCTACGACTTAAACGACTCTATTCCTGAAACAGTAGACGTAT

TCGTTGGTGAAATGTCGGCTAACGTAGTACACTTGTTTGAATTACTACCAATGATGAGATTACCTCTAGCT

CAAATTAACGCATCTGTTACATTTGCAGTTTTATGGTATGGCGCATTAGCTCTAAGAGCACCTAAGAAATG

GGTACGTATTAGAAACGTTAAATATATTCCTGTAAAAAACGTTCATAGCAACTAATAATAAGAGGAGGTAA

ATATATATGGTATTCACATTGGAAGATTTTGTGGGGGATTGGAGACAGACAGCTGGATATAACTTAGACCA

AGTATTAGAACAGGGTGGAGTGTCAAGCTTATTTCAAAACTTAGGTGTGTCAGTGACTCCAATTCAACGTA

TTGTGTTAAGTGGAGAAAACGGTTTAAAAATAGACATTCATGTGATTATTCCGTACGAAGGCCTCAGTGGT

GACCAAATGGGACAAATAGAGAAAATCTTTAAAGTAGTGTACCCTGTGGACGACCATCACTTTAAAGTAAT

-continued

CTTACACTATGGTACGTTAGTAATTGATGGCGTAACGCCAAACATGATAGACTACTTTGGGCGTCCTTATG

AAGGCATTGCCGTGTTTGACGGCAAAAAGATCACCGTGACAGGTACTCTATGGAATGGAAACAAAATCATT

GACGAGCGTTTAATCAACCCAGACGGCTCTTTACTATTTCGGGTAACAATTAACGGCGTGACCGGATGGCG

ATTATGCGAGCGCATTTTAGCCTAATAATTATAGGATAATTGAATAAAAACAGTATAGAGAGCAGATAAAT

ACTGCTCTCTATTTTACTAATAAGGAGGATTTAAATTGCTAAAAAATACAAACTTAGCTAATTATAAAAAA

GTGAATACACGGTTTGGAAATCTTAGTTTTGACGACAAAGGTATTTCTAATGACTTAACGGAAGAACAGCA

AAAAGAATTAGGTAAGCTTCGAGGATTCGAATATATTAAGACAGAACAGAAAACAAAAGAAGAACCTAAGA

AAGAAGAACCTAAGAAAGAAGAACCTAAGAAAGAAGAACCTAAGAAAGAAGAACCTAAGAAAGAAGAACCT

AAGAAAGAAAGTACAGAAAATGAATTAGACAGCTTCTTAGCTAAAGAGCCTTCAATCAAAGAATTAAAAGA

ATTTGCGAGTAAAAAAGGCATTAAAATTGAAAAAACTAAGAAAAATGATATAATTGAAGAACTAAAGAGAG

GGTAATGTATAATGTATGGAGGTTATGA

SEQ ID NO: 43--LP124::COP3

ATGCCAAAAAATAACAAAGAAGAAGAAGTTAAAGAAGTAAACCTTAATTCAGTACAAGAGGACGCGTTAAA

GTCCTTTACAACTGGTTATGGTATCACACCTGATACACAAACAGATGCAGGAGCATTAAGACGTGAGTTCC

TAGACGACCAAATCTCAATGCTTACTTGGACAGAGAATGATTTAACATTCTATAAAGACATCGCTAAAAAA

CCAGCTACATCTACAGTAGCAAAATACGATGTATACATGCAACATGGTAAGGTAGGTCATACTAGATTTAC

TCGTGAGATTGGGGTAGCACCAGTAAGTGACCCTAACATCCGTCAAAAAACAGTAAACATGAAATTTGCTT

CCGATACTAAAAACATCAGTATCGCAGCAGGTCTAGTAAACAACATTCAAGACCCAATGCAAATTTTGACT

GACGATGCTATCGTAAATATTGCTAAAACAATTGAGTGGGCTTCATTCTTTGGAGATTCTGACTTATCAGA

TAGCCCAGAACCACAAGCAGGACTAGAATTTGACGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAATAATAAGAGGAGG

TAAATATATATGGTATTCACATTGGAAGATTTTGTGGGGGATTGGAGACAGACAGCTGGATATAACTTAGA

CCAAGTATTAGAACAGGGTGGAGTGTCAAGCTTATTTCAAAACTTAGGTGTGTCAGTGACTCCAATTCAAC

GTATTGTGTTAAGTGGAGAAAACGGTTTAAAAATAGACATTCATGTGATTATTCCGTACGAAGGCCTCAGT

GGTGACCAAATGGGACAAATAGAGAAAATCTTTAAAGTAGTGTACCCTGTGGACGACCATCACTTTAAAGT

AATCTTACACTATGGTACGTTAGTAATTGATGGCGTAACGCCAAACATGATAGACTACTTTGGGCGTCCTT

ATGAAGGCATTGCCGTGTTTGACGGCAAAAAGATCACCGTGACAGGTACTCTATGGAATGGAAACAAAATC

ATTGACGAGCGTTTAATCAACCCAGACGGCTCTTTACTATTTCGGGTAACAATTAACGGCGTGACCGGATG

GCGATTATGCGAGCGCATTTTAGCCTAATAATTATAGGATAATTGAATAAAAACAGTATAGAGAGCAGATA

AATACTGCTCTCTATTTTACTAATAAGGAGGATTTAAATTGCTAAAAAATACAAACTTAGCTAATTATAAA

-continued

AAAGTGAATACACGGTTTGGAAATCTTAGTTTTGACGACAAAGGTATTTCTAATGACTTAACGGAAGAACA

GCAAAAAGAATTAGGTAAGCTTCGAGGATTCGAATATATTAAGACAGAACAGAAAACAAAAGAAGAACCTA

AGAAAGAAGAACCTAAGAAAGAAGAACCTAAGAAAGAAGAACCTAAGAAAGAAGAACCTAAGAAAGAAGAA

CCTAAGAAAGAAAGTACAGAAAATGAATTAGACAGCTTCTTAGCTAAAGAGCCTTCAATCAAAGAATTAAA

AGAATTTGCGAGTAAAAAAGGCATTAAAATTGAAAAAACTAAGAAAAATGATATAATTGAAGAACTAAAGA

GAGGGTAATGTATAATGTATGGAGGTTATGA

SEQ ID NO: 44 - LP40::COP3
ATGCCAAAAAATAACAAAGAAGAAGAAGTTAAAGAAGTAAACCTTAATTCAGTACAAGAGGATGCGTTAAA

GTCCTTTACAACTGGTTATGGTATCACACCTGATACACAAACAGATGCAGGGGCACTAAGACGTGAGTTCC

TAGACGACCAAATCTCAATGCTTACTTGGACAGAAAATGATTTAACATTCTACAAAGACATCGCTAAAAAA

CCAGCTACATCTACAGTAGCAAAATACGATGTGTACATGCAACACGGTAAAGTAGGTCATACTAGATTTAC

TCGTGAGATTGGGGTAGCACCAGTAAGTGACCCTAACATCCGTCAAAAAACAGTAAACATGAAATTTGCTT

CTGATACTAAAAATATTAGTATCGCAGCAGGTCTAGTAAACAACATTCAAGACCCTATGCAAATTTTGACT

GATGATGCTATCGTAAATATCGCTAAAACAATTGAGTGGGCTTCATTCTTTGGAGATTCTGACTTATCAGA

TAGCCCAGAACCACAAGCAGGATTAGAATTTGATGGCTTGGCTAAACTTATTAACCAAGATAACGTTCATG

ATGCTCGTGGAGCTAGCTTGACTGAAAGCTTGTTAAACCAAGCAGCAGTAATGATTAGTAAAGGTTATGGT

ACACCTACAGATGCTTACATGCCAGTAGGGGTTCAAGCAGACTTTGTTAACCAACAACTTTCTAAACAAAC

ACAACTTGTTCGCGATAACGGAAACAACGTAAGCGTTGGTTTCAACATCCAAGGTTTCCATTCAGCTCGTG

GATTTATCAAACTTCACGGTTCTACAGTAATGGAAAACGAACAAATCTTAGATGAACGTATTCTTGCTTTA

CCAACAGCTCCACAACCAGCTAAGGTAACTGCAACACAAGAAGCAGGTAAAAAAGGACAATTTAGAGCAGA

AGATTTAGCAGCACATGAATATAAAGTTGTTGTAAGTTCTGACGATGCAGAGTCTATTGCAAGTGAAGTGG

CTACAGCTACAGTTACTGCAAAAGATGACGGCGTTAAACTAGAAATCGAATTAGCTCCAATGTATAGCTCT

CGTCCACAATTCGTTTCAATCTATAGAAAAGGTGCAGAAACAGGTTTATTCTACCTAATCGCTCGTGTACC

TGCTAGCAAAGCAGAGAACAACGTAATCACTTTCTACGACTTAAACGACTCTATTCCTGAAACAGTAGACG

TATTCGTTGGTGAAATGTCGGCTAACGTAGTACACTTGTTTGAATTACTACCAATGATGAGATTACCTCTA

GCTCAAATTAACGCATCTGTTACATTTGCAGTTTTATGGTATGGCGCATTAGCTCTAAGAGCACCTAAGAA

ATGGGTACGTATTAGAAACGTTAAATATATTCCTGTAAAAAACGTTCATAGCAACTAATAATAAGAGGAGG

TAAATATATATGGTATTCACATTGGAAGATTTTGTGGGGGATTGGAGACAGACAGCTGGATATAACTTAGA

CCAAGTATTAGAACAGGGTGGAGTGTCAAGCTTATTTCAAAACTTAGGTGTGTCAGTGACTCCAATTCAAC

GTATTGTGTTAAGTGGAGAAAACGGTTTAAAAATAGACATTCATGTGATTATTCCGTACGAAGGCCTCAGT

GGTGACCAAATGGGACAAATAGAGAAAATCTTTAAAGTAGTGTACCCTGTGGACGACCATCACTTTAAAGT

AATCTTACACTATGGTACGTTAGTAATTGATGGCGTAACGCCAAACATGATAGACTACTTTGGGCGTCCTT

ATGAAGGCATTGCCGTGTTTGACGGCAAAAAGATCACCGTGACAGGTACTCTATGGAATGGAAACAAAATC

ATTGACGAGCGTTTAATCAACCCAGACGGCTCTTTACTATTTCGGGTAACAATTAACGGCGTGACCGGATG

GCGATTATGCGAGCGCATTTTAGCCTAATAATTATAGGATAATTGAATAAAAACAGTATAGAGAGCAGATA

AATACTGCTCTCTATTTTACTAATAAGGAGGATTTAAATTGCTAAAAAATACAAACTTAGCTAATTATAAA

AAAGTGAATACACGGTTTGGAAATCTTAGTTTTGACGACAAAGGTATTTCTAATGACTTAACGGAAGAACA

GCAAAAAGAATTAGGTAAGCTTCGAGGATTCGAATATATTAAGACAGAACAGAAAACAAAAGAAGAACCTA

AGAAAGAAGAACCTAAGAAAGAAGAACCTAAGAAAGAAAGTACAGAAAATGAATTAGACAGCTTCTTAGCT

-continued

AAAGAGCCTTCAATCAAAGAATTAAAAGAATTTGCGAGTAAAAAAGGCATTAAAATTGAAAAAACTAAGAA

AAACGATATAATTGAAGAACTAAAGAGAGGGTAATGTATAATGTATGGAGGTTATGAAGGACAAGATTCTT

ACGAATACCCTTACTCACATGGGAACCCTAA

SEQ ID NO: 45 UTR1 (original)
GAGGAGGTAAATATAT

SEQ ID NO: 46 UTR2
ATAATTTTGATTAACTTTAGAGGAGGTAAATATAT

SEQ ID NO: 47 UTR3
AAGGAGATAAATATAT

SEQ ID NO: 48 UTR4
GAGGAGGTAAATA

SEQ ID NO: 49 UTR5
AAGGAGATAAATA

SEQ ID NO: 50 UTR6
ATAATTTTGATTAACTTTAGAGGAGGTAAATA

SEQ ID NO: 51 UTR7
ATAATTTTGATTAACTTTAAAGGAGATAAATATAT

SEQ ID NO: 52 UTR8
ATAATTTTGATTAACTTTAAAGGAGATAAATA

SEQ ID NO: 53 COPD12
ATGGTTTTTACACTAGAGGATTTTGTCGGGGATTGGCGTCAAACTGCCGGATACAACTTAGATCAAGTGTT

AGAACAGGGTGGAGTAAGTAGTCTTTTCCAAAACTTAGGTGTGTCAGTAACTCCTATTCAACGGATTGTTT

TATCTGGAGAGAACGGTTTGAAAATTGATATTCACGTGATAATTCCGTACGAAGGATTAAGCGGAGATCAG

ATGGGGCAAATTGAGAAAATCTTTAAAGTAGTATACCCAGTTGATGACCATCATTTCAAAGTGATTTTACA

TTACGGAACTCTAGTAATTGACGGTGTGACCCCAAATATGATTGACTATTTTGGCCGTCCATACGAAGGAA

TAGCTGTCTTTGACGGTAAAAAAATTACAGTAACTGGAACATTATGGAACGGAAACAAAATCATTGACGAG

CGTTTAATCAATCCGGATGGCTCTTTACTCTTTCGCGTGACGATTAACGGAGTGACAGGTTGGCGTTTGTG

TGAGCGTATTCTTGCCTAATGA

SEQ ID NO: 54 - Ribosome binding site
TAATAAGAGGAGGTAAATATAT

SEQ ID NO: 55 - pMAK upf
TTACGCCAAGCTTGGCTGCAACGTGAGTTCCTAGACGACC

SEQ ID NO: 56 - dbono380
ATATTTACCTCCTCTTATTATTAGTTGCTATGAACGTTTTTTACAGG

SEQ ID NO: 57 - SO472
ATAAGAGGAGGTAAATATATATGGTATTCACATTAGAAGATTTTG

SEQ ID NO: 58 - SO473
ATTCAATTATCCTATAATTATTATGCTAGAATACGTTCACATAA

SEQ ID NO: 59 - SO474
GTGAACGTATTCTAGCATAATAATTATAGGATAATTGAATAAAAAC

SEQ ID NO: 60 - dbono382
ACGACGGCCAGTGAATTCCCTCGTGGTGTTCTGACTCCCG

SEQ ID NO: 64 - SO670
TAATAAGAGGAGGTAAATATATATGGTATTCACATTGGAAGA

SEQ ID NO: 65 - SO671
ATTCAATTATCCTATAATTATTAGGCTAAAATGCGCTCGC

SEQ ID NO: 66 - SO672
GCGAGCGCATTTTAGCCTAATAATTATAGGATAATTGAAT

EQUIVALENTS

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The foregoing description has been presented only for the purposes of illustration and is not intended to limit the invention to the precise form disclosed, but by the claims appended hereto.

What is claimed is:

1. A composition comprising at least one recombinant phage capable of infecting a target microbe, wherein said phage is selected from the group consisting of LP143, A511, LP101, LP124, LP99, LP48, LP125, P100, and LP40 and comprises nucleic acid sequences encoding at least a capsid protein sequence, a ribosome binding site, and a codon-optimized luciferase marker selected from the group consisting of SEQ ID NO:36 (COP2) and SEQ ID NO:37 (COP3).

2. The composition of claim 1, further comprising at least two, three, four, five, or six recombinant phages capable of infecting a target microbe, wherein each of said phage is selected from the group consisting of LP143, A511, LP101, LP124, LP99, LP48, LP125, P100, and LP40 and comprises nucleic acid sequences encoding at least a capsid protein sequence, a ribosome binding site, and a codon-optimized luciferase marker selected from the group consisting of SEQ ID NO:36 (COP2) and SEQ ID NO:37 (COP3).

3. The composition of claim 1, further comprising greater than six recombinant phage capable of infecting a target microbe, wherein each of said phage is selected from the group consisting of LP143, A511, LP101, LP124, LP99, LP48, LP125, P100, and LP40 and comprises at least a capsid protein sequence, a ribosome binding site, and a codon-optimized luciferase marker selected from the group consisting of SEQ ID NO:36 (COP2) and SEQ ID NO:37 (COP3).

4. The composition of claim 1 wherein the ribosome binding site of each phage is identical.

5. The composition of claim 1 wherein the ribosome binding site of each phage is SEQ ID NO: 54.

6. The composition of claim 1, wherein at least one recombinant phage is A511, LP40 or LP124.

7. The composition of claim 1, wherein the composition comprises A511, LP40 and LP124.

8. The composition of claim 1, wherein the phage is A511.

9. The composition of claim 1, wherein the phage is LP40.

10. The composition of claim 1, wherein the phage is LP124.

11. The composition of claim 1, wherein the target microbe is selected from the group consisting of coliform bacteria, *Escherichia, Shigella, Listeria, Clostridium, Vibrio*, Enterobacteriacae, Cronobacter, *Mycobacterium, Staphylococcus, Bacillus, Campylobacter, Pseudomonas, Streptococcus, Acinetobacter, Klebsiella, Campylobacter*, and *Yersinia.*

12. The composition of claim 1, wherein the target microbe belongs to the genus *Listeria.*

13. The composition of claim 12, wherein the target microbe is *Listeria* selected from the group consisting of *Listeria innocua, Listeria monocytogenes, Listeria seeligeri, Listeria ivanovii, Listeria grayi, Listeria marthii, Listeria rocourti, Listeria welshimeri, Listeria floridensis, Listeria aquatic, Listeria cornellensis, Listeria riparia, Listeria weihenstephanensis, Listeria flieschmannii*, and *Listeria grandensis.*

14. The composition of claim 13, wherein the target microbe is *Listeria monocytogenes.*

15. The composition of claim 1 further comprising an aqueous solution, wherein the aqueous solution comprises:

a) at least one nutrient;

b) at least one selective agent suitable to inhibit growth of at least one non-target microbe in an environmental sample or an agricultural sample;

c) at least one vitamin;

d) at least one divalent metal;

e) at least one buffering agent capable of maintaining the composition at pH 7.0-7.5.

16. The composition of claim 15, further comprising at least one agent to prevent the decomposition of a marker substrate.

17. The composition of claim 16, wherein the at least one agent to prevent decomposition of a marker substrate comprises a compound to prevent the decomposition of luciferin.

18. The composition of claim 17, wherein the compound prevents decomposition of luciferin for between 5 and 10 hours.

19. The composition of claim 17, wherein the compound prevents decomposition of luciferin for less than 5 hours.

20. The composition of claim 17, wherein the compound prevents decomposition of luciferin for greater than 10 hours.

21. The composition of claim 17, wherein the at least one agent to prevent decomposition of the luciferin is selected from the group consisting of non-ionic detergents, oxygen scavengers and emulsifiers.

22. The composition of claim 21, wherein the at least one agent to prevent the decomposition of luciferin is selected from the group consisting of sodium metabisulfite, sodium thiosulfate, polysorbate 80, HEPES and lecithin.

23. The composition of claim 15, further comprising at least one agent suitable to neutralize a sanitizer present in an environmental sample.

24. The composition of claim 23, wherein the at least one agent suitable to neutralize a sanitizer is selected from the group consisting of sodium metabisulfite, sodium thiosulfate, polysorbate 80, HEPES and lecithin.

25. The composition of claim 15, wherein the at least one nutrient is selected from a culture medium, alcohol, sugar, sugar derivatives, and combinations thereof.

26. The composition of claim 25, wherein the at least one nutrient is selected from Brain Heart Infusion medium, Tryptic Soy Broth, glucose, glycerol, pyruvate, and combinations thereof.

27. The composition of claim 15, wherein the at least one selective agent suitable to inhibit growth of a non-target microbe is selected from LiCl, acriflavine, nalidixic acid, cycloheximide, and combinations thereof.

28. The composition of claim 15, wherein the at least one vitamin comprises yeast extract.

29. The composition of claim 15, wherein the at least one divalent metal is selected from $CaCl_2$, MgSO4, and combinations thereof.

30. The composition of claim 15, wherein the at least one buffering agent comprises HEPES buffer.

31. The composition of claim 15, wherein the aqueous solution comprises or consists of Tryptic Soy Broth, LiCl, nalidixic acid, yeast extract, glucose, MgSO4, pyruvate, and HEPES.

32. The composition of claim 15, wherein the aqueous solution comprises or consists of Tryptic Soy Broth, LiCl, nalidixic acid, yeast extract, glucose, MgSO4, pyruvate, HEPES, polysorbate 80, lecithin, and potassium phosphate.

33. The composition of claim 1, further comprising a substrate for luciferase.

34. The composition of claim 33, wherein the substrate is luciferin.

35. The composition of claim 1, further comprising a buffer to facilitate a light reaction.

36. A method of determining the presence or absence of a target microbe in an environmental sample, an agricultural sample or both, comprising:

a) contacting an environmental sample, an agricultural sample, or both with a composition of claim 1 to form a test sample; and b) detecting the presence or absence of light thereby determining the presence or absence of a target microbe in an environmental sample or an agricultural sample.

37. The method of claim 36, wherein the environmental sample is selected from the group consisting of an agricultural production facility, a food production facility, a container, a machine, a processing plant, a storage facility, a health care facility, an educational institution, a loading dock, a cargo hold, a sink, a vehicle, an airport, and a customs facility.

38. The method of claim 37, wherein the environmental sample is from a health care facility.

39. The method of claim 38, wherein the health care facility is a clinic, an emergency medical services location, a hospice, a hospital ship, a hospital train, a hospital, a military medical installation, a doctor's office, a long term care facility, respite care facility, or a quarantine station.

40. The method of claim 36, wherein the environmental sample is from a food production facility.

41. The method of claim 40, wherein the food production facility is a farm, a boat, a food distribution facility, a food processing plant, a food retail location, a home, or a restaurant.

42. The method of claim 36, wherein the agricultural sample is stock feed or food supply.

43. The method of 42, wherein the food supply is for human or non-human consumption.

44. The method of 43, wherein the food supply is plant or animal.

45. The method of 44, wherein the food supply is a dairy product, a fruit product, a grain product, a sweet, a vegetable product, a meat product, or a combination thereof.

46. The method of 45, wherein the dairy product is milk, butter, yogurt, cheese, ice cream, queso fresco, a derivative thereof or a combinations thereof.

47. The method of 45, wherein the fruit product is an apple, orange, banana, berry, lemon, or a combination thereof.

48. The method of 45, wherein the grain product is wheat, rice, oats, barley, bread, pasta, or a combination thereof.

49. The method of 45, wherein the sweet product is candy, soft drinks, cake, pie, or a combination thereof.

50. The method of 45, wherein the vegetable product is spinach, carrots, onions, peppers, avocado, broccoli, or a combination thereof.

51. The method of claim 50, wherein the vegetable product is guacamole.

52. The method of claim 45, wherein the meat product is chicken, fish, turkey, pork, beef, or a combination thereof.

53. The method of claim 52, wherein the meat product is whole muscle meat, ground meat, or a combination thereof.

54. The method of claim 52, wherein the meat product is selected from deli turkey, ground beef, or a combination thereof.

55. The method of claim 42, wherein the food supply is a liquid or a solid.

56. A kit comprising a composition of claim 1.

57. A kit comprising: a first container comprising at least one recombinant phage capable of infecting a target microbe, wherein said phage is selected from the group consisting of LP143, A511, LP101, LP124, LP99, LP48, LP125, P100, and LP40 and comprises nucleic acid sequences encoding at least a capsid protein sequence, a ribosome binding site, and a codon-optimized luciferase marker selected from the group consisting of SEQ ID NO:36 (COP2) and SEQ ID NO:37 (COP3); a second container comprising a aqueous solution composition comprising Tryptic Soy Broth, LiCl, nalidixic acid, yeast extract, glucose, MgSO4, pyruvate, HEPES, polysorbate 80, lecithin, and potassium phosphate; a third container containing a substrate; and a fourth container containing a buffer to optimize light detection.

58. The kit of claim 57, further comprising a swab.

59. The kit of claim 57, further comprising a container for facilitating detection of light.

* * * * *

SEQUENCE LISTING

```
<160> NUMBER OF SEQ ID NOS: 103

<210> SEQ ID NO 1
<211> LENGTH: 1653
<212> TYPE: DNA
<213> ORGANISM: Photinus pyralis

<400> SEQUENCE: 1

atggaagacg ccaaaaacat aaagaaaggc ccggcgccat tctatcctct agaggatgga     60

accgctggag agcaactgca taaggctatg aagagatacg ccctggttcc tggaacaatt    120

gcttttacag atgcacatat cgaggtgaac atcacgtacg cggaatactt cgaaatgtcc    180

gttcggttgg cagaagctat gaaacgatat gggctgaata caaatcacag aatcgtcgta    240

tgcagtgaaa actctcttca attctttatg ccggtgttgg gcgcgttatt tatcggagtt    300

gcagttgcgc ccgcgaacga catttataat gaacgtgaat tgctcaacag tatgaacatt    360

tcgcagccta ccgtagtgtt tgtttccaaa aaggggttgc aaaaaatttt gaacgtgcaa    420

aaaaaattac caataatcca gaaaattatt atcatggatt ctaaaacgga ttaccaggga    480

tttcagtcga tgtacacgtt cgtcacatct catctacctc ccggttttaa tgaatacgat    540

tttgtaccag agtcctttga tcgtgacaaa acaattgcac tgataatgaa ttcctctgga    600

tctactgggt tacctaaggg tgtggccctt ccgcatagaa ctgcctgcgt cagattctcg    660

catgccagag atcctatttt tggcaatcaa atcattccgg atactgcgat tttaagtgtt    720

gttccattcc atcacggttt tggaatgttt actacactcg gatatttgat atgtggattt    780

cgagtcgtct taatgtatag atttgaagaa gagctgtttt tacgatccct tcaggattac    840

aaaattcaaa gtgcgttgct agtaccaacc ctattttcat tcttcgccaa aagcactctg    900

attgacaaat acgatttatc taatttacac gaaattgctt ctgggggcgc acctctttcg    960

aaagaagtcg gggaagcggt tgcaaaacgc ttccatcttc cagggatacg acaaggatat   1020

gggctcactg agactacatc agctattctg attacacccg agggggatga taaaccgggc   1080

gcggtcggta aagttgttcc atttttttgaa gcgaaggttg tggatctgga taccgggaaa   1140

acgctgggcg ttaatcagag aggcgaatta tgtgtcagag gacctatgat tatgtccggt   1200

tatgtaaaca atccggaagc gaccaacgcc ttgattgaca aggatggatg gctacattct   1260

ggagacatag cttactggga cgaagacgaa cacttcttca tagttgaccg cttgaagtct   1320

ttaattaaat acaaaggata tcaggtggcc cccgctgaat tggaatcgat attgttacaa   1380

caccccaaca tcttcgacgc gggcgtggca ggtcttcccg acgatgacgc cggtgaactt   1440

cccgccgccg ttgttgtttt ggagcacgga aagacgatga cggaaaaaga gatcgtggat   1500

tacgtcgcca gtcaagtaac aaccgcgaaa aagttgcgcg gaggagttgt gtttgtggac   1560

gaagtaccga aaggtcttac cggaaaactc gacgcaagaa aaatcagaga gatcctcata   1620

aaggccaaga agggcggaaa gtccaaattg taa                                1653
```

<210> SEQ ID NO 2
<211> LENGTH: 550
<212> TYPE: PRT
<213> ORGANISM: Photinus pyralis

<400> SEQUENCE: 2

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val

```
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ser Lys Leu
545                 550
```

<210> SEQ ID NO 3
<211> LENGTH: 516
<212> TYPE: DNA
<213> ORGANISM: Artificial Sequence
<220> FEATURE:
<223> OTHER INFORMATION: Synthetic Polynucleotide

<400> SEQUENCE: 3

```
atggtcttca cactcgaaga tttcgttggg gactggcgac agacagccgg ctacaacctg     60

gaccaagtcc ttgaacaggg aggtgtgtcc agtttgtttc agaatctcgg ggtgtccgta    120

actccgatcc aaaggattgt cctgagcggt gaaaatgggc tgaagatcga catccatgtc    180

atcatcccgt atgaaggtct gagcggcgac caaatgggcc agatcgaaaa aatttttaag    240

gtggtgtacc ctgtggatga tcatcacttt aaggtgatcc tgcactatgg cacactggta    300

atcgacgggg ttacgccgaa catgatcgac tatttcggac ggccgtatga aggcatcgcc    360

gtgttcgacg gcaaaaagat cactgtaaca gggaccctgt ggaacggcaa caaaattatc    420

gacgagcgcc tgatcaaccc cgacggctcc ctgctgttcc gagtaaccat caacggagtg    480

accggctggc ggctgtgcga acgcattctg gcgtaa                             516
```

<210> SEQ ID NO 4
<211> LENGTH: 171
<212> TYPE: PRT
<213> ORGANISM: Artificial Sequence
<220> FEATURE:
<223> OTHER INFORMATION: Polypeptide

<400> SEQUENCE: 4

```
Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30
```

```
Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170
```

<210> SEQ ID NO 5
<211> LENGTH: 1407
<212> TYPE: DNA
<213> ORGANISM: LP40 Phage

<400> SEQUENCE: 5

```
atgccaaaaa ataacaaaga agaagaagtt aaagaagtaa accttaattc agtacaagag     60

gatgcgttaa agtcctttac aactggttat ggtatcacac ctgatacaca aacagatgca    120

ggggcactaa gacgtgagtt cctagacgac caaatctcaa tgcttacttg gacagaaaat    180

gatttaacat tctacaaaga catcgctaaa aaaccagcta catctacagt agcaaaatac    240

gatgtgtaca tgcaacacgg taaagtaggt catactagat ttactcgtga gattggggta    300

gcaccagtaa gtgaccctaa catccgtcaa aaaacagtaa acatgaaatt tgcttctgat    360

actaaaaata ttagtatcgc agcaggtcta gtaaacaaca ttcaagaccc tatgcaaatt    420

ttgactgatg atgctatcgt aaatatcgct aaaacaattg agtgggcttc attctttgga    480

gattctgact tatcagatag cccagaacca caagcaggat tagaatttga tggcttggct    540

aaacttatta accaagataa cgttcatgat gctcgtggag ctagcttgac tgaaagcttg    600

ttaaaccaag cagcagtaat gattagtaaa ggttatggta cacctacaga tgcttacatg    660

ccagtagggg ttcaagcaga ctttgttaac caacaacttt ctaaacaaac acaacttgtt    720

cgcgataacg gaaacaacgt aagcgttggt ttcaacatcc aaggtttcca ttcagctcgt    780

ggatttatca aacttcacgg ttctacagta atggaaaacg aacaaatctt agatgaacgt    840

attcttgctt taccaacagc tccacaacca gctaaggtaa ctgcaacaca agaagcaggt    900

aaaaaaggac aatttagagc agaagattta gcagcacatg aatataaagt tgttgtaagt    960

tctgacgatg cagagtctat tgcaagtgaa gtggctacag ctacagttac tgcaaaagat   1020

gacggcgtta aactagaaat cgaattagct ccaatgtata gctctcgtcc acaattcgtt   1080

tcaatctata gaaaaggtgc agaaacaggt ttattctacc taatcgctcg tgtacctgct   1140

agcaaagcag agaacaacgt aatcactttc tacgacttaa acgactctat tcctgaaaca   1200

gtagacgtat tcgttggtga aatgtcggct aacgtagtac acttgtttga attactacca   1260

atgatgagat tacctctagc tcaaattaac gcatctgtta catttgcagt tttatggtat   1320
```

```
ggcgcattag ctctaagagc acctaagaaa tgggtacgta ttagaaacgt taaatatatt   1380

cctgtaaaaa acgttcatag caactaa                                       1407


<210> SEQ ID NO 6
<211> LENGTH: 468
<212> TYPE: PRT
<213> ORGANISM: LP40 Phage

<400> SEQUENCE: 6

Met Pro Lys Asn Asn Lys Glu Glu Glu Val Lys Glu Val Asn Leu Asn
1               5                   10                  15

Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110

Val Asn Met Lys Phe Ala Ser Asp Thr Lys Asn Ile Ser Ile Ala Ala
        115                 120                 125

Gly Leu Val Asn Asn Ile Gln Asp Pro Met Gln Ile Leu Thr Asp Asp
    130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
    210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
    290                 295                 300

Phe Arg Ala Glu Asp Leu Ala Ala His Glu Tyr Lys Val Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
```

```
        355                 360                 365

Thr Gly Leu Phe Tyr Leu Ile Ala Arg Val Pro Ala Ser Lys Ala Glu
    370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
        435                 440                 445

Lys Lys Trp Val Arg Ile Arg Asn Val Lys Tyr Ile Pro Val Lys Asn
    450                 455                 460

Val His Ser Asn
465


<210> SEQ ID NO 7
<211> LENGTH: 1407
<212> TYPE: DNA
<213> ORGANISM: LP48 phage

<400> SEQUENCE: 7

atgccaaaaa ataacaaaga agaagaagtt aaagaagtaa accttaattc agtacaagag     60

gacgcgttaa agtcctttac aactggttat ggtatcacac ctgatacaca aacagatgca    120

ggagcattaa gacgtgagtt cctagacgac caaatctcaa tgcttacttg gacagagaat    180

gatttaacat tctataaaga catcgctaaa aaaccagcta catctacagt agcaaaatac    240

gatgtataca tgcaacatgg taaggtaggt catactagat ttactcgtga gattggggta    300

gcaccagtaa gtgaccctaa catccgtcaa aaaacagtaa acatgaaatt tgcttccgat    360

actaaaaaca tcagtatcgc agcaggtcta gtaaacaaca ttcaagaccc aatgcaaatt    420

ttgactgacg atgctatcgt aaatattgct aaaacaattg agtgggcttc attctttgga    480

gattctgact tatcagatag cccagaacca caagcaggac tagaatttga cggcttggct    540

aaacttatta accaagataa cgttcatgat gctcgtggag ctagcttgac tgaaagcttg    600

ttaaaccaag cagcagtaat gattagtaaa ggttatggta cacctacaga tgcttacatg    660

ccagtagggg ttcaagcaga ctttgttaac caacaacttt ctaaacaaac acaacttgtt    720

cgcgataacg gaaacaacgt aagcgttggt ttcaacatcc aaggtttcca ttcagctcgt    780

ggatttatca aacttcacgg ttctacagta atggaaaacg aacaaatctt agatgaacgt    840

attcttgctt taccaacagc tccacaacca gctaaggtaa ctgcaacaca agaagcaggt    900

aaaaaaggac aatttagagc agaagattta gcagcacatg aatataaagt tgttgtaagt    960

tctgacgatg cagagtctat tgcaagtgaa gtggctacag ctacagttac tgcaaaagat   1020

gacggcgtta aactagaaat cgaattagct ccaatgtata gctctcgtcc acaattcgtt   1080

tcaatctata gaaaaggtgc agaaacaggt ttattctacc taatcgctcg tgtacctgct   1140

agcaaagcag agaacaacgt aatcactttc tacgacttaa acgactctat tcctgaaaca   1200

gtagacgtat tcgttggtga aatgtcggct aacgtagtac acttgtttga attactacca   1260

atgatgagat tacctctagc tcaaattaac gcatctgtta catttgcagt tttatggtat   1320

ggcgcattag ctctaagagc acctaagaaa tgggtacgta ttagaaacgt taaatatatt   1380

cctgtaaaaa acgttcatag caactaa                                        1407
```

<210> SEQ ID NO 8
<211> LENGTH: 468
<212> TYPE: PRT
<213> ORGANISM: LP48 phage

<400> SEQUENCE: 8

```
Met Pro Lys Asn Asn Lys Glu Glu Glu Val Lys Glu Val Asn Leu Asn
1               5                   10                  15

Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110

Val Asn Met Lys Phe Ala Ser Asp Thr Lys Asn Ile Ser Ile Ala Ala
        115                 120                 125

Gly Leu Val Asn Asn Ile Gln Asp Pro Met Gln Ile Leu Thr Asp Asp
    130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
    210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
    290                 295                 300

Phe Arg Ala Glu Asp Leu Ala Ala His Glu Tyr Lys Val Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
    370                 375                 380
```

```
Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
        435                 440                 445

Lys Lys Trp Val Arg Ile Arg Asn Val Lys Tyr Ile Pro Val Lys Asn
    450                 455                 460

Val His Ser Asn
465


<210> SEQ ID NO 9
<211> LENGTH: 1407
<212> TYPE: DNA
<213> ORGANISM: LP099 Phage

<400> SEQUENCE: 9

atgccaaaaa ataacaaaga agaagaagtt aaagaagtaa accttaattc agtacaagag     60

gacgcgttaa agtcctttac aactggttat ggtatcacac ctgatacaca aacagatgca    120

ggagcattaa gacgtgagtt cctagacgac caaatctcaa tgcttacttg gacagagaat    180

gatttaacat tctataaaga catcgctaaa aaaccagcta catctacagt agcaaaatac    240

gatgtataca tgcaacatgg taaggtaggt catactagat ttactcgtga gattggggta    300

gcaccagtaa gtgaccctaa catccgtcaa aaaacagtaa acatgaaatt tgcttccgat    360

actaaaaaca tcagtatcgc agcaggtcta gtaaacaaca ttcaagaccc aatgcaaatt    420

ttgactgacg atgctatcgt aaatattgct aaaacaattg agtgggcttc attctttgga    480

gattctgact tatcagatag cccagaacca caagcaggac tagaatttga cggcttggct    540

aaacttatta accaagataa cgttcatgat gctcgtggag ctagcttgac tgaaagcttg    600

ttaaaccaag cagcagtaat gattagtaaa ggttatggta cacctacaga tgcttacatg    660

ccagtagggg ttcaagcaga ctttgttaac caacaacttt ctaaacaaac acaacttgtt    720

cgcgataacg gaaacaacgt aagcgttggt ttcaacatcc aaggtttcca ttcagctcgt    780

ggatttatca aacttcacgg ttctacagta atggaaaacg aacaaatctt agatgaacgt    840

attcttgctt taccaacagc tccacaacca gctaaggtaa ctgcaacaca agaagcaggt    900

aaaaaaggac aatttagagc agaagattta gcagcacatg aatataaagt tgttgtaagt    960

tctgacgatg cagagtctat tgcaagtgaa gtggctacag ctacagttac tgcaaaagat   1020

gacggcgtta aactagaaat cgaattagct ccaatgtata gctctcgtcc acaattcgtt   1080

tcaatctata gaaaaggtgc agaaacaggt ttattctacc taatcgctcg tgtacctgct   1140

agcaaagcag agaacaacgt aatcactttc tacgacttaa acgactctat tcctgaaaca   1200

gtagacgtat tcgttggtga aatgtcggct aacgtagtac acttgtttga attactacca   1260

atgatgagat tacctctagc tcaaattaac gcatctgtta catttgcagt tttatggtat   1320

ggcgcattag ctctaagagc acctaagaaa tgggtacgta ttagaaacgt taaatatatt   1380

cctgtaaaaa acgttcatag caactaa                                       1407


<210> SEQ ID NO 10
<211> LENGTH: 468
<212> TYPE: PRT
```

```
<213> ORGANISM: LP099 Phage

<400> SEQUENCE: 10

Met Pro Lys Asn Asn Lys Glu Glu Glu Val Lys Glu Val Asn Leu Asn
1               5                   10                  15

Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110

Val Asn Met Lys Phe Ala Ser Asp Thr Lys Asn Ile Ser Ile Ala Ala
        115                 120                 125

Gly Leu Val Asn Asn Ile Gln Asp Pro Met Gln Ile Leu Thr Asp Asp
    130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
    210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
    290                 295                 300

Phe Arg Ala Glu Asp Leu Ala Ala His Glu Tyr Lys Val Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
    370                 375                 380

Asn Asn Val Ile Thr Phe Tyr Asp Leu Asn Asp Ser Ile Pro Glu Thr
385                 390                 395                 400
```

-continued

```
Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
        435                 440                 445

Lys Lys Trp Val Arg Ile Arg Asn Val Lys Tyr Ile Pro Val Lys Asn
    450                 455                 460

Val His Ser Asn
465
```

<210> SEQ ID NO 11
<211> LENGTH: 1407
<212> TYPE: DNA
<213> ORGANISM: LP101 Phage

<400> SEQUENCE: 11

```
atgccaaaaa ataacaaaga agaagaagtt aaagaagtaa accttaattc agtacaagag     60

gacgcgttaa agtcctttac aactggttat ggtatcacac ctgatacaca aacagatgca    120

ggagcattaa gacgtgagtt cctagacgac caaatctcaa tgcttacttg gacagagaat    180

gatttaacat tctataaaga catcgctaaa aaaccagcta catctacagt agcaaaatac    240

gatgtataca tgcaacatgg taaggtaggt catactagat ttactcgtga gattggggta    300

gcaccagtaa gtgaccctaa catccgtcaa aaaacagtaa acatgaaatt tgcttccgat    360

actaaaaaca tcagtatcgc agcaggtcta gtaaacaaca ttcaagaccc aatgcaaatt    420

ttgactgacg atgctatcgt aaatattgct aaaacaattg agtgggcttc attctttgga    480

gattctgact tatcagatag cccagaacca caagcaggac tagaatttga cggcttggct    540

aaacttatta accaagataa cgttcatgat gctcgtggag ctagcttgac tgaaagcttg    600

ttaaaccaag cagcagtaat gattagtaaa ggttatggta cacctacaga tgcttacatg    660

ccagtagggg ttcaagcaga ctttgttaac caacaacttt ctaaacaaac acaacttgtt    720

cgcgataacg gaaacaacgt aagcgttggt ttcaacatcc aaggtttcca ttcagctcgt    780

ggatttatca aacttcacgg ttctacagta atggaaaacg aacaaatctt agatgaacgt    840

attcttgctt taccaacagc tccacaacca gctaaggtaa ctgcaacaca agaagcaggt    900

aaaaaaggac aatttagagc agaagattta gcagcacatg aatataaagt tgttgtaagt    960

tctgacgatg cagagtctat tgcaagtgaa gtggctacag ctacagttac tgcaaaagat   1020

gacggcgtta aactagaaat cgaattagct ccaatgtata gctctcgtcc acaattcgtt   1080

tcaatctata gaaaaggtgc agaaacaggt ttattctacc taatcgctcg tgtacctgct   1140

agcaaagcag agaacaacgt aatcactttc tacgacttaa acgactctat tcctgaaaca   1200

gtagacgtat tcgttggtga aatgtcggct aacgtagtac acttgtttga attactacca   1260

atgatgagat tacctctagc tcaaattaac gcatctgtta catttgcagt tttatggtat   1320

ggcgcattag ctctaagagc acctaagaaa tgggtacgta ttagaaacgt taaatatatt   1380

cctgtaaaaa acgttcatag caactaa                                       1407
```

<210> SEQ ID NO 12
<211> LENGTH: 468
<212> TYPE: PRT
<213> ORGANISM: LP101 Phage

<400> SEQUENCE: 12

-continued

```
Met Pro Lys Asn Asn Lys Glu Glu Glu Val Lys Glu Val Asn Leu Asn
1               5                   10                  15

Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110

Val Asn Met Lys Phe Ala Ser Asp Thr Lys Asn Ile Ser Ile Ala Ala
        115                 120                 125

Gly Leu Val Asn Asn Ile Gln Asp Pro Met Gln Ile Leu Thr Asp Asp
    130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
    210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
    290                 295                 300

Phe Arg Ala Glu Asp Leu Ala Ala His Glu Tyr Lys Val Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
    370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
```

-continued

```
            420                 425                 430

Val Thr Phe Ala Val Leu Trp Tyr Gly Ala Leu Ala Leu Arg Ala Pro
        435                 440                 445

Lys Lys Trp Val Arg Ile Arg Asn Val Lys Tyr Ile Pro Val Lys Asn
    450                 455                 460

Val His Ser Asn
465
```

<210> SEQ ID NO 13
<211> LENGTH: 1407
<212> TYPE: DNA
<213> ORGANISM: LP124 Phage

<400> SEQUENCE: 13

```
atgccaaaaa ataacaaaga agaagaagtt aaagaagtaa accttaattc agtacaagag     60
gacgcgttaa agtcctttac aactggttat ggtatcacac ctgatacaca aacagatgca    120
ggagcattaa gacgtgagtt cctagacgac caaatctcaa tgcttacttg gacagagaat    180
gatttaacat tctataaaga catcgctaaa aaaccagcta catctacagt agcaaaatac    240
gatgtataca tgcaacatgg taaggtaggt catactagat ttactcgtga gattggggta    300
gcaccagtaa gtgaccctaa catccgtcaa aaaacagtaa acatgaaatt tgcttccgat    360
actaaaaaca tcagtatcgc agcaggtcta gtaaacaaca ttcaagaccc aatgcaaatt    420
ttgactgacg atgctatcgt aaatattgct aaaacaattg agtgggcttc attctttgga    480
gattctgact tatcagatag cccagaacca caagcaggac tagaatttga cggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga ctttgttaac caacaacttt ctaaacaaac acaacttgtt    720
cgcgataacg gaaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900
aaaaaaggac aatttagagc agaagattta gcagcacatg aatataaagt tgttgtaagt    960
tctgacgatg cagagtctat tgcaagtgaa gtggctacag ctacagttac tgcaaaagat   1020
gacggcgtta aactagaaat cgaattagct ccaatgtata gctctcgtcc acaattcgtt   1080
tcaatctata gaaaaggtgc agaaacaggt ttattctacc taatcgctcg tgtacctgct   1140
agcaaagcag agaacaacgt aatcactttc tacgacttaa acgactctat tcctgaaaca   1200
gtagacgtat tcgttggtga aatgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaa                                       1407
```

<210> SEQ ID NO 14
<211> LENGTH: 468
<212> TYPE: PRT
<213> ORGANISM: LP124 Phage

<400> SEQUENCE: 14

```
Met Pro Lys Asn Asn Lys Glu Glu Glu Val Lys Glu Val Asn Leu Asn
1               5                   10                  15

Ser Val Gln Glu Asp Ala Leu Lys Ser Phe Thr Thr Gly Tyr Gly Ile
```

-continued

```
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110

Val Asn Met Lys Phe Ala Ser Asp Thr Lys Asn Ile Ser Ile Ala Ala
        115                 120                 125

Gly Leu Val Asn Asn Ile Gln Asp Pro Met Gln Ile Leu Thr Asp Asp
    130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
    210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
    290                 295                 300

Phe Arg Ala Glu Asp Leu Ala Ala His Glu Tyr Lys Val Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
    370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
        435                 440                 445
```

Lys Lys Trp Val Arg Ile Arg Asn Val Lys Tyr Ile Pro Val Lys Asn
450 455 460

Val His Ser Asn
465

<210> SEQ ID NO 15
<211> LENGTH: 1407
<212> TYPE: DNA
<213> ORGANISM: LP125 Phage

<400> SEQUENCE: 15
atgccaaaaa ataacaaaga agaagaagtt aaagaagtaa accttaattc agtacaagag 60
gacgcgttaa agtcctttac aactggttat ggtatcacac ctgatacaca aacagatgca 120
ggagcattaa gacgtgagtt cctagacgac caaatctcaa tgcttacttg gacagagaat 180
gatttaacat tctataaaga catcgctaaa aaaccagcta catctacagt agcaaaatac 240
gatgtataca tgcaacatgg taaggtaggt catactagat ttactcgtga gattggggta 300
gcaccagtaa gtgaccctaa catccgtcaa aaaacagtaa acatgaaatt tgcttccgat 360
actaaaaaca tcagtatcgc agcaggtcta gtaaacaaca ttcaagaccc aatgcaaatt 420
ttgactgacg atgctatcgt aaatattgct aaaacaattg agtgggcttc attctttgga 480
gattctgact tatcagatag cccagaacca caagcaggac tagaatttga cggcttggct 540
aaacttatta accaagataa cgttcatgat gctcgtggag ctagcttgac tgaaagcttg 600
ttaaaccaag cagcagtaat gattagtaaa ggttatggta cacctacaga tgcttacatg 660
ccagtagggg ttcaagcaga ctttgttaac caacaacttt ctaaacaaac acaacttgtt 720
cgtgataacg gaaacaacgt aagcgttggt ttcaacatcc aaggtttcca ttcagctcgt 780
ggatttatca aacttcacgg ttctacagta atggaaaacg aacaaatctt agatgaacgt 840
attcttgctt taccaacagc tccacaacca gctaaggtaa ctgcaacaca agaagcaggt 900
aaaaaaggac aatttagagc agaagattta gcagcacatg aatataaagt tgttgtaagt 960
tctgacgatg cagagtctat tgcaagtgaa gtggctacag ctacagttac tgcaaaagat 1020
gacggcgtta aactagaaat cgaattagct ccaatgtata gctctcgtcc acaattcgtt 1080
tcaatctata gaaaaggtgc agaaacaggt ttattctacc taatcgctcg tgtacctgct 1140
agcaaagcag agaacaacgt aatcactttc tacgacttaa acgactctat tcctgaaaca 1200
gtagacgtat tcgttggtga aatgtcggct aacgtagtac acttgtttga attactacca 1260
atgatgagat tacctctagc tcaaattaac gcatctgtta catttgcagt tttatggtat 1320
ggcgcattag ctctaagagc acctaagaaa tgggtacgta ttagaaacgt taaatatatt 1380
cctgtaaaaa acgttcatag caactaa 1407

<210> SEQ ID NO 16
<211> LENGTH: 468
<212> TYPE: PRT
<213> ORGANISM: LP125 Phage

<400> SEQUENCE: 16

Met Pro Lys Asn Asn Lys Glu Glu Glu Val Lys Glu Val Asn Leu Asn
1 5 10 15

Ser Val Gln Glu Asp Ala Leu Lys Ser Phe Thr Thr Gly Tyr Gly Ile
20 25 30

Thr Pro Asp Thr Gln Thr Asp Ala Gly Ala Leu Arg Arg Glu Phe Leu
35 40 45

-continued

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110

Val Asn Met Lys Phe Ala Ser Asp Thr Lys Asn Ile Ser Ile Ala Ala
        115                 120                 125

Gly Leu Val Asn Asn Ile Gln Asp Pro Met Gln Ile Leu Thr Asp Asp
    130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
    210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
    290                 295                 300

Phe Arg Ala Glu Asp Leu Ala Ala His Glu Tyr Lys Val Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
    370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
        435                 440                 445

Lys Lys Trp Val Arg Ile Arg Asn Val Lys Tyr Ile Pro Val Lys Asn
    450                 455                 460

Val His Ser Asn
465

<210> SEQ ID NO 17
<211> LENGTH: 1404
<212> TYPE: DNA
<213> ORGANISM: LP143 Phage

<400> SEQUENCE: 17
atgccaaaaa ataacaaaga agaagttaaa gaagtaaacc ttaattcagt acaagaggat 60
gcgttaaagt cctttacgac tggttatggt atcacacctg atacacaaac agatgcagga 120
gcattaagac gtgagttcct agacgaccaa atctcaatgc ttacttggac agagaatgat 180
ttaacattct ataaagacat cgctaaaaaa ccagctacat ctacagtagc aaaatacgat 240
gtatacatgc aacatggtaa ggtaggtcat actagattta ctcgtgagat tggggtagca 300
ccagtaagtg accctaacat ccgtcaaaaa acagtaaata tgaaatttgc ttccgatact 360
aaaaacatca gtatcgcagc aggtctagta aacaacattc aagacccaat gcaaattttg 420
actgacgatg ctatcgtaaa tattgctaaa acaattgagt gggcttcatt ctttggagat 480
tctgacttat cagatagccc agaaccacaa gcaggactag aatttgacgg cttggctaaa 540
cttattaacc aagataacgt tcatgatgct cgtggagcta gcttgactga aagcttgtta 600
aaccaagcag cagtaatgat tagtaaaggt tatggtacac ctacagatgc ttacatgcca 660
gtaggggttc aagcagactt tgttaaccaa caactttcta aacaaacaca acttgttcgc 720
gataacggaa acaacgtaag cgttggtttc aacatccaag gtttccattc agctcgtgga 780
tttatcaaac ttcacggttc tacagtaatg gaaaacgaac aaatcttaga tgaacgtatt 840
cttgctttac caacagctcc acaaccagct aaggtaactg caacacaaga agcaggtaaa 900
aaaggacaat ttagagcaga agatttagca gcacatgaat ataaagttgt tgtaagttct 960
gacgatgcag agtctattgc aagtgaagtg gctacagcta cagttactgc aaaagatgac 1020
ggcgttaaac tagaaatcga attagctcca atgtatagct ctcgtccaca attcgtttca 1080
atctatagaa aaggtgcaga aacaggttta ttctacctaa tcgctcgtgt acctgctagc 1140
aaagcagaga acaacgtaat cactttctac gacttaaacg actctattcc tgaaacagta 1200
gacgtattcg ttggtgaaat gtcggctaac gtagtacact tgtttgaatt actaccaatg 1260
atgagattac ctctagctca aattaacgca tctgttacat ttgcagtttt atggtatggc 1320
gcattagctc taagagcacc taagaaatgg gtacgtatta gaaacgttaa atatattcct 1380
gtaaaaaacg ttcatagcaa ctaa 1404

<210> SEQ ID NO 18
<211> LENGTH: 467
<212> TYPE: PRT
<213> ORGANISM: LP143 Phage

<400> SEQUENCE: 18

Met Pro Lys Asn Asn Lys Glu Glu Val Lys Glu Val Asn Leu Asn Ser
1 5 10 15

Val Gln Glu Asp Ala Leu Lys Ser Phe Thr Thr Gly Tyr Gly Ile Thr
20 25 30

Pro Asp Thr Gln Thr Asp Ala Gly Ala Leu Arg Arg Glu Phe Leu Asp
35 40 45

Asp Gln Ile Ser Met Leu Thr Trp Thr Glu Asn Asp Leu Thr Phe Tyr
50 55 60

-continued

```
Lys Asp Ile Ala Lys Lys Pro Ala Thr Ser Thr Val Ala Lys Tyr Asp
65                  70                  75                  80

Val Tyr Met Gln His Gly Lys Val Gly His Thr Arg Phe Thr Arg Glu
                85                  90                  95

Ile Gly Val Ala Pro Val Ser Asp Pro Asn Ile Arg Gln Lys Thr Val
            100                 105                 110

Asn Met Lys Phe Ala Ser Asp Thr Lys Asn Ile Ser Ile Ala Ala Gly
        115                 120                 125

Leu Val Asn Asn Ile Gln Asp Pro Met Gln Ile Leu Thr Asp Asp Ala
    130                 135                 140

Ile Val Asn Ile Ala Lys Thr Ile Glu Trp Ala Ser Phe Phe Gly Asp
145                 150                 155                 160

Ser Asp Leu Ser Asp Ser Pro Glu Pro Gln Ala Gly Leu Glu Phe Asp
                165                 170                 175

Gly Leu Ala Lys Leu Ile Asn Gln Asp Asn Val His Asp Ala Arg Gly
            180                 185                 190

Ala Ser Leu Thr Glu Ser Leu Leu Asn Gln Ala Ala Val Met Ile Ser
        195                 200                 205

Lys Gly Tyr Gly Thr Pro Thr Asp Ala Tyr Met Pro Val Gly Val Gln
    210                 215                 220

Ala Asp Phe Val Asn Gln Gln Leu Ser Lys Gln Thr Gln Leu Val Arg
225                 230                 235                 240

Asp Asn Gly Asn Asn Val Ser Val Gly Phe Asn Ile Gln Gly Phe His
                245                 250                 255

Ser Ala Arg Gly Phe Ile Lys Leu His Gly Ser Thr Val Met Glu Asn
            260                 265                 270

Glu Gln Ile Leu Asp Glu Arg Ile Leu Ala Leu Pro Thr Ala Pro Gln
        275                 280                 285

Pro Ala Lys Val Thr Ala Thr Gln Glu Ala Gly Lys Lys Gly Gln Phe
    290                 295                 300

Arg Ala Glu Asp Leu Ala Ala His Glu Tyr Lys Val Val Val Ser Ser
305                 310                 315                 320

Asp Asp Ala Glu Ser Ile Ala Ser Glu Val Ala Thr Ala Thr Val Thr
                325                 330                 335

Ala Lys Asp Asp Gly Val Lys Leu Glu Ile Glu Leu Ala Pro Met Tyr
            340                 345                 350

Ser Ser Arg Pro Gln Phe Val Ser Ile Tyr Arg Lys Gly Ala Glu Thr
        355                 360                 365

Gly Leu Phe Tyr Leu Ile Ala Arg Val Pro Ala Ser Lys Ala Glu Asn
    370                 375                 380

Asn Val Ile Thr Phe Tyr Asp Leu Asn Asp Ser Ile Pro Glu Thr Val
385                 390                 395                 400

Asp Val Phe Val Gly Glu Met Ser Ala Asn Val Val His Leu Phe Glu
                405                 410                 415

Leu Leu Pro Met Met Arg Leu Pro Leu Ala Gln Ile Asn Ala Ser Val
            420                 425                 430

Thr Phe Ala Val Leu Trp Tyr Gly Ala Leu Ala Leu Arg Ala Pro Lys
        435                 440                 445

Lys Trp Val Arg Ile Arg Asn Val Lys Tyr Ile Pro Val Lys Asn Val
    450                 455                 460

His Ser Asn
465
```

<210> SEQ ID NO 19
<211> LENGTH: 1404
<212> TYPE: DNA
<213> ORGANISM: A511 phage

<400> SEQUENCE: 19
atgccaaaaa ataacaaaga agaagttaaa gaagtaaacc ttaattcagt acaagaggat 60
gcgttaaagt cctttacgac tggttatggt atcacacctg atacacaaac agatgcagga 120
gcattaagac gtgagttcct agacgaccaa atctcaatgc ttacttggac agagaatgat 180
ttaacattct ataaagacat cgctaaaaaa ccagctacat ctacagtagc aaaatacgat 240
gtatacatgc aacatggtaa ggtaggtcat actagattta ctcgtgagat tggggtagca 300
ccagtaagtg accctaacat ccgtcaaaaa acagtaaata tgaaatttgc ttccgatact 360
aaaaacatca gtatcgcagc aggtctagta aacaacattc aagacccaat gcaaattttg 420
actgacgatg ctatcgtaaa tattgctaaa acaattgagt gggcttcatt ctttggagat 480
tctgacttat cagatagccc agaaccacaa gcaggactag aatttgacgg cttggctaaa 540
cttattaacc aagataacgt tcatgatgct cgtggagcta gcttgactga aagcttgtta 600
aaccaagcag cagtaatgat tagtaaaggt tatggtacac ctacagatgc ttacatgcca 660
gtaggggttc aagcagactt tgttaaccaa caactttcta aacaaacaca acttgttcgc 720
gataacggaa acaacgtaag cgttggtttc aacatccaag gtttccattc agctcgtgga 780
tttatcaaac ttcacggttc tacagtaatg gaaaacgaac aaatcttaga tgaacgtatt 840
cttgctttac caacagctcc acaaccagct aaggtaactg caacacaaga agcaggtaaa 900
aaaggacaat ttagagcaga agatttagca gcacatgaat ataaagttgt tgtaagttct 960
gacgatgcag agtctattgc aagtgaagtg gctacagcta cagttactgc aaaagatgac 1020
ggcgttaaac tagaaatcga attagctcca atgtatagct ctcgtccaca attcgtttca 1080
atctatagaa aaggtgcaga aacaggttta ttctacctaa tcgctcgtgt acctgctagc 1140
aaagcagaga acaacgtaat cactttctac gacttaaacg actctattcc tgaaacagta 1200
gacgtattcg ttggtgaaat gtcggctaac gtagtacact tgtttgaatt actaccaatg 1260
atgagattac ctctagctca aattaacgca tctgttacat ttgcagtttt atggtatggc 1320
gcattagctc taagagcacc taagaaatgg gtacgtatta gaaacgttaa atatattcct 1380
gtaaaaaacg ttcatagcaa ctaa 1404

<210> SEQ ID NO 20
<211> LENGTH: 467
<212> TYPE: PRT
<213> ORGANISM: A511 Phage

<400> SEQUENCE: 20

Met Pro Lys Asn Asn Lys Glu Glu Val Lys Glu Val Asn Leu Asn Ser
1 5 10 15

Val Gln Glu Asp Ala Leu Lys Ser Phe Thr Thr Gly Tyr Gly Ile Thr
20 25 30

Pro Asp Thr Gln Thr Asp Ala Gly Ala Leu Arg Arg Glu Phe Leu Asp
35 40 45

Asp Gln Ile Ser Met Leu Thr Trp Thr Glu Asn Asp Leu Thr Phe Tyr
50 55 60

Lys Asp Ile Ala Lys Lys Pro Ala Thr Ser Thr Val Ala Lys Tyr Asp
65 70 75 80

Val Tyr Met Gln His Gly Lys Val Gly His Thr Arg Phe Thr Arg Glu

-continued

```
                85                  90                  95

Ile Gly Val Ala Pro Val Ser Asp Pro Asn Ile Arg Gln Lys Thr Val
            100                 105                 110

Asn Met Lys Phe Ala Ser Asp Thr Lys Asn Ile Ser Ile Ala Ala Gly
        115                 120                 125

Leu Val Asn Asn Ile Gln Asp Pro Met Gln Ile Leu Thr Asp Asp Ala
    130                 135                 140

Ile Val Asn Ile Ala Lys Thr Ile Glu Trp Ala Ser Phe Phe Gly Asp
145                 150                 155                 160

Ser Asp Leu Ser Asp Ser Pro Glu Pro Gln Ala Gly Leu Glu Phe Asp
                165                 170                 175

Gly Leu Ala Lys Leu Ile Asn Gln Asp Asn Val His Asp Ala Arg Gly
            180                 185                 190

Ala Ser Leu Thr Glu Ser Leu Leu Asn Gln Ala Ala Val Met Ile Ser
        195                 200                 205

Lys Gly Tyr Gly Thr Pro Thr Asp Ala Tyr Met Pro Val Gly Val Gln
    210                 215                 220

Ala Asp Phe Val Asn Gln Gln Leu Ser Lys Gln Thr Gln Leu Val Arg
225                 230                 235                 240

Asp Asn Gly Asn Asn Val Ser Val Gly Phe Asn Ile Gln Gly Phe His
                245                 250                 255

Ser Ala Arg Gly Phe Ile Lys Leu His Gly Ser Thr Val Met Glu Asn
            260                 265                 270

Glu Gln Ile Leu Asp Glu Arg Ile Leu Ala Leu Pro Thr Ala Pro Gln
        275                 280                 285

Pro Ala Lys Val Thr Ala Thr Gln Glu Ala Gly Lys Lys Gly Gln Phe
    290                 295                 300

Arg Ala Glu Asp Leu Ala Ala His Glu Tyr Lys Val Val Val Ser Ser
305                 310                 315                 320

Asp Asp Ala Glu Ser Ile Ala Ser Glu Val Ala Thr Ala Thr Val Thr
                325                 330                 335

Ala Lys Asp Asp Gly Val Lys Leu Glu Ile Glu Leu Ala Pro Met Tyr
            340                 345                 350

Ser Ser Arg Pro Gln Phe Val Ser Ile Tyr Arg Lys Gly Ala Glu Thr
        355                 360                 365

Gly Leu Phe Tyr Leu Ile Ala Arg Val Pro Ala Ser Lys Ala Glu Asn
    370                 375                 380

Asn Val Ile Thr Phe Tyr Asp Leu Asn Asp Ser Ile Pro Glu Thr Val
385                 390                 395                 400

Asp Val Phe Val Gly Glu Met Ser Ala Asn Val Val His Leu Phe Glu
                405                 410                 415

Leu Leu Pro Met Met Arg Leu Pro Leu Ala Gln Ile Asn Ala Ser Val
            420                 425                 430

Thr Phe Ala Val Leu Trp Tyr Gly Ala Leu Ala Leu Arg Ala Pro Lys
        435                 440                 445

Lys Trp Val Arg Ile Arg Asn Val Lys Tyr Ile Pro Val Lys Asn Val
    450                 455                 460

His Ser Asn
465
```

<210> SEQ ID NO 21
<211> LENGTH: 1407
<212> TYPE: DNA
<213> ORGANISM: P100 Phage

<400> SEQUENCE: 21

```
atgccaaaaa ataacaaaga agaagaagtt aaagaagtaa accttaattc agtacaagag     60
gacgcgttaa agtcctttac aactggttat ggtatcacac ctgatacaca aacagatgca    120
ggagcattaa gacgtgagtt cctagacgac caaatctcaa tgcttacttg gacagagaat    180
gatttaacat tctataaaga catcgctaaa aaaccagcta catctacagt agcaaaatac    240
gatgtataca tgcaacatgg taaggtaggt catactagat ttactcgtga gattggggta    300
gcaccagtaa gtgaccctaa catccgtcaa aaaacagtaa atatgaaatt tgcttccgat    360
actaaaaaca tcagtatcgc agcaggtcta gtaaacaaca ttcaagaccc aatgcaaatt    420
ttgactgacg atgctatcgt aaatattgct aaaacaattg agtgggcttc attctttgga    480
gattctgact tatcagatag cccagaacca caagcaggac tagaatttga cggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga ctttgttaac caacaacttt ctaaacaaac acagcttgtt    720
cgtgataacg gaaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900
aaaaaaggac aatttagagc agaagactta gcagcacacg aatacaaagt tgttgtaagt    960
tctgacgatg cagagtctat tgcaagtgaa gtggctacag ctacagttac tgcaaaagat   1020
gacggcgtta aactagaaat cgagttagct ccaatgtaca gctcccgtcc acaattcgtt   1080
tcaatctata gaaaaggtgc agaaacaggt ttattctacc taatcgctcg tgtacctgct   1140
agcaaagcag agaacaacgt aatcactttc tatgacttaa acgactctat tcctgaaaca   1200
gtagacgtat tcgttggtga aatgtctgct aacgtagtac acttgtttga attactacca   1260
atgatgagat tacctctagc tcaaattaac gcatctgtta catttgcagt tttatggtat   1320
ggagcattag ctctaagagc acctaagaaa tgggtacgta ttagaaacgt taaatatatt   1380
cctgtaaaaa acgttcatag caactaa                                       1407
```

<210> SEQ ID NO 22
<211> LENGTH: 468
<212> TYPE: PRT
<213> ORGANISM: P100 Phage

<400> SEQUENCE: 22

```
Met Pro Lys Asn Asn Lys Glu Glu Glu Val Lys Glu Val Asn Leu Asn
1               5                   10                  15

Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110
```

```
Val Asn Met Lys Phe Ala Ser Asp Thr Lys Asn Ile Ser Ile Ala Ala
        115                 120                 125

Gly Leu Val Asn Asn Ile Gln Asp Pro Met Gln Ile Leu Thr Asp Asp
    130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
    210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
    290                 295                 300

Phe Arg Ala Glu Asp Leu Ala Ala His Glu Tyr Lys Val Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
    370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
        435                 440                 445

Lys Lys Trp Val Arg Ile Arg Asn Val Lys Tyr Ile Pro Val Lys Asn
    450                 455                 460

Val His Ser Asn
465
```

<210> SEQ ID NO 23
<211> LENGTH: 3729
<212> TYPE: DNA
<213> ORGANISM: Artificial Sequence
<220> FEATURE:
<223> OTHER INFORMATION: Synthetic Polynucleotide

<400> SEQUENCE: 23

-continued atgccaaaaa ataacaaaga agaagaagtt aaagaagtaa accttaattc agtacaagag 60
gacgcgttaa agtcctttac aactggttat ggtatcacac ctgatacaca aacagatgca 120
ggagcattaa gacgtgagtt cctagacgac caaatctcaa tgcttacttg gacagagaat 180
gatttaacat tctataaaga catcgctaaa aaaccagcta catctacagt agcaaaatac 240
gatgtataca tgcaacatgg taaggtaggt catactagat ttactcgtga gattggggta 300
gcaccagtaa gtgaccctaa catccgtcaa aaaacagtaa acatgaaatt tgcttccgat 360
actaaaaaca tcagtatcgc agcaggtcta gtaaacaaca ttcaagaccc aatgcaaatt 420
ttgactgacg atgctatcgt aaatattgct aaaacaattg agtgggcttc attctttgga 480
gattctgact tatcagatag cccagaacca caagcaggac tagaatttga cggcttggct 540
aaacttatta accaagataa cgttcatgat gctcgtggag ctagcttgac tgaaagcttg 600
ttaaaccaag cagcagtaat gattagtaaa ggttatggta cacctacaga tgcttacatg 660
ccagtagggg ttcaagcaga ctttgttaac caacaacttt ctaaacaaac acaacttgtt 720
cgcgataacg gaaacaacgt aagcgttggt ttcaacatcc aaggtttcca ttcagctcgt 780
ggatttatca aacttcacgg ttctacagta atggaaaacg aacaaatctt agatgaacgt 840
attcttgctt taccaacagc tccacaacca gctaaggtaa ctgcaacaca agaagcaggt 900
aaaaaaggac aatttagagc agaagattta gcagcacatg aatataaagt tgttgtaagt 960
tctgacgatg cagagtctat tgcaagtgaa gtggctacag ctacagttac tgcaaaagat 1020
gacggcgtta aactagaaat cgaattagct ccaatgtata gctctcgtcc acaattcgtt 1080
tcaatctata gaaaaggtgc agaaacaggt ttattctacc taatcgctcg tgtacctgct 1140
agcaaagcag agaacaacgt aatcactttc tacgacttaa acgactctat tcctgaaaca 1200
gtagacgtat tcgttggtga aatgtcggct aacgtagtac acttgtttga attactacca 1260
atgatgagat tacctctagc tcaaattaac gcatctgtta catttgcagt tttatggtat 1320
ggcgcattag ctctaagagc acctaagaaa tgggtacgta ttagaaacgt taaatatatt 1380
cctgtaaaaa acgttcatag caactaagag gaggtaaata tatatggaag acgccaaaaa 1440
cataaagaaa ggcccggcgc cattctatcc tctagaggat ggaaccgctg gagagcaact 1500
gcataaggct atgaagagat acgccctggt tcctggaaca attgctttta cagatgcaca 1560
tatcgaggtg aacatcacgt acgcggaata cttcgaaatg tccgttcggt tggcagaagc 1620
tatgaaacga tatgggctga atacaaatca cagaatcgtc gtatgcagtg aaaactctct 1680
tcaattcttt atgccggtgt tgggcgcgtt atttatcgga gttgcagttg cgcccgcgaa 1740
cgacatttat aatgaacgtg aattgctcaa cagtatgaac atttcgcagc ctaccgtagt 1800
gtttgtttcc aaaaaggggt tgcaaaaaat tttgaacgtg caaaaaaaat taccaataat 1860
ccagaaaatt attatcatgg attctaaaac ggattaccag ggatttcagt cgatgtacac 1920
gttcgtcaca tctcatctac ctcccggttt taatgaatac gattttgtac cagagtcctt 1980
tgatcgtgac aaaacaattg cactgataat gaattcctct ggatctactg ggttacctaa 2040
gggtgtggcc cttccgcata gaactgcctg cgtcagattc tcgcatgcca gagatcctat 2100
ttttggcaat caaatcattc cggatactgc gattttaagt gttgttccat tccatcacgg 2160
ttttggaatg tttactacac tcggatattt gatatgtgga tttcgagtcg tcttaatgta 2220
tagatttgaa gaagagctgt ttttacgatc ccttcaggat tacaaaattc aaagtgcgtt 2280
gctagtacca accctatttt cattcttcgc caaaagcact ctgattgaca aatacgattt 2340

```
atctaattta cacgaaattg cttctggggg cgcacctctt tcgaaagaag tcggggaagc   2400
ggttgcaaaa cgcttccatc ttccagggat acgacaagga tatgggctca ctgagactac   2460
atcagctatt ctgattacac ccgaggggga tgataaaccg ggcgcggtcg gtaaagttgt   2520
tccatttttt gaagcgaagg ttgtggatct ggataccggg aaaacgctgg gcgttaatca   2580
gagaggcgaa ttatgtgtca gaggacctat gattatgtcc ggttatgtaa acaatccgga   2640
agcgaccaac gccttgattg acaaggatgg atggctacat tctggagaca tagcttactg   2700
ggacgaagac gaacacttct tcatagttga ccgcttgaag tctttaatta aatacaaagg   2760
atatcaggtg gcccccgctg aattggaatc gatattgtta caacacccca acatcttcga   2820
cgcgggcgtg gcaggtcttc ccgacgatga cgccggtgaa cttccagccg ccgttgttgt   2880
tttggagcac ggaaagacga tgacggaaaa agagatcgtg gattacgtcg ccagtcaagt   2940
aacaaccgcg aaaaagttgc gcggaggagt tgtgtttgtg gacgaagtac cgaaaggtct   3000
taccggaaaa ctcgacgcaa gaaaaatcag agagatcctc ataaaggcca agaagggcgg   3060
aaagtccaaa ttgtaataat tataggataa ttgaataaaa acagtataga gagcagataa   3120
atactgctct ctattttact aataaggagg atttaaattg ctaaaaaata caaacttagc   3180
taattataaa aaagtgaata cacggtttgg aaatcttagt tttgacgaca aaggtatttc   3240
taatgactta acggaagaac agcaaaaaga attaggtaag cttcgaggat tcgaatatat   3300
taagacagaa cagaaaacaa aagaagaacc taagaaagaa gaacctaaga aagaaagtac   3360
agaaaatgaa ttagacagct tcttagctaa agagccttca atcaaagaat taaaagaatt   3420
tgcgagtaaa aaaggcatta aaattgaaaa aactaagaaa aatgatataa ttgaagaact   3480
aaagagaggg taatgtataa tgtatggagg ttatgaagga caagattctt acgaataccc   3540
ttactcacat gggaacccta agcatgtaga gccagaaaaa gttgacgaat atgttctttc   3600
tgattatggt tggactgcgg aaacaattaa agcatacatg tatggtgttc gtgtagtaga   3660
ccctgaaaca ggagaggaaa tgggagacac cttctacaat catattatag aggttgccgt   3720
tgataaggc                                                           3729
```

<210> SEQ ID NO 24
<211> LENGTH: 3789
<212> TYPE: DNA
<213> ORGANISM: Artificial Sequence
<220> FEATURE:
<223> OTHER INFORMATION: Synthetic Polynucleotide

<400> SEQUENCE: 24

```
atgccaaaaa ataacaaaga agaagaagtt aaagaagtaa accttaattc agtacaagag     60
gacgcgttaa agtcctttac aactggttat ggtatcacac ctgatacaca aacagatgca    120
ggagcattaa gacgtgagtt cctagacgac caaatctcaa tgcttacttg gacagagaat    180
gatttaacat tctataaaga catcgctaaa aaaccagcta catctacagt agcaaaatac    240
gatgtataca tgcaacatgg taaggtaggt catactagat ttactcgtga gattggggta    300
gcaccagtaa gtgaccctaa catccgtcaa aaaacagtaa acatgaaatt tgcttccgat    360
actaaaaaca tcagtatcgc agcaggtcta gtaaacaaca ttcaagaccc aatgcaaatt    420
ttgactgacg atgctatcgt aaatattgct aaaacaattg agtgggcttc attctttgga    480
gattctgact tatcagatag cccagaacca caagcaggac tagaatttga cggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
```

-continued ccagtagggg ttcaagcaga ctttgttaac caacaacttt ctaaacaaac acaacttgtt 720
cgcgataacg gaaacaacgt aagcgttggt ttcaacatcc aaggtttcca ttcagctcgt 780
ggatttatca aacttcacgg ttctacagta atggaaaacg aacaaatctt agatgaacgt 840
attcttgctt taccaacagc tccacaacca gctaaggtaa ctgcaacaca agaagcaggt 900
aaaaaaggac aatttagagc agaagattta gcagcacatg aatataaagt tgttgtaagt 960
tctgacgatg cagagtctat tgcaagtgaa gtggctacag ctacagttac tgcaaaagat 1020
gacggcgtta aactagaaat cgaattagct ccaatgtata gctctcgtcc acaattcgtt 1080
tcaatctata gaaaaggtgc agaaacaggt ttattctacc taatcgctcg tgtacctgct 1140
agcaaagcag agaacaacgt aatcactttc tacgacttaa acgactctat tcctgaaaca 1200
gtagacgtat tcgttggtga aatgtcggct aacgtagtac acttgtttga attactacca 1260
atgatgagat tacctctagc tcaaattaac gcatctgtta catttgcagt tttatggtat 1320
ggcgcattag ctctaagagc acctaagaaa tgggtacgta ttagaaacgt taaatatatt 1380
cctgtaaaaa acgttcatag caactaagag gaggtaaata tatatggaag acgccaaaaa 1440
cataaagaaa ggcccggcgc cattctatcc tctagaggat ggaaccgctg gagagcaact 1500
gcataaggct atgaagagat acgccctggt tcctggaaca attgctttta cagatgcaca 1560
tatcgaggtg aacatcacgt acgcggaata cttcgaaatg tccgttcggt tggcagaagc 1620
tatgaaacga tatgggctga atacaaatca cagaatcgtc gtatgcagtg aaaactctct 1680
tcaattcttt atgccggtgt tgggcgcgtt atttatcgga gttgcagttg cgcccgcgaa 1740
cgacatttat aatgaacgtg aattgctcaa cagtatgaac atttcgcagc ctaccgtagt 1800
gtttgtttcc aaaaaggggt tgcaaaaaat tttgaacgtg caaaaaaaat taccaataat 1860
ccagaaaatt attatcatgg attctaaaac ggattaccag ggatttcagt cgatgtacac 1920
gttcgtcaca tctcatctac ctcccggttt taatgaatac gattttgtac cagagtcctt 1980
tgatcgtgac aaaacaattg cactgataat gaattcctct ggatctactg ggttacctaa 2040
gggtgtggcc cttccgcata gaactgcctg cgtcagattc tcgcatgcca gagatcctat 2100
ttttggcaat caaatcattc cggatactgc gattttaagt gttgttccat tccatcacgg 2160
ttttggaatg tttactacac tcggatattt gatatgtgga tttcgagtcg tcttaatgta 2220
tagatttgaa gaagagctgt ttttacgatc ccttcaggat tacaaaattc aaagtgcgtt 2280
gctagtacca accctatttt cattcttcgc caaaagcact ctgattgaca aatacgattt 2340
atctaattta cacgaaattg cttctggggg cgcacctctt tcgaaagaag tcggggaagc 2400
ggttgcaaaa cgcttccatc ttccagggat acgacaagga tatgggctca ctgagactac 2460
atcagctatt ctgattacac ccgaggggga tgataaaccg ggcgcggtcg gtaaagttgt 2520
tccatttttt gaagcgaagg ttgtggatct ggataccggg aaaacgctgg gcgttaatca 2580
gagaggcgaa ttatgtgtca gaggacctat gattatgtcc ggttatgtaa acaatccgga 2640
agcgaccaac gccttgattg acaaggatgg atggctacat tctggagaca tagcttactg 2700
ggacgaagac gaacacttct tcatagttga ccgcttgaag tctttaatta aatacaaagg 2760
atatcaggtg gcccccgctg aattggaatc gatattgtta caacacccca acatcttcga 2820
cgcgggcgtg gcaggtcttc ccgacgatga cgccggtgaa cttcccgccg ccgttgttgt 2880
tttggagcac ggaaagacga tgacggaaaa agagatcgtg gattacgtcg ccagtcaagt 2940
aacaaccgcg aaaaagttgc gcggaggagt tgtgtttgtg gacgaagtac cgaaaggtct 3000

-continued

```
taccggaaaa ctcgacgcaa gaaaaatcag agagatcctc ataaaggcca agaagggcgg   3060

aaagtccaaa ttgtaataat tataggataa ttgaataaaa acagtataga gagcagataa   3120

atactgctct ctattttact aataaggagg atttaaattg ctaaaaaata caaacttagc   3180

taattataaa aaagtgaata cacggtttgg aaatcttagt tttgacgaca aaggtatttc   3240

taatgactta acggaagaac agcaaaaaga attaggtaag cttcgaggat tcgaatatat   3300

taagacagaa cagaaaacaa aagaagaacc taagaaagaa gaacctaaga aagaagaacc   3360

taagaaagaa gaacctaaga aagaagaacc taagaaagaa gaacctaaga aagaaagtac   3420

agaaaatgaa ttagacagct tcttagctaa agagccttca atcaaagaat taaaagaatt   3480

tgcgagtaaa aaaggcatta aaattgaaaa aactaagaaa aatgatataa ttgaagaact   3540

aaagagaggg taatgtataa tgtatggagg ttatgaagga caagattctt acgaataccc   3600

ttactcacat gggaacccta agcatgtaga gccagaaaaa gttgacgaat atgttctttc   3660

tgattatggt tggactgcgg aaacaattaa agcatacatg tatggtgttc gtgtagtaga   3720

ccctgaaaca ggagaggaaa tgggagacac cttctacaat catattatag aggttgccgt   3780

tgataaggc                                                           3789
```

<210> SEQ ID NO 25
<211> LENGTH: 3789
<212> TYPE: DNA
<213> ORGANISM: Artificial Sequence
<220> FEATURE:
<223> OTHER INFORMATION: Synthetic Polynucleotide

<400> SEQUENCE: 25

```
atgccaaaaa ataacaaaga agaagaagtt aaagaagtaa accttaattc agtacaagag     60

gacgcgttaa agtcctttac aactggttat ggtatcacac ctgatacaca aacagatgca    120

ggagcattaa gacgtgagtt cctagacgac caaatctcaa tgcttacttg gacagagaat    180

gatttaacat tctataaaga catcgctaaa aaaccagcta catctacagt agcaaaatac    240

gatgtataca tgcaacatgg taaggtaggt catactagat ttactcgtga gattggggta    300

gcaccagtaa gtgaccctaa catccgtcaa aaaacagtaa acatgaaatt tgcttccgat    360

actaaaaaca tcagtatcgc agcaggtcta gtaaacaaca ttcaagaccc aatgcaaatt    420

ttgactgacg atgctatcgt aaatattgct aaaacaattg agtgggcttc attctttgga    480

gattctgact tatcagatag cccagaacca caagcaggac tagaatttga cggcttggct    540

aaacttatta accaagataa cgttcatgat gctcgtggag ctagcttgac tgaaagcttg    600

ttaaaccaag cagcagtaat gattagtaaa ggttatggta cacctacaga tgcttacatg    660

ccagtagggg ttcaagcaga ctttgttaac caacaacttt ctaaacaaac acaacttgtt    720

cgcgataacg gaaacaacgt aagcgttggt ttcaacatcc aaggtttcca ttcagctcgt    780

ggatttatca aacttcacgg ttctacagta atggaaaacg aacaaatctt agatgaacgt    840

attcttgctt taccaacagc tccacaacca gctaaggtaa ctgcaacaca agaagcaggt    900

aaaaaaggac aatttagagc agaagattta gcagcacatg aatataaagt tgttgtaagt    960

tctgacgatg cagagtctat tgcaagtgaa gtggctacag ctacagttac tgcaaaagat   1020

gacggcgtta aactagaaat cgaattagct ccaatgtata gctctcgtcc acaattcgtt   1080

tcaatctata gaaaaggtgc agaaacaggt ttattctacc taatcgctcg tgtacctgct   1140

agcaaagcag agaacaacgt aatcactttc tacgacttaa acgactctat tcctgaaaca   1200

gtagacgtat tcgttggtga aatgtcggct aacgtagtac acttgtttga attactacca   1260
```

-continued

```
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaagag gaggtaaata tatatggaag acgccaaaaa   1440
cataaagaaa ggcccggcgc cattctatcc tctagaggat ggaaccgctg gagagcaact   1500
gcataaggct atgaagagat acgccctggt tcctggaaca attgctttta cagatgcaca   1560
tatcgaggtg aacatcacgt acgcggaata cttcgaaatg tccgttcggt tggcagaagc   1620
tatgaaacga tatgggctga atacaaatca cagaatcgtc gtatgcagtg aaaactctct   1680
tcaattcttt atgccggtgt tgggcgcgtt atttatcgga gttgcagttg cgcccgcgaa   1740
cgacatttat aatgaacgtg aattgctcaa cagtatgaac atttcgcagc ctaccgtagt   1800
gtttgtttcc aaaaaggggt tgcaaaaaat tttgaacgtg caaaaaaaat taccaataat   1860
ccagaaaatt attatcatgg attctaaaac ggattaccag ggatttcagt cgatgtacac   1920
gttcgtcaca tctcatctac ctcccggttt taatgaatac gattttgtac cagagtcctt   1980
tgatcgtgac aaaacaattg cactgataat gaattcctct ggatctactg ggttacctaa   2040
gggtgtggcc cttccgcata gaactgcctg cgtcagattc tcgcatgcca gagatcctat   2100
ttttggcaat caaatcattc cggatactgc gattttaagt gttgttccat tccatcacgg   2160
ttttggaatg tttactacac tcggatattt gatatgtgga tttcgagtcg tcttaatgta   2220
tagatttgaa gaagagctgt ttttacgatc ccttcaggat tacaaaattc aaagtgcgtt   2280
gctagtacca accctatttt cattcttcgc caaaagcact ctgattgaca aatacgattt   2340
atctaattta cacgaaattg cttctggggg cgcacctctt tcgaaagaag tcggggaagc   2400
ggttgcaaaa cgcttccatc ttccagggat acgacaagga tatgggctca ctgagactac   2460
atcagctatt ctgattacac ccgaggggga tgataaaccg ggcgcggtcg gtaaagttgt   2520
tccatttttt gaagcgaagg ttgtggatct ggataccggg aaaacgctgg gcgttaatca   2580
gagaggcgaa ttatgtgtca gaggacctat gattatgtcc ggttatgtaa acaatccgga   2640
agcgaccaac gccttgattg acaaggatgg atggctacat tctggagaca tagcttactg   2700
ggacgaagac gaacacttct tcatagttga ccgcttgaag tctttaatta aatacaaagg   2760
atatcaggtg gcccccgctg aattggaatc gatattgtta caacacccca acatcttcga   2820
cgcgggcgtg gcaggtcttc ccgacgatga cgccggtgaa cttcccgccg ccgttgttgt   2880
tttggagcac ggaaagacga tgacggaaaa agagatcgtg gattacgtcg ccagtcaagt   2940
aacaaccgcg aaaaagttgc gcggaggagt tgtgtttgtg gacgaagtac cgaaaggtct   3000
taccggaaaa ctcgacgcaa gaaaaatcag agagatcctc ataaaggcca agaagggcgg   3060
aaagtccaaa ttgtaataat tataggataa ttgaataaaa acagtataga gagcagataa   3120
atactgctct ctattttact aataaggagg atttaaattg ctaaaaaata caaacttagc   3180
taattataaa aaagtgaata cacggtttgg aaatcttagt tttgacgaca aaggtatttc   3240
taatgactta acggaagaac agcaaaaaga attaggtaag cttcgaggat tcgaatatat   3300
taagacagaa cagaaaacaa aagaagaacc taagaaagaa gaacctaaga aagaagaacc   3360
taagaaagaa gaacctaaga aagaagaacc taagaaagaa gaacctaaga aagaaagtac   3420
agaaaatgaa ttagacagct tcttagctaa agagccttca atcaaagaat taaaagaatt   3480
tgcgagtaaa aaaggcatta aaattgaaaa aactaagaaa aatgatataa ttgaagaact   3540
aaagagaggg taatgtataa tgtatggagg ttatgaagga caagattctt acgaataccc   3600
```

ttactcacat gggaacccta agcatgtaga gccagaaaaa gttgacgaat atgttctttc 3660
tgattatggt tggactgcgg aaacaattaa agcatacatg tatggtgttc gtgtagtaga 3720
ccctgaaaca ggagaggaaa tgggagacac cttctacaat catattatag aggttgccgt 3780
tgataaggc 3789

<210> SEQ ID NO 26
<211> LENGTH: 3789
<212> TYPE: DNA
<213> ORGANISM: Artificial Sequence
<220> FEATURE:
<223> OTHER INFORMATION: Synthetic Polynucleotide

<400> SEQUENCE: 26
atgccaaaaa ataacaaaga agaagaagtt aaagaagtaa accttaattc agtacaagag 60
gacgcgttaa agtcctttac aactggttat ggtatcacac ctgatacaca aacagatgca 120
ggagcattaa gacgtgagtt cctagacgac caaatctcaa tgcttacttg gacagagaat 180
gatttaacat tctataaaga catcgctaaa aaaccagcta catctacagt agcaaaatac 240
gatgtataca tgcaacatgg taaggtaggt catactagat ttactcgtga gattggggta 300
gcaccagtaa gtgaccctaa catccgtcaa aaaacagtaa acatgaaatt tgcttccgat 360
actaaaaaca tcagtatcgc agcaggtcta gtaaacaaca ttcaagaccc aatgcaaatt 420
ttgactgacg atgctatcgt aaatattgct aaaacaattg agtgggcttc attctttgga 480
gattctgact tatcagatag cccagaacca caagcaggac tagaatttga cggcttggct 540
aaacttatta accaagataa cgttcatgat gctcgtggag ctagcttgac tgaaagcttg 600
ttaaaccaag cagcagtaat gattagtaaa ggttatggta cacctacaga tgcttacatg 660
ccagtagggg ttcaagcaga ctttgttaac caacaacttt ctaaacaaac acaacttgtt 720
cgcgataacg gaaacaacgt aagcgttggt ttcaacatcc aaggtttcca ttcagctcgt 780
ggatttatca aacttcacgg ttctacagta atggaaaacg aacaaatctt agatgaacgt 840
attcttgctt taccaacagc tccacaacca gctaaggtaa ctgcaacaca agaagcaggt 900
aaaaaaggac aatttagagc agaagattta gcagcacatg aatataaagt tgttgtaagt 960
tctgacgatg cagagtctat tgcaagtgaa gtggctacag ctacagttac tgcaaaagat 1020
gacggcgtta aactagaaat cgaattagct ccaatgtata gctctcgtcc acaattcgtt 1080
tcaatctata gaaaaggtgc agaaacaggt ttattctacc taatcgctcg tgtacctgct 1140
agcaaagcag agaacaacgt aatcactttc tacgacttaa acgactctat tcctgaaaca 1200
gtagacgtat tcgttggtga aatgtcggct aacgtagtac acttgtttga attactacca 1260
atgatgagat tacctctagc tcaaattaac gcatctgtta catttgcagt tttatggtat 1320
ggcgcattag ctctaagagc acctaagaaa tgggtacgta ttagaaacgt taaatatatt 1380
cctgtaaaaa acgttcatag caactaagag gaggtaaata tatatggaag acgccaaaaa 1440
cataaagaaa ggcccggcgc cattctatcc tctagaggat ggaaccgctg gagagcaact 1500
gcataaggct atgaagagat acgccctggt tcctggaaca attgctttta cagatgcaca 1560
tatcgaggtg aacatcacgt acgcggaata cttcgaaatg tccgttcggt tggcagaagc 1620
tatgaaacga tatgggctga atacaaatca cagaatcgtc gtatgcagtg aaaactctct 1680
tcaattcttt atgccggtgt tgggcgcgtt atttatcgga gttgcagttg cgcccgcgaa 1740
cgacatttat aatgaacgtg aattgctcaa cagtatgaac atttcgcagc ctaccgtagt 1800
gtttgtttcc aaaaaggggt tgcaaaaaat tttgaacgtg caaaaaaaat taccaataat 1860
ccagaaaatt attatcatgg attctaaaac ggattaccag ggatttcagt cgatgtacac 1920
gttcgtcaca tctcatctac ctcccggttt taatgaatac gattttgtac cagagtcctt 1980
tgatcgtgac aaaacaattg cactgataat gaattcctct ggatctactg ggttacctaa 2040
gggtgtggcc cttccgcata gaactgcctg cgtcagattc tcgcatgcca gagatcctat 2100
ttttggcaat caaatcattc cggatactgc gattttaagt gttgttccat tccatcacgg 2160
ttttggaatg tttactacac tcggatattt gatatgtgga tttcgagtcg tcttaatgta 2220
tagatttgaa gaagagctgt ttttacgatc ccttcaggat tacaaaattc aaagtgcgtt 2280
gctagtacca accctatttt cattcttcgc caaaagcact ctgattgaca aatacgattt 2340
atctaattta cacgaaattg cttctggggg cgcacctctt tcgaaagaag tcggggaagc 2400
ggttgcaaaa cgcttccatc ttccagggat acgacaagga tatgggctca ctgagactac 2460
atcagctatt ctgattacac ccgaggggga tgataaaccg ggcgcggtcg gtaaagttgt 2520
tccatttttt gaagcgaagg ttgtggatct ggataccggg aaaacgctgg gcgttaatca 2580
gagaggcgaa ttatgtgtca gaggacctat gattatgtcc ggttatgtaa acaatccgga 2640
agcgaccaac gccttgattg acaaggatgg atggctacat tctggagaca tagcttactg 2700
ggacgaagac gaacacttct tcatagttga ccgcttgaag tctttaatta aatacaaagg 2760
atatcaggtg gcccccgctg aattggaatc gatattgtta caacacccca acatcttcga 2820
cgcgggcgtg gcaggtcttc ccgacgatga cgccggtgaa cttcccgccg ccgttgttgt 2880
tttggagcac ggaaagacga tgacggaaaa agagatcgtg gattacgtcg ccagtcaagt 2940
aacaaccgcg aaaaagttgc gcggaggagt tgtgtttgtg gacgaagtac cgaaaggtct 3000
taccggaaaa ctcgacgcaa gaaaaatcag agagatcctc ataaaggcca agaagggcgg 3060
aaagtccaaa ttgtaataat tataggataa ttgaataaaa acagtataga gagcagataa 3120
atactgctct ctattttact aataaggagg atttaaattg ctaaaaaata caaacttagc 3180
taattataaa aaagtgaata cacggtttgg aaatcttagt tttgacgaca aaggtatttc 3240
taatgactta acggaagaac agcaaaaaga attaggtaag cttcgaggat tcgaatatat 3300
taagacagaa cagaaaacaa aagaagaacc taagaaagaa gaacctaaga aagaagaacc 3360
taagaaagaa gaacctaaga aagaagaacc taagaaagaa gaacctaaga aagaaagtac 3420
agaaaatgaa ttagacagct tcttagctaa agagccttca atcaaagaat taaaagaatt 3480
tgcgagtaaa aaaggcatta aaattgaaaa aactaagaaa aatgatataa ttgaagaact 3540
aaagagaggg taatgtataa tgtatggagg ttatgaagga caagattctt acgaataccc 3600
ttactcacat gggaacccta agcatgtaga gccagaaaaa gttgacgaat atgttctttc 3660
tgattatggt tggactgcgg aaacaattaa agcatacatg tatggtgttc gtgtagtaga 3720
ccctgaaaca ggagaggaaa tgggagacac cttctacaat catattatag aggttgccgt 3780
tgataaggc 3789

<210> SEQ ID NO 27
<211> LENGTH: 3729
<212> TYPE: DNA
<213> ORGANISM: Artificial Sequence
<220> FEATURE:
<223> OTHER INFORMATION: Synethic Polynucleotide

<400> SEQUENCE: 27
atgccaaaaa ataacaaaga agaagaagtt aaagaagtaa accttaattc agtacaagag 60

-continued

```
gacgcgttaa agtcctttac aactggttat ggtatcacac ctgatacaca aacagatgca    120
ggagcattaa gacgtgagtt cctagacgac caaatctcaa tgcttacttg gacagagaat    180
gatttaacat tctataaaga catcgctaaa aaaccagcta catctacagt agcaaaatac    240
gatgtataca tgcaacatgg taaggtaggt catactagat ttactcgtga gattggggta    300
gcaccagtaa gtgaccctaa catccgtcaa aaaacagtaa acatgaaatt tgcttccgat    360
actaaaaaca tcagtatcgc agcaggtcta gtaaacaaca ttcaagaccc aatgcaaatt    420
ttgactgacg atgctatcgt aaatattgct aaaacaattg agtgggcttc attctttgga    480
gattctgact tatcagatag cccagaacca caagcaggac tagaatttga cggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga ctttgttaac caacaacttt ctaaacaaac acaacttgtt    720
cgtgataacg gaaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900
aaaaaaggac aatttagagc agaagattta gcagcacatg aatataaagt tgttgtaagt    960
tctgacgatg cagagtctat tgcaagtgaa gtggctacag ctacagttac tgcaaaagat   1020
gacggcgtta aactagaaat cgaattagct ccaatgtata gctctcgtcc acaattcgtt   1080
tcaatctata gaaaaggtgc agaaacaggt ttattctacc taatcgctcg tgtacctgct   1140
agcaaagcag agaacaacgt aatcactttc tacgacttaa acgactctat tcctgaaaca   1200
gtagacgtat tcgttggtga aatgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaagag gaggtaaata tatatggaag acgccaaaaa   1440
cataaagaaa ggcccggcgc cattctatcc tctagaggat ggaaccgctg gagagcaact   1500
gcataaggct atgaagagat acgccctggt tcctggaaca attgctttta cagatgcaca   1560
tatcgaggtg aacatcacgt acgcggaata cttcgaaatg tccgttcggt tggcagaagc   1620
tatgaaacga tatgggctga atacaaatca cagaatcgtc gtatgcagtg aaaactctct   1680
tcaattcttt atgccggtgt tgggcgcgtt atttatcgga gttgcagttg cgcccgcgaa   1740
cgacatttat aatgaacgtg aattgctcaa cagtatgaac atttcgcagc ctaccgtagt   1800
gtttgtttcc aaaaaggggt tgcaaaaaat tttgaacgtg caaaaaaaat taccaataat   1860
ccagaaaatt attatcatgg attctaaaac ggattaccag ggatttcagt cgatgtacac   1920
gttcgtcaca tctcatctac ctcccggttt taatgaatac gattttgtac cagagtcctt   1980
tgatcgtgac aaaacaattg cactgataat gaattcctct ggatctactg ggttacctaa   2040
gggtgtggcc cttccgcata gaactgcctg cgtcagattc tcgcatgcca gagatcctat   2100
ttttggcaat caaatcattc cggatactgc gattttaagt gttgttccat tccatcacgg   2160
ttttggaatg tttactacac tcggatattt gatatgtgga tttcgagtcg tcttaatgta   2220
tagatttgaa gaagagctgt ttttacgatc ccttcaggat tacaaaattc aaagtgcgtt   2280
gctagtacca accctatttt cattcttcgc caaaagcact ctgattgaca aatacgattt   2340
atctaattta cacgaaattg cttctggggg cgcacctctt tcgaaagaag tcggggaagc   2400
ggttgcaaaa cgcttccatc ttccagggat acgacaagga tatgggctca ctgagactac   2460
```

atcagctatt ctgattacac ccgaggggga tgataaaccg ggcgcggtcg gtaaagttgt 2520
tccatttttt gaagcgaagg ttgtggatct ggataccggg aaaacgctgg gcgttaatca 2580
gagaggcgaa ttatgtgtca gaggacctat gattatgtcc ggttatgtaa acaatccgga 2640
agcgaccaac gccttgattg acaaggatgg atggctacat tctggagaca tagcttactg 2700
ggacgaagac gaacacttct tcatagttga ccgcttgaag tctttaatta aatacaaagg 2760
atatcaggtg gcccccgctg aattggaatc gatattgtta caacacccca acatcttcga 2820
cgcgggcgtg gcaggtcttc ccgacgatga cgccggtgaa cttccagccg ccgttgttgt 2880
tttggagcac ggaaagacga tgacggaaaa agagatcgtg gattacgtcg ccagtcaagt 2940
aacaaccgcg aaaaagttgc gcggaggagt tgtgtttgtg gacgaagtac cgaaaggtct 3000
taccggaaaa ctcgacgcaa gaaaaatcag agagatcctc ataaaggcca agaagggcgg 3060
aaagtccaaa ttgtaataat tataggataa ttgaataaaa acagtataga gagcagataa 3120
atactgctct ctattttact aataaggagg atttaaattg ctaaaaaata caaacttagc 3180
taattataaa aaagtgaata cacggtttgg aaatcttagt tttgacgaca aaggtatttc 3240
taatgactta acggaagaac agcaaaaaga attaggtaag cttcgaggat tcgaatatat 3300
taagacagaa cagaaaacaa aagaagaacc taagaaagaa gaacctaaga aagaaagtac 3360
agaaaatgaa ttagacagct tcttagctaa agagccttca atcaaagaat taaaagaatt 3420
tgcgagtaaa aaaggcatta aaattgaaaa aactaagaaa aatgatataa ttgaagaact 3480
aaagagaggg taatgtataa tgtatggagg ttatgaagga caagattctt acgaataccc 3540
ttactcacat gggaacccta agcatgtaga gccagaaaaa gttgacgaat atgttctttc 3600
tgattatggt tggactgcgg aaacaattaa agcatacatg tatggtgttc gtgtagtaga 3660
ccctgaaaca ggagaggaaa tgggagacac cttctacaat catattatag aggttgccgt 3720
tgataaggc 3729

<210> SEQ ID NO 28
<211> LENGTH: 3786
<212> TYPE: DNA
<213> ORGANISM: Artificial Sequence
<220> FEATURE:
<223> OTHER INFORMATION: Synthetic Polynucleotide

<400> SEQUENCE: 28
atgccaaaaa ataacaaaga agaagttaaa gaagtaaacc ttaattcagt acaagaggat 60
gcgttaaagt cctttacgac tggttatggt atcacacctg atacacaaac agatgcagga 120
gcattaagac gtgagttcct agacgaccaa atctcaatgc ttacttggac agagaatgat 180
ttaacattct ataaagacat cgctaaaaaa ccagctacat ctacagtagc aaaatacgat 240
gtatacatgc aacatggtaa ggtaggtcat actagattta ctcgtgagat tggggtagca 300
ccagtaagtg accctaacat ccgtcaaaaa acagtaaata tgaaatttgc ttccgatact 360
aaaaacatca gtatcgcagc aggtctagta aacaacattc aagacccaat gcaaattttg 420
actgacgatg ctatcgtaaa tattgctaaa acaattgagt gggcttcatt ctttggagat 480
tctgacttat cagatagccc agaaccacaa gcaggactag aatttgacgg cttggctaaa 540
cttattaacc aagataacgt tcatgatgct cgtggagcta gcttgactga aagcttgtta 600
aaccaagcag cagtaatgat tagtaaaggt tatggtacac ctacagatgc ttacatgcca 660
gtaggggttc aagcagactt tgttaaccaa caactttcta aacaaacaca acttgttcgc 720

-continued

```
gataacggaa acaacgtaag cgttggtttc aacatccaag gtttccattc agctcgtgga    780
tttatcaaac ttcacggttc tacagtaatg gaaaacgaac aaatcttaga tgaacgtatt    840
cttgctttac caacagctcc acaaccagct aaggtaactg caacacaaga agcaggtaaa    900
aaaggacaat ttagagcaga agatttagca gcacatgaat ataaagttgt tgtaagttct    960
gacgatgcag agtctattgc aagtgaagtg gctacagcta cagttactgc aaaagatgac   1020
ggcgttaaac tagaaatcga attagctcca atgtatagct ctcgtccaca attcgtttca   1080
atctatagaa aaggtgcaga aacaggttta ttctacctaa tcgctcgtgt acctgctagc   1140
aaagcagaga acaacgtaat cactttctac gacttaaacg actctattcc tgaaacagta   1200
gacgtattcg ttggtgaaat gtcggctaac gtagtacact tgtttgaatt actaccaatg   1260
atgagattac ctctagctca aattaacgca tctgttacat ttgcagtttt atggtatggc   1320
gcattagctc taagagcacc taagaaatgg gtacgtatta gaaacgttaa atatattcct   1380
gtaaaaaacg ttcatagcaa ctaagaggag gtaaatatat atggaagacg ccaaaaacat   1440
aaagaaaggc ccggcgccat tctatcctct agaggatgga accgctggag agcaactgca   1500
taaggctatg aagagatacg ccctggttcc tggaacaatt gcttttacag atgcacatat   1560
cgaggtgaac atcacgtacg cggaatactt cgaaatgtcc gttcggttgg cagaagctat   1620
gaaacgatat gggctgaata caaatcacag aatcgtcgta tgcagtgaaa actctcttca   1680
attctttatg ccggtgttgg gcgcgttatt tatcggagtt gcagttgcgc ccgcgaacga   1740
catttataat gaacgtgaat tgctcaacag tatgaacatt tcgcagccta ccgtagtgtt   1800
tgtttccaaa aaggggttgc aaaaaatttt gaacgtgcaa aaaaaattac caataatcca   1860
gaaaattatt atcatggatt ctaaaacgga ttaccaggga tttcagtcga tgtacacgtt   1920
cgtcacatct catctacctc ccggttttaa tgaatacgat tttgtaccag agtcctttga   1980
tcgtgacaaa acaattgcac tgataatgaa ttcctctgga tctactgggt tacctaaggg   2040
tgtggccctt ccgcatagaa ctgcctgcgt cagattctcg catgccagag atcctatttt   2100
tggcaatcaa atcattccgg atactgcgat tttaagtgtt gttccattcc atcacggttt   2160
tggaatgttt actacactcg gatatttgat atgtggattt cgagtcgtct taatgtatag   2220
atttgaagaa gagctgtttt tacgatccct tcaggattac aaaattcaaa gtgcgttgct   2280
agtaccaacc ctattttcat tcttcgccaa aagcactctg attgacaaat acgatttatc   2340
taatttacac gaaattgctt ctgggggcgc acctctttcg aaagaagtcg gggaagcggt   2400
tgcaaaacgc ttccatcttc cagggatacg acaaggatat gggctcactg agactacatc   2460
agctattctg attacacccg agggggatga taaaccgggc gcggtcggta aagttgttcc   2520
attttttgaa gcgaaggttg tggatctgga taccgggaaa acgctgggcg ttaatcagag   2580
aggcgaatta tgtgtcagag gacctatgat tatgtccggt tatgtaaaca atccggaagc   2640
gaccaacgcc ttgattgaca aggatggatg gctacattct ggagacatag cttactggga   2700
cgaagacgaa cacttcttca tagttgaccg cttgaagtct ttaattaaat acaaaggata   2760
tcaggtggcc cccgctgaat tggaatcgat attgttacaa caccccaaca tcttcgacgc   2820
gggcgtggca ggtcttcccg acgatgacgc cggtgaactt cccgccgccg ttgttgtttt   2880
ggagcacgga aagacgatga cggaaaaaga gatcgtggat tacgtcgcca gtcaagtaac   2940
aaccgcgaaa aagttgcgcg gaggagttgt gtttgtggac gaagtaccga aaggtcttac   3000
cggaaaactc gacgcaagaa aaatcagaga gatcctcata aaggccaaga agggcggaaa   3060
gtccaaattg taataattat aggataattg aataaaaaca gtatagagag cagataaata   3120
```

ctgctctcta ttttactaat aaggaggatt taaattgcta aaaaatacaa acttagctaa 3180
ttataaaaaa gtgaatacac ggtttggaaa tcttagtttt gacgacaaag gtatttctaa 3240
tgacttaacg gaagaacagc aaaaagaatt aggtaagctt cgaggattcg aatatattaa 3300
gacagaacag aaaacaaaag aagaacctaa gaaagaagaa cctaagaaag aagaacctaa 3360
gaaagaagaa cctaagaaag aagaacctaa gaaagaagaa cctaagaaag aaagtacaga 3420
aaatgaatta gacagcttct tagctaaaga gccttcaatc aaagaattaa aagaatttgc 3480
gagtaaaaaa ggcattaaaa ttgaaaaaac taagaaaaat gatataattg aagaactaaa 3540
gagagggtaa tgtataatgt atggaggtta tgaaggacaa gattcttacg aataccctta 3600
ctcacatggg aaccctaagc atgtagagcc agaaaaagtt gacgaatatg ttctttctga 3660
ttatggttgg actgcggaaa caattaaagc atacatgtat ggtgttcgtg tagtagaccc 3720
tgaaacagga gaggaaatgg gagacacctt ctacaatcat attatagagg ttgccgttga 3780
taaggc 3786

<210> SEQ ID NO 29
<211> LENGTH: 3786
<212> TYPE: DNA
<213> ORGANISM: Artificial Sequence
<220> FEATURE:
<223> OTHER INFORMATION: Synthetic Polynucleotide

<400> SEQUENCE: 29
atgccaaaaa ataacaaaga agaagttaaa gaagtaaacc ttaattcagt acaagaggat 60
gcgttaaagt cctttacgac tggttatggt atcacacctg atacacaaac agatgcagga 120
gcattaagac gtgagttcct agacgaccaa atctcaatgc ttacttggac agagaatgat 180
ttaacattct ataaagacat cgctaaaaaa ccagctacat ctacagtagc aaaatacgat 240
gtatacatgc aacatggtaa ggtaggtcat actagattta ctcgtgagat tggggtagca 300
ccagtaagtg accctaacat ccgtcaaaaa acagtaaata tgaaatttgc ttccgatact 360
aaaaacatca gtatcgcagc aggtctagta aacaacattc aagacccaat gcaaattttg 420
actgacgatg ctatcgtaaa tattgctaaa acaattgagt gggcttcatt ctttggagat 480
tctgacttat cagatagccc agaaccacaa gcaggactag aatttgacgg cttggctaaa 540
cttattaacc aagataacgt tcatgatgct cgtggagcta gcttgactga aagcttgtta 600
aaccaagcag cagtaatgat tagtaaaggt tatggtacac ctacagatgc ttacatgcca 660
gtaggggttc aagcagactt tgttaaccaa caactttcta aacaaacaca acttgttcgc 720
gataacggaa acaacgtaag cgttggtttc aacatccaag gtttccattc agctcgtgga 780
tttatcaaac ttcacggttc tacagtaatg gaaaacgaac aaatcttaga tgaacgtatt 840
cttgctttac caacagctcc acaaccagct aaggtaactg caacacaaga agcaggtaaa 900
aaaggacaat ttagagcaga agatttagca gcacatgaat ataaagttgt tgtaagttct 960
gacgatgcag agtctattgc aagtgaagtg gctacagcta cagttactgc aaaagatgac 1020
ggcgttaaac tagaaatcga attagctcca atgtatagct ctcgtccaca attcgtttca 1080
atctatagaa aaggtgcaga aacaggttta ttctacctaa tcgctcgtgt acctgctagc 1140
aaagcagaga acaacgtaat cactttctac gacttaaacg actctattcc tgaaacagta 1200
gacgtattcg ttggtgaaat gtcggctaac gtagtacact tgtttgaatt actaccaatg 1260
atgagattac ctctagctca aattaacgca tctgttacat ttgcagtttt atggtatggc 1320
gcattagctc taagagcacc taagaaatgg gtacgtatta gaaacgttaa atatattcct 1380
gtaaaaaacg ttcatagcaa ctaagaggag gtaaatatat atggaagacg ccaaaaacat 1440
aaagaaaggc ccggcgccat tctatcctct agaggatgga accgctggag agcaactgca 1500
taaggctatg aagagatacg ccctggttcc tggaacaatt gcttttacag atgcacatat 1560
cgaggtgaac atcacgtacg cggaatactt cgaaatgtcc gttcggttgg cagaagctat 1620
gaaacgatat gggctgaata caaatcacag aatcgtcgta tgcagtgaaa actctcttca 1680
attctttatg ccggtgttgg gcgcgttatt tatcggagtt gcagttgcgc ccgcgaacga 1740
catttataat gaacgtgaat tgctcaacag tatgaacatt tcgcagccta ccgtagtgtt 1800
tgtttccaaa aaggggttgc aaaaaatttt gaacgtgcaa aaaaaattac caataatcca 1860
gaaaattatt atcatggatt ctaaaacgga ttaccaggga tttcagtcga tgtacacgtt 1920
cgtcacatct catctacctc ccggttttaa tgaatacgat tttgtaccag agtcctttga 1980
tcgtgacaaa acaattgcac tgataatgaa ttcctctgga tctactgggt tacctaaggg 2040
tgtggccctt ccgcatagaa ctgcctgcgt cagattctcg catgccagag atcctatttt 2100
tggcaatcaa atcattccgg atactgcgat tttaagtgtt gttccattcc atcacggttt 2160
tggaatgttt actacactcg gatatttgat atgtggattt cgagtcgtct taatgtatag 2220
atttgaagaa gagctgtttt tacgatccct tcaggattac aaaattcaaa gtgcgttgct 2280
agtaccaacc ctattttcat tcttcgccaa aagcactctg attgacaaat acgatttatc 2340
taatttacac gaaattgctt ctgggggcgc acctctttcg aaagaagtcg gggaagcggt 2400
tgcaaaacgc ttccatcttc cagggatacg acaaggatat gggctcactg agactacatc 2460
agctattctg attacacccg agggggatga taaaccgggc gcggtcggta aagttgttcc 2520 atttttgaa gcgaaggttg tggatctgga taccgggaaa acgctgggcg ttaatcagag 2580
aggcgaatta tgtgtcagag gacctatgat tatgtccggt tatgtaaaca atccggaagc 2640
gaccaacgcc ttgattgaca aggatggatg gctacattct ggagacatag cttactggga 2700
cgaagacgaa cacttcttca tagttgaccg cttgaagtct ttaattaaat acaaaggata 2760
tcaggtggcc cccgctgaat tggaatcgat attgttacaa caccccaaca tcttcgacgc 2820
gggcgtggca ggtcttcccg acgatgacgc cggtgaactt cccgccgccg ttgttgtttt 2880
ggagcacgga aagacgatga cggaaaaaga gatcgtggat tacgtcgcca gtcaagtaac 2940
aaccgcgaaa aagttgcgcg gaggagttgt gtttgtggac gaagtaccga aaggtcttac 3000
cggaaaactc gacgcaagaa aaatcagaga gatcctcata aaggccaaga agggcggaaa 3060
gtccaaattg taataattat aggataattg aataaaaaca gtatagagag cagataaata 3120
ctgctctcta ttttactaat aaggaggatt taaattgcta aaaaatacaa acttagctaa 3180
ttataaaaaa gtgaatacac ggtttggaaa tcttagtttt gacgacaaag gtatttctaa 3240
tgacttaacg gaagaacagc aaaaagaatt aggtaagctt cgaggattcg aatatattaa 3300
gacagaacag aaaacaaaag aagaacctaa gaaagaagaa cctaagaaag aagaacctaa 3360
gaaagaagaa cctaagaaag aagaacctaa gaaagaagaa cctaagaaag aaagtacaga 3420
aaatgaatta gacagcttct tagctaaaga gccttcaatc aaagaattaa aagaatttgc 3480
gagtaaaaaa ggcattaaaa ttgaaaaaac taagaaaaat gatataattg aagaactaaa 3540
gagagggtaa tgtataatgt atggaggtta tgaaggacaa gattcttacg aataccctta 3600
ctcacatggg aaccctaagc atgtagagcc agaaaaagtt gacgaatatg ttctttctga 3660
ttatggttgg actgcggaaa caattaaagc atacatgtat ggtgttcgtg tagtagaccc 3720
tgaaacagga gaggaaatgg gagacacctt ctacaatcat attatagagg ttgccgttga 3780
taaggc 3786

<210> SEQ ID NO 30
<211> LENGTH: 3729
<212> TYPE: DNA
<213> ORGANISM: Artificial Sequence
<220> FEATURE:
<223> OTHER INFORMATION: Synthetic Polynucleotide

<400> SEQUENCE: 30
atgccaaaaa ataacaaaga agaagaagtt aaagaagtaa accttaattc agtacaagag 60
gacgcgttaa agtcctttac aactggttat ggtatcacac ctgatacaca aacagatgca 120
ggagcattaa gacgtgagtt cctagacgac caaatctcaa tgcttacttg gacagagaat 180
gatttaacat tctataaaga catcgctaaa aaaccagcta catctacagt agcaaaatac 240
gatgtataca tgcaacatgg taaggtaggt catactagat ttactcgtga gattggggta 300
gcaccagtaa gtgaccctaa catccgtcaa aaaacagtaa atatgaaatt tgcttccgat 360
actaaaaaca tcagtatcgc agcaggtcta gtaaacaaca ttcaagaccc aatgcaaatt 420
ttgactgacg atgctatcgt aaatattgct aaaacaattg agtgggcttc attctttgga 480
gattctgact tatcagatag cccagaacca caagcaggac tagaatttga cggcttggct 540
aaacttatta accaagataa cgttcatgat gctcgtggag ctagcttgac tgaaagcttg 600
ttaaaccaag cagcagtaat gattagtaaa ggttatggta cacctacaga tgcttacatg 660
ccagtagggg ttcaagcaga ctttgttaac caacaacttt ctaaacaaac acagcttgtt 720
cgtgataacg gaaacaacgt aagcgttggt ttcaacatcc aaggtttcca ttcagctcgt 780
ggatttatca aacttcacgg ttctacagta atggaaaacg aacaaatctt agatgaacgt 840
attcttgctt taccaacagc tccacaacca gctaaggtaa ctgcaacaca agaagcaggt 900
aaaaaaggac aatttagagc agaagactta gcagcacacg aatacaaagt tgttgtaagt 960
tctgacgatg cagagtctat tgcaagtgaa gtggctacag ctacagttac tgcaaaagat 1020
gacggcgtta aactagaaat cgagttagct ccaatgtaca gctcccgtcc acaattcgtt 1080
tcaatctata gaaaaggtgc agaaacaggt ttattctacc taatcgctcg tgtacctgct 1140
agcaaagcag agaacaacgt aatcactttc tatgacttaa acgactctat tcctgaaaca 1200
gtagacgtat tcgttggtga aatgtctgct aacgtagtac acttgtttga attactacca 1260
atgatgagat tacctctagc tcaaattaac gcatctgtta catttgcagt tttatggtat 1320
ggagcattag ctctaagagc acctaagaaa tgggtacgta ttagaaacgt taaatatatt 1380
cctgtaaaaa acgttcatag caactaagag gaggtaaata tatatggaag acgccaaaaa 1440
cataaagaaa ggcccggcgc cattctatcc tctagaggat ggaaccgctg gagagcaact 1500
gcataaggct atgaagagat acgccctggt tcctggaaca attgctttta cagatgcaca 1560
tatcgaggtg aacatcacgt acgcggaata cttcgaaatg tccgttcggt tggcagaagc 1620
tatgaaacga tatgggctga atacaaatca cagaatcgtc gtatgcagtg aaaactctct 1680
tcaattcttt atgccggtgt tgggcgcgtt atttatcgga gttgcagttg cgcccgcgaa 1740
cgacatttat aatgaacgtg aattgctcaa cagtatgaac atttcgcagc ctaccgtagt 1800
gtttgtttcc aaaaaggggt tgcaaaaaat tttgaacgtg caaaaaaaat taccaataat 1860
ccagaaaatt attatcatgg attctaaaac ggattaccag ggatttcagt cgatgtacac 1920

```
gttcgtcaca tctcatctac ctcccggttt taatgaatac gattttgtac cagagtcctt   1980

tgatcgtgac aaaacaattg cactgataat gaattcctct ggatctactg ggttacctaa   2040

gggtgtggcc cttccgcata gaactgcctg cgtcagattc tcgcatgcca gagatcctat   2100

ttttggcaat caaatcattc cggatactgc gattttaagt gttgttccat tccatcacgg   2160

ttttggaatg tttactacac tcggatattt gatatgtgga tttcgagtcg tcttaatgta   2220

tagatttgaa gaagagctgt ttttacgatc ccttcaggat tacaaaattc aaagtgcgtt   2280

gctagtacca accctatttt cattcttcgc caaaagcact ctgattgaca aatacgattt   2340

atctaattta cacgaaattg cttctggggg cgcacctctt tcgaaagaag tcggggaagc   2400

ggttgcaaaa cgcttccatc ttccagggat acgacaagga tatgggctca ctgagactac   2460

atcagctatt ctgattacac ccgaggggga tgataaaccg ggcgcggtcg gtaaagttgt   2520

tccatttttt gaagcgaagg ttgtggatct ggataccggg aaaacgctgg gcgttaatca   2580

gagaggcgaa ttatgtgtca gaggacctat gattatgtcc ggttatgtaa acaatccgga   2640

agcgaccaac gccttgattg acaaggatgg atggctacat tctggagaca tagcttactg   2700

ggacgaagac gaacacttct tcatagttga ccgcttgaag tctttaatta aatacaaagg   2760

atatcaggtg gcccccgctg aattggaatc gatattgtta caacacccca acatcttcga   2820

cgcgggcgtg gcaggtcttc ccgacgatga cgccggtgaa cttcccgccg ccgttgttgt   2880

tttggagcac ggaaagacga tgacggaaaa agagatcgtg gattacgtcg ccagtcaagt   2940

aacaaccgcg aaaaagttgc gcggaggagt tgtgtttgtg gacgaagtac cgaaaggtct   3000

taccggaaaa ctcgacgcaa gaaaaatcag agagatcctc ataaaggcca agaagggcgg   3060

aaagtccaaa ttgtaataat tataggataa ttgaataaaa acagtataga gagcagataa   3120

atactgctct ctattttact aataaggagg atttaaattg ctaaaaaata caaacttagc   3180

taattataaa aaagtgaata cacgatttgg aaatcttagt tttgatgata aaggtatttc   3240

taatgaccta acggaagagc agcaaaaaga attaggtaag cttagaggat tcgaatatat   3300

taagacagaa cagaaaacga aagaagaacc taagaaagaa gaacctaaga aagaaagtac   3360

agaaaatgaa ttagacagct tcttagctaa agaaccttca atcaaagaat taaaagaatt   3420

tgcgagtaaa aaaggcatta aaattgaaaa aactaagaaa aatgatataa ttgaagaact   3480

aaagagaggg taatgtacaa tgtatggagg ttatgaagga caagattctt acgaataccc   3540

ttactcacac gggaacccta agcatgtaga gccagaaaaa gttgacgaat atgttctttc   3600

tgattatggc tggactgcgg aaacaattaa agcatacatg tatggtgttc gtgtagtaga   3660

ccctgaaaca ggagaggaaa tgggagacac cttctacaat catattatag aggttgccgt   3720

tgataaggc                                                           3729
```

<210> SEQ ID NO 31
<211> LENGTH: 2658
<212> TYPE: DNA
<213> ORGANISM: Artificial Sequence
<220> FEATURE:
<223> OTHER INFORMATION: Synthetic Polynucleotide

<400> SEQUENCE: 31

```
atgccaaaaa ataacaaaga agaagaagtt aaagaagtaa accttaattc agtacaagag     60

gacgcgttaa agtcctttac aactggttat ggtatcacac ctgatacaca aacagatgca    120

ggagcattaa gacgtgagtt cctagacgac caaatctcaa tgcttacttg gacagagaat    180

gatttaacat tctataaaga catcgctaaa aaaccagcta catctacagt agcaaaatac    240
```

-continued

```
gatgtataca tgcaacatgg taaggtaggt catactagat ttactcgtga gattggggta    300
gcaccagtaa gtgaccctaa catccgtcaa aaaacagtaa acatgaaatt tgcttccgat    360
actaaaaaca tcagtatcgc agcaggtcta gtaaacaaca ttcaagaccc aatgcaaatt    420
ttgactgacg atgctatcgt aaatattgct aaaacaattg agtgggcttc attctttgga    480
gattctgact tatcagatag cccagaacca caagcaggac tagaatttga cggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga ctttgttaac caacaacttt ctaaacaaac acaacttgtt    720
cgcgataacg gaaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900
aaaaaaggac aatttagagc agaagattta gcagcacatg aatataaagt tgttgtaagt    960
tctgacgatg cagagtctat tgcaagtgaa gtggctacag ctacagttac tgcaaaagat   1020
gacggcgtta aactagaaat cgaattagct ccaatgtata gctctcgtcc acaattcgtt   1080
tcaatctata gaaaaggtgc agaaacaggt ttattctacc taatcgctcg tgtacctgct   1140
agcaaagcag agaacaacgt aatcactttc tacgacttaa acgactctat tcctgaaaca   1200
gtagacgtat tcgttggtga aatgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaataa taagaggagg taaatatata tggtcttcac   1440
actcgaagat ttcgttgggg actggcgaca gacagccggc tacaacctgg accaagtcct   1500
tgaacaggga ggtgtgtcca gtttgtttca gaatctcggg gtgtccgtaa ctccgatcca   1560
aaggattgtc ctgagcggtg aaaatgggct gaagatcgac atccatgtca tcatcccgta   1620
tgaaggtctg agcggcgacc aaatgggcca gatcgaaaaa atttttaagg tggtgtaccc   1680
tgtggatgat catcacttta aggtgatcct gcactatggc acactggtaa tcgacggggt   1740
tacgccgaac atgatcgact atttcggacg gccgtatgaa ggcatcgccg tgttcgacgg   1800
caaaaagatc actgtaacag ggaccctgtg gaacggcaac aaaattatcg acgagcgcct   1860
gatcaacccc gacggctccc tgctgttccg agtaaccatc aacggagtga ccggctggcg   1920
gctgtgcgaa cgcattctgg cgtaataatt ataggataat tgaataaaaa cagtatagag   1980
agcagataaa tactgctctc tattttacta ataaggagga tttaaattgc taaaaaatac   2040
aaacttagct aattataaaa aagtgaatac acggtttgga aatcttagtt ttgacgacaa   2100
aggtatttct aatgacttaa cggaagaaca gcaaaaagaa ttaggtaagc ttcgaggatt   2160
cgaatatatt aagacagaac agaaaacaaa agaagaacct aagaaagaag aacctaagaa   2220
agaagaacct aagaaagaag aacctaagaa agaagaacct aagaaagaag aacctaagaa   2280
agaaagtaca gaaaatgaat tagacagctt cttagctaaa gagccttcaa tcaaagaatt   2340
aaaagaattt gcgagtaaaa aaggcattaa aattgaaaaa actaagaaaa atgatataat   2400
tgaagaacta aagagagggt aatgtataat gtatggaggt tatgaaggac aagattctta   2460
cgaataccct tactcacatg ggaaccctaa gcatgtagag ccagaaaaag ttgacgaata   2520
tgttctttct gattatggtt ggactgcgga aacaattaaa gcatacatgt atggtgttcg   2580
```

tgtagtagac cctgaaacag gagaggaaat gggagacacc ttctacaatc atattataga 2640
ggttgccgtt gataaggc 2658

<210> SEQ ID NO 32
<211> LENGTH: 2598
<212> TYPE: DNA
<213> ORGANISM: Artificial Sequence
<220> FEATURE:
<223> OTHER INFORMATION: Synthetic Polynucleotide

<400> SEQUENCE: 32
atgccaaaaa ataacaaaga agaagaagtt aaagaagtaa accttaattc agtacaagag 60
gacgcgttaa agtcctttac aactggttat ggtatcacac ctgatacaca aacagatgca 120
ggagcattaa gacgtgagtt cctagacgac caaatctcaa tgcttacttg gacagagaat 180
gatttaacat tctataaaga catcgctaaa aaccagcta catctacagt agcaaaatac 240
gatgtataca tgcaacatgg taaggtaggt catactagat ttactcgtga gattggggta 300
gcaccagtaa gtgaccctaa catccgtcaa aaaacagtaa acatgaaatt tgcttccgat 360
actaaaaaca tcagtatcgc agcaggtcta gtaaacaaca ttcaagaccc aatgcaaatt 420
ttgactgacg atgctatcgt aaatattgct aaaacaattg agtgggcttc attctttgga 480
gattctgact tatcagatag cccagaacca caagcaggac tagaatttga cggcttggct 540
aaacttatta accaagataa cgttcatgat gctcgtggag ctagcttgac tgaaagcttg 600
ttaaaccaag cagcagtaat gattagtaaa ggttatggta cacctacaga tgcttacatg 660
ccagtagggg ttcaagcaga ctttgttaac caacaacttt ctaaacaaac acaacttgtt 720
cgtgataacg gaaacaacgt aagcgttggt ttcaacatcc aaggtttcca ttcagctcgt 780
ggatttatca aacttcacgg ttctacagta atggaaaacg aacaaatctt agatgaacgt 840
attcttgctt taccaacagc tccacaacca gctaaggtaa ctgcaacaca agaagcaggt 900
aaaaaaggac aatttagagc agaagattta gcagcacatg aatataaagt tgttgtaagt 960
tctgacgatg cagagtctat tgcaagtgaa gtggctacag ctacagttac tgcaaaagat 1020
gacggcgtta aactagaaat cgaattagct ccaatgtata gctctcgtcc acaattcgtt 1080
tcaatctata gaaaaggtgc agaaacaggt ttattctacc taatcgctcg tgtacctgct 1140
agcaaagcag agaacaacgt aatcactttc tacgacttaa acgactctat tcctgaaaca 1200
gtagacgtat tcgttggtga aatgtcggct aacgtagtac acttgtttga attactacca 1260
atgatgagat tacctctagc tcaaattaac gcatctgtta catttgcagt tttatggtat 1320
ggcgcattag ctctaagagc acctaagaaa tgggtacgta ttagaaacgt taaatatatt 1380
cctgtaaaaa acgttcatag caactaataa taagaggagg taaatatata tggtcttcac 1440
actcgaagat ttcgttgggg actggcgaca gacagccggc tacaacctgg accaagtcct 1500
tgaacaggga ggtgtgtcca gtttgtttca gaatctcggg gtgtccgtaa ctccgatcca 1560
aaggattgtc ctgagcggtg aaaatgggct gaagatcgac atccatgtca tcatcccgta 1620
tgaaggtctg agcggcgacc aaatgggcca gatcgaaaaa atttttaagg tggtgtaccc 1680
tgtggatgat catcacttta aggtgatcct gcactatggc acactggtaa tcgacggggt 1740
tacgccgaac atgatcgact atttcggacg gccgtatgaa ggcatcgccg tgttcgacgg 1800
caaaaagatc actgtaacag ggaccctgtg gaacggcaac aaaattatcg acgagcgcct 1860
gatcaacccc gacggctccc tgctgttccg agtaaccatc aacggagtga ccggctggcg 1920
gctgtgcgaa cgcattctgg cgtaataatt ataggataat tgaataaaaa cagtatagag 1980

```
agcagataaa tactgctctc tattttacta ataaggagga tttaaattgc taaaaaatac   2040

aaacttagct aattataaaa aagtgaatac acggtttgga aatcttagtt ttgacgacaa   2100

aggtatttct aatgacttaa cggaagaaca gcaaaaagaa ttaggtaagc ttcgaggatt   2160

cgaatatatt aagacagaac agaaaacaaa agaagaacct aagaaagaag aacctaagaa   2220

agaaagtaca gaaaatgaat tagacagctt cttagctaaa gagccttcaa tcaaagaatt   2280

aaaagaattt gcgagtaaaa aaggcattaa aattgaaaaa actaagaaaa atgatataat   2340

tgaagaacta aagagagggt aatgtataat gtatggaggt tatgaaggac aagattctta   2400

cgaataccct tactcacatg ggaaccctaa gcatgtagag ccagaaaaag ttgacgaata   2460

tgttctttct gattatggtt ggactgcgga aacaattaaa gcatacatgt atggtgttcg   2520

tgtagtagac cctgaaacag gagaggaaat gggagacacc ttctacaatc atattataga   2580

ggttgccgtt gataaggc                                                 2598
```

<210> SEQ ID NO 33
<211> LENGTH: 2649
<212> TYPE: DNA
<213> ORGANISM: Artificial Sequence
<220> FEATURE:
<223> OTHER INFORMATION: Synthetic Polynucleotide

<400> SEQUENCE: 33

```
atgccaaaaa ataacaaaga agaagttaaa gaagtaaacc ttaattcagt acaagaggat     60

gcgttaaagt cctttacgac tggttatggt atcacacctg atacacaaac agatgcagga    120

gcattaagac gtgagttcct agacgaccaa atctcaatgc ttacttggac agagaatgat    180

ttaacattct ataaagacat cgctaaaaaa ccagctacat ctacagtagc aaaatacgat    240

gtatacatgc aacatggtaa ggtaggtcat actagattta ctcgtgagat tggggtagca    300

ccagtaagtg accctaacat ccgtcaaaaa acagtaaata tgaaatttgc ttccgatact    360

aaaaacatca gtatcgcagc aggtctagta aacaacattc aagacccaat gcaaattttg    420

actgacgatg ctatcgtaaa tattgctaaa acaattgagt gggcttcatt ctttggagat    480

tctgacttat cagatagccc agaaccacaa gcaggactag aatttgacgg cttggctaaa    540

cttattaacc aagataacgt tcatgatgct cgtggagcta gcttgactga aagcttgtta    600

aaccaagcag cagtaatgat tagtaaaggt tatggtacac ctacagatgc ttacatgcca    660

gtaggggttc aagcagactt tgttaaccaa caactttcta aacaaacaca acttgttcgc    720

gataacggaa acaacgtaag cgttggtttc aacatccaag gtttccattc agctcgtgga    780

tttatcaaac ttcacggttc tacagtaatg gaaaacgaac aaatcttaga tgaacgtatt    840

cttgctttac caacagctcc acaaccagct aaggtaactg caacacaaga agcaggtaaa    900

aaaggacaat ttagagcaga agatttagca gcacatgaat ataaagttgt tgtaagttct    960

gacgatgcag agtctattgc aagtgaagtg gctacagcta cagttactgc aaaagatgac   1020

ggcgttaaac tagaaatcga attagctcca atgtatagct ctcgtccaca attcgtttca   1080

atctatagaa aaggtgcaga aacaggttta ttctacctaa tcgctcgtgt acctgctagc   1140

aaagcagaga acaacgtaat cactttctac gacttaaacg actctattcc tgaaacagta   1200

gacgtattcg ttggtgaaat gtcggctaac gtagtacact tgtttgaatt actaccaatg   1260

atgagattac ctctagctca aattaacgca tctgttacat ttgcagtttt atggtatggc   1320

gcattagctc taagagcacc taagaaatgg gtacgtatta gaaacgttaa atatattcct   1380
```

```
gtaaaaaacg ttcatagcaa ctaagaggag gtaaatatat atggtcttca cactcgaaga   1440
tttcgttggg gactggcgac agacagccgg ctacaacctg gaccaagtcc ttgaacaggg   1500
aggtgtgtcc agtttgtttc agaatctcgg ggtgtccgta actccgatcc aaaggattgt   1560
cctgagcggt gaaaatgggc tgaagatcga catccatgta atcatcccgt atgaaggtct   1620
gagcggcgac caaatgggcc agatcgaaaa aatttttaag gtggtgtacc ctgtggatga   1680
tcatcacttt aaggtgatcc tgcactatgg cacactggta atcgacgggg ttacgccgaa   1740
catgatcgac tatttcggac ggccgtatga aggcatcgcc gtgttcgacg gcaaaaagat   1800
cactgtaaca gggaccctgt ggaacggcaa caaaattatc gacgagcgcc tgatcaaccc   1860
cgacggctcc ctgctgttcc gagtaaccat caacggagtg accggctggc ggctgtgcga   1920
acgcattctg gcgtaataat tataggataa ttgaataaaa acagtataga gagcagataa   1980
atactgctct ctattttact aataaggagg atttaaattg ctaaaaaata caaacttagc   2040
taattataaa aaagtgaata cacggtttgg aaatcttagt tttgacgaca aaggtatttc   2100
taatgactta acggaagaac agcaaaaaga attaggtaag cttcgaggat tcgaatatat   2160
taagacagaa cagaaaacaa aagaagaacc taagaaagaa gaacctaaga aagaagaacc   2220
taagaaagaa gaacctaaga aagaagaacc taagaaagaa gaacctaaga aagaaagtac   2280
agaaaatgaa ttagacagct tcttagctaa agagccttca atcaaagaat taaaagaatt   2340
tgcgagtaaa aaaggcatta aaattgaaaa aactaagaaa aatgatataa ttgaagaact   2400
aaagagaggg taatgtataa tgtatggagg ttatgaagga caagattctt acgaataccc   2460
ttactcacat gggaacccta agcatgtaga gccagaaaaa gttgacgaat atgttctttc   2520
tgattatggt tggactgcgg aaacaattaa agcatacatg tatggtgttc gtgtagtaga   2580
ccctgaaaca ggagaggaaa tgggagacac cttctacaat catattatag aggttgccgt   2640
tgataaggc                                                           2649
```

<210> SEQ ID NO 34
<211> LENGTH: 2592
<212> TYPE: DNA
<213> ORGANISM: Artificial Sequence
<220> FEATURE:
<223> OTHER INFORMATION: Synthetic Polynucleotide

<400> SEQUENCE: 34

```
atgccaaaaa ataacaaaga agaagaagtt aaagaagtaa accttaattc agtacaagag     60
gacgcgttaa agtcctttac aactggttat ggtatcacac ctgatacaca aacagatgca    120
ggagcattaa gacgtgagtt cctagacgac caaatctcaa tgcttacttg gacagagaat    180
gatttaacat tctataaaga catcgctaaa aaaccagcta catctacagt agcaaaatac    240
gatgtataca tgcaacatgg taaggtaggt catactagat ttactcgtga gattggggta    300
gcaccagtaa gtgaccctaa catccgtcaa aaaacagtaa atatgaaatt tgcttccgat    360
actaaaaaca tcagtatcgc agcaggtcta gtaaacaaca ttcaagaccc aatgcaaatt    420
ttgactgacg atgctatcgt aaatattgct aaaacaattg agtgggcttc attctttgga    480
gattctgact tatcagatag cccagaacca caagcaggac tagaatttga cggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga ctttgttaac caacaacttt ctaaacaaac acagcttgtt    720
cgtgataacg gaaacaacgt aagcgttggt ttcaacatcc aaggtttcca ttcagctcgt    780
```

```
ggatttatca aacttcacgg ttctacagta atggaaaacg aacaaatctt agatgaacgt     840

attcttgctt taccaacagc tccacaacca gctaaggtaa ctgcaacaca agaagcaggt     900

aaaaaaggac aatttagagc agaagactta gcagcacacg aatacaaagt tgttgtaagt     960

tctgacgatg cagagtctat tgcaagtgaa gtggctacag ctacagttac tgcaaaagat    1020

gacggcgtta aactagaaat cgagttagct ccaatgtaca gctcccgtcc acaattcgtt    1080

tcaatctata gaaaaggtgc agaaacaggt ttattctacc taatcgctcg tgtacctgct    1140

agcaaagcag agaacaacgt aatcactttc tatgacttaa acgactctat tcctgaaaca    1200

gtagacgtat tcgttggtga aatgtctgct aacgtagtac acttgtttga attactacca    1260

atgatgagat tacctctagc tcaaattaac gcatctgtta catttgcagt tttatggtat    1320

ggagcattag ctctaagagc acctaagaaa tgggtacgta ttagaaacgt taaatatatt    1380

cctgtaaaaa acgttcatag caactaagag gaggtaaata tatatggtct tcacactcga    1440

agatttcgtt ggggactggc gacagacagc cggctacaac ctggaccaag tccttgaaca    1500

gggaggtgtg tccagtttgt ttcagaatct cggggtgtcc gtaactccga tccaaaggat    1560

tgtcctgagc ggtgaaaatg ggctgaagat cgacatccat gtcatcatcc cgtatgaagg    1620

tctgagcggc gaccaaatgg gccagatcga aaaaattttt aaggtggtgt accctgtgga    1680

tgatcatcac tttaaggtga tcctgcacta tggcacactg gtaatcgacg gggttacgcc    1740

gaacatgatc gactatttcg gacggccgta tgaaggcatc gccgtgttcg acggcaaaaa    1800

gatcactgta acagggaccc tgtggaacgg caacaaaatt atcgacgagc gcctgatcaa    1860

ccccgacggc tccctgctgt tccgagtaac catcaacgga gtgaccggct ggcggctgtg    1920

cgaacgcatt ctggcgtaat aattatagga taattgaata aaaacagtat agagagcaga    1980

taaatactgc tctctatttt actaataagg aggatttaaa ttgctaaaaa atacaaactt    2040

agctaattat aaaaaagtga atacacgatt tggaaatctt agttttgatg ataaaggtat    2100

ttctaatgac ctaacggaag agcagcaaaa agaattaggt aagcttagag gattcgaata    2160

tattaagaca gaacagaaaa cgaaagaaga acctaagaaa gaagaaccta agaaagaaag    2220

tacagaaaat gaattagaca gcttcttagc taaagaacct tcaatcaaag aattaaaaga    2280

atttgcgagt aaaaaaggca ttaaaattga aaaaactaag aaaaatgata taattgaaga    2340

actaaagaga gggtaatgta caatgtatgg aggttatgaa ggacaagatt cttacgaata    2400

cccttactca cacgggaacc ctaagcatgt agagccagaa aaagttgacg aatatgttct    2460

ttctgattat ggctggactg cggaaacaat taaagcatac atgtatggtg ttcgtgtagt    2520

agaccctgaa acaggagagg aaatgggaga caccttctac aatcatatta tagaggttgc    2580

cgttgataag gc                                                        2592
```

<210> SEQ ID NO 35
<211> LENGTH: 2613
<212> TYPE: DNA
<213> ORGANISM: Artificial Sequence
<220> FEATURE:
<223> OTHER INFORMATION: Synthetic Polynucleotide

<400> SEQUENCE: 35

```
atgccaaaaa ataacaaaga agaagaagtt aaagaagtaa accttaattc agtacaagag      60

gatgcgttaa agtcctttac aactggttat ggtatcacac ctgatacaca aacagatgca     120

ggggcactaa gacgtgagtt cctagacgac caaatctcaa tgcttacttg gacagaaaat     180
```

-continued

```
gatttaacat tctacaaaga catcgctaaa aaaccagcta catctacagt agcaaaatac    240
gatgtgtaca tgcaacacgg taaagtaggt catactagat ttactcgtga gattggggta    300
gcaccagtaa gtgaccctaa catccgtcaa aaaacagtaa acatgaaatt tgcttctgat    360
actaaaaata ttagtatcgc agcaggtcta gtaaacaaca ttcaagaccc tatgcaaatt    420
ttgactgatg atgctatcgt aaatatcgct aaaacaattg agtgggcttc attctttgga    480
gattctgact tatcagatag cccagaacca caagcaggat tagaatttga tggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga ctttgttaac caacaacttt ctaaacaaac acaacttgtt    720
cgcgataacg gaaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900
aaaaaaggac aatttagagc agaagattta gcagcacatg aatataaagt tgttgtaagt    960
tctgacgatg cagagtctat tgcaagtgaa gtggctacag ctacagttac tgcaaaagat   1020
gacggcgtta aactagaaat cgaattagct ccaatgtata gctctcgtcc acaattcgtt   1080
tcaatctata gaaaaggtgc agaaacaggt ttattctacc taatcgctcg tgtacctgct   1140
agcaaagcag agaacaacgt aatcactttc tacgacttaa acgactctat tcctgaaaca   1200
gtagacgtat tcgttggtga aatgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaataa taagaggagg taaatatata tggtcttcac   1440
actcgaagat ttcgttgggg actggcgaca gacagccggc tacaacctgg accaagtcct   1500
tgaacaggga ggtgtgtcca gtttgtttca gaatctcggg gtgtccgtaa ctccgatcca   1560
aaggattgtc ctgagcggtg aaaatgggct gaagatcgac atccatgtca tcatcccgta   1620
tgaaggtctg agcggcgacc aaatgggcca gatcgaaaaa atttttaagg tggtgtaccc   1680
tgtggatgat catcacttta aggtgatcct gcactatggc acactggtaa tcgacggggt   1740
tacgccgaac atgatcgact atttcggacg gccgtatgaa ggcatcgccg tgttcgacgg   1800
caaaaagatc actgtaacag ggaccctgtg gaacggcaac aaaattatcg acgagcgcct   1860
gatcaacccc gacggctccc tgctgttccg agtaaccatc aacggagtga ccggctggcg   1920
gctgtgcgaa cgcattctgg cgtaataatt ataggataat tgaataaaaa cagtatagag   1980
agcagataaa tactgctctc tattttacta ataaggagga tttaaattgc taaaaaatac   2040
aaacttagct aattataaaa aagtgaatac acggtttgga aatcttagtt ttgacgacaa   2100
aggtatttct aatgacttaa cggaagaaca gcaaaaagaa ttaggtaagc ttcgaggatt   2160
cgaatatatt aagacagaac agaaaacaaa agaagaacct aagaaagaag aacctaagaa   2220
agaagaacct aagaaagaaa gtacagaaaa tgaattagac agcttcttag ctaaagagcc   2280
ttcaatcaaa gaattaaaag aatttgcgag taaaaaaggc attaaaattg aaaaaactaa   2340
gaaaaacgat ataattgaag aactaaagag agggtaatgt ataatgtatg gaggttatga   2400
aggacaagat tcttacgaat acccttactc acatgggaac cctaagcatg tagagccaga   2460
aaaagttgac gaatatgttc tttctgatta tggttggact gcggaaacaa ttaaagcata   2520
catgtatggt gttcgtgtag tagaccctga aacaggagag gaaatgggag acaccttcta   2580
```

caatcatatt atagaggttg ccgttgataa ggc 2613

<210> SEQ ID NO 36
<211> LENGTH: 532
<212> TYPE: DNA
<213> ORGANISM: Artificial Sequence
<220> FEATURE:
<223> OTHER INFORMATION: Synthetic Polynucleotide

<400> SEQUENCE: 36
gaggaggtaa atatatatgg tattcacatt agaagatttt gtaggggatt ggcgacaaac 60
agcgggatat aacttagatc aagttttgga acagggtgga gtctcaagcc tctttcaaaa 120
tcttggagtg agtgttactc ctattcaaag aattgtacta tctggtgaaa atggcttaaa 180
gattgatata catgttatca ttccatacga aggcttatcg ggtgatcaaa tgggtcaaat 240
tgagaaaatc tttaaagtag tgtatcctgt agacgatcat catttcaaag ttattcttca 300
ctatggtacg cttgtgatag acggggttac accaaatatg attgattact ttggtcggcc 360
gtatgaaggc attgctgttt ttgacgggaa aaaaatcacc gtcactggaa ctttatggaa 420
tggtaacaaa atcattgatg aacgtttgat aaatccagat ggatccttac ttttccgcgt 480
gacaatcaac ggagtaacgg gctggagatt atgtgaacgt attctagcat aa 532

<210> SEQ ID NO 37
<211> LENGTH: 516
<212> TYPE: DNA
<213> ORGANISM: Artificial Sequence
<220> FEATURE:
<223> OTHER INFORMATION: Synthetic Polynucleotide

<400> SEQUENCE: 37
atggtattca cattggaaga ttttgtgggg gattggagac agacagctgg atataactta 60
gaccaagtat tagaacaggg tggagtgtca agcttatttc aaaacttagg tgtgtcagtg 120
actccaattc aacgtattgt gttaagtgga gaaaacggtt taaaaataga cattcatgtg 180
attattccgt acgaaggcct cagtggtgac caaatgggac aaatagagaa aatctttaaa 240
gtagtgtacc ctgtggacga ccatcacttt aaagtaatct tacactatgg tacgttagta 300
attgatggcg taacgccaaa catgatagac tactttgggc gtccttatga aggcattgcc 360
gtgtttgacg gcaaaaagat caccgtgaca ggtactctat ggaatggaaa caaaatcatt 420
gacgagcgtt taatcaaccc agacggctct ttactatttc gggtaacaat taacggcgtg 480
accggatggc gattatgcga gcgcatttta gcctaa 516

<210> SEQ ID NO 38
<211> LENGTH: 2442
<212> TYPE: DNA
<213> ORGANISM: Artificial Sequence
<220> FEATURE:
<223> OTHER INFORMATION: Synthetic Polynucleotide

<400> SEQUENCE: 38
atgccaaaaa ataacaaaga agaagttaaa gaagtaaacc ttaattcagt acaagaggat 60
gcgttaaagt cctttacgac tggttatggt atcacacctg atacacaaac agatgcagga 120
gcattaagac gtgagttcct agacgaccaa atctcaatgc ttacttggac agagaatgat 180
ttaacattct ataaagacat cgctaaaaaa ccagctacat ctacagtagc aaaatacgat 240
gtatacatgc aacatggtaa ggtaggtcat actagattta ctcgtgagat tggggtagca 300

-continued

```
ccagtaagtg accctaacat ccgtcaaaaa acagtaaata tgaaatttgc ttccgatact    360

aaaaacatca gtatcgcagc aggtctagta aacaacattc aagacccaat gcaaattttg    420

actgacgatg ctatcgtaaa tattgctaaa acaattgagt gggcttcatt ctttggagat    480

tctgacttat cagatagccc agaaccacaa gcaggactag aatttgacgg cttggctaaa    540

cttattaacc aagataacgt tcatgatgct cgtggagcta gcttgactga aagcttgtta    600

aaccaagcag cagtaatgat tagtaaaggt tatggtacac ctacagatgc ttacatgcca    660

gtaggggttc aagcagactt tgttaaccaa caactttcta aacaaacaca acttgttcgc    720

gataacggaa acaacgtaag cgttggtttc aacatccaag gtttccattc agctcgtgga    780

tttatcaaac ttcacggttc tacagtaatg gaaaacgaac aaatcttaga tgaacgtatt    840

cttgctttac caacagctcc acaaccagct aaggtaactg caacacaaga agcaggtaaa    900

aaaggacaat ttagagcaga agatttagca gcacatgaat ataaagttgt tgtaagttct    960

gacgatgcag agtctattgc aagtgaagtg gctacagcta cagttactgc aaaagatgac   1020

ggcgttaaac tagaaatcga attagctcca atgtatagct ctcgtccaca attcgtttca   1080

atctatagaa aaggtgcaga aacaggttta ttctacctaa tcgctcgtgt acctgctagc   1140

aaagcagaga acaacgtaat cactttctac gacttaaacg actctattcc tgaaacagta   1200

gacgtattcg ttggtgaaat gtcggctaac gtagtacact tgtttgaatt actaccaatg   1260

atgagattac ctctagctca aattaacgca tctgttacat ttgcagtttt atggtatggc   1320

gcattagctc taagagcacc taagaaatgg gtacgtatta gaaacgttaa atatattcct   1380

gtaaaaaacg ttcatagcaa ctaataataa gaggaggtaa atatatatgg tattcacatt   1440

agaagatttt gtaggggatt ggcgacaaac agcgggatat aacttagatc aagttttgga   1500

acagggtgga gtctcaagcc tctttcaaaa tcttggagtg agtgttactc ctattcaaag   1560

aattgtacta tctggtgaaa atggcttaaa gattgatata catgttatca ttccatacga   1620

aggcttatcg ggtgatcaaa tgggtcaaat tgagaaaatc tttaaagtag tgtatcctgt   1680

agacgatcat catttcaaag ttattcttca ctatggtacg cttgtgatag acggggttac   1740

accaaatatg attgattact ttggtcggcc gtatgaaggc attgctgttt ttgacgggaa   1800

aaaaatcacc gtcactggaa ctttatggaa tggtaacaaa atcattgatg aacgtttgat   1860

aaatccagat ggatccttac ttttccgcgt gacaatcaac ggagtaacgg gctggagatt   1920

atgtgaacgt attctagcat aataattata ggataattga ataaaaacag tatagagagc   1980

agataaatac tgctctctat tttactaata aggaggattt aaattgctaa aaaatacaaa   2040

cttagctaat tataaaaaag tgaatacacg gtttggaaat cttagttttg acgacaaagg   2100

tatttctaat gacttaacgg aagaacagca aaaagaatta ggtaagcttc gaggattcga   2160

atatattaag acagaacaga aaacaaaaga agaacctaag aaagaagaac ctaagaaaga   2220

agaacctaag aaagaagaac ctaagaaaga agaacctaag aaagaagaac ctaagaaaga   2280

aagtacagaa aatgaattag acagcttctt agctaaagag ccttcaatca aagaattaaa   2340

agaatttgcg agtaaaaaag gcattaaaat tgaaaaaact aagaaaaatg atataattga   2400

agaactaaag agagggtaat gtataatgta tggaggttat ga                      2442
```

<210> SEQ ID NO 39
<211> LENGTH: 2445
<212> TYPE: DNA
<213> ORGANISM: Artificial Sequence
<220> FEATURE:
<223> OTHER INFORMATION: Synthetic Polynucleotide

<400> SEQUENCE: 39

```
atgccaaaaa ataacaaaga agaagaagtt aaagaagtaa accttaattc agtacaagag     60
gacgcgttaa agtcctttac aactggttat ggtatcacac ctgatacaca aacagatgca    120
ggagcattaa gacgtgagtt cctagacgac caaatctcaa tgcttacttg gacagagaat    180
gatttaacat tctataaaga catcgctaaa aaaccagcta catctacagt agcaaaatac    240
gatgtataca tgcaacatgg taaggtaggt catactagat ttactcgtga gattggggta    300
gcaccagtaa gtgaccctaa catccgtcaa aaaacagtaa acatgaaatt tgcttccgat    360
actaaaaaca tcagtatcgc agcaggtcta gtaaacaaca ttcaagaccc aatgcaaatt    420
ttgactgacg atgctatcgt aaatattgct aaaacaattg agtgggcttc attctttgga    480
gattctgact tatcagatag cccagaacca caagcaggac tagaatttga cggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga ctttgttaac caacaacttt ctaaacaaac acaacttgtt    720
cgcgataacg gaaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900
aaaaaaggac aatttagagc agaagattta gcagcacatg aatataaagt tgttgtaagt    960
tctgacgatg cagagtctat tgcaagtgaa gtggctacag ctacagttac tgcaaaagat   1020
gacggcgtta aactagaaat cgaattagct ccaatgtata gctctcgtcc acaattcgtt   1080
tcaatctata gaaaaggtgc agaaacaggt ttattctacc taatcgctcg tgtacctgct   1140
agcaaagcag agaacaacgt aatcactttc tacgacttaa acgactctat tcctgaaaca   1200
gtagacgtat tcgttggtga aatgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaataa taagaggagg taaatatata tggtattcac   1440
attagaagat tttgtagggg attggcgaca aacagcggga tataacttag atcaagtttt   1500
ggaacagggt ggagtctcaa gcctctttca aaatcttgga gtgagtgtta ctcctattca   1560
aagaattgta ctatctggtg aaaatggctt aaagattgat atacatgtta tcattccata   1620
cgaaggctta tcgggtgatc aaatgggtca aattgagaaa atctttaaag tagtgtatcc   1680
tgtagacgat catcatttca aagttattct tcactatggt acgcttgtga tagacggggt   1740
tacaccaaat atgattgatt actttggtcg gccgtatgaa ggcattgctg tttttgacgg   1800
gaaaaaaatc accgtcactg gaactttatg gaatggtaac aaaatcattg atgaacgttt   1860
gataaatcca gatggatcct tacttttccg cgtgacaatc aacggagtaa cgggctggag   1920
attatgtgaa cgtattctag cataataatt ataggataat tgaataaaaa cagtatagag   1980
agcagataaa tactgctctc tattttacta ataaggagga tttaaattgc taaaaaatac   2040
aaacttagct aattataaaa aagtgaatac acggtttgga aatcttagtt ttgacgacaa   2100
aggtatttct aatgacttaa cggaagaaca gcaaaaagaa ttaggtaagc ttcgaggatt   2160
cgaatatatt aagacagaac agaaaacaaa agaagaacct aagaaagaag aacctaagaa   2220
agaagaacct aagaaagaag aacctaagaa agaagaacct aagaaagaag aacctaagaa   2280
```

```
agaaagtaca gaaaatgaat tagacagctt cttagctaaa gagccttcaa tcaaagaatt   2340

aaaagaattt gcgagtaaaa aaggcattaa aattgaaaaa actaagaaaa atgatataat   2400

tgaagaacta aagagagggt aatgtataat gtatggaggt tatga                   2445


<210> SEQ ID NO 40
<211> LENGTH: 2445
<212> TYPE: DNA
<213> ORGANISM: Artificial Sequence
<220> FEATURE:
<223> OTHER INFORMATION: Synthetic Polynucleotide

<400> SEQUENCE: 40

atgccaaaaa ataacaaaga agaagaagtt aaagaagtaa accttaattc agtacaagag     60

gatgcgttaa agtcctttac aactggttat ggtatcacac ctgatacaca aacagatgca    120

ggggcactaa gacgtgagtt cctagacgac caaatctcaa tgcttacttg gacagaaaat    180

gatttaacat tctacaaaga catcgctaaa aaaccagcta catctacagt agcaaaatac    240

gatgtgtaca tgcaacacgg taaagtaggt catactagat ttactcgtga gattggggta    300

gcaccagtaa gtgaccctaa catccgtcaa aaaacagtaa acatgaaatt tgcttctgat    360

actaaaaata ttagtatcgc agcaggtcta gtaaacaaca ttcaagaccc tatgcaaatt    420

ttgactgatg atgctatcgt aaatatcgct aaaacaattg agtgggcttc attctttgga    480

gattctgact tatcagatag cccagaacca caagcaggat tagaatttga tggcttggct    540

aaacttatta accaagataa cgttcatgat gctcgtggag ctagcttgac tgaaagcttg    600

ttaaaccaag cagcagtaat gattagtaaa ggttatggta cacctacaga tgcttacatg    660

ccagtagggg ttcaagcaga ctttgttaac caacaacttt ctaaacaaac acaacttgtt    720

cgcgataacg gaaacaacgt aagcgttggt ttcaacatcc aaggtttcca ttcagctcgt    780

ggatttatca aacttcacgg ttctacagta atggaaaacg aacaaatctt agatgaacgt    840

attcttgctt taccaacagc tccacaacca gctaaggtaa ctgcaacaca agaagcaggt    900

aaaaaaggac aatttagagc agaagattta gcagcacatg aatataaagt tgttgtaagt    960

tctgacgatg cagagtctat tgcaagtgaa gtggctacag ctacagttac tgcaaaagat   1020

gacggcgtta aactagaaat cgaattagct ccaatgtata gctctcgtcc acaattcgtt   1080

tcaatctata gaaaaggtgc agaaacaggt ttattctacc taatcgctcg tgtacctgct   1140

agcaaagcag agaacaacgt aatcactttc tacgacttaa acgactctat tcctgaaaca   1200

gtagacgtat tcgttggtga aatgtcggct aacgtagtac acttgtttga attactacca   1260

atgatgagat tacctctagc tcaaattaac gcatctgtta catttgcagt tttatggtat   1320

ggcgcattag ctctaagagc acctaagaaa tgggtacgta ttagaaacgt taaatatatt   1380

cctgtaaaaa acgttcatag caactaataa taagaggagg taaatatata tggtattcac   1440

attagaagat tttgtagggg attggcgaca aacagcggga tataacttag atcaagtttt   1500

ggaacagggt ggagtctcaa gcctctttca aaatcttgga gtgagtgtta ctcctattca   1560

aagaattgta ctatctggtg aaaatggctt aaagattgat atacatgtta tcattccata   1620

cgaaggctta tcgggtgatc aaatgggtca aattgagaaa atctttaaag tagtgtatcc   1680

tgtagacgat catcatttca aagttattct tcactatggt acgcttgtga tagacggggt   1740

tacaccaaat atgattgatt actttggtcg gccgtatgaa ggcattgctg tttttgacgg   1800

gaaaaaaatc accgtcactg gaactttatg gaatggtaac aaaatcattg atgaacgttt   1860

gataaatcca gatggatcct tacttttccg cgtgacaatc aacggagtaa cgggctggag   1920
```

```
attatgtgaa cgtattctag cataataatt ataggataat tgaataaaaa cagtatagag   1980

agcagataaa tactgctctc tattttacta ataaggagga tttaaattgc taaaaaatac   2040

aaacttagct aattataaaa aagtgaatac acggtttgga aatcttagtt ttgacgacaa   2100

aggtatttct aatgacttaa cggaagaaca gcaaaaagaa ttaggtaagc ttcgaggatt   2160

cgaatatatt aagacagaac agaaaacaaa agaagaacct aagaaagaag aacctaagaa   2220

agaagaacct aagaaagaaa gtacagaaaa tgaattagac agcttcttag ctaaagagcc   2280

ttcaatcaaa gaattaaaag aatttgcgag taaaaaaggc attaaaattg aaaaaactaa   2340

gaaaaacgat ataattgaag aactaaagag agggtaatgt ataatgtatg gaggttatga   2400

aggacaagat tcttacgaat acccttactc acatgggaac cctaa                  2445
```

```
<210> SEQ ID NO 41
<211> LENGTH: 532
<212> TYPE: DNA
<213> ORGANISM: Artificial Sequence
<220> FEATURE:
<223> OTHER INFORMATION: Synthetic Polynucleotide

<400> SEQUENCE: 41

gaggaggtaa atatatatgg tattcacatt agaagatttt gtaggggatt ggcgacaaac     60

agcgggatat aacttagatc aagttttgga acagggtgga gtctcaagcc tctttcaaaa    120

tcttggagtg agtgttactc ctattcaaag aattgtacta tctggtgaaa atggcttaaa    180

gattgatata catgttatca ttccatacga aggcttatcg ggtgatcaaa tgggtcaaat    240

tgagaaaatc tttaaagtag tgtatcctgt agacgatcat catttcaaag ttattcttca    300

ctatggtacg cttgtgatag acggggttac accaaatatg attgattact ttggtcggcc    360

gtatgaaggc attgctgttt ttgacgggaa aaaaatcacc gtcactggaa ctttatggaa    420

tggtaacaaa atcattgatg aacgtttgat aaatccagat ggatccttac ttttccgcgt    480

gacaatcaac ggagtaacgg gctggagatt atgtgaacgt attctagcat aa            532
```

```
<210> SEQ ID NO 42
<211> LENGTH: 2442
<212> TYPE: DNA
<213> ORGANISM: Artificial Sequence
<220> FEATURE:
<223> OTHER INFORMATION: Synthetic Polynucleotide

<400> SEQUENCE: 42

atgccaaaaa ataacaaaga agaagttaaa gaagtaaacc ttaattcagt acaagaggat     60

gcgttaaagt cctttacgac tggttatggt atcacacctg atacacaaac agatgcagga    120

gcattaagac gtgagttcct agacgaccaa atctcaatgc ttacttggac agagaatgat    180

ttaacattct ataaagacat cgctaaaaaa ccagctacat ctacagtagc aaaatacgat    240

gtatacatgc aacatggtaa ggtaggtcat actagattta ctcgtgagat tggggtagca    300

ccagtaagtg accctaacat ccgtcaaaaa acagtaaata tgaaatttgc ttccgatact    360

aaaaacatca gtatcgcagc aggtctagta aacaacattc aagacccaat gcaaattttg    420

actgacgatg ctatcgtaaa tattgctaaa acaattgagt gggcttcatt ctttggagat    480

tctgacttat cagatagccc agaaccacaa gcaggactag aatttgacgg cttggctaaa    540

cttattaacc aagataacgt tcatgatgct cgtggagcta gcttgactga aagcttgtta    600

aaccaagcag cagtaatgat tagtaaaggt tatggtacac ctacagatgc ttacatgcca    660
```

```
gtaggggttc aagcagactt tgttaaccaa caactttcta aacaaacaca acttgttcgc    720
gataacggaa acaacgtaag cgttggtttc aacatccaag gtttccattc agctcgtgga    780
tttatcaaac ttcacggttc tacagtaatg gaaaacgaac aaatcttaga tgaacgtatt    840
cttgctttac caacagctcc acaaccagct aaggtaactg caacacaaga agcaggtaaa    900
aaaggacaat ttagagcaga agatttagca gcacatgaat ataaagttgt tgtaagttct    960
gacgatgcag agtctattgc aagtgaagtg gctacagcta cagttactgc aaaagatgac   1020
ggcgttaaac tagaaatcga attagctcca atgtatagct ctcgtccaca attcgtttca   1080
atctatagaa aaggtgcaga aacaggttta ttctacctaa tcgctcgtgt acctgctagc   1140
aaagcagaga acaacgtaat cactttctac gacttaaacg actctattcc tgaaacagta   1200
gacgtattcg ttggtgaaat gtcggctaac gtagtacact tgtttgaatt actaccaatg   1260
atgagattac ctctagctca aattaacgca tctgttacat ttgcagtttt atggtatggc   1320
gcattagctc taagagcacc taagaaatgg gtacgtatta gaaacgttaa atatattcct   1380
gtaaaaaacg ttcatagcaa ctaataataa gaggaggtaa atatatatgg tattcacatt   1440
ggaagatttt gtgggggatt ggagacagac agctggatat aacttagacc aagtattaga   1500
acagggtgga gtgtcaagct tatttcaaaa cttaggtgtg tcagtgactc caattcaacg   1560
tattgtgtta agtggagaaa acggtttaaa aatagacatt catgtgatta ttccgtacga   1620
aggcctcagt ggtgaccaaa tgggacaaat agagaaaatc tttaaagtag tgtaccctgt   1680
ggacgaccat cactttaaag taatcttaca ctatggtacg ttagtaattg atggcgtaac   1740
gccaaacatg atagactact ttgggcgtcc ttatgaaggc attgccgtgt ttgacggcaa   1800
aaagatcacc gtgacaggta ctctatggaa tggaaacaaa atcattgacg agcgtttaat   1860
caacccagac ggctctttac tatttcgggt aacaattaac ggcgtgaccg gatggcgatt   1920
atgcgagcgc attttagcct aataattata ggataattga ataaaaacag tatagagagc   1980
agataaatac tgctctctat tttactaata aggaggattt aaattgctaa aaaatacaaa   2040
cttagctaat tataaaaaag tgaatacacg gtttggaaat cttagttttg acgacaaagg   2100
tatttctaat gacttaacgg aagaacagca aaaagaatta ggtaagcttc gaggattcga   2160
atatattaag acagaacaga aaacaaaaga agaacctaag aaagaagaac ctaagaaaga   2220
agaacctaag aaagaagaac ctaagaaaga agaacctaag aaagaagaac ctaagaaaga   2280
aagtacagaa aatgaattag acagcttctt agctaaagag ccttcaatca aagaattaaa   2340
agaatttgcg agtaaaaaag gcattaaaat tgaaaaaact aagaaaaatg atataattga   2400
agaactaaag agagggtaat gtataatgta tggaggttat ga                      2442
```

<210> SEQ ID NO 43
<211> LENGTH: 2445
<212> TYPE: DNA
<213> ORGANISM: Artificial Sequence
<220> FEATURE:
<223> OTHER INFORMATION: Synthetic Polynucleotide

<400> SEQUENCE: 43

```
atgccaaaaa ataacaaaga agaagaagtt aaagaagtaa accttaattc agtacaagag     60
gacgcgttaa agtcctttac aactggttat ggtatcacac ctgatacaca aacagatgca    120
ggagcattaa gacgtgagtt cctagacgac caaatctcaa tgcttacttg gacagagaat    180
gatttaacat tctataaaga catcgctaaa aaaccagcta catctacagt agcaaaatac    240
gatgtataca tgcaacatgg taaggtaggt catactagat ttactcgtga gattggggta    300
```

```
gcaccagtaa gtgaccctaa catccgtcaa aaaacagtaa acatgaaatt tgcttccgat    360
actaaaaaca tcagtatcgc agcaggtcta gtaaacaaca ttcaagaccc aatgcaaatt    420
ttgactgacg atgctatcgt aaatattgct aaaacaattg agtgggcttc attctttgga    480
gattctgact tatcagatag cccagaacca caagcaggac tagaatttga cggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga ctttgttaac caacaacttt ctaaacaaac acaacttgtt    720
cgcgataacg gaaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900
aaaaaaggac aatttagagc agaagattta gcagcacatg aatataaagt tgttgtaagt    960
tctgacgatg cagagtctat tgcaagtgaa gtggctacag ctacagttac tgcaaaagat   1020
gacggcgtta aactagaaat cgaattagct ccaatgtata gctctcgtcc acaattcgtt   1080
tcaatctata gaaaaggtgc agaaacaggt ttattctacc taatcgctcg tgtacctgct   1140
agcaaagcag agaacaacgt aatcactttc tacgacttaa acgactctat tcctgaaaca   1200
gtagacgtat tcgttggtga aatgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaataa taagaggagg taaatatata tggtattcac   1440
attggaagat tttgtggggg attggagaca gacagctgga tataacttag accaagtatt   1500
agaacagggt ggagtgtcaa gcttatttca aaacttaggt gtgtcagtga ctccaattca   1560
acgtattgtg ttaagtggag aaaacggttt aaaaatagac attcatgtga ttattccgta   1620
cgaaggcctc agtggtgacc aaatgggaca aatagagaaa atctttaaag tagtgtaccc   1680
tgtggacgac catcacttta aagtaatctt acactatggt acgttagtaa ttgatggcgt   1740
aacgccaaac atgatagact actttgggcg tccttatgaa ggcattgccg tgtttgacgg   1800
caaaaagatc accgtgacag gtactctatg gaatggaaac aaaatcattg acgagcgttt   1860
aatcaaccca gacggctctt tactatttcg ggtaacaatt aacggcgtga ccggatggcg   1920
attatgcgag cgcattttag cctaataatt ataggataat tgaataaaaa cagtatagag   1980
agcagataaa tactgctctc tattttacta ataaggagga tttaaattgc taaaaaatac   2040
aaacttagct aattataaaa aagtgaatac acggtttgga aatcttagtt ttgacgacaa   2100
aggtatttct aatgacttaa cggaagaaca gcaaaaagaa ttaggtaagc ttcgaggatt   2160
cgaatatatt aagacagaac agaaaacaaa agaagaacct aagaaagaag aacctaagaa   2220
agaagaacct aagaaagaag aacctaagaa agaagaacct aagaaagaag aacctaagaa   2280
agaaagtaca gaaaatgaat tagacagctt cttagctaaa gagccttcaa tcaaagaatt   2340
aaaagaattt gcgagtaaaa aaggcattaa aattgaaaaa actaagaaaa atgatataat   2400
tgaagaacta aagagagggt aatgtataat gtatggaggt tatga                  2445
```

<210> SEQ ID NO 44
<211> LENGTH: 2445
<212> TYPE: DNA
<213> ORGANISM: Artificial Sequence
<220> FEATURE:

<223> OTHER INFORMATION: Synthetic Polynucleotide

<400> SEQUENCE: 44

```
atgccaaaaa ataacaaaga agaagaagtt aaagaagtaa accttaattc agtacaagag     60
gatgcgttaa agtcctttac aactggttat ggtatcacac ctgatacaca aacagatgca    120
ggggcactaa gacgtgagtt cctagacgac caaatctcaa tgcttacttg gacagaaaat    180
gatttaacat tctacaaaga catcgctaaa aaaccagcta catctacagt agcaaaatac    240
gatgtgtaca tgcaacacgg taaagtaggt catactagat ttactcgtga gattggggta    300
gcaccagtaa gtgaccctaa catccgtcaa aaaacagtaa acatgaaatt tgcttctgat    360
actaaaaata ttagtatcgc agcaggtcta gtaaacaaca ttcaagaccc tatgcaaatt    420
ttgactgatg atgctatcgt aaatatcgct aaaacaattg agtgggcttc attctttgga    480
gattctgact tatcagatag cccagaacca caagcaggat tagaatttga tggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga ctttgttaac caacaacttt ctaaacaaac acaacttgtt    720
cgcgataacg gaaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900
aaaaaaggac aatttagagc agaagattta gcagcacatg aatataaagt tgttgtaagt    960
tctgacgatg cagagtctat tgcaagtgaa gtggctacag ctacagttac tgcaaaagat   1020
gacggcgtta aactagaaat cgaattagct ccaatgtata gctctcgtcc acaattcgtt   1080
tcaatctata gaaaaggtgc agaaacaggt ttattctacc taatcgctcg tgtacctgct   1140
agcaaagcag agaacaacgt aatcactttc tacgacttaa acgactctat tcctgaaaca   1200
gtagacgtat tcgttggtga aatgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaataa taagaggagg taaatatata tggtattcac   1440
attggaagat tttgtggggg attggagaca gacagctgga tataacttag accaagtatt   1500
agaacagggt ggagtgtcaa gcttatttca aaacttaggt gtgtcagtga ctccaattca   1560
acgtattgtg ttaagtggag aaaacggttt aaaaatagac attcatgtga ttattccgta   1620
cgaaggcctc agtggtgacc aaatgggaca aatagagaaa atctttaaag tagtgtaccc   1680
tgtggacgac catcacttta aagtaatctt acactatggt acgttagtaa ttgatggcgt   1740
aacgccaaac atgatagact actttgggcg tccttatgaa ggcattgccg tgtttgacgg   1800
caaaaagatc accgtgacag gtactctatg gaatggaaac aaaatcattg acgagcgttt   1860
aatcaaccca gacggctctt tactatttcg ggtaacaatt aacggcgtga ccggatggcg   1920
attatgcgag cgcattttag cctaataatt ataggataat tgaataaaaa cagtatagag   1980
agcagataaa tactgctctc tattttacta ataaggagga tttaaattgc taaaaaaatac   2040
aaacttagct aattataaaa aagtgaatac acggtttgga aatcttagtt ttgacgacaa   2100
aggtatttct aatgacttaa cggaagaaca gcaaaaagaa ttaggtaagc ttcgaggatt   2160
cgaatatatt aagacagaac agaaaacaaa agaagaacct aagaaagaag aacctaagaa   2220
agaagaacct aagaaagaaa gtacagaaaa tgaattagac agcttcttag ctaaagagcc   2280
```

ttcaatcaaa gaattaaaag aatttgcgag taaaaaaggc attaaaattg aaaaaactaa 2340
gaaaaacgat ataattgaag aactaaagag agggtaatgt ataatgtatg gaggttatga 2400
aggacaagat tcttacgaat acccttactc acatgggaac cctaa 2445

<210> SEQ ID NO 45
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 45
gaggaggtaa atatat 16

<210> SEQ ID NO 46
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 46
ataattttga ttaactttag aggaggtaaa tatat 35

<210> SEQ ID NO 47
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 47
aaggagataa atatat 16

<210> SEQ ID NO 48
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 48
gaggaggtaa ata 13

<210> SEQ ID NO 49
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 49
aaggagataa ata 13

<210> SEQ ID NO 50
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 50
ataattttga ttaactttag aggaggtaaa ta 32

<210> SEQ ID NO 51
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 51
ataattttga ttaactttaa aggagataaa tatat 35

<210> SEQ ID NO 52
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 52
ataattttga ttaactttaa aggagataaa ta 32

<210> SEQ ID NO 53
<211> LENGTH: 519
<212> TYPE: DNA
<213> ORGANISM: Artificial Sequence
<220> FEATURE:
<223> OTHER INFORMATION: Synthetic Polynucleotide

<400> SEQUENCE: 53
atggttttta cactagagga ttttgtcggg gattggcgtc aaactgccgg atacaactta 60
gatcaagtgt tagaacaggg tggagtaagt agtcttttcc aaaacttagg tgtgtcagta 120
actcctattc aacggattgt tttatctgga gagaacggtt tgaaaattga tattcacgtg 180
ataattccgt acgaaggatt aagcggagat cagatggggc aaattgagaa aatctttaaa 240
gtagtatacc cagttgatga ccatcatttc aaagtgattt tacattacgg aactctagta 300
attgacggtg tgaccccaaa tatgattgac tattttggcc gtccatacga aggaatagct 360
gtctttgacg gtaaaaaaat tacagtaact ggaacattat ggaacggaaa caaaatcatt 420
gacgagcgtt taatcaatcc ggatggctct ttactctttc gcgtgacgat taacggagtg 480
acaggttggc gtttgtgtga gcgtattctt gcctaatga 519

<210> SEQ ID NO 54
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 54
taataagagg aggtaaatat at 22

<210> SEQ ID NO 55
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 55
ttacgccaag cttggctgca acgtgagttc ctagacgacc 40

<210> SEQ ID NO 56
<211> LENGTH: 47

<212> TYPE: DNA
<213> ORGANISM: Artificial Sequence
<220> FEATURE:
<223> OTHER INFORMATION: Synthetic Oligonucleotide

<400> SEQUENCE: 56
atatttacct cctcttatta ttagttgcta tgaacgtttt ttacagg 47

<210> SEQ ID NO 57
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 57
ataagaggag gtaaatatat atggtattca cattagaaga ttttg 45

<210> SEQ ID NO 58
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 58
attcaattat cctataatta ttatgctaga atacgttcac ataa 44

<210> SEQ ID NO 59
<211> LENGTH: 46
<212> TYPE: DNA
<213> ORGANISM: Artificial Sequence
<220> FEATURE:
<223> OTHER INFORMATION: Synthetic Oligonucleotide

<400> SEQUENCE: 59
gtgaacgtat tctagcataa taattatagg ataattgaat aaaaac 46

<210> SEQ ID NO 60
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 60
acgacggcca gtgaattccc tcgtggtgtt ctgactcccg 40

<210> SEQ ID NO 61
<211> LENGTH: 500
<212> TYPE: DNA
<213> ORGANISM: A511 phage

<400> SEQUENCE: 61
taattatagg ataattgaat aaaaacagta tagagagcag ataaatactg ctctctattt 60
tactaataag gaggatttaa attgctaaaa aatacaaact tagctaatta taaaaaagtg 120
aatacacggt ttggaaatct tagttttgac gacaaaggta tttctaatga cttaacggaa 180
gaacagcaaa aagaattagg taagcttcga ggattcgaat atattaagac agaacagaaa 240
acaaaagaag aacctaagaa agaagaacct aagaaagaag aacctaagaa agaagaacct 300
aagaaagaag aacctaagaa agaagaacct aagaaagaaa gtacagaaaa tgaattagac 360
agcttcttag ctaaagagcc ttcaatcaaa gaattaaaag aatttgcgag taaaaaaggc 420
attaaaattg aaaaaactaa gaaaaatgat ataattgaag aactaaagag agggtaatgt 480
ataatgtatg gaggttatga 500

<210> SEQ ID NO 62
<211> LENGTH: 500
<212> TYPE: DNA
<213> ORGANISM: LP124 Phage

<400> SEQUENCE: 62
taattatagg ataattgaat aaaaacagta tagagagcag ataaatactg ctctctattt 60
tactaataag gaggatttaa attgctaaaa aatacaaact tagctaatta taaaaaagtg 120
aatacacggt ttggaaatct tagttttgac gacaaaggta tttctaatga cttaacggaa 180
gaacagcaaa aagaattagg taagcttcga ggattcgaat atattaagac agaacagaaa 240
acaaaagaag aacctaagaa agaagaacct aagaaagaag aacctaagaa agaagaacct 300
aagaaagaag aacctaagaa agaagaacct aagaaagaaa gtacagaaaa tgaattagac 360
agcttcttag ctaaagagcc ttcaatcaaa gaattaaaag aatttgcgag taaaaaaggc 420
attaaaattg aaaaaactaa gaaaaatgat ataattgaag aactaaagag agggtaatgt 480
ataatgtatg gaggttatga 500

<210> SEQ ID NO 63
<211> LENGTH: 500
<212> TYPE: DNA
<213> ORGANISM: LP40 Phage

<400> SEQUENCE: 63
taattatagg ataattgaat aaaaacagta tagagagcag ataaatactg ctctctattt 60
tactaataag gaggatttaa attgctaaaa aatacaaact tagctaatta taaaaaagtg 120
aatacacggt ttggaaatct tagttttgac gacaaaggta tttctaatga cttaacggaa 180
gaacagcaaa aagaattagg taagcttcga ggattcgaat atattaagac agaacagaaa 240
acaaaagaag aacctaagaa agaagaacct aagaaagaag aacctaagaa agaaagtaca 300
gaaaatgaat tagacagctt cttagctaaa gagccttcaa tcaaagaatt aaaagaattt 360
gcgagtaaaa aaggcattaa aattgaaaaa actaagaaaa acgatataat tgaagaacta 420
aagagagggt aatgtataat gtatggaggt tatgaaggac aagattctta cgaataccct 480
tactcacatg ggaaccctaa 500

<210> SEQ ID NO 64
<211> LENGTH: 42
<212> TYPE: DNA
<213> ORGANISM: Artificial Sequence
<220> FEATURE:
<223> OTHER INFORMATION: Synethic Oligonucleotide

<400> SEQUENCE: 64
taataagagg aggtaaatat atatggtatt cacattggaa ga 42

<210> SEQ ID NO 65
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 65
attcaattat cctataatta ttaggctaaa atgcgctcgc 40

<210> SEQ ID NO 66
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 66
gcgagcgcat tttagcctaa taattatagg ataattgaat 40

<210> SEQ ID NO 67
<211> LENGTH: 16
<212> TYPE: DNA
<213> ORGANISM: Artificial Sequence
<220> FEATURE:
<223> OTHER INFORMATION: Synethic Oligonucleotide

<400> SEQUENCE: 67
gaggaggtaa atatat 16

<210> SEQ ID NO 68
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 68
atgtttttgg cgtcttccat atatatttac ctcctcttag ttgctatgaa cgtttt 56

<210> SEQ ID NO 69
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 69
aaaacgttca tagcaactaa gaggaggtaa atatatatgg aagacgccaa aaacat 56

<210> SEQ ID NO 70
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 70
attcaattat cctataatta ttacaatttg gactttccgc 40

<210> SEQ ID NO 71
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 71
gcggaaagtc caaattgtaa taattatagg ataattgaat 40

<210> SEQ ID NO 72
<211> LENGTH: 40
<212> TYPE: DNA
<213> ORGANISM: Artificial Sequence
<220> FEATURE:

<223> OTHER INFORMATION: Synthetic Oligonucleotide

<400> SEQUENCE: 72
acgacggcca gtgaattccc agttactaac tgctctaatg 40

<210> SEQ ID NO 73
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 73
acgacggcca gtgaattccc agttactaac tgttctaatg 40

<210> SEQ ID NO 74
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 74
cctctagctc aaattaacgc atctgt 26

<210> SEQ ID NO 75
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 75
tggctctaca tgcttagggt tcc 23

<210> SEQ ID NO 76
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 76
tcttcgagtg tgaagaccat atatatttac ctcctcttag ttgc 44

<210> SEQ ID NO 77
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 77
ctaagaggag gtaaatatat atggtcttca cactcgaaga ttt 43

<210> SEQ ID NO 78
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 78
attcaattat cctataatta ttacgccaga atgcgttcgc 40

<210> SEQ ID NO 79
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 79
gcgaacgcat tctggcgtaa taattatagg ataattgaat aaa 43

<210> SEQ ID NO 80
<211> LENGTH: 65
<212> TYPE: DNA
<213> ORGANISM: Artificial Sequence
<220> FEATURE:
<223> OTHER INFORMATION: Synthetic Oligonucleotide

<400> SEQUENCE: 80
aaaacgttca tagcaactaa taataagagg aggtaaatat atatggtctt cacactcgaa 60
gattt 65

<210> SEQ ID NO 81
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 81
atatttacct cctcttatta ttagttgcta tgaacgtttt ttacagg 47

<210> SEQ ID NO 82
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 82
tgctatatta taggaacatg ggaa 24

<210> SEQ ID NO 83
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 83
tgcttacatg ccagtagggg t 21

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 84
gtatgaaggt ctgagcggcg 20

<210> SEQ ID NO 85
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 85
gatctggccc atttggtcgc 20

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 86
cgcatagaac tgcctgcgtc 20

<210> SEQ ID NO 87
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 87
caccccaaca tcttcgacgc 20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 88
gcgcaactgc aactccgata 20

<210> SEQ ID NO 89
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 89

His His His His His His
1 5

<210> SEQ ID NO 90
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 90
attcaattat cctataatta ttaatggtga tggtgatgat gacctccacc tgctgccgcc 60
agaatgcgtt cgcaca 76

<210> SEQ ID NO 91
<211> LENGTH: 46
<212> TYPE: DNA
<213> ORGANISM: Artificial Sequence
<220> FEATURE:
<223> OTHER INFORMATION: Synthetic Oligonucleotide

<400> SEQUENCE: 91
atcatcacca tcaccattaa taattatagg ataattgaat aaaaac 46

<210> SEQ ID NO 92
<211> LENGTH: 67
<212> TYPE: DNA
<213> ORGANISM: Artificial Sequence
<220> FEATURE:
<223> OTHER INFORMATION: Synthetic Polynucleotide

<400> SEQUENCE: 92
attcaattat cctataatta ttaatggtga tggtgatgat gtgctgccgc cagaatgcgt 60
tcgcaca 67

<210> SEQ ID NO 93
<211> LENGTH: 80
<212> TYPE: DNA
<213> ORGANISM: Artificial Sequence
<220> FEATURE:
<223> OTHER INFORMATION: Synthetic Polynucleotide

<400> SEQUENCE: 93
taataagagg aggtaaatat atatgcatca tcaccatcac catggtggag gtgcagcagt 60
cttcacactc gaagatttcg 80

<210> SEQ ID NO 94
<211> LENGTH: 80
<212> TYPE: DNA
<213> ORGANISM: Artificial Sequence
<220> FEATURE:
<223> OTHER INFORMATION: Synthetic Polynucleotide

<400> SEQUENCE: 94
agcaactaat aataagagga ggtaaatata tatgcatcat caccatcacc atgcagcagt 60
cttcacactc gaagatttcg 80

<210> SEQ ID NO 95
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 95
catcatcacc atcaccat 18

<210> SEQ ID NO 96
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 96

Ala Ala Gly Gly Gly His His His His His His
1 5 10

<210> SEQ ID NO 97
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 97

-continued gcagcaggtg gaggtcatca tcaccatcac cat 33

<210> SEQ ID NO 98
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 98

Ala Ala His His His His His His
1 5

<210> SEQ ID NO 99
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 99
gcagcacatc atcaccatca ccat 24

<210> SEQ ID NO 100
<211> LENGTH: 11
<212> TYPE: PRT
<213> ORGANISM: Artificial Sequence
<220> FEATURE:
<223> OTHER INFORMATION: Synthetic Polynucleotide

<400> SEQUENCE: 100

His His His His His His Gly Gly Gly Ala Ala
1 5 10

<210> SEQ ID NO 101
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 101
catcatcacc atcaccatgg tggaggtgca gca 33

<210> SEQ ID NO 102
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 102

His His His His His His Ala Ala
1 5

<210> SEQ ID NO 103
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 103
catcatcacc atcaccatgc agca 24